(12) United States Patent
Hutchison et al.

(10) Patent No.: US 7,863,454 B2
(45) Date of Patent: Jan. 4, 2011

(54) 3-SUBSTITUTED-6-ARYL PYRIDINES

(75) Inventors: Alan J. Hutchison, Madison, CT (US); Jun Yuan, Guilford, CT (US); Kyungae Lee, Guilford, CT (US); George D. Maynard, Clinton, CT (US); Bertrand L. Chenard, Waterford, CT (US); Nian Liu, Edison, NJ (US); Qin Guo, Branford, CT (US); Zihong Guo, Southbury, CT (US); Peter Hrnciar, Hamden, CT (US)

(73) Assignee: Novartis International Pharmaceutical Ltd., Hamilton (BM)

( * ) Notice: Subject to any disclaimer, the term of this patent is extended or adjusted under 35 U.S.C. 154(b) by 146 days.

(21) Appl. No.: 12/041,038

(22) Filed: Mar. 3, 2008

(65) Prior Publication Data

US 2009/0176980 A1 Jul. 9, 2009

Related U.S. Application Data

(62) Division of application No. 10/704,364, filed on Nov. 7, 2003, now Pat. No. 7,342,115.

(60) Provisional application No. 60/425,281, filed on Nov. 8, 2002.

(51) Int. Cl.
*C07D 401/04* (2006.01)
(52) U.S. Cl. .................................................. 546/275.7
(58) Field of Classification Search ............... 546/275.7
See application file for complete search history.

(56) References Cited

PUBLICATIONS

Balant et al., "Metabolic Considerations, etc.," in Manfred ed., Burger's Medicinal Chemistry and Drug Discovery, 5th ed. vol. 1:Principles and Practice, John Wiley & Sons, Inc., 1995.*

Vippagunta et al.m "Crystalline Solids", Advanced Drug Delivery Reviews 48 (2001) 3-26.*
Jain et al., "Polymorphism in Pharmacy", Indian Drugs, 1986, 23(6), 315-329.*
Guillory (in Brittain ed.), "Polymorphism, etc.," NY: Marcel Dekker, Inc., 1999, 1-2, 183-226.*

* cited by examiner

*Primary Examiner*—Patricia L Morris
(74) *Attorney, Agent, or Firm*—Peter F. Corless; Dwight D. Kim; Edwards Angell Palmer & Dodge LLP

(57) ABSTRACT

3-substituted-6-aryl pyridines of Formula I are provided:

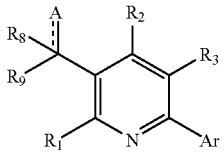

Formula I wherein $R_1$, $R_2$, $R_3$, $R_8$, $R_9$, A and Ar are defined herein. Such compounds are ligands of C5a receptors. Preferred compounds of Formula I bind to C5a receptors with high affinity and exhibit neutral antagonist or inverse agonist activity at C5a receptors. The present invention also relates to pharmaceutical compositions comprising such compounds, and to the use of such compounds in treating a variety of inflammatory, cardiovascular, and immune system disorders. In addition, the present invention provides labeled 3-substituted-6-aryl pyridines, which are useful as probes for the localization of C5a receptors.

4 Claims, No Drawings

3-SUBSTITUTED-6-ARYL PYRIDINES

CROSS-REFERENCE TO RELATED APPLICATIONS

This application is a divisional of U.S. patent application Ser. No. 10/704,364 (now U.S. Pat. No. 7,342,115), filed on Nov. 7, 2003, which claims priority to U.S. Provisional Application 60/425,281, filed Nov. 8, 2002.

FIELD OF THE INVENTION

This invention relates generally to 3-substituted-6-aryl pyridines that act as modulators of mammalian complement C5a receptors, and to pharmaceutical compositions comprising such modulators. The present invention further relates to the use of such modulators in treating a variety of inflammatory and immune system disorders and as probes for the localization of C5a receptors.

BACKGROUND OF THE INVENTION

C5a, a 74 amino acid peptide, is generated in the complement cascade by the cleavage of the complement protein C5 by the complement C5 convertase enzyme. C5a has both anaphylatoxic (e.g., bronchoconstricting and vascular spasmogenic) and chemotactic effects. Therefore, it is active in engendering both the vascular and cellular phases of inflammatory responses. Because it is a plasma protein and, therefore, generally almost instantly available at a site of an inciting stimulus, it is a key mediator in terms of initiating the complex series of events that results in augmentation and amplification of an initial inflammatory stimulus. The anaphylatoxic and chemotactic effects of the C5a peptide are believed to be mediated through its interaction with the C5a receptor (CD88 antigen), a 52 kD membrane bound G-protein coupled receptor (GPCR). C5a is a potent chemoattractant for polymorphonuclear leukocytes, bringing neutrophils, basophils, eosinophils and monocytes to sites of inflammation and/or cellular injury. C5a is one of the most potent chemotactic agents known for a wide variety of inflammatory cell types. C5a also "primes" or prepares neutrophils for various antibacterial functions (e.g., phagocytosis). Additionally, C5a stimulates the release of inflammatory mediators (e.g., histamines, TNF-α, IL-1, IL-6, IL-8, prostaglandins, and leukotrienes) and the release of lysosomal enzymes and other cytotoxic components from granulocytes. Among its other actions, C5a also promotes the production of activated oxygen radicals and the contraction of smooth muscle.

Considerable experimental evidence implicates increased levels of C5a in a number of autoimmune diseases and inflammatory and related disorders. Agents that block the binding of C5a to its receptor other agents, including inverse agonists, which modulate signal transduction associated with C5a-receptor interactions, can inhibit the pathogenic events, including chemotaxis, associated with anaphylatoxin activity contributing to such inflammatory and autoimmune conditions. The present invention provides such agents, and has further related advantages.

SUMMARY OF THE INVENTION

The present invention provides compounds that modulate, and preferably inhibit, C5a receptor activation and/or C5a receptor-mediated signal transduction. Such C5a receptor modulators are preferably high affinity C5a receptor ligands and act as antagonists (e.g., inverse agonists) of complement C5a receptors, such as human C5a receptors. Within certain aspects, C5a receptor modulators provided herein are 3-substituted-6-aryl pyridines of Formula I or a pharmaceutically acceptable form thereof:

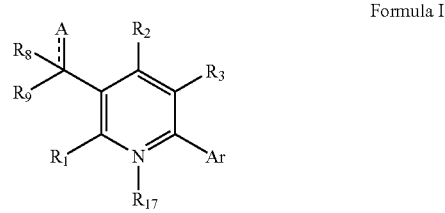

Formula I

Within Formula I,

Ar is optionally substituted phenyl, optionally substituted naphthyl, optionally substituted pyridyl, optionally substituted pyrimidinyl, optionally substituted thienyl, optionally substituted indanyl, optionally substituted indenyl, optionally substituted benzisoxazolyl, optionally substituted indazolyl or optionally substituted indolyl; preferred Ar groups are substituted with from 0 to 4 substituents independently chosen from $R_x$;

A is $OR_4$, $NR_4R_5$, $CHR_6R_7$ or $CR_6R_7$ (including compounds in which ---- represents a single or double bond);

$R_1$ is chosen from:
  (i) hydrogen, halogen, amino, and cyano; and
  (ii) optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkyl), optionally substituted alkoxy (preferably optionally substituted $C_1$-$C_6$alkoxy), optionally substituted haloalkyl (preferably optionally substituted $C_1$-$C_4$haloalkyl), optionally substituted haloalkoxy (preferably optionally substituted $C_1$-$C_4$haloalkoxy), optionally substituted mono- and dialkylamino (preferably optionally substituted mono- and di-($C_1$-$C_6$alkyl)amino), optionally substituted cycloalkyl-alkyl (preferably optionally substituted ($C_3$-$C_7$cycloalkyl)$C_0$-$C_4$alkyl), optionally substituted heterocycloalkyl-alkyl (preferably optionally substituted (3- to 7-membered heterocycloalkyl)$C_0$-$C_4$alkyl) and optionally substituted $S(O_n)$alkyl (preferably optionally substituted —$S(O_n)C_1$-$C_4$alkyl); wherein certain preferred $R_1$ groups are substituted with from 0 to 4 substituents independently chosen from $R_x$;

$R_2$ is halogen, cyano or $XR_y$;

$R_3$ is hydrogen, halogen, hydroxy, amino, cyano, optionally substituted alkyl (preferably optionally substituted $C_1$-$C_4$alkyl), optionally substituted alkenyl (preferably optionally substituted $C_2$-$C_4$alkenyl), optionally substituted alkynyl (preferably optionally substituted $C_2$-$C_4$alkynyl), optionally substituted alkoxy (preferably optionally substituted $C_1$-$C_4$alkoxy), optionally substituted haloalkyl (preferably optionally substituted $C_1$-$C_2$haloalkyl), optionally substituted haloalkoxy (preferably optionally substituted $C_1$-$C_2$haloalkoxy), optionally substituted mono- or di-alkylamino (preferably optionally substituted mono- or di-($C_1$-$C_4$alkyl)amino) or optionally substituted —$S(O_n)$alkyl (preferably optionally substituted —$S(O_n)C_1$-$C_4$alkyl);

$R_4$ is:
  (i) hydrogen, optionally substituted alkyl (preferably optionally substituted $C_1$-$C_8$alkyl), optionally substituted alkenyl (preferably optionally substituted $C_2$-$C_8$alkenyl), optionally substituted alkynyl (preferably optionally substituted $C_2$-$C_8$alkynyl), optionally substituted cycloalkyl-alkyl (preferably optionally substituted ($C_3$-$C_7$cycloalkyl)$C_0$-$C_4$alkyl, optionally substituted mono- or di-alkylamino or mono- or di-alkylamino-alkyl (preferably optionally substituted mono- or di-($C_1$-$C_4$alkylamino)$C_0$-$C_4$alkyl), optionally substituted heterocycloalkyl or optionally substituted heterocycloalkylalkyl (preferably optionally substituted (3- to 7-membered heterocycloalkyl)$C_0$-$C_4$alkyl), optionally substituted phenyl or optionally substituted phenyl-alkyl (preferably optionally substituted phenyl$C_0$-$C_4$alkyl), optionally substituted pyridyl or optionally substituted pyridyl-alkyl (preferably optionally substituted pyridyl$C_0$-$C_4$alkyl), optionally substituted pyrimidinyl or optionally substituted pyrimidinyl-alkyl (preferably optionally substituted pyrimidinyl$C_0$-$C_4$alkyl), optionally substituted thienyl or optionally substituted thienyl-alkyl (preferably optionally substituted thienyl$C_0$-$C_4$alkyl), optionally substituted imidazolyl or optionally substituted imidazolyl-alkyl (preferably optionally substituted imidazolyl$C_0$-$C_4$alkyl), optionally substituted pyrrolyl or optionally substituted pyrrolyl-alkyl (preferably optionally substituted pyrrolyl$C_0$-$C_4$alkyl), optionally substituted pyrazolyl or optionally substituted pyrazolyl-alkyl (preferably optionally substituted pyrazolyl$C_0$-$C_4$alkyl), optionally substituted benzoisothiazolyl, or optionally substituted tetrahydronaphthyl; preferably each $R_4$ is substituted with from 0 to 4 substituents independently chosen from $R_x$, optionally substituted $C_2$-$C_4$alkanoyl, optionally substituted mono- and di-($C_1$-$C_4$alkyl)amino($C_1$-$C_4$alkyl), optionally substituted mono- and di-$C_1$-$C_4$alkylamino ($C_1$-$C_4$alkoxy), optionally substituted (3- to 7-membered heterocycloalkyl)$C_0$-$C_4$alkyl and $XR_y$; or (ii) joined to $R_5$ or $R_8$, in combination with the nitrogen to which $R_4$ is bound, to form an optionally substituted 3- to 10-membered heterocycle substituted with from 0 to 4 substituents independently chosen from $R_x$, oxo and YZ;

$R_5$ is:
(i) hydrogen;
(ii) optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkynyl), optionally substituted carbocycle or carbocycle-alkyl (preferably optionally substituted ($C_3$-$C_7$carbocycle)$C_0$-$C_4$alkyl), wherein preferred $R_5$ groups are substituted with from 0 to 3 substituents independently chosen from halogen, hydroxy, amino, cyano, optionally substituted $C_1$-$C_4$alkyl, optionally substituted $C_1$-$C_4$alkoxy, methylamino, dimethylamino, trifluoromethyl and trifluoromethoxy; or
(iii) joined to $R_4$ to form an optionally substituted heterocycle;

$R_6$ is:
(i) hydrogen, halogen, hydroxy, cyano, amino, optionally substituted alkyl (preferably optionally substituted $C_1$-$C_6$alkyl), optionally substituted alkenyl (preferably optionally substituted $C_1$-$C_6$alkenyl), optionally substituted alkynyl (preferably optionally substituted $C_2$-$C_6$alkynyl), optionally substituted mono- or dialkylamino or mono- or dialkylamino-alkyl (preferably optionally substituted mono- or di-($C_1$-$C_6$alkylamino) $C_0$-$C_6$alkyl), optionally substituted carbocycle or carbocycle-alkyl (preferably optionally substituted ($C_3$-$C_{10}$carbocycle)$C_0$-$C_4$alkyl) or optionally substituted heterocycle or heterocycle-alkyl (preferably optionally substituted (3- to 10-membered heterocycle)$C_0$-$C_4$alkyl), wherein preferred $R_6$ groups are substituted with from 0 to 4 substituents independently chosen from $R_x$, oxo, optionally substituted mono- and di-($C_1$-$C_4$alkylamino)$C_1$-$C_4$alkyl, optionally substituted mono- and di-$C_1$-$C_4$alkylamino($C_1$-$C_4$alkoxy), optionally substituted $C_2$-$C_4$alkanoyl, optionally substituted $C_2$-$C_4$alkanoyloxy, and YZ; or (ii) joined to $R_7$ or $R_8$, in combination with the carbon atom to which $R_6$ is bound, to form a 3- to 10-membered carbocycle or heterocycle, each of which is substituted with from 0 to 4 substituents independently chosen from $R_x$, oxo, optionally substituted mono- and di-($C_1$-$C_4$alkylamino)$C_1$-$C_4$alkyl, optionally substituted mono- and di-$C_1$-$C_4$alkylamino($C_1$-$C_4$alkoxy), optionally substituted $C_2$-$C_4$alkanoyl and optionally substituted $C_2$-$C_4$alkanoyloxy;

$R_7$ is hydrogen, halogen, hydroxy, cyano, amino, optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkynyl), optionally substituted alkoxy (preferably optionally substituted $C_1$-$C_6$alkoxy), optionally substituted cycloalkyl or cycloalkyl-alkyl (preferably optionally substituted ($C_3$-$C_7$cycloalkyl)$C_0$-$C_4$alkyl); or $R_7$ is taken in combination with 16 to form an optionally substituted carbocycle or heterocycle;

$R_8$ is:
(i) hydrogen, halogen, hydroxy, optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkynyl), optionally substituted alkoxy (preferably optionally substituted $C_1$-$C_6$alkoxy), optionally substituted alkylamino (preferably optionally substituted $C_1$-$C_6$alkylamino) or optionally substituted cycloalkyl or cycloalkyl-alkyl (preferably optionally substituted $C_3$-$C_7$cycloalkyl $C_0$-$C_4$alkyl);
(ii) taken in combination with $R_9$ to form a $C_5$-$C_7$cycloalkyl ring or a 5- to 7-membered heterocycloalkyl ring, each of which is substituted with from 0 to 4 substituents independently chosen from halogen, hydroxy, $C_1$-$C_2$alkyl and $C_1$-$C_2$alkoxy;
(iii) taken in combination with $R_9$ to form an oxo group; or
(iv) taken in combination with $R_4$ or $R_6$ to form an optionally substituted 3- to 10

$R_9$ is:
(i) absent, hydrogen, halogen, hydroxy, optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkynyl), optionally substituted alkoxy (preferably optionally substituted $C_1$-$C_6$alkoxy), optionally substituted alkyl amino (preferably optionally substituted $C_1$-$C_6$alkylamino) Or optionally substituted cycloalkyl or cycloalkyl-alkyl (preferably optionally substituted $C_3$-$C_7$cycloalkyl$C_0$-$C_4$alkyl);
(ii) taken in combination with $R_5$ to form an optionally substituted $C_5$-$C_7$cycloalkyl ring or optionally substituted 5- to 7-membered heterocycloalkyl ring; or (iii) taken in combination with $R_5$ to form an oxo group;

$R_{17}$ is absent or oxygen;

X is a single bond, —$CR_AR_B$—, —O—, —C(=O)—, —C(=O)O—, —S(O)$_n$, or —$NR_B$—; and $R_y$ is:
(i) hydrogen; or
(ii) optionally substituted alkyl (preferably optionally substituted $C_1$-$C_{10}$alkyl), optionally substituted alkenyl (preferably optionally substituted $C_2$-$C_{10}$alkenyl), optionally substituted alkynyl (preferably optionally substituted $C_2$-$C_{10}$alkynyl), optionally substituted carbocycle or carbocycle-alkyl (preferably optionally substituted $C_3$-$C_{10}$-carbocycle$C_0$-$C_4$alkyl) or optionally substituted heterocycle or heterocycle-alkyl (preferably optionally substituted (3- to 10-membered heterocycle) $C_0$-$C_4$alkyl), wherein certain preferred $R_y$ are substituted with from 0 to 6 substituents independently selected from $R_x$, oxo, optionally substituted —NH($C_1$-$C_6$alkanoyl), optionally substituted —N($C_1$-$C_6$alkyl)$C_1$-$C_6$alkanoyl, optionally substituted —NHS(O$_n$)$C_1$-$C_6$alkyl, optionally substituted —N(S(O$_n$)$C_1$-$C_6$alkyl)$_2$, optionally substituted —S(O$_n$)NH$C_1$-$C_6$alkyl and optionally substituted —S(O$_n$)N($C_1$-$C_6$alkyl)$_2$;

Y is a single bond, —$CR_AR_B$—, —$NR_B$— or —O—;

Z is independently selected at each occurrence from 3- to 7-membered carbocycles and heterocycles, each of which is substituted with from 0 to 4 substituents independently selected from halogen, oxo, —COOH, hydroxy, amino, cyano, optionally substituted $C_1$-$C_6$alkyl optionally substituted $C_1$-$C_6$alkoxy, optionally substituted $C_1$-$C_6$haloalkyl, optionally substituted $C_1$-$C_6$haloalkoxy, optionally substituted mono- and di-($C_1$-$C_6$alkyl)amino and optionally substituted S(O$_n$)$C_1$-$C_6$alkyl; and $R_A$ and $R_B$ are independently selected at each occurrence from:
(i) hydrogen; and
(ii) optionally substituted alkyl (preferably optionally substituted $C_1$-$C_{10}$alkyl), optionally substituted alkenyl (preferably optionally substituted $C_2$-$C_{10}$alkenyl), optionally substituted alkynyl (preferably optionally substituted $C_2$-$C_{10}$alkynyl), optionally substituted saturated or partially saturated ($C_3$-$C_{10}$carbocycle)$C_0$-$C_4$alkyl and optionally substituted saturated or partially saturated (3- to 10-membered heterocycle)$C_0$-$C_4$alkyl; each of which is preferably substituted with from 0 to 6 substituents independently selected from oxo, hydroxy, halogen, cyano, amino, optionally substituted $C_1$-$C_6$alkoxy, optionally substituted mono- and di-($C_1$-$C_4$alkyl)amino, —COOH, —C(=O)NH$_2$, optionally substituted —NHC(=O)($C_1$-$C_6$alkyl), optionally substituted —N($C_1$-$C_6$alkyl)C(=O)($C_1$-$C_6$alkyl), optionally substituted —NHS(O$_n$)$C_1$-$C_6$alkyl, optionally substituted —S(O$_n$)$C_1$-$C_6$alkyl, optionally substituted —S(O$_n$)NH$C_1$-$C_6$alkyl, optionally substituted —S(O$_n$)N($C_1$-$C_6$alkyl)$C_1$-$C_6$alkyl and Z;

$R_x$ is independently chosen at each occurrence from halogen, hydroxy, amino, cyano, nitro, —COOH, —C(=O)NH$_2$, optionally substituted alkoxycarbonyl (preferably optionally substituted $C_1$-$C_6$alkoxycarbonyl), optionally substituted —C(=O)NH-alkyl (preferably optionally substituted —C(=O)NH$C_1$-$C_6$alkyl), optionally substituted —C(=O)N(alkyl)$_2$ (preferably optionally substituted —C(=O)N($C_1$-$C_6$alkyl)$_2$), optionally substituted alkyl (preferably optionally substituted $C_1$-$C_6$alkyl), optionally substituted alkenyl (preferably optionally substituted $C_2$-$C_6$alkenyl), optionally substituted alkynyl (preferably optionally substituted $C_2$-$C_6$alkynyl), optionally substituted mono- or dialkylamino (preferably optionally substituted mono and di($C_1$-$C_6$alkyl)amino), optionally substituted alkoxy (preferably optionally substituted $C_1$-$C_6$alkoxy), optionally substituted hydroxyalkyl (preferably optionally substituted $C_1$-$C_2$hydroxyalkyl), optionally substituted haloalkyl (preferably optionally substituted $C_1$-$C_2$haloalkyl), optionally substituted haloalkoxy (preferably optionally substituted $C_1$-$C_2$haloalkoxy), optionally substituted cycloalkyl or cycloalkyl-alkyl preferably optionally substituted ($C_3$-$C_7$cycloalkyl)$C_0$-$C_4$alkyl), and optionally substituted —S(O$_n$)-alkyl (preferably optionally substituted —S(O$_n$)$C_1$-$C_6$alkyl); and n is independently selected at each occurrence from 0, 1 and 2.

Within further aspects, 3-substituted-6-aryl pyridines of Formula I further satisfy one or more of Formulas II-XVIX, provided herein, or are a pharmaceutically acceptable form thereof.

In certain embodiments, C5a receptor modulators provided herein exhibit high affinity for C5a receptor (i.e., an affinity constant for binding to C5a receptor of less than 1 micromolar) or very high affinity for C5a receptor (i.e., an affinity constant for binding to the C5a receptor of less than 100 nanomolar). In certain embodiments, such modulators exhibit an affinity for human C5a receptor that is higher than for rat or mouse C5a receptor, preferably at least five times higher, more preferably ten times higher. Affinity of a compound for C5a receptor may be determined, for example, via a radioligand binding assay, such as the assay provided in Example 60.

Within certain aspects, modulators as described herein are C5a receptor antagonists, such as inverse agonists. Certain such compounds exhibit an EC$_{50}$ of 1 micromolar or less, 500 nM or less, 100 nM or less, or 25 nM or less, in a standard in vitro C5a receptor-mediated chemotaxis assay (such as the assay provided in Example 55) or a calcium mobilization assay (as described in Example 62).

Within further aspects, C5a receptor antagonists are essentially free of C5a receptor agonist activity (i.e., exhibit less than 5% agonist activity in a GTP binding assay as described in Example 61).

The present invention further provides, within other aspects, pharmaceutical compositions comprising at least one C5a receptor modulator as described herein, in combination with a physiologically acceptable carrier or excipient. Processes for preparing such pharmaceutical compositions are also provided. Such compositions are particularly useful in the treatment of C5a-mediated inflammation, such as inflammation associated with various inflammatory and immune system disorders.

Within further aspects, methods are provided for inhibiting signal-transducing activity of a cellular C5a receptor, comprising contacting a cell expressing a C5a receptor with at least one C5a receptor modulator as described herein, and thereby reducing signal transduction by the C5a receptor.

Methods are further provided for inhibiting binding of C5a to C5a receptor in vitro, comprising contacting C5a receptor with at least one C5a receptor modulator as described herein, under conditions and in an amount sufficient to detectably inhibit C5a binding to C5a receptor.

The present invention further provides methods for inhibiting binding of C5a to C5a receptor in a human patient, comprising contacting cells expressing C5a receptor with at least one C5a receptor modulator as described herein.

Within further aspects, the present invention provides methods for treating a patent in need of anti-inflammatory treatment or immunomodulatory treatment. Such methods generally comprise administering to the patient a C5a receptor modulatory amount of a C5a receptor modulator as described herein. Treatment of humans, domesticated companion animals (pets) or livestock animals suffering such conditions is contemplated by the present invention. In certain such aspects, methods are provided for treating a patient suffering from cystic fibrosis, rheumatoid arthritis, psoriasis, cardiovascular disease, reperfusion injury, or bronchial asthma comprising administering to the patient a C5a receptor modulatory amount of a C5a receptor modulator as described herein. In further such aspects, methods are provided for treating a patient suffering from stroke, myocardial infarction, atherosclerosis, ischemic heart disease, or ischemia-reperfusion injury comprising administering to the patient a C5a receptor modulatory amount of a C5a receptor modulator as described herein.

The present invention further provides methods for inhibiting C5a receptor-mediated cellular chemotaxis (preferably leukocyte (e.g., neutrophil) chemotaxis), comprising contacting mammalian white blood cells with a C5a receptor modulatory amount of a C5a receptor modulator as described herein. In certain embodiments, the white blood cells are primate white blood cells, such as human white blood cells.

Within further aspects, the present invention provides methods for using a C5a receptor modulator as described herein as a probe for the localization of receptors, particularly C5a receptors. Such localization may be achieved, for example, in tissue sections (e.g., via autoradiography) or in vivo (e.g., via positron emission tomography, PET, or single positron emission computed tomography, SPECT, scanning and imaging). Within certain such aspects, the present invention provides methods for localizing C5a receptors in a tissue sample, comprising: (a) contacting the tissue sample containing C5a receptors with a detectably labeled compound as described herein under conditions that permit binding of the compound to C5a receptors; and (b) detecting the bound compound. Such methods may, optionally, further comprise a step of washing the contacted tissue sample, prior to detection, Suitable detectable labels include, for example, radiolabels such as $^{125}$I, tritium, $^{14}$C, $^{32}$P and $^{99}$Tc.

The present invention also provides packaged pharmaceutical preparations, comprising: (a) a pharmaceutical composition as described herein in a container; and (b) instructions for using the composition to treat a patient suffering from one or more conditions responsive to C5a receptor modulation, such as rheumatoid arthritis, psoriasis, cardiovascular disease, reperfusion injury, bronchial asthma, stroke, myocardial infarction, atherosclerosis ischemic heart disease, or ischemia-reperfusion injury.

In yet another aspect, the present invention provides methods for preparing the compounds disclosed herein, including the intermediates.

These and other aspects of the present invention will become apparent upon reference to the following detailed description.

DETAILED DESCRIPTION OF THE INVENTION

As noted above, the present invention provides 3-substituted-6-aryl pyridines that modulate C5a receptor activation and/or C5a receptor-mediated signal transduction. Such compounds may be used in vitro or in vivo to modulate (preferably inhibit) C5a receptor activity in a variety of contexts.

Chemical Description and Terminology

Compounds provided herein are generally described using standard nomenclature. For compounds having asymmetric centers, it should be understood that (unless otherwise specified) all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise is specified. Where a compound exists in various tautomeric forms, a recited compound is not limited to any one specific tautomer, but rather is intended to encompass all tautomeric forms. Recited compounds are further intended to encompass compounds in which one or more atoms are replaced with an isotope (i.e., an atom having the same atomic number but a different mass number). By way of general example, and without limitation, isotopes of hydrogen include tritium and deuterium and isotopes of carbon include $^{11}$C, $^{13}$C, and $^{14}$C.

Certain compounds are described herein using a general formula that includes variables (e.g., R, $R_1$-$R_6$, Ar). Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted or substituted with up to two R* groups and R* at each occurrence is selected independently from the definition of R*. Also, combinations of substituents and/or variables are permissible only if such combinations result in stable compounds.

The term "3-substituted-6-aryl pyridine," as used herein, refers to compounds of Formula I, as well as pharmaceutically acceptable forms thereof. Such compounds may, but need not, further satisfy one or more additional Formulas provided herein.

"Pharmaceutically acceptable forms" of the compounds recited herein include pharmaceutically acceptable salts, esters, hydrates, clathrates and prodrugs of such compounds. As used herein, a pharmaceutically acceptable salt is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2 hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by *Remington's Pharmaceutical Sciences,* 17th ed., Mack Publishing Company, Easton, Pa., p. 1418 (1985).

A "prodrug" is a compound that may not fully satisfy the structural requirements of Formula I (or another Formula as provided herein) but is modified in vivo, following administration to a patient, to produce such a compound. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein.

A "C5a receptor modulatory amount" is an amount that, upon administration, results in a concentration of C5a receptor modulator at a C5a receptor that is sufficient to inhibit chemotaxis of white blood cells in an In vitro assay and/or alter C5a receptor activity or activation as measured by an in vitro calcium mobilization assay. In a chemotaxis assay (see Example 55), the level of C5a-induced chemotaxis observed in a control assay (i.e., one to which a compound as provided herein has not been added) is significantly higher (measured as $p \leq 5.05$ using a conventional parametric statistical analysis method such as a student's T-test) than the level observed in an assay to which a compound or form thereof as described herein has been added. Within such an assay, the C5a is generally from the same species as the cells used in the assay. In a calcium mobilization assay (see Example 62), a concentration of compound that alters C5a receptor activity or activation may inhibit C5a-induced calcium mobilization or may itself increase or decrease C5a receptor-mediated calcium mobilization in the absence of C5a.

A "therapeutically effective amount" is an amount of a compound or form thereof as provided herein that, upon administration, results in a discernible benefit in a patient. Such benefit may be confirmed using standard clinical procedures.

A "substituent," as used herein, refers to a molecular moiety that is covalently bonded to an atom within a molecule of interest. For example, a "ring substituent" may be a moiety such as a halogen, alkyl group, haloalkyl group or other substituent described herein that is covalently bonded to an atom (preferably a carbon or nitrogen atom) that is a ring member. The term "substituted," as used herein, means that any one or more hydrogens on the designated atom is replaced with a selection from the indicated substituents, provided that the designated atom's normal valence is not exceeded, and that the substitution results in a stable compound (i.e., a compound that can be isolated, characterized and tested for biological activity). When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone.

The phrase "optionally substituted" indicates that a group may either be unsubstituted or substituted at one or more of any of the available positions, typically 1, 2, 3, 4, or 5 positions, by one or more suitable substituents such as those disclosed herein. Optional substitution may also be indicated by the phrase "substituted with from 0 to X sub-substituents," in which X is the maximum number of substituents.

Suitable substituents include, for example, halogen, cyano, amino, hydroxy, nitro, azido, carboxamido, —COOH, $SO_2NH_2$, alkyl (e.g., $C_1$-$C_8$alkyl), alkenyl (e.g., $C_2$-$C_8$alkenyl), alkynyl (e.g., $C_2$-$C_8$alkynyl), alkoxy (e.g., $C_1$-$C_8$alkoxy), alkyl ether (e.g., $C_2$-$C_8$alkyl ether), alkylthio (e.g., $C_1$-$C_8$alkylthio), haloalkyl a $C_1$-$C_8$haloalkyl), hydroxyalkyl (e.g., $C_1$-$C_8$hydroxyalkyl), aminoalkyl (e.g., $C_1$-$C_8$-aminoalkyl), haloalkoxy (e.g., $C_1$-$C_8$haloalkoxy), alkanoyl (e.g., $C_1$-$C_8$alkanoyl), alkanone (erg, $C_1$-$C_8$alkanone), alkanoyloxy (e.g., $C_1$-$C_8$alkanoyloxy, alkoxycarbonyl (e.g., $C_1$-$C_8$alkoxycarbonyl), mono- and di-($C_1$-$C_1$alkyl)amino, mono- and di-($C_1$-$C_8$alkyl)amino$C_1$-$C_8$alkyl, mono- and di-($C_1$-$C_8$alkyl)carboxamido, mono- and di-($C_1$-$C_8$alkyl)sulfonamido, alkylsulfinyl (e.g., $C_1$-$C_8$alkylsulfinyl), alkylsulfonyl (e.g., $C_1$-$C_8$alkylsulfonyl), aryl (e.g., phenyl), arylalkyl (e.g., ($C_6$-$C_{18}$aryl)$C_1$-$C_8$alkyl, such as benzyl and phenethyl), aryloxy (e.g., $C_6$-$C_{18}$aryloxy such as phenoxy), arylalkoxy (e.g., ($C_6$-$C_{18}$aryl)$C_1$-$C_8$alkoxy) and/or 3- to 8-membered heterocyclic groups such as coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino or pyrrolidinyl. Certain groups within the formulas provided herein are optionally substituted with from 1 to 3, 1 to 4 or 1 to 5 independently selected substituents.

A dash ("-") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, and where specified, having the specified number of carbon atoms. Thus, the term $C_1$-$C_6$alkyl, as used herein, indicates an alkyl group having from 1 to 6 carbon atoms. "$C_0$-$C_4$alkyl" refers to a bond or a $C_1$-$C_4$alkyl group. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, n-propyl, isopropyl, n-butyl, sec-butyl, tert-butyl, pentyl, 2-pentyl, isopentyl, neopentyl, hexyl, 2-hexyl, 3-hexyl, and 3-methylpentyl. In certain embodiments, preferred alkyl groups are methyl, ethyl, propyl, butyl, and 3-pentyl. "Aminoalkyl" is an alkyl group as defined herein substituted with one or more —$NH_2$ substituents. "Hydroxyalkyl" is a hydroxy group as defined herein substituted with one or more —OH substituents.

"Alkenyl" refers to a straight or branched hydrocarbon chain comprising one or more unsaturated carbon-carbon bonds, such as ethenyl and propenyl. Alkenyl groups include $C_2$-$C_8$alkenyl, $C_2$-$C_6$alkenyl and $C_2$-$C_4$alkenyl groups which have from 2 to 8, 2 to 6 or 2 to 4 carbon atoms, respectively), such as ethenyl, allyl or isopropenyl.

"Alkynyl" refers to straight or branched hydrocarbon chains comprising one or more triple carbon-carbon bonds. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively. Alkynyl groups include for example groups such as ethynyl and propynyl.

By "alkoxy," as used herein, is meant an alkyl, alkenyl or alkynyl group as described above attached via an oxygen bridge. Alkoxy groups include $C_1$-$C_6$alkoxy and $C_1$-$C_4$alkoxy groups, which have from 1 to 6 or 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are specific alkoxy groups. Similarly "alkylthio" refers to an alkyl, alkenyl or alkynyl group as described above attached via a sulfur bridge.

The term "alkanoyl" refers to an alkyl group as defined above attached through a carbonyl bridge. Alkanoyl groups include $C_2$-$C_8$alkanoyl, $C_2$-$C_6$alkanoyl and $C_2$-$C_4$alkanoyl groups, which have from 2 to 8, 2 to 6 or 2 to 4 carbon atoms, respectively. "$C_1$alkanoyl" refers to —(C=O)—H, which (along with $C_2$-$C_8$alkanoyl) is encompassed by the term "$C_1$-$C_8$alkanoyl." Ethanoyl is $C_2$alkanoyl.

An "alkanone" is an alkyl group as defined above with the indicated number of carbon atoms substituted at least one position with an oxo group. "$C_3$-$C_8$alkanone," "$C_3$-$C_6$alkanone" and "$C_3$-$C_4$alkanone" refer to an alkanone having from 3 to 8, 6 or 4 carbon atoms, respectively. By way of example, a $C_3$ alkanone group has the structure —$CH_2$—(C=O)—$CH_3$.

Similarly, "alkyl ether" refers to a linear or branched ether substituent linked via a carbon-carbon bond. Alkyl ether groups include $C_2$-$C_8$alkyl ether, $C_2$-$C_6$alkyl ether and $C_2$-$C_4$alkyl ether groups, which have 2 to 8, 6 or 4 carbon atoms, respectively. By way of example, a $C_2$ alkyl ether group has the structure —$CH_2$—O—$CH_3$.

The term "alkoxycarbonyl" refers to an alkoxy group linked via a carbonyl (i.e., a group having the general structure —C(=O)—O-alkyl). Alkoxycarbonyl groups include $C_2$-$C_8$, $C_2$-$C_6$ and $C_2$-$C_4$alkoxycarbonyl groups, which have from 2 to 8, 6 or 4 carbon atoms, respectively.

"Alkanoyloxy," as used herein, refers to an alkanoyl group linked via an oxygen bridge (e.g., a group having the general structure —O—C(=O)-alkyl). Alkanoyloxy groups include $C_2$-$C_8$, $C_2$-$C_6$ and $C_2$-$C_4$alkanoyloxy groups, which have from 2 to 8, 6 or 4 carbon atoms, respectively.

"Alkylamino" refers to a secondary or tertiary amine having the general structure —NH-alkyl or —N(alkyl)(alkyl), wherein each alkyl may be the same or different. Such groups include, for example, mono- and di-($C_3$-$C_8$alkyl)amino groups, in which each alkyl may be the same or different and may contain from 1 to 8 carbon atoms, as well as mono- and di-($C_1$-$C_6$alkyl)amino groups and mono- and di-($C_1$-$C_4$alkyl) amino groups. "Mono- or di-($C_1$-$C_4$alkylamino)$C_0$-$C_4$alkyl" refers to a mono- and di-($C_1$-$C_4$alkyl)amino group that is linked via a direct bond or a $C_1$-$C_4$ alkyl group (i.e., a group having the general structure —$C_0$-$C_4$alkyl-NH-alkyl or —$C_0$-$C_4$alkyl-N(alkyl)(alkyl) in which each alkyl may be the same or different. Similarly, "alkylaminoalkoxy" refers to an alkylamino group linked via an alkoxy group.

The term "aminocarbonyl" or "carboxamido" refers to an amide group (i.e. —(C=O)NH$_2$) "Mono- or di-($C_1$-$C_6$alkyl) aminocarbonyl" refers to an amide group in which one or both of the hydrogen atoms is replaced with an independently chosen $C_1$-$C_6$alkyl. Such groups may also be indicated by "—C(=O)NHalkyl" or "—C(=O)N(alkyl)alkyl."

The term "halogen" refers to fluorine, chlorine, bromine and iodine. A "haloalkyl" is a branched or straight-chain alkyl group, substituted with 1 or more halogen atoms (e.g., "halo$C_1$-$C_8$alkyl" groups have from 1 to 8 carbon atoms; "halo$C_1$-$C_6$alkyl" groups have from 1 to 6 carbon atoms). Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Within certain compounds provided herein, not more than 5 or 3 haloalkyl groups are present. The term "haloalkoxy" refers to a haloalkyl group as defined above attached via an oxygen bridge. "Halo$C_1$-$C_8$alkoxy" groups have 1 to 8 carbon atoms.

A "carbocycle" is any saturated, partially saturated, or aromatic group having 1 or 2 fused, pendant or spiro rings, with 3 to 8 atoms in each ring, and with all ring members being carbon. The term "carbocycle" encompasses aromatic groups such as phenyl and naphthyl, as well as groups that comprise both aromatic and nonaromatic rings (e.g., tetrahydronaphthyl), and groups with saturated and partially saturated rings (such as cyclohexyl and cyclohexenyl). When substitutions are indicated, carbocycles may be substituted on any ring atom where such substitution results in a stable compound. The term "$C_3$-$C_{10}$carbocycle" refers to such groups having from 3 to 10 ring members. A "$C_3$-$C_{10}$carbocycle$C_0$-$C_4$alkyl" group is a $C_3$-$C_{10}$carbocycle that is linked via a direct bond or a $C_1$-$C_4$alkyl group.

Certain carbocycles are "cycloalkyl" (i.e. a saturated or partially saturated carbocycle). Such groups typically contain from 3 to about 8 ring carbon atoms; in certain embodiments, such groups have from 3 to 7 ring carbon atoms. Examples of cycloalkyl groups include cyclopropyl, cyclobutyl, cyclopentyl and cyclohexyl, as well as such groups modified by the presence Of one or more double or triple bonds (e.g. cyclohexenyl) and bridged or caged saturated ring groups such as norbornane or adamantane. If substituted, any ring carbon atom may be bonded to any indicated substituent.

In the term "(cycloalkyl)alkyl", "cycloalkyl" and "alkyl" are as defined above, and the point of attachment is on the alkyl group. This term encompasses, but is not limited to, cyclopropylmethyl, cyclohexylmethyl and cyclohexylethyl. "($C_3$-$C_7$cycloalkyl)$C_0$-$C_4$alkyl" refers to 3- to 7-membered cycloalkyl rings that are linked via a direct bond or a $C_1$-$C_4$alkyl.

Other carbocycles are "aryl" (i.e., carbocycles that comprise at least one aromatic ring). In addition to the aromatic ring(s), additional non-aromatic ring(s) may be present in an aryl group. Representative aryl groups include phenyl, naphthyl (e.g., 1-naphthyl and 2-naphthyl), biphenyl, tetrahydronaphthyl and indanyl.

The term "arylalkyl" refers to an aryl group that is linked via an alkyl group. Certain arylalkyl groups are aryl$C_0$-$C_2$alkyl, in which an aryl group is linked via a direct bond or a methylene or ethylene moiety. Such groups include, for example, groups in which phenyl or naphthyl is linked via a bond or $C_1$-$C_2$alkyl, such as benzyl, 1-phenyl-ethyl and 2-phenyl-ethyl.

The term "aryloxy" refers to an aryl group linked via a an oxygen (i.e., a group having the general structure —O-aryl). Phenoxy is a representative aryloxy group.

A "heteroatom" is an atom other than carbon, such as oxygen, sulfur or nitrogen.

The term "heterocycle" or "heterocyclic group" is used to indicate saturated, partially unsaturated, or aromatic groups having 1 or 2 fused, pendent or spiro rings, with 3 to 8 atoms in each ring, and in at least one ring from 1 to 4 heteroatoms independently selected from N, O and S, with remaining atoms being carbon. Certain heterocycles are 3- to 10-membered monocyclic or bicyclic groups; other are 4- to 6-membered monocyclic groups. The heterocyclic ring may be attached at any heteroatom or carbon atom that results in a stable structure, and may be substituted on carbon and/or nitrogen atom(s) if the resulting compound is stable. Any nitrogen and/or sulfur heteroatoms may optionally be oxidized, and any nitrogen may optionally be quaternized.

Variations on the term "(heterocycle)alkyl" refer to a heterocycle that is linked via a direct bond or alkyl group. Such groups include, for example, (3- to 10-membered heterocycle)$C_0$-$C_4$alkyl groups, in which the heterocycle contains from 3 to 10 ring members and is linked via a direct bond or $C_1$-$C_4$alkyl. Unless otherwise specified, the heterocycle portion of such groups may be saturated, partially saturated or aromatic. "(4 to 6-membered heterocycloalkyl)$C_0$-$C_4$alkyl" refers to a heterocycloalkyl group of 4 to 6 ring members that is linked via a direct bond or a $C_1$-$C_4$alkyl.

Certain heterocycles are "heteroaryl" (i.e., groups that comprise at least one aromatic ring having from 1 to 4 heteroatoms). When the total number of S and 0 atoms in a heteroaryl group exceeds 1, then these heteroatoms are not adjacent to one another; preferably the total number of S and 0 atoms in a heteroaryl is not more than 1, 2 or 3, more preferably 1 or 2 and most preferably not more than 1. Examples of heteroaryl groups include pyridyl, furanyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

Other heterocycles are referred to herein as "heterocycloalkyl" (i.e., saturated or partially saturated heterocycles). Heterocycloalkyl groups have 1 or 2 rings, each with from 3 to about 8 ring atoms, and more typically from 5 to 7 ring atoms. Examples of heterocycloalkyl groups include morpholinyl, piperazinyl, piperidinyl and pyrrolidinyl.

Additional examples of heterocyclic groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"A C5a receptor" is a G-protein coupled receptor that specifically binds C5a peptide. Certain preferred C5a receptors are human, such as the protein product of the sequence that produces the human C5a receptor PCR product described by Gerard and Gerard (1991) Nature 349:614-17. The human C5a receptor may also be that described by Boulay (1991) Biochemistry 30(12):2993-99 (nucleotide sequence encoding the receptor is available at GENBANK Accession No. M162505). Non-primate C5a receptors include the rat C5a receptor (encoded by the nucleotide sequence having GENBANK Accession No. X65862, Y09613 or AB003042), canine C5a receptor (encoded by the nucleotide sequence having GENBANK Accession No. X65860), and guinea pig C5a receptor (encoded by the nucleotide sequence having GENBANK Accession No. U86103).

A "C5a receptor modulator" (also referred to herein as a "modulator") is any compound that modulates C5a receptor activation and/or activity (i.e., C5a receptor-mediated signal transduction, as measured using a C5a receptor-mediated chemotaxis, radioligand binding assay, or calcium mobilization assay as provided herein). In certain embodiments, such a modulator may be exhibit an affinity constant for binding to a C5a receptor of less than 1 micromolar in a standard C5a receptor radioligand binding assay; and/or an $EC_{50}$ of less than 1 micromolar in a standard C5a receptor-mediated chemotaxis assay or calcium mobilization assay. In other embodiments the a C5a receptor modulator may exhibit an affinity constant or $EC_{50}$ of less than 500 nM, 200 nM, 100 nM, 50 nM, 25 nM, 10 nM or 5 nM in such an assay. A modulator may be a C5a receptor agonist or antagonist, although, for certain purposes described herein, a modulator preferably inhibits C5a activation resulting from binding of C5a (i.e., the modulator is an antagonist). In addition, or alternatively, a modulator may act as an inverse agonist of C5a receptor In certain embodiments, modulators provided herein modulate activation and/or activity of a primate C5a receptor, such as human C5a receptor, which may be a cloned, recombinantly expressed receptor or a naturally expressed receptor. For treating non-human animals of any particular species, a compound exhibiting high affinity for the C5a receptor of that particular species is preferred.

Certain C5a receptor modulators exhibit high activity in a standard in vitro C5a receptor mediated chemotaxis assay, as specified in Example 55, herein. Such compounds exhibit an $EC_{50}$ of 4 μM or less in such a standard C5a mediated chemotaxis assay, preferably an $EC_{50}$ of 1 μM or less in such an assay, more preferably an $EC_{50}$ of 0.1 μM or less in such an assay, and even more preferably and $EC_{50}$ of 10 nM or less in such an assay.

An "Inverse agonist" of a C5a receptor is a compound that reduces the activity of the C5a receptor below its basal activity level in the absence of added C5a. Inverse agonists may also inhibit the activity of C5a at the C5a receptor, and/or may inhibit binding of C5a to the C5a receptor. The ability of a compound to inhibit the binding of C5a to the C5a receptor may be measured by a binding assay, such as the radioligand binding assay given in Example 60. The basal activity of the C5a receptor may be determined from a GTP binding assay, such as the assay of Example 61. The reduction of C5a receptor may also be determined from a GTP binding assay or a calcium mobilization assay such as the assay of Example 62.

A neutral antagonist of the C5a receptor is a compound which inhibits the activity of C5a at the C5a receptor, but does not significantly change the basal activity of the C5a receptor. Neutral antagonists of the C5a receptor may inhibit the binding of C5a to the C5a receptor.

A "partial agonist" of the C5a receptor elevates the activity of the C5a receptor above the basal activity level of the receptor in the absence of C5a, but does not elevate the activity of the C5a receptor to the level brought about by saturating levels of the natural agonist, C5a. Partial agonist compounds may inhibit the binding of C5a to the C5a receptor. Partial agonists of the C5a receptor usually elevate the activity of the C5a receptor, producing a level of elevation ranging from 5% to 90% of the activity level brought about by receptor-saturating concentrations of the natural agonist, C5a.

C5A Receptor Modulators

As noted above, the present invention provides C5a receptor modulators. Such modulators may be used to alter C5a receptor activity in a variety of contexts, including in the treatment of patients suffering from diseases or disorders responsive to C5a receptor modulation, such as autoimmune disorders and inflammatory conditions C5a receptor modulators may also be used within a variety of in vitro assays (e.g., assays for receptor activity), as probes for detection and localization of C5a receptor and as standards in assays of ligand binding and C5a receptor-mediated signal transduction.

C5a receptor modulators provided herein are 3-substituted-6-aryl pyridines of Formula I (as well as pharmaceutically acceptable forms thereof) that detectably alter, preferably decrease, C5a receptor activation and/or signal transduction activity at submicromolar concentrations. In certain embodiments, C5a receptor modulators provided herein further satisfy Formula II, or are a pharmaceutically acceptable form thereof.

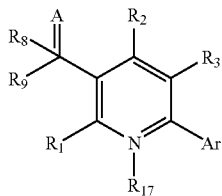

Formula II

Within compounds of Formula II, the variables are as described for Formula I, except that:

at least one of $R_1$, $R_2$ and $R_3$ is not hydrogen;

$R_4$ is:
- (i) $C_1$-$C_8$alkyl, $C_2$-$C_8$alkenyl, $C_2$-$C_8$alkynyl, ($C_3$-$C_7$cycloalkyl)$C_0$-$C_4$alkyl, mono- or di-($C_1$-$C_4$alkylamino)$C_0$-$C_4$alkyl, (3- to 7-membered heterocycloalkyl)$C_0$-$C_4$alkyl, phenyl$C_0$-$C_4$alkyl, pyridyl$C_0$-$C_4$alkyl, pyrimidinyl$C_0$-$C_4$alkyl, thienyl$C_0$-$C_4$alkyl, imidazolyl$C_0$-$C_4$alkyl, pyrrolyl$C_0$-$C_4$alkyl, pyrazolyl$C_0$-$C_4$alkyl, benzoisothiazolyl or tetrahydronapthyl, each of which is substituted with from 0 to 4 substituents independently chosen from $R_x$, $C_2$-$C_4$alkanoyl, mono- and di-($C_1$-$C_4$alkyl)amino($C_1$-$C_4$alkyl), mono- and di-$C_1$-$C_4$alkylamino($C_1$-$C_4$alkoxy), (3- to 7-membered heterocycloalkyl)$C_0$-$C_4$alkyl and $XR_y$; or
- (ii) joined to $R_5$ to form, with die nitrogen to which $R_4$ and $R_5$ are bound, a heterocycle substituted with from 0 to 4 substituents independently chosen from $R_x$, oxo and YZ;

$R_5$ is not hydrogen if $R_4$ is $C_1$-$C_4$alkyl;

$R_6$ is:
- (i) halogen, hydroxy, cyano, amino, $C_2$-$C_6$alkenyl, $C_2$-$C_6$alkynyl, mono- or di-($C_1$-$C_6$alkylamino)$C_0$-$C_6$alkyl, ($C_3$-$C_{10}$carbocycle)$C_0$-$C_4$alkyl or (3- to 10-membered heterocycle)$C_0$-$C_4$alkyl, each of which is substituted with from 0 to 4 substituents independently chosen from $R_x$, oxo, mono- and di-$C_1$-$C_4$alkylamino ($C_1$-$C_4$alkyl), mono- and di-$C_1$-$C_4$alkylamino($C_1$-$C_4$alkoxy), $C_2$-$C_4$alkanoyl, $C_2$-$C_4$alkanoyloxy and YZ; or
- (ii) joined to $R_7$ to form, with the carbon atom to which $R_6$ and $R_7$ are bound, a 3- to 10-membered carbocycle or heterocycle, each of which is substituted with from 0 to 4 substituents independently chosen from $R_x$, oxo, mono- and di-($C_1$-$C_4$alkylamino)$C_1$-$C_4$alkyl, mono- and di-$C_1$-$C_4$alkylamino($C_1$-$C_4$alkoxy), $C_2$-$C_4$alkanoyl and $C_2$-$C_4$alkanoyloxy;

$R_{17}$ is absent if $R_6$ is $C_1$-$C_6$alkenyl;

$R_8$ is:
- (i) hydrogen, halogen, hydroxy, $C_1$-$C_6$alkyl, $C_2$-$C_6$alkenyl, $C_1$-$C_6$alkynyl, $C_1$-$C_6$alkoxy, $C_1$-$C_6$alkylamino or $C_3$-$C_7$cycloalkyl $C_0$-$C_4$alkyl; or
- (ii) joined to $R_9$ to form a $C_5$-$C_7$ cycloalkyl ring or a 5- to 7-membered heterocycloalkyl ring, each of which is substituted with from 0 to 4 substituents independently chosen from halogen, hydroxy, $C_1$-$C_2$alkyl and $C_1$-$C_2$alkoxy; and $R_9$ is:
- (i) absent, hydrogen, hydroxy, $C_1$-$C_6$alkyl, $C_2$-$C_6$alkenyl, $C_2$-$C_6$alkynyl, $C_1$-$C_6$alkoxy, $C_1$-$C_6$alkylamino or $C_3$-$C_7$cycloalkyl $C_0$-$C_4$alkyl; or
- (ii) joined to $R_8$ to form an optionally substituted $C_5$-$C_7$ cycloalkyl ring or 5- to 7-membered heterocycloalkyl ring.

Within certain compounds of Formula I or Formula II, $R_1$ is hydrogen, halogen, amino, cyano, $C_1$-$C_6$alkyl, $C_2$-$C_6$alkenyl, $C_2$-$C_6$alkynyl, $C_1$-$C_6$alkoxy, haloalkyl, haloalkoxy, mono- or di-($C_1$-$C_6$)alkylamino, ($C_3$-$C_7$cycloalkyl)$C_0$-$C_4$alkyl, (3- to 7-membered heterocycloalkyl)$C_0$-$C_4$alkyl or —S(O$_n$)$C_1$-$C_6$alkyl. For example, $R_1$ may be chosen from cyano, $C_1$-$C_4$alkyl and $C_1$-$C_4$alkoxy. In certain compounds, $R_1$ is methyl.

$R_2$, within certain compounds of Formula I or II, is not hydrogen. In certain such compounds, $R_2$ is halogen, cyano or $XR_y$, wherein X is a single bond, —O—, —C(=O)—, —S(O)$_n$— or —NR$_B$—; and $R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4- to 10-membered heterocycle)$C_0$-$C_4$alkyl, each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$aminoalkyl, $C_1$-$C_8$alkoxy and $C_3$-$C_7$cycloalkyl. Representative X groups are those in which X is a single bond, —O—, —C(=O)—, —SO$_2$—, —NH— or —N(CH$_3$)—; and $R_y$ is $C_1$-$C_6$alkyl, $C_1$-$C_6$alkenyl, ($C_3$-$C_7$cycloalkyl)$C_0$-$C_2$alkyl, phenyl$C_0$-$C_2$alkyl, morpholinyl$C_0$-$C_2$alkyl, piperidinyl$C_0$-$C_2$alkyl, pyrrolidinyl$C_0$-$C_2$alkyl, piperazinyl$C_0$-$C_2$alkyl, pyranyl$C_0$-$C_2$alkyl, tetrahydropyranyl$C_0$-$C_2$alkyl, tetrahydrofuranyl$C_0$-$C_2$alkyl, azetidinyl$C_0$-$C_2$alkyl, 1,1-dioxo-isothiazolyl$C_0$-$C_2$alkyl, benzodioxolyl$C_0$-$C_2$alkyl, benzo[1,4]dioxanyl$C_0$-$C_2$alkyl, benzoxazolyl$C_0$-$C_2$alkyl, benzisoxazolyl$C_0$-$C_2$alkyl, or mono- or di-($C_1$-$C_6$alkylamino)$C_1$-$C_4$alkyl, each of which is substituted with from 0 to 2 substituents independently chosen from hydroxy, halogen, cyano, amino, oxo, COOH, —C(O)NH$_2$, —SO$_9$NH$_2$, —SO$_2$NH($C_1$-$C_4$alkyl), $C_1$-$C_6$alkyl and $C_1$-$C_6$alkoxy.

Certain $R_2$ groups have the formula: $X_1$—(CH$_2$)$_m$—$R_y$, wherein: $X_1$ is a bond or —O-m is 0, 1, 2 or 3; and $R_y$ is phenyl, piperidin-1-yl, piperazin-1-yl, morpholin-1-yl or benzisoxazolyl; each of which is substituted with from 0 to 4 substituents independently chosen from hydroxy, halogen, cyano, amino, —COOH, —C(=O)NH$_2$, —SO$_2$NH$_2$, —SO$_2$NH($C_1$-$C_4$alkyl), $C_1$-$C_6$alkyl and $C_1$-$C_6$alkoxy. Such $R_2$ groups include, for example, phenyl, benzyl, phenoxy, piperidin-1-yl, piperidin-1-ylmethyl, piperazin-1-yl, piperazin-1-ylmethyl, morpholin-1-yl, morpholin-1-ylmethyl, morpholin-1-ylethyl or morpholin-1-ylpropyl; each of which is substituted with from 0 to 4 substituents independently chosen from hydroxy, amino, —COOH, —C(=O)NH$_2$, $C_1$-$C_6$alkyl and $C_1$-$C_6$alkoxy.

Within certain compounds of Formula I or II, $R_3$ is hydrogen, methyl, chloro, fluoro, trifluoromethyl or cyano. Representative $R_3$ groups are hydrogen or methyl. In certain compounds provided herein $R_1$ is cyano, $C_1$-$C_4$alkyl Or $C_1$-$C_4$alkoxy and $R_3$ is hydrogen Or methyl.

Ar, within certain compounds of Formula I or II, is phenyl, pyridyl, pyrimidinyl, indazolyl or indolyl, each of which is substituted with from 1 to 3 substituents independently chosen from $R_x$. Representative Ar groups include (a) phenyl substituted with 2 or 3 substituents independently chosen from halogen, hydroxy, amino, cyano, nitro, —COOH, —C(=O)NH$_2$, $C_1$-$C_4$alkyl, mono- and di-($C_1$-$C_4$alkyl) amino, $C_1$-$C_4$alkoxy, $C_1$-$C_2$haloalkyl, $C_1$-$C_2$haloalkoxy and ($C_3$-$C_7$cycloalkyl)$C_0$-$C_4$alkyl; and (b) indazolyl or indolyl substituted with from 1 to 3 substituents independently chosen from halogen, hydroxy, amino, cyano, nitro, —COOH, —C(=O)NH$_2$, $C_1$-$C_4$alkyl, mono- and di-($C_1$-$C_4$alkyl) amino, $C_1$-$C_4$alkoxy, $C_1$-$C_2$haloalkyl, $C_1$-$C_2$haloalkoxy and ($C_3$-$C_7$cycloalkyl)$C_0$-$C_4$alkyl.

Within certain compounds of Formula I or II, $R_8$ and $R_9$ are independently chosen from hydrogen, halogen, hydroxy, $C_1$-$C_4$alkyl, $C_3$-$C_6$cycloalkyl and $C_1$-$C_4$alkoxy.

As noted above, $R_{17}$ in Formula I and Formula II is absent or oxygen. Compounds of Formula II in which $R_{17}$ is absent have the general Formula IIa and those in which $R_{17}$ is oxygen have the general Formula IIb:

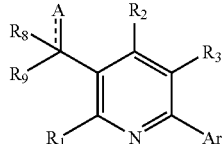

Formula IIa

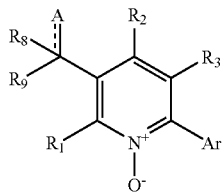

Formula IIb

Compounds of Formula I or II include those in which A is $N_4R_5$. Within certain such compounds, $R_4$ is chosen from $C_1$-$C_8$alkyl, $C_1$-$C_8$alkenyl, $C_1$-$C_8$alkynyl, $(C_3$-$C_7$cycloalkyl)$C_0$-$C_4$alkyl, phenyl$C_0$-$C_4$alkyl, pyridyl$C_0$-$C_4$alkyl, pyrimidinyl$C_0$-$C_4$alkyl, thienyl$C_0$-$C_4$alkyl, imidazolyl$C_0$-$C_4$alkyl, pyrrolyl$C_0$-$C_4$alkyl, pyrazolyl$C_0$-$C_4$alkyl, indolyl$C_0$-$C_4$alkyl, indazolyl$C_0$-$C_4$alkyl, benzocycloheptenyl$C_0$-$C_4$alkyl, decahydronaphthyl$C_0$-$C_4$alkyl, benzoisothiazolyl$C_0$-$C_4$alkyl, tetrahydroquinolinyl$C_0$-$C_4$alkyl and tetrahydronaphthyl$C_0$-$C_4$alkyl, each of which is substituted with from 0 to 4 groups independently chosen from $R_x$, mono- and di-$C_1$-$C_4$alkylamino($C_1$-$C_4$alkyl), mono- and di-$C_1$-$C_4$alkylamino($C_1$-$C_4$alkoxy), (3- to 7-membered heterocycloalkyl)$C_0$-$C_4$alkyl, $C_1$-$C_4$alkoxycarbonyl, $C_2$-$C_4$alkanoyl and $C_2$-$C_4$alkanoyloxy; and $R_5$ is $C_1$-$C_6$alkyl, $C_2$-$C_6$alkenyl or ($C_3$-$C_7$-carbocycle)$C_0$-$C_4$alkyl.

Within other such compounds, $R_4$ and $R_5$ are joined to form a saturated or partially saturated heterocycle containing 1 or 2 fused or spiro rings; wherein the heterocycle is substituted with from 0 to 4 substituents independently chosen from halogen, hydroxy, amino, cyano, —COOH, —C(=O)NH$_2$, $C_1$-$C_6$alkyl, $C_2$-$C_6$alkenyl, $C_2$-$C_6$alkynyl, mono- and di-($C_1$-$C_6$alkyl)amino, $C_1$-$C_6$alkoxy, $C_1$-$C_2$haloalkyl, $C_1$-$C_2$haloalkoxy, ($C_3$-$C_7$cycloalkyl)$C_0$-$C_4$alkyl, —S(O$_n$)$C_1$-$C_6$alkyl and phenyl. For example, $R_4$ and $R_5$ may be joined to form a saturated 4- to 7-membered heterocyclic ring (e.g., azepanyl, morpholinyl, pyrrolidinyl, piperadinyl or piperidinyl) that is substituted with from 0 to 3 substituents independently chosen from halogen, hydroxy, amino, cyano, $C_1$-$C_2$alkyl, $C_1$-$C_2$alkoxy, trifluoromethyl, difluoromethyl, trifluoromethoxy and difluoromethoxy. Alternatively, $R_4$ and $R_5$ may be joined to form a heterocycle containing 2 rings; wherein each of the rings is substituted with from 0 to 3 substituents independently chosen from halogen, hydroxy, amino, cyano, $C_1$-$C_2$alkyl, $C_1$-$C_2$alkoxy, trifluoromethyl, difluoromethyl, trifluoromethoxy and difluoromethoxy. Such heterocycles include, for example, tetrahydroquinolinyl, tetrahydroisoquinolinyl, decahydroquinolinyl, decahydroisoquinolinyl, indazolyl, indolinyl, phenylimidazolyl and benzoxazinyl.

Certain compounds in which A is NR$_4$R$_5$ satisfy Formula III:

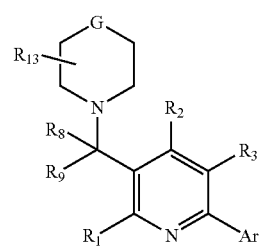

Formula III or are a pharmaceutically acceptable form thereof. Within Formula III:
  $R_{13}$ represents from 0 to 3 substituents independently chosen from: (i) $R_x$; and (ii) phenyl and pyridyl, each of which is substituted with from 0 to 4 substituents independently chosen from halogen, hydroxy, amino, cyano, $C_1$-$C_4$alkyl, $C_1$-$C_4$alkoxy, ($C_3$-$C_7$cycloalkyl)$C_0$-$C_4$alkyl, $C_1$-$C_2$haloalkyl, $C_1$-$C_2$haloalkoxy and mono- and di-($C_1$-$C_4$alkyl)amino;
  G is CH$_2$, sulfur, oxygen or NR$_E$; wherein R$_E$ is: (i) hydrogen; or (ii) $C_1$-$C_6$alkyl, ($C_3$-$C_7$cycloalkyl)$C_0$-$C_4$alkyl, phenyl or a 5- or 6-membered heteroaryl ring, each of which is substituted with from 0 to 3 substituents independently chosen from $R_x$; and
  Ar, $R_1$, $R_2$, $R_3$, $R_8$ and $R_9$ are as described above for Formula I or Formula II.

Within certain compounds of Formula III, G is oxygen and/or R)$_3$ represents from 0 to 2 substituents independently chosen from halogen, methyl, methoxy, ethyl and phenyl.

Other compounds in which A is NR$_4$R$_5$ satisfy Formula IV:

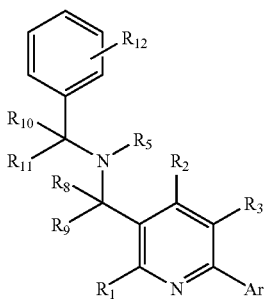

Formula IV or are a pharmaceutically acceptable form thereof. Within Formula IV:
  $R_{10}$ and $R_{11}$ are independently chosen from hydrogen, $C_1$-$C_6$alkyl, $C_1$-$C_2$haloalkyl and $C_3$-$C_7$cycloalkyl($C_0$-$C_2$alkyl);
  $R_{12}$ represents from 0 to 3 substituents independently chosen from $R_x$, mono- and di-($C_1$-$C_4$alkyl)amino($C_1$-$C_4$alkyl), mono- and di-($C_1$-$C_4$alkyl)amino($C_1$-$C_4$alkoxy) and YZ; or two adjacent $R_{12}$ groups are joined to form a fused 5- to 7-membered carbocyclic or heterocyclic ring; and
  Ar, $R_1$, $R_2$, $R_3$, $R_5$, $R_8$ and $R_9$ are as described above for Formula I or Formula II.

Within certain compounds of Formula IV, $R_{12}$ represents from 0 to 3 substituents independently chosen from halogen, hydroxy, amino, cyano, $C_1$-$C_4$alkyl, mono- and di-($C_1$-$C_2$alkyl)amino, $C_1$-$C_4$alkoxy, $C_1$-$C_2$haloalkyl, $C_1$-$C_2$haloalkoxy and ($C_3$-$C_7$cycloalkyl)$C_0$-$C_2$alkyl.

Other compounds in which A is $NR_4R_5$ satisfy Formula V:

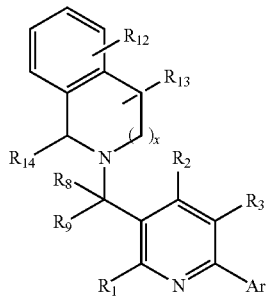

Formula V or are a pharmaceutically acceptable form thereof. Within Formula V:

$R_{12}$ and $R_{13}$ independently represent from 0 to 3 substituents independently chosen from $R_x$;

$R_{14}$ is hydrogen, $C_1$-$C_6$alkyl, $C_2$-$C_6$alkenyl, $C_2$-$C_6$alkynyl, $C_1$-$C_2$haloalkyl or ($C_3$-$C_7$cycloalkyl)$C_0$-$C_2$alkyl;

x is 0, 1 or 2; and

Ar, $R_1$, $R_2$, $R_3$, $R_8$ and $R_9$ are as described above for Formula I or Formula II.

Within certain compounds of Formula V, x is 1; $R_{12}$ and $R_{13}$ independently represent from 0 to 2 substituents independently chosen from halogen, methyl, methoxy and ethyl; and/or $R_{14}$ is hydrogen, $C_1$-$C_6$alkyl, $C_2$-$C_6$alkenyl or $C_3$-$C_7$cycloalkyl($C_0$-$C_2$alkyl).

Other compounds in which A is $NR_4R_5$ satisfy Formula VI:

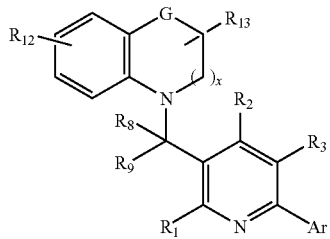

Formula VI or are a pharmaceutically acceptable form thereof. Within Formula VI:

$R_{12}$ and $R_{13}$ independently represent from 0 to 3 substituents independently chosen from $R_x$;

G is $CH_2$, NH, sulfur or oxygen;

x is 0.1 or 2; and

Ar, $R_1$, $R_2$, $R_3$, $R_8$ and $R_9$ are as described above for Formula I or Formula II.

Within certain compounds of Formula VI, x is 1; and/or $R_{12}$ and $R_{13}$ independently represent from 0 to 2 substituents independently chosen from halogen, methyl, methoxy and ethyl.

Still further compounds in which A is $NR_4R_5$ satisfy Formula VII:

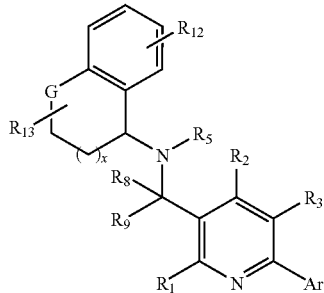

Formula VII or are a pharmaceutically acceptable form thereof. Within Formula VII:

$R_{12}$ and $R_{13}$ independently represent from 0 to 3 substituents independently chosen from $R_x$;

G is $CH_2$, NH or oxygen;

x is 0, 1 or 2; and

Ar, $R_1$, $R_2$, $R_3$, $R_5$, $R_8$ and $R_9$ are as described above for Formula I or Formula II.

Within certain compounds of Formula VII, x is 1 and/or G is $CH_2$. $R_{12}$ and $R_{13}$, in certain compounds of Formula VII, independently represent from 0 to 3 substituents independently chosen from halogen, hydroxy, amino, cyano, $C_1$-$C_4$alkyl, mono- and di-($C_1$-$C_2$alkyl)amino, $C_1$-$C_4$alkoxy, $C_1$-$C_2$haloalkyl, $C_1$-$C_2$haloalkoxy, and ($C_3$-$C_7$cycloalkyl)$C_0$-$C_2$alkyl. For example, in certain such compounds, $R_{12}$ and $R_{13}$ independently represent from 0 to 2 substituents independently chosen from halogen, $C_1$-$C_2$alkyl and $C_1$-$C_2$alkoxy. Representative compounds of Formula VII include those in which $R_5$ is $C_1$-$C_6$alkyl; and $R_{12}$ and $R_{13}$ each represent from 0 to 2 substituents independently chosen from halogen, methyl, methoxy and ethyl.

Within certain compounds of Formula I or Formula II, A is $OR_4$; and $R_4$ is $C_1$-$C_6$alkyl, $C_2$-$C_6$alkenyl, phenyl$C_0$-$C_4$alkyl, naphthyl$C_0$-$C_4$alkyl, pyridyl$C_0$-$C_4$alkyl, pyrimidinyl$C_0$-$C_4$alkyl, thienyl$C_0$-$C_4$alkyl, imidazolyl$C_0$-$C_4$alkyl or pyrrolyl$C_0$-$C_4$alkyl, each of which is substituted with from 0 to 4 substituents independently chosen from $R_x$, mono and di-($C_1$-$C_4$alkyl)amino($C_1$-$C_4$alkyl), mono- and di-$C_1$-$C_4$alkylamino ($C_1$-$C_4$alkoxy), (3- to 7-membered heterocycloalkyl)$C_0$-$C_4$alkyl, $C_1$-$C_4$alkoxycarbonyl and $C_2$-$C_4$alkanoyl. In certain such compounds, $R_4$ is phenyl, benzyl, pyridyl or pyridylmethyl, each of which is substituted with from 0 to 4 substituents independently chosen from $R_x$, mono- and di-$C_1$-$C_4$alkylamino($C_0$-$C_4$alkyl), mono- and di-$C_1$-$C_4$alkylamino ($C_1$-$C_4$alkoxy), (3- to 7-membered heterocycloalkyl)$C_0$-$C_4$alkyl and $C_2$-$C_4$alkanoyl. In other such compounds, $R_4$ is $C_1$-$C_6$alkyl or $C_2$-$C_6$alkenyl, each of which is substituted with from 0 to 3 substituents independently chosen from halogen, hydroxy, amino, cyano, mono- and di-($C_1$-$C_4$alkyl)amino, $C_1$-$C_4$alkoxy, $C_1$-$C_2$haloalkyl, $C_1$-$C_2$haloalkoxy and ($C_3$-$C_7$cycloalkyl)$C_0$-$C_4$alkyl. For example, such $R_4$ groups include $C_1$-$C_6$alkyl and $C_2$-$C_6$alkenyl.

Certain compounds in which A is OR$_4$ satisfy Formula VIII:

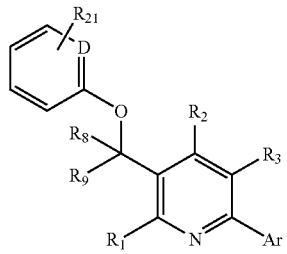

Formula VIII or are a pharmaceutically acceptable form thereof. Within Formula VIII:
D is CH or N;
R$_{21}$ represents from 0 to 3 substituents independently chosen from R$_x$ and LR$_d$; or two adjacent R$_{21}$ groups are joined to form a fused 5- to 7-membered carbocyclic or heterocyclic ring that is substituted with from 0 to 3 substituents independently chosen from R$_x$;
L is a single bond or —CH$_2$—; and
R$_d$ is piperazinyl, morpholinyl, piperidinyl or pyrrolidinyl; with the remaining variables as described for Formula I or Formula II.

Within certain compounds of Formula VIII, R$_{21}$ represents from 0 to 3 substituents independently chosen from R$_x$, and LR$_d$. Within further compounds of Formula VIII, the group designated:

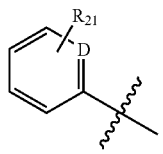

is chosen from naphthyl, tetrahydronaphthyl, benzofuranyl, benzodioxolyl, indanyl, indolyl, indazolyl, benzodioxolyl, benzol[1,4]dioxanyl and benzoxazolyl, each of which is substituted with from 0 to 3 substituents independently chosen from R$_x$.

Within certain compounds of Formula I or Formula II, A is CHR$_6$R$_7$. Representative R$_6$ groups include (i) C$_2$-C$_6$alkenyl, C$_2$-C$_6$alkynyl, mono- and di-(C$_1$-C$_6$alkyl)aminoC$_0$-C$_6$alkyl, (C$_3$-C$_7$cycloalkyl)C$_0$-C$_4$alkyl, benzyl, decahydronaphthyl, tetrahydronaphthyl, dihydronaphthyl, and C$_3$-C$_7$cycloalkyl (C$_1$-C$_4$alkyl), each of which is substituted with from 0 to 4 substituents independently chosen from R$_x$, mono- and di-C$_1$-C$_4$alkylamino(C$_1$-C$_4$alkyl), mono- and di-C$_1$-C$_4$alkylamino (C$_1$-C$_4$alkoxy), C$_2$-C$_4$alkanoyl, C$_2$-C$_4$alkanoyloxy and YZ; and (ii) groups that are joined to R$_7$ to form, with the carbon atom to which R$_6$ and R$_7$ are bound, a 4- to 11-membered carbocycle or heterocycle, each of which is substituted with from 0 to 4 groups independently chosen from R$_x$, oxo, mono- and di-(C$_1$-C$_4$alkylamino)C$_1$-C$_4$alkyl, mono- and di-C$_1$-C$_4$alkylamino(C$_1$-C$_4$alkoxy), C$_2$-C$_4$alkanoyl and C$_2$-C$_4$alkanoyloxy. Representative R$_7$ groups include hydrogen, halogen, hydroxy, and groups that are joined to R$_6$ to form an optionally substituted carbocycle or heterocycle. In certain embodiments, R$_6$ is (C$_3$-C$_7$cycloalkyl)C$_0$-C$_4$alkyl and R$_7$ is hydrogen. In other embodiments, R$_6$ and R$_7$ are joined to form dihydronaphthalenyl, tetrahydronaphthalenyl, cyclohexyl, tetrahydropyranyl or pyrrolidinyl, each of which is substituted with from 0 to 4 groups independently chosen from R$_x$.

Certain compounds in which A is CHR$_6$R$_7$ satisfy Formula IX:

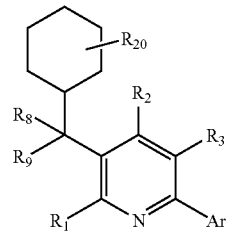

Formula IX or are a pharmaceutically acceptable form thereof. Within Formula IX, R$_{20}$ represents from 0 to 3 groups independently chosen from halogen, hydroxy, amino, cyano, C$_1$-C$_2$alkyl, C$_1$-C$_2$alkoxy, trifluoromethyl, difluoromethyl, trifluoromethoxy and difluoromethoxy; and the remaining variables are as described for Formula I or Formula II. In certain such compounds, R$_8$ is halogens hydroxy, C$_1$-C$_6$alkyl or C$_1$-C$_6$alkoxy; and R$_9$ is hydrogen, C$_1$-C$_6$alkyl or C$_1$-C$_6$alkoxy.

Within certain compounds of Formula I or Formula II, A is CR$_6$R$_7$. One representative class of such compounds satisfies Formula X:

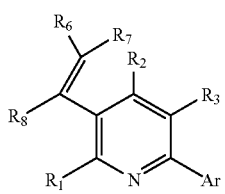

Formula X or are a pharmaceutically acceptable form thereof. Within certain compounds of Formula X, R$_6$ and R$_7$ are joined to form a 3- to 10-membered carbocycle or heterocycle, each of which is substituted with from 0 to 4 substituents independently chosen from R$_x$.

Other compounds in which A is CR$_6$R$_7$ satisfy Formula XI:

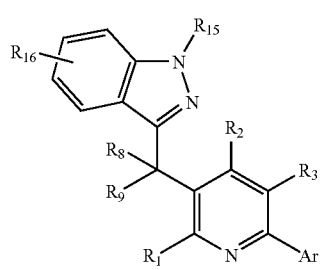

Formula XI or are a pharmaceutically acceptable form thereof, wherein R$_{15}$ is hydrogen, methyl or ethyl; R$_{16}$ represents from 0 to 3 substituents independently chosen from halogen, hydroxy, amino, cyano, C$_1$-C$_2$alkyl, C$_1$-C$_2$alkoxy, trifluoromethyl, difluoromethyl, trifluoromethoxy and difluoromethoxy; and the remaining variables are as described for Formula I or Formula II.

Still further compounds in which A is $CR_6R_7$ satisfy Formula II:

Formula XII

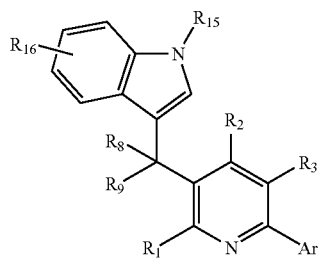

or are a pharmaceutically acceptable form thereof, wherein $R_{15}$ is hydrogen, methyl or ethyl; $R_{16}$ represents from 0 to 3 substituents independently chosen from halogen, hydroxy, amino, cyano, $C_1$-$C_2$alkyl, $C_1$-$C_2$alkoxy, trifluoromethyl, difluoromethyl, trifluoromethoxy and difluoromethoxy; and the remaining variables are as described for Formula I or Formula II.

Certain compounds in which A is $CHR_6R_7$ or $C_6R_7$ satisfy Formula XIII:

Formula XIII

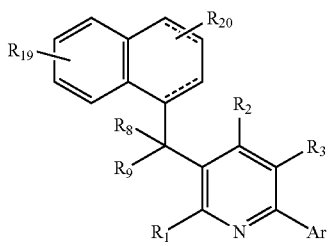

or are a pharmaceutically acceptable form thereof, wherein $R_{19}$ and $R_{20}$ each represent from 0 to 3 substituents independently chosen from halogen, hydroxy, amino, cyano, $C_1$-$C_2$alkyl, $C_1$-$C_2$alkoxy, trifluoromethyl, difluoromethyl, trifluoromethoxy and difluoromethoxy and the remaining variables are as described for Formula I or Formula II.

For Formulas III-XIII, certain representative compounds satisfy the following criteria:

$R_1$ is hydrogen, cyano, $C_1$-$C_4$alkyl or $C_1$-$C_4$alkoxy;
$R_2$ is hydrogen, halogen, cyano or $XR_y$, wherein:
  X is a single bond, —O—, —C(=O)—, —S(O)$_n$— or —NR$_B$—; and
  $R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4- to 10-membered heterocycle)$C_0$-$C_4$alkyl each of which is substituted with from 0 to 2 substituents independently chosen from hydroxy, halogen, cyano, amino, —COON, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$alkoxy and $C_3$-$C_7$cycloalkyl;
$R_3$ is hydrogen, methyl, chloro, fluoro, trifluoromethyl or cyano;

$R_8$ and $R_9$ are independently chosen from hydrogen, halogen, hydroxy, $C_1$-$C_6$alkyl, $C_1$-$C_6$alkenyl, ($C_3$-$C_6$cycloalkyl)$C_0$-$C_4$alkyl and $C_1$-$C_6$alkoxy; and
Ar is phenyl, pyridyl, pyrimidinyl, benzisoxazolyl, indazolyl or indolyl, each of which is substituted with from 1 to 3 substituents independently chosen from $R_x$.

Also provided herein are compounds of Formula I that further satisfy Formula MV:

Formula XIV

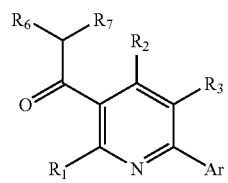

or are a pharmaceutically acceptable form thereof, wherein Ar, $R_1$, $R_2$, $R_3$, $R_6$ and $R_7$ are as described for Formula I. Within certain compounds of Formula XIV, $R_6$ and $R_7$ are joined to form naphthyl, dihydronaphthalenyl, tetrahydronaphthalenyl, cyclohexyl, tetrahydropyranyl or pyrrolidinyl, each of which is substituted with from 0 to 4 groups independently chosen from $R_x$.

Also provided herein are compounds of Formula I that further satisfy Formula XV:

Formula XV

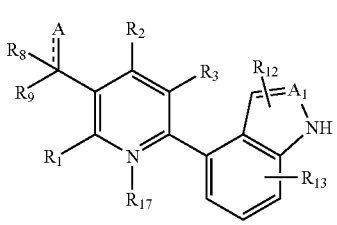

or are a pharmaceutically acceptable form thereof, wherein $A_1$ is CH or N; $R_{12}$ and $R_{13}$ independently represent from 0 to 3 substituents independently chosen from $R_x$; and the remaining variables are as described for Formula I or Formula II. In certain such compounds, $A_1$ is N and/or $R_{12}$ and $R_{13}$ independently represent 0, 1 or 2 substituents independently chosen from methyl, ethyl and isopropyl. Within certain compounds of Formula XV:

$R_1$ is hydrogen, cyano, $C_1$-$C_4$alkyl or $C_1$-$C_4$alkoxy;
$R_2$ is hydrogen, halogen, cyano or $XR_y$, wherein:
  X is a single bond, —O—, —S(O)$_n$— or —NR$_B$—; and
  $R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4- to 10-membered heterocycle)$C_0$-$C_4$alkyl each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$alkoxy and $C_3$-$C_7$cycloalkyl;
$R_3$ is hydrogen, methyl, chloro, fluoro, trifluoromethyl or cyano; and
$R_8$ and $R_9$ are independently chosen from hydrogen, halogen, hydroxy, $C_1$-$C_6$alkyl, $C_1$-$C_6$alkenyl, ($C_3$-$C_6$cycloalkyl)$C_0$-$C_4$alkyl and $C_1$-$C_6$alkoxy.

Certain compounds of Formula I further satisfy Formula XVI:

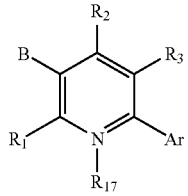

Formula XVI or are a pharmaceutically acceptable form thereof, wherein Ar, $R_1$, $R_2$, $R_3$ and $R_{17}$ are as described for Formula I, and B is a branched $C_4$-$C_{10}$alkyl, $C_4$-$C_{10}$alkenyl or $C_4$-$C_{10}$alkynyl, each of which is substituted with from 0 to 4 substituents independently chosen from $R_x$. Within certain compounds of Formula XVI:

Ar is phenyl, pyridyl, pyrimidinyl, benzisoxazolyl, indazolyl or indolyl, each of which is substituted with from 1 to 3 substituents independently chosen from $R_x$;

B is branched $C_6$-$C_{10}$alkyl or $C_6$-$C_{10}$alkenyl, each of which is substituted with from 0 to 2 substituents independently chosen from halogen, hydroxy, amino or $C_1$-$C_4$alkoxy;

$R_1$ is hydrogen, cyano, $C_1$-$C_4$alkyl or $C_1$-$C_4$alkoxy;

$R_2$ is hydrogen, halogen, cyano or $XR_y$, wherein:
X is a single bond, —O—, —S(O)$_n$— or —NR$_B$—; and
$R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4 to 10-membered heterocycle)$C_0$-$C_4$alkyl each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$alkoxy and $C_3$-$C_7$cycloalkyl; and $R_3$ is hydrogen, methyl, chloro, fluoro, trifluoromethyl or cyano.

Also provided herein are compounds of Formula I that further satisfy Formula XVII:

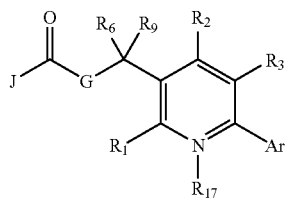

Formula XVII or are a pharmaceutically acceptable form thereof wherein Ar, $R_1$, $R_2$, $R_3$, $R_1$, $R_9$ and $R_{17}$ are as described for Formula I; G is O or NH; and J is phenyl or a 6-membered heteroaryl ring, each of which is substituted with from 0 to 4 substituents independently chosen from $R_x$.

Compounds of Formula I that further satisfy Formula XVIII (or are a pharmaceutically acceptable form thereof) are also provided:

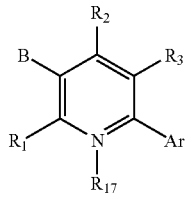

Formula XVIII wherein Ar, $R_1$, $R_2$, $R_3$ and $R_{17}$ are as described for Formula I, and B is a 5- or 6-membered carbocyclic or heterocyclic ring, each of which is substituted with from 0 to 4 substituents independently chosen from $R_x$. Within certain compounds of Formula XVIII:

Ar is phenyl, pyridyl, pyrimidinyl, benzisoxazolyl, indazolyl or indolyl, each of which is substituted with from 1 to 3 substituents independently chosen from $R_x$;

B is pyrrolidinyl or pyrazolyl, each of which is substituted with from 0 to 2 substituents independently chosen from $R_x$;

$R_1$ is hydrogen, cyano, $C_1$-$C_4$alkyl or $C_1$-$C_4$alkoxy;

$R_2$ is hydrogen, halogen, cyano or $XR_y$, wherein:
X is a single bond, —O—, —S(O)$_n$— or —NR$_B$—; and
$R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4- to 10-membered heterocycle)$C_0$-$C_4$alkyl each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$alkoxy and $C_3$-$C_7$cycloalkyl; and $R_3$ is hydrogen, methyl, chloro, fluoro, trifluoromethyl or cyano.

Still further compounds of Formula I additionally satisfy Formula XVIX:

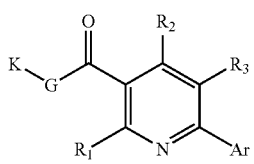

Formula XVIX or are a pharmaceutically acceptable form thereof, wherein Ar, $R_1$, $R_2$ and $R_3$ are as described for Formula I; G is O or NR$_k$ wherein $R_k$ is (i) hydrogen; or (ii) joined to J to form a 4- to 10-membered carbocycle or heterocycle, each of which is substituted with from 0 to 4 substituents independently chosen from $R_x$; and K is: (i) a 4- to 10-membered carbocycle or heterocycle, each of which is substituted with from 0 to 4 substituents independently chosen from $R_x$; or (ii) Joined to $R_k$ to for an optionally substituted 4- to 10-membered heterocycle.

Within certain compounds of Formula XVIX:

Ar is phenyl, pyridyl, pyrimidinyl, benzisoxazolyl, indazolyl or indolyl, each of which is substituted with from 1 to 3 substituents independently chosen from $R_x$;

K is phenyl or joined to $R_k$ to form a 6- to 10-membered heterocycle, each of which is substituted with from 0 to 4 substituents independently selected from halogen, hydroxy, amino, cyano, $C_1$-$C_6$alkyl, $C_1$-$C_6$alkoxy, $C_1$-$C_6$haloalkyl, and $C_1$-$C_6$haloalkoxy;

$R_1$ is hydrogen, cyano, $C_1$-$C_4$alkyl of $C_1$-$C_4$alkoxy;

$R_2$ is halogen, cyano or $XR_y$, wherein:

X is —O—, —S(O)$_n$— or —$NR_B$—; and $R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, phenyl$C_0$-$C_4$alkyl or (4- to 10-membered heterocycle)$C_0$-$C_4$alkyl each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1$-$C_8$alkoxy and $C_3$-$C_7$cycloalkyl; and $R_3$ is hydrogen, methyl, chloro, fluoro, trifluoromethyl or cyano.

Certain compounds according to the Formulas provided herein, which have two or more stereogenic centers, have a diastereomeric excess of at least 50%. For example, such compounds may have a diastereomeric excess of at least 60%, 70%, 80%, 85%, 90%, 95%, or 98%. Certain such compounds have a diastereomeric excess of at least 99%.

Certain compounds according to the Formulas provided herein, which have one or more stereogenic center, have an enantiomeric excess of at least 50%. For example, such compounds may have an enantiomeric excess of at least 60%, 70%, 80%, 85%, 90%, 95%, or 98%. Certain such compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence oaf a resolving agent, or chromatography, using for example a chiral HPLC column 3-substituted-6-aryl pyridines and pharmaceutically acceptable forms thereof provided herein detectably alter (modulate) C5a receptor activity and/or ligand binding, as determined using a standard in vitro C5 receptor-mediated chemotaxis assay (described in Example 55), radioligand binding (described in Example 60), or C5a receptor-mediated calcium mobilization assay (described in Example 62). Preferred compounds exhibit an $EC_{50}$ of about 500 nM or less in such a standard C5a receptor-mediated chemotaxis, radioligand binding, and/or calcium mobilization assay, more preferably an $EC_{50}$ of about 250 nM or less in such an assay, still more preferably an $EC_{50}$ of about 200, 150, 100, 50, 25, 10, or 5 nM or less in such an assay.

Initial characterization of compounds can be conveniently carried out using a C5a receptor binding assay or functional assay, such as set forth in the Examples, and may be expedited by applying such assays in a high throughput screening setting. Additional assays suitable for determining the effects of small molecule compounds on C5a receptor binding and receptor modulatory activity, as well as assays suitable for measuring their effects on C5a-induced neutropenia in vivo, can be found in the published literature, for example in U.S. Pat. No. 5,807,824, which is incorporated herein by reference for its disclosure in this regard in Examples 6-9, columns 19-23, as well as for its discussion of complement and inflammation at columns 1-2. Those of skill in the art will recognize that such assays can be readily adapted to the use of cells or animals of different species as deemed appropriate.

In certain embodiments, preferred compounds have favorable pharmacological properties, including oral bioavailability (such that a sub-lethal or preferably a pharmaceutically acceptable oral dose, preferably less than 2 grams, more preferably of less than or equal to one gram, can provide a detectable in viva effect such as a reduction of C5a-induced neutropenia), ability to inhibit leukocyte chemotaxis at nanomolar concentrations and preferably at sub-nanomolar concentrations, low toxicity (a preferred compound is nontoxic when a C5a receptor-modulatory amount is administered to a subject), minimal side effects (a preferred compound produces side effects comparable to placebo when a C5a receptor-modulatory amount of the compound is administered to a subject), low serum protein binding, and a suitable in vitro and in vivo half-life (a preferred compound exhibits an in vitro half-life that is equal to an in vivo half-life allowing for Q.I.D. dosing, preferably T.I.D. dosing, more preferably B.I.D. dosing, and most preferably once-a-day dosing). Distribution in the body to sites of complement activity is also desirable (e.g., compounds used to treat CNS disorders will preferably penetrate the blood brain barrier, while low brain levels of compounds used to treat peripheral disorders are typically preferred).

Routine assays that are well known in the art may be used to assess these properties, and identify superior compounds for a particular use. For example, assays used to predict bioavailability include transport across human intestinal cell monolayers, such as Caco-2 cell monolayers. Penetration of the blood brain barrier of a compound in humans may be predicted from the brain levels of the compound in laboratory animals given the compound (e.g., intravenously). Serum protein binding may be predicted from albumin binding assays, such as those described by Oravcová, et al. (1996) *Journal of Chromatography B* 677:1-27. Compound half-life is inversely proportional to the frequency of dosage of a compound required to achieve an C5a receptor modulatory amount. In vitro half-lives of compounds may be predicted from assays of microsomal half-life as described by Kuhnz and Gieschen (1998) *Drug Metabolism and Disposition* 26:1120-27.

As noted above, preferred compounds provided herein are nontoxic. In general, the term "nontoxic" as used herein shall be understood in a relative sense and is intended to refer to any substance that has been approved by the United States Food and Drug Administration ("FDA") for administration to mammals (preferably humans) or, in keeping with established criteria, is susceptible to approval by the FDA for administration to mammals (preferably humans). In addition, a highly preferred nontoxic compound generally satisfies one or more of the following criteria: (1) does not substantially inhibit cellular ATP production; (2) does not significantly prolong heart QT intervals; (3) does not cause substantial liver enlargement, and (4) does not cause substantial release of liver enzymes.

As used herein, a compound that "does not substantially inhibit cellular ATP production" is a compound that satisfies the criteria set forth in Example 64, herein. In other words, cells treated as described in Example 64 with 100 µM of such a compound exhibit ATP levels that are at least 50% of the ATP levels detected in untreated cells. In more highly preferred embodiments, such cells exhibit ATP levels that are at least 80% of the ATP levels detected in untreated cells.

A compound that "does not significantly prolong heart QT intervals" is a compound that does not result in a statistically significant prolongation of heart QT intervals (as determined by electrocardiography) in guinea pigs, minipigs or dogs upon administration of twice the minimum dose yielding a therapeutically effective in vivo concentration. In certain preferred embodiments, a dose of 0.01, 0.05, 0.1, 0.5, 1, 5, 10, 40 or 50 mg/kg administered parenterally or orally does not result in a statistically significant prolongation of heart QT intervals. By "statistically significant" is meant results varying from control at the p<0.1 level or more preferably at the p<0.05 level of significance as measured using a standard parametric assay of statistical significance such as a student's T test.

A compound "does not cause substantial liver enlargement" if daily treatment of laboratory rodents (e.g., mice or rats) for 5-10 days with twice the minimum dose that yields a therapeutically effective in vivo concentration results in an increase in liver to body weight ratio that is no more than 100% over matched controls. In more highly preferred embodiments, such doses do not cause liver enlargement of more than 75% or 50% over matched controls. If non-rodent mammals (e.g., dogs) are used, such doses should not result in an increase of liver to body weight ratio of more than 50%, preferably not more than 25%, and more preferably not more than 10% over matched untreated controls. Preferred doses within such assays include 0.01, 0.05, 0.1, 0.5, 1, 5, 10, 40 or 50 mg/kg administered parenterally or orally.

Similarly, a compound "does not promote substantial release of liver enzymes" if administration of twice the minimum dose yielding a therapeutically effective in vivo concentration does not elevate serum levels of ALT, LDH or AST in laboratory rodents by more than 100% over matched mock-treated controls. In more highly preferred embodiments, such doses do not elevate such serum levels by more than 75% or 50% over matched controls. Alternately, a compound "does not promote substantial release of liver enzymes" if, in an in vitro hepatocyte assay, concentrations (in culture media or other such solutions that are contacted and incubated with hepatocytes in vitro) equivalent to two-fold the minimum in vivo therapeutic concentration of the compound do not cause detectable release of any of such liver enzymes into culture medium above baseline levels seen in media from matched mock-treated control cells. In more highly preferred embodiments, there is no detectable release of any of such liver enzymes into culture medium above baseline levels when such compound concentrations are five-fold, and preferably ten-fold the minimum in vivo therapeutic concentration of the compound.

In other embodiments, certain preferred compounds do not inhibit or induce microsomal cytochrome P450 enzyme activities, such as CYP1A2 activity, CYP2A6 activity, CYP2C9 activity CYP2C19 activity, CYP2D6 activity, CYP2E1 activity or CYP3A4 activity at a concentration equal to the minimum therapeutically effective in vivo concentration.

Certain preferred compounds are not clastogenic or mutagenic (e.g. as determined using standard assays such as the Chinese hamster ovary cell vitro micronucleus assay, the mouse lymphoma assay, the human lymphocyte chromosomal aberration assay, the rodent bone marrow micronucleus assay, the Ames test or the like) at a concentration equal to the minimum therapeutically effective in vivo concentration. In other embodiments, certain preferred compounds do not induce sister chromatid exchange (e.g., in Chinese hamster ovary cells) at such concentrations.

In certain embodiments, preferred compounds exert their receptor-modulatory effects with high specificity. This means that they only bind to, activate, or inhibit the activity of certain receptors other than C5a receptors with affinity constants of greater than 100 nanomolar, preferably greater than 1 micromolar, more preferably greater than 4 micromolar. Also provided herein are highly specific C5a receptor modulatory compounds that exhibit 200-fold greater affinity for the C5a receptor that for other cellular receptors. Such receptors include neurotransmitter receptors such as alpha- or beta-adrenergic receptors, muscaric receptors (particularly m1, m2 or m3 receptors), dopamine receptors, and metabotropic glutamate receptors; as well as histamine receptors and cytokine receptors (e.g., interleukin receptors, particularly IL-8 receptors). Such receptors may also include $GABA_A$ receptors, bioactive peptide receptors (other than C5a receptors and C3a receptors, including NPY or VIP receptors), neurokinin receptors, bradykinin receptors, and hormone receptors (e.g., CRF receptors, thyrotropin releasing hormone receptors or melanin-concentrating hormone receptors). Compounds that act with high specificity generally exhibit fewer undesirable side effects.

Within certain embodiments, modulators provided herein do not bind detectably to receptors that do not mediate inflammatory responses, such as GABA receptors, MCH receptors, NPY receptors, dopamine receptors, serotonin receptors and VR1 receptors, with high or even moderate affinity. In addition, or alternatively, certain preferred C5a receptor modulators exhibit an affinity for C5a receptor that is substantially higher than for receptors that do not mediate inflammatory responses (e.g., at least five times higher, at least ten times higher or at least 100 times higher). Assays for evaluating binding to receptors that do not mediate inflammatory responses include, for example, those described in U.S. Pat. No. 6,310,9212 which is incorporated herein by reference for its disclosure of a $GABA_A$ receptor binding assays in Examples 14, columns 16-17, in U.S. patent application Ser. No. 10/152,189 which is incorporated herein by reference for its disclosure of an MCH receptor binding assay in Example 2, pages 104-105, in U.S. Pat. No. 6,362,186, which is incorporated herein by reference for its disclosure of Cad, and NPY receptor binding assays in Examples 19, columns 45-46, in U.S. Pat. No. 6,355,644, which is incorporated herein by reference for its disclosure of a dopamine receptor binding assay at column 10, and in U.S. Pat. No. 6,482,611, which is incorporated herein by reference or its disclosure of VR1 receptor binding assays in Examples 4-5, column 14. It will be apparent that the C5a receptor modulators provided herein may, but need not, bind to one or more other receptors known to mediate inflammatory responses, such as C3a receptors and/or $A_3$ receptors.

Certain preferred compounds are C5a receptor antagonists that do not possess significant (e.g., greater than 5%) agonist activity in any of the C5a receptor-mediated functional assays discussed herein. Specifically, this undesired agonist activity can be evaluated, for example, in the GTP binding assay of Example 61, by measuring small molecule mediated GTP binding in the absence of the natural agonist, C5a. Similarly, in a calcium mobilization assay (e.g., that of Example 62) a small molecule compound can be directly assayed for the ability of the compound to stimulate calcium levels in the absence of the natural agonist, C5a. The preferred extent of C5a agonist activity exhibited by compounds provided herein is less than 10%, 51% or 2% of the response elicited by the natural agonist, C5a.

Also preferred, in certain embodiments, are C5a receptor modulators that inhibit the occurrence of C5a-induced oxidative burst (OB) in inflammatory cells (e.g., neutrophil) as can be conveniently determined using an in vitro neutrophil OB assay.

For detection purposes, compounds provided herein may be isotopically-labeled or radiolabeled. Accordingly, compounds recited in Formula I (or any other formula specifically recited herein) may have one or more atoms replaced by an atom of the same element having an atomic mass or mass number different from the atomic mass or mass number usually found in nature. Examples of isotopes that can be present in compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{32}P$, $^{35}S$, $^{18}F$ and $^{36}Cl$.

In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Pharmaceutical Compositions

The present invention also provides pharmaceutical compositions comprising one or more C5a receptor modulators provided herein, together with at least one physiologically acceptable carrier or excipient. Pharmaceutical compositions may comprise, for example, one or more of water, buffers (e.g., neutral buffered saline or phosphate buffered saline) ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. As noted above, other active ingredients may (but need not) be included in the pharmaceutical compositions provided herein.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch).

Compositions intended for oral use may further comprise one or more components such as sweetening agents, flavoring agents, coloring agents and/or preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions contain the active material(s) in admixture with excipients suitable for the manufacture of aqueous suspensions. Such excipients include suspending agents (e.g., sodium carboxymethylcellulose, methylcellulose, hydropropylmethylcellulose, sodium alginate, polvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also comprise one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil), a mineral oil (e.g., liquid paraffin) or a mixture thereof. Suitable emulsifying agents include naturally-occurring gums (e.g., gum acacia or gum tragacanth), naturally-occurring phosphatides (e.g., soy bean lecithins and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). An emulsion may also comprise one or more sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

Formulations for topical administration typically comprise a topical vehicle combined with active agent(s), with or without additional optional components. Suitable topical vehicles and additional components are well known in the art, and it will be apparent that the choice of a vehicle will depend on the particular physical form and mode of delivery. Topical vehicles include water; organic solvents such as alcohols (e.g., ethanol or isopropyl alcohol) or glycerin; glycols (e.g., butylene, isoprene or propylene glycol); aliphatic alcohols (e.g., lanolin); mixtures of water and organic solvents and mixtures of organic solvents such as alcohol and glycerin; lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile); and hydrocarbon-based materials such as microsponges and polymer matrices. A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatin-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids and emulsions. The physical appearance and viscosity of such forms can be governed by the presence and amount of emulsifier(s) and viscosity adjuster(s) present in the formulation-Solids are generally firm and non-pourable and commonly are formulated as bars or sticks, or in particulate form; solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity; both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product reels can be prepare with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels and often do not contain emulsifiers. Liquid topical products often contain solvents, emulsifiers, moisturizers, emollients, fragrances, dyes/colorants, preservatives and other active ingredients that increase or enhance the efficacy of the final product.

Suitable emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or non-ionic gums such as hydroxyethylcellulose, xanthan gum, magnesium aluminum silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylcellulose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations. Suitable preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerin, propylene glycol, and butylene glycol. Suitable emollients include lanolin alcohol, lanolin, lanolin derivatives, cholesterol, petrolatum, isostearyl neopentanoate and mineral oils. Suitable fragrances and colors include, but are not limited to, FD&C Red No. 40 and FD&C Yellow No. 5. Other suitable additional ingredients that may be included a topical formulation include, but are not limited to, abrasives, absorbents, anti-caking agents, anti-foaming agents, anti-static agents, astringents (e.g., witch hazel, alcohol and herbal extracts such as chamomile extract), binders/excipients, buffering agents, chelating agents, film forming agents, conditioning agents, propellants, opacifying agents, pH adjusters and protectants.

An example of a suitable topical vehicle for formulation of a gel is: hydroxypropylcellulose (2.1%); 70/30 isopropyl alcohol/water (90.9%); propylene glycol (5.1%); and Polysorbate 80 (1.9%). An example of a suitable topical vehicle for formulation as a foam is: cetyl alcohol (1.1%); stearyl alcohol (0.5%; Quaternium 52 (1.0%); propylene glycol (2.0%); Ethanol 95 PGF3 (61.05%); deionized water (30.05%); P75 hydrocarbon propellant (4.30%). All percents are by weight.

Typical modes of delivery for topical compositions include application using the fingers; application using a physical applicator such as a cloth, tissue, swab, stick or brush; spraying (including mist, aerosol or foam spraying); dropper application; sprinkling; soaking; and rinsing. Controlled release vehicles can also be used.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectable compositions, and adjuvants such as local anesthetics, preservatives and/or buffering agents can be dissolved in the vehicle.

C5a modulators described herein may be formulated as inhaled formulations, including sprays, mists, or aerosols. Such formulations are particularly useful for the treatment of asthma or other respiratory conditions. For inhalation formulations, the compounds provided herein may be delivered via any inhalation methods known to those skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Formulations suitable for nasal administration, wherein the carrier is a solid, include a coarse powder having a particle size, for example, in the range of 20 to 500 microns which is administered in the manner in which snuff is administered (i.e., by rapid inhalation through the nasal passage from a container of the powder held close up to the nose). Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon, for example, the site of implantation, the rate and expected duration of release and the nature of the condition to be treated or prevented.

In addition to or together with the above modes of administration, a modulator may be conveniently added to food or drinking water (e.g., for administration to non-human animals including companion animals (such as dogs and cats) and livestock). Animal feed and drinking water compositions may be formulated so that the animal takes in an appropriate quantity of the composition along with its diet. It may also be convenient to present the composition as a premix for addition to feed or drinking water.

Modulators are generally administered in a therapeutically effective amount. Preferred systemic doses range from about 0.1 mg to about 140 mg per kilogram of body weight per day (about 0.5 mg to about 7 g per patient per day), with oral doses generally being about 5-20 fold higher than intravenous doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

Packaged pharmaceutical compositions are also provided herein, comprising a C5a receptor modulatory amount of at least one C5a receptor antagonist in a container (preferably sealed) and instructions for using the C5a receptor antagonist to treat a condition responsive to C5a receptor modulation (e.g., rheumatoid arthritis, psoriasis, cardiovascular disease, reperfusion injury, bronchial asthma, chronic pulmonary obstructive disorder (COPD), fibrosis, cystic fibrosis, Alzheimer's disease, stroke, myocardial infarction, atherosclerosis, ischemic heart disease or ischemia-reperfusion injury). The active agent(s) may be formulated for administration in a single pharmaceutical preparation (e.g., within the same pharmaceutical composition). Alternatively, each of the active agents may be formulated for separate administration, by the same or different routes of administration. Within a packaged pharmaceutical preparation, a C5a receptor modulatory amount may be packaged as a single dose unit; alternatively, multiple doses may be packaged together for convenience. The C5a receptor modulator may be presented in any suitable container including, but not limited to, a plastic, paper, metal or glass package such as an ampoule, bottle, vial, blister package, infusion bag, syringe, inhaler or tube. For example, a packaged pharmaceutical preparation for oral administration of an active agent may comprise a blister package containing rows of tablets. Instructions may be present on a label attached to the container or on exterior packaging, or may be provided as a package insert.

Methods of Use

C5a modulators provided herein may be used as agonists or (preferably) antagonists, such as inverse agonists, of C5a receptors in a variety of contexts, both in vitro and in vivo. Within certain aspects, C5a antagonists may be used to inhibit the binding of C5a receptor ligand (e.g., C5a) to C5a receptor in vitro or in vivo. In general, such methods comprise the step of contacting a C5a receptor with a sufficient concentration of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), or in a cultured or isolated cell. Within certain embodiments, the C5a receptor is expressed by a cell present in a patient, and the aqueous solution is a body fluid. In general, the concentration of C5a receptor modulator contacted with the receptor should be sufficient to inhibit C5a binding to C5a receptor in vitro as measured, for example, using a calcium mobilization assay or chemotaxis assay as described herein.

Also provided herein are methods for modulating, preferably inhibiting, the signal-transducing activity of a C5a receptor. Such modulation may be achieved by contacting a C5a receptor (either in vitro or in vivo) with a C5a receptor modulatory amount of one or more C5a receptor modulators provided herein under conditions suitable for binding of the modulator(s) to the receptor. The receptor may be present in solution or suspension, in a cultured or isolated cell preparation or within a patient. Modulation of signal transducing activity may be assessed by detecting an effect on calcium ion conductance (also referred to as calcium mobilization or flux) or by detecting an effect on C5a receptor-mediated cellular chemotaxis. C5a receptor modulator(s) provided herein are preferably administered to a patient (e.g., a human) orally or topically, and are present within at least one body fluid of the animal while modulating C5a receptor signal-transducing activity.

The present invention further provides methods for treating patients suffering from conditions responsive to C5a receptor modulation. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is responsive to C5a receptor modulations if modulation of C5a receptor activity results in alleviation of the condition or a symptom thereof. Patients may include primates (especially humans), domesticated companion animals (such as dogs, cats, horses) and livestock (such as cattle, pigs, sheep), with dosages as described herein.

Conditions that are responsive to C5a receptor modulation include the following:

Autoimnnmune disorders—e.g., rheumatoid arthritis, systemic lupus erythematosus (and associated glomerulonephritis), psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage, immunovasculitis, tissue graft rejection, and hyperacute rejection of transplanted organs.

For asthma therapy, C5a receptor antagonists provided herein may be used to prevent or decrease the severity of both acute early please asthma attack and the late phase reactions that follow such an asthma attack.

Inflammatory disorders and related conditions—e.g., neutropenia, sepsis, septic shock, Alzheimer's disease, stroke, inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), cystic fibrosis, and multiple organ dysfunction syndrome (MODS). Also included are pathologic sequellae associated with insulin-dependent diabetes to mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement) such as extracorporeal post-dialysis syndrome, or in association with contact with other artificial vessel or container surfaces (e.g., ventricular assist devices, artificial heart machines, transfusion tubing, blood storage bags, plasmapheresis, plateletpheresis, and the like).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. For example, a C5a receptor modulatory amount of a compound provided herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

HIV infection and AIDS—C5a receptor modulators provided herein may be used to inhibit HIV infection, delay AIDS progression or decrease the severity of symptoms of HIV infection and AIDS.

In a further aspect, C5a receptor modulators may be used to perfuse a donor organ prior to transplantation of the organ into a recipient patient. Such perfusion is preferably carried out using a solution (e.g., pharmaceutical composition) comprising a concentration of the modulator that is sufficient to inhibit C5a receptor-mediated effects in vitro and or in vivo. Such perfusion preferably reduces the severity or frequency of one or more of the inflammatory sequelae following organ transplantation when compared to that occurring in control (including, without restriction, historical control) transplant recipients who have received transplants of donor organs that have not been so perfused.

Within further aspects, C5a antagonists provided herein may be used to treat Alzheimer's disease, multiple sclerosis, and cognitive function decline associated with cardiopulmonary bypass surgery and related procedures. Such methods comprise administration of a therapeutically effective amount of a C5a antagonist provided herein to a patient afflicted with one or more of the above conditions, or who is considered to be at risk for the development of one or more such conditions.

Suitable patients include those patients suffering from or susceptible to a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient a C5a receptor modulatory amount of one or more compounds or forms thereof provided herein. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

As noted above, certain compounds and compositions provided herein are useful as inhibitors of C5a receptor-mediated chemotaxis (e.g., they may be used as standards in assays of such chemotaxis). Accordingly, methods are provided herein for inhibiting C5a receptor-mediated cellular chemotaxis, preferably leukocyte (e.g., neutrophil) chemotaxis. Such methods comprise contacting white blood cells (particularly primate white blood cells, especially human white blood cells) with one or more compounds provided herein.

Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound as described herein has been added.

Dosage levels of the order of from about 0.1 mg to about 140 mg per kilogram of body weight per day are useful in the treatment or prevention of conditions involving pathogenic C5a activity (about 0.5 mg to about 7 g per human patient per day). The amount of active ingredient that may be combined with the carrier materials to produce a single dosage form to will vary depending upon the host treated and the particular mode of administration. Dosage unit forms will generally contain between from about 1 mg to about 500 mg of an active ingredient. For compounds administered orally, transdermally, intravenously, or subcutaneously, it is preferred that sufficient amount of the compound be administered to achieve a serum concentration of 5 ng (nanograms)/mL–10 µg (micrograms)/mL serum, more preferably sufficient C5a receptor modulator to achieve a serum concentration of 20 ng-1 µg/mL serum should be administered, most preferably sufficient C5a receptor modulator to achieve a serum concentration of 50 ng mL-200 ng mL serum should be administered.

For direct injection into the synovium (for the treatment of arthritis) sufficient C5a receptor modulator should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Within separate aspects, the present invention provides a variety of non-pharmaceutical in vitro and in vivo uses for the compounds provided herein. For example, such compounds may be labeled and used as probes for the detection and localization of C5a receptor (in samples such as cell preparations or tissue sections, preparations or fractions thereof). Compounds may also be used as positive controls in assays for C5a receptor activity, as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium, as described herein), and incubated with a sample for a suitable incubation time (e.g., deter-mined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. Within one preferred embodiment, a modulator linked to a fluorescent marker, such as fluorescein, is contacted with the cells, which are then analyzed (or isolated) by fluorescence activated cell sorting (FACS).

Preparation of Compounds

Representative methods for preparing compounds of Formula I and Formula II are shown in Schemes 1-14. Those skilled in the art will recognize that the reagents and synthetic transformations in the following Schemes can be readily modified to produce additional compounds of Formula I and Formula II. When a protecting group is required, an optional deprotection step may be employed. Suitable protecting groups and methodology for protection and deprotection such as those described in *Protecting Groups in Organic Synthesis* by T. Greene are well known. Compounds and intermediates requiring protection/deprotection will be readily apparent.

| | |
|---|---|
| $Ac_2O$ | acetic anhydride |
| BOP | benzotriazol-1-yloxy-tris(dimethylamino)-phosphonium hexafluorophospate |
| n-BuLi | n-butyl lithium |
| $CDCl_3$ | deuterated chloroform |
| DCE | 1,2-dichlorethane |
| DCM | dichloromethane |
| DEAD | diethyl azidocarboxylate |
| DIBAL-H | diisobutylaluminum hydride |
| DIEA | diiosopropylethylamine |
| DMA | N,N-dimethylacetamide |
| DMAP | 4-N,N-dimethylaminopyridine |
| DMF | N,N-dimethylformamide |
| DPPF | 1,1'-bis(diphenylphosphino)ferrocene |
| EtOAc | ethyl acetate |
| HOAc | acetic acid |
| HPLC | high pressure liquid chromatography |
| $^1H$ NMR | proton nuclear magnetic resonance |
| Hz | hertz |
| LAH | lithium aluminum hydride |
| LDA | lithium diisopropylamide |
| LC/MS | liquid chromatography/mass spectrometry |
| MEK | methyl ethyl ketone (2-butanone) |
| MHz | megahertz |
| MS | mass spectrometry |
| (M + 1) | mass + 1 |
| NMP | N-methyl-2-pyrrolidone |
| NBS | N-bromosuccinimde |
| δ | chemical shift |
| $Pd(PPh_3)_4$ | tetrakis(triphenylphosphine) palladium (0) |
| $POCl_3$ | phosphorous oxychloride |
| PrMgCl | n-propylmagnesium chloride |
| PTLC | preparative thin layer chromatography |
| THF | tetrahydrofuran |
| TMSCN | trimethylsilylcyanide |
| 18-C-6 | 18-crown-6 |

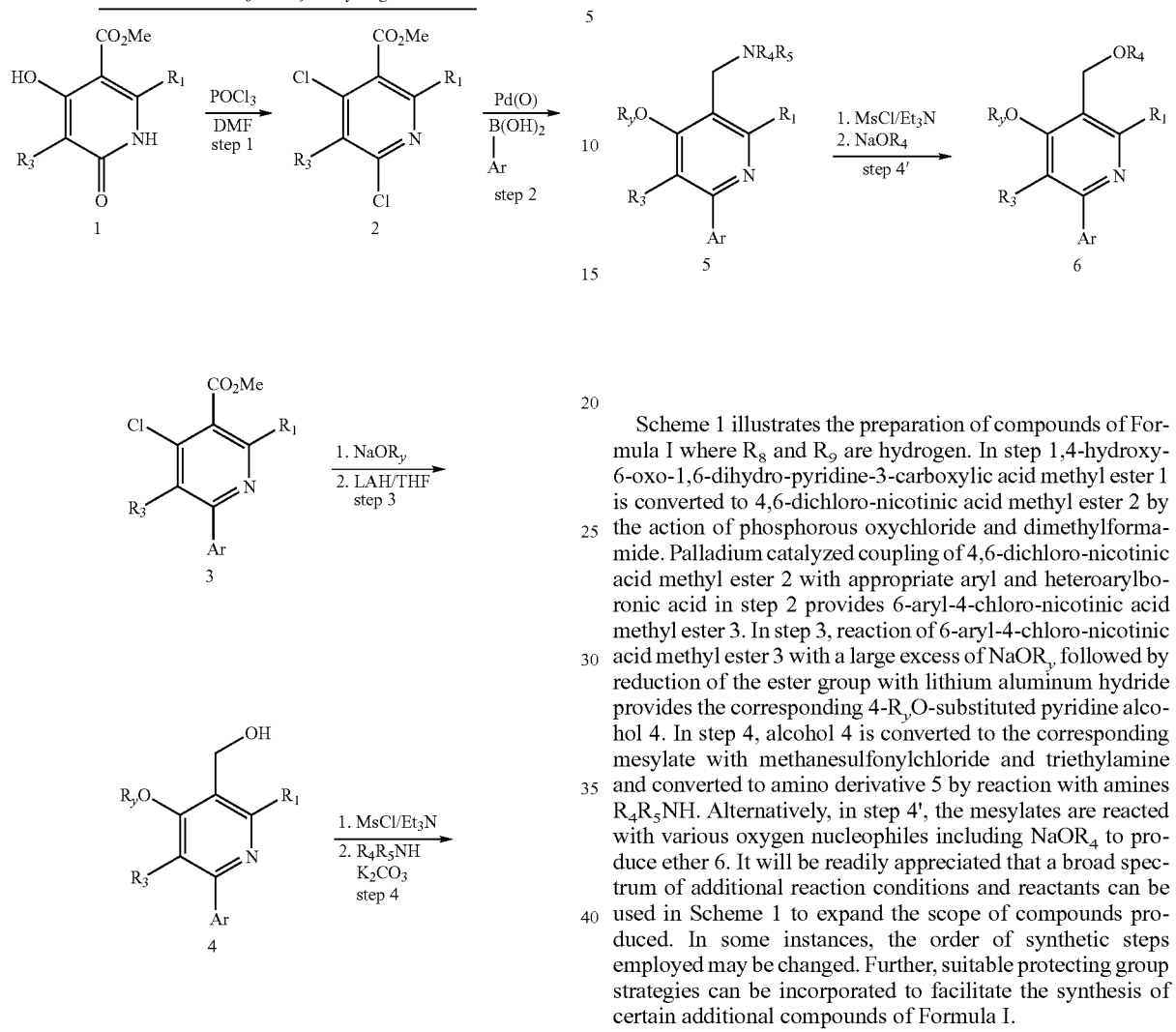

-continued

Scheme 1 illustrates the preparation of compounds of Formula I where $R_8$ and $R_9$ are hydrogen. In step 1, 4-hydroxy-6-oxo-1,6-dihydro-pyridine-3-carboxylic acid methyl ester 1 is converted to 4,6-dichloro-nicotinic acid methyl ester 2 by the action of phosphorous oxychloride and dimethylformamide. Palladium catalyzed coupling of 4,6-dichloro-nicotinic acid methyl ester 2 with appropriate aryl and heteroarylboronic acid in step 2 provides 6-aryl-4-chloro-nicotinic acid methyl ester 3. In step 3, reaction of 6-aryl-4-chloro-nicotinic acid methyl ester 3 with a large excess of $NaOR_y$ followed by reduction of the ester group with lithium aluminum hydride provides the corresponding 4-$R_y$O-substituted pyridine alcohol 4. In step 4, alcohol 4 is converted to the corresponding mesylate with methanesulfonylchloride and triethylamine and converted to amino derivative 5 by reaction with amines $R_4R_5NH$. Alternatively, in step 4', the mesylates are reacted with various oxygen nucleophiles including $NaOR_4$ to produce ether 6. It will be readily appreciated that a broad spectrum of additional reaction conditions and reactants can be used in Scheme 1 to expand the scope of compounds produced. In some instances, the order of synthetic steps employed may be changed. Further, suitable protecting group strategies can be incorporated to facilitate the synthesis of certain additional compounds of Formula I.

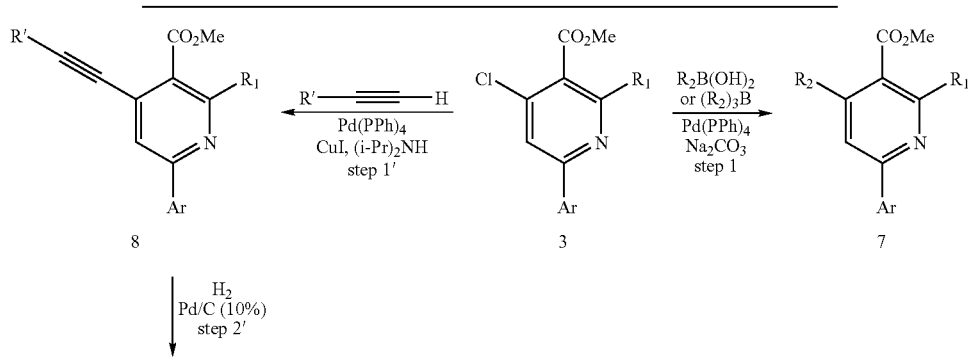

Scheme 2. Preparation of compounds of Formula I and Formula II where $R_2$ is connected to the pyridyl core by a carbon-carbon bond

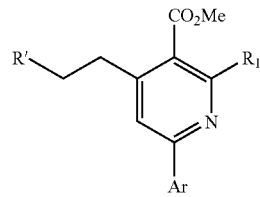

9

Scheme 2 illustrates two methods for preparing intermediates wherein $R_2$ is connected to the pyridyl core by a carbon-carbon bond. In step 1, 4-chloropyridine 3 is reacted with an appropriate boronic acid or trialkylborane to obtain ester 7. Alternatively, in step 1', palladium coupling with an alkyne provides alkyne 8 which may be optionally hydrogenated to 4-alkylpyridine 9. It is readily apparent that 4-chloropyridine 3 may be utilized in a wide variety of additional coupling strategies to produce further examples wherein $R_2$ is connected to the pyridine ring by a carbon-carbon bond.

Scheme 3 provides a route for preparing ethers and amines wherein $R_8$ is alkyl, alkynyl or alkenyl. In step 1, a Grignard reagent is added to aldehyde or ester 10 to provide secondary alcohol 11. Reaction of alcohol 11 with an aryl or heteroaryl alcohol in the presence of triphenylphosphine and DEAD provides aryl or heteroaryl ether 12 in step 2. In step 2', alcohol 11 is converted to the corresponding chloride and reacted with amine $R_4R_5NH$ in the presence of base to obtain amine 13. Alternatively, in step 2", alcohol 11 is reacted with sodium hydride and an alkyl iodide to form ether 14.

Scheme 3. Preparation of ethers and amines of Formula I wherein $R_8$ is alkyl, alkynyl or alkenyl

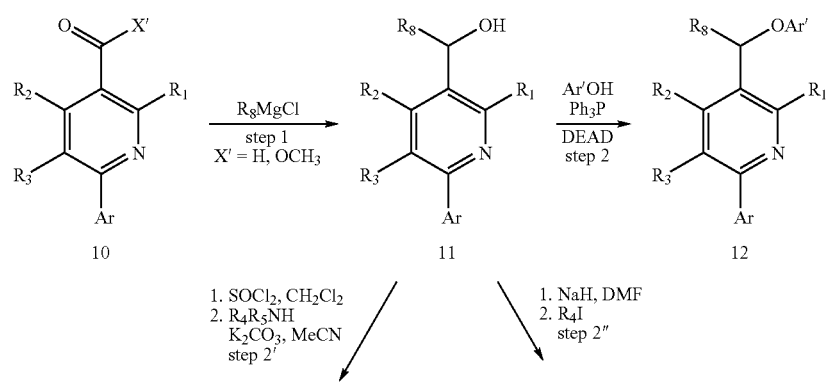

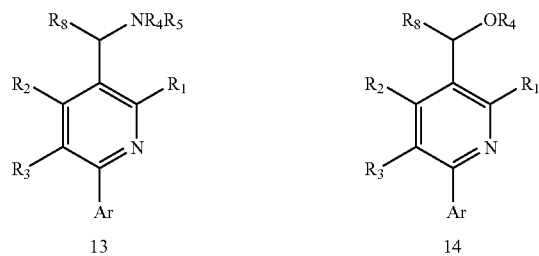

Scheme 4. Preparation of compounds wherein $R_1$ is introduced by nucleophilic aromatic subtitution

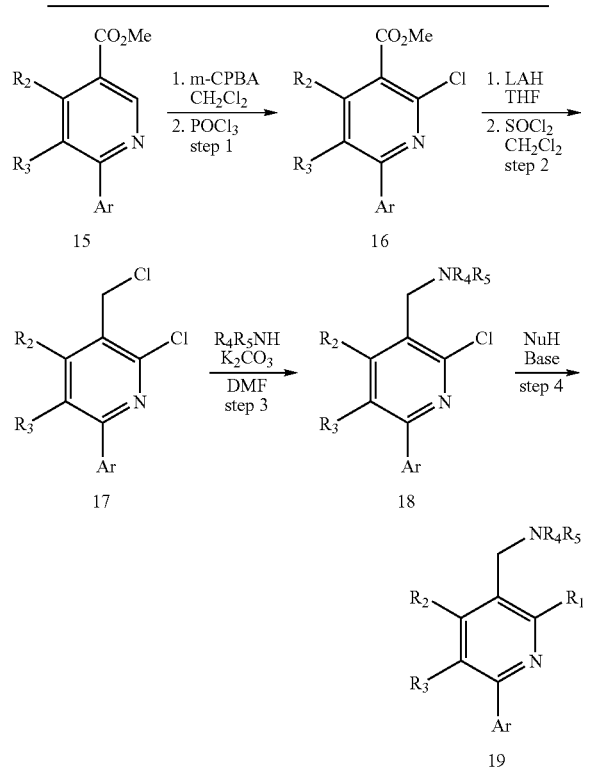

$R_1$ = alkoxy, alkylamino, or dialkylamino

Scheme 4 illustrates a route for preparing compounds of Formula I wherein $R_1$ is introduced by nucleophilic aromatic substitution. In step 1, pyridine ester 15 is converted to the corresponding pyridine N-oxide by the action of meta-chlorobenzoic acid, and the N-oxide is subsequently reacted with phosphorous oxychloride to provide the 2-chloropyridine 16. Reduction with lithium aluminum hydride followed by reaction with thionyl chloride in step 2 provides dichloride 17. In step 3, nucleophilic displacement with an amine gives the 3-aminomethyl-2-chloropyridine 18. The 3-aminomethyl-2-chloropyridine 18 is reacted with any of a variety of oxygen and nitrogen nucleophiles (NuH) in the presence of base to provide the corresponding 2-substituted compound 19, wherein $R_1$ is alkoxy, alkylamino or dialkylamino.

Scheme 5. Preparation of compounds of Formula I and Formula II wherein $R_1$ is cyano

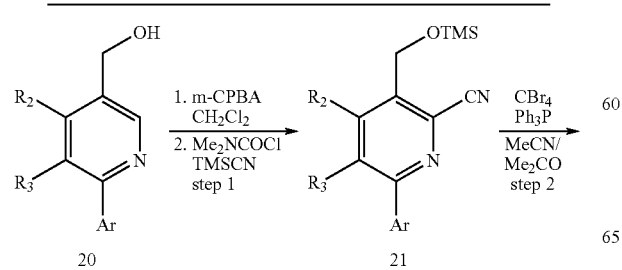

Scheme 5 shows a route for preparing compounds of Formula I where $R_1$ is cyano. In step 1, alcohol 20 is oxidized to the corresponding pyridine N-oxide with meta-chloroperoxybenzoic acid. Subsequent reaction with N,N-dimethylcarbamoyl chloride and trimethylsilylcyanide results in formation of 2-cyanopyridine derivative 21 as the trimethylsilylether. Trimethlylsilylether 21 is converted to the corresponding bromide 22 by reaction with carbon tetrabromide and triphenylphosphine in step 2. Bromide 22 is reacted with a variety of amines in step 3 to provide the desired 2-cyanopyridine 23. Alternatively, bromide 22 may be reacted with an alkoxide (e.g., $NaOR_4$) to obtain additional compounds of Formula I.

Scheme 6. Preparation of compounds of Formula I wherein $R_8$ is alkyl

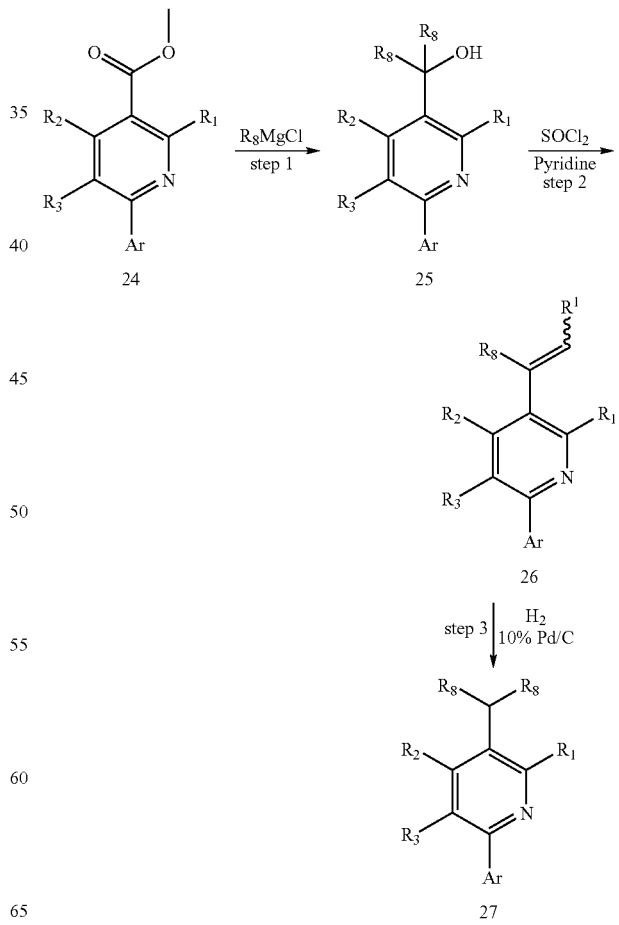

Scheme 6 illustrates a route to synthesize compounds of Formula I wherein $R_8$ is alkyl (and $R_8=R_9$). In step 1, pyridine ester 24 is reacted with excess Grignard reagent to obtain alcohol 25 along with varying amounts of secondary alcohol resulting from mono-addition and reduction. In step 2, alcohol 25 is eliminated to the corresponding alkene 26 by the action of thionyl chloride in pyridine or under a variety of other dehydrating conditions. In step 3, alkene 26 is hydrogenated to obtain alkyl-substituted pyridine 27.

$R_4$ and $R_5$ are as previously defined for Formula I. In step 1, alcohol 28 is oxidized to the corresponding aldehyde which is homologated to the alpha, beta-unsaturated esters and then the ester is hydrolyzed to the acid 29. Acid 29 undergoes [3+2]cyclization with methoxymethyl trimethylsilylmethylamine to give pridylpyrrolidine carboxylic acid 30 in step 2. Acid 30 is reacted with various amines via BOP coupling in step 3 to provide the desired amide 31.

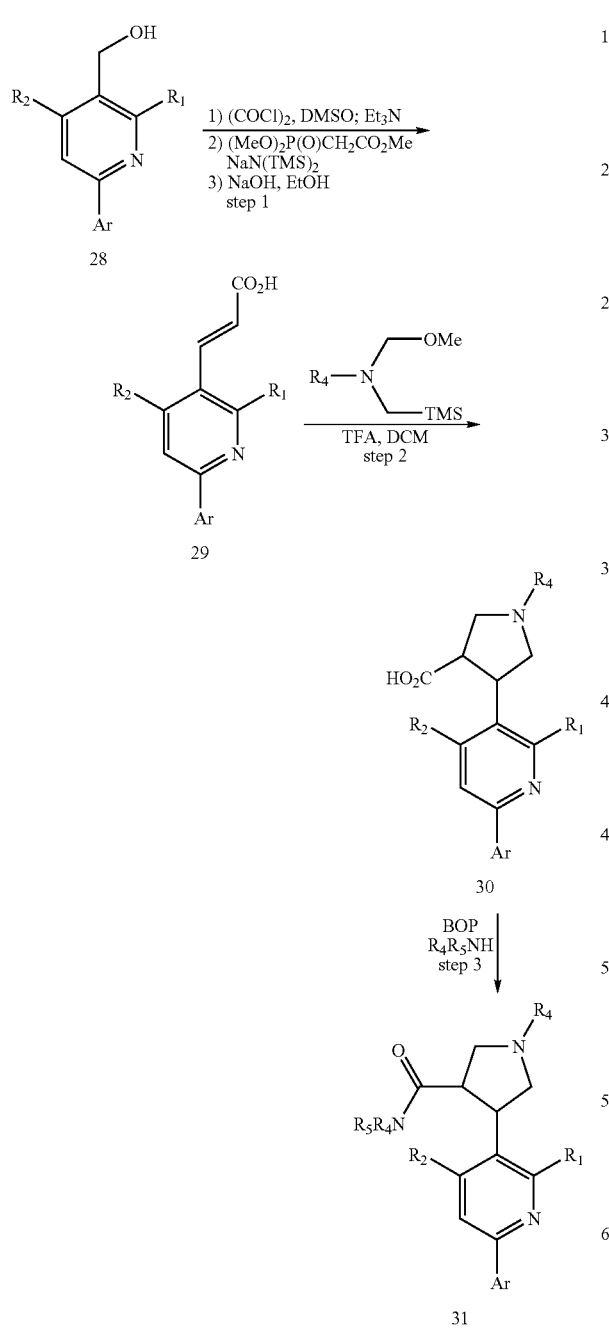

Scheme 7. Preparation of compounds of Formula I wherein $R_8$ and $R_9$ are substituted pyrrolidine

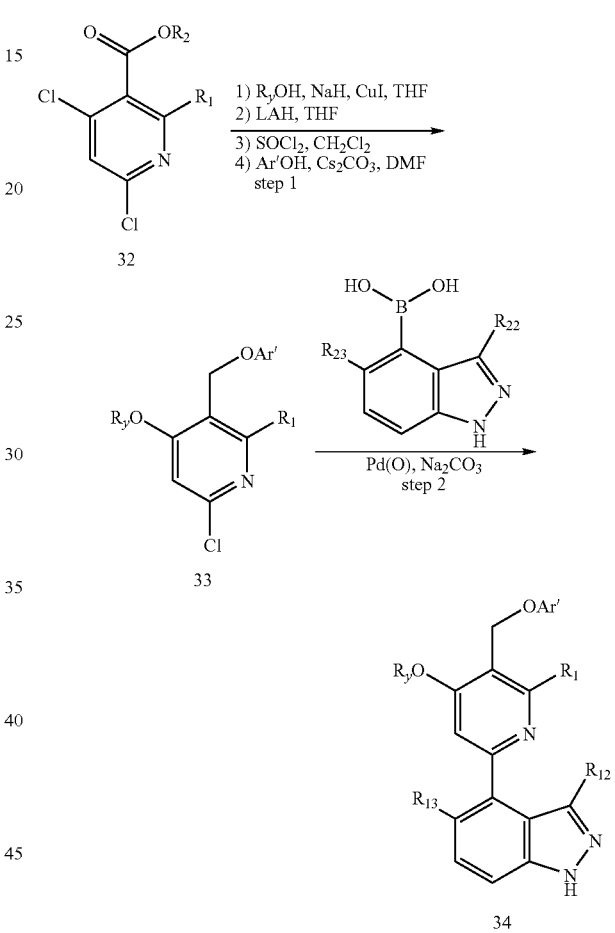

Scheme 8. Preparation of compounds of Formula I where Ar is substituted indazole Scheme 8 illustrates a route for preparing compounds of Formula I or II where Ar is an indazole. In step 1, the 4-chloro group in the dichloropyridine 32 is replaced by an alkoxy group, followed by reduction and chlorination to give the chloromethylpyridine. The intermediate chloride is displaced by phenol or a hydroxylated aromatic heterocycle (Ar'OH) in the presence of a base such as cesium carbonate to yield 33 which is subsequently coupled with various substituted indazole 4-boronic acids to provide the desired pyridyl indazole 34. Alternatively, Scheme 8 can be modified incorporating previously described steps from Schemes 1-7 to produce a variety of other compounds of Formula I or II wherein Ar is indazole. For example, amines of the formula $R_4R_5NH$ may be used in place of Ar'OH in step 1 of Scheme 8 to produce compounds of formula I wherein A is $R_4R_5N$ and Ar is indazole.

Scheme 7 illustrates a route for preparing compounds of Formula I wherein $R_8$ and $R_9$ are substituted pyrrolidine and

Scheme 9. Preparation of 3,5-disubstituted indazole 4-boronic acids

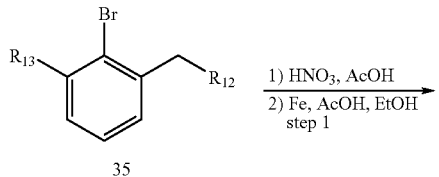

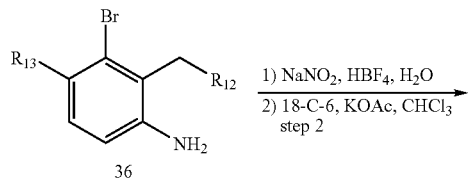

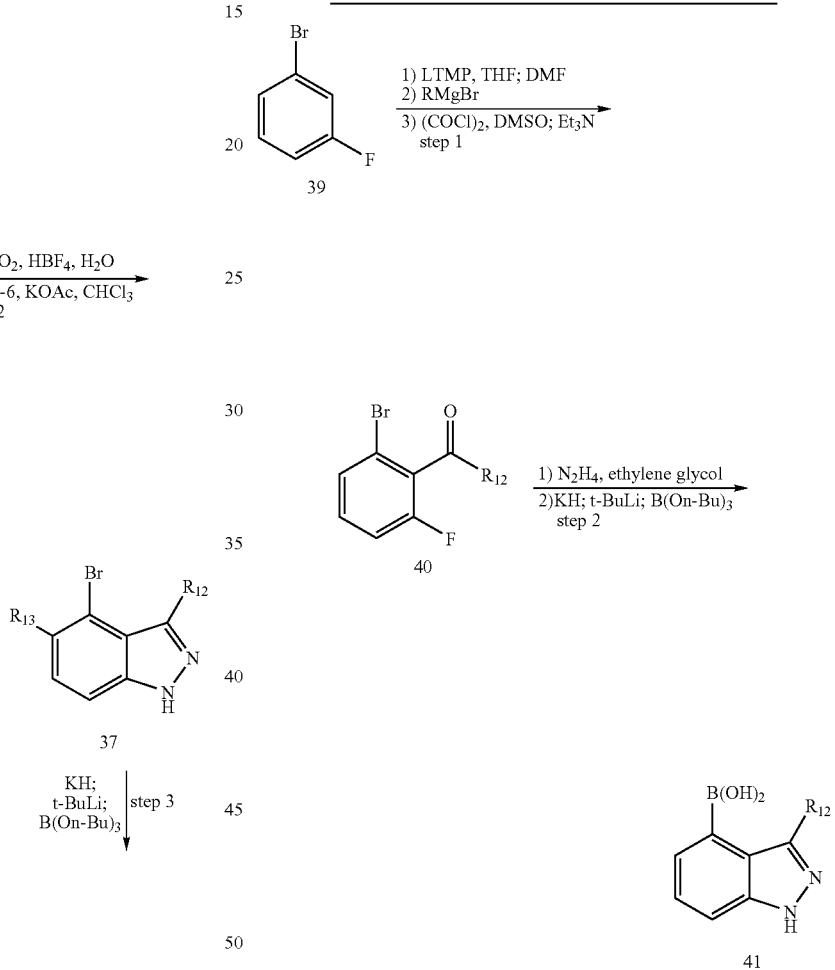

Scheme 9 illustrates a route for preparing 3,5-disubstituted indazole-4-boronic acids. In step 1, substituted bromobenzene 35 is nitrated and then reduced to give the bromoaniline 36 which is converted to the corresponding diazonium salt and cyclized to the bromoindazole 37 in the presence of phase transfer catalyst in step 2. The bromoindazole 37 is converted to the corresponding indazole boronic acid 38 in step 3. In Scheme 9, $R_{12}$ and $R_{13}$ are generally a small alkyl group such as methyl, ethyl, propyl or isopropyl.

Scheme 10 illustrates a route for preparing 3-alkylindazole-4-boronic acids. In step 1, 3-bromofluorobenzene is lithiated regioselectively and quenched with DMF to yield 2-bromo-6-fluoro-benzaldehyde. The benzaldehyde is reacted with any of various alkyl Grignard reagents to give the corresponding secondary alcohol which is subsequently oxidized to ketone 40. Cyclocondensation with hydrazine yields the corresponding 3-substituted-4-bromoindazole which is converted to the corresponding boronic acid 41 in step 2. In Scheme 10, $R_{12}$ is generally a small alkyl group such as methyl, ethyl, propyl or isopropyl.

Scheme 11. Preparation of compounds of Formula I wherein $R_2$ is aryl

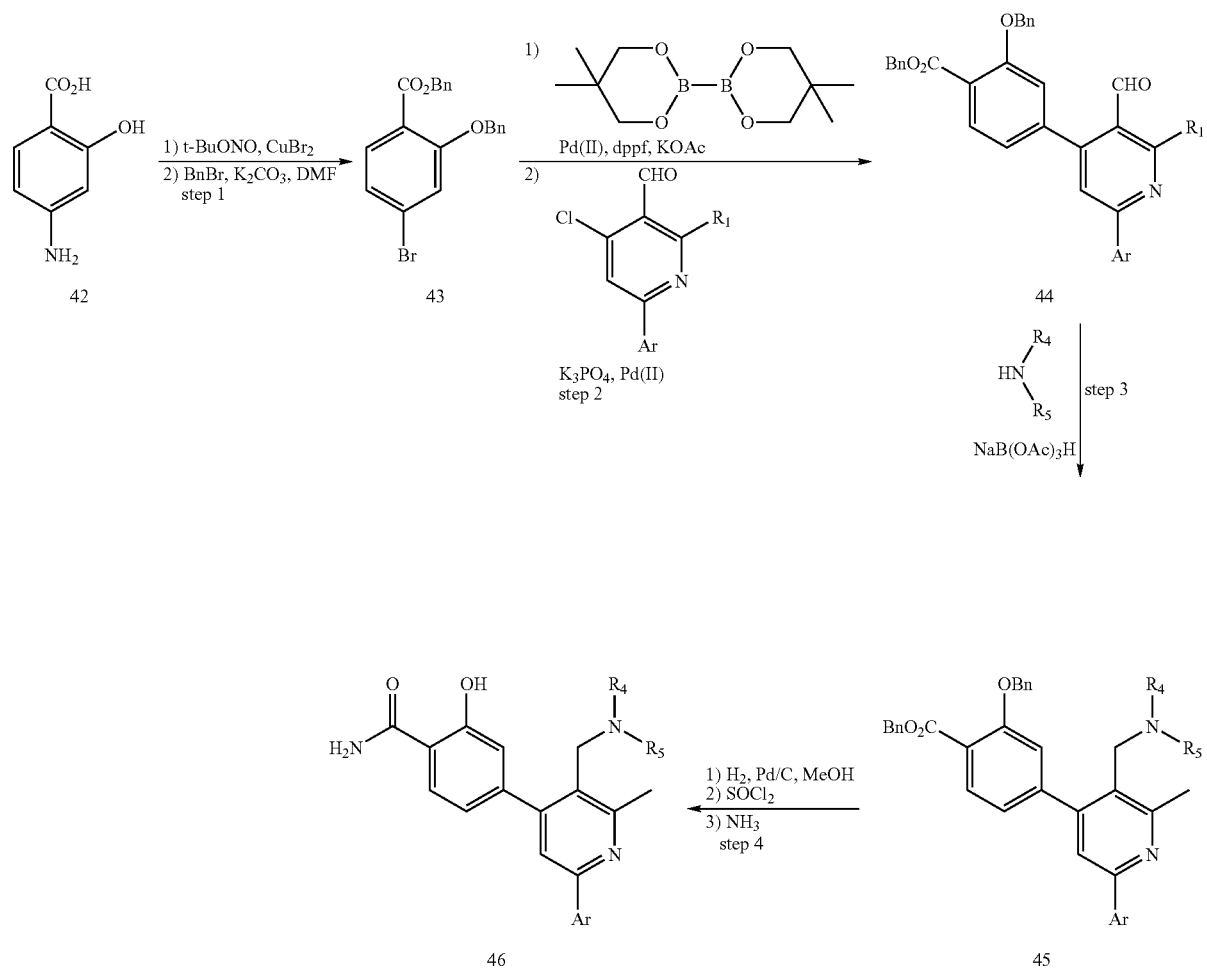

Scheme 11 shows a route for preparing compounds of Formula I or II where $R_2$ is aryl, including salicylic acid derivatives. In step 1, the amino group in 4-aminosalicylic acid 42 is converted to a bromo group via an intermediate diazonium compound, followed by introduction of a benzyl protecting group to give 43. In step 2, 43 is converted to the corresponding boronate and coupled with chloropyridine to give the 2,4-diarylpyridine 44. Reductive amination (step 3) is followed by deprotection and amidation in step 4 to produce 46. Those skilled in the art will recognize that various aryl and heteroaryl boronic acids may be substituted for the boronate of 43 to produce a variety of additional compounds of Formula I wherein $R_2$ is aryl or heteroaryl. Additionally, various other steps may be modified as described in Schemes 1-7 to produce a variety of compounds of Formula I wherein $R_2$ is aryl or heteroaryl.

Scheme 12. Preparation of compounds of Formula I wherein $R_2$ is chloro, cyano, aminoalkyl and substituted aminoalkyl

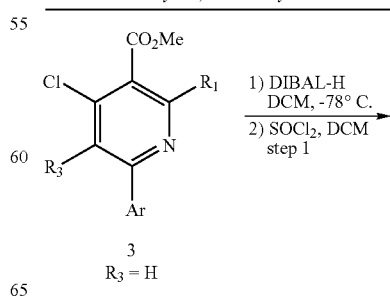

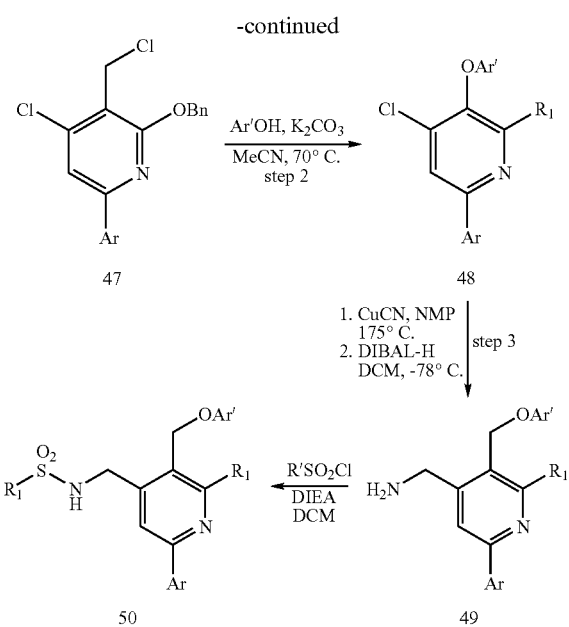

Scheme 12 illustrates a route for producing compounds of Formula I wherein $R_2$ is chloro, cyano, aminomethyl or substituted aminomethyl. In step 1, ester 3 is reduced to the corresponding alcohol and converted to chloromethyl derivative 47. Chloromethyl derivative 47 is reacted with an appropriate phenol or hydroxyheterocycle (Ar'OH) in step 2 to obtain ether 48. In step 3, reaction of 48 with copper cyanide in NMP with heating yields the corresponding 4-cyanopyridine derivative which is subsequently reduced to aminomethyl pyridine 49. In step 4, aminomethyl pyridine 49 is reacted with an alkylsulfonyl chloride (R'SO$_2$Cl) in the presence of DIEA to obtain the corresponding sulfonamide 50. Those skilled in the art will recognize that aminomethylpyridine 49 may also be alkylated or acylated under standard literature conditions to obtain a variety of other compounds of Formula I. In an additional modification of this Scheme, chloromethyl compound 47, may be reacted with a variety of nucleophiles such as amines ($R_4R_5NH$) to obtain compounds of Formula I wherein A is $NR_4R_5$ and $R_2$ is chloro, cyano, aminomethyl or substituted aminomethyl. ($R_yOH$) to produce 4-alkoxypyridine 52. In step 2, the same alcohol ($R_yOH$) is used in the esterification and the displacement reaction to avoid mixtures arising from transesterification. In step 3,4-alkoxypyridine ester 52 is reduced to the corresponding alcohol and subsequently converted to picolyl chloride 53. Step 4 entails reaction of 53, with amine

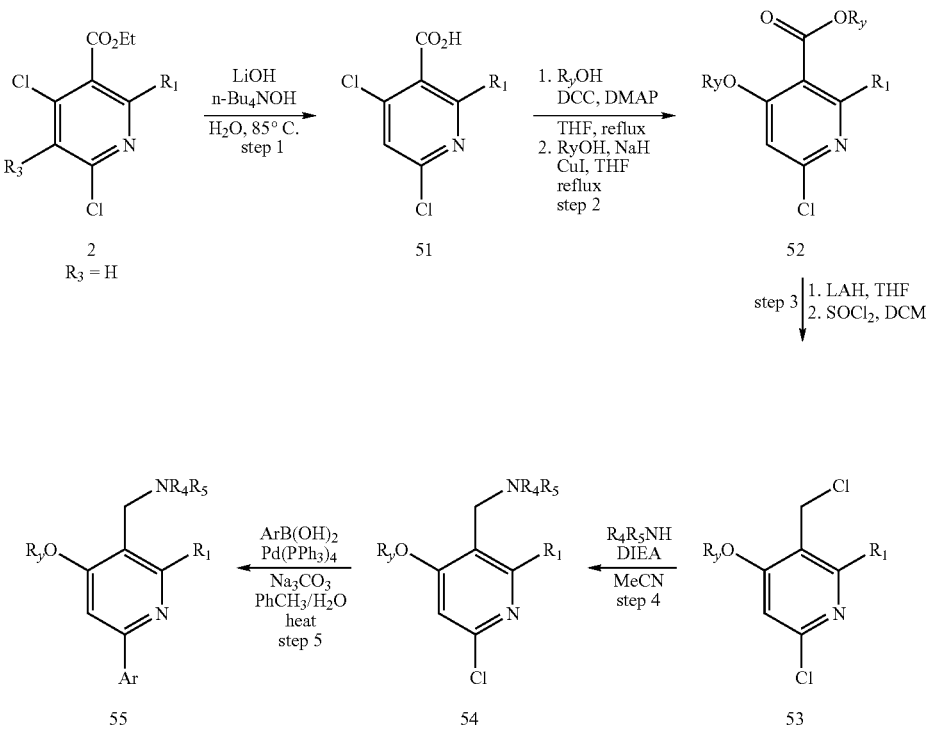

Scheme 13 illustrates an alternative route for producing compounds of Formula I wherein $R_2$ is $R_yO$ and Ar is installed late in the synthesis. In step 1, ester 9 is hydrolyzed to the corresponding carboxylic acid 51. In step 2, acid 51 is converted to the corresponding ester followed by selective displacement of the 4-chloro group with an appropriate alcohol ($R_4R_5NH$) to produce 2-chloropyridine 54. In step 5,2-chloropyridine serves as a versatile intermediate for palladium catalyzed coupling reaction with aryl and heteroaryl boronic acids to produce 55 according to Formula I. Those skilled in the art will recognize that a variety of straightforward modifications to Scheme 13 can be used to produce additional compounds of Formula I.

Scheme 14. Preparation of compounds of Formula I wherein $R_2$ is alkylaminomethyl or dialkylaminomethyl and Ar is indazole

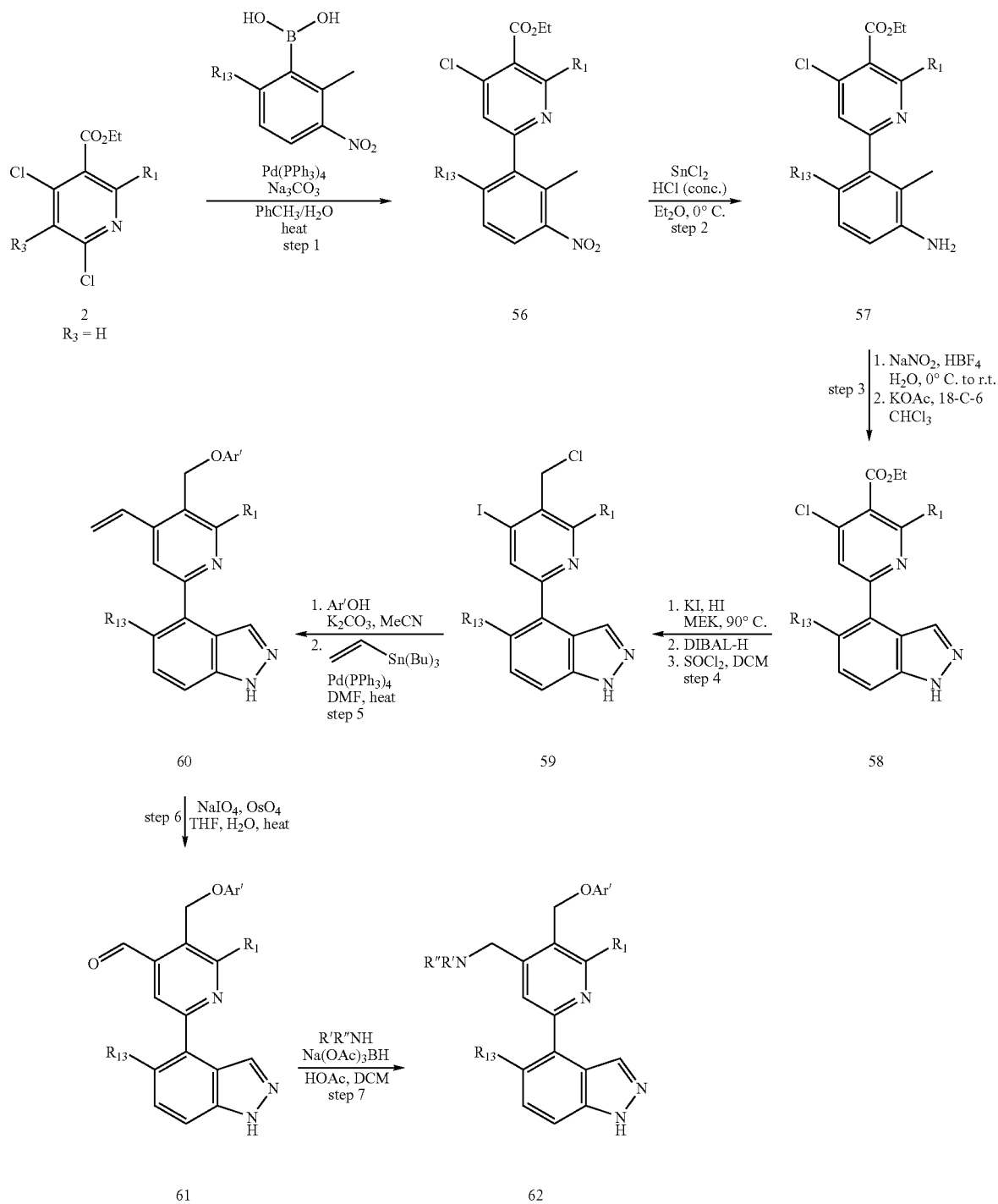

Scheme 14 illustrates a route to compounds of Formula I or II wherein $R_2$ is alkylaminomethyl or dialkylaminomethyl and Ar is indazole. In step 1, pyridine ester 2 is coupled with an appropriate 3-nitroboronic acid (obtained as described in the experimental section) to obtain the corresponding aryl-substituted pyridine derivative 56. Reduction of the nitro group of 56 with tin (II) chloride in step 2 provides the corresponding aniline 57. In step 3, aniline 57 is converted to indazole 58 via base-facilitated cyclization of an intermediate diazonium salt. In step 4, halogen exchange reaction with 58 provides the corresponding 4-iodopyridine ester which is subsequently reduced to the corresponding alcohol and converted to picolyl chloride 59. In step 5, picolyl chloride 59 is reacted with Ar'OH as in the presence of base to form the corresponding ether followed by Stille coupling to produce vinyl pyridine 60. Oxidation of the vinyl group in 60 in step 6 provides aldehyde 61. Compound 61 serves as a versatile intermediate for producing a variety of alkylaminomethyl and dialkyaminomethylpyridines 62 via reductive amination with alkylamines and dialkylamines (R'R"NH) as illustrated in step 7.

Specific examples for the preparation of compounds of Formula I and Formula II (and the other Formulas provided herein) by the methods illustrated in the above Schemes are provided in the following Examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

EXAMPLES

Example 1

Preparation of Certain Starting Materials

A. Synthesis of 2,6-diethylphenylboronic Acid

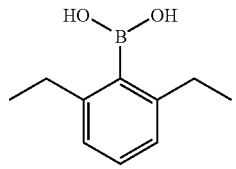

2,6-Diethyl bromobenzene (38.2 g, 180.2 mmol) is added dropwise through an additional funnel over a 1 hour period to a solution of n-BuLi (2.0 M in cyclohexane, 99.1 mL, 198.2 mmol) in THF (380 mL) at −75° C. After addition, the reaction mixture is stirred at −75° C. for 30 minutes; trimethyl borate (28.1 g, 270.3 mmol) is added slowly over a 40 minute period. The reaction mixture is warmed to room temperature overnight. 2N HCl (250 mL) is added slowly and the resulting mixture is stirred for 1 hour. The organic layer is separated and the aqueous layer is extracted with ether (2×200 mL). The combined organic layers are dried over anhydrous $Na_2SO_4$ and the solvents are removed in vacuo. Hexane (400 mL) is added to the residue and a white precipitate is formed. Filtration and drying in vacuo give 2,6-diethylphenyl boronic acid as a white solid. $^1$H NMR: ($CDCl_3$) 7.22 (t, 1H), 7.04 (s, 2H), 4.65 (s, 2H), 2.64 (q, 4H), 1.22 (t, 6H).

B. Synthesis of 2,6-dimethyl-3-methoxybenzeneboronic Acid

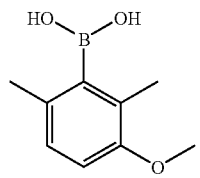

Step 1. Preparation of Aldehyde

A solution of 2-bromo-m-xylene (4.2 g, 23 mmol) in dichloromethane (5 mL) at 78° C. is added dropwise to a solution of titanium tetrachloride (5.0 mL, 45 mmol) and dichloromethyl methyl ether (2.3 mL, 25 mmol) in dichloromethane (20 mL). After the addition is complete, the mixture is allowed to warm to room temperature and stirred for and additional 4 hours before being poured onto ice water. The reaction is extracted with dichloromethane. The organic fraction is washed with water, dried ($Na_2SO_4$), and concentrated to give the aldehyde as a pale yellow solid (4.7 g), which is used in the next step without further purification: $^1$H NMR ($CDCl_3$) 10.1 (s, 1H), 7.68 (d, 1H), 7.22 (d, 1H), 2.79 (s, 3H), 2.45 (s, 3H).

Step 2. Preparation of Methyl Ether

M-chloroperoxybenzoic acid (68%, 8.4 g, 33 mmol) is added to a solution of the above aldehyde (4.7 g) in dichloromethane (120 mL). The mixture is stirred at reflux overnight and concentrated in vacuo. The residue is dissolved in ethyl acetate and washed successively with saturated $NaHCO_3$ (3 times), saturated $NaHSO_3$, and water. The organic fraction is dried ($Na_2SO_4$) and concentrated to give the crude formate (4.4 g). The formate is treated with potassium carbonate (4 g) in ethanol (80 mL) at room temperature for 20 minutes, followed by filtration and concentration to give the corresponding alcohol. The crude alcohol is dissolved in acetone (160 mL) and dimethyl sulfate (2-7 mL, 29 mmol), and potassium carbonate (8.0 g, 58 mmol) is added. The mixture is stirred at reflux for 5 hours. After cooling to room temperature, filtration, concentration, and flash chromatography provide the desired methyl ether as a colorless oil (3.3 g). $^1$H NMR ($CDCl_3$) 7.02 (d, 1H), 6.73 (d, 1H), 3.80 (s, 3H), 2.37 (s, 3H), 2.35 (s, 3H).

Step 3. Preparation of 2,6-dimethyl-3-methoxybenzeneboronic Acid

A solution of 2,4-dimethyl-3-bromoanisole (3.3 g, 15 mmol) in THF (15 mL) is added dropwise at −78° C. to a solution of n-butyllithium (11 mL of 1.6M in hexane, 17 mmol) in THF (35 mL). After 30 minutes, trimethyl borate (2.3 mL, 20 mmol) is added and the mixture is allowed to warm to room temperature overnight. The mixture is poured onto 10% HCl and extracted with ethyl acetate. The organic fraction is washed with saturated brine, dried ($Na_2SO_4$), and concentrated to give the desired product as a brownish oil. $^1$H NMR ($CDCl_3$) 6.98 (d, 1H), 6.75 (d, 1H), 4.64 br s), 3.80 (s, 3H), 2.27 (s, 3H), 2.22 (s, 3H).

C. Synthesis of 4,6-dichloro-2-methyl-nicotinic Acid Ethyl Ester

Step 1. Synthesis of 4-Hydroxy-2-methyl-6-oxo-1,6-dihydro-pyridine-3-carboxylic acid ethyl ester

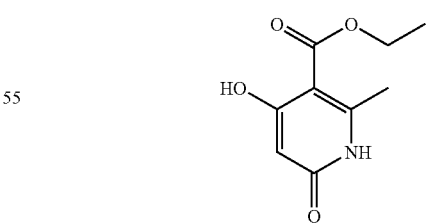

A mixture of 2,4,6-trichloro-phenol (157.6 g, 0.8 mol), malonic acid (52 g, 0.5 mol), and $POCl_3$ (98 mL, 1.05 mol) is heated at reflux for 4 hours. The reaction mixture is cooled slightly and poured into a mixture of ice, water, and ether with stirring. The solid is collected by filtration and dried in vacuo to give malonic acid bis(2,4,6-trichloro-phenyl)ester.

A mixture of malonic acid bis(2,4,6-trichloro-phenyl)ester (13.3 g, 0.03 mol) and ethyl 3-aminocrotonate (3.87 g, 0.03 mol) in bromobenzene (25 mL) is heated at 155° C. for 30 minutes. The mixture is cooled to room temperature. Ethyl acetate (50 mL) and ether (50 mL) are added. The solid is collected and purified by filtration through a short silica gel column (25% ethyl acetate/ether) to give 4-hydroxy-2-methyl-6-oxo-1,6-dihydropyridine-3-carboxylic acid ethyl ester. $^1$H NMR: (CDCl$_3$) 5.85 (s, 1H), 4.38 (q, 2H), 2.68 (s, 3H), 1.39 (t, 3H).

Step 2. Synthesis of 4,6-Dichloro-2-methyl-nicotinic Acid Ethyl Ester

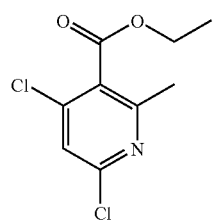

A mixture of 4-hydroxy-2-methyl-6-oxo-1,6-dihydro-pyridine-3-carboxylic acid ethyl ester (2.6 g, 13.2 mmol) and POCl$_3$ (8.2 g, 52.8 mmol) is heated at 140° C. for 2 hours. The volatile material is removed in vacuo. The residue is poured into ice-water. The mixture is neutralized to pH 5 with sodium carbonate powder. The aqueous solution is extracted with ethyl acetate (3×50 mL). The combined organic layers are dried and the solvent is removed. The crude product is purified via flash chromatography (ethyl acetate/hexanes 1:6) to give 4,6-dichloro-2-methyl-nicotinic acid ethyl ester as a colorless oil. $^1$H NMR: (CDCl$_3$) 7.22 (s, 1H), 4.43 (q, 2H), 2.54 (s, 3H), 1.20 (t, 3H).

D. Synthesis of 4,6-Dichloro-2-trifluoromethyl-Nicotinic Acid Methyl Ester

Step 1. Synthesis of 4-Hydroxy-6-oxo-2-trifluoromethyl-1,6-dihydro-pyridine-3-carboxylic Acid Methyl Ester

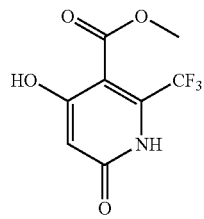

Dimethyl 1,3-acetonedicarboxylate (34.8 g, 0.2 mol) is slowly added to a solution of potassium t-butoxide (22.4 g, 0.2 mol) in THF (300 mL) at 60° C. After addition, the reaction mixture is stirred at 60° C. for 2 hours. The reaction is allowed to cool to 40° C. and trifluoroacetonitrile gas (100 g, 1.05 mol) is slowly bubbled slowly into the above mixture. The reaction temperature is maintained at 50° C. overnight. The volatile material is removed in vacuo. The residue is dissolved in water (200 mL) and the solution is poured into hydrogen chloride solution (conc. HCl/water 80 mL: 200 mL). The white solid is collected by filtration and dried. After being triturated with chloroform (200 mL), the title product is obtained as a white solid. $^1$H NMR: (CDCl$_3$) 6.29 (s, 1H), 3.76 (s, 3H).

Step 2. Synthesis of 4,6-Dichloro-2-trifluoromethyl-nicotinic Acid Methyl Ester

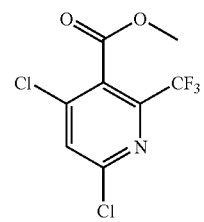

A mixture of 4-hydroxy-6-oxo-2-trifluoromethyl-1,6-dihydro-pyridine-3-carboxylic acid methyl ester (23.7 g, 100 mmol), DMF (29.2 g 400 mmol) and POCl$_3$ (61.2 g, 400 mmol) is heated at 90° C. for 16 hours. The volatile material is removed in vacuo. The residue is poured into ice-water. The mixture is neutralized to pH 5 with sodium carbonate powder. The aqueous solution is extracted with ethyl acetate (3×100 mL). The combined organic layers are dried and the solvent is removed. The crude is purified by flash column (ethyl acetate/hexanes 1:6) to give 4,6-dichloro-2-trifluoromethyl-nicotinic acid methyl ester as a colorless oil. $^1$H NMR: (CDCl$_3$) 7.64 (s, 1H), 4.00 (s, 3H).

E. Synthesis of 6-Chloro-4-methoxy-nicotinic Acid Methyl Ester

Step 1. Synthesis of 4,6-Dichloro-nicotinic Acid Methyl Ester

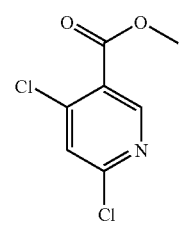

A suspension of 1,6-dihydro-4-hydroxy-6-oxo-pyridine-3-carboxylic acid methyl ester (10.0 g, prepared according to *J. Heterocyclic Chemistry* 20(5):1363-6, 1983) in 100 mL of POCl$_3$ is heated at 140° C. for 0.5 hour. Excess POCl$_3$ is removed in vacuo. Ice water, NaHCO$_3$ and EtOAc are added to the residue. The organic layer is separated and the aqueous layer is extracted with EtOAc. The combined organic layers are washed with water, dried over Na$_2$SO$_4$, and the solvent is removed. The crude is purified by a silica gel column (100% CH$_2$Cl$_2$) to give 4,6-dichloro-nicotinic acid methyl ester. $^1$H NMR (CDCl$_3$) 8.82 (s, 1H), 7.45 (s, 1H), 3.95 (s, 3H).

Similar procedures are applied to the synthesis of 4,6-dichloro-nicotinic acid ethyl ester.

Step 2. Synthesis of 6-Chloro-4-methoxy-nicotinic Acid Methyl Ester

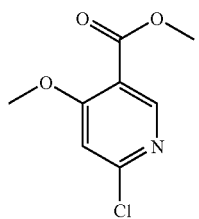

A mixture of 4,6-dichloro-nicotinic acid methyl ester (6.0 g, 29 mmol), NaOMe (2.0 g, 37 mmol) in THF (60 mL) is stirred overnight at room temperature. The solvent is removed in vacuo. Ice-cold dilute HCl solution is added to the solution. The mixture is neutralized with NaHCO$_3$ and extracted with EtOAc. The extract is washed with water, dried, and concentrated. The residue is triturated with hexane until solid is formed. The solid is collected by filtration to give 6-chloro-4-methoxy-nicotinic acid methyl ester. $^1$H NMR (CDCl$_3$) 8.72 (s, 1H), 6.91 (s, 1H), 3.97 (s, 3H), 3.90 (s, 3H).

A similar procedure is applied in the synthesis of 6-(2,6-diethyl-phenyl)-4-ethoxy-nicotinic acid ethyl ester.

F. Synthesis of (S)-Methyl-(1,2,3,4-tetrahydro-naphthalen-1-yl)-amine

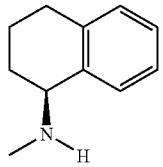

Ethyl chloroformate (7.74 g, 71.3 mmol) is added dropwise to a mixture of (S)-1,2,3,4-tetrahydro-naphthalen-1-ylamine (10.0 g, 67.9 mmol) and K$_2$CO$_3$ (18.8 g, 136 mmol) in CH$_3$CN (100 mL). The resulting mixture is stirred at room temperature overnight. Water (100 mL) is added and the mixture is extracted with ether (2×100 mL). The combined extract is washed with 1 N HCl (2×TO mL), water, dried (Na$_2$SO$_4$), and concentrated in vacuo to give (S)-(1,2,3,4-tetrahydro-naphthalen-1-yl)-carbamic acid ethyl ester as a solid.

(1,2,3,4-Tetrahydro-naphthalen-1-yl)-carbamic acid ethyl ester (5.0 g, 22.8 mmol) is added slowly under nitrogen to a suspension of LiAlH$_4$ (2.6 g, 68 mmol) in THF (50 mL). The resulting mixture is heated at 75° C. with stirring for 2 hours. On cooling, Na$_2$SO$_4$.10H$_2$O (15.0 g) and ether (100 mL) are added to the mixture. The resulting mixture is stirred at room temperature for 1 hour, filtered through celite, and concentrated in vacuo. 1 N HCl (20 mL) and ether (20 mL) are added to the residue. The organic layer is separated and discarded. The aqueous layer is basified with 1 N NaOH and extracted with CH$_2$Cl$_2$ (2×25 mL). The combined extract is washed with water (2×), dried (Na$_2$SO$_4$) and concentrated to give (S)-methyl-(1,2,3,4-tetrahydro-naphthalen-1-yl)-amine as an oil. $[\alpha]^{RT}$=−10.6 (0.02, EtOH). $^1$H NMR (CDCl$_3$) 7.30 (m, 1H), 7.06-7.20 (m, 3H), 3.66 (t, 1H), 2.78 (m, 2H), 2.50 (s, 3H), 1.70-2.00 (m, 4H).

Similar procedures are applied in the synthesis of the following amines:
(R)-Methyl(1,2,3,4-tetrahydro-naphthalen-1-yl)-amine;
(S)-Ethyl-(1,2,3,4-tetrahydro-napthalen-1-yl)-amine;
(S)-Propyl-(1,2,3,4-tetrahydro-naphthalen-1-yl)-amine;
(S)-Indan-1-yl-methyl-amine;
(±)Methyl-(1,2,3,4-tetrahydro-naphthalen-1-yl)-amine; and
(±)Indan-1-yl-methyl-amine.

G. Synthesis of 5-Methylindole-4-boronic Acid

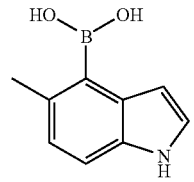

Fuming nitric acid (>90% yellow fuming HNO$_3$) is slowly added to a solution of 2-bromo-in-xylene (20 g, 150 mmol) in acetic acid (100 mL) cooled in an ice bath (above freezing point. The resulting mixture is allowed to warm to room temperature, stirred for 1 hour, and heated at 80° C. for 2 hours or until the reaction is complete by GC/MS analysis following micro-scale base work-up. The reaction mixture is cooled to room temperature and poured into ice/water with stirring. The resulting yellow precipitates are collected by suction filtration and air dried to obtain 2,6-dimethyl-3-nitro-bromobenzene.

Bredereck's reagent (tert-butoxybis(dimethylamino) methane (16 g, 91 mmol) is added to a solution of 2,6-dimethyl-3-nitrobromobenzene (20 g, 87 mmol) in anhydrous DMF (120 mL) at room temperature. The reaction mixture is heated at 120-125° C. under N$_2$ for 5 hours or until starting material is mostly consumed according to TLC. The reaction mixture is allowed to cool to room temperature, poured into water (300 mL), and extracted with dichloromethane (100 mL×3). The combined extracts are dried over anhydrous sodium sulfate, filtered, and concentrated to obtain a mixture of enamines as a dark brown oil. This material is used in the next step without purification.

The crude mixture is dissolved in acetic acid/water (250 mL of 4:1), cooled to 0° C. and treated with zinc dust (57 g, 870 mmol) added slowly in portions. After complete addition, the reaction mixture is heated at 110° C. for 4 hours. Zinc is removed by filtration through a celite pad and the filtrate is extracted with dichloromethane (100 mL×3). The combined extracts are dried over anhydrous sodium sulfate, concentrated, and purified by flash chromatography on silica gel (EtOAc/Hexane 1:20) to obtain 4-bromo-5-methylindole as a light purple oil.

A solution of 4-bromo-5-methylindole (800 mg, 3.8 mmol) in anhydrous ether (8 mL) is added with stirring to a suspension of potassium hydride (560 mg, 4.2 mmol, 30% dispersion in mineral oil) in anhydrous ether at 0° C. under argon. The resulting mixture is cooled to −78° C. and tert-butyl-lithium (4.9 ml, of 1.7 M in pentane, 8.4 mmol) is slowly added. The resulting cream-colored mixture is stirred at −78° C. for 1 hour. Tributylborate (3.1 mL, 11.4 mmol) is slowly added and the reaction mixture is stirred for 1 hour at −78° C. before being allowed to slowly warm to room temperature. More anhydrous ether is added to facilitate stirring. After stirring for 24 hours, the resulting sticky mixture is diluted with ether and transferred in portions with stirring to a pre-cooled solution of 1 M phosphoric acid (50 mL). After stirring for 30 minutes, the acidic mixture is extracted with diethyl ether (75 mL×3) and the combined extracts are extracted with 1 N sodium hydroxide (20 ml×4). The combined base extracts are cooled with an ice bath, acidified with 1 M phosphoric acid and extracted with ethyl acetate (20 ml×3). The combined extracts are washed with brine (20 mL), dried over anhydrous sodium sulfate, filtered and concentrated to obtain a beige residue. The residue is triturated with hexane to obtain the desired 5-methylindole-4-boronic acid as a beige gum (230 mg).

H. Synthesis of 6-isopropyl-2-methyl-3-nitrobenzeneboronic Acid

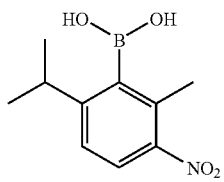

6-Isopropyl-2-methylbenzeneboronic acid (8 g) is added portionwise over 1 hour to 90% $HNO_3$ (50 mL) at $-40°$ C., maintaining an internal temperature below $-30°$ C. After addition, the mixture is stirred at $-40$ to $-30°$ C. for 15 minutes, then poured onto ice, and diluted with water. The solid is collected by filtration, washed with water and dried to give 6-isopropyl-2-methyl-3-nitrobenzeneboronic acid as a white solid. $^1$H NMR (DMSO-d6) 7.78 (d, 2H), 7.30 (d, 2H), 2.85 (m, 1H), 2.38 (s, 3H), 1.15 (d, 6H).

I. Synthesis of 4-Hydroxy-piperidine-4-carboxylic Acid Amide

Step 1. Synthesis of 1-Benzyl-4-hydroxy-piperidine-4-carboxylic Acid Amide

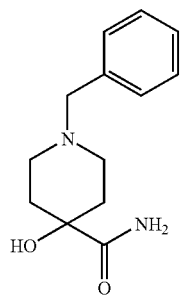

1-Benzyl-4-hydroxy-piperidine-4-carbonitrile (5 g, 23.12 mmol) is dissolved in a mixture of $H_2SO_4$ (18 mL) and $H_2O$ (2 mL) at 0° C. The mixture is warmed to room temperature for 14 hours, transferred into cold 2 N NaOH and adjusted to pH>8. The solid is filtered and washed with $H_2O$, and dried over sodium sulfate to give the crude product.

Step 2. Synthesis of 4-Hydroxy-piperidine-4-carboxylic Acid Amide

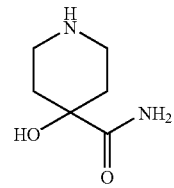

Pd/C (150 mg) and HOAc (2 mL) are added to a solution of 1-benzyl-4-hydroxy-piperidine-4-carboxylic acid amide (2 g, 8.5 mmol) in MeOH. The mixture is shaken under $H_2$ (40 psi) for 14 hours. The catalyst is removed by filtration and the solvent is removed in vacuo to give the title product. $^1$H NMR ($CD_3OD$) 2-96 (m, 4H), 2.05 (m, 2H), 1.49 (m, 2H).

J. Synthesis of 5-Isopropyl-1H-Indazole-4-boronic Acid

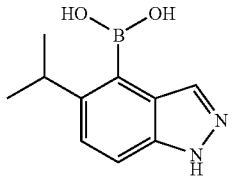

Step 1. Preparation of 4-Bromo-5-isopropyl-1H-indazole

Nitric acid (30 mL, fuming) is added slowly to an ice-cold solution of 2-isopropyl-6-methyl-bromobenzene (10 g, 213 mmol) in acetic acid (60 mL). The mixture is heated 1 hour at 90° C. and cooled to room temperature. The reaction mixture is poured into 200 mL ice-water and extracted with $CH_2Cl_2$ (3×60 mL). The combined extracts are washed with 1 N NaOH (3×40 mL) and then water (40 mL), dried ($Na_2SO_4$), and concentrated to yield crude 2-isopropyl-6-methyl-5-nitro-bromobenzene which is dissolved in AcOH (75 mL)/EtOH (75 mL). To this is added Fe power (5.3 g, 95 mmol) and the mixture is refluxed for 2 hours. The mixture is cooled to room temperature, diluted with water, and neutralized with solid $Na_2CO_3$. The mixture is extracted with EtOAc, dried ($Na_2SO_4$), and concentrated in vacuo. The residue is purified by flash chromatography (elution with Hex/EtOAc 4:1) to yield 3-bromo-4-isopropyl-2-methyl-aniline. A solution of $NANO_2$ (798 mg, 12 mmol) in $H_2O$ (10 mL) is added dropwise at 0° C. to a slurry of 3-bromo-4-isopropyl-2-methyl-aniline (2.4 g, 11 mmol) in $HBF_4$ (15 mL)-$H_2O$ (15 mL), and the mixture is stirred for 1 hour at 0° C. The resulting solid is filtered, washed with cold water and then $Et_2O$, and dried under reduced pressure to yield the diazonium salt as a beige solid. The diazonium salt is added in one portion to mixture of KOAc (1.5 g, 15 mmol) and 18-C-6 (98 mg, 0.37 mmol) in ethanol-free $CHCl_3$ (70 mL) at room temperature. The mixture is stirred for 1 hour and the resulting solid is removed by filtration. The filtrate is washed with water, dried ($Na_2SO_4$), and concentrated in vacuo. The residue is purified by flash chromatography (elution with Hex/EtOAc 4:1) to yield 4-bromo-5-isopropyl-1H-indazole. $^1$H NMR ($CDCl_3$) 8.03 (br s, 1H), 7.41 (d, 1H), 7.35 (d, 1H), 3.55 (m, 1H), 1.24 (d, 6H).

Step 2. Preparation of 5-Isopropyl-1H-indazole-4-boronic Acid

A solution of 4-bromo-5-isopropyl-1H-indazole (116 g, 6.9 mmol) in Et$_2$O (4 mL) is added slowly to a suspension of KH (1.0 g of 30% dispersion in mineral oil, 7.7 mmol) in Et$_2$O (20 mL) at 0° C. and the mixture is stirred for 20 minutes. After cooling to −78° C., t-BuLi (8.9 mL of 1.7 M in Hex, 15 mmol) is added and the resulting mixture is stirred for 40 minutes at −78° C. To this is added B(On-Bu)$_3$ (5.6 mL, 21 mmol) and the mixture is stirred for 24 hours at room temperature. The reaction mixture is quenched with 1N H$_3$PO$_4$ and extracted with Et$_2$O— The combined Et$_2$O layers are back-extracted with 1N NaOH (3×10 mL). The combined NaOH extracts are acidified with 1N H$_3$PO$_4$ and extracted with EtOAc. The EtOAc extracts are washed with saturated brine, dried (MgSO$_4$), and concentrated to yield 5-isopropyl-1H-indazole-4-boronic acid. $^1$H NMR (CDCl$_3$) 7.85 (s, 1H), 7.42 (d, 1H), 7.37 (d, 1H), 3.6 (br s, 2H), 2.88 (m, 1H), 1.32 (d, 6H).

K. Synthesis of 3-Isopropyl-1H-indazole-4-boronic Acid

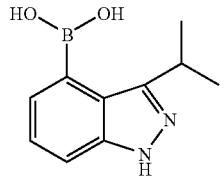

Step 1. Preparation of 1-(2-Bromo-6-fluoro-phenyl)-2-methyl-propan-1-one

To a solution of n-BuLi (25 mL of 1.6 M solution in hexane, 40 mmol) in THF (100 mL) is added 2,2,6,6-teramethylpiperidine (6.8 mL, 40 mmol) at −78° C. and the mixture is stirred for 20 minutes. To this is added 3-bromofluorobenzene (7.0 g, 40 mmol). After stirring for 3 hours at −78° C., DMF (15 mL, 200 mmol) is added and the mixture is warmed to room temperature and stirred for 1 hour. The mixture is quenched with 1N HCl and extracted with EtOAc. The combined extracts are dried (MgSO$_4$) and concentrated in vacuo. The residue is purified by flash chromatography (elution with Hex/EtOAc 10:1) to Held 2-bromo-6-fluoro-benzaldehyde. $^1$H NMR (CDCl$_3$) 10.4 (s, 1H), 7.48-7.39 (m, 2H), 7.18-7.14 (m, 1H).

Isopropylmagnesium chloride (18 mL of 2 M in Et$_2$O, 35 mmol) is added to a solution of 2-bromo-6-fluoro-benzaldehyde (6.0 g, 30 mmol) in THF (40 mL) at −78° C. and the mixture is stirred for 1 hour at 0° C. The mixture is poured into saturated NH$_4$Cl and extracted with EtOAc. The resulting crude alcohol is oxidized directly by Swern oxidation to yield 1-(2-bromo-6-fluoro-phenyl)-2-methyl-propan-1-one. $^1$H NMR (CDCl$_3$) 7.38 (d, 1H), 7.22 (m, 1H), 7.03 (t, 1H), 3.10 (m, 1H), 1.11 (d, 6H).

Step 2. Preparation of 3-Isopropyl-1H-indazole-4-boronic Acid

A mixture of 1-(2-bromo-6-fluoro-phenyl)-2-methyl-propan-1-one (1.1 g, 4.5 mmol) and anhydrous hydrazine (0.17 mL, 5.4 mmol) in ethylene glycol (10 mL) is heated for 16 hours at 160° C. Water is added and the mixture is extracted with CH$_2$Cl$_2$. The combined extracts are dried (MgSO$_4$) and concentrated in vacuo. The residue is purified by flash chromatography to yield 4-bromo-3-isopropyl-1H-indazole. $^1$H NMR (CDCl$_3$) 10.1 (br s, 1H), 7.38 (d, 1H), 7.32 (d, 1H), 7.17 (t, 1H), 3.99 (m, 1H), 1.43 (d, 6H).

4-Bromo-3-isopropyl-1H-indazole is converted to the corresponding boronic acid following analogous procedures to that given in the preceding example. $^1$H NMR (CD$_3$OD) 7.44 (d, 1H), 7.32 (t, 1H), 7.05 (d, 1H), 3.56 (m, 1H), 1.38 (d, 6H). LCMS (m/z): 205.45 (MH)$^+$ Example 2

Synthesis of (±)[6-(2,6-Diethyl-phenyl)-4-methoxy-2-methyl-pyridin-3-ylmethyl]-methyl-(1,2,3,4-tetrahydro-naphthalen-1-YL)-amine Step 1. Synthesis of 4-Chloro-6-(2,6-diethyl-phenyl)-2-methyl-nicotinic acid ethyl ester

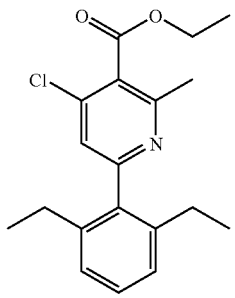

A mixture of 4,6-dichloro-2-methyl-nicotinic acid ethyl ester (1.2 g, 5.1 mmol), 2,6-diethyl-phenyl boronic acid (2.18 g, 12.2 mmol), sodium carbonate (2 M aqueous solution, 12.2 mL, 24.4 mmol), and Pd(PPh$_3$)$_4$ (284 mg, 0.26 mmol) is refluxed in toluene for 48 hours and then cooled to room temperature. The organic layer is separated and the aqueous layer is extracted with ethyl acetate (2×50 mL). The organic Layers are combined, dried, and solvent removed. The crude product is purified by flash column (hexanes/ethyl acetate 8:1) to give 4-chloro-6-(2,6-diethyl-phenyl)-2-methyl-nicotinic acid ethyl ester. $^1$H NMR: (CDCl$_3$) 7.26 (t, 1H), 7.18 (s, 1H), 7.13 (d, 2H), 4.47 (q, 2H), 2.62 (s, 3H), 2.28 (q, 4H), 1.44 (t, 3H), 1.04 (t, 6H).

Step 2. Synthesis of 6-(2,6-diethyl-phenyl)-4-methoxy-2-methyl-nicotinic Acid Methyl Ester

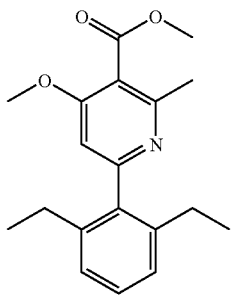

A mixture of 4-chloro-6-(2,6-diethyl-phenyl)-2-methyl-nicotinic acid ethyl ester (165 mg, 0.5 mmol) and sodium methoxide (0.5 M in methanol, 4 mL, 2.0 mmol) is heated at 65° C. for 16 hours. The volatile material is removed in vacuo and the residue is partitioned between ethyl acetate (50 ml) and water (20 mL). The organic layer is separated and the aqueous layer is extracted with ethyl acetate (2×20 mL). The combined organic extract is dried and concentrated in vacuo.

The crude product is purified by PTLC (hexanes/ethyl acetate 4:1) to give 6-(2,6-diethyl-phenyl)-4-methoxy-2-methyl-nicotinic acid methyl ester. $^1$H NMR: (CDCl$_3$) 7.26 (m, 2H), 7.13 (d, 2H), 3.98 (s, 3H), 3.85 (s, 3H), 2.56 (s, 3H), 2.32 (m, 4H), 1.04 (t, 6H).

Step 3. Synthesis of [6-(2,6-Diethyl-phenyl)-4-methoxy-2-methyl-pyridin-3-yl]-methanol

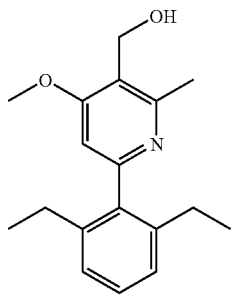

A solution of LiAlH$_4$ (1 M in THF, 1 mL, 1 mmol) is added to a solution of 6-(2,6-diethyl-phenyl)-4-methoxy-2-methyl-nicotinic acid methyl ester (122 mg, 0.39 mmol) in THF (5 mL) at 0° C. The mixture is warmed to room temperature and stirred for 2 hours. The mixture is cooled to 0° C. and Na$_2$SO$_4$.10H$_2$O is added to quench the reaction. The mixture is filtered through Celite and the filtrate is concentrated in vacuo. The crude product is purified by PTLC (hexanes/ethyl acetate 3:1) to give [6-(2,6-diethyl-phenyl)-4-methoxy-2-methyl-pyridin-3-yl]-methanol as a white solid. $^1$H NMR: (CDCl$_3$) 7.26 (m, 1H), 7.13 (d, 2H), 6.68 (S, 1H), 4.82 (d, 2H), 3.87 (s, 3H), 2.65 (s, 3H), 2.33 (m, 4H), 1.05 (t, 6H).

Step 4. Synthesis of (±)[6-(2,6-Diethyl-phenyl)-4-methoxy-2-methyl-pyridin-3-ylmethyl]-methyl-(1,2,3,4-tetrahydro-naphthalen-1-yl)-amine

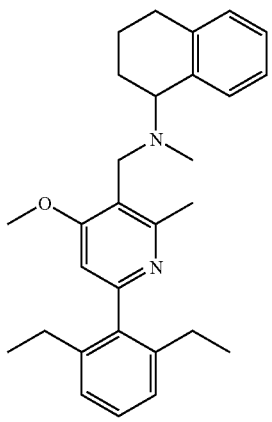

SOCl$_2$ (0.5 mL) is added to a solution of [6-(2,6-diethyl-phenyl)-4-methoxy-2-methyl-pyridin-3-yl]-methanol (40 mg, 0.14 mmol) in CH$_2$Cl$_2$ (1 mL). The mixture is stirred at room temperature for 1 hour. The volatile material is removed in vacuo. K$_2$CO$_3$ (58 mg, 0.42 mmol), (±)methyl-(1,2,3,4-naphthalen-1-yl)-amine (68 mg, 0.42 mmol) (prepared as described above), and acetonitrile (2 mL) are added to the resulting residue. The mixture is stirred at room temperature for 16 hours. The reaction is diluted with ethyl acetate (2 mL) and water (2 mL). The organic layer is separated and the aqueous layer is extracted with ethyl acetate (2×2 mL). The combined organic layers are dried and the solvent removed. The crude product is purified by PTLC (hexanes/ethyl acetate 6:1) to give (±)[6-(2,6-diethyl-phenyl)-4-methoxy-2-methyl-pyridin-3-ylmethyl]-methyl-(1,2,3,4-tetrahydro-naphthalen-1-yl)-amine. $^1$H NMR: (CDCl$_3$) 7.65 (d, 1H), 7.16 (m, 1H), 7.08 (m, 5H), 6.63 (S, 1H), 3.92 (m, 1H), 3.81 (m, 5N), 2.71 (m, 5H), 2.34 (m, 4H), 2.10 (m, 5H), 1.80 (m, 2H), 1.04 (t, 6H).

Example 3

Synthesis of (s)-[6-(2,6-Diethyl-phenyl)-4-methoxy-2-trifluoromethyl-pyridin-3-ylmethyl]-methyl-(1,2,3,4-tetrahydro-naphthalen-1-yl)-amine Step 1. Synthesis of 4-Chloro-6-(2,6-diethyl-phenyl)-2-trifluoromethyl-nicotinic Acid Methyl Ester

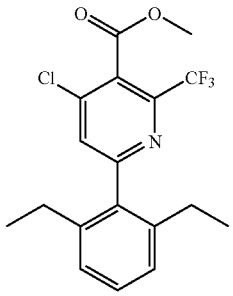

A mixture of 4,6-dichloro-2-trifluoromethyl-nicotinic acid methyl ester (1.0 g, 3.7 mmol), 2,6-diethyl-phenyl boronic acid (0.78 g, 4.4 mmol), sodium carbonate (2 M aqueous solution, 4.4 mL, 8.8 mmol), and Pd(PPh$_3$)$_4$ (206 mg, 0.18 mmol) is refluxed in toluene for 48 hours and then cooled to room temperature. The organic layer is separated and the aqueous layer is extracted with ethyl acetate (2×50 mL). The combined organic layers are dried and the solvent removed. The crude product is purified by flash column (hexanes/ethyl acetate 8:1) to give 4-chloro-6-(2,6-diethylphenyl)-2-trifluoromethyl-nicotinic acid methyl ester as a white solid. $^1$H NMR: (CDCl$_3$) 7.58 (s, 1H), 7.25 (t, 1H), 7.20 (d, 2H), 4.02 (s, 2.28 (q, 4H), 1.04 (t, 6H).

Step 2. Synthesis of 6-(2,6-diethyl-phenyl)-2-trifluoromethoxy-4-methoxy-nicotinic Acid Methyl Ester

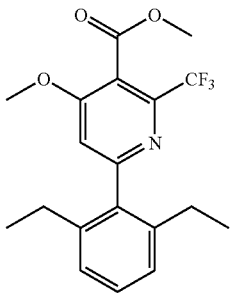

A mixture of 4-Chloro-6-(2,6-diethyl-phenyl)-2-trifluoromethyl-nicotinic acid methyl ester (1.0 mg, 2.7 mmol) and sodium methoxide (4.4 M in methanol, 2 mL, 8.8 mmol) is heated at 60° C. for 2 hours. The volatile material is removed in vacuo and the residue partitioned between ethyl acetate (50 mL) and water (20 mL). The organic layer is separated and the aqueous layer is extracted with ethyl acetate (2×20 mL). The combined organic layers are dried and solvent removed to give the title product. $^1$H NMR: (CDCl$_3$) 7.28 (t, 1H), 7.18 (d, 2H), 6.98 (s, 1H), 3.98 (s, 3H), 3.85 (s, 3H), 2.32 (q, 4H), 1.04 (t, 6H).

Step 3. Synthesis of [6-(2,6-Diethyl-phenyl)-4-methoxy-2-trifluoromethyl-pyridin-3-yl]-methanol

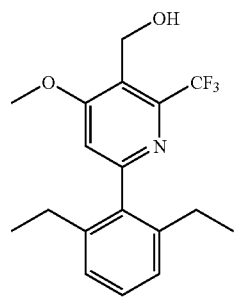

A solution of LiAlH$_4$ (1 M in THF, 2 mL, 2 mmol) is added to a solution of 6-(2,6-diethyl-phenyl)-4-methoxy-2-trifluoromethyl-nicotinic acid methyl ester (200 mg, 0.54 mmol) in THF (5 mL) at 0° C. The mixture is warmed to room temperature and stirred for 2 hours. The mixture is cooled to 0° C. and Na$_2$SO$_4$.10H$_2$O is added to quench the reaction. The mixture is filtered through Celite and the filtrate is concentrated in vacuo. The crude product is purified by PTLC (hexanes/ethyl acetate 3:1) to give [6-(2,6-diethyl-phenyl)-4-methoxy-2-trifluoromethyl-pyridin-3-yl]-methanol as a white solid. $^1$H NMR: (CDCl$_3$) 7.28 (t, 1H), 7.14 (d, 2H), 6.99 (S, 1H), 4.92 (d, 2H), 3.97 (s, 3H), 2.28 (m, 4H), 1.05 (m, 6H).

Step 4. Synthesis of (S)-[6-(2,6-Diethyl-phenyl)-4-methoxy-2-trifluoromethyl-pyridin-3-ylmethyl]-methyl-(1,2,3,4-tetrahydro-naphthalen-1-yl)-amine

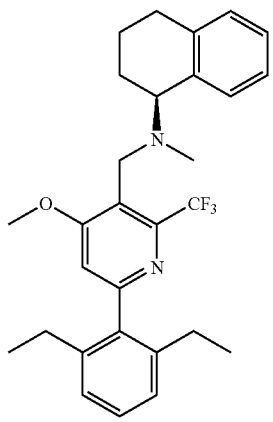

Methanesulfonyl chloride (0.42 g, 3.7 mmol) and triethylamine (0.37 g, 3.7 mmol) are added to a solution of [6-(2,6-diethyl-phenyl)-4-methoxy-2-trifluoromethyl-pyridin-3-yl]-methanol (1.0 g, 3.0 mmol) in DCM (1 mL) and the mixture is stirred at room temperature for 1 hour. The volatile material is removed in vacuo. K$_2$CO$_3$ (1.3 g, 9.3 mmol), (S)-methyl-(1,2,3,4-naphthalen-1-yl)-amine (1.5 g, 9.3 mmol), and acetonitrile (20 mL) are added to the residue. The mixture is stirred at room temperature for 16 hours. The reaction is diluted with ethyl acetate (20 mL) and water (20 mL). The organic layer is separated and the aqueous layer is extracted with ethyl acetate (2×20 mL). The combined organic layers are dried and solvent removed. The crude product is purified by PTLC (hexanes/ethyl acetate 6:1) to give (S)-[6-(2,6-diethyl-phenyl)-4-methoxy-2-trifluoromethyl-pyridin-3-ylmethyl]-methyl-(1,2,3,4-tetrahydro-naphthalen-1-yl)-amine. $^1$H NMR: (CDCl$_3$) 7.68 (d, 1H), 7.29 (m, 1H), 7.12 (m, 5H), 6.95 (S, 1H), 4.04 (m, 3H), 3.91 (s, 3H), 2.76 (m, 2H), 2.35 (m, 4H), 2.06 (m, 5H), 1.80 (m, 2H), 1.07 (t, 6H). [α]$_D$=+10.7 (16.7 mg/l mL benzene).

Example 4

Synthesis of (S)-6-(2,6-Diethyl-phenyl)-4-methoxy-3-{[methyl-(1,2,3,4-tetrahydro-naphthalen-1-yl)-amino]-methyl}-pyridine-2-carbonitrile Step 1. Synthesis of 6-(2,6-diethyl-phenyl)-4-methoxy-nicotinic Acid Methyl Ester

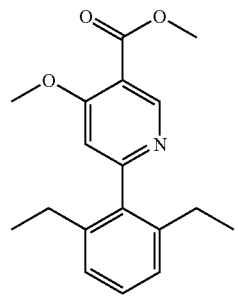

A mixture of 6-chloro-4-methoxy-nicotinic acid methyl ester (4.0 g, 19.8 mmol), 2,6-diethylphenyl boronic acid (7.0 g, 39.3 mmol), Na$_2$CO$_3$ (2M in H$_2$O, 39 mL) and Pd(PPh$_3$)$_4$ (2.0 g, 1.7 mmol) in toluene (200 mL) is heated overnight at 80° C. under argon. On cooling, hexane (200 mL) is added and the organic layer separated. The organic layer is washed with 1N NaOH and water, dried (Na$_2$SO$_4$) and concentrated. The residue is purified by silica gel column (hexane/EtOAc 4:1) to give 6-(2,6-diethyl-phenyl)-4-methoxy-nicotinic acid methyl ester. $^1$H NMR (CDCl$_3$) 8.99 (s, 1H), 7.30 (m, 1H), 7.15 (d, 2H), 6.89 (s, 1H), 3.95 (s, 3H), 3.94 (s, 3H), 2.34 (m, 4H), 1.06 (t, 6H).

6-(2,6-Diethyl-phenyl)-4-ethoxy-nicotinic acid ethyl ester is synthesized via a similar procedure.

Step 2. Synthesis of 4-Chloro-6-(2,6-diethyl-phenyl)-nicotinic Acid Methyl Ester

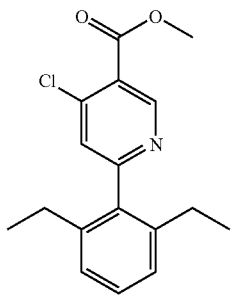

A mixture of 6-(2,6-diethyl-phenyl)-4-methoxy-nicotinic acid methyl ester (4.0 g, 13.4 mmol), DMF (10 mL) and POCl₃ (10 mL) is heated at 80° C. overnight. The volatile material is removed in vacuo. Ice water, NaHCO₃ and hexane (50 mL) are added to the residue. The organic layer is separated and the aqueous layer is extracted with hexane (2×30 mL). The combined organic layer is washed with water, dried, and concentrated. The crude product is purified by silica gel chromatography (1% MeOH in CH₂Cl₂) to give 4-chloro-6-(2,6-diethyl-phenyl)-nicotinic acid methyl ester. ¹H NMR (CDCl₃) 9.12 (s, 1H), 7.40 (s, 1H), 7.30 (d, 1H), 7.15 (d, 2H), 4.00 (s, 3H), 2.30 (q, 4H), 1.05 (t, 6H).

A similar procedure is applied in the synthesis of 4-chloro-6-(2,6-diethyl-phenyl)-nicotinic acid ethyl ester. ¹H NMR (CDCl₃) 9.13 (s, 1H), 7.40 (s, 1H), 7.30 (t, 1H), 7.18 (d, 2H), 4.42 (q, 2H), 2.30 (q, 4H), 1.43 (t, 3H), 1.05 (t, 6H).

Step 3. Synthesis of [6-(2,6-diethyl-phenyl)-4-methoxy-pyridin-3-yl]-methanol

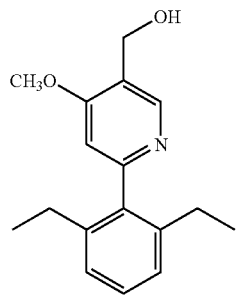

A solution of LiAlH₄ (1 M in THF, 15 mL) is added dropwise to a solution of 6-(2,6-diethyl-phenyl)-4-methoxy-nicotinic acid methyl ester (1.5 g, 5 mmol) in THF (10 mL). The reaction mixture is stirred at room temperature for 6 hours, then diluted with ether (10 mL) and quenched with Na₂SO₄·10H₂O (10 g). The resulting mixture is stirred for one hour, filtered through celite and concentrated to give [6-(2,6-diethyl-phenyl)-4-methoxy-pyridin-3-yl]-methanol. ¹H NMR (CDCl₃) 8.47 (s, 1H), 7.28 (t, 1H), 7.13 (d, 2H), 6.79 (s, 1H), 4.72 (s, 2H), 3.89 (s, 3H), 2.55 (br, 1H), 2.34 (m, 4H), 1.06 (t, 6H).

A similar procedure is applied in the synthesis of [6-(2,6-diethyl-phenyl)-4-ethoxy-pyridin-3-yl]-methanol. ¹H NMR (CDCl₃) 8.45 (s, 1H), 7.30 (t, 1H), 7.12 (d, 2H), 6.78 (s, 1H), 4.72 (s, 2H), 4.10 (q, 2H), 2.35 (m, 4H), 1.42 (t, 3H), 1.02 (t, 6H).

Step 4. Synthesis of [6-(2,6-Diethyl-phenyl)-4-methoxy-pyridin-3-yl]-methanol N-oxide

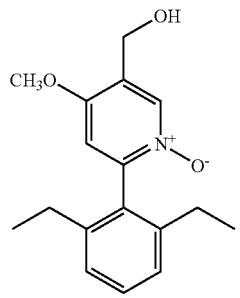

A mixture of [6-(2,6-diethyl-phenyl)-4-methoxy-pyridin-3-yl]-methanol (1.0 g, 3.69 mmol) and 3-chloroperoxybenzoic acid (77%, 910 mg) in CH₂Cl₂ (10 mL) is stirred at room temperature for 2 hours. The mixture is diluted with CH₂Cl₂ (10 mL) and washed with saturated Na₂CO₃, brine, dried, and evaporated at reduce pressure to give [6-(2,6-diethyl-phenyl)-4-methoxy-pyridin-3-yl]-methanol N-oxide. ¹H NMR (CDCl₃) 8.48 (s, 1H), 7.36 (t, 1H), 7.20 (d, 2H), 6.66 (s, 1H), 4.69 (s, 2H), 3.82 (s, 3H), 2.47 (m, 2H), 2.26 (m, 2H), 1.10 (t, 6H).

Step 5. Synthesis of 6-(2,6-Diethyl-phenyl)-4-methoxy-3-trimethyl-silanyloxymethyl-pyridine-2-carbonitrile

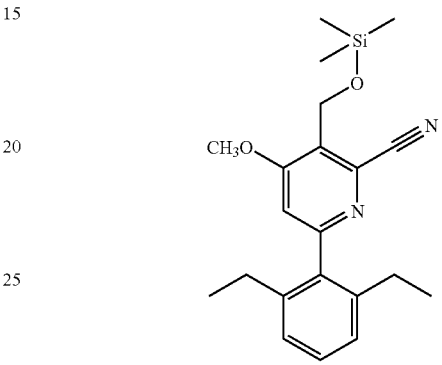

Dimethylcarbamoyl chloride (374 mg, 3.48 mmol) is added to a stirred solution of [6-(2,6-diethyl-phenyl)-4-methoxy-pyridin-3-yl]-methanol N-oxide (500 mg, 1.74 mmol) in dichloroethane (10 mL) under nitrogen. After 15 minutes, TMSCN (700 mg, 7 mmol) is added once and the resulting mixture is stirred at room temperature for 2 days. Water and CH₂Cl₂ are added to the mixture. The organic layer is separated, washed with water, dried and concentrated. The crude product is purified by PTLC (4:1 hexane and EtOAc) to give 6-(2,6-diethyl-phenyl)-4-methoxy-3-trimethylsilanyloxymethyl-pyridine-2-carbonitrile. ¹H NMR (CDCl₃) 7.33 (t, 1H), 7.16 (d, 2H), 6.94 (s, 1H), 4.90 (s, 2H), 3.91 (s, 3H), 2.30 (m, 4H), 1.05 (t, 6H), 0.00-0.22 (9H).

Step 6. Synthesis of (S)-6-(2,6-Diethyl-phenyl)-4-methoxy-3-{[methyl-(1,2,3,4-tetrahydro-naphthalen-1-yl)-amino]methyl}-pyridine-2-carbonitrile

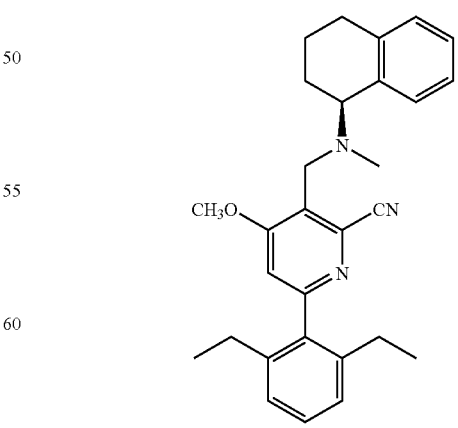

A stirred solution of 6-(2,6-diethyl-phenyl)-4-methoxy-3-trimethylsilanyloxy methyl-pyridine-2-carbonitrile (200 mg, 0.54 mmol) in CH₃CN (5 mL) is treated with CBr₄ (270 mg, 0.81 mmol) and triphenylphosphine (215 mg, 0.81 mmol) at 0° C. under nitrogen. After one hour, acetone (50 mg) is added and the resulting mixture is stirred at room temperature overnight. Water (5 mL) and ether (10 mL) are then added to the mixture, and the organic layer is separated. The organic layer is washed with water, dried, and concentrated to give 3-bromomethyl-6-(2,6-diethyl-phenyl)-4-methoxy-pyridine-2-carbonitrile.

A mixture of 3-bromomethyl-6-(2,6-diethyl-phenyl)-4-methoxy-pyridine-2-carbonitrile (40 mg), K₂CO₃ (50 mg) and (S)-methyl(1,2,3,4-tetrahydro-naphthalen-1-yl)-amine (40 mg) in CH₃CN (2 mL) is stirred at room temperature overnight. Hexane (5 mL) and water (5 mL) are added to the mixture. The organic layer is separated, washed, once with brine, dried (Na₂SO₄), and concentrated. The crude is purified by PTLC (4.1 hexane/EtOAc) to give (S)-6-(2,6-diethyl-phenyl)-4-methoxy-3-{[methyl-(1,2,3,4-tetrahydro-naphthalen-1-yl)-amino]-methyl}-pyridine-2-carbonitrile. ¹H NMR (CDCl₃) 7.72 (d, 1H), 7.35 (t, 1H), 7.07-7.17 (m, 5H), 6.92 (s, 1H), 4.05 (m, 1H), 3.97 (d, 2H), 3.89 (s, 3H), 2.75 (m, 2H), 2.32 (m, 4H), 2.2 (s, 3H), 2.09 (m, 2H), 2.70-2.95 (m, 2H), 1.08 (t, 6H).

Similar procedures are applied in the synthesis of the following compounds:
- 6-(2,6-Diethyl-phenyl)-4-methoxy-3-{[methyl-(1,2,3,4-tetrahydronaphthalen-1-yl)-amino]-methyl}-pyridine-2-carbonitrile;
- (S)-6-(2,6-Diethyl-phenyl)-3-{[ethyl-(1,2,3,4-tetrahydro-naphthalen-1-yl)-amino]-methyl}4-methoxy-pyridine-2-carbonitrile;
- 6-(2,6-Diethyl-phenyl)-3-(1-ethyl-3,4-dihydro-1H-isoquinolin-2-ylmethyl)-4-methoxy-pyridine-2-carbonitrile; and
- 6-(2,6-Diethyl-phenyl)-3-[(indan-1-yl-methyl-amino)-methyl]-4-methoxy-pyridine-2-carbonitrile.

Example 5

Synthesis of (S)-(6-(2,6-diethyl-phenyl)-4-ethyl-3-{[methyl-(1,2,3,4-tetrahydro-napthalen-1-yl)-amino]-methyl}-pyridin-2-yl)-methyl-amine Step 1. Synthesis of 6-(2,6-Diethyl-phenyl)-4-ethyl-nicotinic Acid Methyl Ester

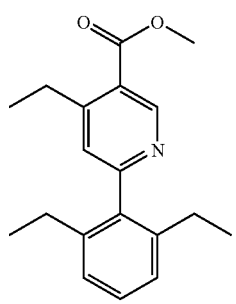

A mixture of 4-chloro-6-(2,6-diethyl-phenyl)-nicotinic acid methyl ester (2.5 g, 8.2 mmol), Et₃B (1M in Hexane, 49 mL, 49 mmol), Na₂CO₃ (2M in H₂O, 12.3 mL) and Pd(PPh₃)₄ (500 mg) in toluene (36 mL) is heated at 80° C. under argon for 2 days. On cooling, hexane (50 mL) is added and the organic layer separated. The organic layer is washed with saturated Na₂CO₃ and water, dried (Na₂SO₄), and concentrated. The residue is purified by silica gel chromatography (hexane/EtOAc 4:1) to give 6-(2,6-diethyl-phenyl)-4-ethyl-nicotinic acid methyl ester. ¹H NMR (CDCl₃) 9.15 (s, 1H), 7.30 (m, 1H), 7.21 (s, 1H), 7.15 (d, 2H), 3.97 (s, 3H), 3.06 (q, 2H), 2.31 (m, 4H), 1.26 (t, 3H), 1.03 (t, 6H).

Step 2. Synthesis of 2-Chloro-6-(2,6-diethyl-phenyl)-4-ethyl-nicotinic Acid Methyl Ester

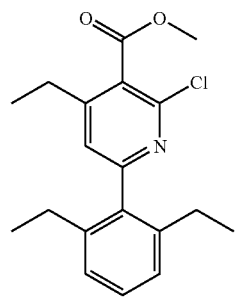

A mixture of 6-(2,6-diethyl-phenyl)-4-ethyl-nicotinic acid methyl ester (2.1 g, 7.1 mmol) and 3-chloroperoxybenzoic acid (77%, 1.9 g) in CH₂Cl₂ (50 mL) is stirred at room temperature overnight. The mixture is diluted with ether (600 mL) and washed with saturated Na₂CO₃, then brine, and dried. Concentration at reduced pressure gives 6-(2,6-diethyl-phenyl)-4-ethyl-nicotinic acid methyl ester N-oxide. ¹H NMR (CDCl₃) 8.89 (s, 1H), 7.26 (t, 1H), 7.19 (m, 3H), 3.95 (s, 3H), 3.02 (q, 2H), 2.04 (m, 2H), 2.30 (m, 2H), 1.26 (t, 3H), 1.11 (t, 6H).

A mixture of 6-(2,6-diethyl-phenyl)-4-ethyl-nicotinic acid methyl ester N-oxide (1.7 g) and POCl₃ (10 mL) is heated at 80° C. for 2 hours. The volatile material is removed in vacuo. Ice water and ether is added to the residue. The organic layer is separated and the aqueous layer is extracted with ether. The combined extract is washed with brine, dried, and concentrated to give 2-chloro-6-(2,6-diethyl-phenyl)-4-ethyl-nicotinic acid methyl ester. ¹H NMR (CDCl₃) 7.26 (t, 1H), 7.12 (d, 3H), 4.02 (s, 3H), 2.69 (q, 2H), 2.32 (m, 4H), 1.25 (t, 3H), 1.07 (t, 6H).

Step 3. Synthesis of (S)-[2-Chloro-6-(2,6-diethyl-phenyl)-4-ethyl-pyridin-3-ylmethyl]-methyl-(1,2,3,4-tetrahydro-naphthalen-1-yl)-amine

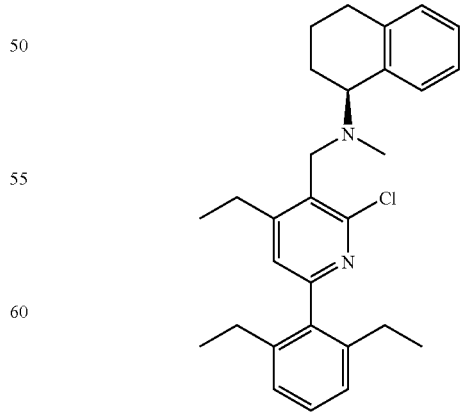

A stirred solution of LiAlH₄ (1M in TI-RF, 3 mL) in ether (10 mL) is treated with AlCl₃ (133 mg) under nitrogen. After 30 minutes, 2-chloro-6-(2,6-diethyl-phenyl)-4-ethyl-nicotinic acid methyl ester (250 mg) in 5 mL of ether is added. The resulting mixture is heated at reflux for 2 hours. On cooling, Na$_2$SO$_4$.10H$_2$O (1.0 g) is added. The mixture is stirred at room temperature for one hour and filtered through Celite. The filtrate is concentrated in vacuo. CH$_2$Cl$_2$ (5 mL) and SOCl$_2$ (0.5 mL) are added to the residue. The resulting mixture is stirred at room temperature for one hour. The volatile material is removed in vacuo. K$_2$CO$_3$ (500 mg) and (S)-methyl-(1,2,3,4-tetrahydro-naphthalen-1-yl)-amine (200 mg) in DMF (5 ml) are added to the residue and the reaction mixture is stirred at room temperature overnight. Hexane (20 mL) and water (5 mL) are added to the mixture. The organic layer is separated, washed once with brine, dried (Na$_2$SO$_4$) and concentrated. The crude product is purified by PTLC (4:1 hexane/EtOAc) to give (S)-[2-chloro-6-(2,6-diethyl-phenyl)-4-ethyl-pyridin-3-ylmethyl]-methyl-(1,2,3,4-tetrahydro-naphthalen-1-yl)-amine. $^1$H NMR (CDCl$_3$) 7.62 (d, 1H), 7.11-7.30 (m, 7H), 4.02 (m, 3H), 3.01 (m, 2H), 2.80 (m, 2H), 2.39 (m, 4H), 2.15 (m, 5H), 1.85-2.00 (m, 2H), 1.33 (t, 3H), 1.09 (t, 6H).

Step 4. Synthesis of (S)-(6-(2,6-Diethyl-phenyl)-4-ethyl-3-{[methyl-(1,2,3,4-tetrahydro-naphthalen-1-yl)-amino]-methyl}-pyridin-2-yl)-methyl-amine

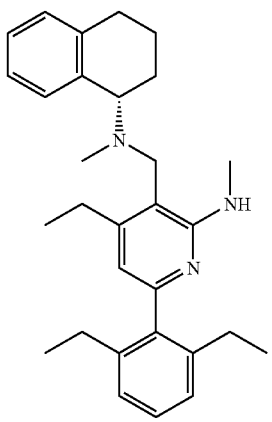

A mixture of (S)-[2-chloro-6-(2,6-diethyl-phenyl)-4-ethyl-pyridin-3-ylmethyl]-methyl-(1,2,3,4-tetrahydro-naphthalen-1-yl)-amine (50 mg), anhydrous MeNH$_2$ (2 mL) and NMP (3 mL) is heated in a sealed tube at 110° C. overnight. On cooling, water (10 mL) and hexane (20 mL) are added and the organic layer is separated. The organic layer is washed with brine, dried and concentrated. The residue is purified by PTLC (8:1 Hexane/EtOAc) to give the desired product. $^1$H NMR (CDCl$_3$) 7.45 (d, 1H), 7.10-7.26 (m, 6H), 6.82 (br, 1H), 6.32 (s, 1H), 3.95 (m, 1H), 3.77 (m, 2H), 2.30 (s, 3H), 2.75 (m, 2H, 2.65 (m, 2H), 2.42 (m, 4H), 2.11 (s, 3H), 1.80-2.10 (m, 2H), 1.07-1.27 (m, 9H).

Example 6

2-(2,6-Diethyl-phenyl)-5-(ethoxy-phenyl-methyl)-4-methoxy-pyridine

Step 1. Synthesis of 6-(2,6-Diethyl-phenyl)-4-ethoxy-pyridine-3-carbaldehyde

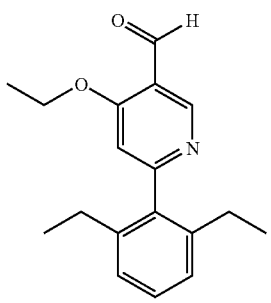

A solution of dry DMSO (2.5 g, 32 mmol) in CH$_2$Cl$_2$ (2 mL) is added dropwise to a solution of oxalyl chloride (2M in CH$_2$Cl$_2$, 7.5 mL) in CH$_2$Cl$_2$ (80 mL) at −78° C. After 10 minutes, a solution of [6-(2,6-diethyl-phenyl)-4-ethoxy-pyridin-3-yl]-methanol (3.4 g, 11.4 mmol) in THF (20 mL) is added to the above mixture. Fifteen minutes after addition, TEA (10 mL) is added and the mixture is stirred at −78° C. for 15 minutes and then warmed to room temperature. The mixture is diluted with ether (100 mL) and washed with water (2×50 mL). The organic layer is dried and concentrated. The crude product is purified on a silica gel:column (4:1 Hexane/EtOAc) to give 6-(2,6-diethyl-phenyl)-4-ethoxy-pyridine-3-carbaldehyde. $^1$H NMR (CDCl$_3$) 10.53 (s, 1H), 8.98 (s, 1H), 7.30 (t, 1H), 7.15 (d, 2H), 6.89 (s, 1H), 4.20 (q, 2H), 2.34 (m, 4H), 1.54 (t, 3H), 1.06 (t, 9H).

Similar procedures are used in the synthesis of 6-(2,6-diethyl-phenyl)-4-methoxy-pyridine-3-carbaldehyde and 6-(2,6-diethyl-phenyl)-4-isopropoxy-pyridine-3-carbaldehyde.

Step 2. Synthesis of [6-(2,6-Diethyl-phenyl)-4-methoxy-pyridin-3-yl]-phenyl-methanol

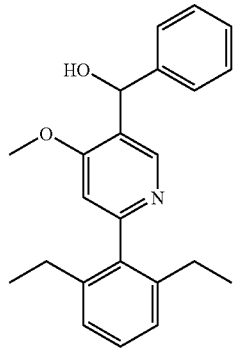

Phenyllithium (1M in THF, 0.26 mL) is added dropwise to a solution of 6-(2,6-diethyl-phenyl)-4-methoxy-pyridine-3-carbaldehyde (70 mg, 0.26 mmol) in ether (4 mL) at room temperature. The mixture is stirred for 2 hours, then treated with aqueous NH$_4$Cl solution (4 mL) and diluted with ether (10 mL). The organic layer is separated, dried and concentrated. The crude is purified by PTLC (4:1 hexane/EtOAc) to give [6-(2,6-diethyl-phenyl)-4-methoxy-pyridin-3-yl]-phenyl-methanol. ¹H NMR (CDCl₃) 8.51 (s, 1H), 7.26-7.43 (m, 6H), 7.15 (d, 2H), 6.76 (s, 1H), 6.06 (s, 1H), 3.82 (s, 3H), 3.21 (s, 1H), 2.32 (m, 4H), 1.05 (m, 6H).

Step 3. Synthesis of 2-(2,6-Diethyl-phenyl)-5-(ethoxy-phenyl-methyl)-4-methoxy-pyridine

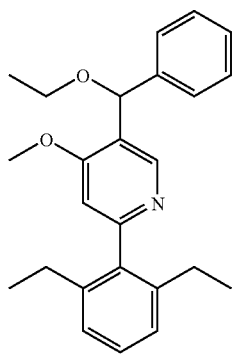

NaH (60% in mineral oil, 8 mg) is added to a solution of [6-(2,6-diethyl-phenyl)-4-methoxy-pyridin-3-yl]-phenyl-methanol (18 mg) in DIM (1 mL). The resulting mixture is stirred at room temperature for 15 minutes. The mixture is then treated with iodoethane (20 mg) and stirred at the same temperature for 1 hour. Aqueous NH₄Cl solution (5 mL) and hexane (5 mL) are added to the mixture. The organic layer is separated, dried, and concentrated in vacuo. The crude product is purified by PTLC (4:1 hexane/EtOAc) to give 2-(2,6-diethyl-phenyl)-5-(ethoxy-phenyl-methyl)-4-methoxy-pyridine. ¹H NMR (CDCl₃) 8.66 (s, 1H), 7.45 (d, 2H), 7.35 (t, 2H), 7.26 (m, 2H), 7.14 (m, 2H), 6.71 (s, 1H), 5.74 (s, 1H), 3.80 (s, 3H), 3.56 (q, 2H), 2.33 (m, 4H), 1.27 (t, 3H), 1.05 (m, 6H).

Example 7

Synthesis of Cyclohexyl-[6-(2,6-diethyl-phenyl)-4-ethoxy-pyridin-3-yl]-methanol

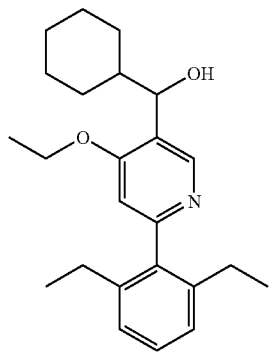

A cyclohexylmagnesium chloride solution (2 M in THF, 1 mL) is slowly added to a solution of 6-(2,6-diethyl-phenyl)-4-ethoxy-pyridine-3-carbaldehyde (prepared as described D above) (142 mg, 0.5 mmol) in ether (2 mL) at 0° C., and the resulting mixture is stirred at room temperature for 30 minutes. Saturated ammonium chloride solution (1 mL) is added to quench the reaction. The organic layer is separated and dried over anhydrous Na₂SO₄. The solvents are removed in vacuo and the crude is purified with PTLC (hexanes/ethyl acetate 3:1) to give cyclohexyl-[6-(2,6-diethyl-phenyl)-4-ethoxy-pyridin-3-yl]-methanol. ¹H NMR: (CDCl₃) 8.40 (s, 1H), 7.28 (t, 1H), 7.16 (d, 2H), 6.76 (S, 1H), 4.54 (t, 1H), 4.08 (q, 2H), 2.32 (m, 4H), 2.05 (br, 1H), 1.75 (m, 4H), 1.40 (m, 4H), 1.05 (m, 10H).

Example 8

Synthesis of 5-(Cyclohexyl-ethoxy-methyl)-2-(2,6-diethyl-phenyl)-4-ethoxy-pyridine Step 1. Synthesis of Racemic Mixture Sodium hydride (60% in mineral oil, 12 mg, 0.3 mmol) is added to a solution of cyclohexyl-[6-(2,6-diethyl-phenyl)-4-ethoxy-pyridin-3-yl]-methanol (74 mg, 0.2 mmol) in DMF (0.5 mL) at room temperature. The resulting mixture is stirred for 30 minutes. Iodoethane (31 mg, 0.2 mmol) is then added and the mixture is stirred for an additional 1 hour. Water (1 mL) is added to the above mixture and the aqueous layer is extracted with ethyl acetate (2×2 mL). The combined organic layers are dried and concentrated in vacuo. The crude product is purified with PTLC (hexanes/ethyl acetate 6:1) to give 5-(cyclohexyl-ethoxy-methyl)-2-(2,6-diethyl-phenyl)-4-ethoxy-pyridine. ¹H NMR: (CDCl₃) 8.50 (s, 1H), 7.28 (t, 1H), 7.12 (d, 2H), 6.70 (S, 1H), 4.45 (d, 1H), 4.03 (q, 2H), 3.34 (m, 2H), 2.34 (m, 4H), 2.02 (br, 1H), 1.73 (m, 4H), 1.21 (m, 4H), 1.05 (m, 13H).

Step 2. Separation of (±) and (−)5-(Cyclohexyl-ethoxy-methyl)-2-(2,6-diethyl-phenyl)-4-ethoxy-pyridine Two isomers are obtained by chiral HPLC separation (Chiralpak AD column, 250*4.6 mm, mobile Phase Hexane/IPA/DEA=500:10:1, flow rate 1.0 mL/min).

Example 9

Synthesis of Cyclopentyl-[6-(2,6-diethyl-phenyl)-4-ethoxy-pyridin-3-yl]-methanol

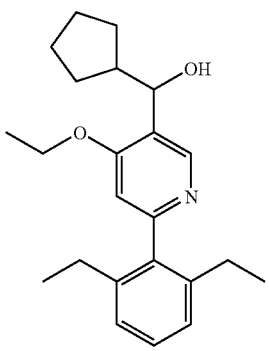

Cyclopentyl magnesium chloride solution (2 M in THF, 2 mL, 4 mmol) is slowly added to a solution of 6-(2,6-diethyl-phenyl)-4-ethoxy-nicotinic acid ethyl ester (prepared by a route analogous to that given in Example 2) (163 mg, 0.5 mmol) in ether (5 mL) at 0° C. The mixture is stirred at room temperature for 30 minutes. Saturated ammonium chloride solution (2 mL) is added and the organic solution is separated. The organic layer is separated and dried over anhydrous $Na_2SO_4$. The solvents are removed in vacuo and the crude is purified with PTLC (hexanes/EtOAc 3:1) to give cyclopentyl-[6-(2,6-diethyl-phenyl)-4-ethoxy-pyridin-3-yl]-methanol. $^1$H NMR: (CDCl$_3$) 8.44 (s, 1H), 7.28 (t, 1H), 7.12 (d, 2H), 6.74 (S, 1H), 4.61 (t, 1H), 4.06 (q, 2H), 2.29 (m, 4H), 1.92 (m, 1H), 1.47 (m, 10H), 1.21 (m, 1H), 1.02 (m, 6H).

Example 10

Synthesis of 4-[6-(2,6-diethyl-phenyl)-4-methoxy-pyridin-3-yl]-heptan-4-ol and 1-[6-(2,6-diethyl-phenyl)-4-methoxy-pyridin-3-yl]-butan-1-ol

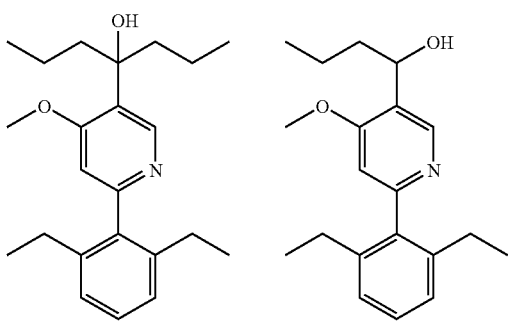

A solution of PrMgCl (2M in ether, 1.5 mL) is added dropwise to a solution of 6-(2,6-diethyl-phenyl)-4-methoxy-nicotinic acid methyl ester (300 mg, 1 mmol) in ether (10 mL) at room temperature. After the mixture is stirred for 2 hours, aqueous NH$_4$Cl solution (10 mL) is added and the organic layer separated. The aqueous layer is extracted with ether (1×) and the organic layers are combined, dried, and concentrated in vacuo. The residue is separated by PTLC purification (4:1 hexane/EtOAc) to give 4-[6-(2,6-diethyl-phenyl)-4-methoxy-pyridin-3-yl]-heptan-4-ol (A) and 1-[6-(2,6-diethyl-phenyl)-4-methoxy-pyridin-3-yl]-butan-1-ol (B). $^1$H NMR (CDCl$_3$) A: 8.51 (s, 1H), 7.30 (t, 1H), 7.16 (d, 2H), 6.77 (s, 1H), 3.87 (s, 3H), 3.04 (s, 1H), 2.33 (m, 4H), 2.03 (m, 2H), 1.83 (m, 2H), 1.19-1.36 (m, 4H), 1.05 (t, 6H), 0.91 (t, 6H). $^1$H NMR (CDCl$_3$) B: 8.49 (s, 1H), 7.30 (m, 1H), 7.15 (m, 2H), 6.77 (s, 1H), 4.91 (m, 1H), 3.87 (s, 3H), 1.81-1.95 (m, 2H), 1.30-1.60 (m, 2H), 1.07 (t, 6H), 0.96 (t, 3H).

Example 11

Synthesis of 2-(2,6-Diethyl-phenyl)-4-methoxy-5-(1-propyl-but-1-enyl)-pyridine

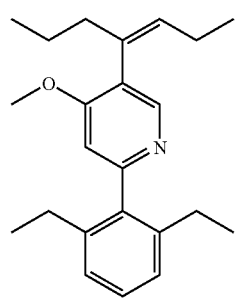

SOCl$_2$ (0.5 mL) is added to a solution of 4-[6-(2,6-diethyl-phenyl)-4-methoxy-pyridin-3-yl]-heptan-4-ol in anhydrous pyridine (5 mL) at 0° C. under nitrogen. The resulting mixture is stirred at room temperature overnight. The volatile materials are removed in vacuo. The residue is treated with water (5 mL), aqueous Na$_2$CO$_3$ (5 mL), and ether. The organic layer is separated and the aqueous is extracted with ether (2×10 mL). The combined extract is washed with brine, dried, and concentrated in vacuo. The crude is purified by PTLC (8:1 hexane/EtOAc) to give 2-(2,6-diethyl-phenyl)-4-methoxy-5-(1-propyl-but-1-enyl)-pyridine. $^1$H NMR (CDCl$_3$) 8.26 (s, 1H), 7.29 (t, 1H), 7.16 (d, 2H), 6.72 (s, 1H), 5.55 (t, 1H), 3.82 (s, 1H), 2.22-2.37 (m, 8H), 1.30 (m, 2H), 0.87-1.10 (m, 9H).

Example 12

Synthesis of 2-(2,6-diethyl-phenyl)-4-methoxy-5-(1-propyl-butyl)-pyridine

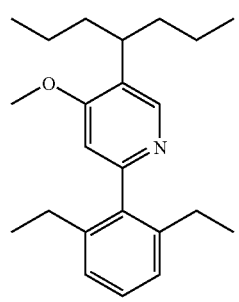

A mixture of 2-(2,6-diethyl-phenyl)-4-methoxy-5 (1-propyl-but-1-enyl)-pyridine (20 mg) and 10% Pd/C (20 mg) in MeOH (1 mL) is hydrogenated at 50 psi overnight. The mixture is filtered through celite and washed with MeOH. The filtrate is concentrated to give 2-(2,6-diethyl-phenyl)-4-methoxy-5-(1-propyl-butyl)-pyridine. $^1$H NMR (CDCl$_3$) 8.29 (s, 1H), 7.26 (d, 1H), 7.13 (d, 2H), 6.71 (s, 1H), 3.81 (s, 3H), 3.00 (m, 1H), 2.37 (m, 4H), 1.65 (m, 4H), 1.23 (m, 4H), 1.07 (t, 6H), 0.86 (t, 6H).

Similar procedures are applied in the synthesis of 4-azetidin-1-yl-2-(2,6-diethyl phenyl)-5-(1-propyl-butyl)-pyridine. ¹H NMR (CDCl₃) 8.15 (s, 1H), 7.26 (t, 1H), 7.11 (d, 2H), 6.14 (s, 1H), 4.10 (m, 4H), 2.84 (m, 1H), 2.35 (m, 6H), 1.62 (m, 4H), 1.26 (m, 4H), 1.07 (t, 6H), 0.88 (t, 6H).

Example 13

Synthesis of 2-(2,6-Diethyl-phenyl)-5-(1-ethoxy-butyl)-4-methoxy-pyridine

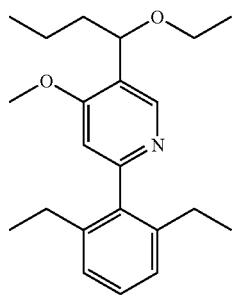

NaH (60% in mineral oil, 12 mg) is added to a solution of 1-[6-(2,6-diethyl-phenyl)-4-methoxy-pyridin-3-yl]-butan-1-ol (24 mg) (see Example 10) in DMF (1 mL). The resulting mixture is stirred at room temperature for 15 minutes. The mixture is then treated with iodoethane (36 mg) and stirred at the same temperature for one hour. Aqueous NH₄Cl solution (5 mL) and EtOAc (5 mL) are added to the mixture. The organic layer is separated, dried, and concentrated in vacuo. The crude is purified by PTLC (4:11 hexane/EtOAc) to give 2-(2,6-diethyl-phenyl)-5-(1-ethoxy-butyl)-4-methoxy-pyridine. ¹H NMR (CDCl₃) 8.54 (s, 1H), 7.29 (t, 1H), 7.14 (d, 2H), 6.74 (s, 1H), 4.68 (m, 1H), 3.83 (s, 3H), 3.41-3.50 (m, 2H), 2.35 (m, 4H), 1.74 (m, 2H), 1.30-1.40 (m, 2H), 1.23 (t, 3H), 1.06 (t, 6H), 0.98 (t, 3H).

Example 14

Synthesis of 4-{1-[6-(2,6-diethyl-phenyl)-4-ethoxy-pyridin-3-yl]-1-propyl-butyl}-morpholine

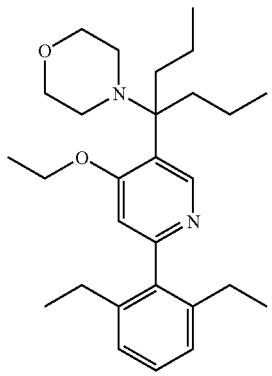

A mixture of 5-(1-chloro-1-propyl-butyl)-2-(2,6-diethyl-phenyl)-4-ethoxy-pyridine (prepared using a synthetic method similar to that given in Example 10) (20 mg, 0.052 mmol) and morpholine (0.5 mL) is heated to 80° C. for 2 hours. Water (1 mL) is added and the aqueous solution is extracted with ethyl acetate (2×2 mL). The combined organic layers are dried and concentrated in vacuo. The crude product is purified with PTLC (hexanes/ethyl acetate 4:1) to give 4-{1-[6-(2,6-diethyl-phenyl)-4-ethoxy-pyridin-3-yl]-1-propyl-butyl}-morpholine. ¹H NMR: (CDCl₃) 8.66 (s, 1H), 7.26 (m, 1H), 7.12 (d, 2H), 6.71 (S, 1H), 4.02 (q, 2H), 3.70 (m, 4H), 2.64 (m, 4H), 2.34 (m, 4H), 1.88 (m, 4H), 1.43 (t, 3H), 1.07 (m, 4H), 1.02 (t, 6H), 0.84 (t, 6H).

Example 15

Synthesis of (S)-[4-Azetidin-1-yl-6-(2,6-diethyl-phenyl)-2-methyl-pyridin-3-ylmethyl]-methyl-(1,2,3,4-tetrahydro-naphthalen-1-yl)-amine Step 1. Synthesis of [4-Azetidin-1-yl-6-(2,6-diethyl-phenyl)-2-methyl-pyridin-3-yl]-methanol

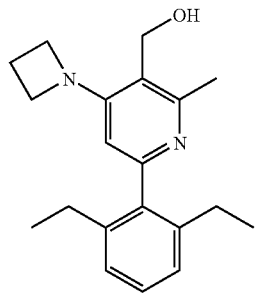

A mixture of 4-chloro-6-(2,6-diethyl-phenyl)-2-methyl-nicotinic acid methyl ester (Example 2, step 1) (500 mg, 1.57 mmol), azetidine hydrochloride (588 mg, 6.29 mmol) and K₂CO₃ (1.08 g, 7.87 mmol) in DMF (5 mL) is heated at 80° C. in a sealed tube overnight. On cooling, water (20 mL) and EtOAc (20 mL) are added. The organic layer is separated and the aqueous layer is extracted with EtOAc (10 mL). The combined organic layer is washed with water, dried, and concentrated to give 4-azetidin-1-yl-6-(2,6-diethyl-phenyl)-2-methyl-nicotinic acid methyl ester as a crude product. A solution of LiAlH₄ (1M in THF, 4.5 mL) is added to a solution of this crude product in THF (5 mL). The reaction mixture is stirred at room temperature overnight, diluted with ether (10 mL), and the reaction quenched with solid Na₂SO₄.10H₂O (1.0 g). The resulting mixture is stirred for 1 hour, filtered through celite and concentrated at reduced pressure. The crude product is purified by PTLC (10% MeOH in CH₂Cl₂) to give the title product. ¹H NMR (CDCl₃) 7.20 (t, 1H), 7.10 (d, 2H), 6.09 (s, 1H), 4.66 (s, 2H), 4.17 (t, 4H), 2.58 (s, 3H), 2.38 (m, 6H), 1.08 (t, 6H).

Step 2. Synthesis of (S)-[4-Azetidin-1-yl-6-(2,6-diethyl-phenyl)-2-methyl-pyridin-3-ylmethyl]-methyl-(1,2,3,4-tetrahydro-naphthalen-1-yl)-amine

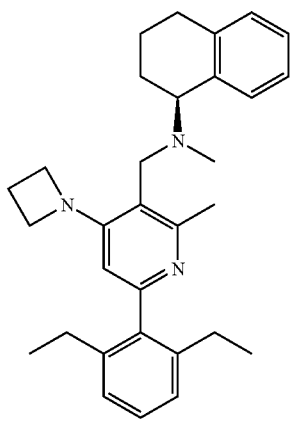

Methanesulfonyl chloride (114 mg, 1 mmol) is added to a solution of [4-azetidin-1-yl-6-(2,6-diethyl-phenyl)-2-methyl-pyridin-3-yl]-methanol (150 mg, 0.5 mmol) and TEA (100 mg) in CH$_2$Cl$_2$ (2 mL). The resulting mixture is stirred at room temperature for 2 hours. The volatile material is removed in vacuo. A mixture of the resulting residue, K$_2$CO$_3$ (138 mg) and (S)-methyl-(1,2,3,4-tetrahydro-naphthalen-1-yl)-amine (240 mg) (prepared by the method given in Example 1) in CH$_3$CN (4 mL) is stirred at room temperature overnight. Hexane (5 ml), ether (5 mL) and water (10 mL) are added to the mixture. The organic layer is separated, washed once with brine, dried (Na$_2$SO$_4$) and concentrated. The crude is purified by PTLC (10% MeOH in CH$_2$CH$_2$) to give (S)-[4-azetidin-1-yl-6-(2,6-diethyl-phenyl)-2-methyl-pyridin-3-yl-methyl]-methyl-(1,2,3,4-tetrahydro-naphthalen-1-yl)-amine. $^1$H NMR (CDCl$_3$) 7.73 (d, 2H), 7.08-7.25 (m, 6H), 6.09 (s, 1H), 4.18 (t, 4H), 3.85 (m, 3H), 2.83 (m, 2H), 2.63 (s, 3H), 2.38 (m, 6H), 2.02 (m, 3H), 1.80 (m, 2H), 1.08 (t, 6H).

Example 16

Synthesis of 4-(3-{1-[6-(2,6-Diethyl-phenyl)-4-ethoxy-pyridin-3-yl]-butoxy}-benzyl)-morpholine Step 1. Synthesis of 1-[6-(2,6-Diethyl-phenyl)-4-ethoxy-pyridin-3-yl]-butan-1-ol

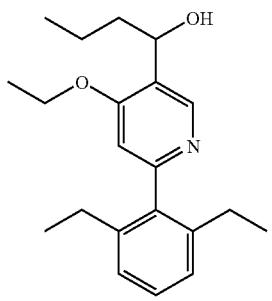

A solution of PrMgCl (2M in ether, 0.15 mL) is added dropwise to a solution of 6-(2,6-diethyl-phenyl)-4-ethoxy-pyridine-3-carbaldehyde (100 mg, 0.59 mmol) in ether (5 mL) at room temperature. After the mixture is stirred for 2 hours, aqueous NH$_4$Cl solution (10 mL) is added and the organic layer is separated. The aqueous layer is extracted with ether (1×) and the organic layers are combined, dried and concentrated in vacuo. The residue is purified by PTLC purification (4:1 hexane/EtOAc) to give 1-[6-(2,6-diethyl-phenyl)-4-ethoxy-pyridin-3-yl]-butan-1-ol. $^1$H NMR (CDCl$_3$) 8.48 (s, 1H), 7.26 (t, 1H), 7.12 (d, 2H), 6.74 (s, 1H), 4.90 (s, 1H), 4.08 (q, 2H), 2.70 (s, 1H), 2.33 (m, 4H), 1.85 (m, 2H), 1.30-1.60 (m, 5H), 0.90-1.05 (m, 9H).

Step 2. Synthesis of 2-(2,6-Diethyl-phenyl)-5-[1-(3-ethoxy-phenoxy)butyl]-4-ethoxy-pyridine

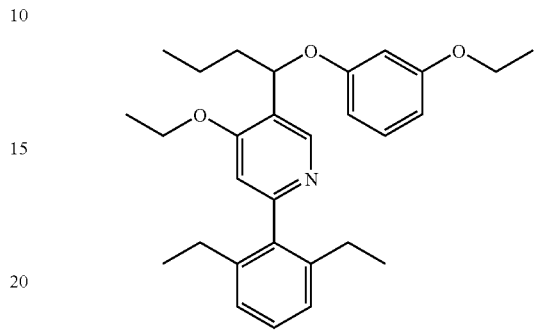

A mixture of 1-[6-(2,6-diethyl-phenyl)-4-ethoxy-pyridin-3-yl]-butan-1-ol (67 mg, 0.20 mmol), 3-ethoxy-phenol (34 mg, 0.25 mmol), triphenylphosphine (65 mg, 0.25 mmol), and DEAD (36 mg, 0.25 mmol) in THF (1 mL) is stirred at room temperature overnight. Aqueous NH$_4$Cl solution (5 mL) and hexane (10 mL) are added to the mixture, and the organic layer is separated. The organic layer is washed with NaHCO$_3$ solution, brine, dried over Na$_2$SO$_4$, and concentrated. The residue is purified by PTLC to give 2-(2,6-diethyl-phenyl)-5-[1-(3-ethoxy-phenoxy)-butyl]-4-ethoxy-pyridine. $^1$H NMR (CDCl$_3$) 8.55 (s, 1H), 7.27 (m, 1H), 7.07-7.14 (m, 3H), 6.73 (s, 1H), 6.43-6.49 (m, 3H), 5.57 (m, 1H), 4.13 (q, 2H), 3.95 (q, 2H), 2.56-2.37 (m, 4H), 1.85-2.05 (m, 2H), 1.40-1.60 (m, 5H), 1.37 (t, 3H), 0.96-1.08 (m, 9H).

Similar procedures are applied in the synthesis of 3-{1-[6-(2,6-diethyl-phenyl)-4-ethoxy-pyridin-3-yl]-butoxy}-benzoic acid methyl ester. $^1$H NMR (CDCl$_3$) 8.55 (s, 1H), 7.55 (m, 2H), 7.30 (m, 2H), 7.05 (m, 3H), 6.75 (s, 1H), 5.63 (m, 1H), 4.05 (q, 2H), 3.85 (s, 3H), 2.20-2.40 (m, 4H), 1.85-2.20 (m, 2H), 1.40-1.60 (m, 5H), 0.90-1.05 (m, 9H).

Step 3. Synthesis of (3-{1-[6-(2,6-Diethyl-phenyl)-4-ethoxy-pyridin-3-yl]-butoxy}-phenyl)-methanol

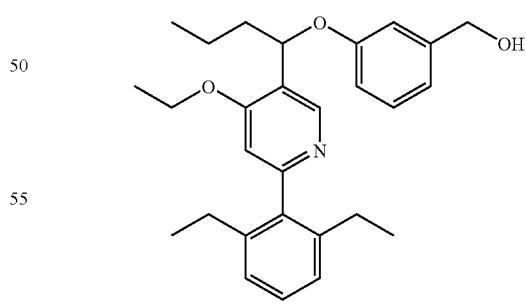

DIBAL-H (1.5 M in Toluene, 0.3 mL) is added dropwise to a solution of 3-{1-[6-(2,6-diethyl-phenyl)-4-ethoxy-pyridin-3-yl]-butoxy}-benzoic acid methyl ester (80 mg, 0.17 mmol) in THF (3 mL) at room temperature. The reaction mixture is stirred for 2 hours, then diluted with ether (5 mL) and treated with Na$_2$SO$_4$.10H$_2$O. The resulting mixture is stirred for one hour and filtered through Celite. Concentration of the filtrate at reduced pressure gives (3-{1-[6-(2,6-diethyl-phenyl)-4-ethoxy-pyridin-3-yl]-butoxy}-phenyl)-methanol. $^1$H NMR (CDCl$_3$) 8.53 (s, 1H), 7.10-7.30 (m, 4H), 6.74-6.90 (m, 4H), 5.60 (m, 1H), 4.51 (s, 2H), 4.13 (, 2l), 2.47 (s, 1H), 2.24-2.37 (m, 4H), 1.80-2.10 (m, 2H), 1.4-1.6 (m, 1H), 0.90-1.05 (m, 9H).

Step 4. Synthesis of 4-(3-{1-[6-(2,6-Diethyl-phenyl)-4-ethoxy-pyridin-3-yl]-butoxy}-benzyl)-morpholine

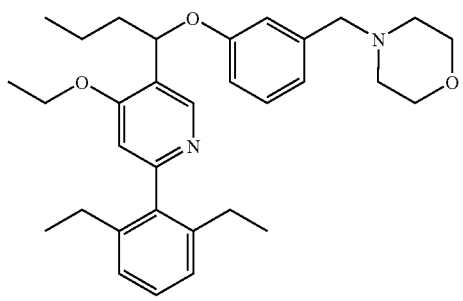

A mixture of (3-{1-[6-(2,6-diethyl-phenyl)-4-ethoxy-pyridin-3-yl]-butoxy}-phenyl)-methanol (50 mg) and SOCl$_2$ (0.2 mL) in CH$_2$Cl$_2$ (1 mL) is stirred at room temperature for one hour. The volatile materials are removed in vacuo. A mixture of the residue, morpholine (60 mg), and K$_2$CO$_3$ (50 mg) in CH$_3$CN (2 mL) is stirred at room temperature overnight. Water (5 mL) and ether (10 mL) are added to the mixture. The organic layer is separated, washed with water, dried and concentrated in vacuo to give 4-(3-{1-[6-(2,6-diethyl-phenyl)-4-ethoxy-pyridin-3-yl]-butoxy}-benzyl)-morpholine. $^1$H NMR (CDCl$_3$) 8.55 (s, 1H), 7.28 (m, 1H), 7.09-7.026 (m, 3H), 6.77-6.91 (m, 2H), 6.74-6.77 (m, 2H), 5.60 (m, 1H), 4.17 (q, 2H), 3.68 (m, 4H), 3.42 (s, 2H), 2.24-2.42 (m, 8H), 1.80-2.10 (m, 2H), 1.40-1.60 (m, 5H), 0.90-1.05 (m, 9H).

Example 17

Synthesis of 3-[6-(2,6-Diethyl-phenyl)-4-ethoxy-2-methyl-pyridin-3-ylmethoxy]-benzoic Acid Methyl Ester Step 1. Synthesis of [6-(2,6-Diethyl-phenyl)-4-ethoxy-2-methyl-pyridin-3-yl]-methanol

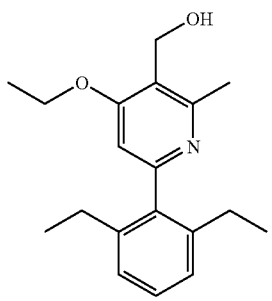

A solution of LiAlH$_4$ (1 M in THF, 20 mL) is added dropwise to a solution of 6-(2,6-diethyl-phenyl)-4-ethoxy-2-methyl-nicotinic acid ethyl ester (2.3 g, 6.7 mmol) in THF (20 mL). The reaction mixture is stirred at room temperature for 4 hours, diluted with ether (10 mL), and quenched with Na$_2$SO$_4$.10H$_2$O (10 g). The resulting mixture is stirred for one hour, filtered through Celite, and concentrated in vacuo to give [6-(2,6-diethyl-phenyl)-4-ethoxy-2-methyl-pyridin-3-yl]-methanol.

Step 2. Synthesis of 3-[6-(2,6-Diethyl-phenyl)-4-ethoxy-2-methyl-pyridin-3-ylmethoxy]-benzoic acid methyl ester

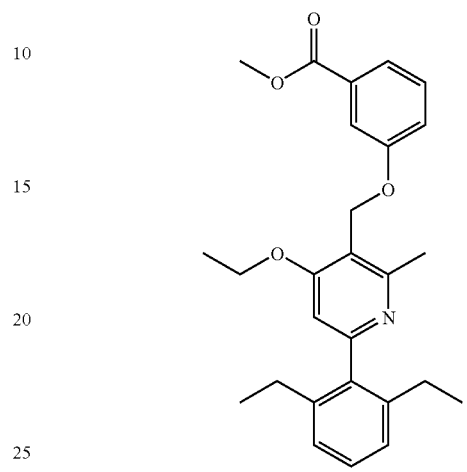

A mixture of [6-(2,6-diethyl-phenyl)-4-ethoxy-2-methyl-pyridin-3-yl]-methanol (1.8 g) and SOCl$_2$ (2 mL) in CH$_2$Cl$_2$ (10 mL) is stirred at room temperature for one hour. The volatile materials are removed in vacuo to give 3-chloromethyl-6-(2,6-diethyl-phenyl)-4-ethoxy-2-methyl-pyridine.

A mixture of the above chloride (800 mg), 3-hydroxy-benzoic acid methyl ester (770 mg), and K$_2$CO$_3$ (2.0 g) in CH$_3$CN (20 mL) is stirred at room temperature overnight. Water (50 mL) and ether (50 mL) are added to the mixture. The organic layer is separated, washed with water, dried and concentrated in vacuo. The crude product is purified by PTLC to give 3-[6-(2,6-diethyl-phenyl)-4-ethoxy-2-methyl-pyridin-3-ylmethoxy]-benzoic acid methyl ester. $^1$H NMR (CDCl$_3$) 7.67-7.77 (m, 2H), 7.15-7.39 (m, 3H), 7.12 (d, 2H), 6.67 (s, 1H), 5.29 (s, 2H), 4.09 (q, 2H), 3.93 (s, 3H), 2.62 (s, 3H), 2.36 (m, 4H), 1.41 (t, 3H), 1.08 (t, 6H).

Example 18

Synthesis of 4-{1-[6-(2,6-Diethyl-phenyl)-4-ethoxy-pyridin-3-yl]-butyl}-morpholine

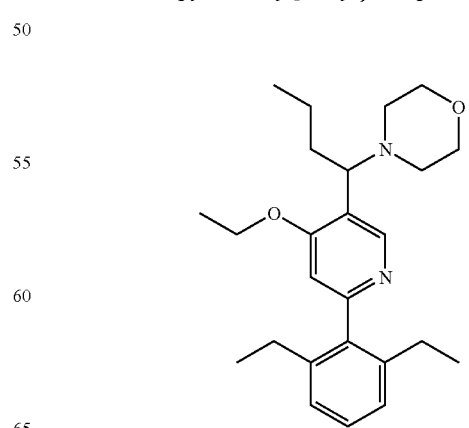

A mixture of 1-[6-(2,6-diethyl-phenyl)-4-ethoxy-pyridin-3-yl]-butan-1-ol (29 mg), and SOCl₂ (0.2 mL) in CH₂Cl₂ (1 mL) is stirred at room temperature for one hour. The volatile materials are removed in vacuo to give 5-(1-chloro-butyl)-2-(2,6-diethyl-phenyl)-4-ethoxy-pyridine.

A mixture of the above chloride, morpholine (50 mg), and K₂CO₃ (50 mg) in CH₃CN (3 mL) is stirred at 50° C. overnight. Water (5 mL) and ether (5 mL) are added to the mixture. The organic layer is separated, washed with water, dried and concentrated in vacuo. The crude product is purified by PTLC to give 4-{1-[6-(2,6-diethyl-phenyl)-4-ethoxy-pyridin-3-yl]-butyl}-morpholine. ¹H NMR (CDCl₃) 8.42 (s, 1H), 7.250 (t, 1H), 7.15 (d, 2H), 6.75 (s, 1H), 4.05 (q, 2H), 3.70 (m, 4H), 2.120-2.60 (m, 9H), 1.70-2.00 (m, 2H), 1.40 (t, 3H), 1.25 (m, 2H), 1.05 (t, 6H), 0.90 (t, 3H).

Example 19

Synthesis of (R)-[6-(2,6-diethyl-phenyl)-4-methoxy-2-methyl-pyridin-3-ylmethyl]-methyl-(1,2,3,4-tetrahydro-naphthalen-1-yl)-amine

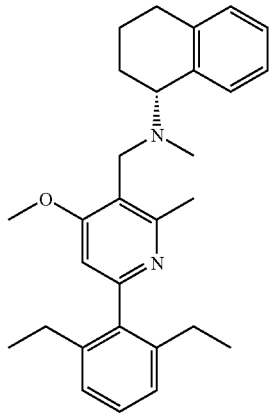

(R)-[6-(2,6-Diethyl-phenyl)-4-methoxy-2-methyl-pyridin-3-ylmethyl]-methyl-(1,2,3,4-tetrahydro-naphthalen-1-yl)-amine is synthesized from 6-(2,6-diethyl-phenyl)-4-ethoxy-2-methyl-pyridin-3-yl]-methanol and (R)-methyl-(1,2,3,4-naphthalen-1-yl)-amine via the procedure given in Example 3, step 4.

¹H NMR (CDCl₃) 7.76 (d, 2H), 7.25 (m, 1H), 7.07-7.20 (m, 5H), 6.63 (s, 1H), 3.90 (m, 1H), 3.81 (5, H), 2.72-2.82 (m, 2H), 2.71 (s, 3H), 2.38 (m, 4H), 2.10 (m, 5H), 1.62-1.95 (m, 2H), 1.07 (m, 6H).

Example 20

Synthesis of 4-{1-[6-(2,6-diethyl-phenyl)-4-ethoxy-pyridin-3-yl]-butyl}-morpholine

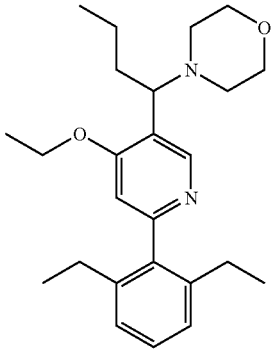

A mixture of 1-[6-(2,6-diethyl-phenyl)-4-ethoxy-pyridin-3-yl]-butan-1-ol (29 mg) and SOCl₂ (0.2 mL) in CH₂Cl₂ (1 ml) is stirred at room-temperature for one hour. The volatile materials are removed in vacuo to give 5-(1-chlorobutyl)-2-(2,6-diethyl-phenyl)-4-ethoxy-pyridine.

A mixture of the above chloride, morpholine (50 mg), and K₂CO₃ (50 mg) in CH₃CN (3 mL) is stirred at 50° C. overnight. Water (5 mL) and ether (5 mL) are added to the mixture. The organic layer is separated, washed with water, dried and concentrated in vacuo. The crude is purified by PTLC to give 4-{1-[6-(2,6-diethyl-phenyl)-4-ethoxy-pyridin-3-yl]-butyl}-morpholine, ¹H NMR (CDCl₃) 8.42 (s, 1H), 7.250 (t, 1H), 7.15 (d, 2H), 6.75 (s, 1H), 4.05 (q, 2H), 3.70 (m, 4H), 2.20-2.60 (m, 9), 1.70-2.00 (m, 2H), 1.40 (t, 3H), 1.25 (m, 2H), 1.05 (t, 6H), 0.90 (t, 3H).

Example 21

Synthesis of (S)-[6-(2,6-diethyl)-2,4-dimethyl-pyridin-3-ylmethyl]-methyl-(1,2,3,4-tetrahydro-naphthalen-1-yl)-amine

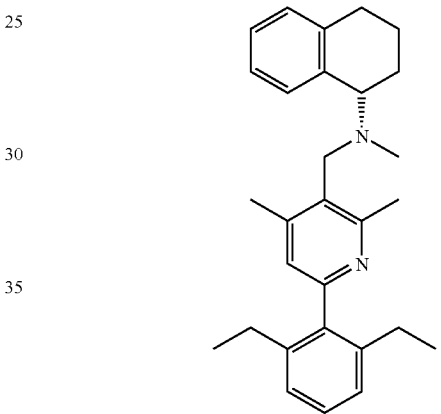

Step 1. Preparation of 6-(2,6-Diethyl-phenyl)-2,4-dimethyl-nicotinic Acid Ethyl Ester A mixture of 4-chloro-6-(2,6-diethyl-phenyl)-2-methyl-nicotinic acid ethyl ester (0.49 g, 1.5 mmol), methylboronic acid (1.8 g, 29 mmol), and tetrakis(triphenylphosphine)palladium (0.086 g, 0.074 mmol) in toluene (30 mL) is stirred for 10 minutes under N₂ atmosphere. A solution of sodium carbonate (6.3 g, 59 mmol) in water (20 mL) is added and the mixture is heated at 100° C. for 48 hours. After cooling to room temperature, the reaction mixture is diluted with water (20 mL) and extracted with EtOAc. The combined extracts are washed with saturated brine, dried (Na₂SO₄), and concentrated in vacuo. The residue is purified by flash chromatography (elution with hexane/EtOAc 20/1) to give 6-(2,6-diethyl-phenyl)-2,4-dimethyl-nicitinic acid ethyl ester as a colorless oil. ¹H NMR (CDCl₃) 7.27 (dd, 1H), 7.12 (d, 2H), 6.96 (s, 1H), 4.47 (q, 2H), 2.60 (s, 3H), 2.38 (s, 3H), 2.36-2.28 (m, 4H), 1.45 (t, 3H), 1.05 (t, 6H).

Step 2. Preparation of [6-(2,6-Diethyl-phenyl)-2,4-dimethyl-pyridin-3-yl]-methanol LiAlH₄ (2.4 mL of 1M solution in THF, 2.44 mmol) is added to a solution of 6-(2,6-diethyl-phenyl)-2,4-dimethyl-nicotinic acid ethyl ester (380 mg, 1.22 mmol) in THF (10 mL) at 0° C. The mixture is stirred for 1 hour at ambient temperature. After quenching with water, the mixture is extracted with EtOAc. The combined extracts are washed with saturated brine, dried (Na₂SO₄), and concentrated to give the crude alcohol as a colorless oil which is used in the next step without further purification. NMR (CDCl₃) 7.26 (t, 1H), 7.13 (d, 2H), 6.93 (s, 1H), 4.82 (s, 2H), 2.68 (s, 3H), 2.46 (s, 3H), 2.37-2.28 (m, 4H), 1.05 (t, 6H).

Step 3. Preparation of [6-(2,6-Diethyl)-2,4-dimethyl-pyridin-3-ylmethyl]-methyl-(1,2,3,4-tetrahydro-naphthalen-1-yl)-amine The crude alcohol is dissolved in CH₂Cl₂ (10 mL) and treated with SOCl₂ (8 mL of 2M solution in CH₂Cl₂). After stirring for 30 minutes at room temperature, the mixture is concentrated to give the crude chloride, which is then dissolved in CH₃CN (25 mL). Potassium carbonate (843 mg, 6.10 mmol) and (S)-methyl-(1,2,3,4-tetrahydro-naphthalen-1-yl)-amine (393 mg, 2.44 mmol) are added to the solution of chloride in CH₃CN. After heating for 18 hours at 85° C., the mixture is extracted with EtOAc. The combined extracts are dried over Na₂SO₄, concentrated, and purified by flash chromatography (elution with Hex/EtOAc 10/1) to give (S)-[6-(2,6-diethyl)-2,4-dimethyl-pyridin-3-ylmethyl]-methyl-(1,2,3,4-tetrahydro-naphthalen-1-yl)-amine as a colorless oil. $^1$H NMR (CDCl₃) 7.62 (d, 1H), 7.29-7.24 (m, 1H), 7.19-7.07 (m, 5H), 6.93 (s, 1H), 4.00-3.97 (m, 1H), 3.86 (s, 2H), 2.88-2.78 (m, 2H), 2.72 (s, 3H), 2.50 (s, 3H), 2.39-2.32 (m, 4H), 2.13-2.2.07 (m, 2H), 2.06 (s, 3H), 1.95-1.76 (m, 2H), 1.06 (t, 6H).

Example 22

Synthesis of (S)-[6-(2,6-Diethyl-phenyl)-4-ethyl-2-methyl-pyridin-3-ylmethyl]-methyl-(1,2,3,4-tetrahydro-naphthalen-1-yl)-amine

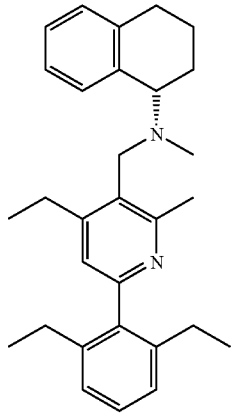

Step 1. Preparation of 6-(2,6-Diethyl-phenyl)-4-ethyl-2-methyl-nicotinic Acid Ethyl Ester A mixture of 4-chloro-6-(2,6-diethyl-phenyl)-2-methyl-nicotinic acid ethyl ester (251 mg, 0.76 mmol), triethylborane (4.6 mL of 1 M solution in hexane, 4.6 mmol), Pd(PPh₃)₄ (26 mg, 0.023 mmol), and Na₂CO₃ (1.27 g, 6 mL of 2M solution in H₂O) in toluene (20 mL) is heated for 48 hours at 95° C. After cooling to room temperature the mixture is diluted with water (10 mL) and extracted with EtOAc. The combined extracts are washed with saturated brine, dried (Na₂SO₄), concentrated, and purified by flash chromatography (elution with hexane/EtOAc 10:1) to yield 159 mg 6-(2,6-diethyl-phenyl)-4-ethyl-2-methyl-nicotinic acid ethyl ester as a colorless oil: $^1$H NMR (CDCl₃) 7.29 (dd, 1H), 7.13 (d, 2H), 7.00 (s, 1H), 4.47 (q, 2H), 2.68 (q, 2H), 2.59 (s, 3H), 2.0-2.3.7 (m, 4H), 1.45 (t, 3H), 1.24 (t, 3H), 1.05 (t, 6H).

Step 2. Preparation of Amine 6-(2,6-Diethyl-phenyl)-4-ethyl-2-methyl-nicotinic acid ethyl ester (159 mg, 0.49 mmol) is converted to (S)-[6-(2,6-Diethyl-phenyl)-4-ethyl-2-methyl-pyridin-3-ylmethyl]-methyl-(1,2,3,4-tetrahydro-naphthalen-1-yl)-amine (142 mg) as a colorless oil as described in Example 21. $^1$H NMR (CDCl₃) 7.62 (d, 1H), 7.30-7.25 (m, 1H), 7.19-7.07 (m, 5H), 6.99 (s, 1H), 4.02-3.97 (m, 1H), 3.86 (s, 2H), 2.89 (q, 2H), 2.88-2.78 (m, 2H), 2.74 (s, 3H), 2.41-2.34 (m, 4H), 2.13-1.75 (m, 4H), 2.07 (s, 3H), 1.25 (t, 3H), 1.06 (t, 6H).

Example 23

Synthesis of (S)-[6-(2,6-Diethyl-phenyl)-4-(3-methoxy-propyl)-2-methyl-pyridin-3-ylmethyl]-methyl-(1,2,3,4-tetrahydro-naphthalen-1-yl)-amine

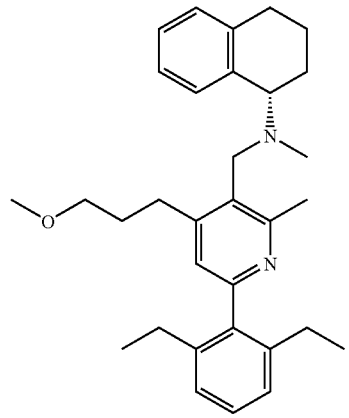

Step 1. Preparation of 6-(2,6-Diethyl-phenyl)-4-(3-methoxy-propyn-1-yl)-2-methyl-nicotinic acid ethyl ester A mixture of 4-bromo-6-(2,6-diethyl-phenyl)-2-methyl-nicotinic ethyl ester (308 mg, 0.82 mmol), methyl propargyl ether (0.69 mL, 8.2 mmol), Pd(PPh₃)₄ (95 mg, 0.082 mmol), and copper iodide (8 mg, 0.041 mmol) in diisopropylamine (8 mL) is heated at 105° C. in a sealed tube. After filtration through celite, the filtrate is concentrated in vacuo and the residue purified by flash chromatography to give 6-(2,6-diethyl-phenyl)-4-(3-methoxy-propyn-1-yl)-2-methyl-nicotinic acid ethyl ester as a yellow oil. $^1$H NMR (CDCl₃) 7.36-7.29 (m, 2H), 7.20-7.15 (m, 2H), 4.47 (q, 2H), 4.32 (s, 2H), 3.41 (s, 3H), 2.62 (s, 3H), 2.38-2.27 (m, 4H), 1.41 (t, 3H), 1.06 (t, 6H).

Step 2. Preparation of 6-(2,6-Diethyl)-4-(3-methoxypropyl)-2-methyl-nicotinic acid ethyl ester and 6-(2,6-Diethyl-phenyl)-2-methyl-4-propyl-nicotinic acid ethyl ester A mixture of 6-(2,6-diethyl-phenyl)-4-(3-methoxy-prop-1-ynyl)-2-methyl-nicotinic acid ethyl ester (160 mg, 0.44 mmol) and 10% Pd/C (40 mg, 25 wt %) in MeOH (20 mL) is hydrogenated for 18 hours at 55 psi (Parr shaker). After filtration through celite, the filtrate is concentrated in vacuo and the residue purified by flash chromatography to give 6-(2,6-diethyl)-4-(3-methoxypropyl)-2-methyl-nicotinic acid ethyl ester and 6-(2,6-diethyl-phenyl)-2-methyl-4-propyl-nicotinic acid ethyl ester.

6-(2,6-Diethyl)-4-(3-methoxypropyl)-2-methyl-nicotinic acid ethyl ester: $^1$H NMR (CDCl₃) 7.26 (t, 1H), 7.12 (d, 2H), 7.00 (s, 1H), 4.43 (q, 2H), 3.37 (t, 2H), 3.30 (s, 3H), 2.72 (t, 2H), 2.59 (s, 3H), 2.38-2.25 (m, 4H), 1.92-1.83 (m, 2H), 1.41 (t, 3H), 1.04 (t, 6H).

6-(2,6-Diethyl-phenyl)-2-methyl-4-propyl-nicotinic acid ethyl ester: $^1$H NMR (CDCl$_3$) 7.25 (t, 1H), 7.18 (d, 2H), 6.99 (s, 1H), 4.43 (q, 2H), 2.62 (q, 2H), 2.60 (s, 3H), 2.38-2.27 (m, 4H), 1.64 (q, 2H), 1.42 (t, 3H), 1.13 (t, 6H), 0.95 (t, 3H).

Step 3. Preparation of (S)-[6-(2,6-Diethyl-phenyl)-4-(3-methoxy-propyl)-2-methyl-pyridin-3-ylmethyl]-methyl-(1,2,3,4-tetrahydro-naphthalen-1-yl)-amine LiAlH$_4$ (0.34 mL of 1M solution in THF, 0.34 mmol) is added to a solution of 6-(2,6-dDiethyl-phenyl)-4-(3-methoxypropyl)-2-methyl-nicotinic acid ethyl ester (64 mg, 0.17 mmol) in THF (6 mL) at 0° C. The mixture is stirred for 1 hour at ambient temperature. After quenching with water the mixture is extracted with EtOAc. The combined extracts are washed with saturated brine, dried (Na$_2$SO$_4$), and concentrated to give the crude alcohol as a colorless oil.

The alcohol is dissolved in CH$_2$Cl$_2$, (6 mL). SOCl$_2$ (0.8 mL of 2 M solution in CH$_2$Cl$_2$, 1.7 mmol) is added and the mixture is stirred for 1 hour at room temperature. After concentration in vacuo, the residue is dissolved in CH$_3$CN (8 mL) and treated with potassium carbonate (117 mg, 0.85 mmol) and (S)-methyl-(1,2,3,4-tetrahydro-naphthalen-1-yl)-amine (55 mg, 0.34 mmol). After heating for 18 hours at 85° C., the mixture is poured onto water and extracted with EtOAc. The combined extracts are dried (Na$_2$SO$_4$), concentrated, and purified by flash chromatography (elution with hexane/EtOAc 10:1) to give (S)-[6-(2,6-diethyl-phenyl)-4-(3-methoxy-propyl)-2-methyl-pyridin-3-ylmethyl]-methyl-(1,2,3,4-tetrahydro-naphthalen-1-yl)-amine as a colorless oil. $^1$H NMR (CDCl$_3$) 7.60 (d, 1H), 7.29-7.24 (m, 1H), 7.18-7.07 (m, 5H), 6.97 (s, 1H), 4.01-3.97 (m, 1H), 3.87 (s, 2H), 3.41 (t, 2H), 3.34 (s, 3H), 2.97-2.88 (m, 2H), 2.84-2.73 (m, 2H), 2.75 (s, 3H), 2.38-2.31 (m, 4H), 2.11-1.95 (m, 2H), 2.06 (s, 3H), 1.90 (q, 2H), 1.94-1.74 (m, 2H), 1.05 (t, 6H).

Example 24

Synthesis of 6-(2,6-Diethyl-phenyl)-3-(1-ethoxy-butyl)-2-methyl-4-propyl-pyridine

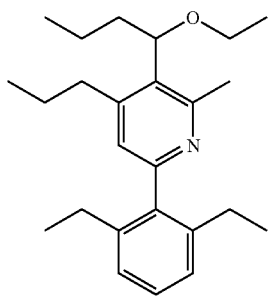

LiAlH$_4$ (0.48 mL of 1M solution in THF, 0.48 mmol) is added to a solution of 6-(2,6-Diethyl-phenyl)-2-methyl-4-propyl-nicotinic acid ethyl ester (40 mg, 0.2 mmol) in THF (3 mL) at room temperature and the mixture is stirred for 18 hours. After quenching with water, the mixture is extracted with EtOAc. The combined extracts are washed with saturated brine, dried (Na$_2$SO$_4$), and concentrated to provide the crude alcohol.

Dimethylsulfoxide (28 mg, 0.36 mmol) is added to a solution of oxalyl chloride (23 mg, 0.18 mmol) in CH$_2$Cl$_2$ (1 mL) at −78° C. The mixture is stirred for 15 minutes. A solution of the crude alcohol in CH$_2$Cl$_2$ (1 mL) is added to this mixture. After stirring for 1 hour at 78° C., triethylamine (61 mg, 0.60 mmol) is added. The resulting mixture is warmed to room temperature, and stirred for 15 minutes. The mixture is quenched with water and extracted with CH$_2$Cl$_2$. The combined extracts are washed with saturated brine, dried (Na$_2$SO$_4$), and concentrated to give the crude aldehyde which is then dissolved in THF (2 mL). N-propyl magnesium chloride (0.12 mL of 2M solution in ether, 0.24 mmol) at 0° C. is added to the solution of aldehyde in THF and the mixture is stirred for 30 minutes at room temperature. After quenching with water the mixture is extracted with EtOAc. The combined extracts are dried (Na$_2$SO$_4$) and concentrated to give the crude sec-alcohol.

A solution of the crude sec-alcohol in DMF (0.5 mL) at 0° C. is added to a suspension of NaH (14 mg, 0.60 mmol) in DMF (2 mL) and the mixture is stirred for 45 minutes at room temperature. Iodoethane (187 mg, 1.2 mmol) is added and the resulting mixture is stirred for 18 hours at room temperature. Water is added and the mixture is extracted with ether. The combined extracts are washed with saturated brine, dried (Na$_2$SO$_4$), concentrated, and chromatographed on silica gel to give 6-(2,6-diethyl-phenyl)-3-(1-ethoxy-butyl)-2-methyl-4-propyl-pyridine as a colorless oil. $^1$H NMR (CDCl$_3$) 7.26 (dd, 1H), 7.11 (d, 2H), 6.91 (s, 1H), 4.79-4.74 (m, 1H), 3.36 (q, 2H), 2.76 (m, 2H), 2.67 (s, 3H), 2.39-2.30 (m, 4H), 2.11-2.03 (m, 1H), 1.70-1.56 (m, 4H), 1.44-1.32 (m, 1H), 1.21 (t, 3H), 1.06-0.96 (m, 12H).

Example 25

Synthesis of 6-(2,6-Diethyl-phenyl)-3-(1-ethoxy-butyl)-4-(3-methoxy-propyl)-2-methyl-pyridine

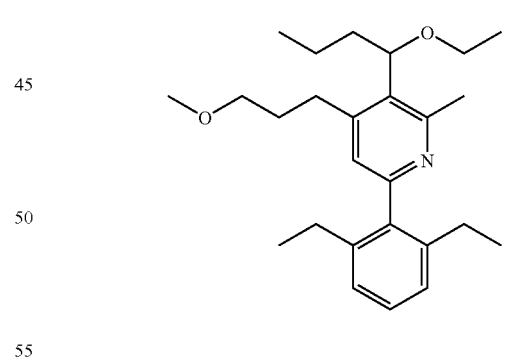

6-(2,6-Diethyl-phenyl)-4-(3-methoxy-prop-1-ynyl)-2-methyl-nicotinic acid ethyl ester (130 mg, 0.36 mmol) is converted to 6-(2,6-diethyl-phenyl)-3-(1-ethoxy-butyl)-4-(3-methoxy-propyl)-2-methyl-pyridine via the methods described in Example 24. $^1$H NMR (CDCl$_3$) 7.26 (dd, 1H), 7.11 (d, 2H), 6.93 (s, 1H), 4.79-4.75 (m, 1H), 3.41 (q, 2H), 3.37 (q, 2H), 3.35 (s, 3H), 2.86 (m, 2H), 2.67 (s, 3H), 2.38-2.29 (m, 4H), 2.09-2.04 (m, 1H), 1.91-1.81 (m, 2H), 1.68-1.61 (m, 2H), 1.40-1.34 (m, 1H), 1.21 (t, 3H), 1.06-0.96 (m, 9H).

Example 26

Synthesis of (S)-4-(6-(2,6-diethyl-phenyl)-2-methyl-3-{[methyl-(1,2,3,4-tetrahydro-napthalen-1-yl)-amino]-methyl}-pyridin-4-yl)-2-methyl-butan-2-ol

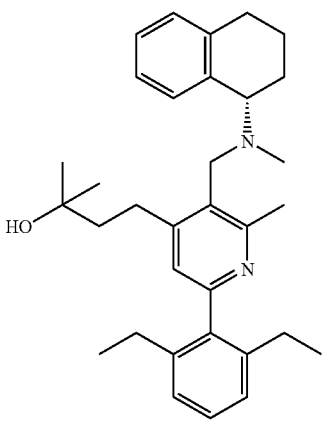

Step 1. Preparation of 4-[3-(tert-butyl-dimethyl-silanyloxy)-3-methyl-but-1-ynyl]-6-(2,6-diethyl-phenyl)-2-methyl-nicotinic acid ethyl ester A mixture of 4-bromo-6-(2,6-diethyl-phenyl)-2-methyl-nicotinic ethyl ester (274 mg, 0.73 mmol), tert-butyl-(1,1-dimethyl-prop-2-ynyloxy)-dimethyl-silane (724 mg, 0.37 mmol), Pd(PPh$_3$)$_4$ (84 mg, 0.082 mmol), and copper iodide (7 mg, 0.037 mmol) in diisopropylamine (8 mL) is heated at 105° C. in a sealed tube. The filtrate is concentrated in vacuo. The residue is purified by flash chromatography to give 4-[3-(tert-butyl-dimethyl-silanyloxy)-3-methyl-but-1-ynyl]-6-(2,6-diethyl-phenyl)-2-methyl-nicotinic acid ethyl ester as a pale yellow oil. $^1$H NMR (CDCl$_3$) 7.38-7.31 (m, 2H), 7.17-7.12 (m, 2H), 4.43 (q, 2H), 2.62 (s, 3H), 2.38-2.25 (m, 4H), 1.56 (s, 6H), 1.44 (t, 3H), 1.06 (t, 6H), 0.83 (s, 9H), 0.15 (s, 6H).

Step 2. Preparation of 4-[3-(tert-Butyl-dimethyl-silanyloxy)-3-methyl-butyl]-6-(2,6-diethyl phenyl)-2-methyl-nicotinic acid ethyl ester A mixture of 4-[3-(tert-butyl-dimethyl-silanyloxy)-3-methyl-but-1-ynyl]-6-(2,6-diethyl-phenyl)-2-methyl-nicotinic acid ethyl ester (318 mg, 0.64 mmol) and 10% Pd/C (32 mg, 10 wt %) in MeOH (30 mL) is hydrogenated for 18 hours at 55 psi (Parr shaker). After filtering through celite, the filtrate is concentrated, and the residue purified by flash chromatography to give 4-[3-(tert-butyl-dimethyl-silanyloxy)-3-methyl-butyl]-6-(2,6-diethyl-phenyl)-2-methyl-nicotinic acid ethyl ester as a colorless oil.

Step 3 Preparation of (S)-[4-[3-(tert-Butyl-dimethyl-silanyloxy)-3-methyl-butyl]-6-(2,6-diethyl-phenyl)-2-methyl-pyridin-3-ylmethyl]-methyl-(1,2,3,4-tetrahydro-naphthalen-1-yl)-amine 4-[3-(tert-Butyl-dimethyl-silanyloxy)-3-methyl-butyl]-6-(2,6-diethyl-phenyl)-2-methyl-nicotinic acid ethyl ester (250 mg, 0.50 mmol) is converted to (S)-[4-[3-(tert-butyl-dimethyl-silanyloxy)-3-methyl-butyl]-6-(2,6-diethyl-phenyl)-2-methyl-pyridin-3-ylmethyl]-methyl-(1,2,3,4-tetrahydro-naphthalen-1-yl)-amine as a pale yellow oil by the procedure described above. $^1$H NMR (CDCl$_3$) 7.64-7.60 (m, 1H), 7.23 (t, 1H), 7.19-7.02 (m, 5H), 6.97 (s, 1H), 4.00-3.94 (m, 1H), 3.84 (s, 2H), 2.98-2.71 (m, 4H), 2.74 (s, 3H), 2.40-2.31 (m, 4H), 2.19-2.08 (m, 2H), 2.07 (s, 3H), 1.91-1.675 (m, 4H), 1.30 (s, 6H), 1.08 (t, 6H), 0.89 (s, 9H), 0.05 (s, 6H).

Step 4. Preparation of (S)-4-(6-(2,6-Diethyl-phenyl)-2-methyl-3-{[methyl-(1,2,3,4-tetrahydro-naphthalen-1-yl)-amino]-methyl}-pyridin-4-yl)-2-methyl-butan-2-ol A solution of (S)-[4-[3-(tert-Butyl-dimethyl-silanyloxy)-3-methyl-butyl]-6-(2,6-diethyl-phenyl)-2-methyl-pyridin-3-ylmethyl]-methyl-(1,2,3,4-tetrahydro-naphthalen-1-yl)-amine (120 mg, 0.20 mmol) in THF (8 mL) is treated with tetrabutylammonium fluoride (1.6 mL of 1M solution in THF, 1.6 mmol) at 0° C. The mixture is stirred for 24 hours at room temperature. Aqueous work-up followed by purification by PTLC yields (S)-4-(6-(2,6-Diethyl-phenyl)-2-methyl-3-{[methyl-(1,2,3,4-tetrahydro-naphthalen-1-yl)-amino]-methyl}-pyridin-4-yl)-2-methyl-butan-2-ol as a colorless oil. $^1$H NMR (CDCl$_3$) 7.65-7.62 (m, 1H), 7.26 (dd, 1H), 7.18-7.06 (m, 5H), 6.96 (s, 1H), 4.02-3.97 (m, 1H), 3.88 (s, 2H), 2.99-2.93 (m, 2H), 2.84-2.2.72 (m, 2H), 2.74 (s, 3H), 2.53 (br s, 1H), 2.39-2.31 (m, 4H), 2.14-2.1.95 (m, 2H), 2.08 (s, 3H), 1.92-1.73 (m, 4H, 1.30 (s, 6H), 1.05 (t, 6H).

Example 27

Synthesis of 4-[6-(2,6-Diethyl-phenyl)-3-(1-ethoxy-butyl)-2-methyl-pyridin-4-yl]-2-methyl-butan-2-ol

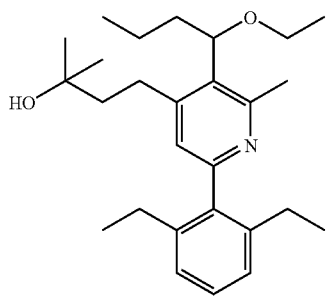

4-[3-(tert-Butyl-dimethyl-silanyloxy)-3-methyl-butyl]-6-(2,6-diethyl-phenyl)-2-methyl-nicotinic acid ethyl ester (125 mg, mmol) (prepared by the method provided in Example 26) is converted to 4-[6-(2,6-diethyl-phenyl)-3-(1-ethoxy-butyl)-2-methyl-pyridin-4-yl]-2-methyl-butan-2-ol (21 mg) by the method described in Example 24. $^1$H NMR (CDCl$_3$) 7.26 (dd, 1H), 7.11 (d, 2H), 6.91 (s, 1H), 4.77 (dd, 1H), 3.44-3.36 (m, 2H), 2.87-2.80 (m, 1H), 2.66 (s, 3H), 2.38-2.29 (m, 4H), 2.12-2.04 (m, 1H), 1.76-1.64 (m, 4H), 1.40-1.24 (m, 2H), 1.28 (s, 6H), 1.23 (t, 3H), 1.04 (t, 6H), 0.98 (t, 3H).

Example 28

Synthesis of 6-(2,6-Diethyl-phenyl)-3-(1-ethoxy-butyl)-2-ethyl-4-methoxy-pyridine

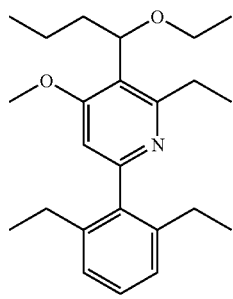

LDA (19 mg, 89 μL of 2 M solution in THF, 0.18 mmol) at −78° C. is added to a solution of 6-(2,6-diethyl-phenyl)-4-methoxy-2-methyl-nicotinic acid methyl ester (27 mg, 0.086 mmol). The mixture is stirred for 30 minutes at 78° C. Methyl iodide (15 μL, 0.24 mmol) is added and the resulting yellow mixture is stirred for 10 minutes at −78° C. After quenching with saturated NH$_4$Cl the mixture is extracted with EtOAc. The combined extracts are dried, concentrated, and purified by flash-chromatography to give 6-(2,6-diethyl-phenyl)-2-ethyl-4-methoxy-nicotinic acid methyl ester.

The ester intermediate is converted to 6-(2,6-diethyl-phenyl)-3-(1-ethoxy-butyl)-2-ethyl-4-methoxy-pyridine by methods provided above. $^1$H NMR (CDCl$_3$) 7.27 (dd, 1H), 7.13 (d, 2H), 6.59 (s, 1H), 4.96 (dd, 1H), 3.80 (s, 3H), 3.48-3.35 (m, 3H), 3.01 (q, 2H), 2.42-2.31 (m, 4H), 2.10-2.00 (m, 1H), 1.76-1.49 (m, 2H), 1.21 (t, 6H), 1.67 (t, 3H), 1.09 (t, 3H), 096 (t, 3H).

Example 29

Synthesis of [6-(2,6-Diethyl-phenyl)-4-methoxy-2-methyl-pyridin-3-yl]-naphthalen-1-yl-methanone

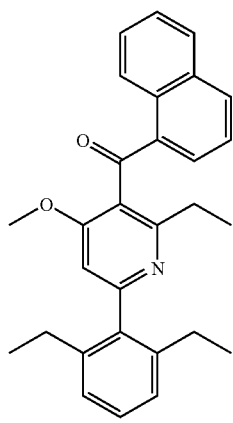

Step 1. Preparation of 4-Iodo-1,2-dihydro-naphthalene

A solution of I$_2$ (14 g, 56 mmol) in ether (100 mL) added slowly at 5° C. over a 50 minute period to a solution of (3,4-dihydro-2H-naphthalen-1-ylidene)-hydrazine (4.5 g, 28 mmol, prepared from α-tetralone and hydrazine) and tent-butyl-tetramethylguanidine (43 g, 251 mmol, prepared from tetramethylurea, triphosgene, and tert-butylamine) in ether (100 mL). After the addition is complete, the mixture is stirred for 30 minutes and the ether (100 mL) is removed. The residue is heated for 1 hour at 90° C. and then cooled to room temperature. The mixture is diluted with ether and washed successively with 1N HCl, aq. Na$_2$S$_2$O$_3$, aq. NaHCO$_3$, and then saturated brine. The organic layers are dried, concentrated, and purified by flash chromatography (elution with hexane only) to give 6.4 g 4-iodo-1,2-dihydro-naphthalene: $^1$H NMR (CDCl$_3$) 7.42 (d, 1H), 7.26-7.14 (m, 2H), 7.01 (d, 1H), 6.83 (t, 1H), 2.84 (t, 2H), 2.39-2.32 (m, 2H).

Step 2. Preparation of [6-(2,6-Diethyl-phenyl)-4-methoxy-2-methyl-pyridin-3-yl]-(3,4-dihydro-naphthalen-1-yl)-methanol N-BuLi (0.33 mL of 1.6 M in hexane, 0.53 mmol) is added dropwise at −78° C. to a solution of 4-iodo-1,2-dihydro-naphthalene (125 mg, 0.49 mmol) in THF (7 ml) and the mixture is stirred for 10 minutes. A solution of the pyridine carboxaldehyde (126 mg, 0.44 mmol) in THF (4 mL) is added dropwise. The mixture is stirred for 10 minutes at −78° C. and then allowed to warm to room temperature before quenching with saturated NH$_4$Cl and dichloromethane. The organic fraction is separated, dried (Na$_2$SO$_4$), concentrated, and chromatographed on silica gel to give [6-(2,6-diethyl-phenyl)-4-methoxy-2-methyl-pyridin-3-yl]-(3,4-dihydro-naphthalen-1-yl)-methanol as a white foam. $^1$H NMR (CDCl$_3$) 7.74 (d, 1H), 7.35-7.14 (m, 6H), 6.90 (s, 1H), 6.12 (d, 1H), 5.64-5.60 (m, 1H), 3.83 (s, 3H), 3.71 (d, 1H), 2.82-2.2.69 (m, 2H), 2.55 (s, 3H), 2.42-2.23 (m, 5H), 1.17-1.02 (m, 6H).

Step 3. Preparation of [6-(2,6-Diethyl-phenyl)-4-methoxy-2-methyl-pyridin-3-yl]-naphthalen-1-yl-methanone Manganese dioxide (390 mg, 4.5 mmol) is added to a solution of [6-(2,6-diethyl-phenyl)-4-methoxy-2-methyl-pyridin-3-yl]-(3,4-dihydro-naphthalen-1-yl)-methanol (63 mg, 0.15 mmol) in dichloromethane (10 mL). The mixture is stirred overnight at room temperature. The mixture is filtered on celite and the filtrate concentrated and chromatographed on silica gel to give [6-(2,6-diethyl-phenyl)-4-methoxy-2-methyl-pyridin-3-yl]-naphthalen-1-yl-methanone. $^1$H NMR (CDCl$_3$) 9.22 (d, 1H), 8.09 (d, 1H), 7.95 (d, 1H), 7.74 (t, 2H), 7.62 (t, 1H), 7.50 (t, 1H), 7.32 (t, 1H), 7.18 (d, 2H), 6.77 (s, 1H), 3.69 (s, 3H), 2.50-2.42 (m, 4H), 2.47 (s, 3H), 1.14 (t, 6H).

Example 30

Synthesis of [6-(2,6-Diethylphenyl)-4-methoxy-2-methyl-pyridin-3-yl]-(1,2,3,4-tetrahydronaphthalene-1-yl)methanone

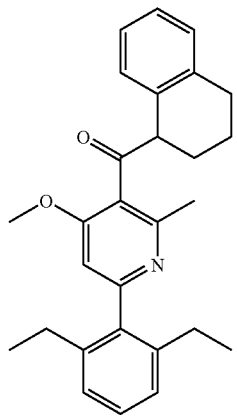

Step 1. Preparation of [6-(2,6-Diethyl-phenyl)-4-methoxy-2-methyl-pyridin-3-yl]-(1,2,3,4-tetrahydro-naphthalen-1-yl)-methanol 10% Palladium on carbon (15 mg) is added to a solution of [6-(2,6-diethyl-phenyl)-4-methoxy-2-methyl-pyridin-3-yl]-(3,4-dihydro-naphthalen-1-yl)-methanol (141 mg, 0.34 mmol, step 2, Example 29) in methanol (25 mL) and the reaction mixture is submitted to hydrogenation (Parr shaker) at 55 psi for 4 hours. The resulting mixture is filtered on celite and the filtrate concentrated in vacuo to give crude [6-(2,6-diethyl-phenyl)-4-methoxy-2-methyl-pyridin-3-yl]-(1,2,3,4-tetrahydro-naphthalen-1-yl)-methanol, which is used in the next step without further purification.

Step 2. Preparation of [6-(2,6-diethylphenyl)-4-methoxy-2-methylpyridin-3-yl]-(1,2,3,4-tetrahydronaphthalene-1-yl)methanone Dimethyl sulfoxide (60 µL, 0.85 mmol) is added at −78° C. to a solution of oxalyl chloride (36 µL, 0.41 mmol) in dichloromethane (2 mL). After stirring at −78° C. for 10 minutes, a solution of [6-(2,6-diethyl-phenyl)-4-methoxy-2-methyl-pyridin-3-yl]-(1,2,3,4-tetrahydro-naphthalen-1-yl)-methanol (138 mg) in dichloromethane (2 mL) is added and the mixture is stirred for 40 minutes more. Triethylamine (0.24 mL, 1.7 mmol) is then added.

After 10 minutes, the mixture is allowed to warm to room temperature and quenched with water. Extraction with dichloromethane, drying ($Na_2SO_4$), and concentration followed by flash chromatography provides [6-(2,6-diethylphenyl)-4-methoxy-2-methylpyridin-3-yl]-(1,2,3,4-tetrahydronaphthalene-1-yl)methanone. $^1$H NMR ($CDCl_3$) 7.30 (dd, 1H), 7.16-7.12 (m, 4H), 7.0 (t, 1H), 6.9 (d, 1H), 6.6 (s, 1H), 4.4 (s, 1H), 3.8 (s, 3H), 2.90-2.76 (m, 2H), 2.43-2.33 (m, 4H), 2.3 (s, 3H), 2.03-1.84 (m, 4H), 1.15-1.04 (m, 6H).

Example 31

Synthesis of 6-(2,6-diethyl-phenyl)-3-[ethoxy-(1,2,3,4-tetrahydro-naphthalen-1-yl)-methyl]-4-methoxy-2-methyl-pyridine

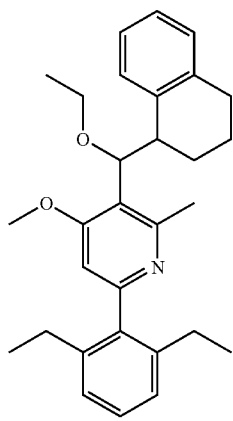

A solution of [6-(2,6-diethyl-phenyl)-4-methoxy-2-methyl-pyridin-3-yl]-(3,4-dihydro-naphthalen-1-yl)-methanol (75 mg, 0.18 mmol) in DMF (1 mL) is added to a suspension of NaH (22 mg, 0.90 mmol) in DMF (5 mL). The mixture is stirred for 1 hour at room temperature. Iodoethane 10.14 mL, 1.8 mmol) is added and the resulting mixture is stirred for 18 hours at room temperature, quenched with water, and extracted with ether. The combined extracts are washed with saturated brine, dried ($Na_2SO_4$) and concentrated. The residue is chromatographed on silica gel to give 6-(2,6-diethyl-phenyl)-3-[ethoxy-(1,2,3,4-tetrahydro-naphthalen-1-yl)-methyl]-4-methoxy-2-methyl-pyridine as a colorless oil. $^1$H NMR ($CDCl_3$) 7.71-7.68 (m, 1H), 7.32-7.26 (m, 1H), 7.21-7.10 (m, 5H), 6.67 (s, 1H), 5.04 (d, 1H), 3.80 (s, 3H), 3.51-3.46 (m, 1H), 3.36-3.19 (m, 2H), 2.89-2.2.72 (m, 2H), 2.75 (s, 3H), 2.47-2.38 (m, 4H), 1.90-1.81 (m, 1H), 1.69-1.59 (m, 2H), 1.41-1.1.32 (m, 1H), 1.17-1.08 (m, 9H).

Example 32

Synthesis of 4-[4-Isopropoxy-5-(5-isopropyl-2-methyl-phenoxy-methyl)-6-methyl-pyridin-2-yl]-5-methyl-1H-indole

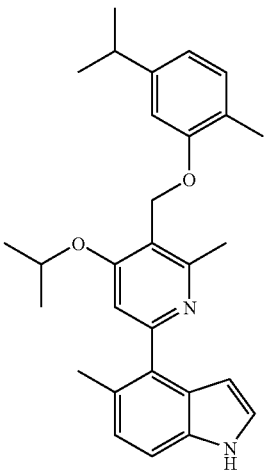

The title compound is prepared from 4,6-dichloro-2-methyl-nicotinic acid ethyl ester and 5-methylindole-4-boronic acid following analogous procedures to those given above.

Example 33

Synthesis of [6-(2,6-Diethyl-phenyl)-4-methanesulfinyl-2-methyl-pyridin-3-ylmethyl]-methyl-(1,2,3,4-tetrahydro-naphthalen-1-yl)-amine Step 1. Synthesis of [6-(2,6-Diethyl-phenyl)-4-methylsulfanyl-pyridin-3-yl]-methanol

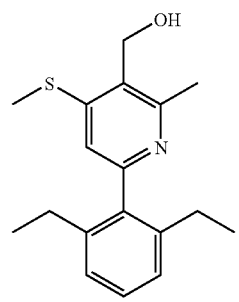

A mixture of 4-chloro-6-(2,6-diethyl-phenyl)-2-methyl-nicotinic acid ethyl ester (200 mg, 0.60 mmol) and sodium thiomethoxide (126 mg, 1.80 mmol) in DMF (5 mL) is heated at 70° C. overnight. After cooling, water (20 mL) is added and the resulting mixture is extracted with EtOAc. The combined extracts are washed with brine, dried over sodium sulfate and concentrated. The residue is chromatographed on silica gel to give 6-(2,6-diethyl-phenyl)-2-methyl-4-methylsulfanyl-nicotinic acid ethyl ester.

A solution of LiAlH$_4$ (1 M in THF, 1 ml, 1 mmol) is added to a solution of 6-(2,6-diethyl-phenyl)-2-methyl-4-methylsulfanyl-nicotinic acid ethyl ester (125 mg) in THF (5 mL) at 0° C. The mixture is warmed to room temperature and stirred for 1 hour, cooled to 0° C. and Na$_2$SO$_4$. 10H$_2$O is added to quench the reaction. The mixture is filtered through Celite and the filtrate is concentrated in vacuo to give [6-(2,6-diethylphenyl)-2-methyl-4-methylsulfanyl-pyridin-3-yl]-methanol.

Step 2. Synthesis of [6-(2,6-Diethyl-phenyl)-4-methanesulfinyl-2-methyl-pyridin-3-yl]-methanol and [6-(2,6-diethyl-phenyl)-4-methanesulfonyl-2-methyl-pyridin-3-yl]-methanol

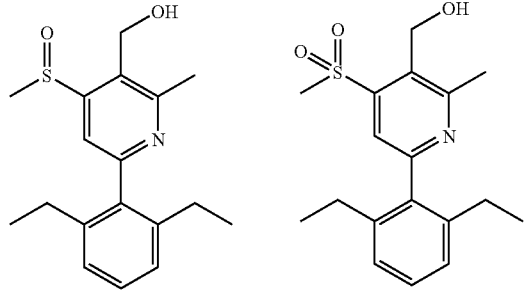

3-Chloroperoxybenzoic acid (77%, 150 mg, 0.67 mmol) is added to a solution of [6-(2,6-diethyl-phenyl)-2-methyl-4-methylsulfanyl-pyridin-3-yl]-methanol (100 mg, 0.33 mmol) at 0° C. The reaction mixture is warmed to room temperature and stirred for 1 hour. The mixture is washed with aqueous Na$_2$CO$_3$, brine, dried over sodium sulfate and concentrated in vacuo and the resulting residue is purified on PTLC (1:1 hexane:EtOAc) to give [6-(2,6-diethyl-phenyl)-4-methanesulfinyl-2-methyl-pyridin-3-yl]-methanol as the more polar product and [6-(2,6-diethyl-phenyl)-4-methanesulfonyl-2-methyl-pyridin-3-yl]-methanol as the less polar product.

Step 3. Synthesis of [6-(2,6-Diethyl-phenyl)-4-methanesulfinyl-2-methyl-pyridin-3-ylmethyl]-methyl-(1,2,3,4-tetrahydro-naphthalen-1-yl)-amine

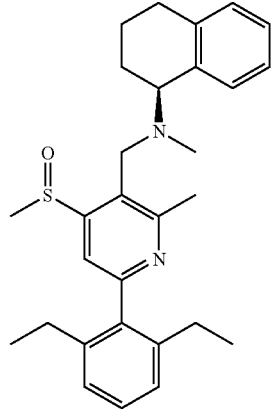

The title compound is obtained from [6-(9,6-diethyl-phenyl)-4-methanesulfinyl-2-methyl-pyridin-3-yl]-methanol in a manner analogous to that described in Example 1F. $^1$H NMR (CDCl$_3$) 7.88 (s, 1H), 7.46-7.36 (m, 2H), 7.26-7.09 (m, 5H), 4.45-4.28 (dd, 2H), 4.09 (m, 1H), 3.29 (s, 3H), 2.80-2.70 (m, 5H), 2.40-1.70 (m, 13H), 1.08 (t, 6H).

Example 34

Synthesis of [6-(2,6-Diethyl-phenyl)-4-methanesulfonyl-2-methyl-pyridin-3-ylmethyl]-methyl-(1,2,3,4-tetrahydro-naphthalen-1-yl)-amine

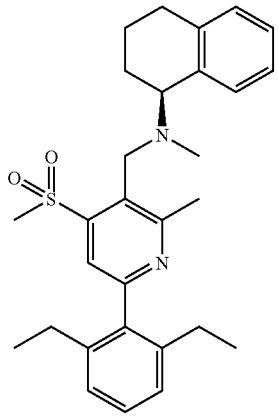

The title compound is obtained from [6-(2,6-diethyl-phenyl)-4-methanesulfonyl-2-methyl-pyridin-3-yl]-methanol in a manner analogous to that described in Example 1F. $^1$H NMR (CDCl$_3$) 7.77 (s, 1H), 7.46 (m, 1H), 7.32 (m, 1H), 7.17-7.05 (m, 5H), 4.37 (dd, 2H), 4.09 (m, 1H), 2.94 (s, 1H), 2.90 (s, 3H), 2.78 (m, 2H), 2.31 (q, 4H), 2.20-1.70 (m, 9H), 1.04 (t, 6H).

Example 35

Synthesis of 6-(2,6-Diethyl-phenyl)-4-isopropoxy-3-(5-isopropyl-2-methyl-phenoxymethyl)-2-methyl-pyridine 1-oxide

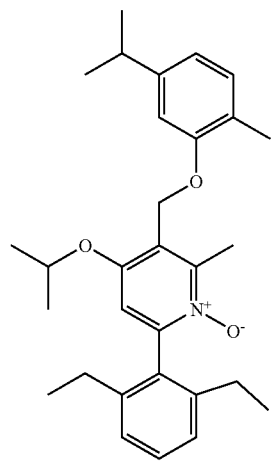

A mixture of 6-(2,6-diethyl-phenyl)-4-isopropoxy-3-(5-isopropyl-2-methyl-phenoxymethyl)-2-methyl-pyridine (250 mg, 0.56 mmol) and 3-chloroperoxy-benzoic acid (77%, 150 mg, 0.67 mmol) in CH$_2$Cl$_2$ (10 mL) is stirred at room temperature for 2 hours. The mixture is diluted with CH$_2$Cl$_2$ (20 mL) and washed with saturated Na$_2$CO$_3$, brine dried over sodium sulfate, and concentrated in vacuo. The residue is purified on PTLC (1:1 hexane EtOAc) to give 6-(2,6-diethyl-phenyl)-4-isopropoxy-3-(5-isopropyl-2-methyl-phenoxymethyl)-2-methyl-pyridine 1-oxide. $^1$H NMR (CDCl$_3$) 7.90 (m, 1H), 7.50-7.04 (m, 3H), 6.90-6.71 (m, 3H), 5.18 (m, 2H), 4.55 (m, 1H), 3.95 (m, 1H), 2.78 (s, 3H), 2.52-2.20 (m, 4H), 2.20 (s, 3H), 1.35 (d, 6H), 1.25 (d, 6H), 1.08 (t, 6H).

Example 36

Synthesis of 4-[6-(2,6-Diethyl-phenyl)-4-isopropoxy-3-(5-isopropyl-2-methyl-phenoxymethyl)-pyridin-2-ylmethyl]-morpholine

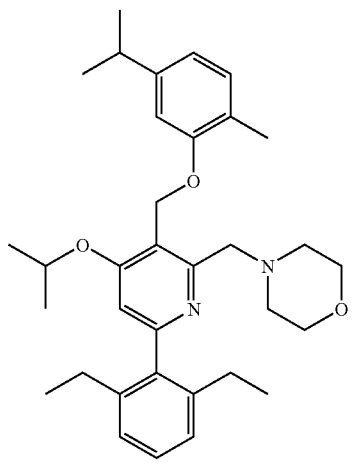

A mixture of 6-(2,6-diethyl-phenyl)-4-isopropoxy-3-(5-isopropyl-2-methyl-phenoxymethyl)-2-methyl-pyridine 1-oxide (150 mL) and POCl$_3$ (5 mL) is heated at 80° C. overnight. After evaporation of excess POCl$_3$ under reduced pressure, the residue is treated with morpholine (5 mL). The mixture is heated at 60° C. for 2 hours and then cooled to room temperature. EtOAc (20 mL) and water (10 mL) are added to the mixture. The organic layer is separated, washed once with brine, dried (Na$_2$SO$_4$) and concentrated. The crude product is purified by PTLC (4:1 hexane:EtOAc) to give 4-[6-(2,6-diethyl-phenyl)-4-isopropoxy-3-(5-isopropyl-2-methyl-phenoxymethyl)-pyridin-2-ylmethyl]-morpholine. $^1$H NMR (CDCl$_3$) 7.25 (m, 1H), 7.20-7.05 (m, 3H), 6.90-6.71 (m, 3H), 5.40 (s, 2H), 4.60 (m, 1H), 3.82 (s, 2H), 3.60 (m, 4H), 2.90 (m, 1H), 2.52-2.28 (m, 8H), 2.20 (s, 3H), 1.35 (d, 6H), 1.25 (d, 6H), 1.08 (t, 6H).

Example 37

Synthesis of (6-(2,6-Diethyl-phenyl)-2-methyl-3-{[methyl-(1,2,3,4-tetrahydro-napthalen-1-yl)-amino]-methyl}-pyridin-4-yl)-pyrrolidin-1-yl-methanone Step 1. Synthesis of (2,6-dichloro-3-hydroxymethyl-pyridin-4-yl)-pyrrolidin-1-yl methanone

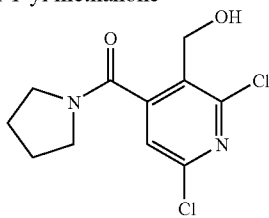

To a solution of 2,6-dichloro-pyridin-4-yl)-pyrrolidin-1-yl-methanone (2.0 g, 8.2 mmol, prepared from commercially available 2,6-dichloro-isonicotinic acid) in THF (50 mL) is added slowly LDA (4 mL, 2M in heptane/THF/ethylbenzene), maintaining an internal temperature below −65° C. The solution is stirred at −78° C. for 1 hour, then treated dropwise ethyl formate (640 mg, 8.6 mmol), again maintaining an internal temperature below −65° C. The resulting mixture is gradually warmed to room temperature and stirred overnight. The mixture is quenched with saturated NH$_4$Cl, extracted with ether and the combined extracts are washed with brine, dried over sodium sulfate and concentrated to give crude 2,6-dichloro-4-(pyrrolidine-1-carbonyl)-pyridine-3-carbaldehyde, which is used directly for the next step.

A mixture of the above aldehyde and sodium borohydride (400 mg, 10 mmol) in EtOH (50 mL) is stirred at room temperature for 1 hour. After evaporation of EtOH, EtOAc (40 mL) and water (40 mL) are added to the residue. The organic layer is separated, washed once with 1 N NaOH, 1N HCl and brine, dried (Na$_2$SO$_4$) and concentrated. The residue is chromatographed on silica gel (1:1 hexane:EtOAc) to give (2,6-dichloro-3-hydroxymethyl-pyridin-4-yl)-pyrrolidin-1-yl-methanone.

Step 2. Synthesis of (2,6-Dichloro-3-{[methyl-(1,2,3,4-tetrahydro-naphthalen-1-yl)-amino]-methyl}-pyridin-4-yl)-pyrrolidin-1-yl-methanone

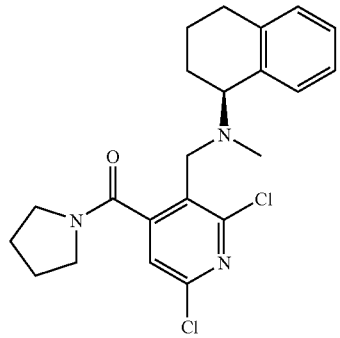

A mixture of (2,6-dichloro-3-hydroxymethyl-pyridin-4-yl)-pyrrolidin-1-yl-methanone (400 mg, 1.45 mmol) and SOCl$_2$ (1 mL) in CH$_2$Cl$_2$ (10 mL) is stirred at room temperature for 1 hour, and then concentrated. The residue is treated with K$_2$CO$_3$ (1.0 g, 7.2 mmol), CH$_3$CN (10 mL) and (S)-methyl-(1,2,3,4-tetrahydro-naphthalen-1-yl)-amine (250 mg, 1.55 mmol). The resulting mixture is stirred at room temperature overnight. EtOAc (50 mL) and water (40 mL) are added to the residue. The organic layer is separated, washed once with brine, dried (Na$_2$SO$_4$) and concentrated. The residue is chromatographed on silica gel (4:1 hexane:EtOAc) to give the title compound.

Step 3. Synthesis of (6-(2,6-diethyl-phenyl)-2-methyl-3-{[methyl-(1,2,3,4-tetrahydro-naphthalen-1-yl)-amino]-methyl}-pyridin-4-yl)-pyrrolidin-1-yl-methanone

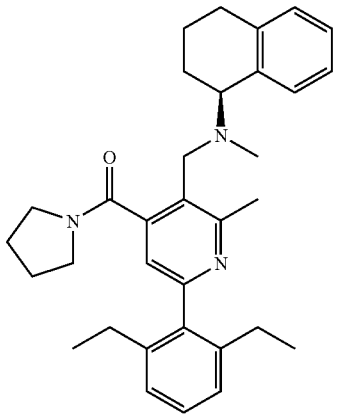

A mixture of (2,6-dichloro-3-{[methyl-(1,2,3,4-tetrahydro-naphthalen-1-yl)-amino]-methyl}-pyridin-4-yl)-pyrrolidin-1-yl-methanone (200 mg, 0.48 mmol), 2,6-diethyl-phenyl boronic acid (85 mg, 0.48 mmol), Na$_2$CO$_3$ (2 M aqueous solution, 0.48 mL, 0.96 mmol), and Pd(PPh$_3$)$_4$ (50 mg) is refluxed in toluene (10 mL) for 18 hours and cooled to room temperature. Methylboronic acid (286 mg, 4.78 mmol), Na$_2$CO$_3$ (2 M aqueous solution, 0.48 mL, 0.96 mmol), and Pd(PPh$_3$)$_4$ (50 mg) are added to the mixture. The resulting mixture is refluxed in toluene for another 18 hours and then cooled to room temperature. Hexane (20 mL) and 1 N NaOH (2 mL) are added. The organic layer is separated, washed with brine, dried over sodium sulfate, and solvent removed. The crude product is purified by flash column (4:1 hexane:EtOAc) to give (6-(2,6-diethyl-phenyl)-2-methyl-3-{[methyl-(1,2,3,4-tetrahydro-naphthalen-1-yl)amino]-methyl}-pyridin-4-yl)-pyrrolidin-1-yl-methanone. $^1$H NMR (CDCl$_3$) 7.51 (m, 1H), 7.28 (m, 1H), 7.14-6.98 (m, 6H), 4.02-3.80 (m, 3H), 3.65 (m, 2H), 3.25 (m, 2H), 2.75-2.34 (m, 5H), 2.10 (m, 4H), 2.05-1.85 (m, 9H), 1.76 (m, 2H), 1.03 (t, 6H).

Example 38

Synthesis of 4-[6-(2,6-Diethyl-phenyl)-3-(2,2-dimethyl-morpholin-4-ylmethyl)-2-methyl-pyridin-4-yloxy]-2-hydroxy-benzamide Step 1. Synthesis of 4-[4-chloro-6-(2,6-diethyl-phenyl)-2-methyl-pyridin-3-ylmethyl]-2,2-dimethyl-morpholine

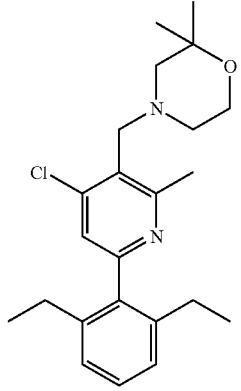

A mixture of 4-chloro-3-chloromethyl-6-(2,6-diethyl-phenyl)-2-methyl-pyridine (310 mg, 1.0 mmol), 2,2-dimethyl-morpholine (150 mg, 1.3 mmol) and K$_2$CO$_3$ (417 mg, 3 mmol) in CH$_3$CN (10 mL) is stirred at room temperature for 16 hours. EtOAc (20 mL) and water (20 ml) are added to the mixture. The organic layer is separated, washed once with brine, dried (Na$_2$SO$_4$) and concentrated to give the title compound.

Step 2. Synthesis of 4-[6-(2,6-diethyl-phenyl)-3-(2,2-dimethyl-morpholin-4-ylmethyl)-2-methyl-pyridin-4-yloxy]-2-hydroxy-benzamide

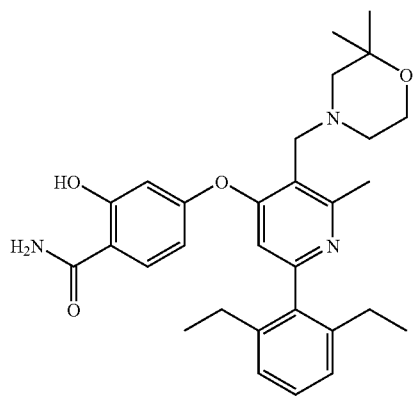

A mixture of 4-[4-chloro-6-(2,6-diethyl-phenyl)-2-methyl-pyridin-3-ylmethyl]-2,2-dimethyl-morpholine (30 mg, 0.08 mmol), 2,4-dihydroxy-benzamide (24 mg, 0.16 mmol), copper powder (10 mg) and K$_2$CO$_3$ (22 mg, 0.16 mmol) in 1-methyl-2-pyrrolidinone (1 mL) is heated at 150° C. overnight. After cooling, EtOAc (10 mL) and water (10 mL) are added to the mixture. The organic layer is separated, washed with brine (3×), dried (Na$_2$SO$_4$) and concentrated. The crude is purified by PTLC (1:1 Hexane/EtOAc) to give to give the title compound. $^1$H NMR (CDCl$_3$) 12.41 (s, 1H), 7.35 (d, 2H), 7.23 (m, 1H), 7.10 (m, 2H), 6.63 (s, 1H), 6.51 (m, 2H), 5.85 (br, 2H), 3.72 (m, 2H), 3.56 (s, 2H), 2.74 (s, 3H), 2.41-2.30 (m, 6H), 1.20 (s, 6H), 1.76 (m, 2H), 1.01 (t, 6H).

Example 39

Synthesis of N-[6-(2,6-Diethyl-phenyl)-3-(5-Isopropyl-2-Methyl-Phenoxy-Methyl)-2-Methyl-Pyridin-4-ylmethyl]-Methanesulfon-amide Step 1. Synthesis of [4-Chloro-6-(2,6-diethyl-phenyl)-2-methyl-pyridin-3-yl]-methanol

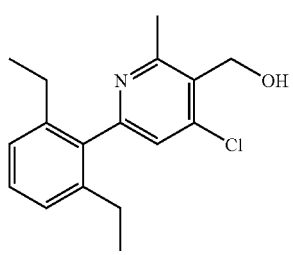

A solution of DIBAL-H (9 mL, 9 mmol, 1M in hexane) is added dropwise to a stirring solution of ethyl ester (1 g, 3 mmol) in CH$_2$Cl$_2$ (10 mL) at −78° C. The mixture is stirred at −78° C. for 2 hours. A saturated Rochelle salt solution (40 mL) is added and warmed to room temperature. The mixture is stirred at room temperature for 3 hours. The organic layer is separated. The aqueous layer is extracted with CH$_2$Cl$_2$ (2×30 mL). The organic layer is washed with brine, dried over sodium sulfate, and evaporated at reduce pressure to give crude product. The crude product is purified by flash column and eluted with 1% methanol in CH$_2$Cl$_2$ to give [4-chloro-6-(2,6-diethyl-phenyl)-2-methyl-pyridin-3-yl]-methanol. $^1$H NMR (CDCl$_3$) 7.28 (m, 1H), 7.16 (m, 3H), 4.92 (d, 2H), 2.74 (s, 3H), 2.34 (m, 4H), 1.07 (t, 6H).

Step 2. Synthesis of 4-Chloro-3-chloromethyl-6-(2,6-diethyl-phenyl)-2-methyl-pyridine

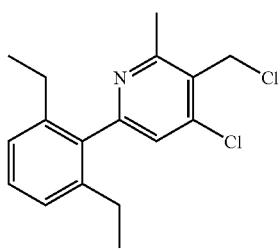

A neat SOCl$_2$ (0.5 mL) is added to a solution of alcohol (625 mg, 2.16 mmol) in CH$_2$Cl$_2$ (15 mL) at room temperature. The mixture is stirred at room temperature for 3 hours. The solvent is removed to dryness in vacuo to give crude 4-chloro-3-chloromethyl-6-(2,6-diethyl-phenyl)-2-methyl-pyridine, which is used for the next step. $^1$H NMR (CDCl$_3$) 7.50 (s, 1H), 7.45 (t, 2H), 7.19 (d, 2H), 4.84 (s, 2H), 3.16 (s, 3H), 2.51 (m, 2H), 2.26 (m, 2H), 1.13 (t, 6H).

Step 3. Synthesis of 4-Chloro-6-(2,6-diethyl-phenyl)-3-(5-isopropyl-2-methyl-phenoxy-methyl)-2-methyl-pyridine

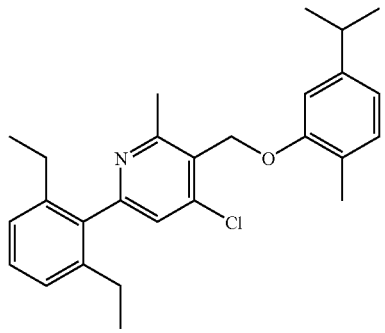

Carvacrol (0.27 mL, 1.78 mmol) and K$_2$CO$_3$ are added to a solution of dichloride (500 mg, 1.62 mmol) in MeCN (10 mL) at room temperature. The mixture is heated to 70° C. for 14 hours. The solvent is removed to dryness in vacuo. This crude product is purified by flash column and eluted with 5% EtOAc in hexane to give 4-chloro-6-(2,6-diethyl-phenyl)-3-(5-isopropyl-2-methyl-phenoxy-methyl)-2-methyl-pyridine. $^1$H NMR (CDCl$_3$) 7.36 (m, 2H), 7.19 (m, 3H), 6.90 (m, 2H), 5.23 (s, 2H), 2.93 (m, 1H), 2.73 (s, 3H), 2.40 (m, 4H), 2.22 (s, 3H), 1.30 (d, 6H), 1.07 (t, 6H).

Step 4. Synthesis of 6-(2,6-Diethyl-phenyl)-3-(5-isopropyl-2-methyl-phenoxymethyl)-2-methyl-isonictinonitrile

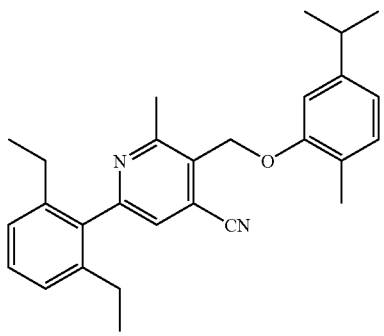

CuCN (915 mg, 10.6 mmol) is added to a solution of chloride (450 mg, 1.06 mmol) in a seal-tube in NMP (3 mL) at room temperature. Argon is bubbled through the solution for 10 minutes. The mixture is heated to 75° C. for 72 hours. H$_2$O (5 mL) and EtOAc (20 mL) are added to the reaction mixture. The organic layer is separated. The organic is washed with brine. The solvent is removed to dryness in vacuo. This crude product is purified by flash column and eluted with 5% EtOAc in hexane to give 6-(2,6-diethyl-phenyl)-3-(5-isopropyl-2-methyl-phenoxymethyl)-2-methyl-isonictino-nitrile. $^1$H NMR (CDCl$_3$) 7.38 (m, 5H), 6.93 (m, 2H), 5.29 (s, 2H), 2.97 (m, 1H), 2.74 (s, 3H), 2.36 (m, 4H), 2.23 (s, 3H), 1.29 (d, 6H), 1.01 (t, 6H).

Step 5. Synthesis of C-[6-(2,6-Diethyl-phenyl)-3-(5-isopropyl-2-methyl-phenoxymethyl)-2-methyl-pyridin-4-yl]-methylamine

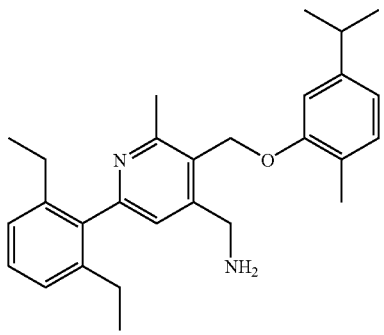

DIBAL-H (4 mL, 4 mmol) is added dropwise to a solution of nitrile (235 mg, 0.557 n mmol) in CH$_2$Cl at −78° C. The mixture is stirred at −78° C. for 3 hours. A saturated Rochelle salt solution (40 ml) is added and warmed to room temperature. The mixture is stirred at room temperature for 3 hours. The organic layer is separated. The aqueous layer is extracted with CH$_2$Cl$_2$ (2×30 mL). The organic layer is washed with brine, dried over sodium sulfate, and evaporated in vacuo to give crude product. The crude product is purified by flash column and eluted with 25% hexane in EtOAc to give C-[6-(2,6-diethyl-phenyl)-3-(5-isopropyl-2-methyl-phenoxymethyl)-2-methyl-pyridin-4yl]-methylamine. $^1$H NMR (CDCl$_3$) 7.26 (m, 2H), 7.19 (m, 3H), 6.90 (m, 2H), 5.19 (s, 2H), 4.47 (m, 2H), 2.92 (m, 1H), 2.70 (s, 3H), 2.38 (m, 4H), 2.20 (s, 3H), 1.32 (d, 6H), 1.03 (t, 6H).

Step 6. Synthesis of N-[6-(2,6-Diethyl-phenyl)-3-(5-isopropyl-2-methyl-phenoxymethyl)-2-methyl-pyridin-4-ylmethyl]-methanesulfonamide

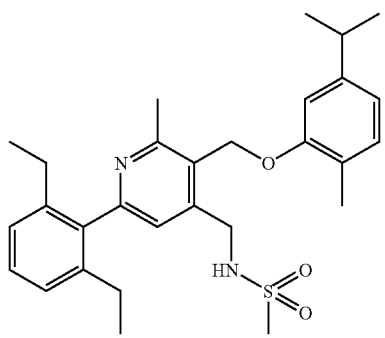

Methanesulfonyl chloride (0.01 mL, 0.12 mmole) is added dropwise to a solution of amine (50 mg, 0.12 mmol) and DIEA (0.04 mL, 0.24 mmol) in CH$_2$Cl$_2$ at 0° C. The mixture is stirred at room temperature for 2 hours. The solvent is removed to dryness in vacuo. The crude product is purified by PTLC and eluted with 1% MeOH in DCM to give N-[6-(2,6-diethyl-phenyl)-3-(5-isopropyl-2-methyl-phenoxymethyl)-2-methyl-pyridin-4-ylmethyl]-methanesulfonamide. $^1$H NMR (CDCl$_3$) 7.29 (m, 3H), 7.18 (m, 2H), 6.86 (m, 2H), 5.20 (s, 2H), 4.50 (d, 2H), 2.90 (m, 1H), 2.83 (s, 3H), 2.71 (s, 3H), 2.38 (m, 4H), 2.01 (s, 3H), 1.29 (d, 6H), 1.07 (t, 6H).

Example 40

Synthesis of 4-[4-(3,3-Dimethyl-Piperidin-1-ylmethyl)-5-(5-Isopropyl-2-Methyl-Phenoxy-Methyl)-6-Methyl-Pyridin-2-Yl]-5-Isopropyl-1H-Indazole Step 1. Synthesis of 4-Chloro-6-(6-isopropyl-2-methyl-3-nitro-phenyl)-2-methyl-nicotinic acid ethyl ester

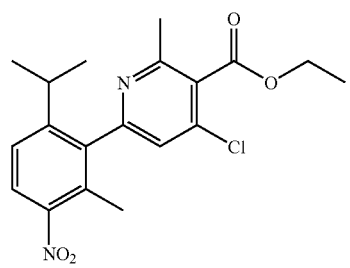

Nitro boronic acid (4.4 g, 19.2 mmol), Na$_2$CO$_3$ (4.1 g, 38.4 mmol) and Pd(PPh$_3$)$_4$ (500 mg) are added to a degassed solution (toluene 80 mL, H$_2$O 20 mL and EtOH 5 mL) of dichloride (3 g, 12.8 mmol) at room temperature. The mixture is heated to 110° C. for 14 hours. The organic layer is separated. The aqueous layer is extracted with EtOAc (2×65 mL). The organic layer is washed with brine, dried over sodium sulfate, and evaporated in vacuo to give the crude product. The crude product is purified by flash column and eluted with 5% EtOAc in hexane to give 4-chloro-6-(6-isopropyl-2-methyl-3-nitro-phenyl)-2-methyl-nicotinic acid ethyl ester. $^1$H NMR (CDCl$_3$) 7.90 (d, 1H), 7.28 (d, 1H), 7.16 (s, 1H), 4.42 (q, 2H), 2.89 (s, 3H), 2.62 (s, 3H), 2.15 (m, 1H), 1.43 (t, 3H), 1.1.3 (t, 6H).

Step 2. Synthesis of 6-(3-Amino-6-isopropyl-2-methyl-phenyl)-4-chloro-2-methyl-nicotinic Acid Ethyl Ester

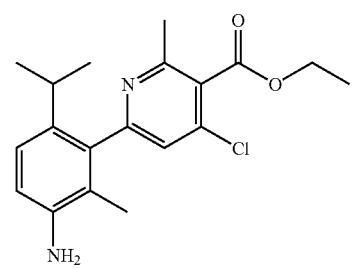

A solution of SnCl$_2$ (7.2 g, 31.8 mmol) in concentrated HCl (20 mL) is added dropwise to a solution of nitro chloride (4.0 g, 10.6 mmol) in EtOH (50 mL) at 0° C. The mixture is warmed to room temperature and stirred for 14 hours. The solvent is removed to dryness in vacuo. Ice (300 g) and 50% NaOH (70 mL) is slowly added and the mixture is stirred for 30 minutes. The mixture is extracted with DCM (4×50 mL). The organic layer is washed with brine, dried over sodium sulfate, and evaporated in vacuo to give crude product. The crude product is purified by flash column and eluted with 1% MeOH in DCM to give 6-(3-Amino-6-isopropyl-2-methyl-phenyl)-4-chloro-2-methyl-nicotinic acid ethyl ester. $^1$H NMR (CDCl$_3$) 7.15 (s, 1H), 7.07 (d, 1H), 6.77 (d, 1H), 4.51 (q, 2H), 3.56 (b, 2H), 2.62 (s, 3H), 2.37 (m, 1H), 1.79 (s, 3H), 1.46 (t, 3H), 1.08 (t, 6H).

Step 3. Synthesis of 3-(4-Chloro-5-ethoxycarbonyl-6-methyl-pyridin-2-yl)-4-isopropyl-2-methyl-benzenediazonium, Tetrafluoroborate

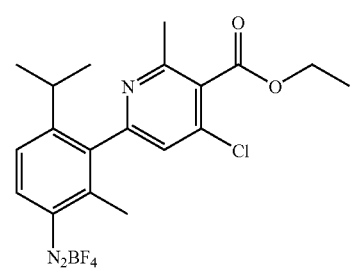

A solution of NaNO$_2$ (5.2 g, 7.5 mmol) in H$_2$O (5 mL) is added dropwise to a solution of amine (2.5 g, 7.3 mmol) and HBF$_4$ in H$_2$O (20 mL) at 0° C. The mixture is warmed to room temperature and stirred for 1 hour. The mixture is neutralized to pH=8.5 by 10 N NaOH. The resulting solid is collected by filtration, washed with H$_2$O (100 mL) and cold ether (50 mL), and dried to give the crude product, which is used for the next step.

Step 4. Synthesis of 4-Chloro-6-(5-isopropyl-1H-indazol-4-yl)2-methyl-nicotinic Acid Ethyl ester

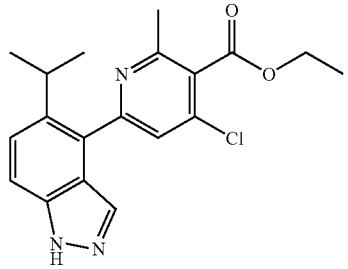

KOAc (746 mg, 7.6 mmol) and 18-Crown-6 (50 mg, 5% mmol) are added to a solution of diazonium salt (1.7 g, 3.8 mmol) in CHCl₃ (20 mL) at room temperature. The mixture is stirred at room temperature for 2 hours. H₂O and DCM are added to the mixture. The organic layer is separated. The aqueous layer is extracted with DCM (2×20 mL). The organic phase is washed with brine, dried over sodium sulfate, and evaporated in vacuo to give crude product. The crude product is purified by flash column and eluted with 0.7% MeOH in DCM to give 4-chloro-6-(5-isopropyl-1H-indazol-4-yl)2-methyl-nicotinic acid ethyl ester ¹H NMR (CDCl₃) 7.81 (s, 1H), 7.57 (d, 1H), 7.52 (d, 1H), 4.57 (q, 2H), 3.13 (m, 1H), 2.68 (s, 3H), 1.50 (t, 3H), 1.26 (t, 6H).

Step 5. Synthesis of 4-iodo-6-(5-isopropyl-1H-indazol-4-yl) 2-methyl-nicotinic acid ethyl ester

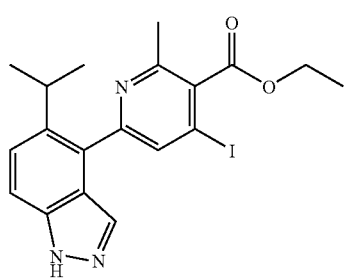

KI (1.8 g, 10.9 mmol) and HI (0.5 mL) are added to a solution of indazole (780 mg, 2.2 mmol) in 2-butanone (10 mL) at room temperature. The mixture is heated to 90° C. for 4 hours. Brine and DCM are added to the mixture. The organic layer is separated. The aqueous layer is extracted with DCM (2×20 mL). The combined organic layers are washed with brine, dried over sodium sulfate, and evaporated in vacuo to give crude product. The crude product is purified by flash column and eluted with 1% MeOH in DCM to give 4-iodo-6-(5-isopropyl-1H-indazol-4-yl)-2-methyl-nicotinic acid ethyl ester. ¹H NMR (CDCl₃) 7.80 (s, 1H), 7.50 (d, 1H), 7.52 (m, 2H), 7.38 (s, 1H), 4.56 (q, 2H), 3.10 (m, 1H), 2.67 (s, 3H), 1.51 (t, 3H), 1.25 (t, 6H).

Step 6. Synthesis of [4-iodo-6-(5-isopropyl-1H-indazol-4-yl) 2-methyl-pyridin-3-yl]-methanol

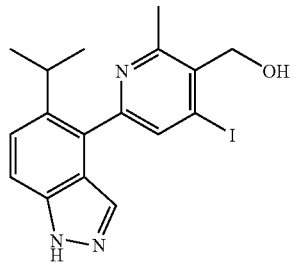

DIBAL-H (4 mL, 6.1 mmol, 1.5 M in hexane) is added dropwise to a solution of indazole ethyl ester (640 mg, 1.57 mmol) in DCM (10 mL) at −78° C. The mixture is stirred at −78° C. for 1 hour. Saturated Rochelle salt solution (40 mL) is added and the mixture is warmed to room temperature and stirred for 3 hours. The organic layer is separated and the aqueous layer is extracted with CH₂Cl₂ (2×30 mL). The combined organic layers are washed with brine, dried over sodium sulfate, and evaporated at reduce pressure to give crude product. The crude product is purified by flash column and eluted with 2-5% MeOH in DCM to give [4-iodo-6-(5-isopropyl-1H-indazol-4-yl)2-methyl-piridin-3-yl]-methanol. ¹H NMR (CDCl₃) 7.86 (s, 1H), 7.58 (d, 1H), 7.53 (m, 2H), 7.18 (s, 1H), 4.90 (m, 2H), 3.34 (m, 1H), 3.08 (m, 1H), 2.74 (s, 3H), 1.28 (t, 6H).

Step 7. Synthesis of 4-(5-Chloromethyl-4-iodo-6-methyl-pyridin-2-yl)-5-isopropyl-1H-indazole

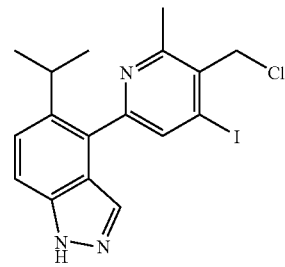

Neat SOCl₂ (1 ml) is added dropwise to a solution of indazole alcohol (640 mg, 1.57 mmol) in DCM (10 mL) at room temperature. The mixture is stirred at room temperature for 1 hour. The solvent is removed to dryness in vacuo to give crude product, which is used for the next step.

Step 8. Synthesis of 4-[4-iodo-5-(5-isopropyl-2-methyl-phenoxymethyl)-6-methyl-pyridin-2-yl)-5-isopropyl-1H-indazole

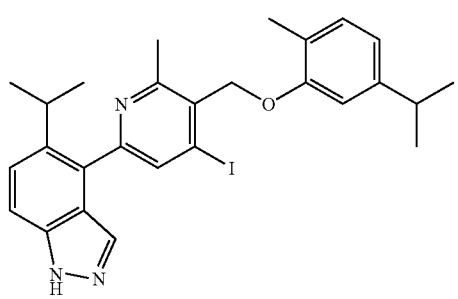

Carvacrol (0.6 mL, 4 mmol) and K$_2$CO$_3$ (559 mg, 4 mmol) are added to a solution of chloride (659 mg, 1.54 mmol) in MeCN (10 mL) at room temperature. The mixture is heated to 70° C. for 14 hours. The solvent is removed to dryness in vacuo. This crude product is purified by flash column and eluted with 1% MeOH in DCM to give 4-[4-iodo-5-(5-isopropyl-2-methyl-phenoxymethyl)-6-methyl-pyridin-2-yl)-5-isopropyl-1H-indazole.

Step 9. Synthesis of 5-Isopropyl-4-[5-(5-isopropyl-2-methyl-phenoxymethyl)-6-methyl-4-vinyl-pyridin-2-yl)-1H-indazole

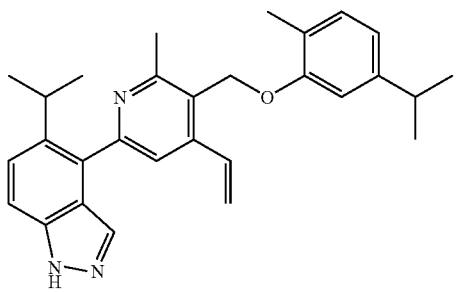

Tributyl(vinyl)tin (0.4 mL, 1.44 mmol) is added to a solution of iodide (390 mg, 0.72 mmol) and Pd(PPh$_3$)$_4$ (100 mg) in DMF (5 mL) at room temperature. The mixture is heated to 100° C. for 3 hours. The solvent is removed to dryness in vacuo. This crude product is purified by flash column and eluted with 1% MeOH in DCM to give 5-isopropyl-4-[5-(5-isopropyl-2-methyl-phenoxymethyl)-6-methyl-4-vinyl-pyridin-2-yl)-1H-indazole.

Step 10. Synthesis of 6-(5-Isopropyl-1H-indazol-4-yl)-3-(5-isopropyl-2-methyl-phenoxy-methyl)-2-methyl-pyridin-4-carbaldehyde

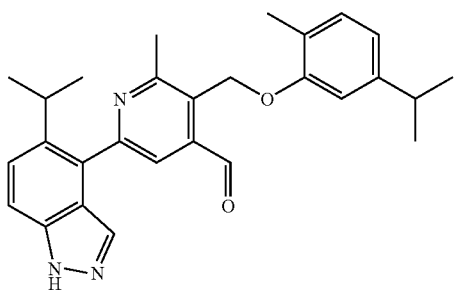

NaIO$_4$ (230 mg, 1.08 mmol) and OSO$_4$ (1 drop, 2.5% wt. in H$_2$O) are added to a solution of vinyl indazole (190 mg, 0.43 mmol) in THF (8 mL) and 120 (2 mL) at room temperature. The mixture is heated to 70° C. for 14 hours. The solvent is removed to dryness in vacuo to give crude 6-(5-isopropyl-1H-indazol-4-yl)-3-(5-isopropyl-2-methyl-phenoxymethyl)-2-methyl-pyridin-4-carbaldehyde.

Step 10. Synthesis of 4-[4-(3,3-Dimethyl-piperidin-1-ylmethyl)-5-(5-isopropyl-2-methyl-phenoxymethyl)-6-methyl-pyridin-2-yl]-5-isopropyl-1H-indazole

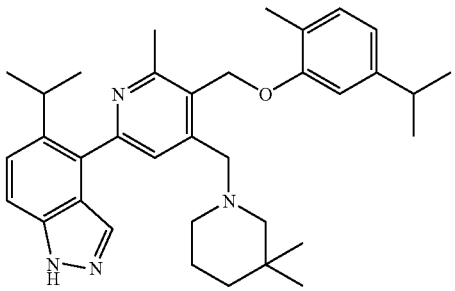

3,3-Dimethyl-piperidine (10 mg, 0.06 mmol) is added to a solution of aldehyde (10 mg, 0.02 mmol) in DCM (2 mL) at room temperature and stirred for 30 minutes. Then, Na(OAc)$_3$BH (14 mg, 0.06 mmol) and HOAc (2 drops) are added to the reaction mixture and stirred for 1 hour at room temperature. DCM and H$_2$O are added to the mixture. The organic layer is separated, washed with brine. The solvent is removed to dryness in vacuo. The crude product is purified by PTLC and eluted with 2% MeOH in DCM to yield 4-[4-(3,3-dimethyl-piperidin-1-ylmethyl)-5-(5-isopropyl-2-methyl-phenoxymethyl)-6-methyl-pyridin 2-yl]-5-isopropyl-1H-indazole. $^1$H NMR (CDCl$_3$) 7.65 (m, 3H), 7.52 (s, 1H), 7.05 (d, 1H), 6.97 (s, 1H), 6.75 (d, 1H), 5.36 (s, 2H), 3.56 (s, 2H), 3.07 (m, 1H), 2.90 (q, 1H), 2.66 (s, 3H), 2.33 (m, 2H), 2-18 (s, 3H), 2.10 (m, 2H), 1.55 (m, 2H), 1.2 (m, 16H), 0.90 (s, 6H).

Example 41

Synthesis Of [6-(2,6-Diethyl-Phenyl)-4-Isopropoxy-Methyl-Pyridin-3-yl]-(7-Trifluoromethyl-3,4-Dihydro-2H-Quinolin-1-yl)-Methanone Step 1. Synthesis of 4-Chloro-6-(2,6-diethyl-phenyl)-2-methyl-nicotinic acid

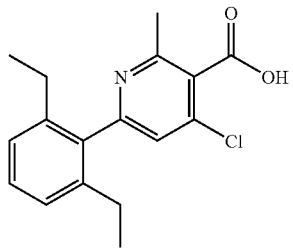

NaOH (360 mg, 9 mmol) is added to a solution of chloro ester (500 mg, 1.5 mmol) in ethyl glycol at room temperature. The mixture is heated to 100° C. for 14 hours. The solvent is removed in vacuo. H$_2$O is added and acidified with 6 N HCl to pH=4. The aqueous layer is extracted with DCM (3×25 mL). The combined organic layer is washed with brine, dried over sodium sulfate, and evaporated in vacuo to give the crude product, which is used for the next step.

Step 2. Synthesis of 4-Chloro-6-(2,6-diethyl-phenyl)-2-methyl-nicotinoyl chloride

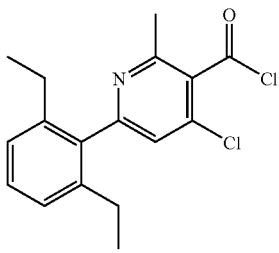

Chloro acid (40 mg, 0.13 mmol) is added to SOCl$_2$ (2 mL) at room temperature. The mixture is heated to 60° C. for 2 hours. The solvent is removed to give crude product in vacuo. The crude product is used for the next step.

Step 3. Synthesis of [4-Chloro-6-(2,6-diethyl-phenyl)-2-methyl-pyridin-3-yl]-(7-trifluoromethyl-3,4-dihydro-2H-quinolin-1-yl)-methanone

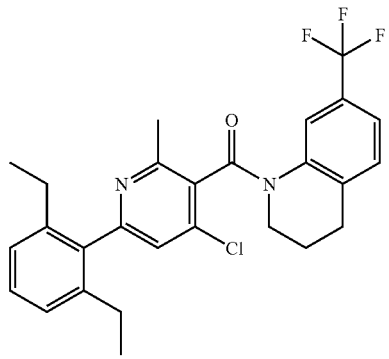

7-Trifluoromethyl-1,2,3,4-tetrahydro-quinoline (14 mg, 0.26 mmol) is added to a solution of acyl chloride (43 mg, 0.13 mmol) and DIEA (34 mg, 0.26 mmol) in THF at room temperature. The mixture is heated to 50° C. for 14 hours. The solvent is removed to dryness. The crude product is purified by PTLC and eluted with 5% EtOAc in hexane to give [4-chloro-6-(2,6-diethyl-phenyl)-2-methyl-pyridin-3-yl]-(7-trifluoro-methyl-3,4-dihydro-2H-quinolin-1-yl)methanone.

Step 4. Synthesis of [6-(2,6-Diethyl-phenyl)-4-isopropoxy-2-methyl-pyridin-3-yl]-(7-trifluoromethyl-3,4-dihydro-2H-quinolin-1-yl)-methanone

A solution of chloride (48 mg, 0.1 mmol) in isopropanol (1 mL) is added to a solution of NaH (15 mg) in isopropanol (3 mL) at room temperature. The mixture is heated to 50° C. for 14 hours. The solvent is removed to dryness. The crude product is purified by PTLC and eluted with 5% EtOAc in hexane to give [6-(2,6-diethyl-phenyl)-4-isopropoxy-2-methyl-pyridin-3-yl]-(7-trifluoromethyl-3,4-dihydro-2H-quinolin-1-yl)-methanone. $^1$H NMR (CDCl$_3$) 7.34 (m, 3H), 7.17 (m, 4H), 4.42 (m, 1H), 2.96 (m, 2H), 2.52 (s, 4H), 2.17 (m, 4H), 1.34 (m, 2H), 1.04 (m, 8H).

Example 42

Synthesis OF 4-[6-[6-(2,6-Diethyl-Phenyl)-3-(5-Isopropyl-2-Methyl-Phenoxymethyl)-2-Methyl-Pyridin-4-ylmethyl]-1-Hydroxy-Cyclohexanecarboxylic Acid Amide Synthesis of 4-[6-(2,6-diethyl-phenyl)-3-(5-isopropyl-2-methyl-phenoxymethyl)-2-methyl-pyridin-4-ylmethyl]-1-hydroxy-cyclohexanecarboxylic acid amide is based on a similar procedure of synthesis of 4-[4-(3,3-dimethyl-piperidin-1-ylmethyl)-5-(5-isopropyl-2-methyl-phenoxy-methyl)-6-methyl-pyridin-2-yl]-5-isopropyl-1H-indazole. $^1$H NMR (CDCl$_3$) 7.31 (m, 3H), 7.16 (m, 3H), 6.92 (m, 1H), 5.30 (s, 2H), 5.26 (s, 2H), 3.64 (m, 2H), 2.95 (m, 1H), 2.71 (m, 7H), 2.37 (m, 4H), 1.59 (m, 4H), 1.25 (d, 6H), 1.08 (t, 6H).

Example 43

Synthesis of (S)-(6-Chloro-4-Cyclopentyloxy-2-Methyl-Pyridin-3-Ylmethyl)-Methyl-(1,2,3,4-Tetrahydro-Naphthalen-1-Yl)-Amine Step 1. Synthesis of 4,6-Dichloro-2-methyl-nicotinic acid

A mixture of 4,6-dichloro-2-methyl-nicothinic acid ethyl ester (10 g, 42.7 mmol), tetrabutylammonium hydroxide (1.0 M solution in water, 0.4 mL), and water (350 mL) is stirred for 5 hours at 85° C. The reaction is cooled to ambient temperature and acidified to pH=2 with concentrated aqueous hydrochloric acid. The product is extracted with methylene chloride (4×150 mL). The combined organic extracts are washed with water (1×100 mL) and brine (1×100 mL), dried (Na$_2$SO$_4$), and concentrated in vacuo to afford 4,6-dichloro-2-methyl-nicotinic acid as colorless oil.

Step 2. Synthesis of 4,6-Dichloro-2-methyl-nicotinic acid cyclopentane ester

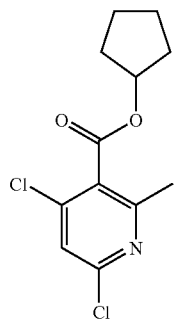

To a solution of 4,6-dichloro-2-methyl-nicotinic acid (8.5 g, 41.3 mmol) in anhydrous tetrahydrofuran (85 mL), 1,3-dicyclohexyl-carbodiimide (9.27 g, 44.9 mmol), 4-(dimethylamino)-pyridine (140 mg, 1.14 mmol), and cyclopentanol (5.1 mL, 4.83 g, 56.2 mmol) are added in succession. The mixture is stirred for 15 minutes at room temperature and brought to reflux at which it is maintained for 1 hour. The reaction is cooled to ambient temperature and all volatiles are removed in vacuo. The residue is dissolved in a mixture of ethyl acetate and hexane (1:12, 200 mL) and the resultant suspension is filtered over a small pad of silica gel (45 g), which is subsequently rinsed with additional 200 mL of the same mixture of hexane and ethyl acetate. The obtained solution is concentrated in vacuo and the residue chromatographed on silica gel (hexane:ethyl acetate 15:1) to afford 4,6-dichloro-2-methyl-nicotinic acid cyclopentane ester as colorless oil.

Step 3. Synthesis of 6-Chloro-4-cyclopentyloxy-2-methyl-nicotinic acid cyclopentyl ester

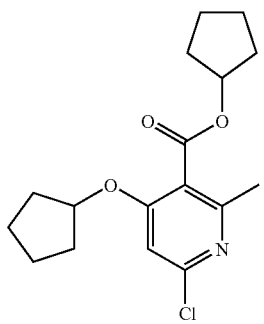

To a suspension of sodium hydride (95%, 11.93 g, 83.9 mmol) in anhydrous tetrahydrofuran (300 mL), cyclopentanol (3.65 mL, 3.46 g, 40.2 mmol) is added, and the resulting mixture is stirred for 45 minutes at ambient temperature. Copper iodide (11.5 g, 8 mmol) followed by a solution of 4,6-dichloro-2-methyl-nicotinic acid cyclopentane ester (10.4 g, 38.1 mmol) in anhydrous tetrahydrofuran (5 mL) is added, and the mixture is heated to reflux for 1 hour. The reaction is cooled to ambient temperature, and a saturated aqueous NH$_4$Cl solution (150 mL) is added. Tetrahydrofuran is removed in vacuo and the product is extracted with ethyl acetate (3×150 mL). The obtained solution is filtered over a small pad of silica gel (45 g) and concentrated in vacuo. The resulting residue is chromatographed on silica gel (Hexane/ethyl acetate 14:1) to afford 6-chloro-4-cyclopentyloxy-2-methyl-nicotinic acid cyclopentyl ester.

Step 4. Synthesis of (6-Chloro-4-cyclopentoxy-2-methyl-pyridin-3-yl)-methanol

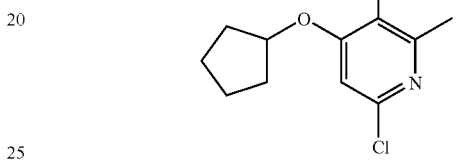

To a solution of the 6-chloro-4-cyclopentyloxy-2-methyl-nicotinic acid cyclopentyl ester (7.4 g, 22.8 mmol) in anhydrous tetrahydrofuran (250 mL) under nitrogen cooled to 0° C., lithium aluminum hydride (10 M solution in tetrahydrofuran, 45.8 mL, 45.8 mmol) is added over period of 15 minutes. The reaction is stirred for 3 hours at ambient temperature, after which a saturated solution of sodium potassium tartarate (300 mL) is slowly added and the mixture is stirred for additional 1 hour. The organic layer is separated and the aqueous solution is extracted with methylene chloride (2×100 mL). The combined organic extracts are washed with washed with brine, dried Na$_2$SO$_4$), and concentrated in vacuo. The residue is dissolved in a mixture of hexane and ethyl acetate (1:1, 150 mL) and filtered over a small pad of silica gel (30 g) which is subsequently rinsed with additional 200 mL of the same mixture of hexane and ethyl acetate. The obtained solution is concentrated in vacuo to give (6-chloro-4-cyclopentoxy-2-methyl-pyridin-3-yl)-methanol as colorless oil.

Step 5. Synthesis of 6-Chloro-3-chloromethyl-4-cyclopentyloxy-2-methyl-pyridine

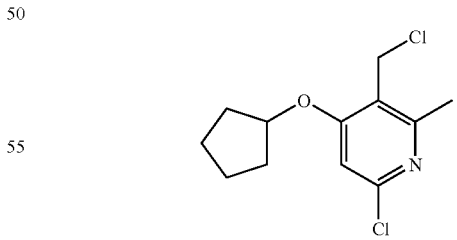

To a solution of (6-chloro-4-cyclopentoxy-2-methyl-pyridin-3-yl)-methanol (3.5 g, 14.5 mmol), a solution of thionyl chloride (2.0 M solution in methylene chloride, 72 mL, 144 mmol) is added, and the mixture is stirred for 2 hours at ambient temperature. All volatiles are removed in vacuo to afford 6-chloro-3-chloromethyl-4-cyclopentyloxy-2-methyl-pyridine hydrochloride salt as a white powder.

Step 6. Synthesis of (S)-(6-Chloro-4-cyclopentyloxy-2-methyl-pyridin-3-ylmethyl)-methyl-(1,2,3,4-tetrahydro-naphthalen-1-yl)-amine

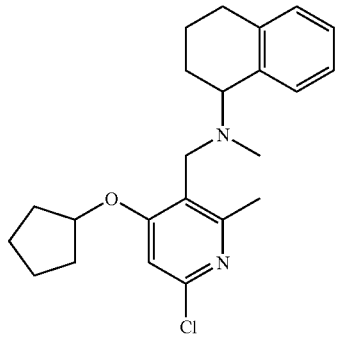

A mixture of 6-chloro-3-chloromethyl-4-cyclopentyloxy-2-methyl-pyridine hydrochloride salt, (S)-methyl-(1,2,3,4-tetrahydro-naphthalen-1-yl)-amine (3.0 g, 18.6 mmol), N,N-diisopropylethylamine (4.0 mL, 22.9 mmol), and anhydrous acetonitrile (50 mL) is stirred for 5 hours at 80° C. The reaction is cooled to ambient temperature and concentrated in vacuo. The obtained residue is dissolved in a mixture of hexane and ethyl:acetate (4:1, 100 mL) and filtered over a small pad of silica gel (35 g), which is subsequently rinsed with additional 100 mL of the same mixture of hexane and ethyl acetate. The filtered solution is concentrated in vacuo and the resultant residue is chromatographed on silica gel (hexane/ethyl Acetate 4:1) to afford (S)-(6-chloro-4-cyclopentyloxy-2-methyl-pyridin-3-ylmethyl)-methyl-(1,2,3,4-tetrahydro-naphthalen-1-yl)-amine. $^1$H NMR: (CDCl$_3$) 7.53 (m, 1H), 7.09 (m, 2H), 7.02 (m, 1H), 6.63 (s, 1H), 4.77 (m, 1H), 3.83 (d, 1H), 3.73 (dd, 1H), 3.56 (d, 1H), 2.73 (m, 2H), 2.63 (s, 3H), 2.07 (m, 2H), 2.04 (s, 3H), 1.98 (m, 2H), 1.82 (m, 4H), 1.68 (m, 4H).

Example 44

Synthesis of {1-Benzyl-4-[6-(2,6-Diethyl-Phenyl)-4-Ethyl-2-Methyl-Pyridin-3-yl]-Pyrrolidin-3-yl}-Pyrrolidin-1-yl-Methanone

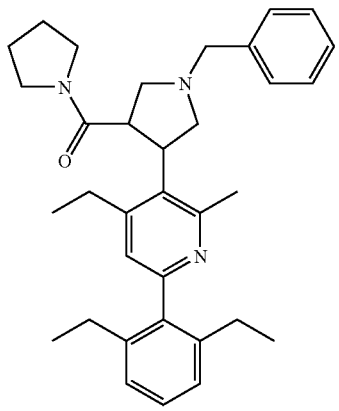

Step 1. Preparation of 3-[6-(2,6-Diethyl-phenyl)-4-ethyl-2-methyl-pyridin-3-yl]-acrylic acid Sodium bis(trimethylsilyl)amide (2.9 mL of 1M solution in THF) is added slowly to a solution of trimethyl phosphonoacetate (0.47 mL, 2.9 mmol) in THF (8 mL). The mixture is stirred for 30 minutes at room temperature and then cooled to −78° C. To this is added a solution of 6-(2,6-diethyl-phenyl)-4-ethyl-2-methyl-pyridine-carbaldehyde (813 mg, 2.9 mmol) in THF (5 mL) which is generated from the pyridylmethanol via Swern oxidation. The resulting mixture is stirred for 1.5 hours at ambient temperature, poured into saturated NH$_4$Cl solution, and the layers are separated. The aqueous layer is extracted with EtOAc and the combined organic layers are dried over sodium sulfate and concentrated in vacuo. The residue is purified by flash chromatography (elution with Hex/EtOAc 8:1) to yield 3-[6-(2,6-diethyl-phenyl)-4-ethyl-2-methylpyridin-3-yl]-acrylic acid methyl ester as a pale yellow oil. $^1$H NMR (CDCl$_3$) 7.91 (d, 1H), 7.29 (m, 2H), 7.18 (d, 2H), 7.01 (s, 1H), 6.10 (d, 1H), 3.83 (s, 3H), 2.72 (q, 2H), 2.60 (s, 3H), 2.34 (m, 4H), 1.21 (t, 3H), 1.04 (m, 6H).

A solution of the ester above (403 mg, 1.2 mmol) in EtOH (5 mL) is treated with NaOH (5 mL of 1 N solution in water). The mixture is heated for 2 hours at 100° C. and concentrated in vacuo. The residue is diluted with EtOAc and acidified to pH 4 with 1 N-HCl. The layers are separated and the aqueous layer is extracted with EtOAc. The combined organic layers are washed with saturated brine, dried (Na$_2$SO$_4$), and concentrated to yield 3-[6-(2,6-diethyl-phenyl)-4-ethyl-2-methylpyridin-3-yl]-acrylic acid as a white foam. $^1$H NMR (CDCl$_3$) 7.64 (d, 1H), 7.29 (dd, 1H), 7.15 (d, 2H), 7.09 (s, 1H), 6.20 (d, 1H), 2.76 (q, 2H), 2.71 (s, 3H), 2.33 (m, 4H), 1.22 (t, 3H), 1.04 (m, 6H).

Step 2. Preparation of 1-Benzyl-4-[6-(2,6-diethyl)-4-ethyl-2-methyl-pyridin-3-yl]-pyrrolidine-3-carboxylic acid N-Methoxymethyl-N-(trimethylsilylmethyl)benzylamine (0.44 mL, 1.7 mmol) and trifluoroacetic acid (8 μl, 0.11 mmol) are added to a solution of 3-[6-(2,6-diethyl-phenyl)-4-ethyl-2-methylpyridin-3-yl]-acrylic acid (367 mg, 1.1 mmol) in CH$_2$Cl$_2$ (8 mL). The mixture is stirred overnight at room temperature, treated with triethylamine (0.1 mL), and concentrated in vacuo. The residue is passed through a short SiO$_2$ column (elution with MeOH/CH$_2$Cl$_2$ 1:10) to yield 1-benzyl-[6-(2,6-diethyl)-4-ethyl-2-methyl-pyridin-3-yl]-pyrrolidine-3-carboxylic acid as a pale yellow foam. $^1$H NMR (CDCl$_3$) 7.43-7.28 (m, 6H), 7.18 (m, 2H), 6.99 (s, 1H), 4.98 (s, 2H), 4.41 (m, 1H), 3.84 (m, 6H), 3.72 (m, 1H), 3.05 (m, 2H), 2.90 (q, 2H), 2.67 (s, 3H), 2.25 (m, 4H), 1.21 (t, 3H), 1.02 (m, 6H). LCMS (m/z): 457.31 (MH)$^+$ Step 3. Preparation of {1-Benzyl-4-[6-(2,6-diethyl-phenyl)-4-ethyl-2-methyl-pyridin-3-yl]-pyrrolidin-3-yl}-pyrrolidin-1-yl-methanone A mixture of 1-benzyl-4-[6-(2,6-diethyl)-4-ethyl-2-methyl-pyridin-3-yl]-pyrrolidine-3-carboxylic acid (38 mg, 0.083 mmol), BOP (40 ma, 0.092 mmol), and diethylamine (43 μl, 0.42 mmol) in CH$_2$Cl$_2$ (2 mL) is stirred for overnight at room temperature. HCl (1 mL of 1 N aqueous solution) is added and the mixture is extracted with CH$_2$Cl$_2$. The combined extracts are dried (Na$_2$SO$_4$) and concentrated in vacuo. The residue is purified by PTLC to yield {1-benzyl-4-[6-(2,6-diethyl-phenyl)-4-ethyl-2-methyl-pyridin-3-yl]-pyrrolidin-3-yl}-pyrrolidin-1-yl-methanone as a colorless oil. $^1$H NMR (CDCl$_3$) 7.39-7.37 (m, 2H), 7.34-7.30 (m, 2H), 7.26-7.22 (m, 2H), 7.09 (m, 2H), 6.88 (s, 1H), 4.25 (m, 1H), 3.90 (d, 1H), 3.62 (d, 1H), 3.46 (m, 1H), 3.41-3.23 (m, 4H), 2.96-

2.83 (m, 4H), 2.76 (s, 3H), 2.66 (m, 2H), 2.29 (m, 4H), 1.77-1.58 (m, 4H), 1.15 (t, 3H), 1.02 (m, 6H). LCMS (m/z): 526.23 (MH)+

Example 45

Synthesis of 4-[4-Isopropoxy-5-(5-Isopropyl-2-Methyl-Phenoxymethyl)-6-Methyl-Pyridin-2-yl]-3-Isopropyl-1H-Indazole

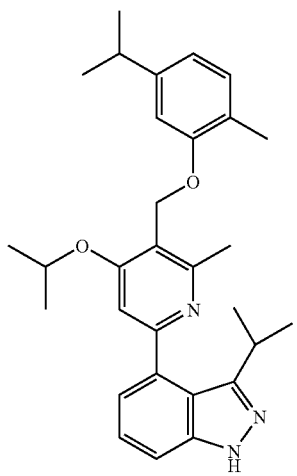

Step 1. Preparation of 6-Chloro-4-isopropoxy-3-(5-isopropyl-2-methyl-phenoxymethyl)-2-methyl-pyridine Anhydrous isopropanol (1.5 mL, 20 mmol) is added to a suspension of NaH (1.5 g of 60% dispersion in mineral oil, 37 mmol) in THF (90 mL) at 0° C. and the mixture is stirred for 30 minutes at ambient temperature. To this is added a solution of 4,6-dichloro-2-methyl-nicotinic acid isopropyl ester (4.6 g, 19 mmol) in THF (10 mL) and CuI (178 mg, 0.94 mmol) The mixture is refluxed for 1 hour, cooled to room temperature, and poured into water-ice mixture. The layers are separated and the aqueous layer is extracted with EtOAc. The combined organic layers are dried (MgSO$_4$) and concentrated in vacuo. The residue is purified by flash chromatography (elution with Hex/EtOAc 6:1) to yield 6-chloro-4-isopropoxy-2-methyl-nicotinic acid isopropyl ester as a pale yellow oil. $^1$H NMR (CDCl$_3$) 6.65 (s, 1H), 5.24 (m, 1H), 4.60 (m, 1H), 2.41 (s, 3H), 1.28 (d, 12H).

LiAlH$_4$ (14 mL of 1 M solution in THF, 14 mmol) is added to a solution of 6-chloro-4-isopropoxy-2-methyl-nicotinic acid isopropyl ester (2.0 g, 7.4 mmol) in THF (10 mL) at 0° C. The mixture is stirred for 3 hours at ambient temperature. After quenching with water, the mixture is extracted with EtOAc. The combined extracts are washed with saturated brine, dried (Na$_2$SO$_4$), and concentrated to give the crude alcohol as a colorless oil which is dissolved in CH$_2$Cl$_2$ (10 mL) and treated with SOCl$_2$ (2.7 mL, 37 mmol). The mixture is stirred for 1 hour at room temperature and concentrated in vacuo. The residue is dissolved in DMF (15 mL). To this is added Cs$_2$CO$_3$ (7.2 g, 11 mmol) and carvacrol (1.6 g, 11 mmol). The mixture is stirred for 16 hours at room temperature, poured into water, and extracted with Et$_2$O. The combined extracts are washed with saturated brine, dried (Na$_2$SO$_4$), and concentrated in vacuo. The residue is purified by flash chromatography (elution with Hex/EtOAc 6:1) to yield 6-chloro-4-isopropoxy-3-(5-isopropyl-2-methyl-phenoxymethyl)-2-methyl-pyridine. $^1$H NMR (CDCl$_3$) 7.05 (d, 1H), 6.82 (s, 1H), 6.79 (d, 1H), 6.724 (s, 1H), 5.02 (s, 2H), 4.60 (m, 1H), 2.88 (m, 1H), 2.59 (s, 3H), 2.12 (s, 3H), 1.37 (d, 6H), 1.24 (d, 6H).

Step 2. Preparation of 4-[4-Isopropoxy-5-(5-isopropyl-2-methyl-phenoxymethyl)-6-methyl-pyridin-2-yl]-5-isopropyl-1H-indazole A mixture of 6-chloro-4-isopropoxy-3-(5-isopropyl-2-methyl-phenoxymethyl)-2-methyl-pyridine (185 mg, 0.53 mmol), 3-isopropyl-1H-indazole-4-boronic acid (109 mg, 0.53 mmol), Pd(PPh$_3$)$_4$ (31 mg, 0.027 mmol), and Na$_2$CO$_3$ (169 mg, 1.6 mmol) in dioxane (8 mL) and water (2 mL) is heated for 24 hours at 100° C. The mixture is poured into water and extracted with EtOAc. The combined extract are dried (Na$_2$SO$_4$) and concentrated in vacuo. The residue is purified by flash chromatography (elution with MeOH/CH$_2$Cl$_2$ 1:10) to yield 4-[4-isopropoxy-5-(5-isopropyl-2-methyl-phenoxymethyl)-6-methyl-pyridin-2-yl]-3-isopropyl-1H-indazole. $^1$H NMR (CDCl$_3$) 9.95 (br s, 1H), 7.45 (d, 1H), 7.39 (t, 1H), 7.13 (d, 1H), 7.09 (d, 1H), 6.92 (m, 2H), 6.78 (d, 1H), 5.20 (s, 2H), 4.68 (m, 1H), 3.19 (m, 1H), 2.88 (m, 1H), 2.64 (s, 3H), 2.20 (s, 3H), 1.99 (d, 6H), 1.24 (d, 6H), 1.11 (d, 6H). LCMS (m/z): 472.63 (MH)+

Example 46

Synthesis of 4-[6-(2,6-Diethyl-Phenyl)-3-(3,3-Dimethyl-Piperidin-1-ylmethyl)-2-Methyl-Pyridin-4-yl]-2-Hydroxy-Benzamide

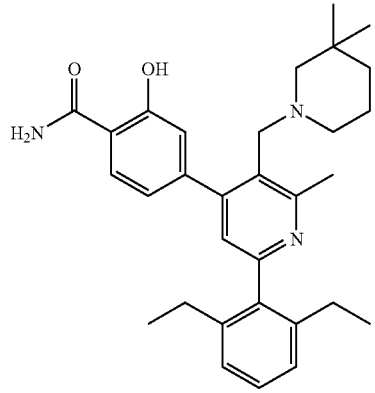

Step 1. Preparation of 2-Benzyloxy-4-bromo Acid Benzyl Ester

A mixture of 4-bromosalicylic acid (17 g, 78 mmol), benzyl bromide (21 mL, 173 mmol), and K$_2$CO$_3$ (38 g, 276 mmol) in DMF (80 mL) is heated for 16 hours at 60° C. The mixture is poured into water and extracted with Et$_2$O. The combined extracts are dried (Na$_2$SO$_4$) and concentrated in vacuo. The residue is purified by flash chromatography (Hex/EtOAc 10:1) to yield 2-benzyloxy-4-bromo acid benzyl ester. $^1$H NMR (CDCl$_3$) 7.78 (d, 1H), 7.44-7.26 (m, 1H), 7.20 (s, 1H), 5.27 (s, 2H), 5.15 (s, 2H), Step 2. Preparation of 2-Benzyloxy-4-[6-(2,6-diethyl-phenyl)-3-formyl-2-methyl-pyridin-4-yl]-benzoic acid benzyl ester A mixture of 2-benzyloxy-4-bromo acid benzyl ester (500 mg, 1.26 mmol), bis(neopentyl glycolato) diboron (313 mg, 1.38 mmol), PdCl$_2$ (dppf) (31 mg, 0.038 mmol), DPPF (21 mg, 0.038 mmol), and KOAc (371 mg, 3.78 mmol) in dioxane (15 mL) is stirred overnight at 90° C. Water is added and the mixture is extracted with EtOAc. The combined extracts are washed with saturated brine, dried (Na$_2$SO$_4$), and concentrated to yield the crude aryl boronate which is dissolved in dioxane (15 mL). To this is added 6-(2,6-diethyl-phenyl)-4-chloro-2-methyl-pyridine-3-carbaldehyde (240 mm, 0.83 mmol), K$_3$PO$_4$ (2.5 mL of 1 M solution in H$_2$O, 2.5 mmol), and PdCl$_2$ (dppf) (20 mg, 0.025 mmol). The mixture is heated for 24 hours at 100° C. and diluted with water. The mixture is extracted with EtOAc and the combined extracts are dried (Na$_2$SO$_4$), and concentrated in vacuo. The residue is purified by flash chromatography to yield 2-benzyloxy-4-[6-(2,6-diethyl-phenyl)-3-formyl-2-methyl-pyridin-4-yl]-benzoic acid benzyl ester as a pale yellow oil. $^1$H NMR (CDCl$_3$) 10.1 (s, 1H), 7.99 (d, 1H), 7.45-7.31 (m, 11H), 7.20-7.16 (m, 3H), 7.12 (d, 2H), 5.39 (s, 2H), 5.19 (s, 2H), 2.93 (s, 3H), 2.40 (m, 4H), 1.09 (m, 6H). LCMS (m/z): 570.47 (MH)$^+$ Step 3. Preparation of 2-Benzyloxy-4-[6-(2,6-diethyl-phenyl)-3-(3,3-dimethyl-piperidin-1-ylmethyl)-2-methyl-pyridin-4-yl]-benzoic Acid Benzyl Ester NaB(OAc)$_3$H (38 mg, 0.65 mmol) is added to a mixture of 2-benzyloxy-4-[6-(2,6-dieethyl-phenyl)-3-formyl-2-methyl-pyridin-4-yl]-benzoic acid benzyl ester (74 mg, 0.13 mmol) and 3,3-dimethylpiperidine (29 mg, 0.26 mmol) in C$_2$Cl$_2$ (4 mL). The mixture is stirred for 6 hours at room temperature and diluted with water. The layers are separated and the aqueous layer is extracted with CH$_2$Cl$_2$. The combined organic layers are dried Na$_2$SO$_4$) and concentrated in vacuo. The residue is purified by PTLC to yield 2-benzyloxy-4-[6-(2,6-diethyl-phenyl)-3-(3,3-dimethyl-piperidin-1-ylmethyl)-2-methyl-pyridin-4-yl]-benzoic acid benzyl ester $^1$H NMR (CDCl$_3$) 7.90 (d, 1H), 7.44-7.25 (m, 2H), 7.12 (d, 2H), 6.96 (d, 1H), 6.90 (s, 1H), 5.39 (s, 2H), 5.18 (s, 2H), 3.32 (s, 2H), 2.75 (s, 3H), 2.40 (m, 4H), 2.05 (br s, 2H), 1.79 (br s, 2H), 1.44 (m, 2H), 1.13 (m, 2H), 1.07 (m, 6H), 0.81 (s, 6H). LCMS (m/z): 667.42 (MH)$^+$ Step 4. Preparation of 4-[6-(2,6-Diethyl-phenyl)-3-(3,3-dimethyl-piperidin-1-ylmethyl)-2-methyl-pyridin-4-yl]-2-hydroxy-benzamide 10% Palladium on carbon (10 mg) is added to a solution of 21-Benzyloxy-4-[6-(2,6-diethyl-phenyl)-3-(3,3-dimethyl-piperidin-1-ylmethyl)-2-methyl-pyridin-4-yl]-benzoic acid benzyl ester (52 mg, 0.078 mmol) in methanol (10 mL) and the reaction mixture is submitted to hydrogenation (Parr shaker) at 55 psi for 24 hours. The resulting mixture is filtered on celite and the filtrate is concentrated in vacuo to give crude debenzylated product (34 mg), which is dissolved in CH$_2$Cl$_2$ (3 mL). SOCl$_2$ (1 mL) is added and the mixture is heated for 1 hour at 95° C., The mixture is concentrated and the residue is dissolved in CH$_2$Cl$_2$ (5 mL). Ammonia gas is bubbled through the mixture for 5 minutes at 0° C. Concentration is followed by PTLC to yield 4-[6-(2,6-diethyl-phenyl)-3-(3,3-dimethyl-piperidin-1-ylmethyl)-2-methyl-pyridin-4-yl]-2-hydroxy-benzamide as a pale yellow oil. $^1$H NMR (CDCl$_3$) 12.2 br s, 1H), 7.38 (d, 1H), 7.26 (t, 1H), 7.11 (d, 2H), 6.97 (s, 1H), 6.93 (s, 1H), 6.82 (d, 1H), 6.10 (br s, 2H), 3.41 (s, 2H), 2.74 (s, 3H), 2.39 (m, 4H), 2.12 (br s, 2H), 1.86 (br s, 2H), 1.47 (m, 2H), 1.13 (m, 2H), 1.05 (m, 6H), 0.82 (s, 6H). LCMS (m/z): 486.72 (MH)$^+$)+

Example 47

Synthesis of 2-(2,6-Diethyl-phenyl)-5-(2,4-diethyl-2H-pyrazol-3-yl)-4-isopropoxy-pyridine and 2-(2,6-Diethyl-phenyl)-5-(1,4-diethyl-1H-pyrazol-3-yl)-4-isopropoxy-pyridine Step 1. Synthesis of 1-[6-(2,6-diethyl-phenyl)-4-isopropoxy-pyridin-3-yl]-butan-1-one

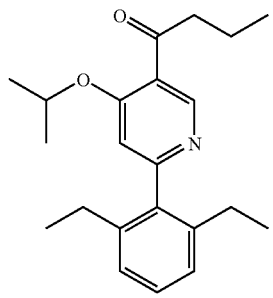

A mixture of 1-[6-(2,6-diethyl-phenyl)-4-isopropoxy-pyridin-3-yl]-butan-1-ol (482 mg, 1.41 mmol, prepared analogously to Example 16) and pyridinium dichromate (1.0 g, 2.82 mmol) in CH$_2$Cl$_2$ (50 mL) is stirred at room temperature overnight. The mixture is washed with brine, dried and concentrated. The residue is chromatographed on silica gel to give 360 mg of 1-[6-(2,6-diethyl-phenyl)-4-isopropoxy-pyridin-3-yl]-butan-1-one.

Step 2. Synthesis of 2-(2,6-diethyl-phenyl)-5-(2,4-diethyl-2H-pyrazol-3-yl)-4-isopropoxy-pyridine and 2-(2,6-diethyl-phenyl)-5-(1,4-diethyl-1H-pyrazol-3-yl)-4-isopropoxy-pyridine

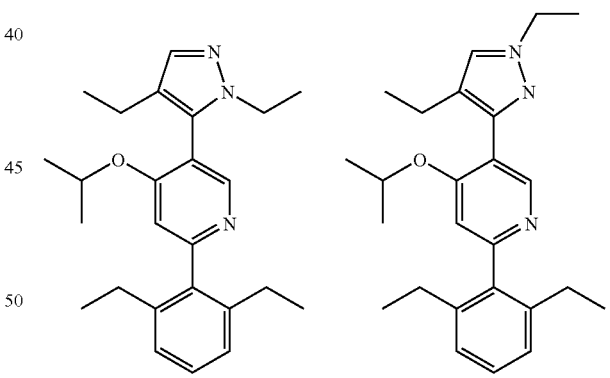

A mixture of 1-[6-(2,6-diethyl-phenyl)$_4$ isopropoxy-pyridin-3-yl]-butan-1-one (100 mg, 0.29 mmol) and tris(dimethylamino)methane (1 mL) is heated with stirring in a sealed tube at 60° C. for 2 hours. After cooling, ether is added to the mixture and the resulting solution is transferred to a flask and concentrated under reduced pressure. The residue is dissolved in EtOH (2 mL) and then mixed with K$_2$CO$_3$ (100 mg) and ethyl hydrazine oxalate (100 mg). The resulting mixture is heated at 80° C. for 4 hours, cooled and evaporated. EtOAc and water are added to the residue. The organic layer is separated washed with brine and concentrated. The residue is purified on PTLC (4:1 hexane:EtOAc) to give 2-(726 diethylphenyl)-5-(2,4-diethyl-2H-pyrazol-3-yl)-4-isopropoxypyridine as the less polar product (A) and 2-(2,6-diethyl-phenyl)-5-(1,4-diethyl-1H-pyrazol-3-yl)-4-isopropoxy-pyridine as the more polar product (B). A: $^1$H NMR (CDCl$_3$) 8.36 (s, 1H), 7.48 (s, 1H), 7.32 (t, 1H), 7.20 (d, 2H), 6.81 (s, 1H), 4.62 (m, 1H), 3.98 (m, 1H), 2.46-2.33 (m, 6H), 1.41-1.00 (m, 18H). B: $^1$H NMR (CDCl$_3$) 8.59 (s, 1H), 7.30 (m, 2H), 7.170 (d, 2H), 6.80 (s, 1H), 4.60 (m, 1H), 4.20 (m, 2H), 2.50-2.30 (m, 6H), 1.55 (t, 3H), 1.30 (d, 2H), 1.20-1.00 (m, 9H).

Example 48

Synthesis of [4-cyclopentyloxy-6-(3-Ethyl-Benzol[D]-Isoxazol-4-yl)-2-Methyl-Pyridin-3-ylmethyl]-Methyl-(1,2,3,4-Tetrahydro-Napthalen-1-yl)-Amine Step 1. Synthesis of 1-(2-Bromo-6-fluoro-phenyl)-propan-1-ol

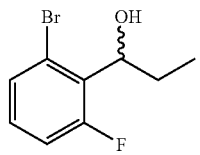

A solution of EtMgBr (35 mL, 35 mmol) in TH-F (1 M) is added dropwise to a solution of 2-bromo-6-fluoro-benzaldehyde (7 g, 34.5 mmol) in THF at −78° C. The mixture is stirred for 1 hour at −78° C. Saturated NH$_4$Cl is added dropwise to the mixture which is subsequently warmed to room temperature and stirred for 1 hour. The organic layer is separated, extracted with THF (3×100 mL. The combined organic layers are washed with brine, dried and solvent is removed in vacuo. The crude product is purified by flash chromatography (5% EtOAc/hexanes) to obtain 1-(2-bromo-6-fluoro-phenyl)-propan-1-ol.

Step 2. Synthesis of 3-Fluoro-2-(1-hydroxypropyl)phenylboronic Acid

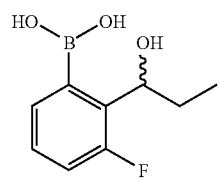

A solution of n-BuLi (2.15 mL, 4.3 mmol) in pentane (2 M) is added dropwise to a solution of 1-(2-bromo-6-fluoro-phenyl)-propan-1-ol (500 mg, 2.15 mmol) in THF at −78° C. The mixture is stirred for 2 hours at −78° C. (i-PrO)$_3$B (41 mL, 4.3 mmol) is added in one portion and the mixture is warmed slowly to room temperature and stirred for 12 hours. 1N HCl (10 mL) is added and the mixture is stirred for 2 hours at room temperature. The organic layer is separated and the aqueous layer is extracted with DCM (3×30 mL). The combined organic layers are dried and solvents are removed in vacuo. The crude product is purified by PTLC eluting with 5% MeOH in DCM to give 3-fluoro-2-(1-hydroxypropyl)phenylboronic acid.

Step 3. Synthesis of 1-[2-(4-Cylopentyloxy-6-methyl-5-{[methyl-(1,2,3,4-tetrahydro-naphthalen-1-yl)amino]-methyl}-pyridin-2-yl)-6-fluoro-phenyl]-propan-1-ol

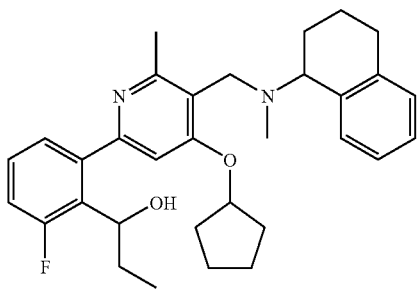

3-Fluoro-2-(1-hydroxypropyl)phenylboronic acid (81 mg, 0.43 mmol), Na$_2$CO$_3$ (126 mg, 1.2 mmol) and Pd(PPh$_3$)$_4$ (10 mg) are added to a degassed solution (toluene 5 mL, H$_2$O 21.6 mL and EtOH 0.8 mL) of (S)-(6-chloro-4-cyclopentyloxy-2-methyl-pyridin-3-ylmethyl)-methyl-(1,2,3,4-tetrahydro-naphthalen-1-yl)amine (prepared as described in Example 43) (150 mg, 0.39 mmol) at room temperature. The mixture is heated to 100° C. for 14 hours. The organic layer is separated and the aqueous layer is extracted with DCM (2×10 mL). The combined organic layers are washed with brine, dried, and evaporated in vacuo to give crude product. The crude product is purified by PTLC and eluted with 2% MeOH in DCM to give 1-[2-(4-cylopentyloxy-6-methyl-5-{[methyl-(1,2,3,4-tetrahydro-naphthalen-1-yl)-amino]methyl}-pyridin-2-yl)-6-fluoro-phenyl]-propan-1-ol.

Step 4. Synthesis of 1-[2-(4-Cylopentyloxy-6-methyl-5-{[methyl-(1,2,3,4-tetrahydro-naphthalen-1-yl)-amino]-methyl}-pyridin-2-yl)-6-fluoro-phenyl]-propan-1-one

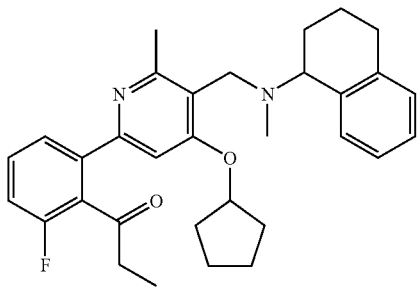

Dess-Martin reagent (170 mg, 0.4 mmol) is added to a solution of 1-[2-(4-cylopentyloxy-6-methyl-5-{[methyl-(1,2,3,4-tetrahydro-naphthalen-1-yl)-amino]-methyl}-pyridin-2-yl)-6-fluoro-pheny]-propan-1-ol (160 mg, 0.32 mmol) in DCM (4 mL) at room temperature and the resulting mixture is stirred for 2 hours, Saturated $Na_2S_2O_3$ is added to the mixture and stirred for 10 minutes. The organic layer is separated and extracted with DCM (2×10 mL). The combined organic layers are dried and solvent is removed in vacuo to give 1-[2-(4-cylopentyloxy-6-methyl-5-{[methyl-(1,2,3,4-tetrahydro-naphthalen-1-yl)-amino]-methyl}-pyridin-2-yl)-6-fluoro-pheny]-propan-1-one which is used in the next step without further purification.

Step 5. Synthesis of 1-[2-(4-Cylopentyloxy-6-methyl-5-{[methyl-(1,2,3,4-tetrahydro-naphthalen-1-yl)-amino]-methyl}-pyridin-2-yl)-6-fluoro-phenyl-propan-1-one oxime

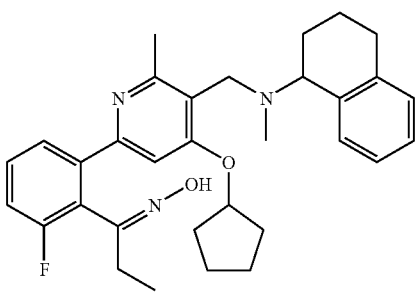

Hydroxylamine hydrochloride (47 mg, 0.7 mmol) is added to a solution of 1-[2-(4-cylopentyloxy-6-methyl-5-{[methyl-(1,2,3,4-tetrahydro-naphthalen-1-yl)-amino]-methyl}-pyridin-2-yl)-6-fluoro-pheny]-propan-1-one (151 mg, 0.3 mmol) in pyridine at room temperature. The mixture is heated to 70° C. for 16 hours. Solvent is removed in vacuo and the crude product is purified by PTLC eluting with 2% MeOH in DCM to give the title product.

Step 5. Synthesis of [4-Cylopentyloxy-6-(3-ethyl-benzol[d]isoxazol-4-yl)-2-methyl-pyridin-3-ylmethyl]-methyl-(1,2,3,4-tetrahydro-naphthalen-1-yl)-amine

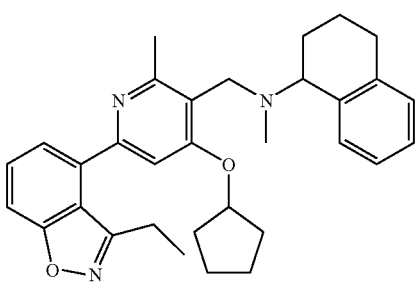

A solution of 1-[2-(4-cylopentyloxy-6-methyl-5-{[methyl-(1,2,3,4-tetrahydro-naphthalen 1-yl)-amino]-methyl}-pyridin-2-yl)-6-fluoro-pheny]-propan-1-one oxime (40 mg, 0.08 mmol) in THF (2 mL) is added to a solution of NaH (2.4 mg, 0.1 mmol) in THF (2 mL) at room temperature. The mixture is heated to 70° C. for 16 hours. Solvent is removed in vacuo and the crude product is purified by PTLC eluting with 1% MeOH in DCM to give [4-cylopentyloxy-6-(3-ethyl-benzol[d]isoxazol-4-yl)-2-methyl-pyridin-3-ylmethyl]-methyl-(1,2,3,4-tetrahydro-naphthalen-1-yl)-amine. $^1$H NMR ($CD_3OD$) 7.58 (m, 2H), 7.32 (d, 2H), 7.11 (m, 3H), 6.84 (s, 1H), 4.87 (m, 1H), 4.04 (d, 1H), 3.81 (m, 1H), 3.68 (d, 1H), 2.87 (m, 7H), 2.17-1.63 (m, 9H), 1.25 (m, 4H), 0.91 (t, 3H).

Example 49

High Speed Synthesis Protocol for Preparation of Aryl and Heteroaryl Ethers Of Formula I

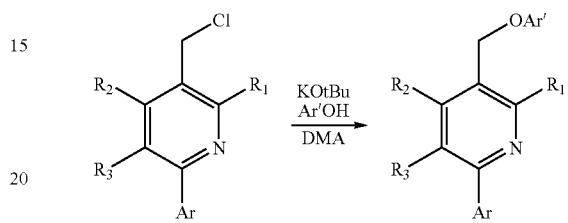

Ar′= aryl or heteroaryl according to $R_4$ in Formula I

A solution of the phenol or hydroxy heterocycle (0.1 mL of 0.3 M in DMA) followed by potassium t-butoxide solution (0.1 mL of 0.3 M in 7:3 DMA/t-BuOH) is added to a solution of chloride (0.1 mL of 0.2 M in DMA). The resulting solution is heated at 50° C. for 2 hours with agitation and then allowed to stand at ambient temperature overnight, Aqueous sodium hydroxide solution (0.5 mL of a 10% solution) is added to the reaction mixture is followed by 0.5 mL of 25% ethyl acetate/hexane. The resulting mixture is agitated and the top layer is removed and delivered to a 500 mg silica gel cartridge. The remaining aqueous layer is extracted with another 0.5 mL of 25% ethyl acetate/hexane and the second organic extract is also delivered to the silica gel cartridge. The cartridge is eluted with 3 mL of 25% ethyl acetate/hexane and the resulting solution of desired product is evaporated, diluted with DMSO and analyzed by t, LC/UV/MS. Aryl ethers of Formula I prepared in this manner are typically >90% pure. For polar analogs (e.g. reaction with hydroxyheterocycles) elution is carried out using ethyl acetate.

Example 50

High Speed Synthesis Protocol for Preparation of Selected Amino Derivatives of Formula I

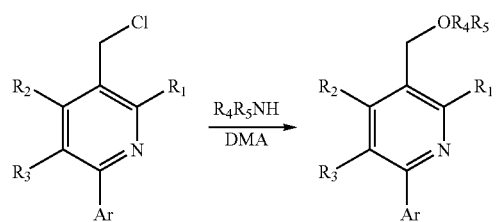

A solution of the appropriate amine (0.15 mL of 0.1 M in toluene) is added to a solution of chloride (0.1 mL of 0.1 M in toluene) and the resulting solution is heated at 90° C. for 16 hours. A solution of aminopropylmorpholine (0.75 mL of 2% in ethyl acetate) is added and heating is continued for an additional hour. The reaction mixture is cooled to ambient temperature, adsorbed onto a 1 g SPE column and eluted with 4 mL of ethyl acetate. The ethyl acetate solution is evaporated and the residue of desired product is diluted with DMSO and analyzed by LC/UV/MS. Amino compounds of Formula I prepared in this manner are typically >90% pure. Note: SPE elution conditions may be varied for polar analogs.

Example 51

Additional 3-Substituted-6-Aryl Pyridines

The compounds shout in Tables I-III are prepared according to the procedures given in the above Schemes and further illustrated in the above Examples.

Unless otherwise specified all starting materials and reagents are of standard commercial grade, and are used without further purification, or are readily prepared from such materials by routine methods. Those skilled in the art of organic synthesis will recognize that starting materials and reaction conditions may be varied to achieve the desired end product.

The chemical groups shown in Tables I-III contain letters $X_n$, where n is an integer. These letters indicate a point of attachment of the group in the structure shown at the top of each table. In some instances the variables used to designate the positions of groups in the structures at the top of Tables I-III differ from the variables used to describe these positions to in similar structures shown elsewhere in the application.

LC/MS data is provided in the tables, along with retention time in minutes and a number (1, 2 or 3) indicating the method used. For Table 3, all LC/MS data was obtained by method 1. The LC/MS methods are as follows:

Method 1:
Analytical HPLC/MS instrumentation: Analyses are performed using a Waters 600 series pump (Waters Corporation, Milford, Mass.), a Waters 996 Diode Array Detector and a Gilson 215 auto-sampler (Gilson Inc, Middleton, Wis.), Micromass® LCT time-of-flight electrospray ionization mass analyzer. Data are acquired using MassLynx™ 4.0 software, with OpenLynx Global Server™, OpenLynx™, and AutoLynx™ processing.
Analytical HPLC conditions: 4.6×50 mm, Chromolith™ SpeedROD RP-18e column (Merck KGaA, Darmstadt, Germany); UV 10 spectra/sec, 220-340 nm summed; flow rate 6.0 mL/min; injection volume 1 µl;
Gradient conditions—mobile phase A is 95% water, 5% methanol with 0.05% TFA; mobile phase B is 95% methanol, 5% water with 0.025% TFA, and the gradient is 0-05 minutes 10-100% B, hold at 100% B to 1.2 minutes, return to 10% B at 1.21 minutes inject-to-inject cycle time is 2.15 minutes.
Analytical MS conditions: capillary voltage 3.5 kV; cone voltage 30V; desolvation and source temperature are 350° C. and 120° C., respectively; mass range 181-750 with a scan time of 0.22 seconds and an inter scan delay of 0.05 minutes.

Method 2:
HPLC instrumentation: Analyses are performed using a Waters 600 series pump (Waters Corporation, Milford, Mass.), a Waters 996 Diode Array Detector and a Gilson 215 autosampler (Gilson Inc, Middleton, Wis.). Data are acquired using MassLynx 4.0 software, with OpenLynx processing.
HPLC conditions: 4.6×50 mm, Chromolith SpeedRod column (Merck AEG); UV 5 spectra/sec, 220, 254 nm; flow rate 6.0 mL/min; injection volume 1-10 µl;
Gradient conditions—Mobile phase A 95% Water, 5% Methanol with 0.05% Formic acid; Mobile phase B 95% Methanol, 5% Water with 0.025% Formic acid;

| Gradient: | |
|---|---|
| Time(mins) | % B |
| 0 | 5 |
| 0.01 | 5 |
| 1.0 | 100 |
| 2 | 100 |
| 2.1 | 5 |

MS instrumentation: LC-MS experiments are performed using a Waters ZMD II Mass Spectrometer.
MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 mins.

Method 3:
HPLC instrumentation: Analyses are performed using a Waters 600 series pump (Waters Corp.), a Waters 996 Diode Array Detector and a Gilson 215 autosampler (Gilson Inc.). Data are acquired using MassLynx 4.0 software, with OpenLynx processing.
HPLC conditions: 4.6×50 mm, XTerra MS C18, 5 µm column (Waters Corp.); UV 10 spectra/sec, 220, 254 nm; flow rate 4.0 mL/min; injection volume 1-10 µl;
Gradient conditions—Mobile phase A 95% Water, 5% Methanol with 0.05% Formic acid; Mobile phase B 95% Methanol, 5% Water with 0.025% Formic acid;

| Gradient: | |
|---|---|
| Time(mins) | % B |
| 0 | 5 |
| 0.01 | 5 |
| 2.0 | 300 |
| 3.50 | 100 |
| 3.51 | 5 |

MS instrumentation: LC-MS experiments are performed using a Waters ZMD II Mass Spectrometer.
MS conditions: Electrospray positive ionization; capillary voltage 3.5 kV; cone voltage 30V; desolvation and source temperature 250° C. and 100° C. respectively; mass range 120-800 with a scan time of 0.5 seconds and an inter scan delay of 0.1 mins,

TABLE I

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 1 | 2-[6-(2,6-Diethyl-phenyl)-4-(1,1-dioxo-1lambda*6*-isothiazolidin-2-ylmethyl)-2-methyl-pyridin-3-ylmethyl]-1-isobutyl-1,2,3,4-tetrahydro-isoquinoline | | | | H | 1.2 | 559.3 | 560.4 | 1 |
| 2 | (Cyclopentyl-phenyl-methyl)-[6-(2,6-diethyl-phenyl)-2-methyl-4-morpholin-4-yl-pyridin-3-ylmethyl]-methyl-amine | | | | H | 1.2 | 511.4 | 512.4 | 1 |
| 3 | (Cyclopentyl-phenyl-methyl)-[6-(2,6-diethyl-phenyl)-4-methoxy-2-methyl-pyridin-3-ylmethyl]-methyl-amine | | | | H | 1.07 | 456.3 | 457.4 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 4 | [6-(2,6-Diethyl-phenyl)-4-methoxy-2-methyl-pyridin-3-ylmethyl]-methyl-(1,2,3,4-tetrahydro-naphthalen-1-yl)-amine |  |  | 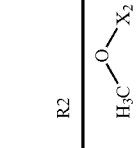 | H | 1.04 | 428.3 | 429.4 | 1 |
| 5 | N-[[6-(2,6-diethylphenyl)-4-(2-methoxyethoxy)-2-methylpyridin-3-yl]methyl]-N-methyl-1,2,3,4-tetrahydronaphthalen-1-amine | 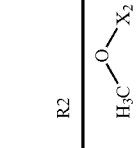 |  |  | H | 1.04 | 472.3 | 473.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 6 | N-{[6-(2,6-diethylphenyl)-4-methoxy-2-methylpyridin-3-yl]methyl}-N-(2,3-dihydro-1,4-benzodioxin-6-ylmethyl)propan-1-amine | CH₃—X₁ | (2,3-dihydro-1,4-benzodioxin-6-ylmethyl)(propyl)amino-CH₂-X₄ | X₂—O—CH₃ | H | 1.03 | 474.3 | 475.4 | 1 |
| 7 | (1S)-N-{[6-(2,6-diethylphenyl)-4-methoxy-2-methylpyridin-3-yl]methyl}-N-methyl-1,2,3,4-tetrahydronaphthalen-1-amine | CH₃—X₁ | (1S)-1,2,3,4-tetrahydronaphthalen-1-yl(methyl)amino-CH₂-X₄ | X₂—O—CH₃ | H | 1.04 | 428.3 | 429.3 | 1 |
| 8 | 4-[6-(2,6-diethylphenyl)-4-methoxypyridin-3-yl]heptan-4-ol | | 4-hydroxyheptan-4-yl-X₄ | H₃C—O—X₂ | H | 1.12 | 355.3 | 356.3 | 1 |

TABLE I-continued
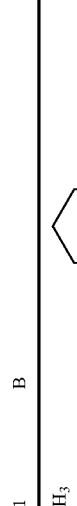
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 9 | N-{[6-(2,6-diethylphenyl)-4-(2-isopropoxyethoxy)-2-methylpyridin-3-yl]methyl}-N-methyl-1,2,3,4-tetrahydronaphthalen-1-amine |  |  |  | H | 1.1 | 500.3 | 501.4 | 1 |
| 10 | 1-{2-[6-(2,6-Diethyl-phenyl)-4-methoxy-2-methyl-pyridin-3-yl]-1-methyl-ethyl}-1,2,3,4-tetrahydroquinoline |  | 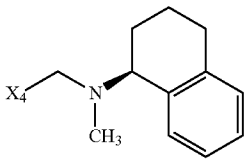 |  | H | 1.05 | 428.3 | 429.3 | 1 |
| 11 | 2-(2,6-diethylphenyl)-4-methoxy-5-[(1Z)-1-propylbut-1-enyl]pyridine | H | 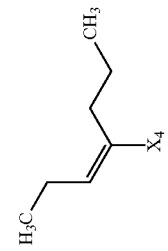 | H₃C—O—X₂ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 12 | 2-(2,6-Diethyl-phenyl)-4-methoxy-5-(1-propyl-but-1-enyl)-pyridine | H | 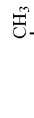 | 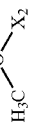 | H | | | | |
| 13 | 2-(2,6-diethylphenyl)-4-methoxy-5-(1-propylbutyl)pyridine | H |  |  | H | 1.16 | 339.3 | 340.3 | 1 |
| 14 | (1S)-N-{[6-(2,6-diethylphenyl)-4-isopropoxy-2-methylpyridin-3-yl]methyl}-N-methyl-1,2,3,4-tetrahydronaphthalen-1-amine |  |  | 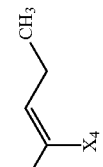 | H | 1.09 | 456.3 | 457.4 | 1 |
| 15 | 4-[(6-(2,6-diethylphenyl)-2-methyl-3-{[methyl(1,2,3,4-tetrahydronaphthalen-1-yl)amino]methyl}pyridin-4-yl)oxy]-2-methylbutan-2-ol |  |  |  | H | | | | |

TABLE I-continued


| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 16 | (1S)-N-{[6-(2,6-diethylphenyl)-4-ethoxy-2-methylpyridin-3-yl]methyl}-N-methyl-1,2,3,4-tetrahydronaphthalen-1-amine | CH₃—X₁ |  | X₂—O—CH₃ | H | | | | |
| 17 | (1S)-N-{[6-(2,6-diethylphenyl)-2-methylpyridin-3-yl]methyl}-N-methyl-1,2,3,4-tetrahydronaphthalen-1-amine | CH₃—X₁ |  | H | H | | | | |
| 18 | (1S)-N-{[6-(2,6-diethylphenyl)-4-(2-methoxyethoxy)-2-methylpyridin-3-yl]methyl}-N-methyl-1,2,3,4-tetrahydronaphthalen-1-amine | CH₃—X₁ |  | X₂—O—CH₃ | H | | | | |
| 19 | 2-(2,6-diethylphenyl)-5-(1-ethoxybutyl)-4-methoxypyridine | H |  | H₃C—O—X₂ | H | | | | |

TABLE I-continued


| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 20 | [6-(2,6-Diethyl-phenyl)-2-methyl-4-morpholin-4-yl-pyridin-3-ylmethyl]-methyl-(1,2,3,4-tetrahydro-naphthalen-1-yl)-amine | X₁—CH₃ |  | 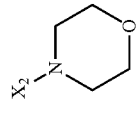 | H | | | | |
| 21 | N-{[6-(2,6-diethylphenyl)-4-methoxy-2,5-dimethylpyridin-3-yl]methyl}-N-methyl-1,2,3,4-tetrahydronaphthalen-1-amine | X₁—CH₃ |  | H₃C—O—X₂ | H₃C—X₃ | 1.09 | 442.3 | 443.2 | 1 |
| 22 | N-{[6-(2,6-diethylpyridin-3-yl]methyl}-N-methyldecahydronaphthalen-1-amine | CH₃—X₁ |  | X₂—O—CH₃ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 23 | (1S)-N-{[4-chloro-6-(2,6-diethylphenyl)-2-methylpyridin-3-yl]methyl}-N-methyl-1,2,3,4-tetrahydronaphthalen-1-amine | CH$_3$—X$_1$ | tetrahydronaphthalenyl-N(CH$_3$)-CH$_2$-X$_4$ | X$_2$—Cl | H | 1.21 | 432.2 | 433.3 | 1 |
| 24 | (1S)-N-{[6-(2,6-diethylphenyl)-4-methoxy-2-(trifluoromethyl)pyridin-3-yl]methyl}-N-methyl-1,2,3,4-tetrahydronaphthalen-1-amine | CF$_3$—X$_1$ | tetrahydronaphthalenyl-N(CH$_3$)-CH$_2$-X$_4$ | X$_2$—O—CH$_3$ | H | 1.17 | 482.3 | 483.3 | 1 |
| 25 | [6-(2,6-diethylphenyl)-4-methoxy-2-methylpyridin-3-yl](3,4-dihydronaphthalen-1-yl)methanol | CH$_3$—X$_1$ | 3,4-dihydronaphthalen-1-yl-CH(OH)-X$_4$ | H$_3$C—O—X$_2$ | H | 1.12 | 413.2 | 414.3 | 1 |

TABLE I-continued

[Structure: pyridine ring with substituents R1, R2, R3 and B group, attached to 2,6-diethylphenyl]

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 26 | (1S)-N-{[6-(2,6-diethylphenyl)-2,4-dimethylpyridin-3-yl]methyl}-N-methyl-1,2,3,4-tetrahydronaphthalen-1-amine | CH₃—X₁ | [tetrahydronaphthalenyl with N(CH₃)-X₄] | H₃C—X₂ | H | 1.15 | 412.3 | 413.3 | 1 |
| 27 | 1-cyclopentyl-N-{[6-(2,6-diethylphenyl)-4-methoxy-2,5-dimethylpyridin-3-yl]methyl}-N-methyl-1-phenylmethanamine | CH₃—X₁ | [cyclopentyl-phenyl-CH with N(CH₃)-X₄] | H₃C—O—X₂ | CH₃—X₁ | 1.14 | 470.3 | 471.3 | 1 |
| 28 | N-{[6-(2,6-diethylphenyl)-4-methoxypyridin-3-yl]methyl}-N-methylpyridin-2-amine | H | [pyridin-2-yl-N(CH₃)-CH₂-X₄] | H₃C—O—X₂ | H | 0.98 | 361.2 | 362.1 | 1 |

TABLE I-continued

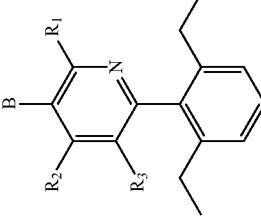

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 29 | 6-(2,6-diethylphenyl)-4-methoxy-3-{[methyl(1,2,3,4-tetrahydronaphthalen-1-yl)amino]methyl}pyridin-2-carbonitrile |  |  |  | H | 1.14 | 439.3 | 440.2 | 1 |
| 30 | 1-{[6-(2,6-diethylphenyl)-4-methoxypyridin-3-yl]methyl}-1,2,3,4-tetrahydroquinoline | H |  |  | H | 1.13 | 386.2 | 387.1 | 1 |
| 31 | N-(cyclopropylmethyl)-N-{[6-(2,6-diethylphenyl)-4-methoxy-2,5-dimethylpyridin-3-yl]methyl}propan-1-amine | 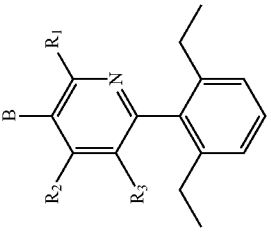 | 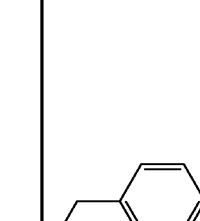 | 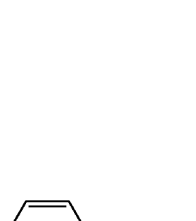 | 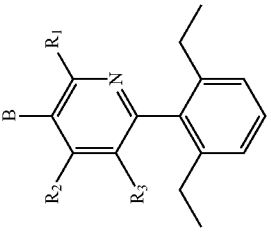 | 1.05 | 394.3 | 395.3 | 1 |
| 32 | N-allyl-N-{[6-(2,6-diethylphenyl)-4-methoxy-2,5-dimethylpyridin-3-yl]methyl}prop-2-en-1-amine | 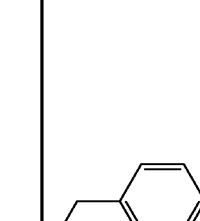 | 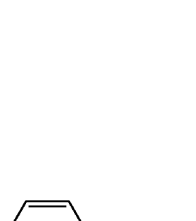 | H₃C—O—X₂ | H₃C—X₃ | 1.04 | 378.3 | 379.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 33 | N-benzyl-N-{[6-(2,6-diethylphenyl)-4-methoxy-2,5-dimethylpyridin-3-yl]methyl}propan-2-amine | X₁—CH₃ | (benzyl, CH₃CH, N, X₄) | H₃C—O—X₂ | H₃C—X₃ | 1.07 | 430.3 | 431.3 | 1 |
| 34 | N-{[6-(2,6-diethylphenyl)-4-methoxy-2,5-dimethylpyridin-3-yl]methyl}-N-ethylethanamine | X₁—CH₃ | (CH₃CH₂, N, CH₃, X₄) | H₃C—O—X₂ | H₃C—X₃ | 0.99 | 354.3 | 355.2 | 1 |
| 35 | N-benzyl-N-{[6-(2,6-diethylphenyl)-4-methoxy-2-methylpyridin-3-yl]methyl}propan-2-amine | X₁—CH₃ | (benzyl, isopropyl, N, X₄) | H₃C—O—X₂ | H | 1.02 | 416.3 | 417.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 36 | 6-(2,6-diethylphenyl)-4-methoxy-2-methyl-3-[(1-naphthyloxy)methyl]pyridine | X₁—CH₃ | 1-naphthyloxy-CH₂-X₄ | H₃C—O—X₂ | H | 1.16 | 411.2 | 412.1 | 1 |
| 37 | 6-(2,6-diethylphenyl)-3-[(3-ethoxyphenoxy)methyl]-4-methoxy-2-methylpyridine | X₁—CH₃ | 3-ethoxyphenoxy-CH₂-X₄ | H₃C—O—X₂ | H | 1.13 | 405.2 | 406.1 | 1 |
| 38 | 2-(2,6-diethylphenyl)-5-(2-ethoxybutyl)-4-isopropoxypyridine | H | CH₃CH₂O-CH(X₄)-CH₂CH₃ | (CH₃)₂CH—O—X₂ | H | 1.15 | 369.3 | 370.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 39 | (1S)-N-{[6-(2,6-diethylphenyl)-4-ethoxy-2-(trifluoromethyl)pyridin-3-yl]methyl}-N-methyl-1,2,3,4-tetrahydronaphthalen-1-amine | F₃C-X₁ | tetrahydronaphthalenyl-N(CH₃)-X₄ | X₂-O-CH₂CH₃ | H | | | | |
| 40 | (1S)-N-{[6-(2,6-diethylphenyl)-4-isopropoxy-2-(trifluoromethyl)pyridin-3-yl]methyl}-N-methyl-1,2,3,4-tetrahydronaphthalen-1-amine | F₃C-X₁ | tetrahydronaphthalenyl-N(CH₃)-X₄ | X₂-O-CH(CH₃)₂ | H | | | | |
| 41 | [6-(2,6-diethylphenyl)-4-methoxy-2-methylpyridin-3-yl](1-naphthyl)methanone | CH₃-X₁ | naphthyl-C(=O)-X₄ | H₃C-O-X₂ | H | 1.14 | 409.2 | 410.2 | 1 |
| 42 | [6-(2,6-diethylphenyl)-4-methoxy-2-methylpyridin-3-yl](1,2,3,4-tetrahydronaphthalen-1-yl)methanone | CH₃-X₁ | tetrahydronaphthalenyl-C(=O)-X₄ | H₃C-O-X₂ | H | 1.16 | 413.2 | 414.1 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 43 | N-{[6-(2,6-diethylphenyl)-4-pyrrolidin-1-yl-2-(trifluoromethyl)pyridin-3-yl]methyl}-N-methyl-1,2,3,4-tetrahydronaphthalen-1-amine | X₁–CF₃ | N-methyl-tetrahydronaphthalenyl-N-CH₂-X₄ | pyrrolidin-N-X₂ | H | 1.25 | 521.3 | 522.4 | 1 |
| 44 | 6-(2,6-diethylphenyl)-3-{[ethyl(1,2,3,4-tetrahydronaphthalen-1-yl)amino]methyl}-4-methoxypyridine-2-carbonitrile | N≡C–X₁ | N-ethyl-tetrahydronaphthalenyl-N-CH₂-X₄ | X₂–O–CH₃ | H | | | | |
| 45 | 2-(2,6-diethylphenyl)-4-isopropoxy-5-(1-propylbutyl)pyridine | H | H₃C–CH₂–CH₂–CH(X₄)–CH₂–CH₂–CH₃ | H₃C–CH(CH₃)–O–X₂ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 46 | N-{[6-(2,6-diethylphenyl)-2,4-dimethylpyridin-3-yl]methyl}-N-methylindan-1-amine | CH₃—X₁ | N-methyl indanyl | H₃C—X₂ | H | 1.1 | 398.3 | 399.3 | 1 |
| 47 | N-{[6-(2,6-diethylphenyl)-2,4-dimethylpyridin-3-yl]methyl}-N-methylchroman-4-amine | CH₃—X₁ | N-methyl chromanyl | H₃C—X₂ | H | 1.16 | 414.3 | 415.3 | 1 |
| 48 | N-{[6-(2,6-diethylphenyl)-4-ethyl-2-methylpyridin-3-yl]methyl}-N-methyl-1,2,3,4-tetrahydronaphthalen-1-amine | CH₃—X₁ | N-methyl tetrahydronaphthalenyl | H₃C—X₂ | H | 1.19 | 426.3 | 427.4 | 1 |
| 49 | 6-(2,6-diethylphenyl)-3-[(1-ethyl-3,4-dihydroisoquinolin-2(1H)-yl)methyl]-4-methoxypyridine-2-carbonitrile | N≡—X₁ | dihydroisoquinolinyl | X₂—O—CH₃ | H | | | | |

TABLE I-continued

[Structure: pyridine with R1, R2, R3, B substituents and 2,6-diethylphenyl group]

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 50 | 6-(2,6-diethylphenyl)-3-{[(2,3-dihydro-1H-inden-1-yl(methyl)amino]methyl}-4-methoxypyridine-2-carbonitrile | N≡C—X1 | [2,3-dihydro-1H-inden-1-yl(methyl)amino]methyl group with X4 | X2—O—CH3 | H | | | | |
| 51 | 6-(2,6-diethylphenyl)-4-methoxy-2-methyl-3-[(2-phenylpiperidin-1-yl)methyl]pyridine | CH3—X1 | 2-phenylpiperidin-1-yl with X4 | X2—O—CH3 | H | 1.03 | 428.3 | 429.4 | 1 |
| 52 | 4-[6-(2,6-diethylphenyl)-4-methylpyridin-3-yl]heptan-4-ol | H | heptan-4-ol group with X4 | H3C—X2 | H | 1.14 | 339.3 | 340.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 53 | N-{[6-(2,6-diethylphenyl)-4-methoxy-2-(trifluoromethyl)pyridin-3-yl]methyl}-N-methylpyridin-2-amine | CF3 | N-methyl-(pyridin-2-yl)aminomethyl | OCH3 | H | 1.14 | 429.2 | 430.1 | 1 |
| 54 | 2-(2,6-diethylphenyl)-5-(1-isopropoxybutyl)-4-methylpyridine | H | 1-isopropoxybutyl | CH3 | H | | | | |
| 55 | 6-(2,6-diethylphenyl)-3-(1-ethoxybutyl)-2-ethyl-4-methoxypyridine | CH2CH3 | 1-ethoxybutyl | OCH3 | H | 1.15 | 369.3 | 370.1 | 1 |

TABLE I-continued
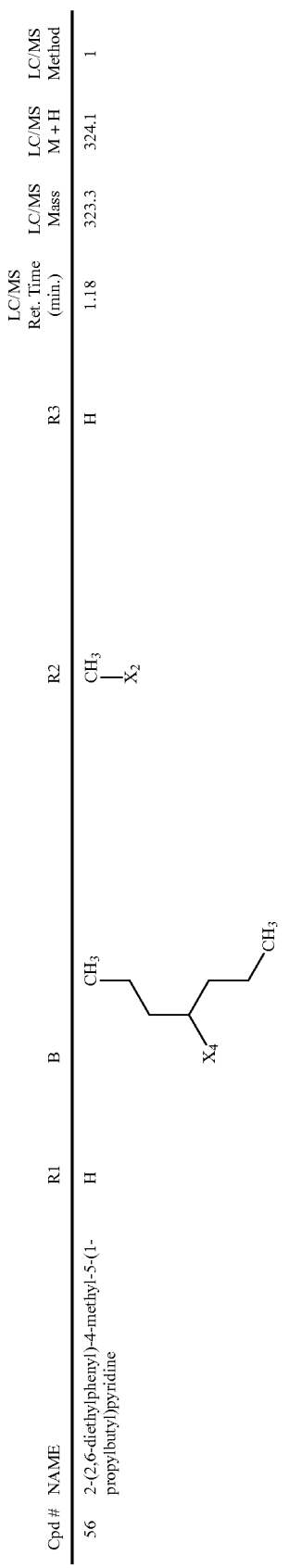
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 56 | 2-(2,6-diethylphenyl)-4-methyl-5-(1-propylbutyl)pyridine | H | 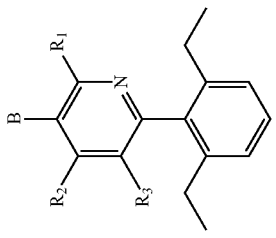 | CH₃—X₂ | H | 1.18 | 323.3 | 324.1 | 1 |
| 57 | 2-(2,6-diethylphenyl)-5-[1-(2-methoxyethoxy)butyl]-4-methylpyridine | H | | H₃C—O—X₂ | H | | | | |
| 58 | 2-(2,6-diethylphenyl)-5-[ethoxy(phenyl)methyl]-4-methoxypyridine | H | 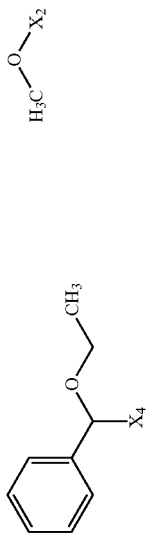 | H₃C—O—X₂ | H | | | | |

TABLE I-continued

| Cpd # | NAME | R1 | B | R2 | R3 | LC/MS Ret. Time (min.) | LC/MS Mass | LC/MS M+H | LC/MS Method |
|---|---|---|---|---|---|---|---|---|---|
| 59 | (1S)-N-{[4-azetidin-1-yl-6-(2,6-diethylphenyl)-2-methylpyridin-3-yl]methyl}-N-methyl-1,2,3,4-tetrahydronaphthalen-1-amine | X₁—CH₃ | [tetrahydronaphthalen-N(CH₃)-CH₂-X₄] | [azetidine-N-X₂] | H | | | | |
| 60 | 6-(2,6-diethylphenyl)-4-methoxy-3-({methyl[(1R)-1,2,3,4-tetrahydronaphthalen-1-yl]amino}methyl)pyridine-2-carbonitrile | N≡C-X₁ | [tetrahydronaphthalen-N(CH₃)-CH₂-X₄] | X₂—O—CH₃ | H | | | | |
| 61 | 2-(2,6-diethylphenyl)-5-(1-ethoxy-5-methylbutyl)-4-methoxypyridine | H | H₃C-CH(-)-CH₂-CH(X₄)-O-CH₂-CH₃ | H₃C—O—X₂ | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 62 | 2-(2,6-diethylphenyl)-5-[1-(3-ethoxyphenoxy)butyl]-4-methylpyridine | H |  |  | H | | | | |
| 63 | [6-(2,6-diethylphenyl)-4-methoxy-2-(trifluoromethyl)pyridin-3-yl]methyl 4-hydroxybenzoate | 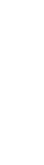 | 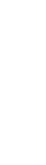 |  | H | | | | |
| 64 | 5-(2-cyclobutyl-1-ethoxyethyl)-2-(2,6-diethylphenyl)-4-methoxypyridine | H |  |  | H | 1.15 | 367.3 | 368.1 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 65 | [6-(2,6-diethylphenyl)-4-methoxy-2-(trifluoromethyl)pyridin-3-yl]methyl 3-hydroxybenzoate | CF3-X1 | 3-hydroxybenzoate-X4 | H3C-O-X2 | H | 1.26 | 459.2 | 460.1 | 1 |
| 66 | 6-(2,6-diethylphenyl)-N,2-dimethyl-3-({methyl[(1S)-1,2,3,4-tetrahydronaphthalen-1-yl]amino}methyl)pyridin-4-amine | CH3-X1 | tetrahydronaphthalenyl-N(CH3)-CH2-X4 | X2-O-CH3 | H | 1.16 | 427.3 | 428.2 | 1 |
| 67 | 2-(2,6-diethylphenyl)-5-(1-ethoxybutyl)-4-[(1Z)-2-(methoxymethyl)pent-1-enyl]pyridine | H | H3C-CH(OCH2CH3)-CH2CH2-X4 | H3C-CH2-CH2-C(=CH-X2)-CH2-O-CH3 | H | 1.29 | 423.3 | 424.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 68 | ethyl 4-[(6-(2,6-diethylphenyl)-4-methoxy-2-methylpyridin-3-yl]methoxy]benzoate | X₁—CH₃ | 4-methoxybenzoate-CH₂-O-X₄ | H₃C—O—X₂ | H | | | | |
| 69 | 4-[4-azetidin-1-yl-6-(2,6-diethylphenyl)pyridin-3-yl]heptan-4-ol | H | heptan-4-ol with X₄ | azetidine N-X₂ | H | 1.14 | 380.3 | 381.2 | 1 |
| 70 | 4-azetidin-1-yl-2-(2,6-diethylphenyl)-5-(1-propylbutyl)pyridine | H | 1-propylbutyl-X₄ | azetidine N-X₂ | H | 1.15 | 364.3 | 365.2 | 1 |
| 71 | (1R)-N-[[2-chloro-6-(2,6-diethylphenyl)-4-ethylpyridin-3-yl]methyl]-N-methyl-1,2,3,4-tetrahydronaphthalen-1-amine | X₁—Cl | tetrahydronaphthalenyl-N(CH₃)-X₄ | H₃C—X₂ | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 72 | 6-(2,6-diethylphenyl)-4-ethyl-N-methyl-3-({methyl[(1R)-methyl-1,2,3,4-tetrahydronaphthalen-1-yl]amino}methyl)pyridin-2-amine |  |  |  | H | | | | |
| 73 | 2-(2,6-diethylphenyl)-5-(1-ethoxybutyl)-4-[2-(methoxymethyl)pentyl]pyridine | H |  |  | H | | | | |
| 74 | (1S)-N-{[4-(cyclopentyloxy)-6-(2,6-diethylphenyl)-2-methylpyridin-3-yl]methyl}-N-methyl-1,2,3,4-tetrahydronaphthalen-1-amine |  |  |  | H | 1.13 | 482.3 | 483.2 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 75 | (1S)-N-{[4-(cyclobutyloxy)-6-(2,6-diethylphenyl)-2-methylpyridin-3-yl]methyl}-N-methyl-1,2,3,4-tetrahydronaphthalen-1-amine |  |  | 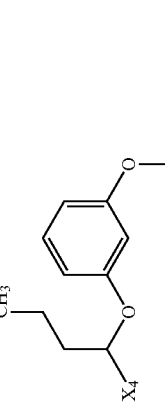 | H | 1.12 | 468.3 | 469.2 | 1 |
| 76 | 2-(2,6-diethylphenyl)-4-ethoxy-5-[1-(3-ethoxyphenoxy)butyl]pyridine | H |  |  | H | 1.21 | 447.3 | 448.2 | 1 |
| 77 | 2-(2,6-diethylphenyl)-3,6-dimethyl-5-({methyl[(1S)-1,2,3,4-tetrahydronaphthalen-1-yl]amino}methyl)pyridin-4-ol | 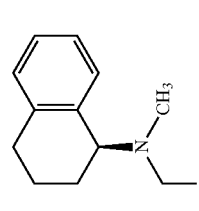 |  | HO—X$_2$ | H$_3$C—X$_3$ | 1.19 | 428.3 | 429.2 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 78 | 5-(2-cyclobutyl-1-ethoxyethyl)-2-(2,6-diethylphenyl)-4-ethoxypyridine | H |  |  | H | 1.17 | 381.3 | 382.1 | 1 |
| 79 | 5-[cyclohexyl(ethoxy)methyl]-2-(2,6-diethylphenyl)-4-ethoxypyridine | H | 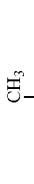 |  | H | 1.19 | 395.3 | 396.2 | 1 |
| 80 | methyl 3-{1-[6-(2,6-diethylphenyl)-4-ethoxypyridin-3-yl]butoxy}benzoate | H | 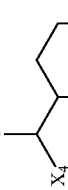 |  | H | 1.18 | 461.3 | 462.2 | 1 |

TABLE I-continued
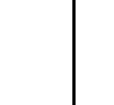
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 81 | 6-(2,6-diethylphenyl)-3-[3,4-dihydronaphthalen-1-yl(ethoxy)methyl]-4-methoxy-2-methylpyridine | 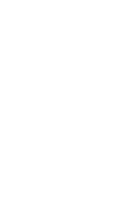 | 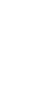 | 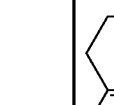 | H | 1.16 | 441.3 | 442.2 | 1 |
| 82 | 6-(2,6-diethylphenyl)-3-[ethoxy(1,2,3,4-tetrahydronaphthalen-1-yl)methyl]-4-methoxy-2-methylpyridine | 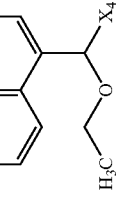 |  | 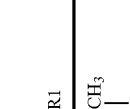 | H | 1.18 | 443.3 | 444.2 | 1 |
| 83 | 1-[6-(2,6-Diethyl-phenyl)-4-ethyl-2-methoxy-pyridin-3-yl]-butan-1-ol | 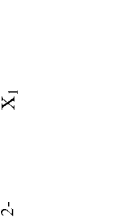 |  | 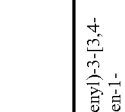 | H | 1.36 | 341.2 | 342.1 | 1 |
| 84 | 6-(2,6-diethylphenyl)-2,4-dimethoxy-3-(1-propylbutyl)pyridine |  |  | H₃C—O—X₂ | H | 1.48 | 369.3 | 370.1 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 85 | 1-[6-(2,6-Diethyl-phenyl)-4-(3-methoxy-propyl)-2-methyl-pyridin-3-yl]-butan-1-one | CH₃—X₁ | (ketone with propyl, X₄) | H₃C—O—CH₂CH₂CH₂—X₂ | H | 1.22 | 367.3 | 368.1 | 1 |
| 86 | 4-{[6-(2,6-diethylpheny)-2,4-dimethylpyridin-3-yl]methyl}morpholine | X₁—CH₂CH₃ | morpholine-CH₂-X₄ | H₃C—X₂ | H | 1.03 | 338.2 | 339.1 | 1 |
| 87 | 2-(2,6-diethylphenyl)-5-(1-ethoxybutyl)-4-(3-methoxypropyl)pyridine | H | H₃C-CH₂-O-CH(CH₂CH₃)—X₄ | H₃C—O—CH₂CH₂CH₂—X₂ | H | | | | |
| 88 | 6-(2,6-diethylphenyl)-3-(1-ethoxybutyl)-2-methyl-4-propylpyridine | CH₃—X₁ | H₃C-CH₂-O-CH(CH₂CH₃)—X₄ | H₃C-CH₂CH₂—X₂ | H | 1.32 | 367.3 | 368.2 | 1 |
| 89 | 6-(2,6-diethylphenyl)-3-(1-ethoxybutyl)-4-(3-methoxypropyl)-2-methylpyridine | CH₃—X₁ | H₃C-CH₂-O-CH(CH₂CH₃)—X₄ | H₃C—O—CH₂CH₂CH₂—X₂ | H | 1.16 | 397.3 | 398.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 90 | 2-(2,6-diethylphenyl)-4-ethoxy-5-(1-propylbutyl)pyridine | H | H₃C—⟨X₄⟩—CH₃ (with propyl chains) | H₃C—O—X₂ | H | 1.16 | 353.3 | 354.2 | 1 |
| 91 | (1S)-N-{[6-(2,6-diethylphenyl)-2-methyl-4-[(3R)-tetrahydrofuran-3-yloxy]pyridin-3-yl]methyl}-N-methyl-1,2,3,4-tetrahydronaphthalen-1-amine | CH₃—X₁ | tetrahydronaphthalen-N(CH₃)-X₄ | (3R)-tetrahydrofuran-3-yloxy-X₂ | H | | | | |
| 92 | (1S)-N-{[6-(2,6-diethylphenyl)-2-methyl-4-[(3S)-tetrahydrofuran-3-yloxy]pyridin-3-yl]methyl}-N-methyl-1,2,3,4-tetrahydronaphthalen-1-amine | CH₃—X₁ | tetrahydronaphthalen-N(CH₃)-X₄ | (3S)-tetrahydrofuran-3-yloxy-X₂ | H | 1.05 | 484.3 | 485.2 | 1 |
| 93 | 4-{1-[6-(2,6-diethylphenyl)-4-ethoxypyridin-3-yl]butyl}morpholine | H | morpholine-CH(CH₂CH₃)-X₄ | X₂—O—CH₂CH₃ | H | | | | |

TABLE I-continued

[Structure: pyridine with R1, B, R2, R3 substituents and 2,6-diethylphenyl group]

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 94 | 2-(2,6-diethylphenyl)-4-(3-methoxypropyl)-5-(1-propylbutyl)pyridine | H | H$_3$C–CH(X$_4$)–CH$_2$CH$_2$CH$_3$ (with propyl) | H$_3$C–O–(CH$_2$)$_3$–X$_2$ | H | | | | |
| 95 | 6-(2,6-diethylphenyl)-3-isopropoxy-2-methyl-1-[(4-phenyl-1H-imidazol-1-yl)methyl]pyridine | X$_1$–CH$_3$ | 4-phenyl-imidazol-1-yl–CH$_2$–X$_4$ | H$_3$C–CH(CH$_3$)–O–X$_2$ | H | 1.06 | 439.3 | 440.2 | 1 |
| 96 | 1-[6-(2,6-Diethyl-phenyl)-4-isopropoxy-2-methyl-pyridin-3-ylmethyl]-1H-benzoimidazole | X$_1$–CH$_3$ | benzoimidazol-1-yl–CH$_2$–X$_4$ | H$_3$C–CH(CH$_3$)–O–X$_2$ | H | 1.04 | 413.2 | 414.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 97 | 1-{[6-(2,6-Diethyl-phenyl)-4-isopropoxy-2-methyl-pyridin-3-yl]methyl}-indoline | | | | H | 1.17 | 414.3 | 415.3 | 1 |
| 98 | 6-(2,6-Diethyl-phenyl)-4-isopropoxy-2-methyl-3-(3-phenyl-[1,2,4]triazol-4-ylmethyl)-pyridine | | | | H | 1.02 | 440.3 | 440.3 | 1 |
| 99 | 1-{[6-(2,6-diethylphenyl)-4-isopropoxy-2-methylpyridin-3-yl]methyl}-1H-indazole | | | | H | 1.13 | 413.2 | 414.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 100 | 1-{[6-(2,6-diethylphenyl)-4-isopropoxy-2-methylpyridin-3-yl]methyl}-1,2,3,4-tetrahydroquinoline | X₁—CH₃ | tetrahydroquinoline-N-CH₂-X₄ | H₃C—O—CH(CH₃)—X₂ | H | 1.19 | 428.3 | 429.2 | 1 |
| 101 | 2-{[6-(2,6-diethylphenyl)-4-isopropoxy-2-methylpyridin-3-yl]methoxy}quinoline | X₁—CH₃ | quinolin-2-yl-O-CH₂-X₄ | H₃C—O—CH(CH₃)—X₂ | H | 1.18 | 440.2 | 441.1 | 1 |
| 102 | (3-{1-[6-(2,6-diethylphenyl)-4-ethoxypyridin-3-yl]butoxy}phenyl)methanol | H | 3-(hydroxymethyl)phenyl-O-CH(CH₂CH₂CH₃)-X₄ | X₂—O—CH₂—CH₃ | H | 1.14 | 433.3 | 434.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 103 | 3-{1-[6-(2,6-diethylphenyl)-4-ethoxypyridin-3-yl]butoxy}benzoic acid | H | | | H | | | | |
| 104 | 4-(3-{1-[6-(2,6-diethylphenyl)-3-ethoxypyridin-3-yl]butoxy}benzyl)morpholine | H | | | H | | | | |
| 105 | 1-(3-{1-[6-(2,6-diethylphenyl)-4-ethoxypyridin-3-yl]butoxy}phenyl)-N-methylmethanamine | H | | | H | | | | |
| 106 | 2-(2,6-diethylphenyl)-4-ethoxy-5-[1-(3-ethoxyphenyl)ethyl]pyridine | H | | | H | 1.21 | 419.2 | 420.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 107 | 2-(2,6-diethylphenyl)-4-ethoxy-5-[1-(pyridin-3-ylmethoxy)butyl]pyridine | H |  |  | H | | | | |
| 108 | methyl 3-[[6-(2,6-diethylphenyl)-4-ethoxy-2-methylpyridin-3-yl]methoxy]benzoate |  |  |  | H | | | | |
| 109 | (1R)-N-{[6-(2,6-diethylphenyl)-4-ethyl-2-methylpyridin-3-yl]methyl}-N-methyl-1,2,3,4-tetrahydronaphthalen-1-amine |  | 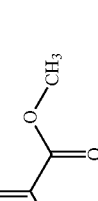 |  | H | 1.23 | 426.3 | 427.3 | 1 |
| 110 | (1R)-N-{[6-(2,6-diethylphenyl)-4-(3-methoxypropyl)-2-methylpyridin-3-yl]methyl}-N-methyl-1,2,3,4-tetrahydronaphthalen-1-amine |  |  |  | H | 1.22 | 470.3 | 471.3 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 111 | 4-[6-(2,6-diethylphenyl)-2-methyl-3-({methyl[(1R)-1,2,3,4-tetrahydronaphthalen-1-yl]amino}methyl)pyridin-4-yl]-2-methylbutan-2-ol |  |  |  | H | 1.22 | 484.3 | 485.4 | 1 |
| 112 | 4-[6-(2,6-diethylphenyl)-3-(1-ethoxybutyl)-2-methylpyridin-4-yl]-2-methylbutan-2-ol | 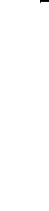 |  |  | H | 1.19 | 411.3 | 412.3 | 1 |
| 113 | 4-(3-{[6-(2,6-diethylphenyl)-4-ethoxy-2-methylpyridin-3-yl]methoxy}benzyl)morpholine |  | 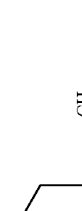 | 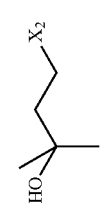 | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 114 | (1S)-N-[[6-(2,6-diethylphenyl)-4-[[(1S)-2-methoxy-1-methylethyl]oxy]-2-methylpyridin-3-yl]methyl]-N-methyl-1,2,3,4-tetrahydronaphthalen-1-amine | CH₃—X₁ | tetrahydronaphthalen-N(CH₃)-CH₂-X₄ | X₂—O—CH(CH₃)—CH₂—O—CH₃ | H | 1.1 | 486.3 | 487.4 | 1 |
| 115 | cyclohexyl[(2,6-diethylphenyl)-4-ethoxypyridin-3-yl]methyanone | H | cyclohexyl-C(=O)-X₄ | X₂—O—CH₂—CH₃ | H | 1.23 | 365.2 | 366.3 | 1 |
| 116 | (1S)-N-[[6-(2,6-diethylphenyl)-4-methoxy-2,5-dimethylpyridin-3-yl]methyl]-N-methyl-1,2,3,4-tetrahydronaphthalen-1-amine | CH₃—X₁ | tetrahydronaphthalen-N(CH₃)-CH₂-X₄ | X₂—O—CH₃ | X₃—CH₃ | 1.12 | 442.3 | 443.2 | 1 |
| 117 | 2-(2,6-diethylphenyl)-4-ethoxy-5-[1-(pyridin-3-yloxy)butyl]pyridine | H | H₃C-CH₂-CH₂-CH(X₄)-O-pyridin-3-yl | H₃C—CH₂—O—X₂ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 118 | 2-(2,6-diethylphenyl)-4-ethoxy-5-[1-(pyridin-2-yloxy)butyl]pyridine | H | | | H | 1.16 | 404.2 | 405.1 | 1 |
| 119 | 2-(2,6-diethylphenyl)-4-ethoxy-5-[1-(pyridin-2-yloxy)butyl]pyridine | H | | | H | 1.19 | 404.2 | 405.1 | 1 |
| 120 | 2-(2,6-diethylphenyl)-4-ethoxy-5-[1-(pyridin-4-yloxy)butyl]pyridine | H | | | H | 1.08 | 404.2 | 405.1 | 1 |
| 121 | 2-(2,6-diethylphenyl)-4-ethoxy-5-[1-(pyridin-4-ylmethoxy)butyl]pyridine | H | | | H | | | | |
| 122 | 2-(2,6-diethylphenyl)-4-ethoxy-5-[1-(pyridin-2-ylmethoxy)butyl]pyridine | H | | | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 123 | (2R,6S)-4-{[6-(2,6-diethylphenyl)-4-ethoxy-2-methylpyridin-3-yl]methyl}-2,6-dimethylmorpholine | CH₃—X₁ | 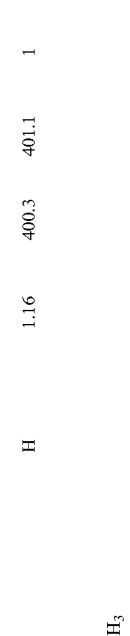 | X₂—O—CH₂CH₃ | H | 1.07 | 396.3 | 397.2 | 1 |
| 124 | 1-{[6-(2,6-diethylphenyl)-4-ethoxy-2-methylpyridin-3-yl]methyl}indoline | CH₃—X₁ |  | X₂—O—CH₂CH₃ | H | 1.16 | 400.3 | 401.1 | 1 |
| 125 | 2-(2,6-diethylphenyl)-4-ethoxy-5-(1-ethoxy-1-propylbutyl)pyridine | H | | H₃C—CH₂—O—X₂ | H | | | | |
| 126 | (1S)-N-{[6-(2,6-diethylphenyl)-4-{[(1R)-2-methoxy-1-methylethyl]oxy}-2-methylpyridin-3-yl]methyl}-N-methyl-1,2,3,4-tetrahydronaphthalen-1-amine | CH₃—X₁ |  | X₂—O—CH(CH₃)—CH₂—OCH₃ | H | 1.11 | 486.3 | 487.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 127 | 5-[cyclopentyl(ethoxy)methyl]-2-(2,6-diethylphenyl)-4-ethoxypyridine | H | cyclopentyl-CH(X4)-O-CH2CH3 | X2-O-CH2CH3 | H | 1.21 | 381.3 | 383.3 | 1 |
| 128 | 4-(2-{[5-[cyclohexyl(ethoxy)methyl]-2-(2,6-diethylphenyl)pyridin-4-yl]oxy}ethyl)morpholine | H | cyclohexyl-CH(X4)-O-CH2CH3 | morpholine-CH2CH2-O-X2 | H | 1.12 | 480.3 | 481.4 | 1 |
| 129 | (1S)-N-{[6-(2,6-diethylphenyl)-2-methyl-4-(tetrahydro-2H-pyran-4-yloxy)pyridin-3-yl]methyl}-N-methyl-1,2,3,4-tetrahydronaphthalen-1-amine | CH3-X1 | tetrahydronaphthalenyl-N(CH3)-CH2-X4 | X2-O-tetrahydropyran | H | 1.07 | 498.3 | 499.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 130 | 5-[(R)-cyclohexyl(ethoxy)methyl]-2-(2,6-diethylphenyl)-4-ethoxypyridine | H | cyclohexyl-CH(X4)-O-CH2-CH3 | X2-O-CH2-CH3 | H | 1.2 | 395.3 | 396.3 | 1 |
| 131 | 5-[(S)-cyclohexyl(ethoxy)methyl]-2-(2,6-diethylphenyl)-4-ethoxypyridine | H | cyclohexyl-CH(X4)-O-CH2-CH3 | X2-O-CH2-CH3 | H | 1.19 | 395.3 | 396.3 | 1 |
| 132 | 5-(Cyclohexyl-ethoxy-methyl)-2-(2,6-diethyl-phenyl)-4-isopropoxy-pyridine | H | cyclohexyl-CH(X4)-O-CH2-CH3 | X2-O-CH(CH3)2 | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 133 | 2-(2,6-diethylphenyl)-4-ethoxy-5-(1-methoxy-1-propylbutyl)pyridine | H | 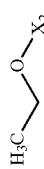 |  | H | 1.16 | 383.3 | 384.3 | 1 |
| 134 | 2-(2,6-diethylphenyl)-4-ethoxy-5-[(1Z)-1-propylbut-1-enyl]pyridine | H | 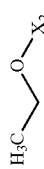 |  | H | 1.18 | 351.3 | 352.2 | 1 |
| 135 | 4-(cyclopentyloxy)-6-(2,6-diethylphenyl)-2-methyl-3-{[(6-methylpyridin-2-yl)oxy]methyl}pyridine | 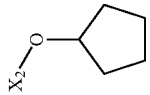 |  |  | H | | | | |
| 136 | 4-{[6-(2,6-diethylphenyl)-4-isopropoxy-2-methylpyridin-3-yl]methyl}-3,4-dihydro-2H-1,4-benzoxazine | 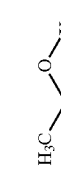 |  | | H | 1.14 | 430.3 | 431.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 137 | 1-{[6-(2,6-diethylphenyl)-4-isopropoxy-2-methylpyridin-3-yl]methyl}-4-ethoxyindoline | X1—CH3 (ethyl) | 4-ethoxyindoline-N-CH2-X4 | H3C-O-CH(CH3)-X2 (isopropoxy) | H | 1.18 | 458.3 | 459.3 | 1 |
| 138 | 1-{[6-(2,6-diethylphenyl)-4-isopropoxy-2-methylpyridin-3-yl]methyl}-6-ethoxyindoline | X1—CH3 (ethyl) | 6-ethoxyindoline-N-CH2-X4 | H3C-O-CH(CH3)-X2 (isopropoxy) | H | 1.18 | 458.3 | 459.3 | 1 |
| 139 | 2-(2,6-diethylphenyl)-5-[ethoxy(tetrahydro-2H-pyran-4-yl)methyl]-4-isopropoxypyridine | H | tetrahydropyran-4-yl-CH(O-CH2-CH3)-X4 | X2-O-CH(CH3)2 (isopropoxy) | H | 1.11 | 411.3 | 412.3 | 1 |

TABLE I-continued
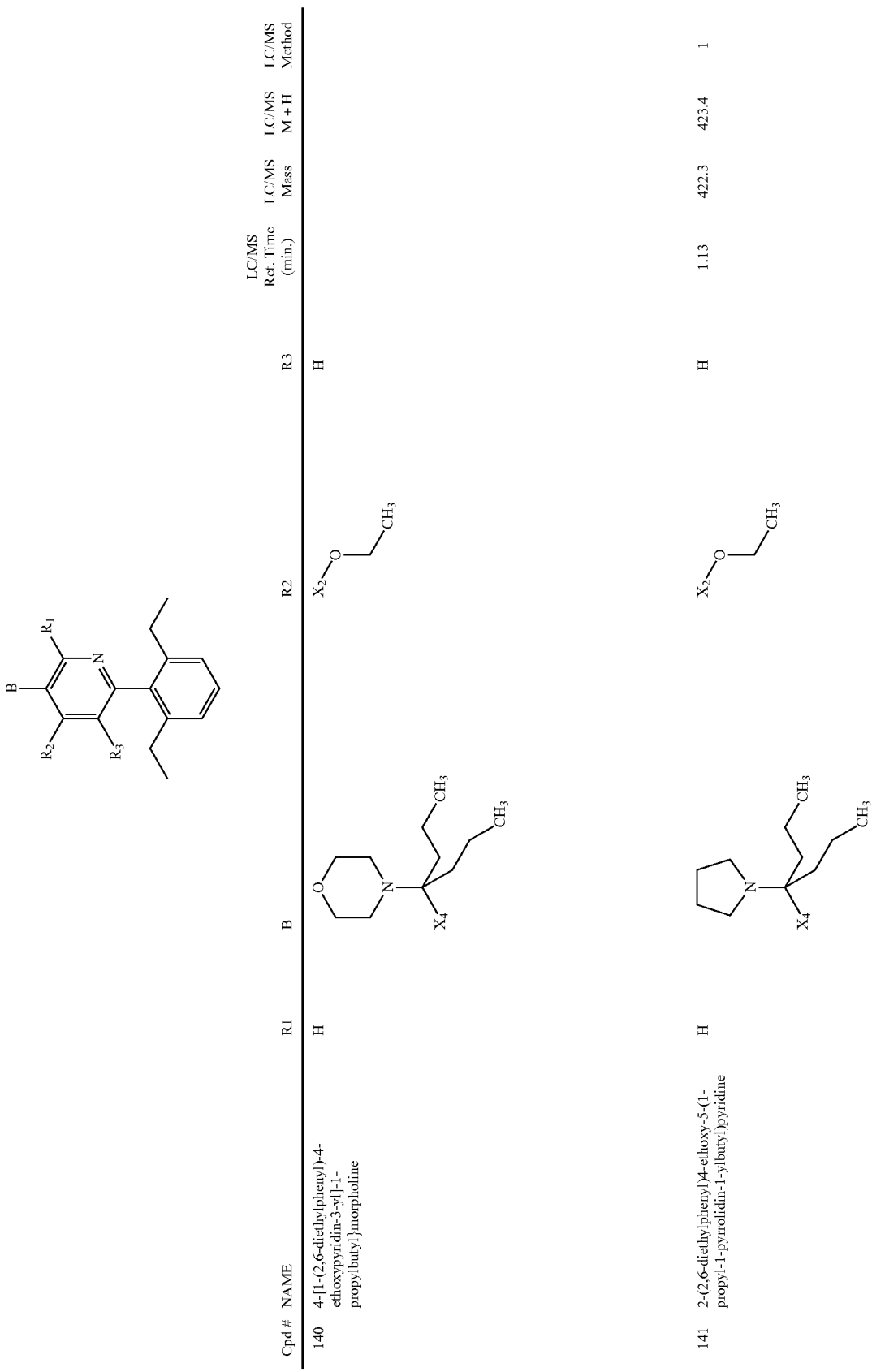
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 140 | 4-[1-(2,6-diethylphenyl)-4-ethoxypyridin-3-yl]-1-propylbutyl}morpholine | H | morpholine-N-C(X4)(CH2CH2CH3)(CH2CH2CH3) | X2—O—CH3 | H | | | | |
| 141 | 2-(2,6-diethylphenyl)4-ethoxy-5-(1-propyl-1-pyrrolidin-1-ylbutyl)pyridine | H | pyrrolidine-N-C(X4)(CH2CH2CH3)(CH2CH2CH3) | X2—O—CH3 | H | 1.13 | 422.3 | 423.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 142 | 4-[6-(2,6-diethylphenyl)-4-ethoxypyridin-3-yl]-N-propylheptan-4-amine | H | | $X_2$—O—CH$_3$ | H | | | | |
| 143 | 2-(2,6-diethylphenyl)-4-ethoxy-5-(1-piperidin-1-yl-1-propylbutyl)pyridine | H | | $X_2$—O—CH$_3$ | H | | | | |
| 144 | 2-(2,6-diethylphenyl)-5-[ethoxy(2-methylphenyl)methyl]-4-isopropoxypyridine | H | | H$_3$C—CH(O—$X_2$)—CH$_3$ | H | 1.17 | 417.3 | 418.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 145 | 2-{[6-(2,6-diethylphenyl)-2-methylpyridin-3-yl]methyl}-1-isobutyl-1,2,3,4-tetrahydroisoquinoline | X₁⁀CH₃ | [1-isobutyl-tetrahydroisoquinoline with N-CH₂-X₄] | CH₃-CH(OCH(CH₃)-X₂) (isopropoxy, via CH₃/H₃C-O-X₂) | H | 1.17 | 484.3 | 485.5 | 1 |
| 146 | 2-(2,6-diethylphenyl)-5-(1-propylbutyl)-4-[(3R)-tetrahydrofuran-3-yloxy]pyridine | H | CH(CH₂CH₂CH₃)₂ with X₄ | (3R)-tetrahydrofuran-3-yloxy (O-X₂) | H | 1.14 | 395.3 | 396.4 | 1 |
| 147 | N-(2-chlorobenzyl)-N-{[6-(2,6-diethylphenyl)-2-methyl-4-(tetrahydro-2H-pyran-4-yloxy)pyridin-3-yl]methyl}-N-methylamine | X₁⁀CH₃ | 2-chlorobenzyl-N(CH₃)-CH₂-X₄ | tetrahydro-2H-pyran-4-yloxy (O-X₂) | H | 1.07 | 492.3 | 493.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 148 | 2-{[6-(2,6-diethylphenyl)-2-methyl-4-(tetrahydro-2H-pyran-4-yloxy)pyridin-3-yl]methyl}-1-isobutyl-1,2,3,4-tetrahydroisoquinoline |  |  |  | H | 1.17 | 526.4 | 527.6 | 1 |
| 149 | 2-{[6-(2,6-diethylphenyl)-2-methyl-4-(tetrahydro-2H-pyran-4-yloxy)pyridin-3-yl]methyl}-1,2,3,4-tetrahydroisoquinoline |  |  |  | H | | | | |
| 150 | 2-{[6-(2,6-diethylphenyl)-2-methyl-4-(tetrahydro-2H-pyran-4-yloxy)pyridin-3-yl]methyl}-1-methyl-1,2,3,4-tetrahydroisoquinoline |  |  |  | H | 1.03 | 484.3 | 485.5 | 1 |

TABLE I-continued


| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 151 | 1-[6-(2,6-diethylphenyl)-2-methyl-4-(tetrahydro-2H-pyran-4-lyoxy)pyridin-3-yl]-N-methyl-N-[2-(trifluoromethyl)benzyl]methanamine | CH₃—X₁ |  |  | H | 1.13 | 526.3 | 527.5 | 1 |
| 152 | N-benzyl-N-{[6-(2,6-diethylphenyl)-2-methyl-4-(tetrahydro-2H-pyran-4-yloxy)pyridin-3-yl]methyl}-2-methylpropan-1-amine | CH₃—X₁ |  |  | H | 1.18 | 500.3 | 501.6 | 1 |
| 153 | 4-[cyclohexyl[6-(2,6-dsiethylphenyl)-4-ethoxypyridin-3-yl]methyl]morpholine | H |  |  | H | 1.15 | 436.3 | 437.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 154 | 2-(2,6-diethylphenyl)-5-(1-propylbutyl)-4-(tetrahydro-2H-pyran-4-yloxy)pyridine | H | [structure: CH3-CH2-CH(X4)-CH2-CH2-CH3] | [structure: X2-O-tetrahydropyran-4-yl] | H | 1.16 | 409.3 | 410.4 | 1 |
| 155 | 6-(2,6-diethylphenyl)-3-[(3,3-dimethylpiperidin-1-yl)methyl]-4-isopropoxy-2-methylpyridine | X1—CH3 | [structure: 3,3-dimethylpiperidin-1-ylmethyl-X4] | [structure: isopropoxy CH3-CH(CH3)-O-X2] | H | 1.03 | 408.3 | 409.4 | 1 |
| 156 | 2-{[6-(2,6-diethylphenyl)-4-isopropoxy-2-methylpyridin-3-yl]methyl}-1,2,3,4-tetrahydroisoquinoline | X1—CH3 | [structure: 1,2,3,4-tetrahydroisoquinolin-2-ylmethyl-X4] | [structure: isopropoxy CH3-CH(CH3)-O-X2] | H | 1.04 | 428.3 | 429.4 | 1 |
| 157 | 1-{[6-(2,6-diethylphenyl)-4-isopropoxy-2-methylpyridin-3-yl]methyl}-3,3,5-trimethylazepane | X1—CH3 | [structure: 3,3,5-trimethylazepan-1-ylmethyl-X4] | [structure: isopropoxy CH3-CH(CH3)-O-X2] | H | 1.08 | 436.3 | 437.5 | 1 |

TABLE I-continued

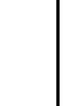

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 158 | N-benzyl-1-[6-(2,6-diethylphenyl)-4-isopropoxy-2-methylpyridin-3-yl]-N-methylmethanamine |  |  |  | H | 1.04 | 416.3 | 417.4 | 1 |
| 159 | N-benzyl-N-{[6-(2,6-diethylphenyl)-4-isopropoxy-2-methylpyridin-3-yl]methyl}ethanamine |  |  |  | H | 1.05 | 430.3 | 431.4 | 1 |
| 160 | N-benzyl-N-{[6-(2,6-diethylphenyl)-4-isopropoxy-2-methylpyridin-3-yl]methyl}propan-1-amine |  |  |  | H | 1.08 | 444.3 | 445.5 | 1 |
| 161 | N-benzyl-N-{[6-(2,6-diethylphenyl)-4-isopropoxy-2-methylpyridin-3-yl]methyl}propan-2-amine |  |  | | H | 1.06 | 444.3 | 445.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 162 | 1-butyl-2-{[6-(2,6-diethylphenyl)-2-methyl-4-pyran-4-yloxy)pyridin-3-yl]methyl}-1,2,3,4-tetrahydroisoquinoline | X₁—CH₃ | (1-butyl-tetrahydroisoquinoline with N–CH₂–X₄) | tetrahydropyran-4-yloxy (O–X₂) | H | | | | |
| 163 | 1-{[6-(2,6-diethylphenyl)-2-methyl-4-(tetrahydro-2H-pyran-4-yloxy)pyridin-3-yl]methyl}-3,3,5-trimethylazepane | X₁—CH₃ | 3,3,5-trimethylazepane (N–CH₂–X₄) | tetrahydropyran-4-yloxy (O–X₂) | H | 1.06 | 478.4 | 479.6 | 1 |
| 164 | 2-(2,6-Diethyl-phenyl)-5-(1-propyl-butyl)-4-(tetrahydro-furan-3-yloxy)-pyridine | H | heptan-4-yl (X₄) | tetrahydrofuran-3-yloxy (O–X₂) | H | | | | |

TABLE I-continued
| Cpd # | NAME | R1 | B | R2 | R3 | LC/MS Ret. Time (min.) | LC/MS Mass | LC/MS M+H | LC/MS Method |
|---|---|---|---|---|---|---|---|---|---|
| 165 | 1-[6-(2,6-diethylphenyl)-4-isopropoxy-2-methylpyridin-3-yl]-N-methyl-N-(2-methylbenzyl)methanamine |  |  |  | H | 1.07 | 430.3 | 431.5 | 1 |
| 166 | 1-[6-(2,6-diethylphenyl)-4-isopropoxy-2-methylpyridin-3-yl]-N-(2-fluorobenzyl)-N-methylmethanamine |  |  |  | H | 1.05 | 434.3 | 435.5 | 1 |
| 167 | N-(2-chlorobenzyl)-N-{[6-(2,6-diethylphenyl)-4-isopropoxy-2-methylpyridin-3-yl]methyl}-N-methylamine |  |  |  | H | 1.08 | 450.2 | 451.5 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 168 | 1-[6-(2,6-diethylphenyl)-2-isopropoxy-2-methylpyridin-3-yl]-N-methyl-N-[2-(trifluoromethyl)benzyl]methanamine |  |  |  | H | 1.15 | 484.3 | 485.5 | 1 |
| 169 | 2-(2,6-diethylphenyl)-5-[(1Z)-1-propylbut-1-enyl]-4-[(3R)-tetrahydrofuran-3-yloxy]pyridine | H |  |  | H | | | | |
| 170 | 4-(1-{6-(2,6-diethylphenyl)-4-[(3R)-tetrahydrofuran-3-yloxy]pyridin-3-yl}-1-propylbutyl)morpholine | H |  |  | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 171 | N-benzyl-N-{[6-(2,6-diethylphenyl)-2-methyl-4-(tetrahydro-2H-pyran-4-yloxy)pyridin-3-yl]methyl}propan-1-amine |  |  |  | H | | | | |
| 172 | N-benzyl-N-{[6-(2,6-diethylphenyl)-2-methyl-4-(tetrahydro-2H-pyran-4-yloxy)pyridin-3-yl]methyl}pentan-2-amine |  |  |  | H | | | | |
| 173 | 1-[6-(2,6-diethylphenyl)-4-isopropoxy-2-methylpyridin-3-yl]-N-methyl-N-(3-methylbenzyl)methanamine |  |  |  | H | 1.07 | 430.3 | 431.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 174 | 1-[6-(2,6-diethylphenyl)-4-isopropoxy-2-methylpyridin-3-yl]-N-(3-fluorobenzyl)-N-methylmethanamine |  |  |  | H | 1.06 | 434.3 | 435.5 | 1 |
| 175 | N-(3-chlorobenzyl)-N-{[6-(2,6-diethylphenyl)-4-isopropoxy-2-methylpyridin-3-yl]methyl}-N-methylamine |  | 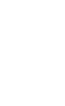 |  | H | 1.09 | 450.2 | 451.5 | 1 |
| 176 | 1-[6-(2,6-diethylphenyl)-4-isopropoxy-2-methylpyridin-3-yl]-N-methyl-N-[3-(trifluoromethyl)benzyl]methanamine |  | 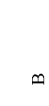 | 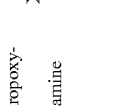 | H | 1.12 | 484.3 | 485.5 | 1 |
| 177 | 6-(2,6-diethylphenyl)-3-{[(3R,5S)-3,5-dimethylpyridin-1-yl]methyl}-4-ethoxy-2-methylpyridine |  | 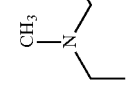 |  | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 178 | 6-(2,6-diethylphenyl)-3-{[(3S,5S)-3,5-dimethylpyridin-1-yl]methyl}-2-methyl-4-(tetrahydro-2H-pyran-4-yloxy)pyridine | X₁—CH₃ | (3S,5S)-3,5-dimethylpiperidinyl-CH₂-X₄ | tetrahydropyran-4-yl-O-X₂ | H | | | | |
| 179 | 6-(2,6-diethylphenyl)-3-{[(3S,5S)-3,5-dimethylpyridin-1-yl]methyl}-4-ethoxy-2-methylpyridine | X₁—CH₃ | (3S,5S)-3,5-dimethylpiperidinyl-CH₂-X₄ | H₃C—O—X₂ | H | | | | |
| 180 | 2-{[6-(2,6-diethylphenyl)-4-ethoxy-2-methylpyridin-3-yl]methyl}-1-isobutyl-1,2,3,4-tetrahydroisoquinoline | X₁—CH₃ | 1-isobutyl-1,2,3,4-tetrahydroisoquinolin-2-yl-CH₂-X₄ | H₃C—O—X₂ | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 181 | 3-{[6-(2,6-diethylphenyl)-2-methyl-3-({methyl[(1S)-1,2,3,4-tetrahydronaphthalen-1-yl]amino}methyl)pyridin-4-yl]oxy}cyclopentanol | CH₃—X₁ |  |  | H | 1.03 | 498.3 | 499.6 | 1 |
| 182 | N-{[6-(2,6-diethylphenyl)-4-ethoxy-2-methylpyridin-3-yl]methyl}-N-methyl-1,2-benzisothiazol-3-amine | CH₃—X₁ | (benzisothiazole-N(CH₃)-X₄) | X₂—O—CH₂CH₃ | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 183 | 1-{1-[6-(2,6-diethylphenyl)-4-ethoxypyridin-3-yl]-1-propylbutyl}-4-methylpiperazine | H |  |  | H | | | | |
| 184 | 1-[6-(2,6-diethylphenyl)-4-isopropoxy-2-methylpyridin-3-yl]-N-methyl-N-(4-methylbenzyl)methanamine | 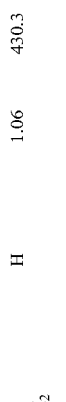 |  |  | H | 1.06 | 430.3 | 431.4 | 1 |
| 185 | 1-[6-(2,6-diethylphenyl)-4-isopropoxy-2-methylpyridin-3-yl]-N-(4-fluorobenzyl)-N-methylmethanamine | 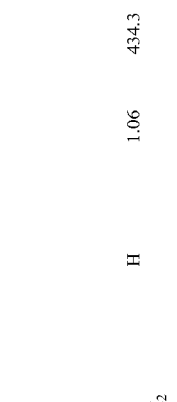 | 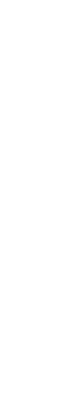 |  | H | 1.06 | 434.3 | 435.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 186 | N-(4-chlorobenzyl)-N-{[6-(2,6-diethylphenyl)-4-isopropoxy-2-methylpyridin-3-yl]methyl}-N-methylamine | $X_1$—CH$_3$ | 4-chlorobenzyl-N(CH$_3$)-CH$_2$-$X_4$ | H$_3$C-CH(O-$X_2$)-CH$_3$ | H | 1.09 | 450.2 | 451.4 | 1 |
| 187 | 1-[6-(2,6-diethylphenyl)-2-methylpyridin-3-yl]-N-methyl-N-[4-(trifluoromethyl)benzyl]methanamine | $X_1$—CH$_3$ | 4-(trifluoromethyl)benzyl-N(CH$_3$)-CH$_2$-$X_4$ | H$_3$C-CH(O-$X_2$)-CH$_3$ | H | 1.11 | 484.3 | 485.5 | 1 |
| 188 | (1R)-N-{[6-(2,6-diethylphenyl)-4-isobutyl-2-methylpyridin-3-yl]methyl}-N-methyl-1,2,3,4-tetrahydronaphthalen-1-amine | CH$_3$—$X_1$ | (1R)-tetrahydronaphthalen-1-yl-N(CH$_3$)-$X_4$ | (CH$_3$)$_2$CH-CH$_2$-$X_2$ | H | 1.23 | 454.3 | 455.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 189 | methyl 1-benzyl-4-[6-(2,6-diethylphenyl)-4-ethyl-2-methylpyridin-3-yl]pyrrolidine-3-carboxylate | CH₃—X₁ | (1-benzyl-pyrrolidine-3-carboxylate, methyl ester, X₄) | H₃C—X₂ (ethyl) | H | 1.08 | 470.3 | 471.5 | 1 |
| 190 | 6-(2,6-diethylphenyl)-4-isopropoxy-3-[(5-isopropoxy-2-methylphenoxy)methyl]-2-methylpyridine | X₁—CH₃ | (5-isopropoxy-2-methylphenoxymethyl, X₄) | CH₃/H₃C-CH-O-X₂ (isopropoxy) | H | 1.23 | 445.3 | 446.5 | 1 |
| 191 | 6-(2,6-diethylphenyl)-4-isopropoxy-2-methyl-3-[(3-methylpiperidin-1-yl)methyl]pyridine | X₁—CH₃ | (3-methylpiperidin-1-ylmethyl, X₄) | CH₃/H₃C-CH-O-X₂ (isopropoxy) | H | 1.02 | 394.3 | 395.4 | 1 |

TABLE I-continued

| Cpd # | NAME | R1 | B | R2 | R3 | LC/MS Ret. Time (min.) | LC/MS Mass | LC/MS M+H | LC/MS Method |
|---|---|---|---|---|---|---|---|---|---|
| 192 | N-{[6-(2,6-diethylphenyl)-4-ethoxy-2-methylpyridin-3-yl]methyl}-N-methylisoquinoline-1-amine | X₁—CH₃ | isoquinoline-N(CH₃)-CH₂-X₄ | H₃C—O—X₂ | H | | | | |
| 193 | 6-(2,6-diethylphenyl)-4-ethyl-2-methyl-3-[(1E)-3-oxo-3-piperidin-1-ylprop-1-enyl]pyridine | CH₃—X₁ | piperidine-C(O)-CH=CH-X₄ | H₃C—X₂ | H | 1.13 | 390.3 | 391.4 | 1 |
| 194 | 2-(2,6-diethylphenyl)-5-[1-(3,3-dimethylpiperidin-1-yl)butyl]-4-ethoxypyridine | H | 3,3-dimethylpiperidine-CH(propyl)-X₄ | H₃C—O—X₂ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 195 | 1-{[6-(2,6-diethylphenyl)-4-isopropoxy-2-methylpyridin-3-yl]methyl}decahydroquinoline | X₁–CH₃ | | | H | 1.04 | 434.3 | 435.5 | 1 |
| 196 | 2-(2,6-diethylphenyl)-5-(1,4-diethyl-1H-pyrazol-3-yl)-4-isopropoxypyridine | H | | | H | 1.12 | 391.3 | 392.4 | 1 |
| 197 | 2-(2,6-diethylphenyl)-5-(1,4-diethyl-1H-pyrazol-5-yl)-4-isopropoxypyridine | H | | | H | 1.17 | 391.3 | 392.4 | 1 |
| 198 | ethyl 1-{[6-(2,6-diethylphenyl)-4-isopropoxy-2-methylpyridin-3-yl]methyl}piperidine-2-carboxylate | X₁–CH₃ | | | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 199 | ethyl 1-{[6-(2,6-diethylphenyl)-4-methoxy-2-methylpyridin-3-yl]methyl}piperidine-2-carboxylate |  |  |  | H | | | | |
| 200 | 2-(2,6-diethylphenyl)-4-isopropoxy-5-(1-tetrahydro-2H-pyran-4-ylbutyl)pyridine | H |  |  | H | | | | |
| 201 | 3-{[(2-benzylpiperidin-1-yl)methyl]-6-(2,6-diethylphenyl)-4-isopropoxy-2-methylpyridine |  |  |  | H | 1.07 | 470.3 | 471.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 202 | 6-(2,6-diethylphenyl)-3-[(3-ethylpiperidin-1-yl)methyl]-4-isopropoxy-2-methylpyridine | X₁―CH₃ | (3-ethylpiperidin-1-yl)methyl with X₄ | H₃C-CH(CH₃)-O-X₂ | H | 1.05 | 408.3 | 409.5 | 1 |
| 203 | 2-(2,6-diethylphenyl)-5-{1-[(3S,5S)-3,5-dimethylpiperidin-1-yl]butyl}-4-ethoxypyridine | H | (3S,5S)-3,5-dimethylpiperidin-1-yl butyl with X₄ | H₃C-CH₂-O-X₂ | H | | | | |
| 204 | 2-(2,6-diethylphenyl)-5-{1-[(3R,5S)-3,5-dimethylpiperidin-1-yl]butyl}-4-ethoxypyridine | H | (3R,5S)-3,5-dimethylpiperidin-1-yl butyl with X₄ | H₃C-CH₂-O-X₂ | H | 1.13 | 422.3 | 423.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 205 | (1S)-N-{[6-(2,6-diethylphenyl)-4-ethyl-2-(4-methoxyphenyl)pyridin-3-yl]methyl}-N-methyl-1,2,3,4-tetrahydronaphthalen-1-amine | 4-methoxyphenyl-X₁ | tetrahydronaphthalenyl-N(CH₃)-CH₂-X₄ | X₂-CH₂-CH₃ | H | 1.26 | 518.3 | 519.3 | 1 |
| 206 | 6-(2,6-diethylphenyl)-4-isopropoxy-2-methyl-3-[(3-phenylpyrrolidin-1-yl)methyl]pyridine | X₁-CH₃ | 3-phenylpyrrolidin-1-yl-CH₂-X₄ | H₃C-CH(O-X₂)-CH₃ | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 207 | 6-(2,6-diethylphenyl)-2-methyl-3-[(3-phenylpyrrolidin-1-yl)methyl]pyridine | 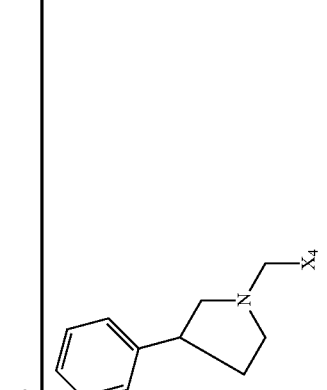 | 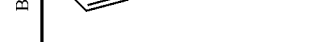 | H | H | | | | |
| 208 | N-{[6-(2,6-diethylphenyl)-4-isopropoxy-2-methylpyridin-3-yl]methyl}-6-methoxy-N-methylpyridin-2-amine |  | 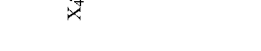 | 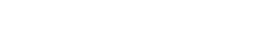 | H | | | | |
| 209 | 4-[6-(2,6-Diethyl-phenyl)-4-ethyl-2-methyl-pyridin-3-yl]-1-isobutyl-pyrrolidine-3-carboxylic acid methyl ester |  |  |  | H | 1.05 | 436.3 | 437.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 210 | methyl 4-[6-(2,6-diethyl)phenyl)-4-ethyl-2-methylpyridin-3-yl]-1-propylpyrrolidine-3-carboxylate | CH₃–X₁ | (pyrrolidine with propyl and methyl ester) | X₂–CH₃ (ethyl) | H | 1.08 | 422.3 | 423.3 | 1 |
| 211 | methyl 2-{1-[6-(2,6-diethylphenyl)-4-ethoxypyridin-3-yl]butyoxy}benzoate | H | (methyl benzoate with butyoxy) | H₃C–O–X₂ | H | | | | |
| 212 | 2-[6-(2,6-Diethyl-phenyl)-4-isopropoxy-2-methyl-pyridin-3-ylmethyl]-(3S)-1,2,3,4-tetrahydro-isoquinoline-3-carboxylic acid methyl ester | X₁–CH₃ | (tetrahydroisoquinoline methyl ester) | H₃C–O–X₂, CH₃ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 213 | [6-(2,6-Diethyl-phenyl)-4-methanesulfinyl]-methyl-pyridin-3-ylmethyl]-methyl-(1S)-(1,2,3,4-tetrahydro-naphthalen-1-yl)-amine | CH₃—X₁ | tetrahydronaphthalen-N(CH₃)-CH₂-X₄ | X₂—S(=O)—CH₃ | H | | | | |
| 214 | [6-(2,6-Diethyl-phenyl)-4-methanesulfonyl-methyl-pyridin-3-ylmethyl]-methyl-(1S)-(1,2,3,4-tetrahydro-naphthalen-1-yl)-amine | CH₃—X₁ | tetrahydronaphthalen-N(CH₃)-CH₂-X₄ | X₂—S(=O)(=O)—CH₃ | H | 1.15 | 476.2 | 477.2 | 1 |
| 215 | [6-(2,6-Diethyl-phenyl)-2-methyl-4-(3-morpholin-4-yl-propyl)-pyridin-3-ylmethyl]-methyl-(1S)-(1,2,3,4-tetrahydro-naphthalen-1-yl)-amine | CH₃—X₁ | tetrahydronaphthalen-N(CH₃)-CH₂-X₄ | morpholin-N-CH₂CH₂CH₂-X₂ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 216 | [6-(2,6-Diethyl-phenyl)-4-(3-dimethylamino-propyl)-2-methyl-pyridin-3-ylmethyl]-methyl-(1S)-(1,2,3,4-tetrahydro-naphthalen-1-yl)-amine | CH₃—X₁ | naphthalenyl-N(CH₃)-CH₂-X₄ | H₃C-N(CH₃)-CH₂CH₂CH₂-X₂ | H | | | | |
| 217 | 2-{[6-(2,6-Diethyl-phenyl)-4-isopropoxy-2-methyl-pyridin-3-ylmethyl]-methyl-amino}-nicotinonitrile | CH₃—X₁ | nicotinonitrile-N(CH₃)-CH₂-X₄ | H₃CCH(CH₃)-O-X₂ | H | | | | |

TABLE I-continued
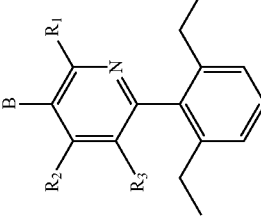
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 218 | 6-(2,6-Diethyl-phenyl)-3-[3-(4-methoxy-phenyl)-piperidin-1-ylmethyl]-2-methyl-pyridine |  |  | H | H | | | | |
| 219 | 6-(2,6-Diethyl-phenyl)-4-isopropoxy-3-[3-(2-methoxy-phenyl)-piperidin-1-ylmethyl]-2-methyl-pyridine |  |  |  | H | 1.09 | 486.3 | 487.3 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 220 | 6-(2,6-Diethyl-phenyl)-3-[3-(2-methoxy-phenyl)-piperidin-1-ylmethyl]-2-methyl-pyridine |  |  | H | H | | | | |
| 221 | 2-(2,6-Diethyl-phenyl)-4-isopropoxy-3-[3-(4-methoxy-phenyl)-piperidin-1-ylmethyl]-2-methyl-pyridine |  | 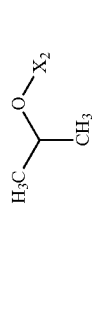 |  | H | | | | |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 222 | 6-(2,6-Diethyl-phenyl)-4-isopropoxy-2-methyl-3-(3-phenyl-piperidin-1-ylmethyl)-pyridine |  |  |  | H | 1.09 | 456.3 | 457.3 | 1 |
| 223 | 3-[6-(2,6-Diethyl-phenyl)-4-isopropoxy-2-methyl-pyridin-3-ylmethoxy]-4-methyl-benzoic acid methyl ester |  |  |  | H | | | | |
| 224 | 2-[6-(2,6-Diethyl-phenyl)-4-isopropoxy-2-methyl-pyridin-3-ylmethyl]-1,2,3,4-tetrahydro-isoquinoline-3-carboxylic acid |  |  |  | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 225 | 1-[6-(2,6-Diethyl-phenyl)-4-isopropoxy-2-methyl-pyridin-3-ylmethyl]-2,3-dihydro-1H-pyrrolo[2,3-b]pyridine | CH₃—X₁ | | | H | | | | |
| 226 | 2-[6-(2,6-Diethyl-phenyl)-4-isopropoxy-2-methyl-pyridin-3-ylmethoxy]-4-methyl-benzoic acid methyl ester | CH₃—X₁ | | | H | 1.17 | 461.3 | 462.2 | 1 |
| 227 | [6-(2,6-Diethyl-phenyl)-4-(1,4-dioxa-spiro[4.5]dec-8-yloxy)-2-methyl-pyridin-3-ylmethyl]-methyl-(1S)-(1,2,3,4-tetrahydro-naphthalen-1-yl)-amine | CH₃—X₁ | | | H | 1.1 | 554.4 | 555.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 228 | 4-(6-(2,6-Diethyl-phenyl)-2-methyl-3-{[methyl-(1S)-(1,2,3,4-tetrahydro-naphthalen-1-yl)-amino]-methyl}-pyridin-4-yloxy)-cyclohexanone | CH₃—X₁ | | | H | | | | |
| 229 | 1-{2-[6-(2,6-Diethyl-phenyl)-4-isopropoxy-2-methyl-pyridin-3-ylmethoxy]-4-methyl-phenyl}-ethanone | CH₃—X₁ | | | H | 1.14 | 445.3 | 446.3 | 1 |
| 230 | 4-(6-(2,6-Diethyl-phenyl)-2-methyl-3-{[methyl-(1S)-(1,2,3,4-tetrahydro-naphthalen-1-yl)-amino]-methyl}-pyridin-4-yloxy)-1-methyl-cyclohexanol | CH₃—X₁ | | | H | 1.11 | 526.4 | 527.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 231 | 6-(2,6-Diethyl-phenyl)-3-(3-ethyl-6-methyl-pyridin-2-yloxymethyl)-4-isopropoxy-2-methyl-pyridine | CH₃—X₁ | (3-ethyl-6-methyl-pyridin-2-yloxymethyl) | X₂—O—CH(CH₃)₂ | H | | | | |
| 232 | 6-(2,6-Diethyl-phenyl)-4-isopropoxy-2-methyl-3-(2-[1,3,4]oxadiazol-2-yl-phenoxymethyl)-pyridine | CH₃—X₁ | (2-[1,3,4]oxadiazol-2-yl-phenoxymethyl) | X₂—O—CH(CH₃)₂ | H | 1.14 | 457.2 | 458.3 | 1 |
| 233 | 4-{1-[6-(2,6-Diethyl-phenyl)-4-ethoxy-pyridin-3-yl]-butyl}-(2R,6R)-2,6-dimethyl-morpholine | H | (2R,6R)-2,6-dimethyl-morpholinyl-butyl | X₂—O—CH₂CH₃ | H | 1.17 | 424.3 | 425.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 234 | 4-{1-[6-(2,6-Diethyl-phenyl)-4-ethoxy-pyridin-3-yl]-butyl}-(2R,6R)-2,6-dimethyl-morpholine | H | | | H | 1.15 | 424.3 | 425.3 | 1 |
| 235 | 4-{1-[6-(2,6-Diethyl-phenyl)-4-ethoxy-pyridin-3-yl]-butyl}-(2S,6S)-2,6-dimethyl-morpholine | H | | | H | 1.16 | 424.3 | 425.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 236 | 4-{1-[6-(2,6-Diethyl-phenyl)-4-ethoxy-pyridin-3-yl]-butyl}-(2S,6S)-2,6-dimethyl-morpholine | H | | | H | 1.16 | 424.3 | 425.3 | 1 |
| 237 | {3-[6-(2,6-Diethyl-phenyl)-4-isopropoxy-2-methyl-pyridin-3-ylmethoxy]-4-methyl-phenyl}-morpholin-4-yl-methanone | CH₃—X₁ | | | H | | | | |

TABLE I-continued

| Cpd # | NAME | R1 | B | R2 | R3 | LC/MS Ret. Time (min.) | LC/MS Mass | LC/MS M+H | LC/MS Method |
|---|---|---|---|---|---|---|---|---|---|
| 238 | {3-[6-(2,6-Diethyl-phenyl)-4-isopropoxy-2-methyl-pyridin-3-ylmethoxy]-4-methyl-phenyl}-pyrrolidin-1-yl-methanone | CH₃—X₁ | (pyrrolidinyl carbonyl-methylphenyl-OX₄) | X₂—O—CH(CH₃)₂ | H | | | | |
| 239 | {3-[6-(2,6-Diethyl-phenyl)-4-isopropoxy-2-methyl-pyridin-3-ylmethoxy]-4-methyl-phenyl}-(4-methyl-piperazin-1-yl)-methanone | CH₃—X₁ | (4-methylpiperazinyl carbonyl-methylphenyl-OX₄) | X₂—O—CH(CH₃)₂ | H | | | | |

TABLE I-continued

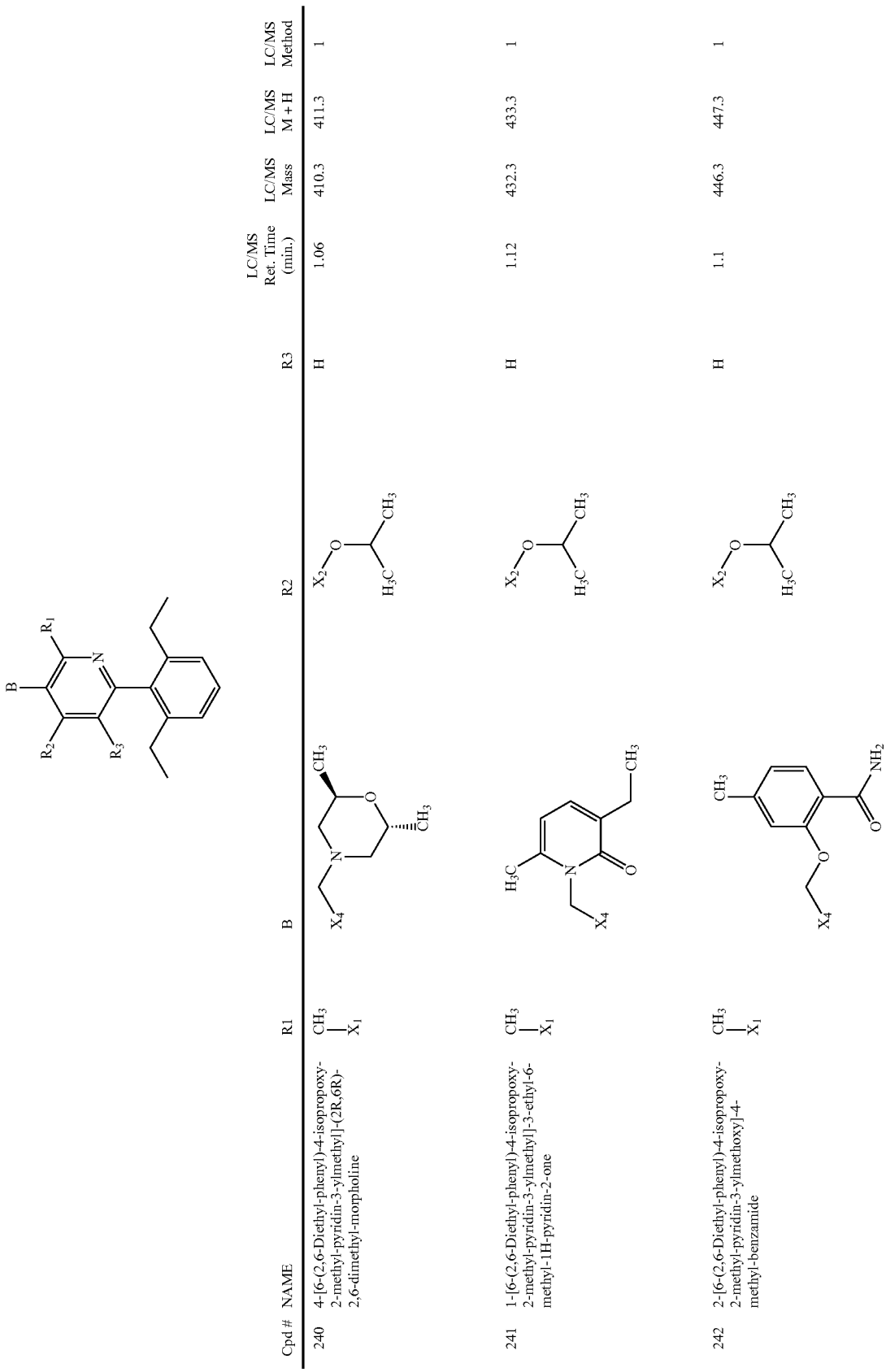

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 240 | 4-[6-(2,6-Diethyl-phenyl)-4-isopropoxy-2-methyl-pyridin-3-ylmethyl]-(2R,6R)-2,6-dimethyl-morpholine | CH₃—X₁ | (2R,6R)-2,6-dimethylmorpholine-N-CH₂-X₄ | X₂—O-CH(CH₃)₂ | H | 1.06 | 410.3 | 411.3 | 1 |
| 241 | 1-[6-(2,6-Diethyl-phenyl)-4-isopropoxy-2-methyl-pyridin-3-ylmethyl]-3-ethyl-6-methyl-1H-pyridin-2-one | CH₃—X₁ | 3-ethyl-6-methyl-pyridin-2(1H)-one-N-CH₂-X₄ | X₂—O-CH(CH₃)₂ | H | 1.12 | 432.3 | 433.3 | 1 |
| 242 | 2-[6-(2,6-Diethyl-phenyl)-4-isopropoxy-2-methyl-pyridin-3-ylmethoxy]-4-methyl-benzamide | CH₃—X₁ | 4-methyl-2-(OCH₂-X₄)-benzamide | X₂—O-CH(CH₃)₂ | H | 1.1 | 446.3 | 447.3 | 1 |

TABLE I-continued
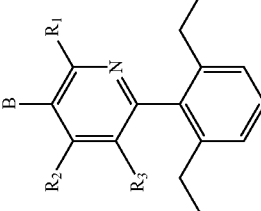
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 243 | 2-[6-(2,6-Diethyl-phenyl)-4-isopropoxy-2-methyl-pyridin-3-ylmethoxy]-4,N-dimethyl-benzamide |  | 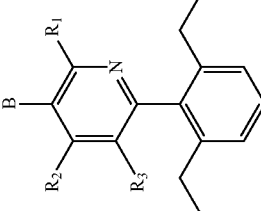 |  | H | | | | |
| 244 | {2-[6-(2,6-Diethyl-phenyl)-4-isopropoxy-2-methyl-pyridin-3-ylmethoxy]-4-methyl-phenyl}-pyrrolidin-1-yl-methanone | 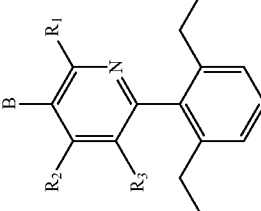 |  |  | H | 1.13 | 500.3 | 501.3 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 245 | 6-(2,6-Diethyl-phenyl)-4-isopropoxy-3-(2-methanesulfonyl-phenoxymethyl)-2-methyl-pyridine |  |  |  | H | 1.1 | 467.2 | 468.2 | 1 |
| 246 | 6-(2,6-Diethyl-phenyl)-4-isopropoxy-3-(2-methanesulfinyl-phenoxymethyl)-2-methyl-pyridine |  |  |  | H | | | | |
| 247 | 6-(2,6-Diethyl-phenyl)-3-[2-(3,4-dimethoxy-phenyl)-piperidin-1-ylmethyl]-4-isopropoxy-2-methyl-pyridine |  |  |  | H | 1.05 | 516.3 | 517.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 248 | N-[6-(2,6-Diethyl-phenyl)-3-(1-isobutyl-3,4-dihydro-1H-isoquinolin-2-ylmethyl)-2-methyl-pyridin-4-ylmethyl]-N-methanesulfonyl-methanesulfonamide | CH₃—X₁ | (1-isobutyl-3,4-dihydroisoquinolin-2-ylmethyl, X₄) | X₂—CH₂—N(SO₂CH₃)₂ | H | | | | |
| 249 | 4-[6-(2,6-Diethyl-phenyl)-4-isopropoxy-2-methyl-pyridin-3-ylmethyl]-6-methyl-3,4-dihydro-2H-pyrido[3,2-b][1,4]oxazine | X₁—CH₃ | (6-methyl-3,4-dihydro-2H-pyrido[3,2-b][1,4]oxazin-4-yl, X₄) | H₃C—CH(X₂)—O—CH₃ (isopropoxy) | H | 1.08 | 445.3 | 446.3 | 1 |
| 250 | 3-[6-(2,6-Diethyl-phenyl)-2-methyl-pyridin-3-ylmethoxy]-4,N-dimethyl-benzamide | CH₃—X₁ | (3-(X₄-methoxy)-4-methyl-N-methyl-benzamide) | X₂—O—CH(CH₃)₂ | H | | | | |

TABLE I-continued

| Cpd # | NAME | R1 | B | R2 | R3 | LC/MS Ret. Time (min.) | LC/MS Mass | LC/MS M+H | LC/MS Method |
|---|---|---|---|---|---|---|---|---|---|
| 251 | 3-[6-(2,6-Diethyl-phenyl)-4-isopropoxy-2-methyl-pyridin-3-ylmethoxy]-N-ethyl-4-methyl-benzamide | CH$_3$—X$_1$ | H$_3$C-NH-C(=O)-Ar(4-CH$_3$, 3-OCH$_2$-X$_4$) | X$_2$-O-CH(CH$_3$)$_2$ | H | | | | |
| 252 | 3-[6-(2,6-Diethyl-phenyl)-4-isopropoxy-2-methyl-pyridin-3-ylmethoxy]-4,N,N-trimethyl-benzamide | CH$_3$—X$_1$ | (CH$_3$)$_2$N-C(=O)-Ar(4-CH$_3$, 3-OCH$_2$-X$_4$) | X$_2$-O-CH(CH$_3$)$_2$ | H | | | | |

TABLE I-continued

| Cpd # | NAME | B | R1 | R2 | R3 | LC/MS Ret. Time (min.) | LC/MS Mass | LC/MS M+H | LC/MS Method |
|---|---|---|---|---|---|---|---|---|---|
| 253 | 4-[4-Cyclopentyloxy-6-(2,6-diethyl-phenyl)-2-methyl-pyridin-3-ylmethyl]-6-methyl-3,4-dihydro-2H-pyrido[3,2-b][1,4]oxazine | | CH₃—X₁ | X₂—O—cyclopentyl | H | 1.14 | 471.3 | 472.3 | 1 |
| 254 | 4-(6-(2,6-Diethyl-phenyl)-2-methyl-3-{[methyl-(1S)-(1,2,3,4-tetrahydro-naphthalen-1-yl)-amino]-methyl}-pyridin-4-yloxy)-1-methyl-cyclohexanol | | CH₃—X₁ | X₂—O—(4-hydroxy-4-methylcyclohexyl) | H | | | | |
| 255 | 2-[6-(2,6-Diethyl-phenyl)-2-methyl-4-morpholin-4-ylmethyl-pyridin-3-ylmethyl]-1-isobutyl-1,2,3,4-tetrahydro-isoquinoline | | CH₃—X₁ | X₂—morpholine | H | 1.16 | 525.4 | 526.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 256 | 1-Benzyl-4-[6-(2,6-diethyl-phenyl)-4-ethyl-2-methyl-pyridin-3-yl]-pyrrolidine-3-carboxylic acid propylamide | CH₃—X₁ | | H₃C—X₂ | H | 1.12 | 497.3 | 498.4 | 1 |
| 257 | 1-Benzyl-4-[6-(2,6-diethyl-phenyl)-4-ethyl-2-methyl-pyridin-3-yl]-pyrrolidine-3-carboxylic acid diethylamide | CH₃—X₁ | | H₃C—X₂ | H | 1.14 | 511.4 | 512.4 | 1 |
| 258 | {1-Benzyl-4-[6-(2,6-diethyl-phenyl)-4-ethyl-2-methyl-pyridin-3-yl]-pyrrolidin-3-yl]}-pyrrolidin-1-yl-methanone | CH₃—X₁ | | H₃C—X₂ | H | 1.16 | 511.4 | 512.4 | 1 |

TABLE I-continued
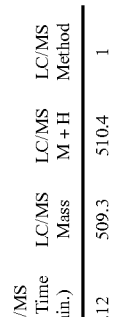
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 259 | 2-[6-(2,6-Diethyl-phenyl)-4-isopropoxy-2-methyl-pyridin-3-ylmethoxy]-6-methyl-nicotinonitrile | CH₃—X₁ |  |  | H | 1.12 | 509.3 | 510.4 | 1 |
| 260 | 2-[6-(2,6-Diethyl-phenyl)-4-isopropoxy-2-methyl-pyridin-3-ylmethoxy]-6-methyl-nicotinonitrile | CH₃—X₁ | 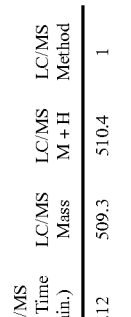 |  | H | 1.13 | 429.2 | 430.2 | 1 |
| 261 | 1-{2-[6-(2,6-Diethyl-phenyl)-4-isopropoxy-2-methyl-pyridin-3-ylmethoxy]-4-methoxy-phenyl}-ethanone | CH₃—X₁ |  |  | H | 1.13 | 461.3 | 462.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 262 | 4-{1-[6-(2,6-Diethyl-phenyl)-4-ethoxy-pyridin-3-yl]-ethyl}-(2R,6R)-2,6-dimethyl-morpholine | H | | | H | 1.07 | 396.3 | 397.3 | 1 |
| 263 | 2-(4-{1-[6-(2,6-Diethyl-phenyl)-4-ethoxy-pyridin-3-yl]-ethyl]-piperazin-1-yl)-ethanol | H | | | H | 1.01 | 411.3 | 412.3 | 1 |
| 264 | 2-{[6-(2,6-Diethyl-phenyl)-4-isopropoxy-2-methyl-pyridin-3-yl]methyl]-methyl-amino}-6-methyl-nicotinonitrile | CH₃—X₁ | | | H | 1.13 | 442.3 | 443.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 265 | 4-{2-[6-(2,6-Diethyl-phenyl)-3-(5-isopropyl-2-methyl-phenoxymethyl)-2-methyl-pyridin-4-yloxy]-propyl}-morpholine | CH₃—X₁ | | | H | 1.12 | 530.4 | 531.4 | 1 |
| 266 | 6-(2,6-Diethyl-phenyl)-4-(1-ethyl-pyrrolidin-3-yloxy)-3-(5-isopropyl-2-methyl-phenoxymethyl)-2-methyl-pyridine | CH₃—X₁ | | | H | 1.11 | 500.3 | 501.4 | 1 |
| 267 | 4-[6-(2,6-Diethyl-phenyl)-3-(2,6-dimethyl-morpholin-4-ylmethyl)-2-methyl-pyridin-4-yloxy]-cyclohexanone | CH₃—X₁ | | | H | 1.09 | 464.3 | 497.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 268 | 4-[6-(2,6-Diethyl-phenyl)-3-((2R,6R)-2,6-dimethyl-morpholin-4-ylmethyl)-2-methyl-pyridin-4-yloxy]-1-methyl-cyclohexanol | CH₃—X₁ | 2,6-dimethylmorpholine-CH₂-X₄ | 4-oxy-1-methylcyclohexanol | H | | | | |
| 269 | 2-[6-(2,6-Diethyl-phenyl)-4-(1,4-dioxa-8-aza-spiro[4.5]dec-8-ylmethyl)-2-methyl-pyridin-3-ylmethyl]-1-isobutyl-1,2,3,4-tetrahydro-isoquinoline | CH₃—X₁ | 1-isobutyl-tetrahydroisoquinoline-CH₂-X₄ | 1,4-dioxa-8-aza-spiro[4.5]dec-8-ylmethyl-X₂ | H | 1.24 | 581.4 | 582.4 | 1 |
| 270 | N-[6-(2,6-Diethyl-phenyl)-3-(1-isobutyl-3,4-dihydro-1H-isoquinolin-2-ylmethyl)-2-methyl-pyridin-4-ylmethyl]-methanesulfonamide | CH₃—X₁ | 1-isobutyl-tetrahydroisoquinoline-CH₂-X₄ | X₂-CH₂CH₂-N(H)-SO₂-CH₃ | H | 1.24 | 533.3 | 534.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 271 | 1-[6-(2,6-Diethyl-phenyl)-3-(1-isobutyl-3,4-dihydro-1H-isoquinolin-2-ylmethyl)-2-methyl-pyridin-4-ylmethyl]-piperidin-4-one | CH₃—X₁ | (1-isobutyl-3,4-dihydroisoquinolin-2-yl group at X₄) | X₂—CH₂—(piperidin-4-one) | H | 0.7 | 537.4 | 309.0 | 1 |
| 272 | {2-[6-(2,6-Diethyl-phenyl)-4-isopropoxy-2-methyl-pyridin-3-ylmethoxy]-4-methyl-phenyl}-methanol | CH₃—X₁ | (2-methoxymethyl-4-methylphenyloxy at X₄) | X₂—O—CH(CH₃)₂ | H | 1.18 | 433.3 | 434.2 | 1 |
| 273 | 4-[6-(2,6-Diethyl-phenyl)-2,4-dimethyl-pyridin-3-ylmethyl]-(2R,6R)-2,6-dimethyl-morpholine | CH₃—X₁ | ((2R,6R)-2,6-dimethylmorpholin-4-ylmethyl at X₄) | X₂—CH₃ | H | 1.16 | 366.3 | 367.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 274 | 4-[6-(2,6-Diethyl-phenyl)-3-((2R,6R)-2,6-dimethyl-morpholin-4-ylmethyl)-2-methyl-pyridin-4-yloxy]-1-methyl-cyclohexanol | CH₃—X₁ | | X₂—O—(cyclohexyl with OH, CH₃) | H | | | | |
| 275 | 4-{2-[6-(2,6-Diethyl-phenyl)-3-(5-isopropyl-2-methyl-phenoxymethyl)-2-methyl-pyridin-4-yloxy]-ethyl}-morpholine | CH₃—X₁ | | X₂—O—CH₂CH₂—morpholine | H | 1.15 | 516.3 | 517.3 | 1 |
| 276 | 4-{2-[6-(2,6-Diethyl-phenyl)-3-(3-ethyl-6-methyl-pyridin-2-yloxymethyl)-2-methyl-pyridin-4-yloxy]-ethyl}-morpholine | CH₃—X₁ | | X₂—O—CH₂CH₂—morpholine | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 277 | N-[6-(2,6-Diethyl-phenyl)-3-(1-isobutyl-3,4-dihydro-1H-isoquinolin-2-ylmethyl)-2-methyl-pyridin-4-ylmethyl]-2-morpholin-4-yl-acetamide | CH₃—X₁ | 1-isobutyl-3,4-dihydroisoquinoline with X₄ on N | X₂—CH₂C(O)N(H)CH₂-morpholine | H | | | | |
| 278 | 4-[6-(2,6-Diethyl-phenyl)-4-methoxy-2-trifluoromethyl-pyridin-3-ylmethyl]-(2R,6R)-2,6-dimethyl-morpholine | CF₃—X₁ | (2R,6R)-2,6-dimethylmorpholine with X₄ on N | X₂—OCH₃ | H | 1.19 | 436.2 | 437.2 | 1 |
| 279 | 1-{2-[6-(2,6-Diethyl-phenyl)-2-methyl-4-(2-morpholin-4-yl-ethoxy)-pyridin-3-ylmethoxy]-4-methoxy-phenyl}-ethanone | CH₃—X₁ | 4-methoxy-2-(acetyl)phenoxy with X₄ | X₂—OCH₂CH₂-morpholine | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 280 | 1-{2-[4-(2-Diethylamino-1-methyl-ethoxy)-6-(2,6-diethyl-phenyl)-2-methyl-pyridin-3-ylmethoxy]-4-methoxy-phenyl}-ethanone | CH₃—X₁ | (4-acetyl-3-methoxyphenoxymethyl group) | X₂—O—CH(CH₃)—CH₂—N(CH₂CH₃)₂ | H | | | | |
| 281 | 4-[6-(2,6-Diethyl-phenyl)-4-isopropoxy-2-methyl-pyridin-3-ylmethyl]-2,2-dimethyl-morpholine | CH₃—X₁ | (2,2-dimethylmorpholin-4-ylmethyl, X₄) | X₂—O—CH(CH₃)₂ | H | 1.11 | 410.3 | 411.3 | 1 |
| 282 | 4-[6-(2,6-Diethyl-phenyl)-3-(5-isopropyl-2-methyl-phenoxymethyl)-4-methyl-pyridin-2-ylmethyl]-morpholine | X₁—(morpholin-4-ylmethyl) | (5-isopropyl-2-methylphenoxymethyl, X₄) | CH₃—X₂ | H | 1.3 | 486.3 | 487.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 283 | N-[6-(2,6-Diethyl-phenyl)-3-(5-isopropyl-2-methyl-phenoxymethyl)-2-methyl-pyridin-4-ylmethyl]-methanesulfonamide | CH₃—X₁ | 5-isopropyl-2-methyl-phenoxymethyl group | X₂—NH—SO₂CH₃ (ethyl linker) | H | | | | |
| 284 | 4-[6-(2,6-Diethyl-phenyl)-3-(5-isopropyl-2-methyl-phenoxymethyl)-2-methyl-pyridin-4-ylmethyl]-morpholine | CH₃—X₁ | 5-isopropyl-2-methyl-phenoxymethyl group | X₂-morpholine | H | 1.23 | 486.3 | 487.5 | 1 |
| 285 | 4-[6-(2,6-Diethyl-phenyl)-4-methoxy-2-trifluoromethyl-pyridin-3-ylmethyl]-(2S,6S)-2,6-dimethyl-morpholine | CF₃—X₁ | (2S,6S)-2,6-dimethyl-morpholine-X₄ | X₂—O—CH₃ | H | 1.13 | 436.2 | 437.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 286 | 6-(2,6-Diethyl-phenyl)-3-(2-isoxazol-5-yl-5-methoxy-phenoxymethyl)-2,4-dimethyl-pyridine | CH₃—X₁ | (structure) | X₂—CH₃ | H | | | | |
| 287 | N-[6-(2,6-Diethyl-phenyl)-3-((2R,6R)-2,6-dimethyl-morpholin-4-ylmethyl)-2-methyl-pyridin-4-ylmethyl]-methanesulfonamide | CH₃—X₁ | (structure) | (structure) | H | 1.06 | 459.3 | 460.4 | 1 |
| 288 | 2-[6-(2,6-Diethyl-phenyl)-4-isopropoxy-2-methyl-pyridin-3-ylmethoxy]-4-methyl-benzenesulfonamide | CH₃—X₁ | (structure) | (structure) | H | 1.14 | 482.2 | 483.2 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 289 | 4-[6-(2,6-Diethyl-phenyl)-4-isopropoxy-2-methyl-pyridin-3-ylmethyl]-2-ethoxy-morpholine | 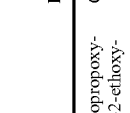 | 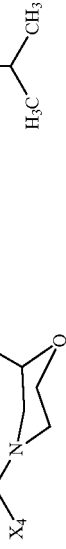 |  | H | 1.1 | 426.3 | 427.3 | 1 |
| 290 | 6-(2,6-Diethyl-phenyl)-2,4-dimethyl-3-(5-methyl-2-oxazol-5-yl-phenoxymethyl)-pyridine |  |  |  | H | 1.21 | 426.2 | 427.2 | 1 |
| 291 | {2-[6-(2,6-Diethyl-phenyl)-3-(92R,6R)-2,6-dimethyl-morpholin-4-ylmethyl)-2-methyl-pyridin-4-yloxy]-ethyl}-dimethyl-amine |  |  | 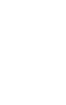 | H | 1.01 | 439.3 | 440.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 292 | {2-[6-(2,6-Dimethyl-phenyl)-3-(5-isopropyl-2-methyl-phenoxymethyl)-2-methyl-pyridin-4-yloxy]-ethyl}-dimethyl-amine | CH₃—X₁ | (5-isopropyl-2-methyl-phenoxymethyl group) | X₂—O—CH₂CH₂—N(CH₃)₂ | H | | | | |
| 293 | {2-[6-(2,6-Diethyl-phenyl)-3-(5-isopropyl-2-methyl-phenoxymethyl)-2-trifluoromethyl-pyridin-4-yloxy]-ethyl}-dimethyl-amine | CF₃—X₁ | (5-isopropyl-2-methyl-phenoxymethyl group) | X₂—O—CH₂CH₂—N(CH₃)₂ | H | 1.29 | 528.3 | 529.3 | 1 |
| 294 | 4-[6-(2,6-Diethyl-phenyl)-4-(1-ethyl-pyrrolidin-3-yloxy)-2-methyl-pyridin-3-ylmethyl]-(2R,6R)-2,6-dimethyl-morpholine | CH₃—X₁ | (2R,6R)-2,6-dimethyl-morpholinylmethyl | X₂—O-(1-ethyl-pyrrolidin-3-yl) | H | 1.01 | 465.3 | 466.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 295 | 4-[6-(2,6-Diethyl-phenyl)-2-methyl-4-(pyridin-3-yloxy)-pyridin-3-ylmethyl]-(2R,6R)-2,6-dimethyl-morpholine | CH₃—X₁ | (2,6-dimethyl-morpholine-N-CH₂-X₄) | X₂—O—(pyridin-3-yl) | H | 1.14 | 445.3 | 446.3 | 1 |
| 296 | 6-(2,6-Diethyl-phenyl)-3-(3-ethyl-6-methyl-pyridin-2-yloxymethyl)-2-methyl-4-(pyridin-3-yloxy)-pyridine | CH₃—X₁ | (6-methyl-3-ethyl-pyridin-2-yl)-O-CH₂-X₄ | X₂—O—(pyridin-3-yl) | H | | | | |
| 297 | 4-[6-(2,6-Diethyl-phenyl)-3-(5-isopropyl-2-methyl-phenoxymethyl)-2-methyl-pyridin-4-ylmethyl]-thiomorpholine 1,1-dioxide | CH₃—X₁ | (5-isopropyl-2-methyl-phenyl)-O-CH₂-X₄ | X₂—CH₂—(thiomorpholine-1,1-dioxide) | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 298 | N-[6-(2,6-Diethyl-phenyl)-3-((2R,6R)-2,6-dimethyl-morpholin-4-ylmethyl)-2-methyl-pyridin-4-ylmethyl]-N-methyl-methanesulfonamide | CH₃—X₁ | (2R,6R)-2,6-dimethylmorpholine-N-CH₂-X₄ | X₂-CH₂-N(CH₃)SO₂CH₃ | H | 1.14 | 473.3 | 474.3 | 1 |
| 299 | 6-(2,6-Diethyl-phenyl)-3-(3-ethyl-6-methyl-pyridin-2-yloxymethyl)-4-(1-ethyl-pyrrolidin-2-yloxy)-2-methyl-pyridine | CH₃—X₁ | 6-methyl-3-ethyl-pyridin-2-yloxy-CH₂-X₄ | X₂-O-(1-ethylpyrrolidin-3-yl) | H | 1.11 | 487.3 | 488.3 | 1 |
| 300 | 4-[4-Cyclopentyloxy-6-((2R,6R)-2,6-diethyl-phenyl)-2-methyl-pyridin-3-ylmethyl]-2,6-dimethyl-morpholine | CH₃—X₁ | (2R,6R)-2,6-dimethylmorpholine-N-CH₂-X₄ | X₂-O-cyclopentyl | H | 1.16 | 436.3 | 437.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 301 | 4-[6-(2,6-Diethyl-phenyl)-2-methyl-4-morpholin-4-ylmethyl-pyridin-3-ylmethyl]-(2R,6R)-2,6-dimethyl-morpholine | CH₃—X₁ | (2R,6R)-2,6-dimethylmorpholinyl-CH₂-X₄ | morpholinyl-CH₂-X₂ | H | | | | |
| 302 | 4-[6-(2,6-Diethyl-phenyl)-4-((1R)-2-methoxy-1-methyl-ethoxy)-2-methyl-pyridin-3-ylmethyl]-(2R,6R)-2,6-dimethyl-morpholine | CH₃—X₁ | (2R,6R)-2,6-dimethylmorpholinyl-CH₂-X₄ | (R)-CH(CH₃)CH₂OCH₃-O-X₂ | H | 1.09 | 440.3 | 441.3 | 1 |
| 303 | 6-(2,6-Diethyl-phenyl)-3-(5-isopropyl-2-methyl-phenoxymethyl)-4-((1R)-2-methoxy-1-methyl-ethoxy)-2-methyl-pyridine | CH₃—X₁ | 5-isopropyl-2-methylphenoxy-CH₂-X₄ | (R)-CH(CH₃)CH₂OCH₃-O-X₂ | H | 1.27 | 475.3 | 476.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 304 | 4-[6-(2,6-Diethyl-phenyl)-4-isopropoxy-2-methyl-pyridin-3-ylmethyl]-2-phenyl-morpholine | CH₃—X₁ |  | 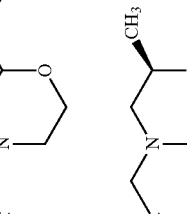 | H | 1.15 | 458.3 | 459.3 | 1 |
| 305 | [6-(2,6-Diethyl-phenyl)-3-((2R,6R)-2,6-dimethyl-morpholin-4-ylmethyl)-2-methyl-pyridin-4-ylmethyl]-bis-(2-ethoxy-ethyl)-amine | CH₃—X₁ |  |  | H | 1.16 | 525.4 | 526.6 | 1 |
| 306 | [6-(2,6-Diethyl-phenyl)-3-((2R,6R)-2,6-dimethyl-morpholin-4-ylmethyl)-2-methyl-pyridin-4-ylmethyl]-(2-ethoxy-ethyl)-amine | CH₃—X₁ |  |  | H | 1.09 | 453.3 | 454.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 307 | N-[6-(2,6-Diethyl-phenyl)-3-(3,4-dihydro-1H-isoquinolin-2-ylmethyl)-2-methyl-pyridin-4-ylmethyl]-C,C,C-trifluoro-methanesulfonamide | CH₃ | | | H | 1.18 | 531.2 | 532.4 | 1 |
| 308 | 2,2,2-Trifluoro-ethanesulfonic acid [6-(2,6-diethyl-phenyl)-3-(3,4-dihydro-1H-isoquinolin-2-ylmethyl)-2-methyl-pyridin-4-ylmethyl]-amide | CH₃ | | | H | 1.13 | 545.2 | 546.5 | 1 |
| 309 | M-[6-(2,6-Diethyl-phenyl)-3-(3,4-dihydro-1H-isoquinolin-2-ylmethyl)-2-methyl-pyridin-4-ylmethyl]-methanesulfonamide | CH₃ | | | H | 1.08 | 477.2 | 478.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 310 | Ethanesulfonic acid [6-(2,6-diethyl-phenyl)-3-(3,4-dihydro-1H-isoquinolin-2-ylmethyl)-2-methyl-pyridin-4-ylmethyl]-amide | CH₃—X₁ | X₄—N(tetrahydroisoquinoline) | X₂—CH₂N(SO₂CH₂CH₃) | H | 1.09 | 491.3 | 492.5 | 1 |
| 311 | Propane-2-sulfonic acid [6-(2,6-diethyl-phenyl)-3-(3,4-dihydro-1H-isoquinolin-2-ylmethyl)-2-methyl-pyridin-4-ylmethyl]-amide | CH₃—X₁ | X₄—N(tetrahydroisoquinoline) | X₂—CH₂N(SO₂CH(CH₃)₂) | H | 1.12 | 505.3 | 506.5 | 1 |
| 312 | 4-[6-(2,6-Diethyl-phenyl)-4-(3-methoxy-phenoxy)-2-methyl-pyridin-3-ylmethyl]-(2R,6R)-2,6-dimethyl-morpholine | CH₃—X₁ | X₄—N((2R,6R)-2,6-dimethylmorpholine) | X₂—O-(3-methoxyphenyl) | H | 1.16 | 474.3 | 475.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 313 | 4-[6-(2,6-Diethyl-phenyl)-3-(3,4-dihydro-1H-isoquinolin-2-ylmethyl)-2-methyl-pyridin-4-yloxy]-benzoic acid ethyl ester | CH₃—X₁ | X₄—(3,4-dihydroisoquinolin-2-ylmethyl) | X₂—O—C₆H₄—C(O)O—CH₂CH₃ | H | | | | |
| 314 | 1-[6-(2,6-Diethyl-phenyl)-4-isopropoxy-2-methyl-pyridin-3-ylmethyl]-6-isopropyl-1H-indazole | CH₃—X₁ | X₄—(6-isopropyl-1H-indazol-1-yl) | X₂—O—CH(CH₃)₂ | H | 1.18 | 455.3 | 456.5 | 1 |
| 315 | [6-(2,6-Diethyl-phenyl)-3-(3,4-dihydro-1H-isoquinolin-2-ylmethyl)-2-methyl-pyridin-4-yl]-methanol | CH₃—X₁ | X₄—(3,4-dihydroisoquinolin-2-ylmethyl) | X₂—CH₂—OH | H | 1.08 | 400.3 | 401.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 316 | 4-[6-(2,6-Diethyl-phenyl)-3-(3,4-dihydro-1H-isoquinolin-2-ylmethyl)-2-methyl-pyridin-4-yloxy]-benzamide | CH₃—X₁ | X₄—(tetrahydroisoquinoline) | X₂—O—(phenyl)—C(O)NH₂ | H | 1.08 | 505.3 | 502.5 | 1 |
| 317 | 3-[6-(2,6-Diethyl-phenyl)-3-(3,4-dihydro-1H-isoquinolin-2-ylmethyl)-2-methyl-pyridin-4-yloxy]-benzaoic acid ethyl ester | CH₃—X₁ | X₄—(tetrahydroisoquinoline) | X₂—O—(phenyl)—C(O)OCH₂CH₃ | H | 1.19 | 534.3 | 535.5 | 1 |
| 318 | 2-[6-(2,6-Diethyl-phenyl)-2-methyl-4-(2-morpholin-4-yl-ethoxy)-pyridin-3-ylmethyl]-1,2,3,4-tetrahydro-isoquinoline | CH₃—X₁ | X₄—(tetrahydroisoquinoline) | X₂—O—CH₂CH₂—morpholine | H | 0.96 | 499.3 | 500.5 | 1 |

TABLE I-continued

[Structure: pyridine with R1, R2, R3 substituents and 2,6-diethylphenyl group, labeled B]

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 319 | 1-[6-(2,6-Diethyl-phenyl)-3-(3,4-dihydro-1H-isoquinolin-2-ylmethyl)-2-methyl-pyridin-4-ylmethyl]-(2S)-pyrrolidine-2-carboxylic acid amide | CH₃—X₁ | [tetrahydroisoquinoline-CH₂-X₄] | [X₂-CH₂-(2S)-pyrrolidine-2-carboxamide] | H | 1.09 | 496.3 | 497.5 | 1 |
| 320 | 4-[6-(2,6-Diethyl-phenyl)-3-(3,4-dihydro-1H-isoquinolin-2-ylmethyl)-2-methyl-pyridin-4-yloxy]-2-hydroxy-benzamide | CH₃—X₁ | [tetrahydroisoquinoline-CH₂-X₄] | [X₂-O-phenyl with OH and C(O)NH₂] | H | 1.11 | 521.3 | 522.5 | 1 |
| 321 | 2-[6-(2,6-Diethyl-phenyl)-3-(3,4-dihydro-1H-isoquinolin-2-ylmethyl)-2-methyl-pyridin-4-yloxy]-benzoic acid ethyl ester | CH₃—X₁ | [tetrahydroisoquinoline-CH₂CH₂-X₄] | [X₂-O-phenyl-C(O)OCH₂CH₃] | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 322 | 4-[6-(2,6-Diethyl-phenyl)-3-((2R,6R)-2,6-dimethyl-morpholin-4-ylmethyl)-2-methyl-pyridin-4-yloxy]-benzamide | CH₃—X₁ | (2R,6R)-2,6-dimethylmorpholinylmethyl-X₄ | X₂—O—(2-hydroxy-4-yl)benzamide | H | 1.21 | 503.3 | 504.3 | 1 |
| 323 | 4-[6-(2,6-Diethyl-phenyl)-3-((2R,6R)-2,6-dimethyl-morpholin-4-ylmethyl)-2-methyl-pyridin-4-yloxy]-2-hydroxy-benzamide | CH₃—X₁ | 2,2-dimethylmorpholinylmethyl-X₄ | X₂—O—(4-yl)benzamide | H | 1.1 | 487.3 | 488.3 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 324 | 4-[6-(2,6-Diethyl-phenyl)-3-(2,2-dimethyl-morpholin-4-ylmethyl)-2-methyl-pyridin-4-yloxy]-benzamide | 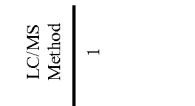 |  | 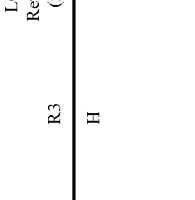 | H | 1.16 | 503.3 | 504.3 | 1 |
| 325 | 4-[6-(2,6-Diethyl-phenyl)-3-(2,2-dimethyl-morpholin-4-ylmethyl)-2-methyl-pyridin-4-yloxy]-2-hydroxy-benzamide |  | 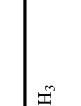 |  | H | 1.18 | 448.2 | 449.2 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 326 | 4-[6-(2,6-Diethyl-phenyl)-2-methyl-3-propoxymethyl-pyridin-4-yloxy]-2-hydroxy-benzamide | CH₃—X₁ | X₄—O—CH₂CH₂—O— (with CH₃) | 4-oxy-2-hydroxybenzamide | H | 1.22 | 448.2 | 449.3 | 1 |
| 327 | 2,2,2-Trifluoro-ethanesulfonic acid [6-(2,6-diethyl-phenyl)-3-((2R,6R)-2,6-dimethyl-morpholin-4-ylmethyl)-2-methyl-pyridin-4-ylmethyl]-amide | CH₃—X₁ | X₄—(2R,6R)-2,6-dimethylmorpholine | X₂—N(H)SO₂CH₂CF₃ | H | 1.16 | 527.2 | 528.2 | 1 |
| 328 | 3,5-Dimethyl-isoxazole-4-sulfonic acid [6-(2,6-diethyl-phenyl)-3-((2R,6R)-2,6-dimethyl-morpholin-4-ylmethyl)-2-methyl-pyridin-4-ylmethyl]-amide | CH₃—X₁ | X₄—(2R,6R)-2,6-dimethylmorpholine | X₂—N(H)SO₂-(3,5-dimethylisoxazole) | H | 1.19 | 540.3 | 541.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 329 | 2,2,2-Trifluoro-ethanesulfonic acid [6-(2,6-diethyl-phenyl)-3-(2,2-dimethyl-morpholin-4-ylmethyl)-2-methyl-pyridin-4-ylmethyl]-amide | CH₃—X₁ | 2,2-dimethylmorpholinyl-CH₂-X₄ | X₂-CH₂CH₂-N(H)SO₂CH₂CF₃ | H | 1.16 | 527.2 | 528.3 | 1 |
| 330 | 4-[4-Benzo[1,3]dioxol-5-yl-6-(2,6-diethyl-phenyl)-2-methyl-pyridin-3-ylmethyl]-(2R,6R)-2,6-dimethyl-morpholine | CH₃—X₁ | (2R,6R)-2,6-dimethylmorpholinyl-CH₂-X₄ | X₂-benzo[1,3]dioxol-5-yl | H | 1.23 | 472.3 | 473.3 | 1 |
| 331 | tert-Butyl-{2-[6-(2,6-diethyl-phenyl)-3-(3,4-dihydro-1H-isoquinolin-2-ylmethyl)-2-methyl-pyridin-4-yloxy]-ethyl}-amine | CH₃—X₁ | 3,4-dihydro-1H-isoquinolin-2-yl-CH₂-X₄ | X₂-O-CH₂CH₂-NH-C(CH₃)₃ | H | 0.99 | 485.3 | 486.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 332 | (2-{6-(2,6-Diethyl-phenyl)-3-(3,4-dihydro-1H-isoquinolin-2-ylmethyl)-2-methyl-pyridin-4-yloxy]-ethyl}-ethyl-amine | CH₃ | 3,4-dihydroisoquinolin-2-ylmethyl | 2-(ethylamino)ethoxy | H | 1.07 | 457.3 | 458.5 | 1 |
| 333 | 4-[6-(2,6-Diethyl-phenyl)-4-isopropoxy-2-methyl-pyridin-3-ylmethyl]-2-hydroxy-benzamide | CH₃ | 4-carbamoyl-3-hydroxyphenylmethyl | isopropoxy | H | | | | |
| 334 | 4-{6-(2,6-Diethyl-phenyl)-3-(2,2-dimethyl-morpholin-4-ylmethyl)-2-trifluoromethyl-pyridin-4-yloxy]-2-hydroxy-benzamide | CF₃ | 2,2-dimethylmorpholin-4-ylmethyl | 4-carbamoyl-3-hydroxyphenoxy | H | 1.25 | 557.3 | 558.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 335 | 4-[6-(2,6-Diethyl-phenyl)-3-(trans-3,5-dimethyl-piperidin-1-ylmethyl)-2-methyl-pyridin-4-yloxy]-2-hydroxy-benzamide | CH₃—X₁ | | | H | 1.1 | 501.3 | 502.5 | 1 |
| 336 | N-[6-(2,6-Diethyl-phenyl)-3-(5-isopropyl-2-methyl-phenoxymethyl)-2-methyl-pyridin-4-yl]-N-methyl-acetamide | CH₃—X₁ | | | H | 1.3 | 458.3 | 459.5 | 1 |
| 337 | 4-[6-(2,6-Diethyl-phenyl)-4-(4-methoxy-benzyl)-2-methyl-pyridin-3-ylmethyl]-(2R,6R)-2,6-dimethyl-morpholine | CH₃—X₁ | | | H | 1.18 | 472.3 | 473.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 338 | 4-[6-(2,6-Diethyl-phenyl)-3-(1,4-dioxa-8-aza-spiro[4.5]dec-8-ylmethyl)-2-methyl-pyridin-4-yloxy]-2-hydroxy-benzamide | CH₃—X₁ | X₄—(1,4-dioxa-8-aza-spiro[4.5]dec-8-ylmethyl) | X₂—O—(2-hydroxy-4-benzamide) | H | 1.08 | 531.3 | 532.5 | 1 |
| 339 | 4-[6-(2,6-Diethyl-phenyl)-2-methyl-3-(3-oxo-piperazin-1-ylmethyl)-pyridin-4-yloxy]-2-hydroxy-benzamide | CH₃—X₁ | X₄—(3-oxo-piperazin-1-ylmethyl) | X₂—O—(2-hydroxy-4-benzamide) | H | 1.13 | 488.2 | 489.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 340 | 2,2,2-Trifluoro-ethanesulfonic acid [6-(2,6-diethyl-phenyl)-2-methyl-3-(3-phenyl-piperidin-1-ylmethyl)-pyridin-4-ylmethyl]-amide | CH₃—X₁ |  | 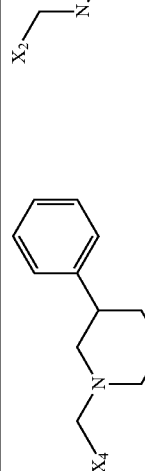 | H | 1.15 | 573.5 | 574.5 | 1 |
| 341 | 4-[6-(2,6-Diethyl-phenyl)-2-methyl-3-(3-phenyl-piperidin-1-ylmethyl)-pyridin-4-ylmethyl]-morpholine | CH₃—X₁ | 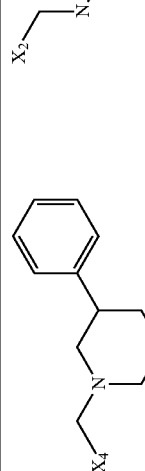 |  | H | 1.13 | 497.3 | 498.5 | 1 |
| 342 | 4-[6-(2,6-Diethyl-phenyl)-3-(3,3-dimethyl-pipieridin-1-ylmethyl)-2-methyl-pyridin-4-yloxy]-2-hydroxy-benzamide | CH₃—X₁ | 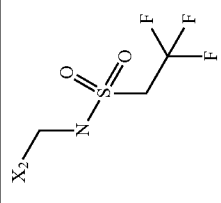 | 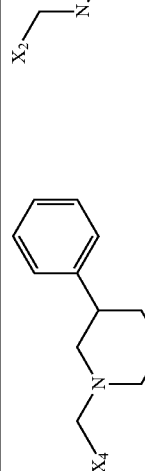 | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 343 | 4-[6-(2,6-Diethyl-phenyl)-2-methyl-3-(4-methyl-piperidin-1-ylmethyl)-pyridin-4-yloxy]-2-hydroxy-benzamide | CH₃—X₁ | 4-methylpiperidin-1-ylmethyl-X₄ | X₂—O-(2-hydroxy-4-benzamide) | H | 1.08 | 487.3 | 488.5 | 1 |
| 344 | 4-[6-(2,6-Diethyl-phenyl)-2-methyl-3-piperidin-1-ylmethyl-pyridin-4-yloxy]-2-hydroxy-benzamide | CH₃—X₁ | piperidin-1-ylmethyl-X₄ | X₂—O-(2-hydroxy-4-benzamide) | H | 1.08 | 473.3 | 474.5 | 1 |

TABLE I-continued
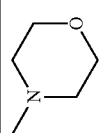
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 345 | 4-[6-(2,6-Diethyl-phenyl)-2-methyl-3-morpholin-4-ylmethyl-pyridin-4-yloxy]-2-hydroxy-benzamide | 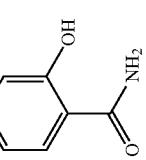 |  |  | H | 1.07 | 475.2 | 476.4 | 1 |
| 346 | 4-[6-(2,6-Diethyl-phenyl)-3-(cis-3,5-dimethyl-piperidin-1-ylmethyl)-2-methyl-pyridin-4-yloxy]-2-hydroxy-benzamide | | | | H | 1.1 | 501.3 | 502.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 347 | 4-[6-(2,6-Diethyl-phenyl)-3-(cis-2,6-dimethyl-piperidin-1-ylmethyl)-2-methyl-pyridin-4-yloxy]-2-hydroxy-benzamide | CH₃—X₁ | (cis-2,6-dimethylpiperidin-1-yl, X₄ linker) | (4-oxy-2-hydroxybenzamide, X₂) | H | 1.09 | 501.3 | 502.5 | 1 |
| 348 | 4-[6-(2,6-Diethyl-phenyl)-2-methyl-3-(4-oxo-piperidin-1-ylmethyl)-pyridin-4-yloxy]-2-hydroxy-benzamide | CH₃—X₁ | (4-oxo-piperidin-1-yl, X₄ linker) | (4-oxy-2-hydroxybenzamide, X₂) | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 349 | 1-[4-(4-Carbamoyl-3-hydroxy-phenoxy)-6-(2,6-diethyl-phenyl)-2-methyl-pyridin-3-ylmethyl]-piperidine-4-carboxylic acid ethyl ester | CH₃—X₁ | piperidine-CH₂-X₄ with 4-CO-O-CH₂CH₃ | X₂—O—(2-OH, 4-CONH₂ phenyl) | H | 1.09 | 545.3 | 546.6 | 1 |
| 350 | 1-[4-(4-Carbamoyl-3-hydroxy-phenoxy)-6-(2,6-diethyl-phenyl)-2-methyl-pyridin-3-ylmethyl]-piperidine-4-carboxylic acid | CH₃—X₁ | piperidine-CH₂-X₄ with 4-COOH | X₂—O—(2-OH, 4-CONH₂ phenyl) | H | 1.07 | 517.3 | 518.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 351 | 4-[6-(2,6-Diethyl-phenyl)-2-methyl-3-(4-methyl-[1,4]diazepan-1-ylmethyl)-pyridin-4-yloxy]-2-hydroxy-benzamide | CH₃—X₁ | (4-methyl-[1,4]diazepan-1-ylmethyl)-X₄ | X₂—O— 2-hydroxy-benzamide | H | | | | |
| 352 | 4-[6-(2,6-Diethyl-phenyl)-3-(4-isopropyl-piperazin-1-ylmethyl)-2-methyl-pyridin-4-yloxy]-2-hydroxy-benzamide | CH₃—X₁ | (4-isopropyl-piperazin-1-ylmethyl)-X₄ | X₂—O— 2-hydroxy-benzamide | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 353 | 4-[6-(2,6-Diethyl-phenyl)-3-(3-dimethylamino-pyrrolidin-1-ylmethyl)-2-methyl-pyridin-4-yloxy]-2-hydroxy-benzamide | CH₃—X₁ | (3-dimethylamino-pyrrolidin-1-ylmethyl) | 2-hydroxybenzamide | H | | | | |
| 354 | 4-(6-(2,6-Diethyl-phenyl)-3-{[ethyl-(2-methoxy-ethyl)-amino]-methyl}-2-methyl-pyridin-4-yloxy)-2-hydroxy-benzamide | CH₃—X₁ | [ethyl-(2-methoxy-ethyl)-amino]-methyl | 2-hydroxybenzamide | H | 1.17 | 491.3 | 492.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 355 | 4-[3-(4-Acetyl-piperazin-1-ylmethyl)-6-(2,6-diethyl-phenyl)-2-methyl-pyridin-4-yloxy]-2-hydroxy-benzamide | CH₃—X₁ | 4-acetylpiperazin-1-ylmethyl (X₄) | 4-(X₂-O)-2-hydroxy-benzamide | H | | | | |
| 356 | 4-[6-(2,6-Diethyl-phenyl)-3-(2,2-dimethyl-morpholin-4-ylmethyl)-2-methyl-pyridin-4-yloxy]-3-fluoro-benzoic acid | CH₃—X₁ | 2,2-dimethyl-morpholin-4-ylmethyl (X₄) | 4-(X₂-O)-3-fluoro-benzoic acid | H | 1.19 | 506.3 | 507.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 357 | 4-[4-Chloro-6-(2,6-diethyl-phenyl)-2-methyl-pyridin-3-ylmethyl]-(2R,6R)-2-methyl-6-phenyl-morpholine | CH₃—X₁ | 2-methyl-6-phenyl-morpholine with X₄ | X₂—Cl | H | 1.42 | 448.2 | 449.2 | 1 |
| 358 | 4-[4-(5-Chloro-pyridin-3-yloxy)-6-(2,6-diethyl-phenyl)-2-methyl-pyridin-3-ylmethyl]-2,2-dimethyl-morpholine | CH₃—X₁ | 2,2-dimethyl-morpholine with X₄ | X₂—O—(5-chloropyridin-3-yl) | H | 1.23 | 479.2 | 480.3 | 1 |
| 359 | 4-[4-Cyclopentyloxy-6-(2,6-diethyl-phenyl)-2-methyl-pyridin-3-ylmethyl]-(2R,6R)-2-methyl-6-phenyl-morpholine | CH₃—X₁ | (2R,6R)-2-methyl-6-phenyl-morpholine with X₄ | X₂—Cl | H | 1.23 | 498.3 | 499.3 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 360 | 4-[3-Cyclopentylaminomethyl-6-(2,6-diethyl-phenyl)-2-methyl-pyridin-4-yloxy]-2-hydroxy-benzamide | 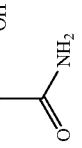 | 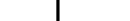 |  | H | 1.14 | 473.3 | 474.3 | 1 |
| 361 | 4-[3-[(Cyclohexyl-methyl-amino)-methyl]-6-(2,6-diethyl-phenyl)-2-methyl-pyridin-4-yloxy]-2-hydroxy-benzamide | 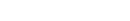 | 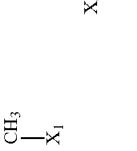 |  | H | 1.15 | 501.3 | 502.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 362 | 4-[3-[(Cyclopropylmethyl-propyl-amino)-methyl]-6-(2,6-diethyl-phenyl)-2-methyl-pyridin-4-yloxy]-2-hydroxy-benzamide | CH₃—X₁ | cyclopropylmethyl-propylaminomethyl group at X₄ | 4-(X₂-O)-2-hydroxy-benzamide | H | 1.15 | 501.3 | 502.3 | 1 |
| 363 | 4-[6-(2,6-Diethyl-phenyl)-4-isopropoxy-3-(2-methyl-phenoxymethyl)-pyridin-2-ylmethyl]-morpholine | X₁-morpholinylmethyl | 2-methyl-5-(isopropyl)-phenoxymethyl at X₄ | isopropoxy (CH₃)₂CH-O-X₂ | | | | | |
| 364 | 1-{4-[6-(2,6-Diethyl-phenyl)-3-(2,2-dimethyl-morpholin-4-ylmethyl)-2-methyl-pyridin-4-yloxy]-2-hydroxy-phenyl}-ethanone | CH₃—X₁ | 2,2-dimethyl-morpholin-4-ylmethyl at X₄ | 4-(X₂-O)-2-hydroxy-phenyl ethanone | H | 1.24 | 502.3 | 503.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 365 | 4-[6-(2,6-Diethyl-phenyl)-2-methyl-3-(3-methyl-piperidin-1-ylmethyl)-pyridin-4-yloxy]-2-hydroxy-benzamide | CH₃—X₁ | 3-methylpiperidine-CH₂-X₄ | 2-hydroxy-4-yloxy-benzamide (X₂—O—) | H | 1.14 | 487.3 | 488.3 | 1 |
| 366 | 4-(Benzo[1,3]dioxol-5-yloxy)-6-(2,6-diethyl-phenyl)-3-(3,3-dimethyl-piperidin-1-ylmethyl)-2-methyl-pyridine | CH₃—X₁ | 3,3-dimethylpiperidine-CH₂-X₄ | indanyl-O-X₂ | H | 1.18 | 486.3 | 487.5 | 1 |
| 367 | 6-(2,6-Diethyl-phenyl)-4-(2,3-dihydro-benzo[1,4]dioxin-6-yloxy)-3-(3,3-dimethyl-piperidin-1-ylmethyl)-2-methyl-pyridine | CH₃—X₁ | 3,3-dimethylpiperidine-CH₂-X₄ | 2,3-dihydro-benzo[1,4]dioxin-6-yloxy-X₂ | H | 1.17 | 500.3 | 502.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 368 | 4-{6-(2,6-Diethyl-phenyl)-2-methyl-3-[(tetrahydro-pyran-4-ylamino)-methyl]-pyridin-4-yloxy}-2-hydroxy-benzamide | CH₃—X₁ | tetrahydropyran-4-yl-aminomethyl | 4-oxy-2-hydroxybenzamide | H | 1.09 | 489.3 | 490.5 | 1 |
| 369 | 4-[6-(2,6-Diethyl-phenyl)-3-(2,2-dimethyl-morpholin-4-ylmethyl)-2-methyl-pyridin-4-yloxy]-benzenesulfonamide | CH₃—X₁ | 2,2-dimethylmorpholin-4-ylmethyl | 4-oxybenzenesulfonamide | H | 1.09 | 523.3 | 524.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 370 | 7-[6-(2,6-Diethyl-phenyl)-3-(3,3-dimethyl-piperidin-1-ylmethyl)-2-methyl-pyridin-4-yloxy]-benzo[e][1,3]oxazine-2,4-dione | CH₃—X₁ | 3,3-dimethyl-piperidin-1-yl-CH₂-X₄ | X₂—O—benzo[e][1,3]oxazine-2,4-dione | H | 1.15 | 527.3 | 528.5 | 1 |
| 371 | 4-[6-(2,6-Diethyl-phenyl)-3-(5-isopropyl-2-methyl-phenoxymethyl)-2-methyl-pyridin-4-yloxy]-2-hydroxy-benzamide | CH₃—X₁ | 5-isopropyl-2-methyl-phenoxymethyl-X₄ | X₂—O—(2-hydroxy-benzamide) | H | 1.28 | 538.3 | 539.5 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 372 | 5-[6-(2,6-Diethyl-phenyl)-3-(3,3-dimethyl-piperidin-1-ylmethyl)-2-methyl-pyridin-4-yloxy]-2-methyl-benzothiazole | CH₃—X₁ | 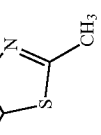 | 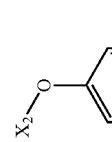 | H | 1.2 | 513.3 | 514.5 | 1 |
| 373 | 2-[6-(2,6-Diethyl-phenyl)-4-(3,5-dimethoxy-phenoxy)-2-methyl-pyridin-3-ylmethyl]-1,2,3,4-tetrahydro-isoquinoline | CH₃—X₁ | (tetrahydroisoquinoline-CH₂-X₄) | (3,5-dimethoxyphenoxy-X₂) | H | 1.22 | 522.3 | 523.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 374 | 2-[6-(2,6-Diethyl-phenyl)-4-(2,3-dihydro-benzo[1,4]dioxin-6-yloxy)-2-methyl-pyridin-3-ylmethyl]-1,2,3,4-tetrahydro-isoquinoline | CH₃—X₁ | X₄–(tetrahydroisoquinoline) | X₂–O–(2,3-dihydrobenzo[1,4]dioxin-6-yl) | H | 1.18 | 520.3 | 521.5 | 1 |
| 375 | 2-[6-(2,6-Diethyl-phenyl)-2-methyl-4-(3-trifluoromethoxy-phenoxy)-pyridin-3-ylmethyl]-1,2,3,4-tetrahydro-isoquinoline | CH₃—X₁ | X₄–(tetrahydroisoquinoline) | X₂–O–(3-trifluoromethoxyphenyl) | H | 1.25 | 546.2 | 547.5 | 1 |
| 376 | {3-[6-(2,6-Diethyl-phenyl)-3-(3,4-dihydro-1H-isoquinolin-2-ylmethyl)-2-methyl-pyridin-4-yloxy]-phenyl}-methanol | CH₃—X₁ | X₄–(tetrahydroisoquinoline) | X₂–O–(3-hydroxymethylphenyl) | H | 1.14 | 492.3 | 493.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 377 | 4-[6-(2,6-Diethyl-phenyl)-3-(3,4-dihydro-1H-isoquinolin-2-ylmethyl)-2-methyl-pyridin-4-yloxy]-2-hydroxy-benzonitrile | CH₃—X₁ | | | H | 1.17 | 503.3 | 504.5 | 1 |
| 378 | [4-Cyclopentyloxy-6-(2,6-diethyl-phenyl)-2-methyl-pyridin-3-ylmethyl]-methyl-(1R)-(1,2,3,4-tetrahydro-naphthalen-1-yl)-amine | CH₃—X₁ | | | H | 1.17 | 482.3 | 483.5 | 1 |
| 379 | 3-[6-(2,6-Diethyl-phenyl)-3-(5-isopropyl-2-methyl-phenoxymethyl)-2-methyl-pyridin-4-yl]propan-1-ol | CH₃—X₁ | | | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 380 | 4-{3-[6-(2,6-Diethyl-phenyl)-3-(5-isopropyl-2-methyl-phenoxymethyl)-2-methyl-pyridin-4-yl]-propyl}-morpholine | CH₃—X₁ | H₃C-CH(CH₃)-Ar-CH₃, O-X₄ | X₂-(CH₂)₃-morpholine | H | | | | |
| 381 | 4-Cyclopentyloxy-6-(2,6-diethyl-phenyl)-2-methyl-3-(3-phenyl-pyrazol-1-ylmethyl)-pyridine | CH₃—X₁ | 3-phenyl-pyrazol-1-yl-CH₂-X₄ | X₂-O-cyclopentyl | H | 1.22 | 465.3 | 466.4 | 1 |
| 382 | {3-[6-(2,6-Diethyl-phenyl)-3-(5-isopropyl-2-methyl-phenoxymethyl)-2-methyl-pyridin-4-yl]propyl}-dimethylamine | CH₃—X₁ | H₃C-CH(CH₃)-Ar-CH₃, O-X₄ | X₂-(CH₂)₃-N(CH₃)₂ | H | 1.16 | 472.3 | 473.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 383 | 4-Cyclopentyloxy-6-(2,6-diethyl-phenyl)-2-methyl-3-(3-methyl-4-phenyl-pyrazol-1-ylmethyl)-pyridine | CH₃—X₁ | (3-methyl-4-phenyl-pyrazol-1-ylmethyl, X₄) | X₂—O-cyclopentyl | H | 1.23 | 479.3 | 480.5 | 1 |
| 384 | 4-[6-(2,6-Diethyl-phenyl)-4-isopropoxy-2-methyl-pyridin-3-ylmethyl]-(2R,6R))-2-methyl-6-phenyl-morpholine | CH₃—X₁ | (2-methyl-6-phenyl-morpholine, X₄) | X₂—O-CH(CH₃)₂ | H | 1.2 | 472.3 | 473.5 | 1 |
| 385 | 4-[6-(2,5-Diethyl-phenyl)-3-(3,3-dimethyl-piperidin-1-ylmethyl)-2-methyl-pyridin-4-yl]-2-hydroxy-benzoic acid | CH₃—X₁ | (3,3-dimethyl-piperidin-1-ylmethyl, X₄) | 2-hydroxy-4-carboxyphenyl (X₂) | H | 1.22 | 486.3 | 487.5 | 1 |

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 386 | N-{2-[6-(2,6-Diethyl-phenyl)-3-(2,2-dimethyl-morpholin-4-ylmethyl)-2-methyl-pyridin-4-yloxy]-ethyl}-methanesulfonamide | 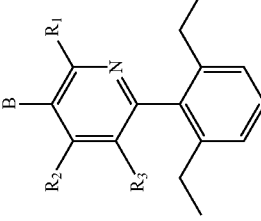 |  | 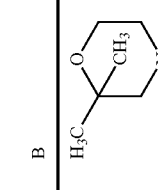 | H | 1.02 | 489.3 | 490.5 | 1 |
| 387 | 4-[6-(2,6-Diethyl-phenyl)-3-(3,3-dimethyl-piperidin-1-ylmethyl)-2-methyl-pyridin-4-yl]-2-hydroxy-benzamide |  | 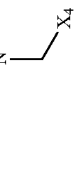 |  | H | 1.18 | 485.3 | 486.5 | 1 |
| 388 | 4-[6-(2,6-Diethyl-phenyl)-3-(3,3-dimethyl-piperidin-1-ylmethyl)-2-methyl-pyridin-4-yl]-2-hydroxy-benzamide |  |  |  | H | 1.03 | 493.3 | 494.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 389 | 4-Isopropoxy-6-(2,6-diethyl-phenyl)-2-methyl-3-((3R)-3-phenyl-piperidin-1-ylmethyl)-pyridine | CH₃—X₁ | (3R)-1-(X₄-methyl)-3-phenylpiperidine | X₂—O—CH(CH₃)₂ | H | 1.12 | 456.3 | 457.5 | 1 |
| 390 | 4-Isopropoxy-6-(2,6-diethyl-phenyl)-2-methyl-3-((3S)-3-phenyl-piperidin-1-ylmethyl)-pyridine | CH₃—X₁ | (3S)-1-(X₄-methyl)-3-phenylpiperidine | X₂—O—CH(CH₃)₂ | H | 1.12 | 456.3 | 457.5 | 1 |
| 391 | 4-Cyclopentyloxy-6-(2,6-diethyl-phenyl)-2-methyl-3-((3R)-3-phenyl-piperidin-1-ylmethyl)-pyridine | CH₃—X₁ | (3R)-1-(X₄-methyl)-3-phenylpiperidine | X₂—O-cyclopentyl | H | 1.15 | 482.3 | 483.5 | 1 |
| 392 | 4-Cyclopentyloxy-6-(2,6-diethyl-phenyl)-2-methyl-3-((3S)-3-phenyl-piperidin-1-ylmethyl)-pyridine | CH₃—X₁ | (3S)-1-(X₄-methyl)-3-phenylpiperidine | X₂—O-cyclopentyl | H | 1.16 | 482.3 | 483.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 393 | {4-[6-(2,6-Diethyl-phenyl)-3-(3,4-dihydro-1H-isoquinolin-2-ylmethyl)-2-methyl-pyridin-4-yloxy]-phenyl}-methanol | CH₃—X₁ | (3,4-dihydroisoquinolin-2-ylmethyl, X₄) | X₂-O-C₆H₄-CH₂OH | H | 1.12 | 492.3 | 493.5 | 1 |
| 394 | 6-[6-(2,6-Diethyl-phenyl)-3-(3,4-dihydro-2H-quinolin-1-ylmethyl)-2-methyl-pyridin-4-yloxy]-benzo[d]isoxazol-3-ylamine | CH₃—X₁ | (3,4-dihydroquinolin-1-ylmethyl, X₄) | X₂-O-benzo[d]isoxazol-3-amine | H | 1.22 | 518.3 | 519.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 395 | 6-[6-(2,6-Diethyl-phenyl)-3-(3,4-dihydro-1H-isoquinolin-2-ylmethyl)-2-methyl-pyridin-4-yloxy]-benzooxazol-2-ylamine | CH₃—X₁ | X₄—N(tetrahydroisoquinoline) | X₂—O-(benzoxazol-2-amine) | H | 1.11 | 518.3 | 519.5 | 1 |
| 396 | 1-[6-(2,6-Diethyl-phenyl)-3-(5-isopropyl-2-methyl-phenoxymethyl)-2-methyl-pyridin-4-ylmethyl]-4-hydroxy-piperidine-4-carboxylic acid amide | CH₃—X₁ | X₄—O-(5-isopropyl-2-methylphenyl) | X₂—N(4-hydroxy-4-carboxamide-piperidine) | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 397 | 4-[6-(2,6-Diethyl-phenyl)-3-[1-(3,3-dimethyl-piperidin-1-yl)-ethyl]-2-methyl-pyridin-4-yloxy]-2-hydroxy-benzamide | CH₃—X₁ |  |  | H | 1.17 | 515.3 | 516.5 | 1 |
| 398 | [6-(2,6-Diethyl-phenyl)-3-(5-isopropyl-2-methyl-phenoxymethyl)-2-methyl-pyridin-4-ylmethyl]-ethyl-(2-methoxy-ethyl)-amine | CH₃—X₁ |  | 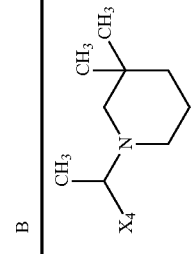 | H | 1.26 | 502.4 | 503.6 | 1 |
| 399 | [6-(2,6-Diethyl-phenyl)-3-(5-isopropyl-2-methyl-phenoxymethyl)-2-methyl-pyridin-4-ylmethyl]-dimethyl-amine | CH₃—X₁ |  |  | H | 1.24 | 444.3 | 445.5 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 400 | 5-[6-(2,6-Diethyl-phenyl)-3-(3,3-dimethyl-piperidin-1-ylmethyl)-2-methyl-pyridin-4-yloxy]-2-(1,4,5,6-tetrahydro-pyrimidin-2-yl)-phenol | CH₃—X₁ |  | | H | 1.05 | 540.3 | 541.6 | 1 |
| 401 | 6-(2,6-Diethyl-phenyl)-3-(5-isopropyl-2-methyl-phenoxymethyl)-2-methyl-4-piperidin-1-ylmethyl-pyridine | CH₃—X₁ | | | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 402 | 6-(2,6-Diethyl-phenyl)-3-(5-isopropyl-2-methyl-phenoxymethyl)-2-methyl-4-pyrrolidin-1-ylmethyl-pyridine | CH₃—X₁ | (5-isopropyl-2-methyl-phenoxymethyl with X₄) | X₂—CH₂-pyrrolidinyl | H | 1.24 | 470.3 | 471.5 | 1 |
| 403 | 1-[6-(2,6-Diethyl-phenyl)-3-(5-isopropyl-2-methyl-phenoxymethyl)-2-methyl-pyridin-4-ylmethyl]-piperidin-4-ol | CH₃—X₁ | (5-isopropyl-2-methyl-phenoxymethyl with X₄) | X₂—CH₂-(4-hydroxypiperidinyl) | H | 1.24 | 500.3 | 501.6 | 1 |
| 404 | {1-[6-(2,6-Diethyl-phenyl)-3-(5-isopropyl-2-methyl-phenoxymethyl)-2-methyl-pyridin-4-ylmethyl]-piperidin-4-yl}-methanol | CH₃—X₁ | (5-isopropyl-2-methyl-phenoxymethyl with X₄) | X₂—CH₂-(4-hydroxymethylpiperidinyl) | H | 1.24 | 514.4 | 515.6 | 1 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 405 | {1-[6-(2,6-Diethyl-phenyl)-3-(5-isopropyl-2-methyl-phenoxymethyl)-2-methyl-pyridin-4-ylmethyl]-piperidin-3-yl]}-methanol |  |  |  | H | 1.24 | 514.4 | 515.6 | 1 |
| 406 | 6-[6-(2,6-Diethyl-phenyl)-3-(3,3-dimethyl-piperidin-1-ylmethyl)-2-methyl-pyridin-4-yloxy]-benzo[d]isoxazol-3-ylamine |  |  |  | H | 1.12 | 498.3 | 499.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 407 | 6-[6-(2,6-Diethyl-phenyl)-3-(3,3-difluoro-piperidin-1-ylmethyl)-2-methyl-pyridin-4-yloxy]-benzo[d]isoxazol-3-ylamine | CH₃—X₁ | 3,3-difluoropiperidinyl-CH₂-X₄ | 3-amino-benzo[d]isoxazol-6-yl-O-X₂ | H | 1.15 | 506.2 | 507.5 | 1 |
| 408 | 6-[6-(2,6-Diethyl-phenyl)-3-(5-isopropyl-2-methyl-phenoxymethyl)-2-methyl-pyridin-4-yloxy]-benzo[d]isoxazol-3-ylamine | CH₃—X₁ | 5-isopropyl-2-methyl-phenoxy-CH₂-X₄ | 3-amino-benzo[d]isoxazol-6-yl-O-X₂ | H | 1.27 | 535.3 | 536.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 409 | {4-[6-(2,6-Diethyl-phenyl)-3-(3,4-dihydro-1H-isoquinolin-2-ylmethyl)-2-methyl-pyridin-4-yloxy]-benzyl}-dimethyl-amine | CH₃—X₁ | 3,4-dihydroisoquinolin-2-yl-CH₂-X₄ | X₂-O-C₆H₄-CH₂-N(CH₃)₂ | H | 1.08 | 519.3 | 520.6 | 1 |
| 410 | 4-[6-(2,6-Diethyl-phenyl)-4-methoxymethyl-2-methyl-pyridin-3-ylmethyl]-(2R,6R)-2-methyl-6-phenyl-morpholine | CH₃—X₁ | (2R,6R)-2-methyl-6-phenyl-morpholin-4-yl-CH₂-X₄ | X₂-CH₂-O-CH₃ | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 411 | 6-(2,6-Diethyl-phenyl)-3-(2,5-dimethyl-phenoxymethyl)-4-isopropoxy-2-methyl-pyridine | $CH_3$—$X_1$ | 2,5-dimethyl-phenoxymethyl (with $X_4$) | $X_2$—O—CH($CH_3$)$_2$ (isopropoxy) | H | 1.22 | 417.3 | 418.4 | 1 |
| 412 | [6-(2,6-Diethyl-phenyl)-4-methoxymethyl-2-methyl-pyridin-3-ylmethyl]-methyl-(1S)-(1,2,3,4-tetrahydro-naphthalen-1-yl)-amine | $CH_3$—$X_1$ | (1S)-N-methyl-tetrahydronaphthalen-1-amine (with $X_4$) | $X_2$—O—$CH_3$ | H | 1.2 | 442.3 | 443.5 | 1 |
| 413 | 4-[6-(2,6-Diethyl-phenyl)-4-methoxymethyl-2-methyl-pyridin-3-ylmethyl]-2-methyl-6-phenyl-morpholine | $CH_3$—$X_1$ | 2-methyl-6-phenyl-morpholine (with $X_4$) | $X_2$—O—$CH_3$ | H | 1.23 | 458.3 | 459.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 414 | 4-Azetidin-1-ylmethyl-6-(2,6-diethyl-phenyl)-3-(5-isopropyl-2-methyl-phenoxymethyl)-2-methyl-pyridine | CH₃—X₁ | | X₂—CH₂-azetidinyl | H | 1.25 | 456.3 | 457.5 | 1 |
| 415 | 6-(2,6-Diethyl-phenyl)-3-(5-isopropyl-2-methyl-phenoxymethyl)-4-(4-methoxy-piperidin-1-ylmethyl)-2-methyl-pyridine | CH₃—X₁ | | X₂—CH₂-(4-methoxypiperidin-1-yl) | H | 1.26 | 514.4 | 515.6 | 1 |
| 416 | 1-[6-(2,6-Diethyl-phenyl)-3-(5-isopropyl-2-methyl-phenoxymethyl)-2-methyl-pyridin-4-yl]-ethane-1,2-diol | CH₃—X₁ | | X₂-CH(OH)-CH₂OH | H | 1.21 | 447.3 | 448.4 | 1 |

TABLE I-continued

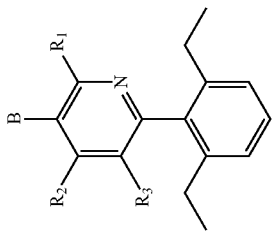

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 417 | 1-[6-(2,6-Diethyl-phenyl)-3-(5-isopropyl-2-methyl-phenoxymethyl)-2-methyl-pyridin-4-ylmethyl]-4-methyl-piperazine | CH₃—X₁ | H₃C-[aryl]-CH₃, X₄-O | X₂-N(piperazine)N-CH₃ | H | 1.17 | 499.4 | 500.6 | 1 |
| 418 | 1-{4-[6-(2,6-Diethyl-phenyl)-3-(5-isopropyl-2-methyl-phenoxymethyl)-2-methyl-pyridin-4-ylmethyl]-piperazin-1-yl}-ethanone | CH₃—X₁ | H₃C-[aryl]-CH₃, X₄-O | X₂-N(piperazine)N-C(O)CH₃ | H | 1.25 | 527.4 | 528.6 | 1 |
| 419 | 4-[6-(2,6-Diethyl-phenyl)-3-(5-isopropyl-2-methyl-phenoxymethyl)-2-methyl-pyridin-4-ylmethyl]-piperazin-2-one | CH₃—X₁ | H₃C-[aryl]-CH₃, X₄-O | X₂-N(piperazin-2-one) | H | 1.23 | 499.3 | 500.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 420 | 6-(2,6-Diethyl-phenyl)-3-(5-isopropyl-2-methyl-phenoxymethyl)-4-((2S)-2-methoxymethyl-pyrrolidin-1-ylmethyl)-2-methyl-pyridine |  |  |  | H | 1.26 | 514.4 | 515.6 | 1 |
| 421 | 6-(2,6-Diethyl-phenyl)-3-(5-isopropyl-2-methyl-phenoxymethyl)-4-((2R)-2-methoxymethyl-pyrrolidin-1-ylmethyl)-2-methyl-pyridine |  |  |  | H | 1.25 | 514.4 | 515.6 | 1 |
| 422 | 1-[6-(2,6-Diethyl-phenyl)-3-(5-isopropyl-2-methyl-phenoxymethyl)-2-methyl-pyridin-4-ylmethyl]-piperidine-4-carboxylic acid |  |  |  | H | 1.25 | 528.3 | 529.6 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 423 | 1-[6-(2,6-Diethyl-phenyl)-3-(5-isopropyl-2-methyl-phenoxymethyl)-2-methyl-pyridin-4-ylmethyl]-azetidine-3-carboxylic acid | CH₃—X₁ | | | H | 1.24 | 500.3 | 501.5 | 1 |
| 424 | [4-Cyclopentyloxy-6-(2,6-diethyl-phenyl)-2-methyl-pyridin-3-ylmethyl]-methyl-(1,2,3,4-tetrahydro-naphthalen-1-yl)-amine | CH₃—X₁ | | | H | 1.16 | 482.3 | 483.5 | 1 |
| 425 | 1-[6-(2,6-Diethyl-phenyl)-3-(5-isopropyl-2-methyl-phenoxymethyl)-2-methyl-pyridin-4-ylmethyl]-4-(2-methoxy-ethyl)-piperazine | CH₃—X₁ | | | H | 1.19 | 543.4 | 544.6 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 426 | 6-(2,6-Diethyl-phenyl)-4-(3,3-dimethyl-piperidin-1-ylmethyl)-3-(5-isopropyl-2-methyl-phenoxymethyl)-2-methyl-pyridine | CH₃–X₁ | (5-isopropyl-2-methyl-3-phenoxymethyl)- group with X₄ | 3,3-dimethyl-piperidin-1-ylmethyl with X₂ | H | 1.3 | 512.4 | 513.6 | 1 |
| 427 | Cyclobutyl-[6-(2,6-diethyl-phenyl)-3-(5-isopropyl-2-methyl-phenoxymethyl)-2-methyl-pyridin-4-ylmethyl]-amine | CH₃–X₁ | (5-isopropyl-2-methyl-3-phenoxymethyl)- group with X₄ | cyclobutyl-N-CH₂-X₂ | H | 1.24 | 470.3 | 471.5 | 1 |
| 428 | [6-(2,6-Diethyl-phenyl)-3-(5-isopropyl-2-methyl-phenoxymethyl)-2-methyl-pyridin-4-ylmethyl]-(3-methoxy-propyl)-amine | CH₃–X₁ | (5-isopropyl-2-methyl-3-phenoxymethyl)- group with X₄ | (3-methoxy-propyl)-N-CH₂-X₂ | H | 1.25 | 488.3 | 489.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 429 | [6-(2,6-Diethyl-phenyl)-3-(5-isopropyl-2-methyl-phenoxymethyl)-2-methyl-pyridin-4-ylmethyl]-isopropyl-amine | CH₃—X₁ | (aryl with X₄-OCH₂-, CH₃, and CH(CH₃)- substituents) | X₂—N(CH(CH₃)₂)— | H | 1.24 | 458.3 | 459.5 | 1 |
| 430 | [6-(2,6-Diethyl-phenyl)-3-(5-isopropyl-2-methyl-phenoxymethyl)-2-methyl-pyridin-4-ylmethyl]-methyl-amine | CH₃—X₁ | (aryl with X₄-OCH₂-, CH₃, and CH(CH₃)- substituents) | X₂—N(CH₃)— | H | 1.23 | 430.3 | 431.5 | 1 |
| 431 | [6-(2,6-Diethyl-phenyl)-3-(5-isopropyl-2-methyl-phenoxymethyl)-2-methyl-pyridin-4-ylmethyl]-(3-methoxy-propyl)-methyl-amine | CH₃—X₁ | (aryl with X₄-OCH₂-, CH₃, and CH(CH₃)- substituents) | X₂—N(CH₃)(CH₂CH₂CH₂OCH₃) | H | 1.25 | 502.4 | 503.6 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 432 | 4-Amino-1-[6-(2,6-diethyl-phenyl)-3-(5-isopropyl-2-methyl-phenoxymethyl)-2-methyl-pyridin-4-ylmethyl]-piperidine-4-carboxylic acid | CH₃—X₁ | H₃C-phenyl-CH₃ with OCH₂X₄ | piperidine-X₂ with NH₂ and COOH at 4-position | H | 1.2 | 543.3 | 544.6 | 1 |
| 433 | 1-[6-(2,6-Diethyl-phenyl)-3-(5-isopropyl-2-methyl-phenoxymethyl)-2-methyl-pyridin-4-ylmethyl]-4-isopropyl-piperazine | CH₃—X₁ | H₃C-phenyl-CH₃ with OCH₂X₄ | piperazine-X₂ with CH(CH₃)₂ | H | 1.19 | 527.4 | 528.6 | 1 |
| 434 | 1-[6-(2,6-Diethyl-phenyl)-3-(5-isopropyl-2-methyl-phenoxymethyl)-2-methyl-pyridin-4-ylmethyl]-(2S)-pyrrolidine-2-carboxylic acid | CH₃—X₁ | H₃C-phenyl-CH₃ with OCH₂X₄ | (2S)-pyrrolidine-X₂ with COOH | H | 1.26 | 514.3 | 515.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 435 | [6-(2,6-Diethyl-phenyl)-2-methyl-4-pyrrolidin-1-ylmethyl-pyridin-3-ylmethyl]-methyl-(1S)-(1,2,3,4-tetrahydro-naphthalen-1-yl)-amine | CH₃—X₁ | | X₂—N(pyrrolidine) | H | | | | |
| 436 | 2-[6-(2,6-Diethyl-phenyl)-2-methyl-4-pyrrolidin-1-ylmethyl-pyridin-3-ylmethyl]-1-methyl-1,2,3,4-tetrahydro-isoquinoline | CH₃—X₁ | | X₂—N(pyrrolidine) | H | 1.18 | 467.3 | 468.3 | 1 |
| 437 | 2-[6-(2,6-Diethyl-phenyl)-2-methyl-4-pyrrolidin-1-ylmethyl-pyridin-3-ylmethyl]-1-propyl-1,2,3,4-tetrahydro-isoquinoline | CH₃—X₁ | | X₂—N(pyrrolidine) | H | 1.23 | 495.4 | 496.4 | 1 |

TABLE I-continued

[Structure: pyridine core with substituents R1, R2, R3 and B, attached to a 2,6-diethylphenyl group]

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 438 | 2-[6-(2,6-Diethyl-phenyl)-2-methyl-4-pyrrolidin-1-ylmethyl-pyridin-3-ylmethyl]-1-isobutyl-1,2,3,4-tetrahydro-isoquinoline | CH₃—X₁ | [isobutyl-tetrahydroisoquinoline group with X₄] | X₂—CH₂-pyrrolidine | H | 1.25 | 509.4 | 510.4 | 1 |
| 439 | 4-{[6-(2,6-Diethyl-phenyl)-3-(5-isopropyl-2-methyl-phenoxymethyl)-2-methyl-pyridin-4-ylmethyl]-methyl-amino}-butyric acid | CH₃—X₁ | [isopropyl-methyl-phenyl with OCH₂-X₄] | X₂—CH₂N(CH₃)CH₂CH₂CH₂COOH | H | 1.27 | 516.3 | 517.4 | 1 |
| 440 | N-(2-{[6-(2,6-Diethyl-phenyl)-3-(5-isopropyl-2-methyl-phenoxymethyl)-2-methyl-pyridin-4-ylmethyl]-amino}-ethyl)-methanesulfonamide | CH₃—X₁ | [isopropyl-methyl-phenyl with OCH₂-X₄] | X₂—CH₂N(CH₃)CH₂CH₂NHSO₂CH₃ | H | 1.25 | 537.3 | 538.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 441 | 1-[6-(2,6-Diethyl-phenyl)-3-(5-isopropyl-2-methyl-phenoxymethyl)-2-methyl-pyridin-4-ylmethyl]-4-methanesulfonyl-piperazine | CH₃—X₁ | isopropyl-methylphenoxymethyl group | X₂—piperazine-methanesulfonyl | H | 1.28 | 563.3 | 564.6 | 1 |
| 442 | (6-(2,6-Diethyl-phenyl)-2-methyl-3-{[methyl-(1S)-(1,2,3,4-tetrahydro-naphthalen-1-yl)-amino]-methyl}-pyridin-4-yl)-pyrrolidin-1-yl-methanone | X₁—CH₃ | (1S)-tetrahydronaphthalen-N(CH₃)-X₄ | pyrrolidinyl-C(=O)-X₂ | H | 1.22 | 495.3 | 496.5 | 1 |
| 443 | [4-Cyclopentyloxy-6-(2,6-diethyl-phenyl)-2-methyl-pyridin-3-ylmethyl]-(1S)-1,2,3,4-tetrahydro-naphthalen-1-yl)-amine | CH₃—X₁ | (1S)-tetrahydronaphthalen-NH-X₄ | X₂—pyrrolidine | H | 1.17 | 468.3 | 469.3 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 444 | 1-[6-(2,6-Diethyl-phenyl)-3-(5-isopropyl-2-methyl-phenoxymethyl)-2-methyl-pyridin-4-ylmethyl]-4-methyl-piperidine-4-carboxylic acid methyl ester |  |  |  | H | 1.29 | 556.4 | 557.5 | 1 |
| 445 | 1-[6-(2,6-Diethyl-phenyl)-3-(5-isopropyl-2-methyl-phenoxymethyl)-2-methyl-pyridin-4-ylmethyl]-4-methyl-piperidine-4-carboxylic acid |  |  |  | H | 1.26 | 542.4 | 543.5 | 1 |
| 446 | [4-Cyclopentyloxy-6-(2,6-diethyl-phenyl)-2-methyl-pyridin-3-ylmethyl]-indan-2-yl-methyl-amine |  |  | | H | 1.15 | 468.3 | 469.4 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 447 | [4-Cyclopentyloxy-6-(2,6-diethyl-phenyl)-2-methyl-pyridin-3-ylmethyl]-methyl-(1,2,3,4-tetrahydro-naphthalen-2-yl)-amine | CH₃—X₁ |  | X₂—O-cyclopentyl | H | 1.16 | 482.3 | 483.4 | 1 |
| 448 | ((2S,3S)-2-Benzyloxy-cyclohexyl)-[4-cyclopentyloxy-6-(2,6-diethyl-phenyl)-2-methyl-pyridin-3-ylmethyl]-methyl-amine | CH₃—X₁ |  | X₂—O-cyclopentyl | H | 1.2 | 540.4 | 541.5 | 1 |
| 449 | ((2S,3S)-2-Benzyloxy-cyclopentyl)-[4-cyclopentyloxy-6-(2,6-diethyl-phenyl)-2-methyl-pyridin-3-ylmethyl]-methyl-amine | CH₃—X₁ |  | X₂—O-cyclopentyl | H | 1.19 | 526.4 | 527.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 450 | 4-[6-(2,6-Diethyl-phenyl)-3-(5-isopropyl-2-methyl-phenoxymethyl)-2-methyl-pyridin-4-yloxy]-benzoic acid |  |  |  | H | 1.31 | 523.3 | 524.4 | 1 |
| 451 | [4-Cyclopentyloxy-6-(2,6-diethyl-phenyl)-2-methyl-pyridin-3-ylmethyl]-methyl-(6,7,8,9-tetrahydro-5H-benzocyclohepten-5-yl)-amine |  |  |  | H | 1.19 | 496.3 | 497.4 | 1 |
| 452 | 4-(6-(2,6-Diethyl-phenyl)-2-methyl-3-{[methyl-(1S)-(1,2,3,4-tetrahydro-naphthalen-1-yl)-amino]-methyl}-pyridin-4-yloxy)-cyclohexanol |  |  | | H | 1.1 | 512.3 | 513.5 | 1 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 453 | [6-(2,6-Diethyl-phenyl)-4-(trans-4-methoxy-cyclohexyloxy)-2-methyl-pyridin-3-ylmethyl]-methyl-(1S)-(1,2,3,4-tetrahydro-naphthalen-1-yl)-amine | CH₃—X₁ | tetrahydronaphthalenyl-N(CH₃)-X₄ | X₂—O-cyclohexyl-OCH₃ (trans) | H | 1.15 | 526.4 | 527.5 | 1 |
| 454 | 6-(2,6-Diethyl-phenyl)-3-(1-ethoxy-butyl)-2-methyl-4-pyrrolidin-1-ylmethyl-pyridine | CH₃—X₁ | CH₃CH₂-O-CH(CH₂CH₂CH₃)-X₄ | X₂—pyrrolidinyl | H | 1.17 | 408.3 | 409.3 | 1 |
| 455 | 3-{[4-(2-Chloro-4-fluoro-phenoxy)-piperidin-1-ylmethyl]-4-cyclopentyloxy-6-(2,6-diethyl-phenyl)-2-methyl-pyridine | X₁—CH₃ | piperidinyl-O-(2-Cl-4-F-phenyl)-X₄ | X₂—O-cyclopentyl | H | | | | |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 456 | 4-(4-Carbamoyl-3-hydroxy-phenoxy)-6-(2,6-diethyl-phenyl)-2-methyl-N-(3-trifluoromethyl-phenyl)-nicotinamide | CH₃—X₁ | 3-(trifluoromethyl)phenyl-NH-C(=O)-X₄ | 4-carbamoyl-3-hydroxyphenoxy-X₂ | H | 1.69 | 563.0 | 564.0 | 2 |
| 457 | 6-(2,6-Diethyl-phenyl)-4-ethoxy-N-(2-fluoro-5-trifluoromethyl-phenyl)-2-methyl-nicotinamide | CH₃—X₁ | 2-fluoro-5-(trifluoromethyl)phenyl-NH-C(=O)-X₄ | ethoxy-X₂ | H | 1.6 | 488.0 | 489.0 | 2 |
| 458 | [6-(2,6-Diethyl-phenyl)-4-isopropoxy-2-methyl-pyridin-3-yl]-(7-trifluoromethyl-3,4-dihydro-2H-quinolin-1-yl)-methanone | CH₃—X₁ | 7-(trifluoromethyl)-3,4-dihydroquinolin-1(2H)-yl-C(=O)-X₄ | isopropoxy-X₂ | H | 1.7 | 510.0 | 511.0 | 2 |

TABLE I-continued
| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 459 | 4-Cyclopentyloxy-6-(2,6-diethyl-phenyl)-3-(3,5-diisopropyl-pyrazol-1-ylmethyl)-2-methyl-pyridine |  |  |  | H | 1.63 | 473.3 | 474.3 | 2 |
| 460 | 4-[6-(2,6-Diethyl-phenyl)-3-(3,3-dimethyl-piperidine-1-carbonyl)-2-methyl-pyridin-4-yloxy]-2-hydroxy-benzamide |  |  | | H | 1.65 | 515.0 | 516.0 | 2 |

TABLE I-continued

| Cpd # | NAME | R1 | B | R2 | R3 | LC/MS Ret. Time (min.) | LC/MS Mass | LC/MS M + H | LC/MS Method |
|---|---|---|---|---|---|---|---|---|---|
| 461 | 4-[6-(2,6-Diethyl-phenyl)-2-methyl-3-(3,3,5-trimethyl-azepane-1-carbonyl)-pyridin-4-yloxy]-2-hydroxy-benzamide | CH₃—X₁ | 3,3,5-trimethyl-azepane-1-carbonyl (X₄) | 4-oxy-2-hydroxy-benzamide (X₂) | H | 1.72 | 543.0 | 544.0 | 2 |
| 462 | 4-Cyclopentyloxy-6-(2,6-diethyl-phenyl)-3-(2-fluoro-5-trifluoromethyl-phenoxymethyl)-2-methyl-pyridine | X₁—CH₃ | 2-fluoro-5-trifluoromethyl-phenoxymethyl (X₄) | cyclopentyloxy (X₂) | H | | | | |

TABLE II

| Cpd. # | NAME | MOLSTRUCTURE | LC/MS Ret. Time (min.) | LC/MS Mass | LC/MS M + H | LC/MS Method |
|---|---|---|---|---|---|---|
| 463 | [4-Ethoxy-6-(2-ethoxy-5-fluoro-phenyl)-2-methyl-pyridin-3-ylmethyl]-methyl-(1S)-(1,2,3,4-tetrahydro-naphthalen-1-yl)-amine | | Chiral 1.07 | 448.3 | 449.2 | 1 |
| 464 | [4-Ethoxy-6-(2-ethoxy-5-fluoro-phenyl)-2-methyl-pyridin-3-ylmethyl]-methyl-(1S)-(1,2,3,4-tetrahydro-naphthalen-1-yl)-amine | | Chiral 1.14 | 474.3 | 475.3 | 1 |
| 465 | [4-Ethoxy-6-(2-ethoxy-5-fluoro-phenyl)-2-methyl-pyridin-3-ylmethyl]-methyl-(1S)-(1,2,3,4-tetrahydro-naphthalen-1-yl)-amine | | Chiral 3.11 | 432.6 | 433.26 | 3 |
| 466 | 4-[5-((2R, 6R)-2,6-Dimethyl-morpholin-4-ylmethyl)-4-isopropoxy-6-methyl-pyridin-2-yl]-5-methyl-1H-indazole | | Chiral 2.12 | 408.5 | 409.25 | 3 |
| 467 | 4-[6-(2,6-Diethyl-4-fluoro-phenyl)-4-isopropoxy-2-methyl-pyridin-3-ylmethyl]-((2R, 6R)-2,6-dimethyl-morpholine) | | Chiral 1.12 | 428.3 | 429.3 | 1 |

TABLE II-continued

| Cpd. # | NAME | MOLSTRUCTURE | | LC/MS Ret. Time (min.) | LC/MS Mass | LC/MS M + H | LC/MS Method |
|---|---|---|---|---|---|---|---|
| 468 | 4-[5-((2R, 6R)-2,6-Dimethyl-morpholin-4-ylmethyl)-4-isopropoxy-6-methyl-pyridin-2-yl]-5-isopropyl-1H-indazole | | Chiral | 1.07 | 436.3 | 437.3 | 1 |
| 469 | 4-[4-Isopropoxy-5-(5-isopropyl-2-methyl-phenoxymethyl)-6-methyl-pyridin-2-yl]-5-isopropyl-1H-indazole | | | 1.25 | 471.3 | 472.5 | 1 |
| 470 | [4-Isopropoxy-6-(5-isopropyl-1H-indazol-4-yl)-2-methyl-pyridin-3-ylmethyl]-methyl-(1S)-(1,2,3,4-tetrahydro-naphthalen-1-yl)-amine | | Chiral | 1.11 | 482.3 | 483.3 | 1 |
| 471 | 3-[5-((2R, 6R)-2,6-Dimethyl-morpholin-4-ylmethyl)-4-isopropoxy-6-methyl-pyridin-2-yl]-2,4-diethyl-phenol | | Chiral | 2.05 | 426.3 | 427.4 | 1 |

TABLE II-continued

| Cpd. # | NAME | MOLSTRUCTURE | | LC/MS Ret. Time (min.) | LC/MS Mass | LC/MS M + H | LC/MS Method |
|---|---|---|---|---|---|---|---|
| 472 | 4-[5-(3-Ethyl-6-methyl-pyridin-2-yloxymethyl)-4-isopropoxy-6-methyl-pyridin-2-yl]-5-isopropyl-1H-indazole | | | 1.18 | 458.3 | 459.4 | 1 |
| 473 | 4-[3-(2,2-Dimethyl-morpholin-4-ylmethyl)-6-(5-isopropyl-1H-indazol-4-yl)-2-methyl-pyridin-4-yloxy]-2-hydroxy-benzamide | | | 2.09 | 529.6 | 530.3 | 3 |
| 474 | [4-Cyclopentyloxy-6-(5-ethyl-3-methyl-1H-indazol-4-yl)-2-methyl-pyridin-3-ylmethyl]-methyl-(1S)-(1,2,3,4-tetrahydro-naphthalen-1-yl)-amine | | Chiral | 1.14 | 508.3 | 509.5 | 1 |
| 475 | 4-[4-Cyclopentyloxy-6-methyl-5-(2-methyl-6-phenyl-morpholin-4-ylmethyl)-pyridin-2-yl]-5-ethyl-3-methyl-1H-indazole | | Chiral | 1.19 | 524.3 | 525.6 | 1 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 476 | 5-Ethyl-4-[4-isopropoxy-5-(5-isopropyl-2-methyl-phenoxymethyl)-6-methyl-pyridin-2-yl]-3-methyl-1H-indazole | | 1.23 | 471.3 | 472.5 | 1 |
| 477 | {2-[4-Isopropoxy-5-(5-isopropyl-2-methyl-phenoxymethyl)-6-methyl-pyridin-2-yl]-3-methoxy-phenyl}-methanol | | 1.22 | 449.3 | 450.4 | 1 |
| 478 | 5-Ethyl-4-[4-isopropoxy-6-methyl-5-((2R,6R)-2-methyl-6-phenyl-morpholin-4-ylmethyl)-pyridin-2-yl]-3-methyl-1H-indazole | Chiral | 1.16 | 498.3 | 499.5 | 1 |
| 479 | 4-[4-Ethoxy-5-(5-isopropyl-2-methyl-phenoxymethyl)-6-methyl-pyridin-2-yl]-5-ethyl-3-methyl-1H-indazole | | 1.22 | 457.3 | 458.4 | 1 |
| 480 | 4-[5-(2,5-Dimethyl-phenoxymethyl)-4-ethoxy-6-methyl-pyridin-2-yl]-5-ethyl-3-methyl-1H-indazole | | 1.18 | 429.2 | 430.4 | 1 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 481 | 3-Ethyl-4-[4-isopropoxy-5-(5-isopropyl-2-methyl-phenoxymethyl)-6-methyl-pyridin-2-yl]-1H-indazole | | 1.23 | 457.3 | 458.4 | 1 |
| 482 | 4-[4-Isopropoxy-5-(5-isopropyl-2-methyl-phenoxymethyl)-6-methyl-pyridin-2-yl]-3-isopropyl-1H-indazole | | 1.24 | 471.3 | 472.5 | 1 |
| 483 | [4-Ethyl-6-(5-ethyl-3-methyl-1H-indazol-4-yl)-2-methyl-pyridin-3-ylmethyl]-methyl-(1S)-(1,2,3,4-tetrahydro-naphthalen-1-yl)-amine | Chiral | 1.16 | 452.3 | 453.5 | 1 |
| 484 | [4-Cyclopentyloxy-6-(3-ethyl-1H-indazol-4-yl)-2-methyl-pyridin-3-ylmethyl]-methyl-(1S)-(1,2,3,4-tetrahydro-naphthalen-1-yl)-amine | Chiral | 1.14 | 494.3 | 495.5 | 1 |
| 485 | [4-Cyclopentyloxy-6-(3-isopropyl-1H-indazol-4-yl)-2-methyl-pyridin-3-ylmethyl]-methyl-(1S)-(1,2,3,4-tetrahydro-naphthalen-1-yl)-amine | Chiral | 1.16 | 508.3 | 509.5 | 1 |

TABLE II-continued

| Cpd. # | NAME | MOLSTRUCTURE | | LC/MS Ret. Time (min.) | LC/MS Mass | LC/MS M + H | LC/MS Method |
|---|---|---|---|---|---|---|---|
| 486 | [4-Cyclopentyloxy-2-methyl-6-(5-methyl-1H-indol-4-yl)-pyridin-3-ylmethyl]-methyl-(1S)-(1,2,3,4-tetrahydro-naphthalen-1-yl)-amine | | | 1.12 | 479.3 | 480.5 | 1 |
| 487 | [6-(3-Bromo-5-methyl-1H-indol-4-yl)-4-cyclopentyloxy-2-methyl-pyridin-3-ylmethyl]-methyl-(1S)-(1,2,3,4-tetrahydro-naphthalen-1-yl)-amine | | | 1.17 | 557.2 | 560.2 | 1 |
| 488 | [4-Cyclopentyloxy-2-methyl-6-(3-methyl-1H-indazol-4-yl)-pyridin-3-ylmethyl]-methyl-(1S)-(1,2,3,4-tetrahydro-naphthalen-1-yl)-amine | | | 1.14 | 493.3 | 494.3 | 1 |
| 489 | [4-Cyclopentyloxy-2-methyl-6-(3-methyl-1H-indazol-4-yl)-pyridin-3-ylmethyl]-methyl-(1S)-(1,2,3,4-tetrahydro-naphthalen-1-yl)-amine | | Chiral | 1.11 | 480.3 | 481.4 | 1 |
| 490 | 4-[4-Isopropoxy-5-(5-isopropyl-2-methyl-phenoxymethyl)-6-methyl-pyridin-2-yl]-3-methyl-1H-indazole | | | 1.23 | 443.3 | 444.3 | 1 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 491 | [4-Cyclopentyloxy-6-(2,6-diethyl-3-nitro-phenyl)-2-methyl-pyridin-3-ylmethyl]-methyl-(1S)-(1,2,3,4-tetrahydro-naphthalen-1-yl)-amine | Chiral | 1.2 | 527.3 | 528.4 | 1 |
| 492 | [6-(3-Amino-2,6-diethyl-phenyl)-4-cyclopentyloxy-2-methyl-pyridin-3-ylmethyl]-methyl-(1S)-(1,2,3,4-tetrahydro-naphthalen-1-yl)-amine | Chiral | 1.12 | 497.3 | 498.4 | 1 |
| 493 | 4-[3-(3,3-Dimethyl-piperidin-1-ylmethyl)-6-(3-isopropyl-1H-indazol-4-yl)-2-methyl-pyridin-4-yloxy]-2-hydroxy-benzamide | | 2.11 | 527.7 | 528.3 | 3 |
| 494 | [4-Cyclopentyloxy-6-(2-isopropyl-6-methyl-phenyl)-2-methyl-pyridin-3-ylmethyl]-methyl-(1S)-(1,2,3,4-tetrahydro-naphthalen-1-yl)-amine | Chiral | | | | |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 495 | 4-[5-(Cyclohexyl-methoxy-methyl)-4-isopropyl-6-methyl-pyridin-2-yl]-5-isopropyl-1H-indazole | | 2.49 | 435.6 | 436.3 | 3 |
| 496 | 4-[5-(Chloro-cyclohexyl-methyl)-6-methyl-pyridin-2-yl]-5-isopropyl-1H-indazole | | 3.01 | 382.0 | 382.2 | 3 |
| 497 | 4-[5-(Chloro-cyclohexyl-methyl)-6-methyl-pyridin-2-yl]-5-isopropyl-1H-indazole | | 2.33 | 421.6 | 422.3 | 3 |
| 498 | 5-Isopropyl-4-[5-(5-isopropyl-2-methyl-phenoxymethyl)-6-methyl-4-vinyl-pyridin-2-yl]-1H-indazole | | 1.83 | 439.0 | 440.0 | 2 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 499 | 1-[6-(5-Isopropyl-1H-indazol-4-yl)-3-(5-isopropyl-2-methyl-phenoxymethyl)-2-methyl-pyridin-4-ylmethyl]-piperidine-4-carboxylic acid ethyl ester |  | 1.65 | 582.0 | 583.0 | 2 |
| 500 | 1-[6-(5-Isopropyl-1H-indazol-4-yl)-3-(5-isopropyl-2-methyl-phenoxymethyl)-2-methyl-pyridin-4-ylmethyl]-piperidine-4-carboxylic acid ethyl ester |  | 1.55 | 554.0 | 555.0 | 2 |
| 501 | 5-Isopropyl-4-[5-(5-isopropyl-2-methyl-phenoxymethyl)-6-methyl-4-piperidin-1-ylmethyl-pyridin-2-yl]-1H-indazole |  | 1.58 | 510.0 | 511.0 | 2 |
| 502 | 4-[4-(3,3-Dimethyl-piperidin-1-ylmethyl)-5-(5-isopropyl-2-methyl-phenoxymethyl)-6-methyl-pyridin-2-yl]-5-isopropyl-1H-indazole |  | 1.76 | 538.0 | 539.0 | 2 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 503 | Isopropyl[6-(5-isopropyl-1H-indazol-4-yl)-3-(5-isopropyl-2-methyl-phenoxymethyl)-2-methyl-pyridin-4-ylmethyl]-amine | 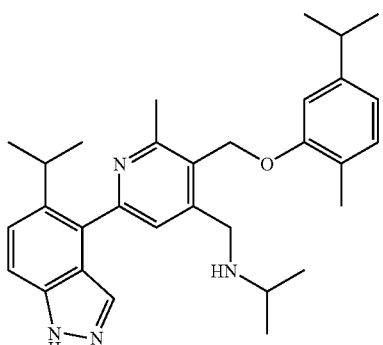 | 1.56 | 484.0 | 485.0 | 2 |
| 504 | Cyclobutyl-[6-(5-isopropyl-1H-indazol-4-yl)-3-(5-isopropyl-2-methyl-phenoxymethyl)-2-methyl-pyridin-4-ylmethyl]-amine |  | 1.55 | 496.0 | 497.0 | 2 |
| 505 | Isobutyl-[6-(5-isopropyl-1H-indazol-4-yl)-3-(5-isopropyl-2-methyl-phenoxymethyl)-2-methyl-pyridin-4-ylmethyl]-amine |  | 1.59 | 498.0 | 499.0 | 2 |
| 506 | (2,2-Dimethyl-propyl)-[6-(5-isopropyl-1H-indazol-4-yl)-3-(5-isopropyl-2-methyl-phenoxymethyl)-2-methyl-pyridin-4-ylmethyl]-amine |  | 1.58 | 512.0 | 513.0 | 2 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 507 | 2-{[6-(5-Isopropyl-1H-indazol-4-yl)-3-(5-isopropyl-2-methyl-phenoxymethyl)-2-methyl-pyridin-4-ylmethyl]-amino}-2-methyl-propan-1-ol |  | 1.53 | 514.0 | 515.0 | 2 |
| 508 | 5-Isopropyl-4-[5-(5-isopropyl-2-methyl-phenoxymethyl)-6-methyl-4-pyrrolidin-1-ylmethyl-pyridin-2-yl]-1H-indazole | 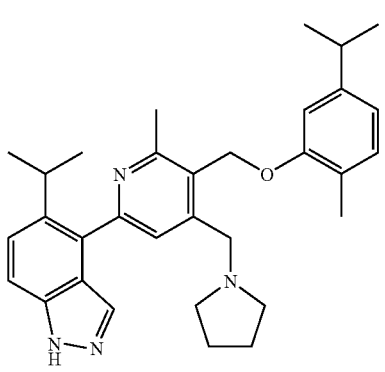 | 1.53 | 496.0 | 497.0 | 2 |
| 509 | 5-Isopropyl-4-[5-(5-isopropyl-2-methyl-phenoxymethyl)-6-methyl-pyridin-2-yl]-1H-indazole | 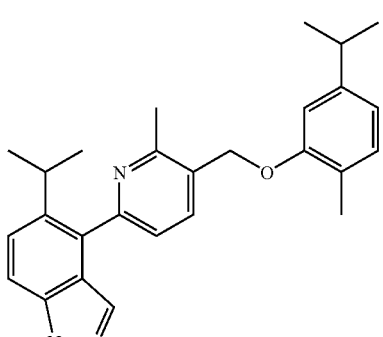 | 1.84 | 413.0 | 414.0 | 2 |

TABLE II-continued

| Cpd. # | NAME | MOLSTRUCTURE | LC/MS Ret. Time (min.) | LC/MS Mass | LC/MS M + H | LC/MS Method |
|---|---|---|---|---|---|---|
| 510 | 5-Isopropyl-4-[5-(5-isopropyl-2-methyl-phenoxymethyl)-4-(4-methoxy-piperidin-1-ylmethyl)-6-methyl-pyridin-2-yl]-1H-indazole | | 1.63 | 540.0 | 541.0 | 2 |
| 511 | (S)-(1,2-Dimethyl-propyl)-[6-(5-isopropyl-1H-indazol-4-yl)-3-(5-isopropyl-2-methyl-phenoxymethyl)-2-methyl-pyridin-4-ylmethyl]-amine | Chiral | 1.57 | 512.0 | 513.0 | 2 |
| 512 | (R)-(1,2-Dimethyl-propyl)-[6-(5-isopropyl-1H-indazol-4-yl)-3-(5-isopropyl-2-methyl-phenoxymethyl)-2-methyl-pyridin-4-ylmethyl]-amine | Chiral | 1.57 | 512.0 | 513.0 | 2 |

TABLE 3
| Cpd # | NAME | R1 | B | R2 | R3 | LC/MS Retention Time | LC/MS Calc. Mass | LC/MS M + H |
|---|---|---|---|---|---|---|---|---|
| 513 | N-{[6-(2,6-diethylphenyl)-4-methoxy-2-methylpyridin-2-yl]methyl}-N,2-dimethyl-1-phenylpropan-1-amine |  | 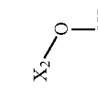 |  | H | 1.17 | 430.3 | 431.4 |
| 514 | N-{[6-(2,6-diethylphenyl)-4-methoxy-2-methylpyridin-3-yl]methyl}-N-methyl-1-phenylbutan-1-amine |  | 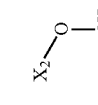 |  | H | 1.14 | 430.3 | 431.4 |
| 515 | N-{[6-(2,6-diethylphenyl)-4-methoxy-2-methylpyridin-3-yl]methyl}-N-methyl-1-phenylpentan-1-amine |  | 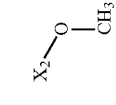 | | H | 1.23 | 444.3 | 445.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 516 | N-{[6-(2,6-diethylphenyl)-4-methoxy-2-methylpyridin-3-yl]methyl}-N,3-dimethyl-1-phenylbutan-1-amine | X₁—CH₃ | (structure with N-CH₃, CH₂-X₄, CH(CH₃)CH₃, phenyl) | X₂—O—CH₃ | H | 1.13 | 444.3 | 445.4 |
| 517 | N-{[6-(2,6-diethylphenyl)-4-methoxy-2-methylpyridin-3-yl]methyl}-N-methyl-1-phenylhexan-1-amine | CH₃—X₁ | (structure with N-CH₃, CH₂-X₄, butyl chain, phenyl) | X₂—O—CH₃ | H | 1.16 | 458.3 | 459.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 518 | N-{[6-(2,6-diethylphenyl)-4-methoxy-2-methylpyridin-3-yl]methyl}-N-methyl-1-phenylheptan-1-amine | CH₃—X₁ | (benzyl-heptyl-N(CH₃)-CH₂-X₄ group) | X₂—O—CH₃ | H | 1.19 | 472.3 | 473.5 |
| 519 | N-benzyl-N-{[6-(2,6-diethylphenyl)-4-methoxy-2-methylpyridin-3-yl]methyl}propan-1-amine | CH₃—X₁ | (benzyl-N(CH₂CH₂CH₃)-CH₂-X₄ group) | H₃C—O—X₂ | H | 1.13 | 416.3 | 417.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 520 | N-benzyl-N-{[6-(2,6-diethylphenyl)-4-methoxy-2-methylpyridin-3-yl]methyl}prop-2-en-1-amine | X₁—CH₃ |  |  | H | 1.15 | 414.3 | 415.4 |
| 521 | N-benzyl-N-{[6-(2,6-diethylphenyl)-4-methoxy-2-methylpyridin-3-yl]methyl}butan-1-amine | H₃C—X₁ |  |  | H | 1.18 | 430.3 | 431.4 |
| 522 | N-benzyl-N-{[6-(2,6-diethylphenyl)-4-methoxy-2-methylpyridin-3-yl]methyl}butan-2-amine | X₁—CH₃ | 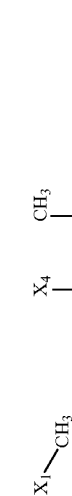 | 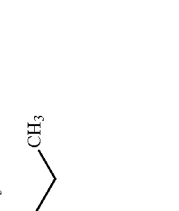 | H | 1.15 | 430.3 | 431.4 |

TABLE 3-continued
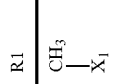
| Cpd # | NAME | R1 | B | R2 | R3 | LC/MS Retention Time | LC/MS Calc. Mass | LC/MS M + H |
|---|---|---|---|---|---|---|---|---|
| 523 | N-benzyl-N-{[6-(2,6-diethylphenyl)-4-methoxy-2-methylpyridin-3-yl]methyl}pentan-1-amine |  |  |  | H | 1.18 | 444.3 | 445.4 |
| 524 | N-benzyl-N-{[6-(2,6-diethylphenyl)-4-methoxy-2-methylpyridin-3-yl]methyl}-3-methylbutan-1-amine | 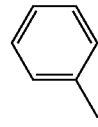 |  |  | H | 1.15 | 444.3 | 445.4 |
| 525 | N-benzyl-N-{[6-(2,6-diethylphenyl)-4-methoxy-2-methylpyridin-3-yl]methyl}pentan-2-amine |  |  |  | H | 1.21 | 444.3 | 445.4 |

TABLE 3-continued
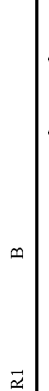
| Cpd # | NAME | R1 | B | R2 | R3 | LC/MS Retention Time | LC/MS Calc. Mass | LC/MS M + H |
|---|---|---|---|---|---|---|---|---|
| 526 | 2-{[6-(2,6-diethylphenyl)-4-methoxy-2-methylpyridin-3-yl]methyl}-1,2,3,4-tetrahydroisoquinoline |  |  | 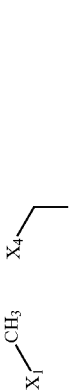 | H | 1.1 | 414.3 | 415.4 |
| 527 | 2-{[6-(2,6-diethylphenyl)-4-methoxy-2-methylpyridin-3-yl]methyl}-1-methyl-1,2,3,4-tetrahydroisoquinoline |  |  | 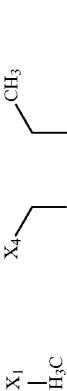 | H | 1.13 | 428.3 | 429.4 |
| 529 | 2-{[6-(2,6-diethylphenyl)-4-methoxy-2-methylpyridin-3-yl]methyl}-1-propyl-1,2,3,4-tetrahydroisoquinoline | 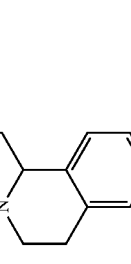 | 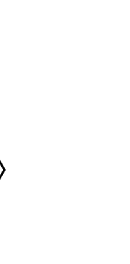 | | H | 1.27 | 442.3 | 443.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 530 | 1-cyclopropyl-2-{[6-(2,6-diethylphenyl)-4-methoxy-2-methylpyridin-3-yl]methyl}-1,2,3,4-tetrahydroisoquinoline | H₃C—X₁ | | X₂—O—CH₃ | H | 1.15 | 440.3 | 441.4 |
| 531 | 1-butyl-2-{[6-(2,6-diethylphenyl)-4-methoxy-2-methylpyridin-3-yl]methyl}-1,2,3,4-tetrahydroisoquinoline | X₁—CH₃ | | X₂—O—CH₃ (H₃C) | H | 1.23 | 456.3 | 457.4 |
| 532 | 2-{[6-(2,6-diethylphenyl)-4-methoxy-2-methylpyridin-3-yl]methyl}-1-isobutyl-1,2,3,4-tetrahydroisoquinoline | X₁—CH₃ | | X₂—O—CH₃ (H₃C) | H | 1.23 | 456.3 | 457.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 533 | 2-{[6-(2,6-diethylphenyl)-4-methoxy-2-methylpyridin-3-yl]methyl}-1-pentyl-1,2,3,4-tetrahydroisoquinoline | 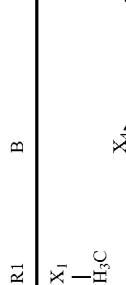 |  | 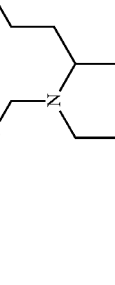 | H | 1.22 | 470.3 | 471.5 |
| 534 | 2-{[6-(2,6-diethylphenyl)-4-methoxy-2-methylpyridin-3-yl]methyl}-1-isopentyl-1,2,3,4-tetrahydroisoquinoline |  | 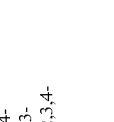 |  | H | 1.21 | 470.3 | 471.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 535 | N-benzyl-N-{[6-(2,6-diethylphenyl)-4-methoxy-2-methylpyridin-3-yl]methyl}cyclohexanamine |  | 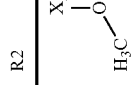 |  | H | 1.17 | 456.3 | 457.4 |
| 536 | N-benzyl-1-cyclopentyl-N-{[6-(2,6-diethylphenyl)-4-methoxy-2-methylpyridin-3-yl]methyl}methanamine | 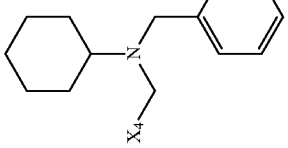 |  |  | H | 1.26 | 456.3 | 457.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 537 | N-benzyl-1-cyclohexyl-N-{[6-(2,6-diethylphenyl)-4-methoxy-3-methylpyridin-3-yl]methyl}methanamine | X₁—CH₃ |  | 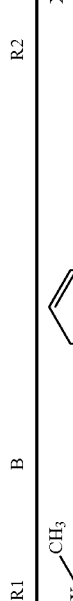 | H | 1.27 | 470.3 | 471.5 |
| 538 | N-benzyl-3-cyclopentyl-N-{[6-(2,6-diethylphenyl)-4-methoxy-2-methylpyridin-3-yl]methyl}propan-1-amine | H₃C—X₁ | 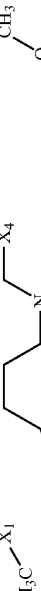 |  | H | 1.26 | 484.3 | 485.5 |
| 539 | N-benzyl-1-[6-(2,6-diethylphenyl)-4-methoxy-2,5-dimethylpyridin-3-yl]-N-methylmethanamine | X₁—H₃C |  | X₂—O—CH₃ | CH₃—X₃ | | | |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 540 | (1R)-N-{[6-(2,6-diethylphenyl)-4-methoxy-2,5-dimethylpyridin-3-yl]methyl}-N-methyl-1-phenylethanamine | | | | | | | |
| 541 | N-{[6-(2,6-diethylphenyl)-4-methoxy-2,5-dimethylpyridin-3-yl]methyl}-N,2-dimethyl-1-phenylpropan-1-amine | | | | | | | |
| 542 | N-{[6-(2,6-diethylphenyl)-4-methoxy-2,5-dimethylpyridin-3-yl]methyl}-N-methyl-1-phenylpentan-1-amine | | | | | 1.21 | 458.3 | 459.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 543 | N-benzyl-N-{[6-(2,6-diethylphenyl)-4-methoxy-2,5-dimethylpyridin-3-yl]methyl}butan-1-amine | H₃C—X₁ | X₄–N(Bn)–CH₂CH₂CH₂–CH₃ | X₂–O–CH₃ | X₃–CH₃ | 1.2 | 444.3 | 445.4 |
| 544 | 2-{[6-(2,6-diethylphenyl)-4-methoxy-2,5-dimethylpyridin-3-yl]methyl}-1,2,3,4-tetrahydroisoquinoline | X₁–H₃C | X₄–(tetrahydroisoquinolin-2-yl) | X₂–O–CH₃ | X₃–CH₃ | 1.13 | 414.3 | 415.4 |
| 545 | 2-{[6-(2,6-diethylphenyl)-4-methoxy-2,5-dimethylpyridin-3-yl]methyl}-1-methyl-1,2,3,4-tetrahydroisoquinoline | X₁–H₃C | X₄–(1-methyl-tetrahydroisoquinolin-2-yl) | X₂–O–CH₃ | X₃–CH₃ | 1.16 | 428.3 | 429.4 |

TABLE 3-continued
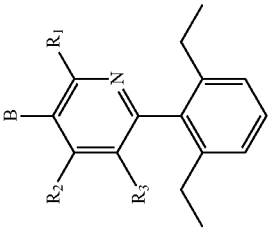
| Cpd # | NAME | R1 | B | R2 | R3 | LC/MS Retention Time | LC/MS Calc. Mass | LC/MS M + H |
|---|---|---|---|---|---|---|---|---|
| 546 | 2-{[6-(2,6-diethylphenyl)-4-methoxy-2,5-dimethylpyridin-3-yl]methyl}-1-propyl-1,2,3,4-tetrahydroisoquinoline | 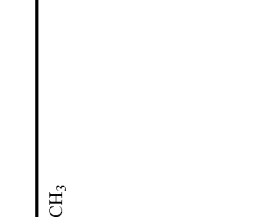 | 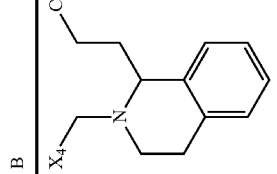 | 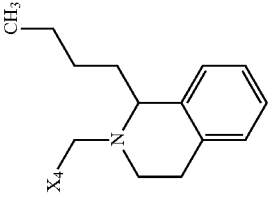 | 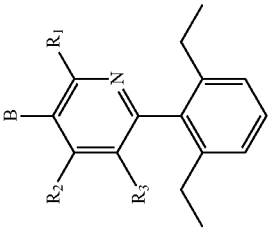 | 1.28 | 456.3 | 457.4 |
| 547 | 1-butyl-2-{[6-(2,6-diethylphenyl)-4-methoxy-2,5-dimethylpyridin-3-yl]methyl}-1,2,3,4-tetrahydroisoquinoline | 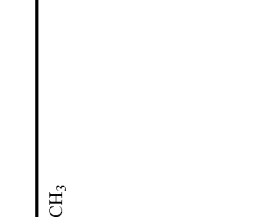 | 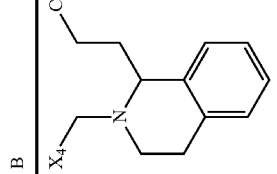 | 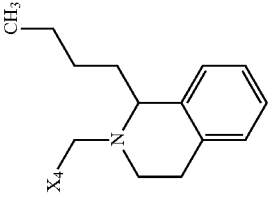 | 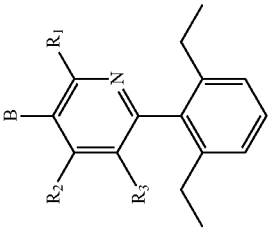 | 1.24 | 470.3 | 471.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 548 | 2-{[6-(2,6-diethylphenyl)-4-methoxy-2,5-dimethylpyridin-3-yl]methyl}-1-isobutyl-1,2,3,4-tetrahydroisoquinoline | X1—CH3 |  |  X2—O—CH3 | CH3—X3 | 1.25 | 470.3 | 471.4 |
| 549 | N-benzyl-N-{[6-(2,6-diethylphenyl)-4-methoxy-2,5-dimethylpyridin-3-yl]methyl}pentan-3-amine | X1—CH3 |  | H3C—O—X2 | H3C—X3 | 1.28 | 458.3 | 459.4 |
| 550 | 1-{[6-(2,6-diethylphenyl)-4-methoxy-2-methylpyridin-3-yl]methyl}-3,3,5-trimethylazepane | X1—CH3 |  | X2—O—CH3 | H | 1.16 | 408.3 | 409.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 551 | N-{[6-(2,6-diethylphenyl)-4-methoxy-2-methylpyridin-3-yl]methyl}-N-ethyl-2-methylprop-2-en-1-amine | CH₃—X₁ | H₃C-C(=CH₂)-CH₂-N(CH₂CH₃)-X₄ | X₂-O-CH₃ | H | 1.14 | 366.3 | 367.4 |
| 552 | N-{[6-(2,6-diethylphenyl)-4-methoxy-2-methylpyridin-3-yl]methyl}-N-pentylpentan-1-amine | CH₃—X₁ | pentyl-N(pentyl)-CH₂-X₄ | X₂-O-CH₃ | H | 1.18 | 424.3 | 425.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 553 | N-{[6-(2,6-diethylphenyl)-4-methoxy-2-methylpyridin-3-yl]methyl}-N-hexylhexan-1-amine | 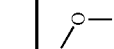 |  |  | H | 1.23 | 452.4 | 453.5 |
| 554 | 1-[6-(2,6-diethylphenyl)-4-methoxy-2-methylpyridin-3-yl]-N-(4-fluorobenzyl)-N-methylmethanamine |  |  |  | H | 1.09 | 406.2 | 407.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 555 | 1-[6-(2,6-diethylphenyl)-4-methoxy-2-methylpyridin-3-yl]-N-(3-fluorobenzyl)-N-methylmethanamine | X1—CH3 | 3-fluorobenzyl-N(CH3)-CH2-X4 | X2-O-CH3 | H | 1.09 | 406.2 | 407.4 |
| 556 | N-(4-chlorobenzyl)-N-{[6-(2,6-diethylphenyl)-4-methoxy-2-methylpyridin-3-yl]methyl}-N-methylamine | X1—CH3 | 4-chlorobenzyl-N(CH3)-CH2-X4 | X2-O-CH3 | H | 1.22 | 422.2 | 423.4 |
| 557 | N-(3-chlorobenzyl)-N-{[6-(2,6-diethylphenyl)-4-methoxy-2-methylpyridin-3-yl]methyl}-N-methylamine | X1—CH3 | 3-chlorobenzyl-N(CH3)-CH2-X4 | X2-O-CH3 | H | 1.14 | 422.2 | 423.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 558 | 1-[6-(2,6-diethylphenyl)-4-methoxy-2-methylpyridin-3-yl]-N-methyl-N-[4-(trifluoromethyl)benzyl]methanamine | X$_1$—CH$_3$ | 4-(trifluoromethyl)benzyl-N(CH$_3$)-CH$_2$-X$_4$ | X$_2$—O—CH$_3$ | H | 1.14 | 456.2 | 457.4 |
| 559 | 1-[6-(2,6-diethylphenyl)-4-methoxy-2-methylpyridin-3-yl]-N-methyl-N-[3-(trifluoromethyl)benzyl]methanamine | X$_1$—CH$_3$ | 3-(trifluoromethyl)benzyl-N(CH$_3$)-CH$_2$-X$_4$ | X$_2$—O—CH$_3$ | H | 1.17 | 456.2 | 457.4 |
| 560 | 1-(4-bromophenyl)-N-{[6-(2,6-diethylphenyl)-4-methoxy-2-methylpyridin-3-yl]methyl}-N-methylmethanamine | X$_1$—CH$_3$ | 4-bromobenzyl-N(CH$_3$)-CH$_2$-X$_4$ | X$_2$—O—CH$_3$ | H | 1.13 | 466.2 | 467.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 561 | 1-{[6-(2,6-diethylphenyl)-4-methoxy-2,5-dimethylpyridin-3-yl]methyl}-3,3,5-trimethylazepane | X₁—CH₃ (H₃C) | 3,3,5-trimethylazepane attached via X₄—CH₂ | X₂—O—CH₃ | CH₃—X₃ | 1.17 | 422.3 | 423.5 |
| 562 | N-(3-chlorobenzyl)-N-{[6-(2,6-diethylphenyl)-4-methoxy-2,5-dimethylpyridin-3-yl]methyl}-N-methylamine | X₁—CH₃ (H₃C) | X₄—CH₂—N(CH₃)—CH₂-(3-chlorophenyl) | X₂—O—CH₃ | CH₃—X₃ | 1.21 | 436.2 | 437.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 563 | 1-(4-bromophenyl)-N-{[6-(2,6-diethylphenyl)-4-methoxy-2,5-dimethylpyridin-3-yl]methyl}-N-methylmethanamine |  |  |  | 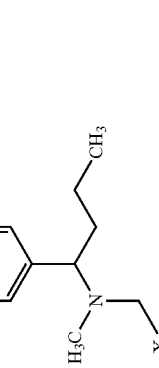 | 1.22 | 480.2 | 481.4 |
| 564 | N-{[6-(2,6-diethylphenyl)-2-methylpyridin-3-yl]methyl}-N,2-dimethyl-1-phenylpropan-1-amine |  |  | H | H | 1.2 | 400.3 | 401.4 |
| 565 | N-{[6-(2,6-diethylphenyl)-2-methylpyridin-3-yl]methyl}-N-methyl-1-phenylbutan-1-amine |  |  | H | H | 1.15 | 400.3 | 401.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 566 | N-{[6-(2,6-diethylphenyl)-2-methylpyridin-3-yl]methyl}-N-methyl-1-phenylpentan-1-amine |  |  | H | H | 1.19 | 414.3 | 415.4 |
| 567 | N-{[6-(2,6-diethylphenyl)-2-methylpyridin-3-yl]methyl}-N,3-dimethyl-1-phenylbutan-1-amine |  |  | H | H | 1.16 | 414.3 | 415.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 568 | N-{[6-(2,6-diethylphenyl)-2-methylpyridin-3-yl]methyl}-N-methyl-1-phenylhexan-1-amine |  | 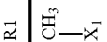 | H | H | 1.2 | 428.3 | 429.5 |
| 569 | N-{[6-(2,6-diethylphenyl)-2-methylpyridin-3-yl]methyl}-N-methyl-1-phenylheptan-1-amine |  |  | H | H | 1.22 | 442.3 | 443.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 570 | N-benzyl-N-{[6-(2,6-diethylphenyl)-2-methylpyridin-3-yl]methyl}ethanamine | 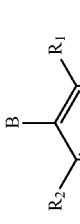 | 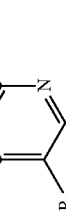 | H | H | 1.12 | 372.3 | 373.4 |
| 571 | N-benzyl-N-{[6-(2,6-diethylphenyl)-2-methylpyridin-3-yl]methyl}propan-2-amine | 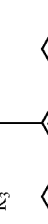 |  | H | H | 1.14 | 386.3 | 387.4 |
| 572 | N-benzyl-N-{[6-(2,6-diethylphenyl)-2-methylpyridin-3-yl]methyl}propan-1-amine |  | 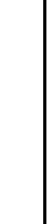 | H | H | 1.15 | 386.3 | 387.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 573 | N-benzyl-N-{[6-(2,6-diethylphenyl)-2-methylpyridin-3-yl]methyl}prop-2-en-1-amine |  |  | H | H | 1.18 | 384.3 | 385.4 |
| 574 | N-benzyl-N-{[6-(2,6-diethylphenyl)-2-methylpyridin-3-yl]methyl}cyclopropanamine |  |  | H | H | 1.19 | 384.3 | 385.4 |
| 575 | N-benzyl-N-{[6-(2,6-diethylphenyl)-2-methylpyridin-3-yl]methyl}butan-1-amine |  | | H | H | 1.17 | 400.3 | 401.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 576 | N-benzyl-N-{[6-(2,6-diethylphenyl)-2-methylpyridin-3-yl]methyl}-2-methylpropan-1-amine |  |  | H | H | 1.23 | 400.3 | 401.4 |
| 577 | N-benzyl-N-{[6-(2,6-diethylphenyl)-2-methylpyridin-3-yl]methyl}butan-2-amine |  |  | H | H | 1.19 | 400.3 | 401.4 |
| 578 | N-benzyl-N-{[6-(2,6-diethylphenyl)-2-methylpyridin-3-yl]methyl}pentan-1-amine |  |  | H | H | 1.22 | 414.3 | 415.4 |

TABLE 3-continued
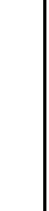
| Cpd # | NAME | R1 | B | R2 | R3 | LC/MS Retention Time | LC/MS Calc. Mass | LC/MS M + H |
|---|---|---|---|---|---|---|---|---|
| 579 | N-benzyl-N-{[6-(2,6-diethylphenyl)-2-methylpyridin-3-yl]methyl}-3-methylbutan-1-amine | 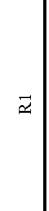 |  | H | H | 1.19 | 414.3 | 415.4 |
| 580 | N-benzyl-N-{[6-(2,6-diethylphenyl)-2-methylpyridin-3-yl]methyl}pentan-2-amine | 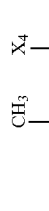 |  | H | H | 1.22 | 414.3 | 415.4 |
| 581 | 2-{[6-(2,6-diethylphenyl)-2-methylpyridin-3-yl]methyl}-1,2,3,4-tetrahydroisoquinoline |  |  | H | H | 1.12 | 370.2 | 371.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 582 | 2-{[6-(2,6-diethylphenyl)-2-methylpyridin-3-yl]methyl}-1-methyl-1,2,3,4-tetrahydroisoquinoline | X₁—CH₃ |  | H | H | 1.12 | 384.3 | 385.4 |
| 583 | 2-{[6-(2,6-diethylphenyl)-2-methylpyridin-3-yl]methyl}-1-ethyl-1,2,3,4-tetrahydroisoquinoline | X₁—CH₃ |  | H | H | 1.15 | 398.3 | 399.4 |
| 584 | 2-{[6-(2,6-diethylphenyl)-2-methylpyridin-3-yl]methyl}-1-propyl-1,2,3,4-tetrahydroisoquinoline | X₁—CH₃ |  | H | H | 1.2 | 412.3 | 413.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 585 | 1-cyclopropyl-2-{[6-(2,6-diethylphenyl)-2-methylpyridin-3-yl]methyl}-1,2,3,4-tetrahydroisoquinoline | H₃C—X₁ | | H | H | 1.15 | 410.3 | 411.4 |
| 586 | 2-{[6-(2,6-diethylphenyl)-2-methylpyridin-3-yl]methyl}-1-isopropyl-1,2,3,4-tetrahydroisoquinoline | X₁—CH₃ | | H | H | 1.19 | 412.3 | 413.4 |
| 587 | 1-butyl-2-{[6-(2,6-diethylphenyl)-2-methylpyridin-3-yl]methyl}-1,2,3,4-tetrahydroisoquinoline | X₁—CH₃ | | H | H | 1.21 | 426.3 | 427.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 588 | 1-cyclobutyl-2-{[6-(2,6-diethylphenyl)-2-methylpyridin-3-yl]methyl}-1,2,3,4-tetrahydroisoquinoline | H₃C—X₁ | | H | H | 1.17 | 424.3 | 425.4 |
| 589 | 2-{[6-(2,6-diethylphenyl)-2-methylpyridin-3-yl]methyl}-1-isobutyl-1,2,3,4-tetrahydroisoquinoline | X₁—CH₃ | | H | H | 1.23 | 426.3 | 427.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 590 | 2-{[6-(2,6-diethylphenyl)-2-methylpyridin-3-yl]methyl}-1-pentyl-1,2,3,4-tetrahydroisoquinoline | 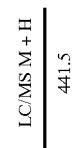 |  | H | H | 1.22 | 440.3 | 441.5 |
| 591 | N-benzyl-N-{[6-(2,6-diethylphenyl)-2-methylpyridin-3-yl]methyl}cyclopentanamine |  | 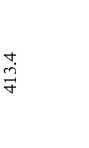 | H | H | 1.16 | 412.3 | 413.4 |
| 592 | N-benzyl-N-{[6-(2,6-diethylphenyl)-2-methylpyridin-3-yl]methyl}pentan-3-amine |  |  | H | H | 1.24 | 414.3 | 415.4 |

TABLE 3-continued
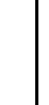
| Cpd # | NAME | R1 | B | R2 | R3 | LC/MS Retention Time | LC/MS Calc. Mass | LC/MS M + H |
|---|---|---|---|---|---|---|---|---|
| 593 | N-benzyl-N-{[6-(2,6-diethylphenyl)-2-methylpyridin-3-yl]methyl}cyclohexanamine | 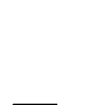 | 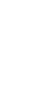 | H | H | 1.21 | 426.3 | 427.5 |
| 594 | N-benzyl-N-{[6-(2,6-diethylphenyl)-2-methylpyridin-3-yl]methyl}hexan-1-amine | 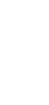 | 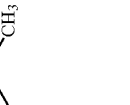 | H | H | 1.22 | 428.3 | 429.5 |
| 595 | N-benzyl-3-cyclopentyl-N-{[6-(2,6-diethylphenyl)-2-methylpyridin-3-yl]methyl}propan-1-amine |  |  | H | H | 1.26 | 454.3 | 455.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 596 | N-benzyl-N-{[6-(2,6-diethylphenyl)-2-methylpyridin-3-yl]methyl}-3-phenylpropan-1-amine | 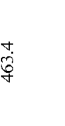 | 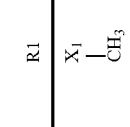 | H | H | 1.21 | 462.3 | 463.4 |
| 597 | 1-{[6-(2,6-diethylphenyl)-2-methylpyridin-3-yl]methyl}-3,3,5-trimethylazepane | 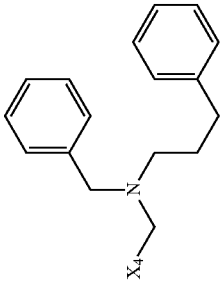 |  | H | H | 1.12 | 378.3 | 379.3 |
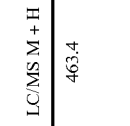

TABLE 3-continued
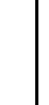
| Cpd # | NAME | R1 | B | R2 | R3 | LC/MS Retention Time | LC/MS Calc. Mass | LC/MS M + H |
|---|---|---|---|---|---|---|---|---|
| 598 | N-{[6-(2,6-diethylphenyl)-2-methylpyridin-3-yl]methyl}-N-ethyl-2-methylprop-2-en-1-amine |  |  | H | H | 1.09 | 336.3 | 337.2 |
| 599 | N-{[6-(2,6-diethylphenyl)-2-methylpyridin-3-yl]methyl}-N-pentylpentan-1-amine |  |  | H | H | 1.16 | 394.3 | 395.3 |

TABLE 3-continued
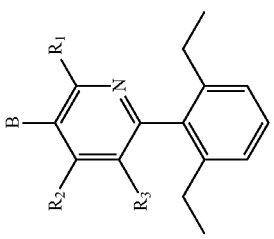
| Cpd # | NAME | R1 | B | R2 | R3 | LC/MS Retention Time | LC/MS Calc. Mass | LC/MS M + H |
|---|---|---|---|---|---|---|---|---|
| 600 | N-{[6-(2,6-diethylphenyl)-2-methylpyridin-3-yl]methyl}-N-hexylhexan-1-amine | CH₃—X₁ | 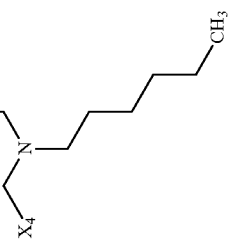 | H | H | 1.2 | 422.4 | 423.3 |
| 601 | 1-[6-(2,6-diethylphenyl)-2-methylpyridin-3-yl]-N-methyl-N-{3-methylbenzyl}methanamine | X₁—CH₃ | 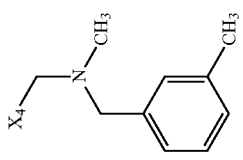 | H | H | 1.12 | 372.3 | 373.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 602 | 1-[6-(2,6-diethylphenyl)-2-methylpyridin-3-yl]-N-(4-fluorobenzyl)-N-methylmethanamine | X₁—CH₃ | X₄—CH₂N(CH₃)CH₂-(4-fluorophenyl) | H | H | 1.11 | 376.2 | 377.2 |
| 603 | N-(4-chlorobenzyl)-N-{[6-(2,6-diethylphenyl)-2-methylpyridin-3-yl]methyl}-N-methylamine | X₁—CH₃ | X₄—CH₂N(CH₃)CH₂-(4-chlorophenyl) | H | H | 1.14 | 392.2 | 393.2 |

TABLE 3-continued
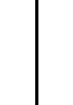
| Cpd # | NAME | R1 | B | R2 | R3 | LC/MS Retention Time | LC/MS Calc. Mass | LC/MS M + H |
|---|---|---|---|---|---|---|---|---|
| 604 | N-(3-chlorobenzyl)-N-{[6-(2,6-diethylphenyl)-2-methylpyridin-3-yl]methyl}-N-methylamine |  | 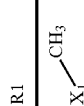 | H | H | 1.14 | 392.2 | 393.2 |
| 605 | 1-[6-(2,6-diethylphenyl)-2-methylpyridin-3-yl]-N-methyl-N-[4-(trifluoromethyl)benzyl]methanamine |  |  | H | H | 1.16 | 426.2 | 427.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 606 | 1-[6-(2,6-diethylphenyl)-2-methylpyridin-3-yl]-N-methyl-N-[3-(trifluoromethyl)benzyl]methanamine | X₁—CH₃ | X₄—N(CH₃)—CH₂—C₆H₄-3-CF₃ | H | H | 1.16 | 426.2 | 427.2 |
| 607 | 1-(4-bromophenyl)-N-{[6-(2,6-diethylphenyl)-2-methylpyridin-3-yl]methyl}-N-methylmethanamine | X₁—CH₃ | X₄—N(CH₃)—CH₂—C₆H₄-4-Br | H | H | 1.14 | 436.2 | 437.1 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 608 | N-benzyl-1-[6-(2,6-diethylphenyl)-4-methoxy-2-methylpyridin-3-yl]-N-methylmethanamine | 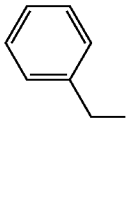 |  |  | H | 1 | 388.3 | 389.2 |
| 609 | N-{[6-(2,6-diethylphenyl)-4-methoxy-2-methylpyridin-3-yl]methyl}-N-methyl-1-phenylpropan-1-amine | 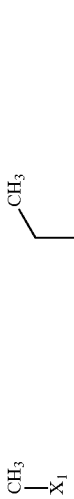 | 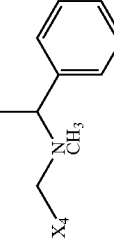 |  | H | 1.02 | 416.3 | 417.2 |
| 610 | N-{[6-(2,6-diethylphenyl)-4-methoxy-2-methylpyridin-3-yl]methyl}-N,2-dimethyl-1-phenylpropan-1-amine |  | 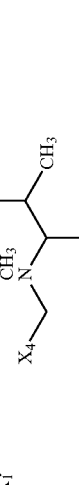 | 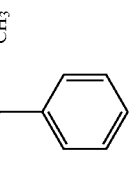 | H | 1.04 | 430.3 | 431.3 |

TABLE 3-continued
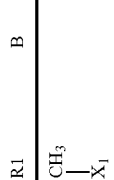
| Cpd # | NAME | R1 | B | R2 | R3 | LC/MS Retention Time | LC/MS Calc. Mass | LC/MS M + H |
|---|---|---|---|---|---|---|---|---|
| 611 | N-{[6-(2,6-diethylphenyl)-4-methoxy-2-methylpyridin-3-yl]methyl}-N-methyl-1-phenylbutan-1-amine | 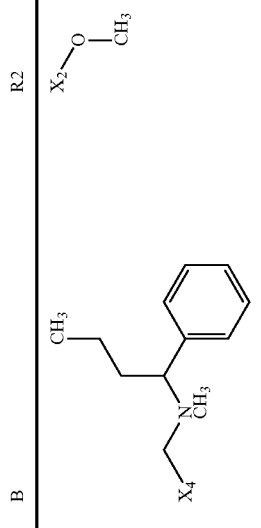 | 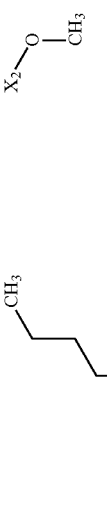 | 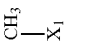 | H | 1.04 | 430.3 | 431.3 |
| 612 | N-{[6-(2,6-diethylphenyl)-4-methoxy-2-methylpyridin-3-yl]methyl}-N-methyl-1-phenylpentan-1-amine | 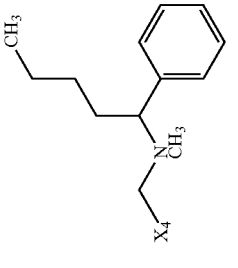 | 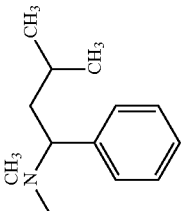 | 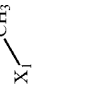 | H | 1.07 | 444.3 | 445.3 |
| 613 | N-{[6-(2,6-diethylphenyl)-4-methoxy-2-methylpyridin-3-yl]methyl}-N,3-dimethyl-1-phenylbutan-1-amine | 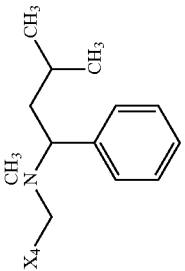 |  | | H | 1.07 | 444.3 | 445.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 614 | N-{[6-(2,6-diethylphenyl)-4-methoxy-2-methylpyridin-3-yl]methyl}-N-methyl-1-phenylhexan-1-amine |  | 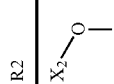 |  | H | 1.1 | 458.3 | 459.3 |
| 615 | N-{[6-(2,6-diethylphenyl)-4-methoxy-2-methylpyridin-3-yl]methyl}-N-methyl-1-phenylheptan-1-amine |  |  |  | H | 1.12 | 472.3 | 473.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 616 | N-benzyl-N-{[6-(2,6-diethylphenyl)-4-methoxy-2-methylpyridin-3-yl]methyl}ethanamine | H₃C—X₁ | X₄—N(CH₂Ph)(CH₂CH₃) | X₂—O—CH₃ | H | 1.01 | 402.3 | 403.2 |
| 617 | N-benzyl-N-{[6-(2,6-diethylphenyl)-4-methoxy-2-methylpyridin-3-yl]methyl}propan-2-amine | X₁—CH₃ | X₄—N(CH₂Ph)CH(CH₃)₂ | X₂—O—CH₃ | H | 1.01 | 416.3 | 417.2 |
| 618 | N-benzyl-N-{[6-(2,6-diethylphenyl)-4-methoxy-2-methylpyridin-3-yl]methyl}propan-1-amine | CH₃—X₁ | X₄—N(CH₂Ph)(CH₂CH₂CH₃) | H₃C—O—X₂ | H | 1.03 | 416.3 | 417.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 619 | N-benzyl-N-{[6-(2,6-diethylphenyl)-4-methoxy-2-methylpyridin-3-yl]methyl}prop-2-en-1-amine | X₁—CH₃ | 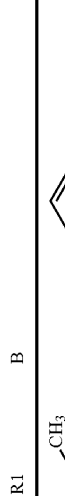 |  | H | 1.04 | 414.3 | 415.2 |
| 620 | N-benzyl-N-{[6-(2,6-diethylphenyl)-4-methoxy-2-methylpyridin-3-yl]methyl}cyclopropanamine |  | 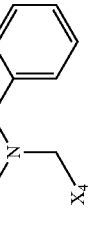 |  | H | 1.09 | 414.3 | 415.2 |
| 621 | N-benzyl-N-{[6-(2,6-diethylphenyl)-4-methoxy-2-methylpyridin-3-yl]methyl}butan-1-amine |  |  |  | H | 1.04 | 430.3 | 431.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 622 | N-benzyl-N-{[6-(2,6-diethylphenyl)-4-methoxy-2-methylpyridin-3-yl]methyl}-2-methylpropan-1-amine |  |  |  | H | 1.12 | 430.3 | 431.3 |
| 623 | N-benzyl-N-{[6-(2,6-diethylphenyl)-4-methoxy-2-methylpyridin-3-yl]methyl}-butan-2-amine |  |  |  | H | 1.05 | 430.3 | 431.3 |
| 624 | N-benzyl-N-{[6-(2,6-diethylphenyl)-4-methoxy-2-methylpyridin-3-yl]methyl}pentan-1-amine |  |  | 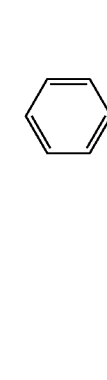 | H | 1.08 | 444.3 | 445.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 625 | N-benzyl-N-{[6-(2,6-diethylphenyl)-4-methoxy-2-methylpyridin-3-yl]methyl}-3-methylbutan-1-amine | X₁—CH₃ | (benzyl-N(CH₂X₄)-CH₂CH₂-CH(CH₃)₂) | X₂—O—CH₃ | H | 1.08 | 444.3 | 445.3 |
| 626 | N-benzyl-N-{[6-(2,6-diethylphenyl)-4-methoxy-2-methylpyridin-3-yl]methyl}pentan-2-amine | H₃C—X₁ | (benzyl-N(X₄)-CH(CH₃)-CH₂CH₂CH₃) | X₂—O—CH₃ | H | 1.08 | 444.3 | 445.3 |
| 627 | 2-{[6-(2,6-diethylphenyl)-4-methoxy-2-methylpyridin-3-yl]methyl}-1,2,3,4-tetrahydroisoquinoline | X₁—CH₃ | (1,2,3,4-tetrahydroisoquinolin-2-yl-X₄) | X₂—O—CH₃ | H | 0.99 | 400.3 | 401.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 628 | 2-{[6-(2,6-diethylphenyl)-4-methoxy-2-methylpyridin-3-yl]methyl}-1-methyl-1,2,3,4-tetrahydroisoquinoline | X₁—CH₃ |  |  | H | 1 | 414.3 | 415.2 |
| 629 | 2-{[6-(2,6-diethylphenyl)-4-methoxy-2-methylpyridin-3-yl]methyl}-1-ethyl-1,2,3,4-tetrahydroisoquinoline | X₁—CH₃ |  |  | H | 1.04 | 428.3 | 429.2 |
| 630 | 2-{[6-(2,6-diethylphenyl)-4-methoxy-2-methylpyridin-3-yl]methyl}-1-propyl-1,2,3,4-tetrahydroisoquinoline | X₁—CH₃ |  |  | H | 1.08 | 442.3 | 443.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 631 | 1-cyclopropyl-2-{[6-(2,6-diethylphenyl)-4-methoxy-2-methylpyridin-3-yl]methyl}-1,2,3,4-tetrahydroisoquinoline | H₃C—X₁ |  | X₂—O—CH₃ | H | 1.03 | 440.3 | 441.2 |
| 632 | 2-{[6-(2,6-diethylphenyl)-4-methoxy-2-methylpyridin-3-yl]methyl}-1-isopropyl-1,2,3,4-tetrahydroisoquinoline | X₁—CH₃ |  | X₂—O—CH₃ | H | 1.07 | 442.3 | 443.3 |
| 633 | 1-butyl-2-{[6-(2,6-diethylphenyl)-4-methoxy-2-methylpyridin-3-yl]methyl}-1,2,3,4-tetrahydroisoquinoline | X₁—CH₃ |  | X₂—O—CH₃ | H | 1.11 | 456.3 | 457.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 634 | 1-cyclobutyl-2-{[6-(2,6-diethylphenyl)-4-methoxy-2-methylpyridin-3-yl]methyl}-1,2,3,4-tetrahydroisoquinoline | H₃C—X₁ | | X₂—O—CH₃ | H | 1.07 | 454.3 | 455.3 |
| 635 | 2-{[6-(2,6-diethylphenyl)-4-methoxy-2-methylpyridin-3-yl]methyl}-1-isobutyl-1,2,3,4-tetrahydroisoquinoline | X₁—CH₃ | | X₂—O—CH₃ | H | 1.12 | 456.3 | 457.3 |
| 636 | 2-{[6-(2,6-diethylphenyl)-4-methoxy-2-methylpyridin-3-yl]methyl}-1-pentyl-1,2,3,4-tetrahydroisoquinoline | X₁—CH₃ | | X₂—O—CH₃ | H | 1.14 | 470.3 | 471.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 637 | 2-{[6-(2,6-diethylphenyl)-4-methoxy-2-methylpyridin-3-yl]methyl}-1-isopentyl-1,2,3,4-tetrahydroisoquinoline | X₁―CH₃ |  |  | H | 1.14 | 470.3 | 471.3 |
| 638 | N-benzyl-N-{[6-(2,6-diethylphenyl)-4-methoxy-2-methylpyridin-3-yl]methyl}cyclopentanamine | X₁―CH₃ |  |  | H | 1.03 | 442.3 | 443.3 |
| 639 | N-benzyl-N-{[6-(2,6-diethylphenyl)-4-methoxy-2-methylpyridin-3-yl]methyl}pentan-3-amine | X₁―CH₃ |  |  | H | 1.16 | 444.3 | 445.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 640 | N-benzyl-N-{[6-(2,6-diethylphenyl)-4-methoxy-2-methylpyridin-3-yl]methyl}cyclohexanamine | 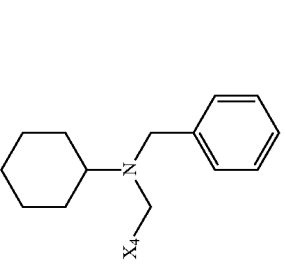 |  | 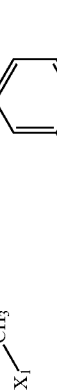 | H | 1.06 | 456.3 | 457.3 |
| 641 | N,N-dibenzyl-1-[6-(2,6-diethylphenyl)-4-methoxy-2-methylpyridin-3-yl]methanamine |  |  | 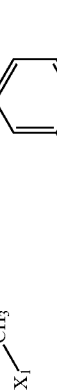 | H | 1.17 | 464.3 | 465.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 642 | N-benzyl-1-cyclopentyl-N-{[6-(2,6-diethylphenyl)-4-methoxy-2-methylpyridin-3-yl]methyl}methanamine | H₃C—X₁ |  |  | H | 1.13 | 456.3 | 457.3 |
| 643 | N-benzyl-N-{[6-(2,6-diethylphenyl)-4-methoxy-2-methylpyridin-3-yl]methyl}hexan-1-amine | H₃C—X₁ | 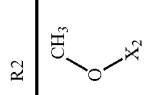 |  | H | 1.11 | 458.3 | 459.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 644 | N-benzyl-1-cyclohexyl-N-{[6-(2,6-diethylphenyl)-4-methoxy-2-methylpyridin-3-yl]methyl}methanamine | 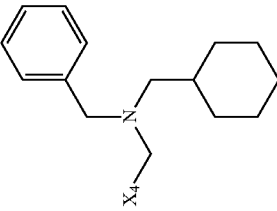 |  |  | H | 1.18 | 470.3 | 471.3 |
| 645 | N-benzyl-N-{[6-(2,6-diethylphenyl)-4-methoxy-2-methylpyridin-3-yl]methyl}-heptan-1-amine |  | 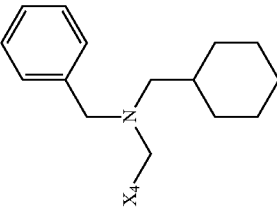 |  | H | 1.15 | 472.3 | 473.3 |

TABLE 3-continued
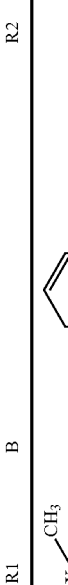
| Cpd # | NAME | R1 | B | R2 | R3 | LC/MS Retention Time | LC/MS Calc. Mass | LC/MS M + H |
|---|---|---|---|---|---|---|---|---|
| 646 | N-benzyl-N-{[6-(2,6-diethylphenyl)-4-methoxy-2-methyl]pyridin-3-yl]methyl}-2-phenylethanamine | 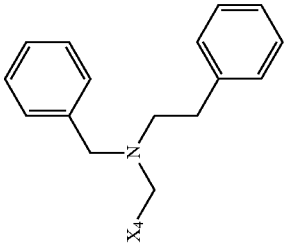 | 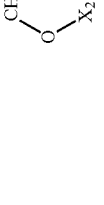 | 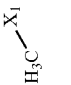 | H | 1.13 | 478.3 | 479.3 |
| 647 | N-benzyl-3-cyclopentyl-N-{[6-(2,6-diethylphenyl)-4-methoxy-2-methyl]pyridin-3-yl]methyl}propan-1-amine |  |  |  | H | 1.14 | 484.3 | 485.3 |
| 648 | N-benzyl-N-{[6-(2,6-diethylphenyl)-4-methoxy-2-methyl]pyridin-3-yl]methyl}-3-phenylpropan-1-amine |  |  | | H | 1.11 | 492.3 | 493.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 649 | 6-(2,6-diethylphenyl)-4-methoxy-2-methyl-3-(phenoxymethyl)pyridine |  |  |  | H | 1.13 | 361.2 | 362.2 |
| 650 | 6-(2,6-diethylphenyl)-4-methoxy-2-methyl-3-[(4-propylphenoxy)methyl]pyridine | 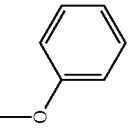 |  |  | H | 1.2 | 403.3 | 404.2 |
| 651 | 3-[(4-butylphenoxy)methyl]-6-(2,6-diethylphenyl)-4-methoxy-2-methylpyridine |  | 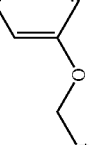 |  | H | 1.22 | 417.3 | 418.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 652 | 3-[(4-sec-butylphenoxy)methyl]-6-(2,6-diethylphenyl)-4-methoxy-2-methylpyridine | 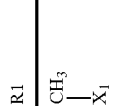 | 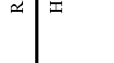 | 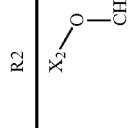 | H | 1.19 | 417.3 | 418.3 |
| 653 | 3-[(4-benzylphenyl)-6-(2,6-diethylphenyl)-4-methoxy-2-methylpyridine |  |  |  | H | 1.19 | 451.3 | 452.3 |
| 654 | 6-(2,6-diethylphenyl)-4-methoxy-2-methyl-3-[(3-propylphenoxy)methyl]pyridine |  |  |  | H | 1.2 | 403.3 | 404.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 655 | 6-(2,6-diethylphenyl)-3-[(3,4-dimethylphenoxy)methyl]-4-methoxy-2-methylpyridine | X1—CH3 |  |  | H | 1.17 | 389.2 | 390.2 |
| 656 | 6-(2,6-diethylphenyl)-3-[(3,5-dimethylphenoxy)methyl]-4-methoxy-2-methylpyridine | X1—CH3 |  |  | H | 1.17 | 389.2 | 390.2 |
| 657 | 6-(2,6-diethylphenyl)-4-methoxy-2-methyl-3-[(3,4,5-trimethylphenoxy)methyl]pyridine | X1—CH3 |  |  | H | 1.18 | 403.3 | 404.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 658 | 6-(2,6-diethylphenyl)-4-methoxy-2-methyl-3-[(5,6,7,8-tetrahydronaphthalen-2-yloxy)methyl]pyridine | X$_1$—CH$_3$ | X$_4$—O—(5,6,7,8-tetrahydronaphthalen-2-yl) | X$_2$—O—CH$_3$ | H | 1.22 | 415.3 | 416.3 |
| 659 | 6-(2,6-diethylphenyl)-4-methoxy-2-methyl-3-[(2-naphthyloxy)methyl]pyridine | X$_1$—CH$_3$ | X$_4$—O—(2-naphthyl) | X$_2$—O—CH$_3$ | H | 1.17 | 411.2 | 412.2 |
| 660 | 6-(2,6-diethylphenyl)-4-methoxy-2-{[(7-methoxy-2-naphthyl)oxy]methyl}-2-methylpyridine | X$_1$—CH$_3$ | X$_4$—O—(7-methoxy-2-naphthyl) | X$_2$—O—CH$_3$ | H | 1.18 | 441.2 | 442.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 661 | 6-(2,6-diethylphenyl)-3-[(3-ethoxyphenoxy)methyl]-4-methoxy-2-methylpyridine | H₃C—X₁ | H₃C—O—(3-phenylene)—O—CH₂—X₄ | X₂—O—CH₃ | H | 1.14 | 405.2 | 406.2 |
| 662 | 6-(2,6-diethylphenyl)-4-methoxy-2-methyl-3-[(3-phenoxyphenoxy)methyl]pyridine | X₁—CH₃ | X₄—CH₂—O—(3-phenoxyphenyl) | X₂—O—CH₃ | H | 1.19 | 453.2 | 454.2 |
| 663 | 6-(2,6-diethylphenyl)-4-methoxy-2-methyl-3-[(4-phenoxyphenoxy)methyl]pyridine | X₁—CH₃ | X₄—CH₂—O—(4-phenoxyphenyl) | X₂—O—CH₃ | H | 1.17 | 453.2 | 454.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 664 | 3-[(1,3-benzodioxol-5-yloxy)methyl]-6-(2,6-diethylphenyl)-4-methoxy-2-methylpyridine | H₃C—X₁ | benzodioxol-CH₂-O-X₄ | X₂—O—CH₃ | H | 1.12 | 405.2 | 406.2 |
| 665 | 6-(2,6-diethylphenyl)-4-methoxy-2-methyl-3-{[4-(trifluoromethoxy)phenoxy]methyl}pyridine | X₁—CH₃ | X₄-CH₂-O-(4-CF₃-phenyl) | X₂—O—CH₃ (H₃C) | H | 1.16 | 429.2 | 430.2 |
| 666 | 6-(2,6-diethylphenyl)-3-{[4-fluoro-3-(trifluoromethyl)phenoxy]methyl}-4-methoxy-2-methylpyridine | X₁—CH₃ | X₄-CH₂-O-(4-F-3-CF₃-phenyl) | X₂—O—CH₃ (H₃C) | H | 1.16 | 447.2 | 448.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 667 | 6-(2,6-diethylphenyl)-3-{[2-fluoro-5-(trifluoromethyl)phenoxy]methyl}-4-methoxy-2-methylpyridine |  | 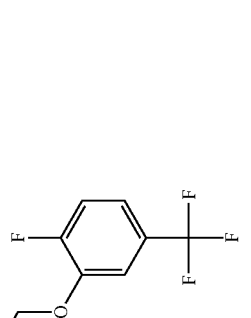 |  | H | 1.17 | 447.2 | 448.2 |
| 668 | 3-{[4-chloro-3-(trifluoromethyl)phenoxy]methyl}-6-(2,6-diethylphenyl)-4-methoxy-2-methylpyridine |  |  |  | H | 1.2 | 463.2 | 464.2 |
| 669 | 3-[(3-chloro-2-fluorophenoxy)methyl]-6-(2,6-diethylphenyl)-4-methoxy-2-methylpyridine |  |  |  | H | 1.16 | 413.2 | 414.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 670 | 3-[(4-chloro-2-fluorophenoxy)methyl]-6-(2,6-diethylphenyl)-4-methoxy-2-methylpyridine | X1—CH3 | (4-chloro-2-fluorophenoxy)methyl-X4 | X2—O—CH3 | H | 1.16 | 413.2 | 414.2 |
| 671 | 3-[(4-chloro-3-fluorophenoxy)methyl]-6-(2,6-diethylphenyl)-4-methoxy-2-methylpyridine | X1—CH3 | (4-chloro-3-fluorophenoxy)methyl-X4 | X2—O—CH3 | H | 1.15 | 413.2 | 414.2 |
| 672 | 3-[(4-chloro-3-methylphenoxy)methyl]-6-(2,6-diethylphenyl)-4-methoxy-2-methylpyridine | X1—CH3 | (4-chloro-3-methylphenoxy)methyl-X4 | X2—O—CH3 | H | 1.19 | 409.2 | 410.2 |
| 673 | 3-[(4-chloro-3-ethylphenoxy)methyl]-6-(2,6-diethylphenyl)-4-methoxy-2-methylpyridine | X1—CH3 | (4-chloro-3-ethylphenoxy)methyl-X4 | X2—O—CH3 | H | 1.21 | 423.2 | 424.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 674 | 3-[(4-chloro-3,5-dimethylphenoxy)methyl]-6-(2,6-diethylphenyl)-4-methoxy-2-methylpyridine |  |  |  | H | 1.2 | 423.2 | 424.2 |
| 675 | 3-[(1,1'-biphenyl-3-yloxy)methyl]-6-(2,6-diethylphenyl)-4-methoxy-2-methylpyridine | 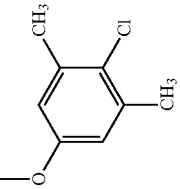 |  |  | H | 1.19 | 437.2 | 438.2 |
| 676 | 6-(2,6-diethylphenyl)-3-[(2,3-difluorophenoxy)methyl]-4-methoxy-2-methylpyridine | |  |  | H | 1.14 | 397.2 | 398.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 677 | 6-(2,6-diethylphenyl)-3-[(2,4-difluorophenoxy)methyl]-4-methoxy-2-methylpyridine | X1—CH3 |  |  | H | 1.12 | 397.2 | 398.2 |
| 678 | 6-(2,6-diethylphenyl)-3-[(2,5-difluorophenoxy)methyl]-4-methoxy-2-methylpyridine | X1—CH3 |  |  | H | 1.13 | 397.2 | 398.2 |
| 679 | 6-(2,6-diethylphenyl)-3-[(2,6-difluorophenoxy)methyl]-4-methoxy-2-methylpyridine | X1—CH3 |  |  | H | 1.12 | 397.2 | 398.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 680 | 6-(2,6-diethylphenyl)-3-[(3,4-difluorophenoxy)methyl]-4-methoxy-2-methylpyridine | X1—CH3 | X4—CH2—O—(3,4-difluorophenyl) | X2—O—CH3 | H | 1.14 | 397.2 | 398.2 |
| 681 | 6-(2,6-diethylphenyl)-3-[(3,5-difluorophenoxy)methyl]-4-methoxy-2-methylpyridine | X1—CH3 | X4—CH2—O—(3,5-difluorophenyl) | X2—O—CH3 | H | 1.15 | 397.2 | 398.2 |
| 682 | 6-(2,6-diethylphenyl)-3-[(4-fluoro-3-methylphenoxy)methyl]-4-methoxy-2-methylpyridine | X1—CH3 | X4—CH2—O—(4-fluoro-3-methylphenyl) | X2—O—CH3 | H | 1.17 | 393.2 | 394.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 683 | 6-(2,6-diethylphenyl)-3-[(2-fluoro-5-methylphenoxy)methyl]-4-methoxy-2-methylpyridine | X₁—CH₃ |  |  | H | 1.15 | 393.2 | 394.2 |
| 684 | 2-(2,6-diethylphenyl)-4-methoxy-3,6-dimethyl-5-(phenoxymethyl)pyridine | X₁—CH₃ |  | X₂—O—CH₃ | CH₃—X₃ | 1.16 | 375.2 | 376.2 |
| 685 | 2-(2,6-diethylphenyl)-4-methoxy-3,6-dimethyl-5-[(3-propylphenoxy)methyl]pyridine | H₃C—X₁ |  | X₂—O—CH₃ | X₃—CH₃ | 1.23 | 417.3 | 418.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 686 | 2-(2,6-diethylphenyl)-5-[(3,4-dimethylphenoxy)methyl]-4-methoxy-3,6-dimethylpyridine | $X_1$—$CH_3$ | $X_4$—(3,4-dimethylphenoxy)methyl | $X_2$—O—$CH_3$ | $CH_3$—$X_3$ | 1.21 | 403.3 | 404.3 |
| 687 | 2-(2,6-diethylphenyl)-5-[(3,5-dimethylphenoxy)methyl]-4-methoxy-3,6-dimethylpyridine | $X_1$—$CH_3$ | $X_4$—(3,5-dimethylphenoxy)methyl | $X_2$—O—$CH_3$ | $CH_3$—$X_3$ | 1.22 | 403.3 | 404.2 |
| 688 | 2-(2,6-diethylphenyl)-4-methoxy-3,6-dimethyl-5-[(3,4,5-trimethylphenoxy)methyl]pyridine | $X_1$—$CH_3$ | $X_4$—(3,4,5-trimethylphenoxy)methyl | $X_2$—O—$CH_3$ | $CH_3$—$X_3$ | 1.22 | 417.3 | 418.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 689 | 2-(2,6-diethylphenyl)-4-methoxy-3,6-dimethyl-5-[(2-naphthyloxy)methyl]pyridine | X1—CH3 | (2-naphthyloxymethyl) | X2—O—CH3 | CH3—X3 | 1.22 | 425.2 | 426.2 |
| 690 | 2-(2,6-diethylphenyl)-4-methoxy-5-{[(7-methoxy-2-naphthyl)oxy]methyl}-3,6-dimethylpyridine | X1—CH3 | (7-methoxy-2-naphthyloxymethyl) | X2—O—CH3 | CH3—X3 | 1.21 | 455.2 | 456.3 |
| 691 | 2-(2,6-diethylphenyl)-5-[(3-ethoxyphenoxy)methyl]-4-methoxy-3,6-dimethylpyridine | H3C—X1 | (3-ethoxyphenoxymethyl) | X2—O—CH3 | X3—CH3 | 1.2 | 419.2 | 420.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 692 | 2-(2,6-diethylphenyl)-4-methoxy-3,6-dimethyl-5-[(3-phenoxyphenoxy)methyl]pyridine | X₁—CH₃ | 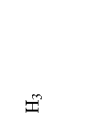 | X₂—O—CH₃ | CH₃—X₃ | 1.23 | 467.2 | 468.3 |
| 693 | 3-[(1,3-benzodioxol-5-yloxy)methyl]-6-(2,6-diethylphenyl)-4-methoxy-2,5-dimethylpyridine | X₁—CH₃ |  | CH₃—O—X₂ | H₃C—X₃ | 1.16 | 419.2 | 420.2 |
| 694 | 2-(2,6-diethylphenyl)-5-{[4-fluoro-3-(trifluoromethyl)phenoxy]methyl}-4-methoxy-3,6-dimethylpyridine | X₁—CH₃ | 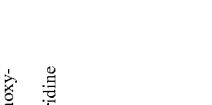 | X₂—O—CH₃ | CH₃—X₃ | 1.21 | 461.2 | 462.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 695 | 2-(2,6-diethylphenyl)-5-{[2-fluoro-5-(trifluoromethyl)phenoxy]methyl}-4-methoxy-3,6-dimethylpyridine | X1—CH3 | (2-fluoro-5-(trifluoromethyl)phenoxymethyl) | X2—O—CH3 | CH3—X3 | 1.21 | 461.2 | 462.2 |
| 696 | 3-[(3-chloro-2-fluorophenoxy)methyl]-6-(2,6-diethylphenyl)-4-methoxy-2,5-dimethylpyridine | X1—CH3 | (3-chloro-2-fluorophenoxymethyl) | X2—O—CH3 | CH3—X3 | 1.21 | 427.2 | 428.2 |
| 697 | 3-[(4-chloro-2-fluorophenoxy)methyl]-6-(2,6-diethylphenyl)-4-methoxy-2,5-dimethylpyridine | X1—CH3 | (4-chloro-2-fluorophenoxymethyl) | X2—O—CH3 | CH3—X3 | 1.21 | 427.2 | 428.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 698 | 3-[(4-chloro-3-fluorophenoxy)methyl]-6-(2,6-diethylphenyl)-4-methoxy-2,5-dimethylpyridine | X₁—CH₃ |  |  |  | 1.22 | 427.2 | 428.2 |
| 699 | 3-[(4-chloro-3-ethylphenoxy)methyl]-6-(2,6-diethylphenyl)-4-methoxy-2,5-dimethylpyridine | X₁—CH₃ |  |  |  | 1.23 | 437.2 | 438.2 |
| 700 | 3-[(4-chloro-3,5-dimethylphenoxy)methyl]-6-(2,6-diethylphenyl)-4-methoxy-2,5-dimethylpyridine | X₁—CH₃ |  |  |  | 1.24 | 437.2 | 438.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 701 | 3-[(1,1'-biphenyl-3-yloxy)methyl]-6-(2,6-diethylphenyl)-4-methoxy-2,5-dimethylpyridine | $X_1$—$CH_3$ |  | $X_2$—O—$CH_3$ | $CH_3$—$X_3$ | 1.23 | 451.3 | 452.3 |
| 702 | 2-(2,6-diethylphenyl)-5-[(2,3-difluorophenoxy)methyl]-4-methoxy-3,6-dimethylpyridine | $X_1$—$CH_3$ |  | $X_2$—O—$CH_3$ | $CH_3$—$X_3$ | 1.18 | 411.2 | 412.2 |
| 703 | 2-(2,6-diethylphenyl)-5-[(2,5-difluorophenoxy)methyl]-4-methoxy-3,6-dimethylpyridine | $X_1$—$CH_3$ |  | $X_2$—O—$CH_3$ | $CH_3$—$X_3$ | 1.19 | 411.2 | 412.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 704 | 6-(2,6-diethylphenyl)-2-methyl-3-[(3-propylphenoxy)methyl]pyridine | X₁—CH₃ |  | H | H | 1.27 | 373.2 | 374.2 |
| 705 | 6-(2,6-dimethylphenyl)-3-[(3,4-dimethylphenoxy)methyl]-2-methylpyridine | X₁—CH₃ | 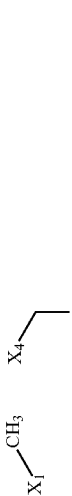 | H | H | 1.24 | 359.2 | 360.2 |
| 706 | 6-(2,6-dimethylphenyl)-3-[(3,5-dimethylphenoxy)methyl]-2-methylpyridine | X₁—CH₃ | 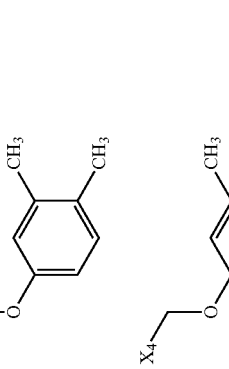 | H | H | 1.25 | 359.2 | 360.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 707 | 6-(2,6-diethylphenyl)-2-methyl-3-[(2-naphthyloxy)methyl]pyridine | X₁—CH₃ | 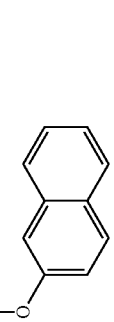 | H | H | 1.25 | 381.2 | 382.2 |
| 708 | 6-(2,6-diethylphenyl)-3-[(3-ethoxyphenoxy)methyl]-2-methylpyridine | X₁—CH₃ |  | H | H | 1.23 | 375.2 | 376.2 |
| 709 | 6-(2,6-diethylphenyl)-2-methyl-3-[(3-phenoxyphenoxy)methyl]pyridine | X₁—CH₃ |  | H | H | 1.28 | 423.2 | 424.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 710 | 6-(2,6-diethylphenyl)-3-{[2-fluoro-5-(trifluoromethyl)phenoxy]methyl}-2-methylpyridine | X₁—CH₃ |  | H | H | 1.25 | 417.2 | 418.2 |
| 711 | 3-[(4-chloro-2-fluorophenoxy)methyl]-6-(2,6-diethylphenyl)-2-methylpyridine | X₁—CH₃ |  | H | H | 1.24 | 383.1 | 384.1 |
| 712 | 3-[(4-chloro-3-fluorophenyl)methyl]-6-(2,6-diethylphenyl)-2-methylpyridine | X₁—CH₃ |  | H | H | 1.25 | 383.1 | 384.1 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 713 | 3-[(1,1'-biphenyl-3-yloxy)methyl]-6-(2,6-diethylphenyl)-2-methylpyridine |  |  | H | H | 1.27 | 407.2 | 408.2 |
| 714 | 6-(2,6-diethylphenyl)-3-[(2,6-difluorophenoxy)methyl]-2-methylpyridine |  |  | H | H | 1.21 | 367.2 | 368.1 |
| 715 | 6-(2,6-diethylphenyl)-3-[(2-fluoro-5-methylphenoxy)methyl]-2-methylpyridine |  | 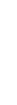 | H | H | 1.23 | 363.2 | 364.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 716 | 6-(2,6-diethylphenyl)-2,4-dimethyl-3-(phenoxymethyl)pyridine |  |  |  | H | 1.16 | 345.2 | 346.2 |
| 717 | 6-(2,6-diethylphenyl)-2,4-dimethyl-3-[(4-propylphenoxy)methyl]pyridine |  |  |  | H | 1.24 | 387.3 | 388.2 |
| 718 | 3-[(4-sec-butylphenoxy)methyl]-6-(2,6-diethylphenyl)-2,4-dimethylpyridine |  |  |  | H | 1.24 | 401.3 | 402.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 719 | 6-(2,6-diethylphenyl)-2,4-dimethyl-3-[(3-propylphenoxy)methyl]pyridine | X₁—CH₃ | 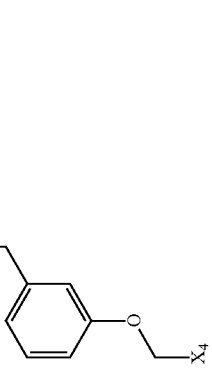 | H₃C—X₂ | H | 1.22 | 387.3 | 388.2 |
| 720 | 6-(2,6-diethylphenyl)-3-[(3,4-dimethylphenoxy)methyl]-2,4-dimethylpyridine | X₁—CH₃ |  | X₂—CH₃ | H | 1.21 | 373.2 | 374.2 |
| 721 | 6-(2,6-diethylphenyl)-3-[(3,5-dimethylphenoxy)methyl]-2,4-dimethylpyridine | X₁—CH₃ |  | X₂—CH₃ | H | 1.2 | 373.2 | 374.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 722 | 6-(2,6-diethylphenyl)-2,4-dimethyl-3-[(3,4,5-trimethylphenoxy)methyl]pyridine | X1—CH3 | (3,4,5-trimethylphenoxymethyl) | X2—CH3 | H | 1.23 | 387.3 | 387.3 |
| 723 | 6-(2,6-diethylphenyl)-2,4-dimethyl-3-[(5,6,7,8-tetrahydronaphthalen-2-yloxy)methyl]pyridine | X1—CH3 | (5,6,7,8-tetrahydronaphthalen-2-yloxymethyl) | X2—CH3 | H | 1.23 | 399.3 | 400.2 |
| 724 | 6-(2,6-diethylphenyl)-2,4-dimethyl-3-[(2-naphthyloxy)methyl]pyridine | X1—CH3 | (2-naphthyloxymethyl) | X2—CH3 | H | 1.21 | 395.2 | 396.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 725 | 6-(2,6-diethylphenyl)-3-{[(7-methoxy-2-naphthyl)oxy]methyl}-2,4-dimethylpyridine | X1—CH3 | (7-methoxy-2-naphthyl-O-CH2-X4) | X2—CH3 | H | 1.18 | 425.2 | 426.2 |
| 726 | 6-(2,6-diethylphenyl)-3-[(3-ethoxyphenoxy)methyl]-2,4-dimethylpyridine | X1—CH3 | (3-ethoxyphenoxy-CH2-X4) | H3C—X2 | H | 1.17 | 389.2 | 390.2 |
| 727 | 6-(2,6-diethylphenyl)-2,4-dimethyl-3-[(3-phenoxyphenoxy)methyl]pyridine | X1—CH3 | (3-phenoxyphenoxy-CH2-X4) | X2—CH3 | H | 1.22 | 437.2 | 438.2 |

TABLE 3-continued

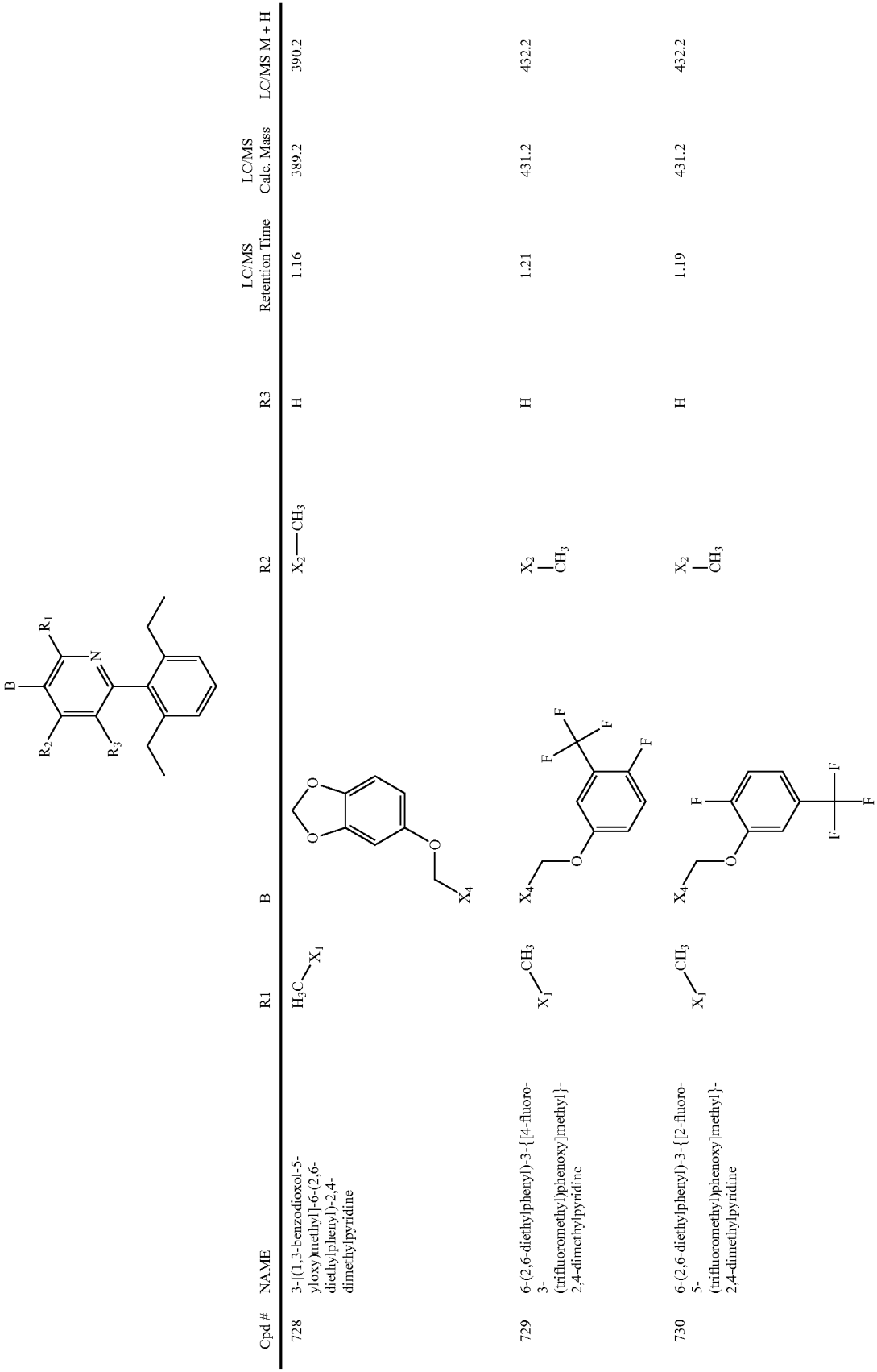

| Cpd # | NAME | R1 | B | R2 | R3 | LC/MS Retention Time | LC/MS Calc. Mass | LC/MS M + H |
|---|---|---|---|---|---|---|---|---|
| 728 | 3-[(1,3-benzodioxol-5-yloxy)methyl]-6-(2,6-diethylphenyl)-2,4-dimethylpyridine | H₃C—X₁ | benzodioxol-O-CH₂-X₄ | X₂—CH₃ | H | 1.16 | 389.2 | 390.2 |
| 729 | 6-(2,6-diethylphenyl)-3-{[4-fluoro-3-(trifluoromethyl)phenoxy]methyl}-2,4-dimethylpyridine | X₁—CH₃ | 4-fluoro-3-CF₃-phenyl-O-CH₂-X₄ | X₂—CH₃ | H | 1.21 | 431.2 | 432.2 |
| 730 | 6-(2,6-diethylphenyl)-3-{[2-fluoro-5-(trifluoromethyl)phenoxy]methyl}-2,4-dimethylpyridine | X₁—CH₃ | 2-fluoro-5-CF₃-phenyl-O-CH₂-X₄ | X₂—CH₃ | H | 1.19 | 431.2 | 432.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 731 | 3-[(4-chloro-3-(trifluoromethyl)phenoxy]methyl]-6-(2,6-diethylphenyl)-2,4-dimethylpyridine | X₁—CH₃ | X₄—O—(4-Cl,3-CF₃-phenyl) | X₂—CH₃ | H | 1.23 | 447.2 | 448.2 |
| 732 | 3-[(4-chloro-2-fluorophenoxy)methyl]-6-(2,6-diethylphenyl)-2,4-dimethylpyridine | X₁—CH₃ | X₄—O—(4-Cl,2-F-phenyl) | X₂—CH₃ | H | 1.19 | 397.2 | 398.1 |
| 733 | 3-[(4-chloro-3-fluorophenoxy)methyl]-6-(2,6-diethylphenyl)-2,4-dimethylpyridine | X₁—CH₃ | X₄—O—(4-Cl,3-F-phenyl) | X₂—CH₃ | H | 1.2 | 397.2 | 398.1 |
| 734 | 3-[(4-chloro-3-methylphenoxy)methyl]-6-(2,6-diethylphenyl)-2,4-dimethylpyridine | X₁—CH₃ | X₄—O—(4-Cl,3-CH₃-phenyl) | X₂—CH₃ | H | 1.21 | 393.2 | 394.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 735 | 3-[(4-chloro-3-ethylphenoxy)methyl]-6-(2,6-diethylphenyl)-2,4-dimethylpyridine | X₁—CH₃ | 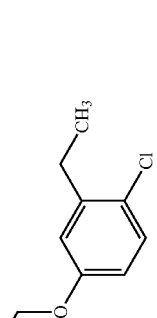 | X₂—CH₃ | H | 1.24 | 407.2 | 408.2 |
| 736 | 3-[(4-chloro-3,5-dimethylphenoxy)methyl]-6-(2,6-diethylphenyl)-2,4-dimethylpyridine | X₁—CH₃ |  | X₂—CH₃ | H | 1.24 | 407.2 | 408.2 |
| 737 | 3-[(1,1'-biphenyl-3-yloxy)methyl]-6-(2,6-diethylphenyl)-2,4-dimethylpyridine | X₁—CH₃ |  | X₂—CH₃ | H | 1.24 | 421.2 | 422.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 738 | 6-(2,6-diethylphenyl)-3-[(2,5-difluorophenoxy)methyl]-2,4-dimethylpyridine | X₁—CH₃ | 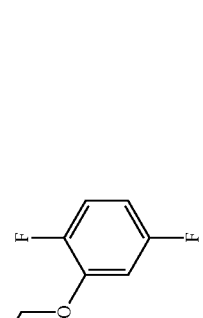 | X₂—CH₃ | H | 1.16 | 381.2 | 382.2 |
| 739 | 6-(2,6-diethylphenyl)-3-[(2,6-difluorophenoxy)methyl]-2,4-dimethylpyridine | X₁—CH₃ |  | X₂—CH₃ | H | 1.16 | 381.2 | 382.2 |
| 740 | 6-(2,6-diethylphenyl)-3-[(3,5-difluorophenoxy)methyl]-2,4-dimethylpyridine | X₁—CH₃ |  | X₂—CH₃ | H | 1.18 | 381.2 | 382.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 741 | 6-(2,6-diethylphenyl)-3-[(4-fluoro-3-methylphenoxy)methyl]-2,4-dimethylpyridine | X₁—CH₃ | (4-fluoro-3-methylphenoxymethyl) | X₂—CH₃ | H | 1.18 | 377.2 | 378.2 |
| 742 | 6-(2,6-diethylphenyl)-3-[(2-fluoro-5-methylphenoxy)methyl]-2,4-dimethylpyridine | X₁—CH₃ | (2-fluoro-5-methylphenoxymethyl) | X₂—CH₃ | H | 1.18 | 377.2 | 378.2 |
| 743 | 6-(2,6-diethylphenyl)-3-[(3,3-dimethylpiperidin-1-yl)methyl]-2,4-dimethylpyridine | X₁—CH₃ | (3,3-dimethylpiperidin-1-ylmethyl) | X₂—CH₃ | H | 1.09 | 364.3 | 365.4 |
| 744 | 1-[[6-(2,6-diethylphenyl)-2,4-dimethylpyridin-3-yl]methyl]-4-phenylpiperazine | X₁—CH₃ | (4-phenylpiperazin-1-ylmethyl) | X₂—CH₃ | H | 1.14 | 413.3 | 414.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 745 | 1-{[6-(2,6-diethylphenyl)-2,4-dimethyl]pyridin-3-yl]methyl}-4-(2-methylphenyl)piperazine | X₁—CH₃ |  | X₂—CH₃ | H | 1.15 | 427.3 | 428.4 |
| 746 | 1-{[6-(2,6-diethylphenyl)-2,4-dimethyl]pyridin-3-yl]methyl}-4-(4-methylphenyl)piperazine | X₁—CH₃ |  | X₂—CH₃ | H | 1.16 | 427.3 | 428.4 |
| 747 | N-{[6-(2,6-diethylphenyl)-2,4-dimethyl]pyridin-3-yl]methyl}-N-methylchroman-4-amine | X₁—CH₃ |  | X₂—CH₃ | H | 1.17 | 414.3 | 415.3 |
| 748 | N-{[6-(2,6-diethylphenyl)-2,4-dimethyl]pyridin-3-yl]methyl}-N-methylthiochroman-4-amine | X₁—CH₃ |  | X₂—CH₃ | H | 1.18 | 430.2 | 431.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 749 | 1-{[6-(2,6-diethylphenyl)-2,4-dimethylpyridin-3-yl]methyl}-4-(2-ethoxyphenyl)piperazine | H₃C—X₁ |  | X₂—CH₃ | H | 1.11 | 457.3 | 458.4 |
| 750 | 4-{[6-(2,6-diethylphenyl)-2,4-dimethylpyridin-3-yl]methyl}-2-methyl-1-(3-methylphenyl)piperazine | X₁—CH₃ |  | X₂—CH₃ | H | 1.11 | 441.3 | 442.4 |
| 751 | 4-{[6-(2,6-diethylphenyl)-2,4-dimethylpyridin-3-yl]methyl}-1-(4-methoxyphenyl)-2-methylpiperazine | X₁—CH₃ |  | X₂—CH₃ | H | 1.05 | 457.3 | 458.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 752 | 1-{[6-(2,6-diethylphenyl)-2,4-dimethylpyridin-3-yl]methyl}-4-(3-methoxyphenyl)piperazine | $X_1$—$CH_3$ |  | $X_2$—$CH_3$ | H | 1.13 | 443.3 | 444.4 |
| 753 | 1-{[6-(2,6-diethylphenyl)-2,4-dimethylpyridin-3-yl]methyl}-4-(3-methylphenyl)piperazine | $X_1$—$CH_3$ |  | $X_2$—$CH_3$ | H | 1.13 | 427.3 | 428.4 |
| 754 | 6-(2,6-diethylphenyl)-3-[(3,5-dimethylpiperidin-1-yl)methyl]-2,4-dimethylpyridine | $X_1$—$CH_3$ |  | $X_2$—$CH_3$ | H | 1.07 | 364.3 | 365.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 755 | N-benzyl-1-[6-(2,6-diethylphenyl)-4-methoxy-5-methylpyridin-3-yl]-N-methylmethanamine | H | 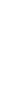 |  |  | 1.12 | 388.3 | 389.4 |
| 756 | N-{[6-(2,6-diethylphenyl)-4-methoxy-5-methylpyridin-3-yl]methyl}-N-methyl-1-phenylpropan-1-amine | H | 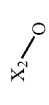 |  | 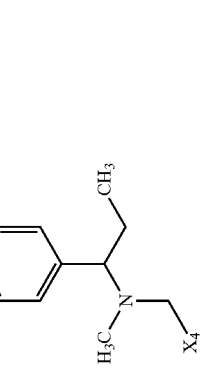 | 1.13 | 416.3 | 417.4 |
| 757 | N-{[6-(2,6-diethylphenyl)-4-methoxy-5-methylpyridin-3-yl]methyl}-N,2-dimethyl-1-phenylpropan-1-amine | H |  |  | | 1.14 | 430.3 | 431.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 758 | N-{[6-(2,6-diethylphenyl)-4-methoxy-5-methylpyridin-3-yl]methyl}-N-methyl-1-phenylbutan-1-amine | H | | | | 1.14 | 430.3 | 431.4 |
| 759 | N-{[6-(2,6-diethylphenyl)-4-methoxy-5-methylpyridin-3-yl]methyl}-N-methyl-1-phenylpentan-1-amine | H | | | | 1.18 | 444.3 | 445.5 |
| 760 | N-{[6-(2,6-diethylphenyl)-4-methoxy-5-methylpyridin-3-yl]methyl}-N,3-dimethyl-1-phenylbutan-1-amine | H | | | | 1.17 | 444.3 | 445.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 761 | N-{[6-(2,6-diethylphenyl)-4-methoxy-5-methylpyridin-3-yl]methyl}-N-methyl-1-phenylhexan-1-amine | H |  |  | 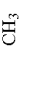 | 1.19 | 458.3 | 459.5 |
| 762 | N-{[6-(2,6-diethylphenyl)-4-methoxy-5-methylpyridin-3-yl]methyl}-N-methyl-1-phenylheptan-1-amine | H |  | 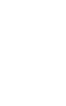 |  | 1.21 | 472.3 | 473.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 763 | N-benzyl-N-{[6-(2,6-diethylphenyl)-4-methoxy-5-methyl]pyridin-3-yl]methyl}propan-2-amine | H | | | | 1.12 | 416.3 | 417.4 |
| 764 | N-benzyl-N-{[6-(2,6-diethylphenyl)-4-methoxy-5-methyl]pyridin-3-yl]methyl}propan-1-amine | H | | | | 1.13 | 416.3 | 417.4 |
| 765 | N-benzyl-N-{[6-(2,6-diethylphenyl)-4-methoxy-5-methyl]pyridin-3-yl]methyl}prop-2-en-1-amine | H | | | | 1.13 | 414.3 | 415.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 766 | N-benzyl-N-{[6-(2,6-diethylphenyl)-4-methoxy-5-methylpyridin-3-yl]methyl}cyclopropanamine | H | | $X_2$—O—$CH_3$ | $H_3C$—$X_3$ | 1.17 | 414.3 | 415.4 |
| 767 | N-benzyl-N-{[6-(2,6-diethylphenyl)-4-methoxy-5-methylpyridin-3-yl]methyl}butan-1-amine | H | | $X_2$—O—$CH_3$ | $X_3$—$CH_3$ | 1.14 | 430.3 | 431.4 |
| 768 | N-benzyl-N-{[6-(2,6-diethylphenyl)-4-methoxy-5-methylpyridin-3-yl]methyl}-2-methylpropan-1-amine | H | | $CH_3$—O—$X_2$ | $CH_3$—$X_3$ | 1.18 | 430.3 | 431.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 769 | N-benzyl-N-{[6-(2,6-diethylphenyl)-4-methoxy-5-methylpyridin-3-yl]methyl}butan-2-amine | H | | H₃C—O—X₂ | H₃C—X₃ | 1.14 | 430.3 | 431.4 |
| 770 | N-benzyl-N-{[6-(2,6-diethylphenyl)-4-methoxy-5-methylpyridin-3-yl]methyl}pentan-1-amine | H | | H₃C—O—X₂ | X₃—CH₃ | 1.16 | 444.3 | 445.5 |
| 771 | N-benzyl-N-{[6-(2,6-diethylphenyl)-4-methoxy-5-methylpyridin-3-yl]methyl}-3-methylbutan-1-amine | H | | X₂—O—CH₃ | CH₃—X₃ | 1.17 | 444.3 | 445.5 |

TABLE 3-continued
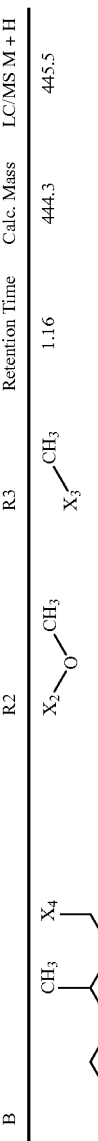
| Cpd # | NAME | R1 | B | R2 | R3 | LC/MS Retention Time | LC/MS Calc. Mass | LC/MS M + H |
|---|---|---|---|---|---|---|---|---|
| 772 | N-benzyl-N-{[6-(2,6-diethylphenyl)-4-methoxy-5-methylpyridin-3-yl]methyl}pentan-2-amine | H |  |  | 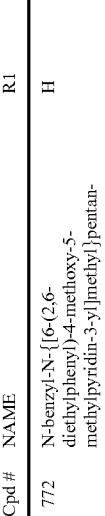 | 1.16 | 444.3 | 445.5 |
| 773 | 2-{[6-(2,6-diethylphenyl)-4-methoxy-5-methylpyridin-3-yl]methyl}-1-methyl-1,2,3,4-tetrahydroisoquinoline | H |  |  |  | 1.13 | 414.3 | 415.4 |
| 774 | 2-{[6-(2,6-diethylphenyl)-4-methoxy-5-methylpyridin-3-yl]methyl}-1-ethyl-1,2,3,4-tetrahydroisoquinoline | H |  |  | | 1.15 | 428.3 | 429.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 775 | 2-{[6-(2,6-diethylphenyl)-4-methoxy-5-methylpyridin-3-yl]methyl}-1-propyl-1,2,3,4-tetrahydroisoquinoline | H | | $X_2$—O—$CH_3$ | $CH_3$—$X_3$ | 1.19 | 442.3 | 443.5 |
| 776 | 1-cyclopropyl-2-{[6-(2,6-diethylphenyl)-4-methoxy-5-methylpyridin-3-yl]methyl}-1,2,3,4-tetrahydroisoquinoline | H | | $CH_3$—O—$X_2$ | $H_3C$—$X_3$ | 1.16 | 440.3 | 441.4 |
| 777 | 2-{[6-(2,6-diethylphenyl)-4-methoxy-5-methylpyridin-3-yl]methyl}-1-isopropyl-1,2,3,4-tetrahydroisoquinoline | H | | $X_2$—O—$CH_3$ | $CH_3$—$X_3$ | 1.18 | 442.3 | 443.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 778 | 1-butyl-2-{[6-(2,6-diethylphenyl)-4-methoxy-5-methylpyridin-3-yl]methyl}-1,2,3,4-tetrahydroisoquinoline | H |  |  | 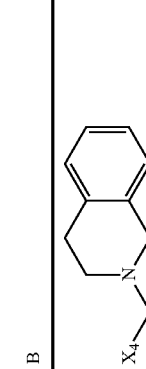 | 1.2 | 456.3 | 457.5 |
| 779 | 1-cyclobutyl-2-{[6-(2,6-diethylphenyl)-4-methoxy-5-methylpyridin-3-yl]methyl}-1,2,3,4-tetrahydroisoquinoline | H |  |  | 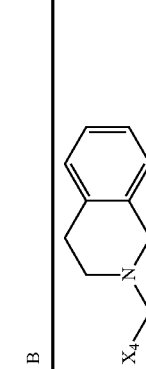 | 1.17 | 454.3 | 455.5 |
| 780 | 2-{[6-(2,6-diethylphenyl)-4-methoxy-5-methylpyridin-3-yl]methyl}-1-isobutyl-1,2,3,4-tetrahydroisoquinoline | H | 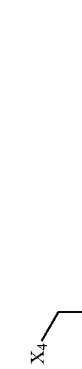 | 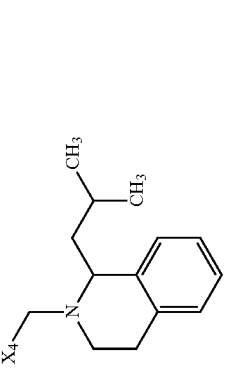 | | 1.21 | 456.3 | 457.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 781 | 2-{[6-(2,6-diethylphenyl)-4-methoxy-5-methylpyridin-3-yl]methyl}-1-pentyl-1,2,3,4-tetrahydroisoquinoline | H | | $X_2$—O—$CH_3$ | $CH_3$—$X_3$ | 1.22 | 470.3 | 471.5 |
| 782 | 2-{[6-(2,6-diethylphenyl)-4-methoxy-5-methylpyridin-3-yl]methyl}-1-isopentyl-1,2,3,4-tetrahydroisoquinoline | H | | $X_2$—O—$CH_3$ | $CH_3$—$X_3$ | 1.21 | 470.3 | 471.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 783 | N-benzyl-N-{[6-(2,6-diethylphenyl)-4-methoxy-5-methylpyridin-3-yl]methyl}cyclopentanamine | H |  |  |  | 1.13 | 442.3 | 443.5 |
| 784 | N-benzyl-N-{[6-(2,6-diethylphenyl)-4-methoxy-5-methylpyridin-3-yl]methyl}pentan-3-amine | H |  |  |  | 1.18 | 444.3 | 445.5 |
| 785 | N-benzyl-N-{[6-(2,6-diethylphenyl)-4-methoxy-5-methylpyridin-3-yl]methyl}cyclohexanamine | H |  |  |  | 1.15 | 456.3 | 457.5 |

TABLE 3-continued
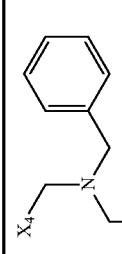
| Cpd # | NAME | R1 | B | R2 | R3 | LC/MS Retention Time | LC/MS Calc. Mass | LC/MS M + H |
|---|---|---|---|---|---|---|---|---|
| 786 | N,N-dibenzyl-1-[6-(2,6-diethylphenyl)-4-methoxy-5-methylpyridin-3-yl]methanamine | H |  |  |  | 1.21 | 464.3 | 465.4 |
| 787 | N-benzyl-1-cyclopentyl-N-{[6-(2,6-diethylphenyl)-4-methoxy-5-methylpyridin-3-yl]methyl}methanamine | H |  |  |  | 1.19 | 456.3 | 457.5 |
| 788 | N-benzyl-N-{[6-(2,6-diethylphenyl)-4-methoxy-5-methylpyridin-3-yl]methyl}hexan-1-amine | H |  |  | | 1.2 | 458.3 | 459.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 789 | N-benzyl-1-cyclohexyl-N-{[6-(2,6-diethylphenyl)-4-methoxy-5-methylpyridin-3-yl]methyl}methanamine | H | 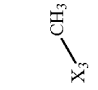 |  | 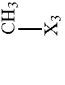 | 1.22 | 470.3 | 471.5 |
| 790 | N-benzyl-N-{[6-(2,6-diethylphenyl)-4-methoxy-5-methylpyridin-3-yl]methyl}heptan-1-amine | H |  |  | 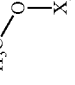 | 1.21 | 472.3 | 473.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 791 | N-benzyl-N-{[6-(2,6-diethylphenyl)-4-methoxy-5-methylpyridin-3-yl]methyl}-3-phenylpropan-1-amine | H | | X2—O—CH3 | CH3—X3 | 1.2 | 492.3 | 493.5 |
| 792 | N-benzyl-1-[6-(2,6-diethylphenyl)-2,4-dimethylpyridin-3-yl]-N-methylmethanamine | X1—CH3 | | X2—CH3 | H | 1.1 | 372.3 | 373.4 |
| 793 | (1R)-N-{[6-(2,6-diethylphenyl)-2,4-dimethylpyridin-3-yl]methyl}-N-methyl-1-phenylethanamine | X1—CH3 | | X2—CH3 | H | 1.1 | 386.3 | 387.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 794 | N-{[6-(2,6-diethylphenyl)-2,4-dimethylpyridin-3-yl]methyl}-N-methyl-1-phenylpropan-1-amine | X₁—CH₃ |  | CH₃—X₂ | H | 1.12 | 400.3 | 401.4 |
| 795 | N-{[6-(2,6-diethylphenyl)-2,4-dimethylpyridin-3-yl]methyl}-N,2-dimethyl-1-phenylpropan-1-amine | X₁—CH₃ |  | X₂—CH₃ | H | 1.19 | 414.3 | 415.4 |
| 796 | N-{[6-(2,6-diethylphenyl)-2,4-dimethylpyridin-3-yl]methyl}-N-methyl-1-phenylbutan-1-amine | X₁—CH₃ |  | CH₃—X₂ | H | 1.13 | 414.3 | 415.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 797 | N-{[6-(2,6-diethylphenyl)-2,4-dimethylpyridin-3-yl]methyl}-N-methyl-1-phenylpentan-1-amine | X₁—CH₃ |  | CH₃—X₂ | H | 1.17 | 428.3 | 429.5 |
| 798 | N-{[6-(2,6-diethylphenyl)-2,4-dimethylpyridin-3-yl]methyl}-N,3-dimethyl-1-phenylbutan-1-amine | X₁—CH₃ |  | X₂—CH₃ | H | 1.15 | 428.3 | 429.5 |
| 799 | N-{[6-(2,6-diethylphenyl)-2,4-dimethylpyridin-3-yl]methyl}-N-methyl-1-phenylhexan-1-amine | X₁—CH₃ |  | CH₃—X₂ | H | 1.19 | 442.3 | 443.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 800 | N-{[6-(2,6-diethylphenyl)-2,4-dimethylpyridin-3-yl]methyl}-N-methyl-1-phenylheptan-1-amine | $X_1$—$CH_3$ | (structure) | $CH_3$—$X_2$ | H | 1.21 | 456.4 | 457.5 |
| 801 | N-benzyl-N-{[6-(2,6-diethylphenyl)-2,4-dimethylpyridin-3-yl]methyl}ethanamine | $X_1$—$CH_3$ | (structure) | $H_3C$—$X_2$ | H | 1.12 | 386.3 | 387.4 |
| 802 | N-benzyl-N-{[6-(2,6-diethylphenyl)-2,4-dimethylpyridin-3-yl]methyl}propan-2-amine | $X_1$—$CH_3$ | (structure) | $X_2$—$CH_3$ | H | 1.17 | 400.3 | 401.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 803 | N-benzyl-N-{[6-(2,6-diethylphenyl)-2,4-dimethylpyridin-3-yl]methyl}propan-1-amine | H₃C—X₁ |  | CH₃—X₂ | H | 1.17 | 400.3 | 401.4 |
| 804 | N-benzyl-N-{[6-(2,6-diethylphenyl)-2,4-dimethylpyridin-3-yl]methyl}prop-2-en-1-amine | X₁—CH₃ |  | X₂—CH₃ | H | 1.18 | 398.3 | 399.4 |
| 805 | N-benzyl-N-{[6-(2,6-diethylphenyl)-2,4-dimethylpyridin-3-yl]methyl}cyclopropanamine | CH₃—X₁ |  | X₂—CH₃ | H | 1.2 | 398.3 | 399.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 806 | N-benzyl-N-{[6-(2,6-diethylphenyl)-2,4-dimethylpyridin-3-yl]methyl}butan-1-amine | X₁—CH₃ | (N-benzyl-butyl, X₄) | H₃C—X₂ | H | 1.21 | 414.3 | 415.4 |
| 807 | N-benzyl-N-{[6-(2,6-diethylphenyl)-2,4-dimethylpyridin-3-yl]methyl}-2-methylpropan-1-amine | X₁—CH₃ | (N-benzyl-isobutyl, X₄) | X₂—CH₃ | H | 1.24 | 414.3 | 415.4 |
| 808 | N-benzyl-N-{[6-(2,6-diethylphenyl)-2,4-dimethylpyridin-3-yl]methyl}butan-2-amine | H₃C—X₁ | (N-benzyl-sec-butyl, X₄) | X₂—CH₃ | H | 1.21 | 414.3 | 415.4 |

TABLE 3-continued
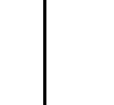
| Cpd # | NAME | R1 | B | R2 | R3 | LC/MS Retention Time | LC/MS Calc. Mass | LC/MS M + H |
|---|---|---|---|---|---|---|---|---|
| 809 | N-benzyl-N-{[6-(2,6-diethylphenyl)-2,4-dimethylpyridin-3-yl]methyl}pentan-1-amine | H₃C—X₁ |  | CH₃—X₂ | H | 1.22 | 428.3 | 429.5 |
| 810 | N-benzyl-N-{[6-(2,6-diethylphenyl)-2,4-dimethylpyridin-3-yl]methyl}-3-methylbutan-1-amine | X₁—CH₃ |  | X₂—CH₃ | H | 1.22 | 428.3 | 429.4 |

TABLE 3-continued
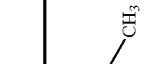
| Cpd # | NAME | R1 | B | R2 | R3 | LC/MS Retention Time | LC/MS Calc. Mass | LC/MS M + H |
|---|---|---|---|---|---|---|---|---|
| 811 | N-benzyl-N-{[6-(2,6-diethylphenyl)-2,4-dimethylpyridin-3-yl]methyl}pentan-2-amine |  |  |  | H | 1.23 | 428.3 | 429.4 |
| 812 | 2-{[6-(2,6-diethylphenyl)-2,4-dimethylpyridin-3-yl]methyl}-1,2,3,4-tetrahydroisoquinoline |  |  | 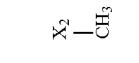 | H | 1.1 | 384.3 | 385.4 |
| 813 | 2-{[6-(2,6-diethylphenyl)-2,4-dimethylpyridin-3-yl]methyl}-1-methyl-1,2,3,4-tetrahydroisoquinoline |  | 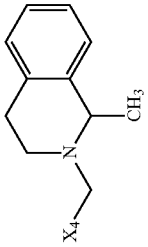 |  | H | 1.11 | 398.3 | 399.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 814 | 2-{[6-(2,6-diethylphenyl-2,4-dimethyl]pyridin-3-yl]methyl}-1-ethyl-1,2,3,4-tetrahydroisoquinoline | X₁—CH₃ |  | X₂—CH₃ | H | 1.18 | 412.3 | 413.4 |
| 815 | 2-{[6-(2,6-diethylphenyl)-2,4-dimethylpyridin-3-yl]methyl}-1-propyl-1,2,3,4-tetrahydroisoquinoline | X₁—CH₃ |  | X₂—CH₃ | H | 1.21 | 426.3 | 427.4 |
| 816 | 1-cyclopropyl-2-{[6-(2,6-diethylphenyl)-2,4-dimethylpyridin-3-yl]methyl}-1,2,3,4-tetrahydroisoquinoline | H₃C—X₁ |  | X₂—CH₃ | H | 1.15 | 424.3 | 425.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 817 | 2-{[6-(2,6-diethylphenyl)-2,4-dimethylpyridin-3-yl]methyl}-1-isopropyl-1,2,3,4-tetrahydroisoquinoline |  |  |  | H | 1.23 | 426.3 | 427.4 |
| 818 | 1-butyl-2-{[6-(2,6-diethylphenyl)-2,4-dimethylpyridin-3-yl]methyl}-1,2,3,4-tetrahydroisoquinoline |  | 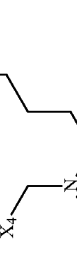 |  | H | 1.23 | 440.3 | 441.5 |
| 819 | 1-cyclobutyl-2-{[6-(2,6-diethylphenyl)-2,4-dimethylpyridin-3-yl]methyl}-1,2,3,4-tetrahydroisoquinoline |  | 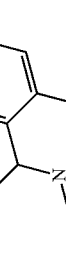 |  | H | 1.21 | 438.3 | 439.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 820 | 2-{[6-(2,6-diethylphenyl)-2,4-dimethylpyridin-3-yl]methyl}-1-isobutyl-1,2,3,4-tetrahydroisoquinoline |  |  |  | H | 1.23 | 440.3 | 441.5 |
| 821 | 2-{[6-(2,6-diethylphenyl)-2,4-dimethylpyridin-3-yl]methyl}-1-pentyl-1,2,3,4-tetrahydroisoquinoline | 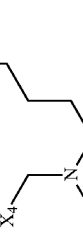 |  |  | H | 1.25 | 454.3 | 455.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 822 | 2-{[6-(2,6-diethylphenyl)-2,4-dimethylpyridin-3-yl]methyl}-1-isopentyl-1,2,3,4-tetrahydroisoquinoline | $X_1$—$CH_3$ |  | $X_2$—$CH_3$ | H | 1.26 | 454.3 | 455.5 |
| 823 | N-benzyl-N-{[6-(2,6-diethylphenyl)-2,4-dimethylpyridin-3-yl]methyl}cyclopentanamine | $X_1$—$CH_3$ |  | $H_3C$—$X_2$ | H | 1.19 | 426.3 | 427.4 |
| 824 | N-benzyl-N-{[6-(2,6-diethylphenyl)-2,4-dimethylpyridin-3-yl]methyl}pentan-3-amine | $H_3C$—$X_1$ |  | $X_2$—$CH_3$ | H | 1.08 | 428.3 | 429.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 825 | N-benzyl-N-{[6-(2,6-diethylphenyl)-2,4-dimethylpyridin-3-yl]methyl}cyclohexanamine | 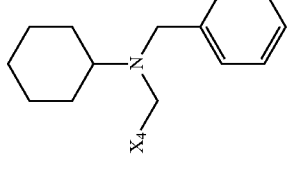 |  |  | H | 1.22 | 440.3 | 441.5 |
| 826 | N-benzyl-1-[6-(2,6-diethylphenyl)-4-isopropoxy-2-methylpyridin-3-yl]-N-methylmethanamine | 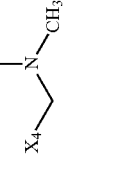 |  |  | H | 1.05 | 416.3 | 417.4 |
| 827 | N-{[6-(2,6-diethylphenyl)-4-isopropoxy-2-methylpyridin-3-yl]methyl}-N-methyl-1-phenylethanamine |  |  |  | H | 1.05 | 430.3 | 431.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 828 | (1S)-N-{[6-(2,6-diethylphenyl)-4-isopropoxy-2-methylpyridin-3-yl]methyl}-N-methyl-1-phenylethanamine | X₁—CH₃ | (CH₃)(N)(CH₃)(H)(phenyl), X₄ | X₂—O—CH(CH₃)₂ | H | 1.05 | 430.3 | 431.4 |
| 829 | | X₁—CH₃ | (CH₃)(N)(CH₃)(H)(phenyl), X₄ | X₂—O—CH(CH₃)₂ | H | 1.06 | 430.3 | 431.4 |
| 830 | N-{[6-(2,6-diethylphenyl)-4-isopropoxy-2-methylpyridin-3-yl]methyl}-N-methyl-1-phenylpropan-1-amine | CH₃—X₁ | (CH₃)(phenyl)(CH)(N-CH₃), X₄ | X₂—O—CH(CH₃)₂ | H | 1.08 | 444.3 | 445.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 831 | N-{[6-(2,6-diethylphenyl)-4-isopropoxy-2-methylpyridin-3-yl]methyl}-N,2-dimethyl-1-phenylpropan-1-amine | 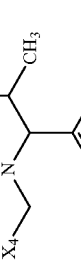 | 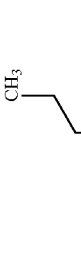 | 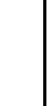 | H | 1.09 | 458.3 | 459.5 |
| 832 | N-{[6-(2,6-diethylphenyl)-4-isopropoxy-2-methylpyridin-3-yl]methyl}-N-methyl-1-phenylbutan-1-amine | 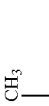 |  |  | H | 1.1 | 458.3 | 459.5 |
| 833 | N-{[6-(2,6-diethylphenyl)-4-isopropoxy-2-methylpyridin-3-yl]methyl}-N-methyl-1-phenylpentan-1-amine | 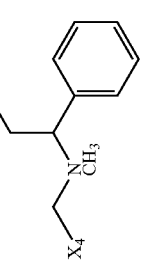 | 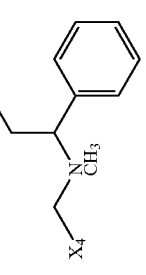 | 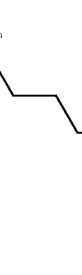 | H | 1.11 | 472.3 | 473.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 834 | N-{[6-(2,6-diethylphenyl)-4-isopropoxy-2-methylpyridin-3-yl]methyl}-N,3-dimethyl-1-phenylbutan-1-amine | 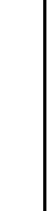 | 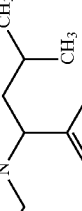 |  | H | 1.1 | 472.3 | 473.5 |
| 835 | N-{[6-(2,6-diethylphenyl)-4-isopropoxy-2-methylpyridin-3-yl]methyl}-N-methyl-1-phenylhexan-1-amine |  | 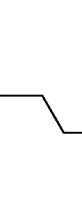 | 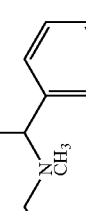 | H | 1.13 | 486.4 | 487.5 |

TABLE 3-continued
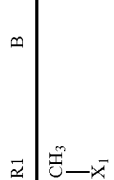
| Cpd # | NAME | R1 | B | R2 | R3 | LC/MS Retention Time | LC/MS Calc. Mass | LC/MS M + H |
|---|---|---|---|---|---|---|---|---|
| 836 | N-{[6-(2,6-diethylphenyl)-4-isopropoxy-2-methylpyridin-3-yl]methyl}-N-methyl-1-phenylheptan-1-amine |  | 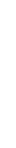 |  | H | 1.16 | 500.4 | 501.5 |
| 837 | N-benzyl-N-{[6-(2,6-diethylphenyl)-4-isopropoxy-2-methylpyridin-3-yl]methyl}ethanamine |  | 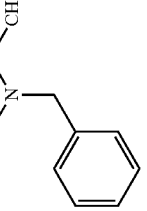 |  | H | 1.08 | 430.3 | 431.4 |
| 838 | N-benzyl-N-{[6-(2,6-diethylphenyl)-4-isopropoxy-2-methylpyridin-3-yl]methyl}propan-2-amine |  |  | 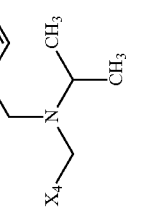 | H | 1.05 | 444.3 | 445.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 839 | N-benzyl-N-{[6-(2,6-diethylphenyl)-4-isopropoxy-2-methyl]pyridin-3-yl]methyl}propan-1-amine | 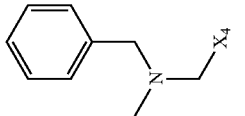 | 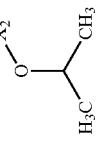 | 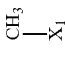 | H | 1.1 | 444.3 | 445.5 |
| 840 | N-benzyl-N-{[6-(2,6-diethylphenyl)-4-isopropoxy-2-methyl]pyridin-3-yl]methyl}prop-2-en-1-amine | 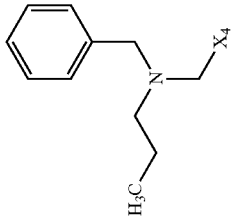 |  |  | H | 1.12 | 442.3 | 443.4 |
| 841 | N-benzyl-N-{[6-(2,6-diethylphenyl)-4-isopropoxy-2-methyl]pyridin-3-yl]methyl}cyclopropanamine | 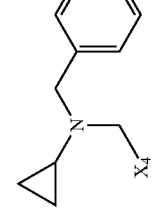 | 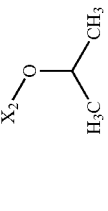 |  | H | 1.18 | 442.3 | 443.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 842 | N-benzyl-N-{[6-(2,6-diethylphenyl)-4-isopropoxy-2-methyl]pyridin-3-yl]methyl}butan-1-amine | H₃C—X₁ |  |  | H | 1.12 | 458.3 | 459.5 |
| 843 | N-benzyl-N-{[6-(2,6-diethylphenyl)-4-isopropoxy-2-methyl]pyridin-3-yl]methyl}-2-methylpropan-1-amine | X₁—CH₃ |  |  | H | 1.21 | 458.3 | 459.5 |
| 844 | N-benzyl-N-{[6-(2,6-diethylphenyl)-4-isopropoxy-2-methyl]pyridin-3-yl]methyl}butan-2-amine | X₁—CH₃ | 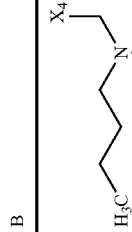 | 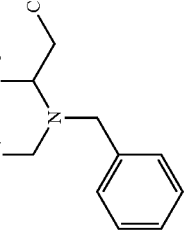 | H | 1.13 | 458.3 | 459.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 845 | N-benzyl-N-{[6-(2,6-diethylphenyl)-4-isopropoxy-2-methylpyridin-3-yl]methyl}pentan-1-amine | CH₃—X₁ |  | 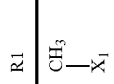 | H | 1.16 | 472.3 | 473.5 |
| 846 | N-benzyl-N-{[6-(2,6-diethylphenyl)-4-isopropoxy-2-methylpyridin-3-yl]methyl}-3-methylbutan-1-amine | X₁—CH₃ | 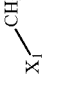 |  | H | 1.15 | 472.3 | 473.5 |
| 847 | N-benzyl-N-{[6-(2,6-diethylphenyl)-4-isopropoxy-2-methylpyridin-3-yl]methyl}pentan-2-amine | H₃C—X₁ |  |  | H | 1.17 | 472.3 | 473.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 848 | 2-{[6-(2,6-diethylphenyl)-4-isopropoxy-2-methylpyridin-3-yl]methyl}-1,2,3,4-tetrahydroisoquinoline | 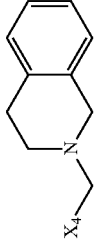 |  |  | H | 1.04 | 428.3 | 429.4 |
| 849 | 2-{[6-(2,6-diethylphenyl)-4-isopropoxy-2-methylpyridin-3-yl]methyl}-1-methyl-1,2,3,4-tetrahydroisoquinoline |  |  |  | H | 1.07 | 442.3 | 443.4 |
| 850 | 2-{[6-(2,6-diethylphenyl)-4-isopropoxy-2-methylpyridin-3-yl]methyl}-1-ethyl-1,2,3,4-tetrahydroisoquinoline |  |  | 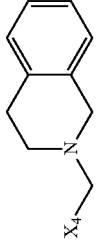 | H | 1.1 | 456.3 | 457.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 851 | 2-{[6-(2,6-diethylphenyl)-4-isopropoxy-2-methylpyridin-3-yl]methyl}-1-propyl-1,2,3,4-tetrahydroisoquinoline |  |  |  | H | 1.11 | 470.3 | 471.5 |
| 852 | 1-cyclopropyl-2-{[6-(2,6-diethylphenyl)-4-isopropoxy-2-methylpyridin-3-yl]methyl}-1,2,3,4-tetrahydroisoquinoline |  | 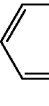 | 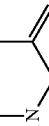 | H | 1.07 | 468.3 | 469.5 |
| 853 | 2-{[6-(2,6-diethylphenyl)-4-isopropoxy-2-methylpyridin-3-yl]methyl}-1-isopropyl-1,2,3,4-tetrahydroisoquinoline |  |  |  | H | 1.16 | 470.3 | 471.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 854 | 1-butyl-2-{[6-(2,6-diethylphenyl)-isopropoxy-2-methylpyridin-3-yl]methyl}-1,2,3,4-tetrahydroisoquinoline | X₁—CH₃ | (1-butyl-tetrahydroisoquinoline with N-CH₂-X₄) | X₂-O-CH(CH₃)₂ | H | 1.16 | 484.3 | 485.5 |
| 855 | 1-cyclobutyl-2-{[6-(2,6-diethylphenyl)-4-isopropoxy-2-methylpyridin-3-yl]methyl}-1,2,3,4-tetrahydroisoquinoline | H₃C—X₁ | (1-cyclobutyl-tetrahydroisoquinoline with N-CH₂-X₄) | X₂-O-CH(CH₃)₂ | H | 1.13 | 482.3 | 483.5 |
| 856 | 2-{[6-(2,6-diethylphenyl)-4-isopropoxy-2-methylpyridin-3-yl]methyl}-1-isobutyl-1,2,3,4-tetrahydroisoquinoline | X₁—CH₃ | (1-isobutyl-tetrahydroisoquinoline with N-CH₂-X₄) | X₂-O-CH(CH₃)₂ | H | 1.2 | 484.3 | 485.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 857 | 2-{[6-(2,6-diethylphenyl)-4-isopropoxy-2-methylpyridin-3-yl]methyl}-1-pentyl-1,2,3,4-tetrahydroisoquinoline |  | 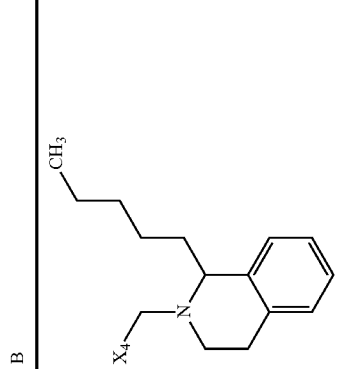 | 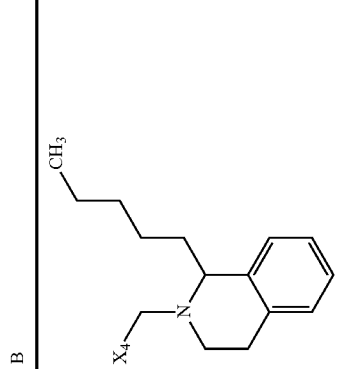 | H | 1.16 | 498.4 | 499.5 |
| 858 | 2-{[6-(2,6-diethylphenyl)-4-isopropoxy-2-methylpyridin-3-yl]methyl}-1-isopentyl-1,2,3,4-tetrahydroisoquinoline |  |  |  | H | 1.17 | 498.4 | 499.5 |

TABLE 3-continued
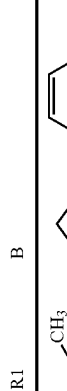
| Cpd # | NAME | R1 | B | R2 | R3 | LC/MS Retention Time | LC/MS Calc. Mass | LC/MS M + H |
|---|---|---|---|---|---|---|---|---|
| 859 | N-benzyl-N-{[6-(2,6-diethylphenyl)-4-isopropoxy-2-methylpyridin-3-yl]methyl}cyclopentanamine | X1—CH3 | 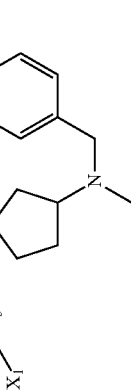 | 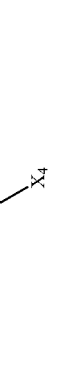 | H | 1.1 | 470.3 | 471.5 |
| 860 | N-benzyl-N-{[6-(2,6-diethylphenyl)-4-isopropoxy-2-methylpyridin-3-yl]methyl}pentan-3-amine | X1—CH3 | 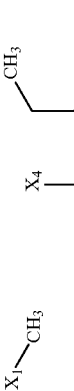 | 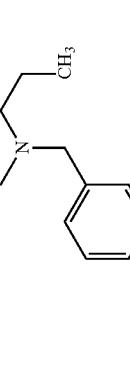 | H | 1.23 | 472.3 | 473.5 |
| 861 | N-benzyl-N-{[6-(2,6-diethylphenyl)-4-isopropoxy-2-methylpyridin-3-yl]methyl}cyclohexanamine | X1—CH3 | 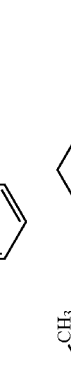 | 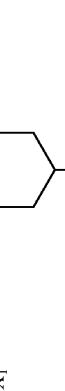 | H | 1.14 | 484.3 | 485.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 862 | N,N-dibenzyl-1-[6-(2,6-diethylphenyl)-4-isopropoxy-2-methylpyridin-3-yl]methanamine |  |  |  | H | 1.22 | 492.3 | 493.5 |
| 863 | N-benzyl-1-cyclopentyl-N-{[6-(2,6-diethylphenyl)-4-isopropoxy-2-methylpyridin-3-yl]methyl}methanamine |  |  |  | H | 1.22 | 484.3 | 485.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 864 | N-benzyl-N-{[6-(2,6-diethylphenyl)-4-isopropoxy-2-methylpyridin-3-yl]methyl}hexan-1-amine | H₃C—X₁ | (N-benzyl-N-hexyl structure with X₄) | X₂—O—CH(CH₃)₂ | H | 1.17 | 486.4 | 487.5 |
| 865 | N-benzyl-1-cyclohexyl-N-{[6-(2,6-diethylphenyl)-4-isopropoxy-2-methylpyridin-3-yl]methyl}methanamine | X₁—CH₃ | (N-benzyl-N-cyclohexylmethyl structure with X₄) | X₂—O—CH(CH₃)₂ | H | 1.26 | 498.4 | 499.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 866 | N-benzyl-N-{[6-(2,6-diethylphenyl)-4-isopropoxy-2-methylpyridin-3-yl]methyl}heptan-1-amine |  |  |  | H | 1.18 | 500.4 | 501.5 |
| 867 | N-benzyl-N-{[6-(2,6-diethylphenyl)-4-isopropoxy-2-methylpyridin-3-yl]methyl}-2-phenylethanamine |  |  |  | H | 1.2 | 506.3 | 507.5 |
| 868 | N-benzyl-3-cyclopentyl-N-{[6-(2,6-diethylphenyl)-4-isopropoxy-2-methylpyridin-3-yl]methyl}propan-1-amine |  |  |  | H | 1.19 | 512.4 | 513.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 869 | N-benzyl-N-{[6-(2,6-diethylphenyl)-4-isopropoxy-2-methylpyridin-3-yl]methyl}-3-phenylpropan-1-amine | X₁—CH₃ |  |  | H | 1.16 | 520.3 | 521.5 |
| 870 | N-{[6-(2,6-diethylphenyl)-4-methoxypyridin-3-yl]methyl}-N-methyl-1-phenylpropan-1-amine | H |  |  | H | 1.07 | 402.3 | 403.3 |
| 871 | N-{[6-(2,6-diethylphenyl)-4-methoxypyridin-3-yl]methyl}-N,2-dimethyl-1-phenylpropan-1-amine | H | 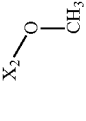 | 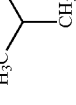 | H | 1.07 | 416.3 | 417.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 872 | N-{[6-(2,6-diethylphenyl)-4-methoxypyridin-3-yl]methyl}-N-methyl-1-phenylbutan-1-amine | H | 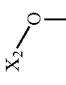 |  | H | 1.1 | 416.3 | 417.3 |
| 873 | N-{[6-(2,6-diethylphenyl)-4-methoxypyridin-3-yl]methyl}-N-methyl-1-phenylpentan-1-amine | H | 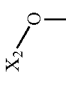 |  | H | 1.12 | 430.3 | 431.3 |
| 874 | N-{[6-(2,6-diethylphenyl)-4-methoxypyridin-3-yl]methyl}-N,3-dimethyl-1-phenylbutan-1-amine | H |  | H₃C—O—X₂ | H | 1.11 | 430.3 | 431.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 875 | N-{[6-(2,6-diethylphenyl)-4-methoxypyridin-3-yl]methyl}-N-methyl-1-phenylhexan-1-amine | H | 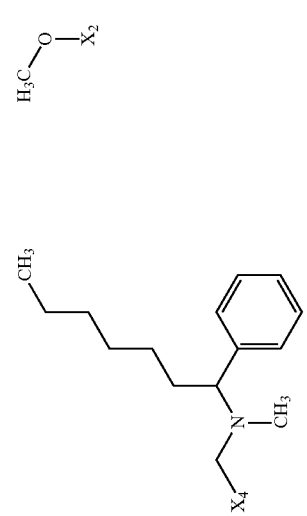 | H₃C−O−X₂ | H | 1.14 | 444.3 | 445.4 |
| 876 | N-{[6-(2,6-diethylphenyl)-4-methoxypyridin-3-yl]methyl}-N-methyl-1-phenylheptan-1-amine | H | | H₃C−O−X₂ | H | 1.17 | 458.3 | 459.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 877 | N-benzyl-N-{[6-(2,6-diethylphenyl)-4-methoxypyridin-3-yl]methyl}propan-2-amine | H |  |  | H | 1.04 | 402.3 | 403.3 |
| 878 | N-benzyl-N-{[6-(2,6-diethylphenyl)-4-methoxypyridin-3-yl]methyl}propan-1-amine | H |  |  | H | 1.06 | 402.3 | 403.3 |
| 879 | N-benzyl-N-{[6-(2,6-diethylphenyl)-4-methoxypyridin-3-yl]methyl}prop-2-en-1-amine | H |  |  | H | 1.06 | 400.3 | 401.3 |

TABLE 3-continued
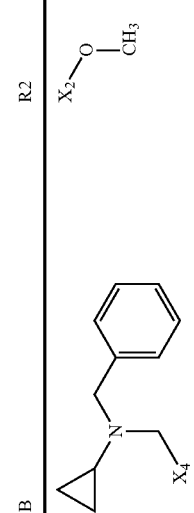
| Cpd # | NAME | R1 | B | R2 | R3 | LC/MS Retention Time | LC/MS Calc. Mass | LC/MS M + H |
|---|---|---|---|---|---|---|---|---|
| 880 | N-benzyl-N-{[6-(2,6-diethylphenyl)-4-methoxypyridin-3-yl]methyl}cyclopropanamine | H | 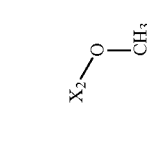 | 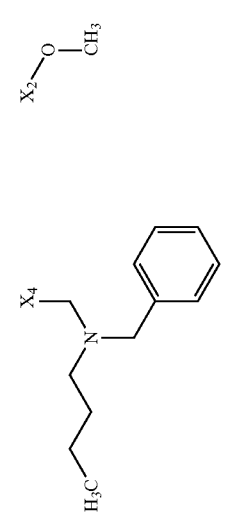 | H | 1.09 | 400.3 | 401.3 |
| 881 | N-benzyl-N-{[6-(2,6-diethylphenyl)-4-methoxypyridin-3-yl]methyl}butan-1-amine | H | 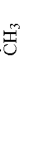 | 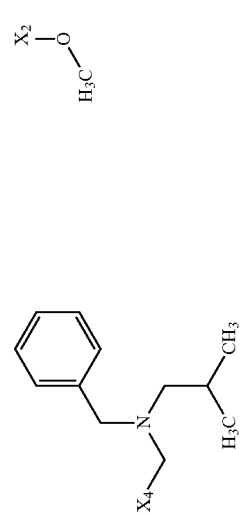 | H | 1.08 | 416.3 | 417.3 |
| 882 | N-benzyl-N-{[6-(2,6-diethylphenyl)-4-methoxypyridin-3-yl]methyl}-2-methylpropan-1-amine | H |  |  | H | 1.11 | 416.3 | 417.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 883 | N-benzyl-N-{[6-(2,6-diethylphenyl)-4-methoxypyridin-3-yl]methyl}butan-2-amine | H | | H₃C—O—X₂ | H | 1.06 | 416.3 | 417.3 |
| 884 | N-benzyl-N-{[6-(2,6-diethylphenyl)-4-methoxypyridin-3-yl]methyl}pentan-1-amine | H | | H₃C—O—X₂ | H | 1.11 | 430.3 | 431.3 |

TABLE 3-continued
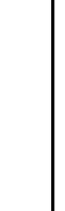
| Cpd # | NAME | R1 | B | R2 | R3 | LC/MS Retention Time | LC/MS Calc. Mass | LC/MS M + H |
|---|---|---|---|---|---|---|---|---|
| 885 | N-benzyl-N-{[6-(2,6-diethylphenyl)-4-methoxypyridin-3-yl]methyl}-3-methylbutan-1-amine | H |  |  | H | 1.1 | 430.3 | 431.3 |
| 886 | N-benzyl-N-{[6-(2,6-diethylphenyl)-4-methoxypyridin-3-yl]methyl}-pentan-2-amine | H |  |  | H | 1.09 | 430.3 | 431.3 |
| 887 | 2-{[6-(2,6-diethylphenyl)-4-methoxypyridin-3-yl]methyl}-1-ethyl-1,2,3,4-tetrahydroisoquinoline | H | 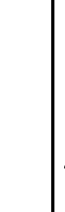 |  | H | 1.09 | 414.3 | 415.3 |

TABLE 3-continued
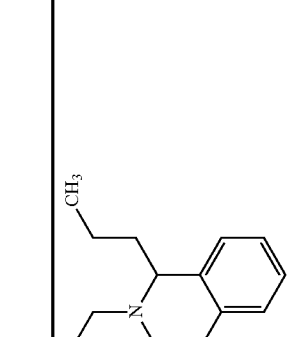
| Cpd # | NAME | R1 | B | R2 | R3 | LC/MS Retention Time | LC/MS Calc. Mass | LC/MS M + H |
|---|---|---|---|---|---|---|---|---|
| 888 | 2-{[6-(2,6-diethylphenyl)-4-methoxypyridin-3-yl]methyl}-1-propyl-1,2,3,4-tetrahydroisoquinoline | H |  | 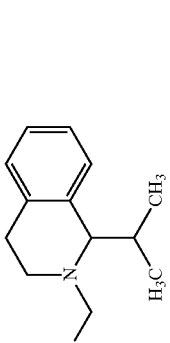 | H | 1.11 | 428.3 | 429.3 |
| 889 | 2-{[6-(2,6-diethylphenyl)-4-methoxypyridin-3-t1]methyl}-1-isopropyl-1,2,3,4-tetrahydroisoquinoline | H |  | 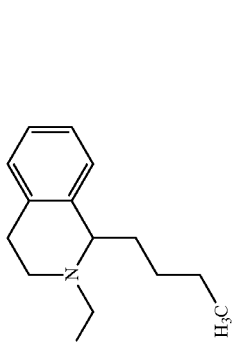 | H | 1.11 | 428.3 | 429.3 |
| 890 | 1-butyl-2-{[6-(2,6-diethylphenyl)-4-methoxypyridin-3-yl]methyl}-1,2,3,4-tetrahydroisoquinoline | H |  |  | H | 1.14 | 442.3 | 443.3 |

TABLE 3-continued
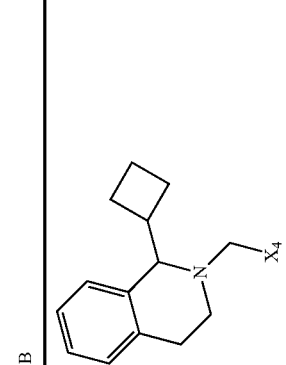
| Cpd # | NAME | R1 | B | R2 | R3 | LC/MS Retention Time | LC/MS Calc. Mass | LC/MS M + H |
|---|---|---|---|---|---|---|---|---|
| 891 | 1-cyclobutyl-2-{[6-(2,6-diethylphenyl)-4-methoxypyridin-3-yl]methyl}-1,2,3,4-tetrahydroisoquinoline | H |  | 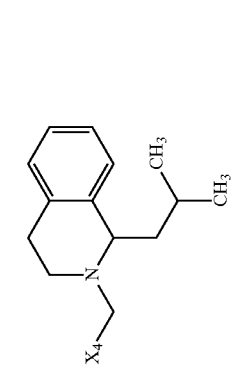 | H | 1.11 | 440.3 | 441.3 |
| 892 | 2-{[6-(2,6-diethylphenyl)-4-methoxypyridin-3-yl]methyl}-1-isobutyl-1,2,3,4-tetrahydroisoquinoline | H |  | | H | 1.15 | 442.3 | 443.3 |

TABLE 3-continued
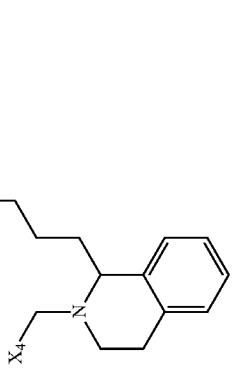
| Cpd # | NAME | R1 | B | R2 | R3 | LC/MS Retention Time | LC/MS Calc. Mass | LC/MS M + H |
|---|---|---|---|---|---|---|---|---|
| 893 | 2-{[6-(2,6-diethylphenyl)-4-methoxypyridin-3-yl]methyl}-1-pentyl-1,2,3,4-tetrahydroisoquinoline | H | 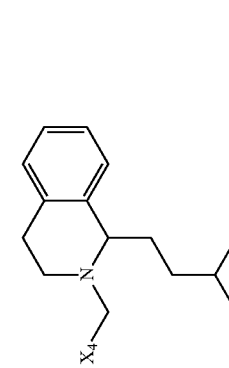 |  | H | 1.16 | 456.3 | 457.4 |
| 894 | 2-{[6-(2,6-diethylphenyl)-4-methoxypyridin-3-yl]methyl}-1-isopentyl-1,2,3,4-tetrahydroisoquinoline | H | 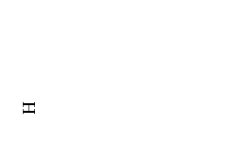 |  | H | 1.16 | 456.3 | 457.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 895 | N-benzyl-N-{[6-(2,6-diethylphenyl)-4-methoxypyridin-3-yl]methyl}cyclopentanamine | H | cyclopentyl-N(benzyl)-CH2-X4 | H3C-O-X2 | H | 1.06 | 428.3 | 429.3 |
| 896 | N-benzyl-N-{[6-(2,6-diethylphenyl)-4-methoxypyridin-3-yl]methyl}pentan-3-amine | H | (CH3CH2)2CH-N(benzyl)-CH2-X4 | H3C-O-X2 | H | 1.12 | 430.3 | 431.3 |
| 897 | N-benzyl-N-{[6-(2,6-diethylphenyl)-4-methoxypyridin-3-yl]methyl}cyclohexanamine | H | cyclohexyl-N(benzyl)-CH2-X4 | X2-O-CH3 | H | 1.07 | 442.3 | 443.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 898 | N,N-dibenzyl-1-[6-(2,6-diethylphenyl)-4-methoxypyridin-3-yl]methanamine | H | (dibenzylaminomethyl, X4) | $X_2$—O—CH$_3$ | H | 1.14 | 450.3 | 451.3 |
| 899 | N-benzyl-1-cyclopentyl-N-{[6-(2,6-diethylphenyl)-4-methoxypyridin-3-yl]methyl}methanamine | H | (N-benzyl-N-cyclopentylmethyl, X4) | CH$_3$—O—$X_2$ | H | 1.13 | 442.3 | 443.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 900 | N-benzyl-N-{[6-(2,6-diethylphenyl)-4-methoxypyridin-3-yl]methyl}hexan-1-amine | H |  |  | H | 1.14 | 444.3 | 445.4 |
| 901 | N-benzyl-1-cyclohexyl-{[6-(2,6-diethylphenyl)-4-methoxypyridin-3-yl]methyl}methanamine | H | 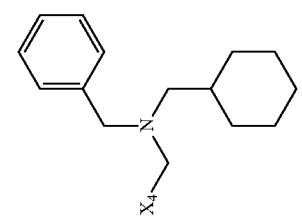 |  | H | 1.17 | 456.3 | 457.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 902 | N-benzyl-N-{[6-(2,6-diethylphenyl)-4-methoxypyridin-3-yl]methyl}heptan-1-amine | H | 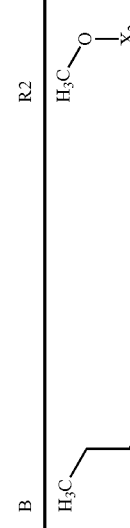 |  | H | 1.16 | 458.3 | 459.4 |
| 903 | N-benzyl-N-{[6-(2,6-diethylphenyl)-4-methoxypyridin-3-yl]methyl}-2-phenylethanamine | H |  | | H | 1.13 | 464.3 | 465.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 904 | N-benzyl-3-cyclopentyl-N-{[6-(2,6-diethylphenyl)-4-methoxypyridin-3-yl]methyl}propan-1-amine | H |  | 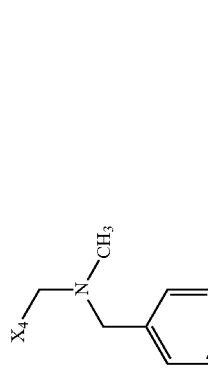 | H | 1.17 | 470.3 | 471.4 |
| 905 | N-benzyl-N-{[6-(2,6-diethylphenyl)-4-methoxypyridin-3-yl]methyl}-3-phenylpropan-1-amine | H | 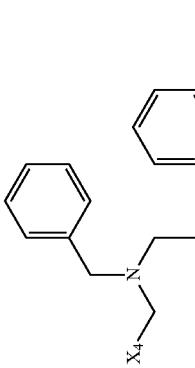 | 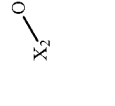 | H | 1.13 | 478.3 | 479.4 |
| 906 | N-(3-chlorobenzyl)-N-{[6-(2,6-diethylphenyl)-5-methoxypyridin-3-yl]methyl}-N-methylamine | H |  |  | CH₃—X₃ | 1.15 | 422.2 | 423.2 |
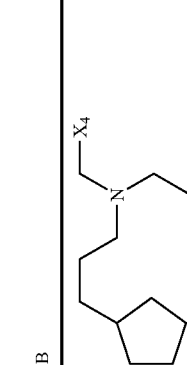

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 907 | 1-{[6-(2,6-diethylphenyl)-2,4-dimethylpyridin-3-yl]methyl}azepane | $X_1$—$CH_3$ |  | $X_2$—$CH_3$ | H | 1.05 | 350.3 | 351.4 |
| 908 | 4-{[6-(2,6-diethylphenyl)-2,4-dimethylpyridin-3-yl]methyl}thiomorpholine | $X_1$—$CH_3$ |  | $X_2$—$CH_3$ | H | 1.07 | 354.2 | 355.3 |
| 909 | | $X_1$—$CH_3$ |  | $X_2$—$CH_3$ | H | 1.09 | 364.3 | 365.4 |
| 910 | 1-{[6-(2,6-diethylphenyl)-2,4-dimethylpyridin-3-yl]methyl}azocane | $X_1$—$CH_3$ |  | $X_2$—$CH_3$ | H | 1.06 | 364.3 | 365.4 |
| 911 | 1-{[6-(2,6-diethylphenyl)-2,4-dimethylpyridin-3-yl]methyl}-3,3,5-trimethylazepane | $X_1$—$CH_3$ |  | $X_2$—$CH_3$ | H | 1.13 | 392.3 | 393.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 912 | 1-{[6-(2,6-diethylphenyl)-2,4-dimethylpyridin-3-yl]methyl}decahydroquinoline |  |  |  | H | 1.07 | 390.3 | 391.4 |
| 913 | N-allyl-N-{[6-(2,6-diethylphenyl)-2,4-dimethylpyridin-3-yl]methyl}prop-2-en-1-amine |  |  |  | H | 1.1 | 348.3 | 349.4 |
| 914 | N-{[6-(2,6-diethylphenyl)-2,4-dimethylpyridin-3-yl]methyl}-N-propylpropan-1-amine |  |  | | H | 1.08 | 352.3 | 353.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 915 | N-(cyclopropylmethyl)-N-{[6-(2,6-diethylphenyl)-2,4-dimethylpyridin-3-yl]methyl}propan-1-amine | H₃C—X₁ | (CH₃, N, cyclopropylmethyl, X₄) | X₂—CH₃ | H | 1.09 | 364.3 | 365.4 |
| 916 | N-{[6-(2,6-diethylphenyl)-2,4-dimethylpyridin-3-yl]methyl}-N-methylhexan-1-amine | X₁—CH₃ | (CH₃, hexyl, N-CH₃, X₄) | CH₃—X₂ | H | 1.13 | 366.3 | 367.4 |
| 917 | N-butyl-N-{[6-(2,6-diethylphenyl)-2,4-dimethylpyridin-3-yl]methyl}butan-1-amine | X₁—CH₃ | (CH₃, propyl, N, propyl-CH₃, X₄) | CH₃—X₂ | H | 1.14 | 380.3 | 381.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 918 | N-{[6-(2,6-diethylphenyl)-2,4-dimethylpyridin-3-yl]methyl}-N-ethyl-2-methylprop-2-en-1-amine | X1—CH3 | H3C-C(=CH2)-CH2-N(CH2CH3)-X4 | CH3—X2 | H | 1.13 | 350.3 | 351.4 |
| 919 | N-{[6-(2,6-diethylphenyl)-2,4-dimethylpyridin-3-yl]methyl}-N-ethylcyclohexanamine | X1—CH3 | cyclohexyl-N(CH3)(CH2-X4) | CH3—X2 | H | 1.08 | 378.3 | 379.4 |
| 920 | N-{[6-(2,6-diethylphenyl)-2,4-dimethylpyridin-3-yl]methyl}-N-pentylpentan-1-amine | X1—CH3 | CH3(CH2)4-N-(CH2)4CH3, CH2-X4 | CH3—X2 | H | 1.17 | 408.4 | 409.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 921 | | X₁—CH₃ | (1-methyl-3,5-dimethylpiperidinyl with X₄) | X₂—CH₃ | H | 1.08 | 364.3 | 365.4 |
| 922 | N-{[6-(2,6-diethylphenyl)-2,4-dimethylpyridin-3-yl]methyl}-N-methyl-N-(4-methylbenzyl)amine | X₁—CH₃ | 4-methylbenzyl-N(CH₃)-X₄ | X₂—CH₃ | H | 1.12 | 386.3 | 387.4 |
| 923 | N-{[6-(2,6-diethylphenyl)-2,4-dimethylpyridin-3-yl]methyl}-N-methyl-N-(3-methylbenzyl)amine | X₁—CH₃ | 3-methylbenzyl-N(CH₃)-X₄ | X₂—CH₃ | H | 1.14 | 386.3 | 387.4 |
| 924 | N-{[6-(2,6-diethylphenyl)-2,4-dimethylpyridin-3-yl]methyl}-N-(4-fluorobenzyl)-N-methylamine | X₁—CH₃ | 4-fluorobenzyl-N(CH₃)-X₄ | X₂—CH₃ | H | 1.11 | 390.2 | 391.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 925 | N-{[6-(2,6-diethylphenyl)-2,4-dimethylpyridin-3-yl]methyl}-N-(3-fluorobenzyl)-N-methylamine | X₁—CH₃ | (3-fluorobenzyl-N(CH₃)-X₄) | X₂—CH₃ | H | 1.14 | 390.2 | 391.4 |
| 926 | N-{[6-(2,6-diethylphenyl)-2,4-dimethylpyridin-3-yl]methyl}-N-(4-methoxybenzyl)-N-methylamine | X₁—CH₃ | (4-methoxybenzyl-N(CH₃)-X₄) | X₂—CH₃ | H | 1.1 | 402.3 | 403.4 |
| 927 | N-{[6-(2,6-diethylphenyl)-2,4-dimethylpyridin-3-yl]methyl}-N-(3-methoxybenzyl)-N-methylamine | X₁—CH₃ | (3-methoxybenzyl-N(CH₃)-X₄) | X₂—CH₃ | H | 1.12 | 402.3 | 403.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 928 | N-(4-chlorobenzyl)-N-{[6-(2,6-diethylphenyl)-2,4-dimethylpyridin-3-yl]methyl}-N-methylamine | X₁—CH₃ | (4-chlorobenzyl-N-methyl-X₄) | X₂—CH₃ | H | 1.15 | 406.2 | 407.4 |
| 929 | N-(3-chlorobenzyl)-N-{[6-(2,6-diethylphenyl)-2,4-dimethylpyridin-3-yl]methyl}-N-methylamine | X₁—CH₃ | (3-chlorobenzyl-N-methyl-X₄) | X₂—CH₃ | H | 1.16 | 406.2 | 407.4 |
| 930 | N-{[6-(2,6-diethylphenyl)-2,4-dimethylpyridin-3-yl]methyl}-N-methyl-N-[4-(trifluoromethyl)benzyl]amine | X₁—CH₃ | (4-trifluoromethylbenzyl-N-methyl-X₄) | X₂—CH₃ | H | 1.17 | 440.2 | 441.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 931 | N-{[6-(2,6-diethylphenyl)-2,4-dimethylpyridin-3-yl]methyl}-N-methyl-N-[3-(trifluoromethyl)benzyl]amine |  |  |  | H | 1.18 | 440.2 | 441.4 |
| 932 | 1-(4-bromophenyl)-N-{[6-(2,6-diethylphenyl)-2,4-dimethylpyridin-3-yl]methyl}-N-methylmethanamine |  |  |  | H | 1.16 | 450.2 | 451.4 |
| 933 | 6-(2,6-diethylphenyl)-4-isopropoxy-2-methyl-3-(pyrrolidin-1-ylmethyl)pyridine |  |  |  | H | 1.01 | 366.3 | 367.4 |
| 934 | 1-{[6-(2,6-diethylphenyl)-4-isopropoxy-2-methylpyridin-3-yl]methyl}azepane |  |  | | H | 1.02 | 394.3 | 395.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 935 | 4-{[6-(2,6-diethylphenyl)-4-isopropoxy-2-methylpyridin-3-yl]methyl}thiomorpholine |  | 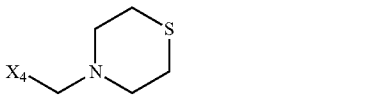 |  | H | 1.04 | 398.2 | 399.4 |
| 936 | 6-(2,6-diethylphenyl)-3-{(3,3-dimethylpiperidin-1-yl)methyl]-4-isopropoxy-2-methylpyridine |  |  |  | H | 1.04 | 408.3 | 409.5 |
| 937 | 1-{[6-(2,6-diethylphenyl)-4-isopropoxy-2-methylpyridin-3-yl]methyl}azocane |  |  |  | H | 1.01 | 408.3 | 409.5 |
| 938 | 1-{[6-(2,6-diethylphenyl)-4-isopropoxy-2-methylpyridin-3-yl]methyl}-3,3,5-trimethylazepane |  |  | | H | 1.07 | 436.3 | 437.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 939 | 1-{[6-(2,6-diethylphenyl)-4-isopropoxy-2-methylpyridin-3-yl]methyl}decahydroquinoline |  |  |  | H | 1.03 | 434.3 | 435.5 |
| 940 | N-{[6-(2,6-diethylphenyl)-4-isopropoxy-2-methylpyridin-3-yl]methyl}-N-methylprop-2-en-1-amine | 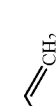 |  |  | H | 1 | 366.3 | 367.4 |
| 941 | N-{[6-(2,6-diethylphenyl)-4-isopropoxy-2-methylpyridin-3-yl]methyl}-N-methylbutan-1-amine |  |  |  | H | 1.03 | 382.3 | 383.5 |
| 942 | N-{[6-(2,6-diethylphenyl)-4-isopropoxy-2-methylpyridin-3-yl]methyl}-N-ethylpropan-2-amine |  |  |  | H | 1.03 | 382.3 | 383.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 943 | N-allyl-N-{[6-(2,6-diethylphenyl)-4-isopropoxy-2-methylpyridin-3-yl]methyl}prop-2-en-1-amine | X₁—CH₃ | CH₂=CH-CH₂-N(X₄)-CH₂-CH=CH₂ | H₃C-CH(O-X₂)-CH₃ | H | 1.03 | 392.3 | 393.5 |
| 944 | N-{[6-(2,6-diethylphenyl)-4-isopropoxy-2-methylpyridin-3-yl]methyl}-N-propylpropan-1-amine | CH₃—X₁ | H₃C-CH₂-CH₂-N(X₄)-CH₂-CH₂-CH₃ | H₃C-CH(O-X₂)-CH₃ | H | 1.04 | 396.3 | 397.5 |
| 945 | N-{[6-(2,6-diethylphenyl)-4-isopropoxy-2-methylpyridin-3-yl]methyl}-N-ethylbutan-1-amine | CH₃—X₁ | CH₃-CH₂-CH₂-CH₂-N(X₄)-CH₂-CH₃ | H₃C-CH(O-X₂)-CH₃ | H | 1.03 | 396.3 | 397.5 |

TABLE 3-continued
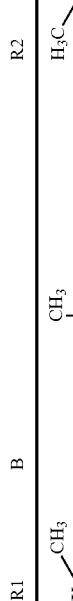
| Cpd # | NAME | R1 | B | R2 | R3 | LC/MS Retention Time | LC/MS Calc. Mass | LC/MS M + H |
|---|---|---|---|---|---|---|---|---|
| 946 | N-(cyclopropylmethyl)-N-{[6-(2,6-diethylphenyl)-4-isopropoxy-2-methylpyridin-3-yl]methyl}propan-1-amine |  |  | 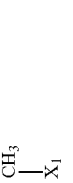 | H | 1.02 | 408.3 | 409.5 |
| 947 | N-{[6-(2,6-diethylphenyl)-4-isopropoxy-2-methylpyridin-3-yl]methyl}-N-methylhexan-1-amine |  |  | 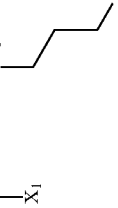 | H | 1.09 | 410.3 | 411.5 |
| 948 | N-butyl-N-{[6-(2,6-diethylphenyl)-4-isopropoxy-2-methylpyridin-3-yl]methyl}butan-1-amine |  |  | | H | 1.06 | 424.3 | 425.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 949 | N-{[6-(2,6-diethylphenyl)-4-isopropoxy-2-methylpyridin-3-yl]methyl}-N-ethyl-2-methylprop-2-en-1-amine | CH$_3$—X$_1$ | H$_3$C-C(=CH$_2$)-CH$_2$-N(CH$_2$CH$_3$)-X$_4$ | X$_2$-O-CH(CH$_3$)$_2$ | H | 1.04 | 394.3 | 395.5 |
| 950 | N-{[6-(2,6-diethylphenyl)-4-isopropoxy-2-methylpyridin-3-yl]methyl}-N-ethylcyclohexanamine | CH$_3$—X$_1$ | cyclohexyl-N(CH$_2$CH$_3$)-X$_4$ | X$_2$-O-CH(CH$_3$)$_2$ | H | 1.03 | 422.3 | 423.5 |
| 951 | N-{[6-(2,6-diethylphenyl)-4-isopropoxy-2-methylpyridin-3-yl]methyl}-N-pentylpentan-1-amine | CH$_3$—X$_1$ | (H$_3$C(CH$_2$)$_4$)$_2$N-X$_4$ | X$_2$-O-CH(CH$_3$)$_2$ | H | 1.13 | 452.4 | 453.6 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 952 | N-{[6-(2,6-diethylphenyl)-4-isopropoxy-2-methylpyridin-3-yl]methyl}-N-hexylhexan-1-amine | CH₃—X₁ | (hexyl)₂N-CH₂-X₄ | X₂-O-CH(CH₃)₂ | H | 1.17 | 480.4 | 481.7 |
| 953 | 6-(2,6-diethylphenyl)-3-[(3,5-dimethylpiperidin-1-yl)methyl]-4-isopropoxy-2-methylpyridine | X₁—CH₃ | 3,5-dimethylpiperidin-1-yl-CH₂-X₄ | X₂-O-CH(CH₃)₂ | H | 1.05 | 408.3 | 409.5 |
| 954 | 1-[6-(2,6-diethylphenyl)-4-isopropoxy-2-methylpyridin-3-yl]-N-methyl-N-(4-methylbenzyl)methanamine | X₁—CH₃ | 4-MeC₆H₄-CH₂-N(CH₃)-CH₂-X₄ | X₂-O-CH(CH₃)₂ | H | 1.09 | 430.3 | 431.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 955 | 1-[6-(2,6-diethylphenyl)-4-isopropoxy-2-methylpyridin-3-yl]-N-methyl-N-(3-methylbenzyl)methanamine | X1—CH3 | (3-methylbenzyl)-N-CH3 | H3C—X2—O—CH(CH3) | H | 1.08 | 430.3 | 431.5 |
| 956 | 1-[6-(2,6-diethylphenyl)-4-isopropoxy-2-methylpyridin-3-yl]-N-(4-fluorobenzyl)-N-methylmethanamine | X1—CH3 | (4-fluorobenzyl)-N-CH3 | H3C—X2—O—CH(CH3) | H | 1.07 | 434.3 | 435.5 |
| 957 | 1-[6-(2,6-diethylphenyl)-4-isopropoxy-2-methylpyridin-3-yl]-N-(3-fluorobenzyl)-N-methylmethanamine | X1—CH3 | (3-fluorobenzyl)-N-CH3 | H3C—X2—O—CH(CH3) | H | 1.07 | 434.3 | 435.5 |
| 958 | 1-[6-(2,6-diethylphenyl)-4-isopropoxy-2-methylpyridin-3-yl]-N-(4-methoxybenzyl)-N-methylmethanamine | X1—CH3 | (4-methoxybenzyl)-N-CH3 | H3C—X2—O—CH(CH3) | H | 1.05 | 446.3 | 447.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 959 | 1-[6-(2,6-diethylphenyl)-4-isopropoxy-2-methylpyridin-3-yl]-N-(3-methoxybenzyl)-N-methylmethanamine | 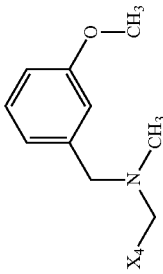 | 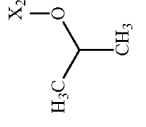 | 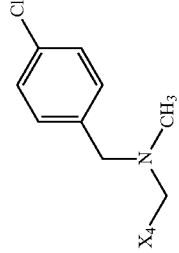 | H | 1.07 | 446.3 | 447.5 |
| 960 | N-(4-chlorobenzyl)-N-{[6-(2,6-diethylphenyl)-4-isopropoxy-2-methylpyridin-3-yl]methyl}-N-methylamine | 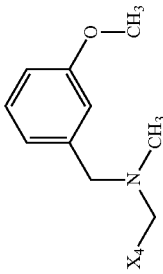 | 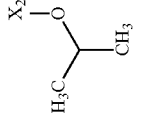 | 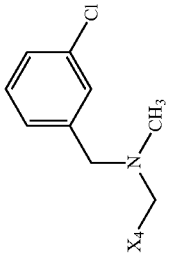 | H | 1.11 | 450.2 | 451.5 |
| 961 | N-(3-chlorobenzyl)-N-{[6-(2,6-diethylphenyl)-4-isopropoxy-2-methylpyridin-3-yl]methyl}-N-methylamine | 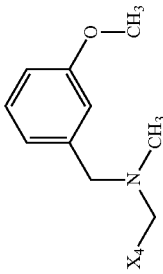 | 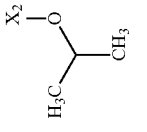 | 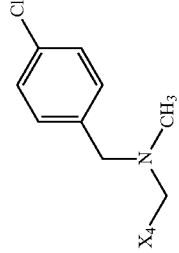 | H | 1.11 | 450.2 | 451.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 962 | 1-[6-(2,6-diethylphenyl)-4-isopropoxy-2-methylpyridin-3-yl]-N-methyl-N-[4-(trifluoromethyl)benzyl]methanamine | X₁—CH₃ | 4-CF₃-benzyl-N(CH₃)-CH₂-X₄ | H₃C-CH(CH₃)-O-X₂ | H | 1.14 | 484.3 | 485.5 |
| 963 | 1-[6-(2,6-diethylphenyl)-4-isopropoxy-2-methylpyridin-3-yl]-N-methyl-N-[3-(trifluoromethyl)benzyl]methanamine | X₁—CH₃ | 3-CF₃-benzyl-N(CH₃)-CH₂-X₄ | H₃C-CH(CH₃)-O-X₂ | H | 1.13 | 484.3 | 485.5 |
| 964 | 1-(4-bromophenyl)-N-{[6-(2,6-diethylphenyl)-4-isopropoxy-2-methylpyridin-3-yl]methyl}-N-methylmethanamine | X₁—CH₃ | 4-Br-benzyl-N(CH₃)-CH₂-X₄ | H₃C-CH(CH₃)-O-X₂ | H | 1.11 | 494.2 | 495.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 965 | N-{[6-((2,6-diethylphenyl)-4-methoxypyridin-3-yl]methyl}-N-hexylhexan-1-amine | H | (dihexylamino-methyl, X4) | (H3C-O-X2, methoxy) | H | 1.18 | 438.4 | 439.5 |
| 966 | N-(4-chlorobenzyl)-N-{[6-(2,6-diethylphenyl)-4-methoxypyridin-3-yl]methyl}-N-methylamine | H | (N-(4-chlorobenzyl)-N-methylaminomethyl, X4) | (X2-O-CH3, methoxy) | H | 1.11 | 408.2 | 409.4 |

TABLE 3-continued
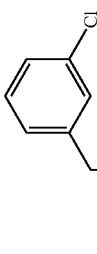
| Cpd # | NAME | R1 | B | R2 | R3 | LC/MS Retention Time | LC/MS Calc. Mass | LC/MS M + H |
|---|---|---|---|---|---|---|---|---|
| 967 | N-(3-chlorobenzyl)-N-{[6-(2,6-diethylphenyl)-4-methoxypyridin-3-yl]methyl}-N-methylamine | H |  | 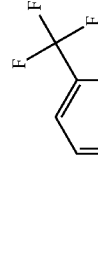 | H | 1.1 | 408.2 | 409.4 |
| 968 | 1-[6-(2,6-diethylphenyl)-4-methoxypyridin-3-yl]-N-methyl-N-[4-(trifluoromethyl)benzyl]methanamine | H |  | 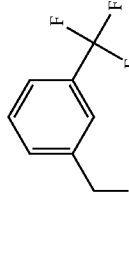 | H | 1.13 | 442.2 | 443.4 |
| 969 | 1-[6-(2,6-diethylphenyl)-4-methoxypyridin-3-yl]-N-methyl-N-[3-(trifluoromethyl)benzyl]methanamine | H |  | 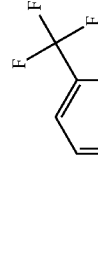 | H | 1.13 | 442.2 | 443.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 970 | 1-(4-bromophenyl)-N-{[6-(2,6-diethylphenyl)-4-methoxypyridin-3-yl]methyl}-N-methylmethanamine | H |  |  | H | 1.11 | 452.1 | 453.3 |
| 971 | N-(cyclopropylmethyl)-N-{[6-(2,6-diethylphenyl)-4-methoxy-5-methylpyridin-3-yl]methyl}-2-phenylethanamine | H |  |  | X₃—CH₃ | 1.16 | 442.3 | 443.3 |
| 972 | N-(cyclobutylmethyl)-N-{[6-(2,6-diethylphenyl)-4-methoxy-5-methylpyridin-3-yl]methyl}-2-phenylethanamine | H |  |  | X₃—CH₃ | 1.17 | 456.3 | 457.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 973 | N-(cyclohexylmethyl)-N-{[6-(2,6-diethylphenyl)-4-methoxy-5-methylpyridin-3-yl]methyl}-2-phenylethanamine | H | | $X_2$—O—$CH_3$ | $H_3C$—$X_3$ | 1.2 | 484.3 | 485.4 |
| 974 | N-{[6-(2,6-diethylphenyl)-4-methoxy-5-methylpyridin-3-yl]methyl}-N-(2-methylbenzyl)-2-phenylethanamine | H | | $X_2$—O—$CH_3$ | $CH_3$—$X_3$ | 1.21 | 492.3 | 493.3 |
| 975 | 5-[(2-benzylpiperidin-1-yl)methyl]-2-(2,6-diethylphenyl)-4-methoxy-3-methylpyridine | H | | $X_2$—O—$CH_3$ | $CH_3$—$X_3$ | 1.15 | 442.3 | 443.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 976 | N-benzyl-N-{[6-(2,6-diethylphenyl)-4-methoxy-5-methyl]pyridin-3-yl]methyl}-3-phenylbutan-1-amine | H |  | 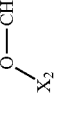 |  | 1.19 | 506.3 | 507.3 |
| 977 | N-benzyl-N-{[6-(2,6-diethylphenyl)-4-methoxy-5-methyl]pyridin-3-yl]methyl}indan-1-amine | H | | | | 1.22 | 490.3 | 491.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 978 | N-(cyclobutylmethyl)-N-{[6-(2,6-diethylphenyl)-4-methoxy-2-methylpyridin-3-yl]methyl}-2-phenylethanamine | 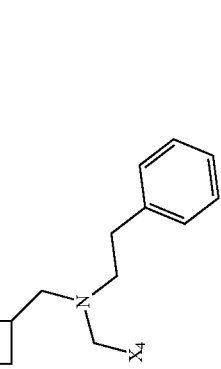 |  |  | H | 1.09 | 456.3 | 457.3 |
| 979 | N-{[6-(2,6-diethylphenyl)-4-methoxy-2-methylpyridin-3-yl]methyl}-N-(2-phenylethyl)pentan-1-amine | 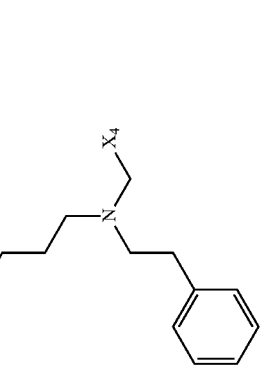 |  |  | H | 1.1 | 458.3 | 459.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 980 | N-(cyclopentylmethyl)-N-{[6-(2,6-diethylphenyl)-4-methoxy-2-methylpyridin-3-yl]methyl}-2-phenylethanamine |  |  |  | H | 1.1 | 470.3 | 471.4 |
| 981 | N-{[6-(2,6-diethylphenyl)-4-methoxy-2-methylpyridin-3-yl]methyl}-N-(2-phenylethyl)hexan-1-amine |  |  |  | H | 1.12 | 472.3 | 473.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 982 | N-(cyclohexylmethyl)-N-{[6-(2,6-diethylphenyl)-4-methoxy-2-methylpyridin-3-yl]methyl}-2-phenylethanamine | X₁—CH₃ | 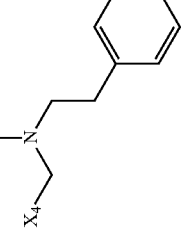 |  | H | 1.14 | 484.3 | 485.4 |
| 983 | N-{[6-(2,6-diethylphenyl)-4-methoxy-2-methylpyridin-3-yl]methyl}-N-(2-phenylethyl)heptan-1-amine | H₃C—X₁ | 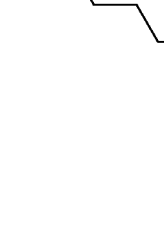 |  | H | 1.15 | 486.4 | 487.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 984 | 2-cyclohexyl-N-{[6-(2,6-diethylphenyl)-4-methoxy-2-methylpyridin-3-yl]methyl}-N-(2-phenylethyl)ethanamine |  |  |  | H | 1.14 | 498.4 | 499.4 |
| 985 | N-{[6-(2,6-diethylphenyl)-4-methoxy-2-methylpyridin-3-yl]methyl}-N-(2-fluorobenzyl)-2-phenylethanamine |  |  |  | H | 1.16 | 496.3 | 497.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 986 | N-{[6-(2,6-diethylphenyl)-4-methoxy-2-methylpyridin-3-yl]methyl}-N-(4-methylbenzyl)-2-phenylethanamine |  | 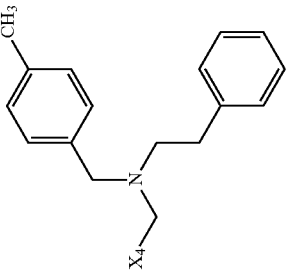 |  | H | 1.14 | 492.3 | 493.4 |
| 987 | N-{[6-(2,6-diethylphenyl)-4-methoxy-2-methylpyridin-3-yl]methyl}-N-(4-fluorobenzyl)-2-phenylethanamine |  | 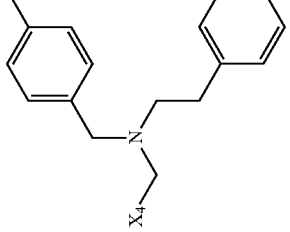 |  | H | 1.15 | 496.3 | 497.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 988 | N-(cycloheptylmethyl)-N-{[6-(2,6-diethylphenyl)-4-methoxy-2-methylpyridin-3-yl]methyl}-2-phenylethanamine |  |  |  | H | 1.17 | 498.4 | 499.4 |
| 989 | N-{[6-(2,6-diethylphenyl)-4-methoxy-2-methylpyridin-3-yl]methyl}-N-(4-methoxybenzyl)-2-phenylethanamine | 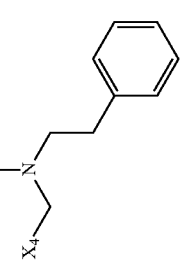 | 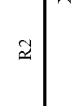 | 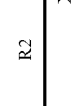 | H | 1.11 | 508.3 | 509.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 990 | N-{[6-(2,6-diethylphenyl)-4-methoxy-2-methylpyridin-3-yl]methyl}-2-phenyl-N-[2-(trifluoromethyl)benzyl]ethanamine |  |  |  | H | 1.22 | 546.3 | 547.4 |
| 991 | 1-[6-(2,6-diethylphenyl)-4-methoxy-2-methylpyridin-3-yl]-N-methyl-N-(2-methylbenzyl)methanamine | 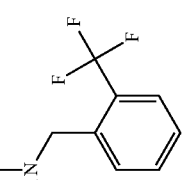 | 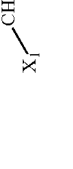 | 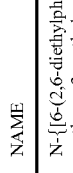 | H | 1.02 | 402.3 | 403.3 |
| 992 | N-(2-chlorobenzyl)-N-{[6-(2,6-diethylphenyl)-4-methoxy-2-methylpyridin-3-yl]methyl}-N-methylamine | 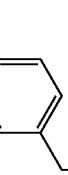 |  | 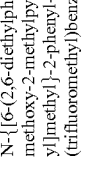 | H | 1.03 | 422.2 | 423.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 993 | 1-[6-(2,6-diethylphenyl)-4-methoxy-2-methylpyridin-3-yl]-N-methyl-N-[2-(trifluoromethyl)benzyl]methanamine | 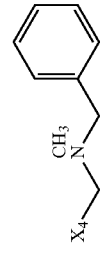 |  |  | H | 1.08 | 456.2 | 457.3 |
| 994 | N-benzyl-N-{[6-(2,6-diethylphenyl)-4-methoxy-2-methylpyridin-3-yl]methyl}-3-phenylbutan-1-amine | 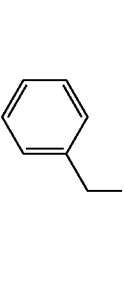 |  |  | H | 1.13 | 506.3 | 507.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 995 | N-benzyl-2-(3-chlorophenyl)-N-{[6-(2,6-diethylphenyl)-4-methoxy-2-methylpyridin-3-yl]methyl}ethanamine |  |  |  | H | 1.18 | 512.3 | 513.3 |
| 996 | N-benzyl-N-{[6-(2,6-diethylphenyl)-4-methoxy-2-methylpyridin-3-yl]methyl}indan-2-amine |  |  |  | H | 1.13 | 490.3 | 491.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 997 | N-benzyl-N-{[6-(2,6-diethylphenyl)-4-methoxy-2-methylpyridin-3-yl]methyl}-2-(4-fluorophenyl)ethanamine | X1—CH3 | 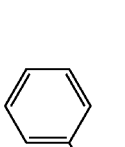 |  | H | 1.14 | 496.3 | 497.3 |
| 998 | N-benzyl-N-{[6-(2,6-diethylphenyl)-4-methoxy-2-methylpyridin-3-yl]methyl}-2-(4-methoxyphenyl)ethanamine | X1—CH3 |  |  | H | 1.12 | 508.3 | 509.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 999 | N-benzyl-N-{[6-(2,6-diethylphenyl)-4-methoxy-2-methylpyridin-3-yl]methyl}-1-(4-methoxyphenyl)propan-2-amine |  |  |  | H | 1.15 | 522.3 | 523.4 |
| 1000 | N-benzyl-N-{[6-(2,6-diethylphenyl)-4-methoxy-2-methylpyridin-4-yl]methyl}-1,2,3,4-tetrahydronaphthalen-2-amine |  |  |  | H | 1.17 | 504.3 | 505.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1001 | N-(cyclobutylmethyl)-N-{[6-(2,6-diethylphenyl)-4-methoxy-2,5-dimethylpyridin-3-yl]methyl}-2-phenylethanamine | H₃C—X₁ | 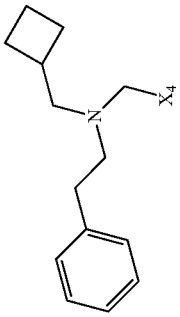 | X₂—O—CH₃ | X₃—CH₃ | 1.15 | 470.3 | 471.4 |
| 1002 | N-(cyclohexylmethyl)-N-{[6-(2,6-diethylphenyl)-4-methoxy-2,5-dimethylpyridin-3-yl]methyl}-2-phenylethanamine | X₁—CH₃ | 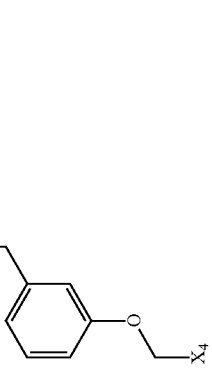 | X₂—O—CH₃ | CH₃—X₃ | 1.19 | 498.4 | 499.4 |
| 1003 | N-(2-chlorobenzyl)-N-{[6-(2,6-diethylphenyl)-4-methoxy-2,5-dimethylpyridin-3-yl]methyl}-N-methylamine | X₁—CH₃ | 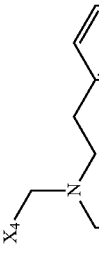 | X₂—O—CH₃ | CH₃—X₃ | 1.1 | 436.2 | 437.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1004 | 1-[6-(2,6-diethylphenyl)-4-methoxy-2,5-dimethylpyridin-3-yl]-N-methyl-N-[2-(trifluoromethyl)benzyl]methanamine | X₁—CH₃ | | X₂—O—CH₃ | CH₃—X₃ | 1.16 | 470.3 | 471.3 |
| 1005 | N-(cyclobutylmethyl)-N-{[6-(2,6-diethylphenyl)-2-methylpyridin-3-yl]methyl}-2-phenylethanamine | X₁—CH₃ | | H | H | 1.17 | 426.3 | 427.5 |
| 1006 | N-(cyclohexylmethyl)-N-{[6-(2,6-diethylphenyl)-2-methylpyridin-3-yl]methyl}-2-phenylethanamine | X₁—CH₃ | | H | H | 1.22 | 454.3 | 455.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1007 | 3-[(2-benzylpiperidin-1-yl)methyl]-6-(2,6-diethylphenyl)-2-methylpyridine | X₁—CH₃ | (2-benzylpiperidin-1-ylmethyl) | H | H | 1.13 | 412.3 | 413.4 |
| 1008 | 1-[6-(2,6-diethylphenyl)-2-methylpyridin-3-yl]-N-methyl-N-(2-methylbenzyl)methanamine | X₁—CH₃ | N-methyl-N-(2-methylbenzyl)aminomethyl | H | H | 1.14 | 372.3 | 373.4 |
| 1009 | N-(2-chlorobenzyl)-N-{[6-(2,6-diethylphenyl)-2-methylpyridin-3-yl]methyl}-N-methylamine | X₁—CH₃ | N-(2-chlorobenzyl)-N-methylaminomethyl | H | H | 1.14 | 392.2 | 393.3 |

TABLE 3-continued
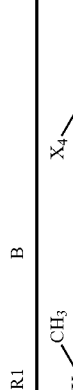
| Cpd # | NAME | R1 | B | R2 | R3 | LC/MS Retention Time | LC/MS Calc. Mass | LC/MS M + H |
|---|---|---|---|---|---|---|---|---|
| 1010 | 1-{6-(2,6-diethylphenyl)-2-methylpyridin-3-yl]-N-methyl-N-[2-(trifluoromethyl)benzyl]methanamine |  |  | H | H | 1.2 | 426.2 | 427.4 |
| 1011 | N-{6-(2,6-diethylphenyl)-2,4-dimethylpyridin-3-yl]-N-(2-phenylethyl)propan-1-amine |  | 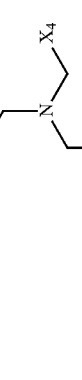 |  | H | 1.16 | 414.3 | 415.4 |
| 1012 | N-(cyclopropylmethyl)-N-{[6-(2,6-dimethylphenyl)-2,4-dimethylpyridin-3-yl]methyl}-2-phenylethanamine | 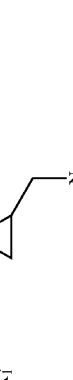 |  | 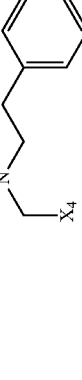 | H | 1.16 | 426.3 | 427.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1013 | N-{[6-(2,6-diethylphenyl)-2,4-dimethylpyridin-3-yl]methyl}-N-(2-phenylethyl)butan-1-amine |  |  |  | H | 1.19 | 428.3 | 429.5 |
| 1014 | N-(cyclobutylmethyl)-N-{[6-(2,6-diethylphenyl)-2,4-dimethylpyridin-3-yl]methyl}-2-phenylethanamine | 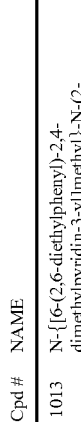 | 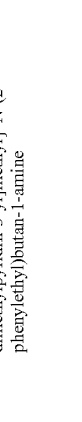 |  | H | 1.2 | 440.3 | 441.5 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1015 | N-{[6-(2,6-diethylphenyl)-2,4-dimethylpyridin-3-yl]methyl}-N-(2-phenylethyl)pentan-1-amine | H₃C—X₁ | (CH₃-pentyl-N(X₄-CH₂-)-CH₂CH₂-phenyl) | X₂—CH₃ | H | 1.21 | 442.3 | 443.5 |
| 1016 | 3-[(2-benzylpiperidin-1-yl)methyl]-6-(2,6-diethylphenyl)-2,4-dimethylpyridine | X₁—CH₃ | (2-benzylpiperidin-1-yl with X₄-CH₂-) | X₂—CH₃ | H | 1.12 | 426.3 | 427.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1017 | 6-(2,6-diethylphenyl)-2,4-dimethyl-3-{[2-(2-phenylethyl)piperidin-1-yl]methyl}pyridine | X₁—CH₃ | 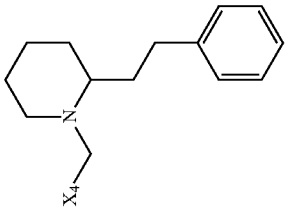 | X₂—CH₃ | H | 1.13 | 440.3 | 441.5 |
| 1018 | 6-(2,6-diethylphenyl)-2,4-dimethyl-3-{[2-(4-phenylbutyl)piperidin-1-yl]methyl}pyridine | X₁—CH₃ |  | X₂—CH₃ | H | 1.17 | 468.4 | 469.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1019 | N-{[6-(2,6-diethylphenyl)-2,4-dimethylpyridin-3-yl]methyl}-N-methyl-N-(2-methylbenzyl)amine |  |  |  | H | 1.14 | 386.3 | 387.4 |
| 1020 | N-{[6-(2,6-diethylphenyl)-2,4-dimethylpyridin-3-yl]methyl}-N-(2-fluorobenzyl)-N-methylamine |  |  |  | H | 1.13 | 390.2 | 391.4 |
| 1021 | N-(2-chlorobenzyl)-N-{[6-(2,6-diethylphenyl)-2,4-dimethylpyridin-3-yl]methyl}-N-methylamine |  |  |  | H | 1.16 | 406.2 | 407.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1022 | N-{[6-(2,6-diethylphenyl)-2,4-dimethylpyridin-3-yl]methyl}-N-(2-methoxybenzyl)-N-methylamine |  |  |  | H | 1.1 | 402.3 | 403.4 |
| 1023 | N-{[6-(2,6-diethylphenyl)-2,4-dimethylpyridin-3-yl]methyl}-N-methyl-N-[2-(trifluoromethyl)benzyl]amine |  | 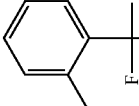 |  | H | 1.18 | 440.2 | 441.4 |
| 1024 | N-{[6-(2,6-diethylphenyl)-4-isopropoxy-2-methylpyridin-3-yl]methyl}-N-methyl-2-phenylethanamine |  | 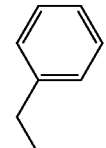 |  | H | 1.07 | 430.3 | 431.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1025 | N-{[6-(2,6-diethylphenyl)-4-isopropoxy-2-methylpyridin-3-yl]methyl}-N-(2-phenylethyl)propan-1-amine |  |  |  | H | 1.1 | 458.3 | 459.5 |
| 1026 | N-(cyclopropylmethyl)-N-{[6-(2,6-diethylphenyl)-4-isopropoxy-2-methylpyridin-3-yl]methyl}-2-phenylethanamine |  | 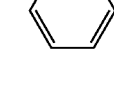 | 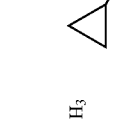 | H | 1.11 | 470.3 | 471.5 |
| 1027 | N-{[6-(2,6-diethylphenyl)-4-isopropoxy-2-methylpyridin-3-yl]methyl}-N-(2phenylethyl)butan-1-amine |  |  | 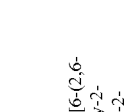 | H | 1.12 | 472.3 | 473.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1028 | N-(cyclobutylmethyl)-N-{[6-(2,6-diethylphenyl)-4-isopropoxy-2-methylpyridin-3-yl]methyl}-2-phenylethanamine |  | 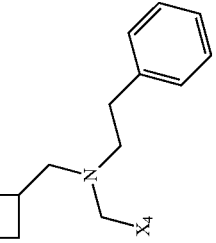 |  | H | 1.13 | 484.3 | 485.5 |
| 1029 | N-{[6-(2,6-diethylphenyl)-4-isopropoxy-2-methylpyridin-3-yl]methyl}-N-(2-phenylethyl)pentan-1-amine |  | 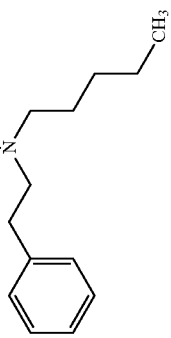 | 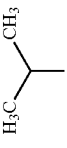 | H | 1.15 | 486.4 | 487.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1030 | N-(cyclopentylmethyl)-N-{[6-(2,6-diethylphenyl)-4-isopropoxy-2-methylpyridin-3-yl]methyl}-2-phenylethanamine |  | 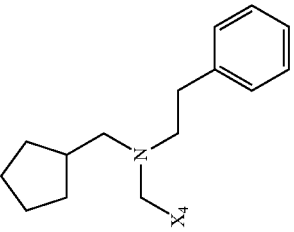 |  | H | 1.17 | 498.4 | 499.6 |
| 1031 | N-{[6-(2,6-diethylphenyl)-4-isopropoxy-2-methylpyridin-3-yl]methyl}-N-(2-phenylethyl)hexan-1-amine |  | 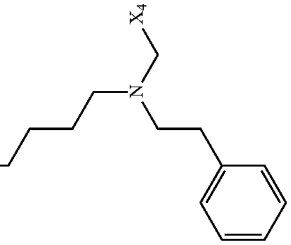 | 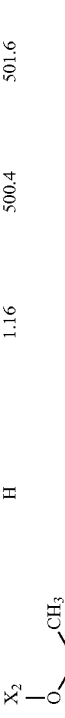 | H | 1.16 | 500.4 | 501.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1032 | N-(cyclohexylmethyl)-N-{[6-(2,6-diethylphenyl)-4-isopropoxy-2-methylpyridin-3-yl]methyl}-2-phenylethanamine | 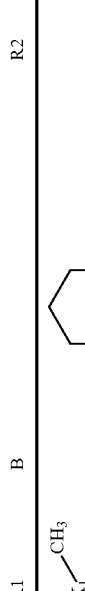 | 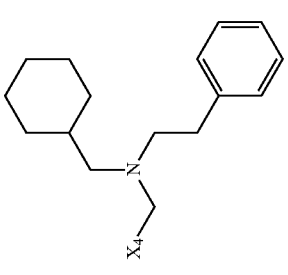 | 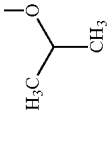 | H | 1.21 | 512.4 | 513.6 |
| 1033 | N-{[6-(2,6-diethylphenyl)-4-isopropoxy-2-methylpyridin-3-yl]methyl}-N-(2-phenylethyl)heptan-1-amine |  |  | 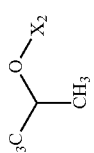 | H | 1.19 | 514.4 | 516.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1034 | 2-cyclohexyl-N-{[6-(2,6-diethylphenyl)-4-isopropoxy-2-methylpyridin-3-yl]methyl}-N-(2-phenylethyl)ethanamine |  | 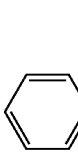 | 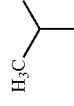 | H | 1.19 | 526.4 | 527.6 |
| 1035 | N-{[6-(2,6-diethylphenyl)-4-isopropoxy-2-methylpyridin-3-yl]methyl}-N-(2-methylbenzyl)-2-phenylethanamine | 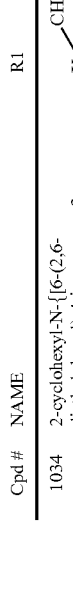 |  | 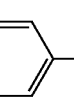 | H | 1.24 | 520.3 | 521.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1036 | N-{[6-(2,6-diethylphenyl)-4-isopropoxy-2-methylpyridin-3-yl]methyl}-N-(2-fluorobenzyl)-2-phenylethanamine |  |  |  | H | 1.23 | 524.3 | 525.5 |
| 1037 | N-{[6-(2,6-diethylphenyl)-4-isopropoxy-2-methylpyridin-3-yl]methyl}-N-(4-methylbenzyl)-2-phenylethanamine |  | 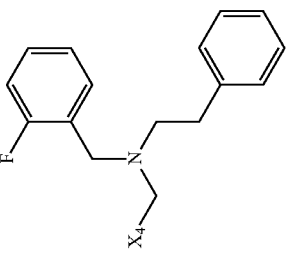 | 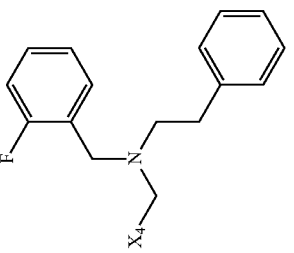 | H | 1.2 | 520.3 | 521.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1038 | N-{[6-(2,6-diethylphenyl)-4-isopropoxy-2-methylpyridin-3-yl]methyl}-N-(4-fluorobenzyl)-2-phenylethanamine |  |  |  | H | 1.21 | 524.3 | 525.6 |
| 1039 | N-(cycloheptylmethyl)-N-{[6-(2,6-diethylphenyl)-4-isopropoxy-2-methylpyridin-3-yl]methyl}-2-phenylethanamine |  |  |  | H | 1.24 | 526.4 | 527.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1040 | N-{[6-(2,6-diethylphenyl)-4-isopropoxy-2-methylpyridin-3-yl]methyl}-N-(2-methoxybenzyl)-2-phenylethanamine |  |  |  | H | 1.14 | 536.3 | 537.6 |
| 1041 | N-{[6-(2,6-diethylphenyl)-4-isopropoxy-2-methylpyridin-3-yl]methyl}-N-(4-methoxybenzyl)-2-phenylethanamine |  |  |  | H | 1.17 | 536.3 | 537.6 |

TABLE 3-continued
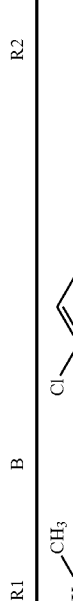
| Cpd # | NAME | R1 | B | R2 | R3 | LC/MS Retention Time | LC/MS Calc. Mass | LC/MS M + H |
|---|---|---|---|---|---|---|---|---|
| 1042 | N-(2-chlorobenzyl)-N-{[6-(2,6-diethylphenyl)-4-isopropoxy-2-methylpyridin-3-yl]methyl}-2-phenylethanamine |  | 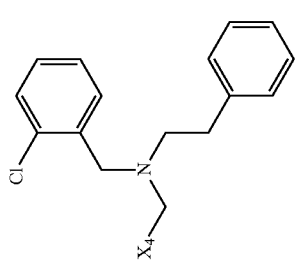 | 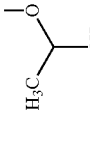 | H | 1.25 | 540.3 | 541.5 |
| 1043 | N-(4-chlorobenzyl)-N-{[6-(2,6-diethylphenyl)-4-isopropoxy-2-methylpyridin-3-yl]methyl}-2-phenylethanamine | 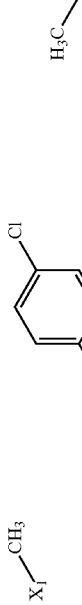 |  | 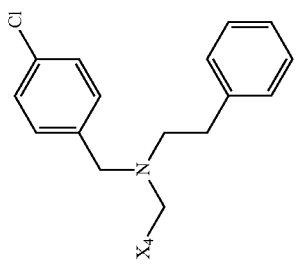 | H | 1.24 | 540.3 | 541.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1044 | N-{[6-(2,6-diethylphenyl)-4-isopropoxy-2-methylpyridin-3-yl]methyl}-2-phenyl-N-[2-(trifluoromethyl)benzyl]ethan-amine |  | 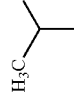 | 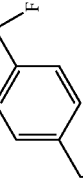 | H | 1.26 | 574.3 | 575.6 |
| 1045 | N-{[6-(2,6-diethylphenyl)-4-isopropoxy-2-methylpyridin-3-yl]methyl}-2-phenyl-N-[4-(trifluoromethyl)ethan-amine | 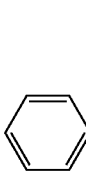 |  | 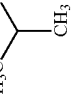 | H | 1.25 | 574.3 | 575.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1046 | 1-{[6-(2,6-diethylphenyl)-4-isopropoxy-2-methylpyridin-3-yl]methyl}-2-phenylazepane |  |  | 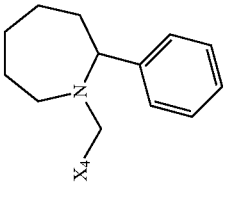 | H | 1.08 | 470.3 | 471.5 |
| 1047 | 3-[(2-benzylpiperidin-1-yl)methyl]-6-(2,6-diethylphenyl)-4-isopropoxy-2-methylpyridine | 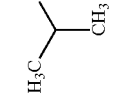 |  |  | H | 1.08 | 470.3 | 471.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1048 | 6-(2,6-diethylphenyl)-4-isopropoxy-2-methyl-3-{[2-(2-phenylethyl)piperidin-1-yl]methyl}pyridine |  |  |  | H | 1.1 | 484.3 | 486.6 |
| 1049 | 6-(2,6-diethylphenyl)-4-isopropoxy-2-methyl-3-{[2-(3-phenylpropyl)piperidin-1-yl]methyl}pyridine |  |  |  | H | 1.11 | 498.4 | 499.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1050 | 6-(2,6-diethylphenyl)-4-isopropoxy-2-methyl-3-{[2-(4-phenyl)butyl]piperidin-1-yl]methyl}pyridine |  |  | | H | 1.14 | 512.4 | 513.6 |
| 1051 | 1-[6-(2,6-diethylphenyl)-4-isopropoxy-2-methylpyridin-3-yl]-N-methyl-N-(2-methylbenzyl)methanamine |  | 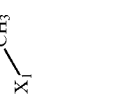 |  | H | 1.07 | 430.3 | 431.4 |
| 1052 | 1-[6-(2,6-diethylphenyl)-4-isopropoxy-2-methylpyridin-3-yl]-N-(2-fluorobenzyl)-N-methylmethanamine |  | 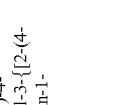 |  | H | 1.06 | 434.3 | 435.4 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1053 | N-(2-chlorobenzyl)-N-{[6-(2,6-diethylphenyl)-4-isopropoxy-2-methylpyridin-3-yl]methyl}-N-methylamine | X₁—CH₃ | 2-chlorobenzyl-N(CH₃)-CH₂-X₄ | H₃C-CH(X₂-O)-CH₃ | H | 1.09 | 450.2 | 451.4 |
| 1054 | 1-[6-(2,6-diethylphenyl)-4-isopropoxy-2-methylpyridin-3-yl]-N-(2-methoxybenzyl)-N-methylmethanamine | X₁—CH₃ | 2-methoxybenzyl-N(CH₃)-CH₂-X₄ | H₃C-CH(X₂-O)-CH₃ | H | 1.05 | 446.3 | 447.5 |
| 1055 | 1-[6-(2,6-diethylphenyl)-4-isopropoxy-2-methylpyridin-3-yl]-N-methyl-N-[2-(trifluoromethyl)benzyl]methanamine | X₁—CH₃ | 2-(trifluoromethyl)benzyl-N(CH₃)-CH₂-X₄ | H₃C-CH(X₂-O)-CH₃ | H | 1.16 | 484.3 | 485.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1056 | N-benzyl-2-(2-chlorophenyl)-N-{[6-(2,6-diethylphenyl)-4-isopropoxy-2-methylpyridin-3-yl]methyl}ethanamine | 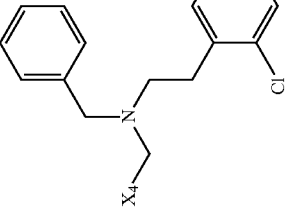 | 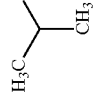 |  | H | 1.24 | 540.3 | 541.5 |
| 1057 | N-benzyl-N-{[6-(2,6-diethylphenyl)-4-isopropoxy-2-methylpyridin-3-yl]methyl}-3-phenylbutan-1-amine | 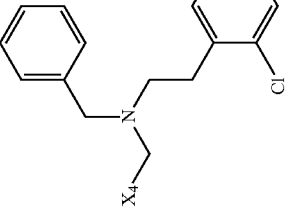 | 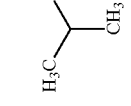 |  | H | 1.18 | 534.4 | 535.6 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1058 | N-benzyl-2-(4-chlorophenyl)-N-{[6-(2,6-diethylphenyl)-4-isopropoxy-2-methylpyridin-3-yl]methyl}ethanamine |  | 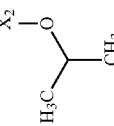 |  | H | 1.22 | 540.3 | 541.5 |
| 1059 | N-benzyl-2-(3-chlorophenyl)-N-{[6-(2,6-diethylphenyl)-4-isopropoxy-2-methylpyridin-3-yl]methyl}ethanamine |  |  | 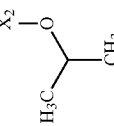 | H | 1.24 | 540.3 | 541.5 |
| 1060 | N-benzyl-N-{[6-(2,6-diethylphenyl)-4-isopropoxy-2-methylpyridin-3-yl]methyl}indan-2-amine | | | | | | | |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1061 | N-benzyl-N-{[6-(2,6-diethylphenyl)-4-isopropoxy-2-methyl]pyridin-3-yl]methyl}indan-1-amine |  | 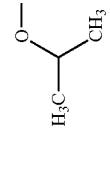 |  | H | 1.24 | 518.3 | 519.6 |
| 1062 | N-benzyl-N-{[6-(2,6-diethylphenyl)-4-isopropoxy-2-methyl]pyridin-3-yl]methyl}-2-(3-fluorophenyl)ethanamine |  | 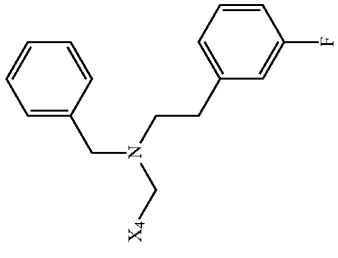 |  | H | 1.21 | 524.3 | 525.5 |

TABLE 3-continued
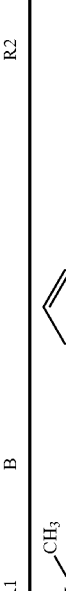
| Cpd # | NAME | R1 | B | R2 | R3 | LC/MS Retention Time | LC/MS Calc. Mass | LC/MS M + H |
|---|---|---|---|---|---|---|---|---|
| 1063 | N-benzyl-N-{[6-(2,6-diethylphenyl)-4-isopropoxy-2-methyl]pyridin-3-yl]methyl}-2-(4-fluorophenyl)ethanamine |  | 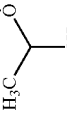 |  | H | 1.2 | 524.3 | 525.6 |
| 1064 | N-benzyl-N-{[6-(2,6-diethylphenyl)-4-isopropoxy-2-methyl]pyridin-3-yl]methyl}-2-(4-methoxyphenyl)ethanamine | 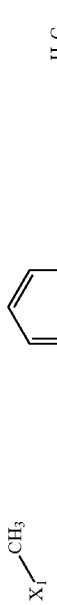 |  | 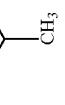 | H | 1.18 | 536.3 | 537.6 |

TABLE 3-continued
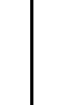
| Cpd # | NAME | R1 | B | R2 | R3 | LC/MS Retention Time | LC/MS Calc. Mass | LC/MS M + H |
|---|---|---|---|---|---|---|---|---|
| 1065 | N-benzyl-N-{[6-(2,6-diethylphenyl)-4-isopropoxy-2-methylpyridin-3-yl]methyl}-1-(4-methoxyphenyl)propan-2-amine |  | 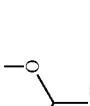 |  | H | 1.22 | 550.4 | 551.6 |
| 1066 | N-benzyl-N-{[6-(2,6-diethylphenyl)-4-isopropoxy-2-methylpyridin-3-yl]methyl}-1,2,3,4-tetrahydronaphthalen-2-amine |  | 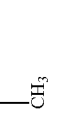 | | H | 1.23 | 532.3 | 533.5 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1067 | N-(cyclobutylmethyl)-N-{[6-(2,6-diethylphenyl)-4-methoxypyridin-3-yl]methyl}-2-phenylethanamine | H |  |  | H | 1.12 | 442.3 | 443.4 |
| 1068 | N-{[6-(2,6-diethylphenyl)-4-methoxypyridin-3-yl]methyl}-N-(2-phenylethyl)pentan-1-amine | H |  |  | H | 1.14 | 444.3 | 445.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1069 | N-(cyclopentylmethyl)-N-{[6-(2,6-diethylphenyl)-4-methoxypyridin-3-yl]methyl}-2-phenylethanamine | H |  | 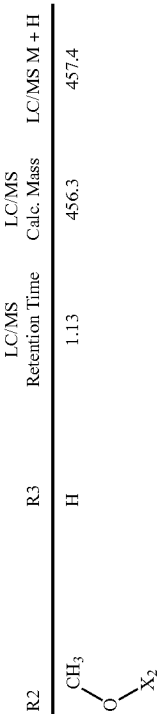 | H | 1.13 | 456.3 | 457.4 |
| 1070 | N-{[6-(2,6-diethylphenyl)-4-methoxypyridin-3-yl]methyl}-N-(2-phenylethyl)hexan-1-amine | H |  |  | H | 1.16 | 458.3 | 459.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1071 | N-(cyclohexylmethyl)-N-{[6-(2,6-diethylphenyl)-4-methoxypyridin-3-yl]methyl}-2-phenylethanamine | H |  | 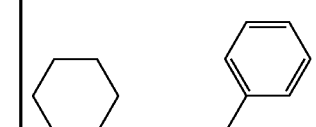 | H | 1.16 | 470.3 | 471.4 |
| 1072 | N-{[6-(2,6-diethylphenyl)-4-methoxypyridin-3-yl]methyl}-N-(2-phenylethyl)heptan-1-amine | H | 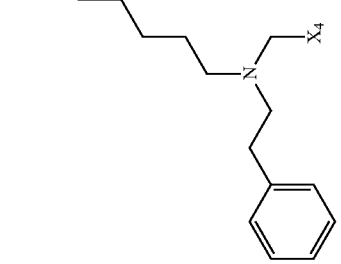 |  | H | 1.18 | 472.3 | 473.4 |

TABLE 3-continued
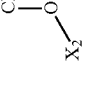
| Cpd # | NAME | R1 | B | R2 | R3 | LC/MS Retention Time | LC/MS Calc. Mass | LC/MS M + H |
|---|---|---|---|---|---|---|---|---|
| 1073 | 2-cyclohexyl-N-{[6-(2,6-diethylphenyl)-4-methoxypyridin-3-yl]methyl}-N-(2-phenylethyl)ethanamine | H |  |  | H | 1.18 | 484.3 | 485.5 |
| 1074 | N-{[6-(2,6-diethylphenyl)-4-methoxypyridin-3-yl]methyl}-N-(2-methylbenzyl)-2-phenylethanamine | H |  |  | H | 1.17 | 478.3 | 479.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1075 | N-{[6-(2,6-diethylphenyl)-4-methoxypyridin-3-yl]methyl}-N-(2-fluorobenzyl)-2-phenylethanamine | H | 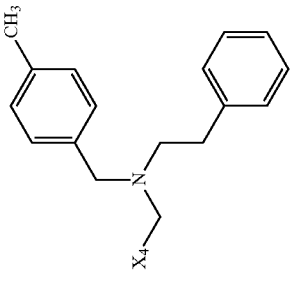 | 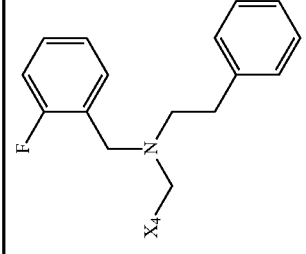 | H | 1.15 | 482.3 | 483.4 |
| 1076 | N-{[6-(2,6-diethylphenyl)-4-methoxypyridin-3-yl]methyl}-N-(4-methylbenzyl)-2-phenylethanamine | H |  |  | H | 1.15 | 478.3 | 479.4 |

TABLE 3-continued
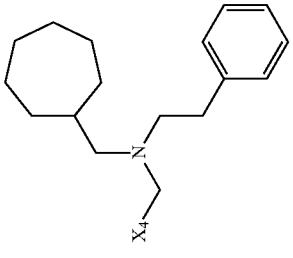
| Cpd # | NAME | R1 | B | R2 | R3 | LC/MS Retention Time | LC/MS Calc. Mass | LC/MS M + H |
|---|---|---|---|---|---|---|---|---|
| 1077 | N-(cycloheptylmethyl)-N-{[6-(2,6-diethylphenyl)-4-methoxypyridin-3-yl]methyl}-2-phenylethanamine | H |  | 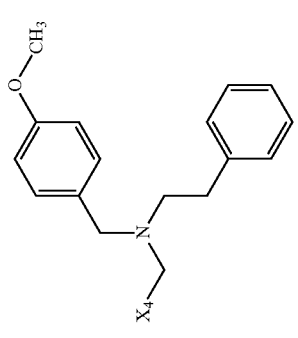 | H | 1.17 | 484.3 | 485.5 |
| 1078 | N-{[6-(2,6-diethylphenyl)-4-methoxypyridin-3-yl]methyl}-N-(4-methoxybenzyl)-2-phenylethanamine | H |  | H₃C-O-X₂ | H | 1.13 | 494.3 | 495.4 |

TABLE 3-continued
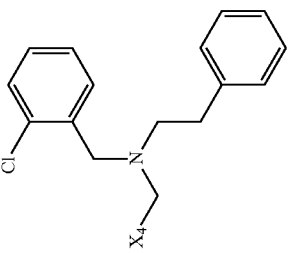
| Cpd # | NAME | R1 | B | R2 | R3 | LC/MS Retention Time | LC/MS Calc. Mass | LC/MS M + H |
|---|---|---|---|---|---|---|---|---|
| 1079 | N-(2-chlorobenzyl)-N-{[6-(2,6-diethylphenyl)-4-methoxypyridin-3-yl]methyl}-2-phenylethanamine | H |  | 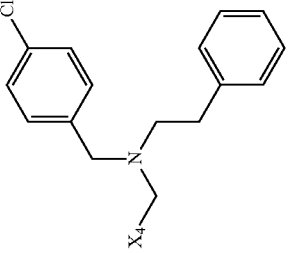 | H | 1.18 | 498.2 | 499.4 |
| 1080 | N-(4-chlorobenzyl)-N-{[6-(2,6-diethylphenyl)-4-methoxypyridin-3-yl]methyl}-2-phenylethanamine | H |  | 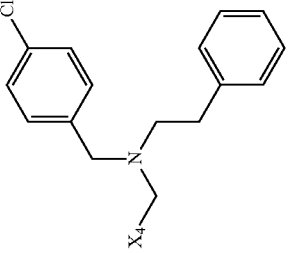 | H | 1.18 | 498.2 | 499.4 |

TABLE 3-continued
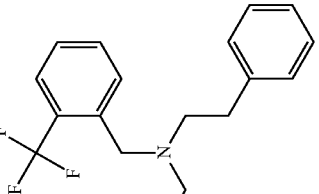
| Cpd # | NAME | R1 | B | R2 | R3 | LC/MS Retention Time | LC/MS Calc. Mass | LC/MS M + H |
|---|---|---|---|---|---|---|---|---|
| 1081 | N-{[6-(2,6-diethylphenyl)-4-methoxypyridin-3-yl]methyl}-2-phenyl-N-[2-(trifluoromethyl)benzyl]ethanamine | H |  | H₃C-O-X₂ | H | 1.22 | 532.3 | 533.4 |
| 1082 | 2-(2,6-diethylphenyl)-4-methoxy-5-[(2-phenylpiperidin-1-yl)methyl]pyridine | H |  | H₃C-O-X₂ | H | 1.06 | 414.3 | 415.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1083 | 1-[[6-(2,6-diethylphenyl)-4-methoxypyridin-3-yl]methyl]-2-phenylazepane | H | (2-phenylazepane-N-CH2-X4) | X2-O-CH3 | H | 1.07 | 428.3 | 429.4 |
| 1084 | N-(2-chlorobenzyl)-N-{[6-(2,6-diethylphenyl)-4-methoxypyridin-3-yl]methyl}-N-methylamine | H | (2-chlorobenzyl-N(CH3)-CH2-X4) | X2-O-CH3 | H | 1.08 | 408.2 | 409.3 |
| 1085 | 1-[6-(2,6-diethylphenyl)-4-methoxypyridin-3-yl]-N-methyl-N-[2-(trifluoromethyl)benzyl]methanamine | H | (2-trifluoromethylbenzyl-N(CH3)-CH2-X4) | X2-O-CH3 | H | 1.12 | 442.2 | 443.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1086 | N-benzyl-N-{[6-(2,6-diethylphenyl)-4-methoxypyridin-3-yl]methyl}-3-phenylbutan-1-amine | H | | | H | 1.15 | 492.3 | 493.4 |
| 1087 | N-benzyl-2-(4-chlorophenyl)-N-{[6-(2,6-diethylphenyl)-4-methoxypyridin-3-yl]methyl}ethanamine | H | | | H | 1.17 | 498.2 | 499.4 |

TABLE 3-continued
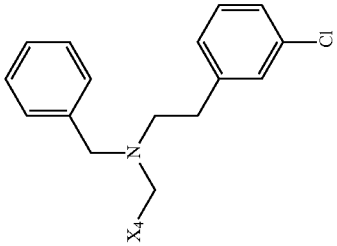
| Cpd # | NAME | R1 | B | R2 | R3 | LC/MS Retention Time | LC/MS Calc. Mass | LC/MS M + H |
|---|---|---|---|---|---|---|---|---|
| 1088 | N-benzyl-2-(3-chlorophenyl)-N-{[6-(2,6-diethylphenyl)-4-methoxypyridin-3-yl]methyl}ethanamine | H |  | 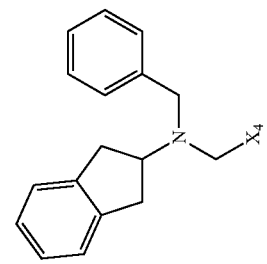 | H | 1.17 | 498.2 | 499.4 |
| 1089 | N-benzyl-N-{[6-(2,6-diethylphenyl)-4-methoxypyridin-3-yl]methyl}indan-2-amine | H | 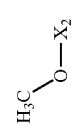 | H₃C—O—X₂ | H | 1.14 | 476.3 | 477.4 |

TABLE 3-continued
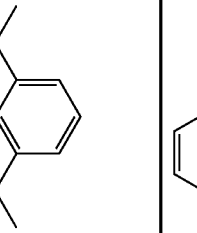
| Cpd # | NAME | R1 | B | R2 | R3 | LC/MS Retention Time | LC/MS Calc. Mass | LC/MS M + H |
|---|---|---|---|---|---|---|---|---|
| 1090 | N-benzyl-N-{[6-(2,6-diethylphenyl)-4-methoxypyridin-3-yl]methyl}indan-1-amine | H | 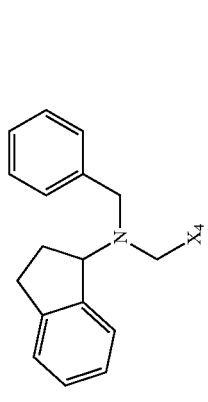 | H₃C—O—X₂ | H | 1.18 | 476.3 | 477.4 |
| 1091 | N-benzyl-N-{[6-(2,6-diethylphenyl)-4-methoxypyridin-3-yl]methyl}-2-(3-fluorophenyl)ethanamine | H | 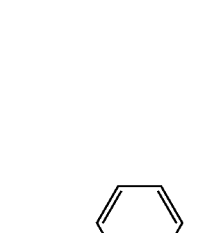 | X₂—O—CH₃ (H₃C—O—X₂) | H | 1.14 | 482.3 | 483.4 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1092 | N-benzyl-N-{[6-(2,6-diethylphenyl)-4-methoxypyridin-3-yl]methyl}-2-(4-fluorophenyl)ethanamine | H | 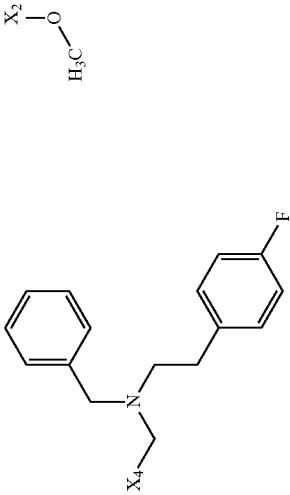 |  | H | 1.14 | 482.3 | 483.4 |
| 1093 | N-benzyl-N-{[6-(2,6-diethylphenyl)-4-methoxypyridin-3-yl]methyl}-2-(4-methoxyphenyl)ethanamine | H | 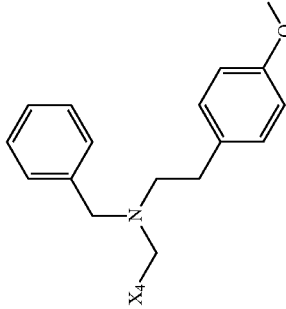 |  | H | 1.13 | 494.3 | 495.4 |

TABLE 3-continued
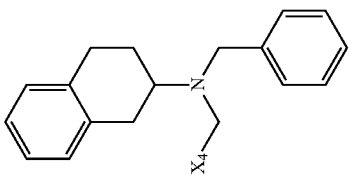
| Cpd # | NAME | R1 | B | R2 | R3 | LC/MS Retention Time | LC/MS Calc. Mass | LC/MS M + H |
|---|---|---|---|---|---|---|---|---|
| 1094 | N-benzyl-N-{[6-(2,6-diethylphenyl)-4-methoxypyridin-3-yl]methyl}-1,2,3,4-tetrahydronaphthalen-2-amine | H | 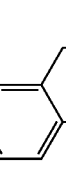 | 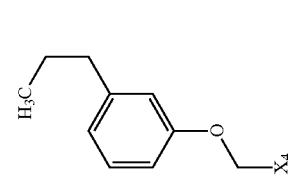 | H | 1.15 | 490.3 | 491.4 |
| 1095 | 2-(2,6-diethylphenyl)-4-methoxy-3-methyl-5-[(3-propylphenoxy)methyl]pyridine | H | 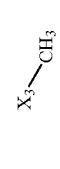 | X2—O—CH3 | X3—CH3 | 1.24 | 403.3 | 404.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1096 | 6-(2,6-diethylphenyl)-4-isopropoxy-2-methyl-3-(phenoxymethyl)pyridine |  | 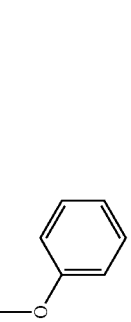 | 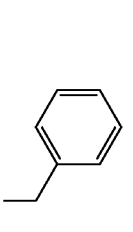 | H | 1.16 | 389.2 | 390.3 |
| 1097 | 6-(2,6-diethylphenyl)-4-isopropoxy-2-methyl-3-[(4-propylphenoxy)methyl]pyridine |  | 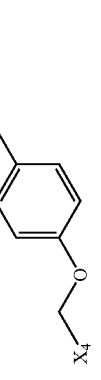 |  | H | 1.22 | 431.3 | 432.3 |
| 1098 | 3-[(4-butylphenoxy)methyl]-6-(2,6-diethylphenyl)-4-isopropoxy-2-methylpyridine |  | 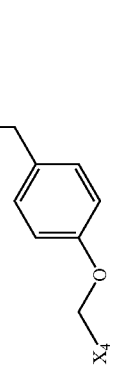 |  | H | 1.24 | 445.3 | 446.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1099 | 3-[(4-sec-butylphenoxy)methyl]-6-(2,6-diethylphenyl)-4-isopropoxy-2-methylpyridine | | | | H | 1.24 | 445.3 | 446.3 |
| 1100 | 3-[(4-tert-butylphenoxy)methyl]-6-(2,6-diethylphenyl)-4-isopropoxy-2-methylpyridine | | | | H | 1.23 | 445.3 | 446.3 |
| 1101 | 3-[(4-benzylphenoxy)methyl]-6-(2,6-diethylphenyl)-4-isopropoxy-2-methylpyridine | | | | H | 1.23 | 479.3 | 480.4 |

TABLE 3-continued
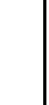
| Cpd # | NAME | R1 | B | R2 | R3 | LC/MS Retention Time | LC/MS Calc. Mass | LC/MS M + H |
|---|---|---|---|---|---|---|---|---|
| 1102 | 6-(2,6-diethylphenyl)-4-isopropoxy-2-methyl-3-{[4-(1-methyl-1-phenylethyl)phenoxy]methyl}pyridine | 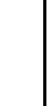 |  |  | H | 1.25 | 507.3 | 508.4 |
| 1103 | 6-(2,6-diethylphenyl)-4-isopropoxy-2-methyl-3-((3-propylphenoxy)methyl]pyridine |  |  |  | H | 1.22 | 431.3 | 432.3 |
| 1104 | 6-(2,6-diethylphenyl)-3-[(3,4-dimethylphenoxy)methyl]-4-isopropoxy-2-methylpyridine |  |  |  | H | 1.2 | 417.3 | 418.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1105 | 6-(2,6-diethylphenyl)-3-[(3,5-dimethylphenoxy)methyl]-4-isopropoxy-2-methylpyridine | X₁—CH₃ | X₄—O—(3,5-dimethylphenyl) | X₂—O—CH(CH₃)CH₃ | H | 1.2 | 417.3 | 418.3 |
| 1106 | 6-(2,6-diethylphenyl)-4-isopropoxy-2-methyl-3-[(3,4,5-trimethylphenoxy)methyl]pyridine | X₁—CH₃ | X₄—O—(3,4,5-trimethylphenyl) | X₂—O—CH(CH₃)CH₃ | H | 1.22 | 431.3 | 432.3 |
| 1107 | 6-(2,6-diethylphenyl)-4-isopropoxy-2-methyl-3-[(5,6,7,8-tetrahydronaphthalen-2-yloxy)methyl]pyridine | X₁—CH₃ | X₄—O—(5,6,7,8-tetrahydronaphthalen-2-yl) | X₂—O—CH(CH₃)CH₃ | H | 1.23 | 443.3 | 444.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1108 | 6-(2,6-diethylphenyl)-4-isopropoxy-2-methyl-3-[(2-naphthyloxy)methyl]pyridine | 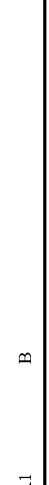 |  |  | H | 1.19 | 439.3 | 440.3 |
| 1109 | 6-(2,6-diethylphenyl)-4-isopropoxy-2-{[(7-methoxy-2-naphthyl)oxy]methyl}-2-methylpyridine | 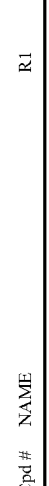 | 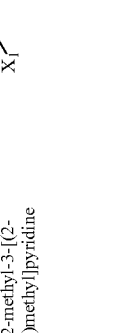 | 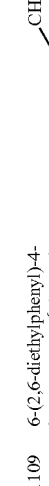 | H | 1.19 | 469.3 | 470.3 |
| 1110 | 6-(2,6-diethylphenyl)-3-[(3-ethoxyphenoxy)methyl]-4-isopropoxy-2-methylpyridine |  |  |  | H | 1.18 | 433.3 | 434.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1111 | 6-(2,6-diethylphenyl)-4-isopropoxy-2-methyl-3-[(4-propoxyphenoxy)methyl]pyridine | CH₃–X₁ | 4-propoxyphenoxymethyl (X₄–O–C₆H₄–O–CH₂CH₂CH₃) | X₂–O–CH(CH₃)₂ | H | 1.19 | 447.3 | 448.3 |
| 1112 | 6-(2,6-diethylphenyl)-4-isopropoxy-2-methyl-3-[(3-phenoxyphenoxy)methyl]pyridine | X₁–CH₃ | 3-phenoxyphenoxymethyl | X₂–O–CH(CH₃)₂ | H | 1.21 | 481.3 | 482.3 |
| 1113 | 6-(2,6-diethylphenyl)-4-isopropoxy-2-methyl-3-[(4-phenoxyphenoxy)methyl]pyridine | X₁–CH₃ | 4-phenoxyphenoxymethyl | X₂–O–CH(CH₃)₂ | H | 1.21 | 481.3 | 482.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1114 | 3-[(1,3-benzodioxol-5-yloxy)methyl]-6-(2,6-diethylphenyl)-4-isopropoxy-2-methylpyridine | H₃C—X₁ | benzodioxol-CH₂-O-X₄ | X₂—O—CH(CH₃)₂ | H | 1.14 | 433.2 | 434.3 |
| 1115 | 6-(2,6-diethylphenyl)-4-isopropoxy-2-methyl-3-{[4-(trifluoromethyl)phenoxy]methyl}pyridine | X₁—CH₃ | X₄-CH₂-O-(4-CF₃-phenyl) | X₂—O—CH(CH₃)₂ | H | 1.19 | 457.2 | 458.3 |
| 1116 | 6-(2,6-diethylphenyl)-3-{[4-fluoro-3-(trifluoromethyl)phenoxy]methyl}-4-isopropoxy-2-methylpyridine | X₁—CH₃ | X₄-CH₂-O-(4-F-3-CF₃-phenyl) | X₂—O—CH(CH₃)₂ | H | 1.19 | 475.2 | 476.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1117 | 6-(2,6-diethylphenyl)-3-{[2-fluoro-5-(trifluoromethyl)phenoxy]methyl}-4-isopropoxy-2-methylpyridine | X1—CH3 | X4—OC6H3(F)(CF3) | H3C-CH(O-X2)-CH3 | H | 1.19 | 475.2 | 476.3 |
| 1118 | 3-{[4-chloro-3-(trifluoromethyl)phenoxy]methyl}-6-(2,6-diethylphenyl)-4-isopropoxy-2-methylpyridine | X1—CH3 | X4—OC6H3(Cl)(CF3) | H3C-CH(O-X2)-CH3 | H | 1.21 | 491.2 | 492.3 |
| 1119 | 3-{[3,5-bis(trifluoromethyl)phenoxy]methyl}-6-(2,6-diethylphenyl)-4-isopropoxy-2-methylpyridine | X1—CH3 | X4—OC6H3(CF3)2 | H3C-CH(O-X2)-CH3 | H | 1.23 | 525.2 | 526.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1120 | 3-[(3-chloro-2-fluorophenoxy)methyl]-6-(2,6-diethylphenyl)-4-isopropoxy-2-methylpyridine | X1—CH3 | 3-chloro-2-fluorophenoxymethyl (X4-O-) | X2-O-CH(CH3)2 | H | 1.18 | 441.2 | 442.2 |
| 1121 | 3-[(4-chloro-2-fluorophenoxy)methyl]-6-(2,6-diethylphenyl)-4-isopropoxy-2-methylpyridine | X1—CH3 | 4-chloro-2-fluorophenoxymethyl (X4-O-) | X2-O-CH(CH3)2 | H | 1.19 | 441.2 | 442.2 |
| 1122 | 3-[(4-chloro-3-fluorophenoxy)methyl]-6-(2,6-diethylphenyl)-4-isopropoxy-2-methylpyridine | X1—CH3 | 4-chloro-3-fluorophenoxymethyl (X4-O-) | X2-O-CH(CH3)2 | H | 1.19 | 441.2 | 442.2 |
| 1123 | 3-[(4-chloro-3-methylphenoxy)methyl]-6-(2,6-diethylphenyl)-4-isopropoxy-2-methylpyridine | X1—CH3 | 4-chloro-3-methylphenoxymethyl (X4-O-) | X2-O-CH(CH3)2 | H | 1.2 | 437.2 | 438.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1124 | 3-[(4-chloro-3-ethylphenoxy)methyl]-6-(2,6-diethylphenyl)-4-isopropoxy-2-methylpyridine |  |  |  | H | 1.22 | 451.2 | 452.3 |
| 1125 | 3-[(4-chloro-3,5-dimethylphenyl)methyl]-6-(2,6-diethylphenyl)-4-isopropoxy-2-methylpyridine |  |  |  | H | 1.23 | 451.2 | 452.3 |
| 1126 | 3-[(1,1'-biphenyl-3-yloxy)methyl]-6-(2,6-diethylphenyl)-4-isopropoxy-2-methylpyridine |  |  |  | H | 1.15 | 465.3 | 370.3 |

TABLE 3-continued
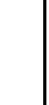
| Cpd # | NAME | R1 | B | R2 | R3 | LC/MS Retention Time | LC/MS Calc. Mass | LC/MS M + H |
|---|---|---|---|---|---|---|---|---|
| 1127 | 6-(2,6-diethylphenyl)-3-[(2,3-difluorophenoxy)methyl]-4-isopropoxy-2-methylpyridine | 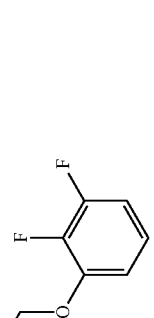 | 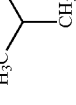 |  | H | 1.16 | 425.2 | 426.2 |
| 1128 | 6-(2,6-diethylphenyl)-3-[(2,4-difluorophenoxy)methyl]-4-isopropoxy-2-methylpyridine |  |  |  | H | 1.16 | 425.2 | 426.2 |
| 1129 | 6-(2,6-diethylphenyl)-4-[(2,5-difluorophenoxy)methyl]-4-isopropoxy-2-methylpyridine |  |  | | H | 1.15 | 425.2 | 426.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1130 | 6-(2,6-diethylphenyl)-3-[(2,6-difluorophenoxy)methyl]-4-isopropoxy-2-methylpyridine | X1—CH3 |  | 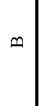 | H | 1.15 | 425.2 | 426.2 |
| 1131 | 6-(2,6-diethylphenyl)-3-[(3,4-difluorophenoxy)methyl]-4-isopropoxy-2-methylpyridine | X1—CH3 | 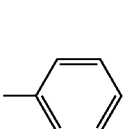 |  | H | 1.17 | 425.2 | 426.3 |
| 1132 | 6-(2,6-diethylphenyl)-3-[(3,5-difluorophenoxy)methyl]-4-isopropoxy-2-methylpyridine | X1—CH3 |  |  | H | 1.17 | 425.2 | 426.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1133 | 6-(2,6-diethylphenyl)-3-[(4-fluoro-3-methylphenoxy)methyl]-4-isopropoxy-2-methylpyridine | 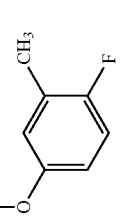 |  |  | H | 1.18 | 421.2 | 422.3 |
| 1134 | 6-(2,6-diethylphenyl)-3-[(2-fluoro-5-methylphenoxy)methyl]-4-isopropoxy-2-methylpyridine | 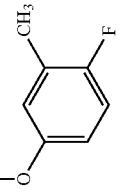 |  |  | H | 1.17 | 421.2 | 422.3 |
| 1135 | 2-(2,6-diethylphenyl)-4-methoxy-5-(phenoxymethyl)pyridine | H |  | | H | 1.11 | 347.2 | 348.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1136 | 2-(2,6-diethylphenyl)-4-methoxy-5-[(4-propylphenoxy)methyl]pyridine | H | 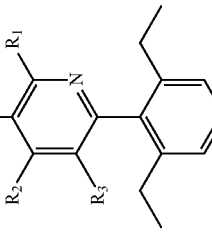 | 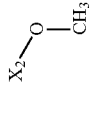 | H | 1.2 | 389.2 | 390.3 |
| 1137 | 5-[(4-butylphenoxy)methyl]-2-(2,6-diethylphenyl)-4-methoxypyridine | H | 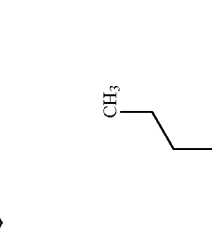 | 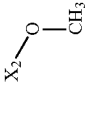 | H | 1.22 | 403.3 | 404.3 |
| 1138 | 5-[(4-sec-butylphenyl)methyl]-2-(2,6-diethylphenyl)-4-methoxypyridine | H | 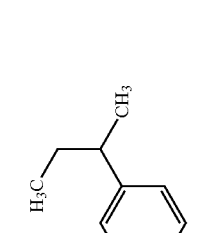 |  | H | 1.21 | 403.3 | 404.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1139 | 5-[(4-tert-butylphenoxy)methyl]-2-(2,6-diethylphenyl)-4-methoxypyridine | H | (4-tert-butylphenoxymethyl group, X4) | X2-OCH3 | H | 1.21 | 403.3 | 404.3 |
| 1140 | 5-[(4-benzylphenoxy)methyl]-2-(2,6-diethylphenyl)-4-methoxypyridine | H | (4-benzylphenoxymethyl group, X4) | X2-OCH3 | H | 1.2 | 437.2 | 438.3 |
| 1141 | 2-(2,6-diethylphenyl)-4-methoxy-5-[(3-propylphenoxy)methyl]pyridine | H | (3-propylphenoxymethyl group, X4) | X2-OCH3 | H | 1.19 | 389.2 | 390.3 |

TABLE 3-continued
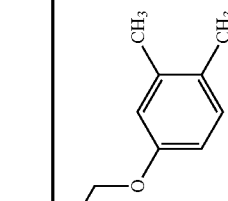
| Cpd # | NAME | R1 | B | R2 | R3 | LC/MS Retention Time | LC/MS Calc. Mass | LC/MS M + H |
|---|---|---|---|---|---|---|---|---|
| 1142 | 2-(2,6-diethylphenyl)-5-[(3,4-dimethylphenoxy)methyl]-4-methoxypyridine | H |  |  | H | 1.16 | 375.2 | 376.2 |
| 1143 | 2-(2,6-diethylphenyl)-5-[(3,5-dimethylphenoxy)methyl]-4-methoxypyridine | H | 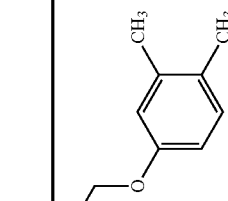 |  | H | 1.17 | 375.2 | 376.2 |
| 1144 | 2-(2,6-diethylphenyl)-4-methoxy-5-[(3,4,5-trimethylphenoxy)methyl]pyridine | H |  | 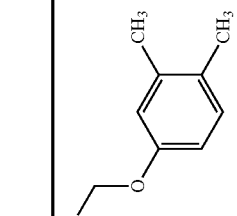 | H | 1.19 | 389.2 | 390.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1145 | 2-(2,6-diethylphenyl)-4-methoxy-5-[(5,6,7,8-tetrahydronaphthalen-2-yloxy)methyl]pyridine | H | | | H | 1.2 | 401.2 | 402.3 |
| 1146 | 2-(2,6-diethylphenyl)-4-methoxy-5-[(2-naphthyloxy)methyl]pyridine | H | | | H | 1.17 | 397.2 | 398.2 |
| 1147 | 2-(2,6-diethylphenyl)-4-methoxy-5-{[(7-methoxy-2-naphthyl)oxy]methyl}pyridine | H | | | H | 1.17 | 427.2 | 428.3 |

TABLE 3-continued
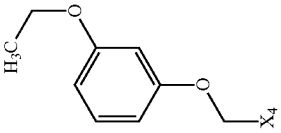
| Cpd # | NAME | R1 | B | R2 | R3 | LC/MS Retention Time | LC/MS Calc. Mass | LC/MS M + H |
|---|---|---|---|---|---|---|---|---|
| 1148 | 2-(2,6-diethylphenyl)-5-[(3-ethoxyphenoxy)methyl]-4-methoxypyridine | H |  | 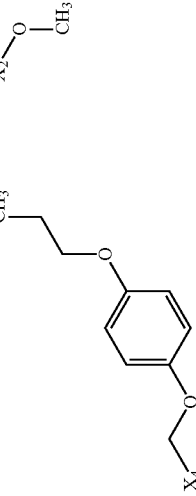 | H | 1.14 | 391.2 | 392.2 |
| 1149 | 2-(2,6-diethylphenyl)-4-methoxy-5-[(4-propoxyphenoxy)methyl]pyridine | H |  | 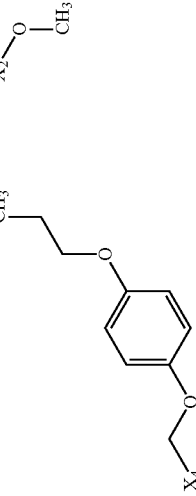 | H | 1.17 | 405.2 | 406.3 |

TABLE 3-continued
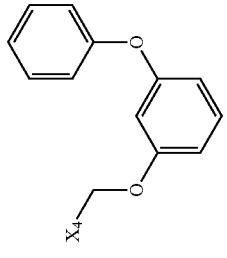
| Cpd # | NAME | R1 | B | R2 | R3 | LC/MS Retention Time | LC/MS Calc. Mass | LC/MS M + H |
|---|---|---|---|---|---|---|---|---|
| 1150 | 2-(2,6-diethylphenyl)-4-methoxy-5-[(3-phenoxyphenoxy)methyl]pyridine | H |  | 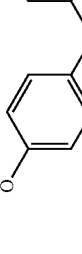 | H | 1.16 | 439.2 | 440.3 |
| 1151 | 2-(2,6-diethylphenyl)-4-methoxy-5-[(4-phenoxyphenoxy)methyl]pyridine | H |  | 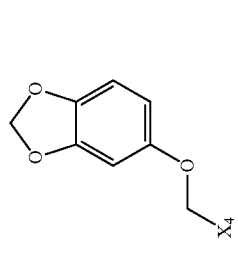 | H | 1.19 | 439.2 | 440.3 |
| 1152 | 5-[(1,3-benzodioxol-5-yloxy)methyl]-2-(2,6-diethylphenyl)-4-methoxypyridine | H |  | X₂—O—CH₃ | H | 1.1 | 391.2 | 392.2 |

TABLE 3-continued
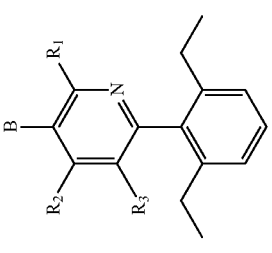
| Cpd # | NAME | R1 | B | R2 | R3 | LC/MS Retention Time | LC/MS Calc. Mass | LC/MS M + H |
|---|---|---|---|---|---|---|---|---|
| 1153 | 2-(2,6-diethylphenyl)-4-methoxy-5-{[4-(trifluoromethyl)phenoxy]methyl}pyridine | H |  | 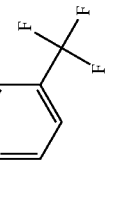 | H | 1.16 | 415.2 | 416.2 |
| 1154 | 2-(2,6-diethylphenyl)-5-{[4-fluoro-3-(trifluoromethyl)phenoxy]methyl}-4-methoxypyridine | H | 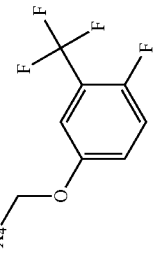 | 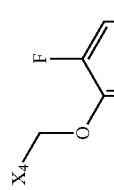 | H | 1.17 | 433.2 | 434.2 |
| 1155 | 2-(2,6-diethylphenyl)-5-{[2-fluoro-5-(trifluoromethyl)phenoxy]methyl}-4-methoxypyridine | H | 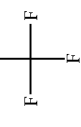 | H₃C-O-X₂ | H | 1.16 | 433.2 | 434.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1156 | 5-[(3-chloro-2-fluorophenoxy)methyl]-2-(2,6-diethylphenyl)-4-methoxypyridine | H | | | H | 1.15 | 399.1 | 400.2 |
| 1157 | 5-[(4-chloro-2-fluorophenoxy)methyl]-2-(2,6-diethylphenyl)-4-methoxypyridine | H | | | H | 1.15 | 399.1 | 400.2 |
| 1158 | 5-[(4-chloro-3-fluorophenoxy)methyl]-2-(2,6-diethylphenyl)-4-methoxypyridine | H | | | H | 1.17 | 399.1 | 400.2 |
| 1159 | 5-[(4-chloro-3-methylphenoxy)methyl]-2-(2,6-diethylphenyl)-4-methoxypyridine | H | | | H | 1.18 | 395.2 | 396.2 |

TABLE 3-continued
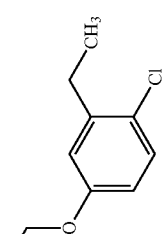
| Cpd # | NAME | R1 | B | R2 | R3 | LC/MS Retention Time | LC/MS Calc. Mass | LC/MS M + H |
|---|---|---|---|---|---|---|---|---|
| 1160 | 5-[(4-chloro-3-ethylphenoxy)methyl]-2-(2,6-diethylphenyl)-4-methoxypyridine | H | 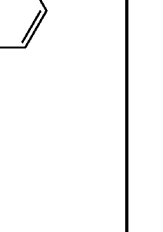 | 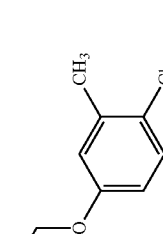 | H | 1.2 | 409.2 | 410.2 |
| 1161 | 5-[(4-chloro-3,5-dimethylphenoxy)methyl]-2-(2,6-diethylphenyl)-4-methoxypyridine | H | 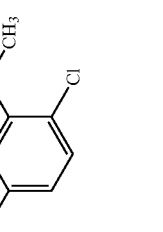 | 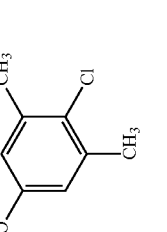 | H | 1.21 | 409.2 | 410.2 |
| 1162 | 5-[[(1,1'-biphenyl-3-yloxy)methyl]-2-(2,6-diethylphenyl)-4-methoxypyridine | H | 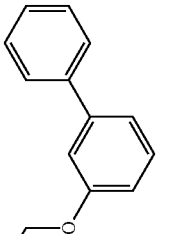 | 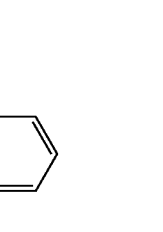 | H | 1.19 | 423.2 | 424.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1163 | 2-(2,6-diethylphenyl)-5-[(2,3-difluorophenoxy)methyl]-4-methoxypyridine | H | 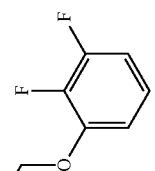 |  | H | 1.13 | 383.2 | 384.2 |
| 1164 | 2-(2,6-diethylphenyl)-5-[(2,4-difluorophenoxy)methyl]-4-methoxypyridine | H | 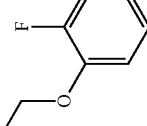 |  | H | 1.13 | 383.2 | 384.2 |
| 1165 | 2-(2,6-diethylphenyl)-5-[(2,5-difluorophenoxy)methyl]-4-methoxypyridine | H | 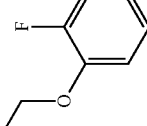 |  | H | 1.13 | 383.2 | 384.2 |

TABLE 3-continued
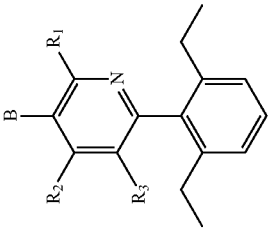
| Cpd # | NAME | R1 | B | R2 | R3 | LC/MS Retention Time | LC/MS Calc. Mass | LC/MS M + H |
|---|---|---|---|---|---|---|---|---|
| 1166 | 2-(2,6-diethylphenyl)-5-[(2-fluoro-5-methylphenoxy)methyl]-4-methoxypyridine | H |  |  | H | 1.15 | 379.2 | 380.2 |
| 1167 | 3-[(2,5-dichlorophenoxy)methyl]-6-(2,6-diethylphenyl)-4-isopropoxy-2-methylpyridine | 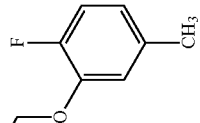 |  |  | H | 1.2 | 457.2 | 458.2 |
| 1168 | 3-[(2,6-dichlorophenyl)-4-isopropoxy-2-methylpyridine | 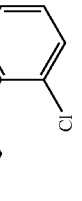 |  | | H | 1.17 | 457.2 | 458.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1169 | 3-[(2-chloro-4-methyl)phenoxy]methyl]-6-(2,6-diethyl)phenyl)-4-isopropoxy-2-methylpyridine | X₁—CH₃ | 2-chloro-4-methylphenoxymethyl (X₄—CH₂—O—Ar) | X₂—O—CH(CH₃)₂ | H | 1.19 | 437.2 | 438.3 |
| 1170 | 3-[(2-chloro-4-(trifluoromethyl)phenoxy]methyl]-6-(2,6-diethyl)phenyl)-4-isopropoxy-2-methylpyridine | X₁—CH₃ | 2-chloro-4-(trifluoromethyl)phenoxymethyl | X₂—O—CH(CH₃)₂ | H | 1.21 | 491.2 | 492.3 |
| 1171 | 6-(2,6-diethyl)phenyl)-4-isopropoxy-2-methyl-3-[(2-(trifluoromethyl)phenoxy]methyl]pyridine | X₁—CH₃ | 2-(trifluoromethyl)phenoxymethyl | X₂—O—CH(CH₃)₂ | H | 1.18 | 457.2 | 458.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1172 | 6-(2,6-diethylphenyl)-4-isopropoxy-3-[(2-methoxyphenoxy)methyl]-2-methylpyridine |  |  |  | H | 1.14 | 419.2 | 420.3 |
| 1173 | 6-(2,6-diethylphenyl)-4-isopropoxy-3-[(2-isopropoxyphenoxy)methyl]-2-methylpyridine |  |  |  | H | 1.18 | 447.3 | 448.3 |
| 1174 | 6-(2,6-diethylphenyl)-3-{[(2,2-dimethyl-2,3-dihydro-1-benzofuran-7-yl)oxy]methyl}-4-isopropoxy-2-methylpyridine |  |  | | H | 1.18 | 459.3 | 460.3 |

TABLE 3-continued
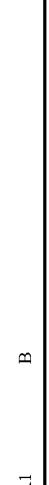
| Cpd # | NAME | R1 | B | R2 | R3 | LC/MS Retention Time | LC/MS Calc. Mass | LC/MS M + H |
|---|---|---|---|---|---|---|---|---|
| 1175 | 6-(2,6-diethylphenyl)-3-[(4-fluoro-2-methoxyphenoxy)methyl]-4-isopropoxy-2-methylpyridine | 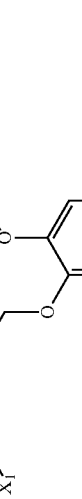 |  |  | H | 1.14 | 437.2 | 438.3 |
| 1176 | 6-(2,6-diethylphenyl)-4-isopropoxy-3-[(2-methoxy-4-methylphenoxy)methyl]-2-methylpyridine | 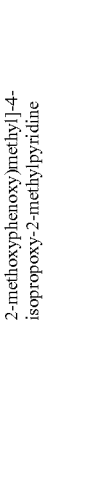 |  |  | H | 1.16 | 433.3 | 434.3 |
| 1177 | 6-(2,6-diethylphenyl)-4-isopropoxy-3-[(2-methoxy-4-propylphenoxy)methyl]-2-methylpyridine | 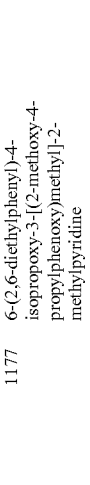 |  | | H | 1.21 | 461.3 | 462.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1178 | 6-(2,6-diethylphenyl)-4-isopropoxy-3-[(2-methoxy-5-methylphenoxy)methyl]-2-methylpyridine | X1—CH3 |  |  | H | 1.16 | 433.3 | 434.3 |
| 1179 | 6-(2,6-diethylphenyl)-3-[(2,3-dimethoxyphenoxy)methyl]-4-isopropoxy-2-methylpyridine | X1—CH3 |  |  | H | 1.14 | 449.3 | 450.3 |
| 1180 | 6-(2,6-diethylphenyl)-3-[(4-fluoro-2-methylphenoxy)methyl]-4-isopropoxy-2-methylpyridine | X1—CH3 | 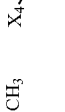 |  | H | 1.18 | 421.2 | 422.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1181 | 3-[(2-chloro-6-fluorophenoxy)methyl]-6-(2,6-diethylphenyl)-4-isopropoxy-2-methylpyridine |  | 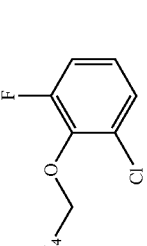 | 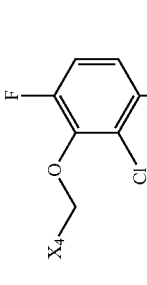 | H | 1.16 | 441.2 | 442.2 |
| 1182 | 3-[(2-chloro-6-fluoro-3-methylphenoxy)methyl]-6-(2,6-diethylphenyl)-4-isopropoxy-2-methylpyridine |  | 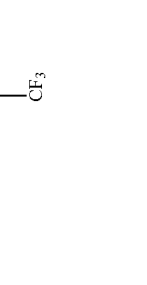 |  | H | 1.19 | 455.2 | 456.3 |
| 1183 | 3-[(2-chloro-6-methylphenoxy)methyl]-6-(2,6-diethylphenyl)-4-isopropoxy-2-methylpyridine | 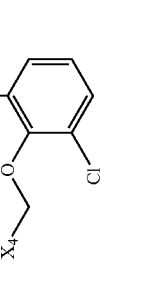 |  | | H | 1.18 | 437.2 | 438.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1184 | 3-[(2-chloro-4,5-dimethylphenoxy)methyl]-6-(2,6-diethylphenyl)-4-isopropoxy-2-methylpyridine |  |  |  | H | 1.2 | 451.2 | 452.3 |
| 1185 | 6-(2,6-diethylphenyl)-4-isopropoxy-2-methyl-3-{[2-(methylthio)phenoxy]methyl}pyridine |  |  |  | H | 1.16 | 435.2 | 436.3 |
| 1186 | 6-(2,6-diethylphenyl)-4-isopropoxy-2-methyl-3-[(1-naphthyloxy)methyl]pyridine |  |  |  | H | 1.2 | 439.3 | 440.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1187 | 3-{[(4-chloro-1-naphthyl)oxy]methyl}-6-(2,6-diethylphenyl)-4-isopropoxy-2-methylpyridine |  |  |  | H | 1.23 | 473.2 | 474.3 |
| 1188 | 6-(2,6-diethylphenyl)-4-isopropoxy-3-{[(4-methoxy-1-naphthyl)oxy]methyl}-2-methylpyridine |  |  |  | H | 1.21 | 469.3 | 470.3 |
| 1189 | 6-(2,6-diethylphenyl)-4-isopropoxy-2-methyl-3-[(2-methylphenoxy)methyl]pyridine |  |  |  | H | 1.17 | 403.3 | 404.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1190 | 6-(2,6-diethylphenyl)-3-[(2,4-dimethylphenoxy)methyl]-4-isopropoxy-2-methylpyridine | X₁—CH₃ | 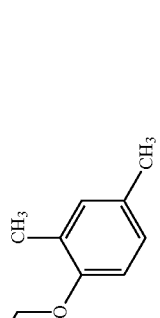 |  | H | 1.19 | 417.3 | 418.3 |
| 1191 | 6-(2,6-diethylphenyl)-3-[(2,5-dimethylphenoxy)methyl]-4-isopropoxy-2-methylpyridine | X₁—CH₃ | 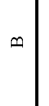 |  | H | 1.2 | 417.3 | 418.3 |
| 1192 | 6-(2,6-diethylphenyl)-4-isopropoxy-3-[(5-isopropyl-2-methylphenoxy)methyl]-2-methylpyridine | X₁—CH₃ |  |  | H | 1.23 | 445.3 | 446.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1193 | 6-(2,6-diethylphenyl)-4-isopropoxy-2-methyl-3-[(2,3,5-trimethylphenoxy)methyl]pyridine |  | 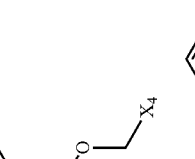 |  | H | 1.21 | 431.3 | 432.3 |
| 1194 | 6-(2,6-diethylphenyl)-4-isopropoxy-2-methyl-3-[(2-propylphenoxy)methyl]pyridine |  |  | 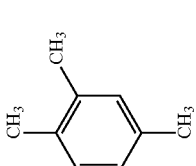 | H | 1.21 | 431.3 | 432.3 |
| 1195 | 3-[(2-benzylphenoxy)methyl]-6-(2,6-diethylphenyl)-4-isopropoxy-2-methylpyridine | 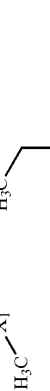 | 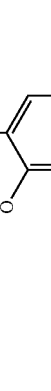 |  | H | 1.23 | 479.3 | 480.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1196 | 6-(2,6-diethylphenyl)-4-isopropoxy-2-methyl-3-[(5,6,7,8-tetrahydronaphthalen-1-yloxy)methyl]pyridine |  | 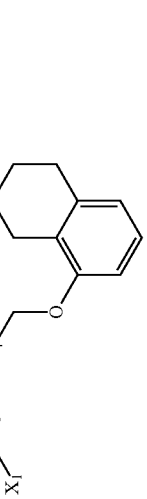 | 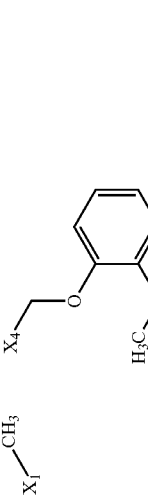 | H | 1.22 | 443.3 | 444.3 |
| 1197 | 6-(2,6-diethylphenyl)-4-isopropoxy-3-[(2-isopropylphenoxy)methyl]-2-methylpyridine |  | 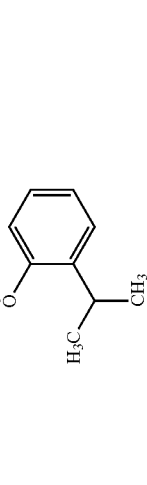 | 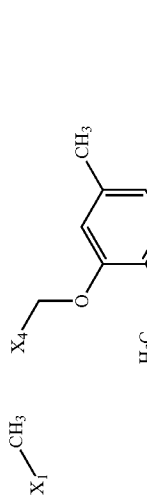 | H | 1.21 | 431.3 | 432.3 |
| 1198 | 6-(2,6-diethylphenyl)-4-isopropoxy-3-[(2-isopropyl-5-methylphenoxy)methyl]-2-methylpyridine |  | 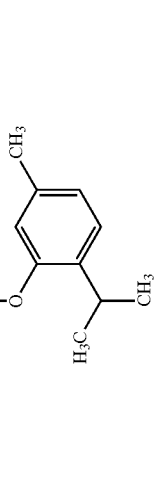 |  | H | 1.23 | 445.3 | 446.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1199 | 3-[(4-chloro-2-isopropyl-5-methyl)phenoxy)methyl]-6-(2,6-diethylphenyl)-4-isopropoxy-2-methylpyridine | X₁—CH₃ | (4-chloro-2-isopropyl-5-methylphenoxymethyl group) | X₂—O—CH(CH₃)₂ | H | 1.25 | 479.3 | 480.3 |
| 1200 | 3-[(2-cyclopentylphenoxy)methyl]-6-(2,6-diethylphenyl)-4-isopropoxy-2-methylpyridine | X₁—CH₃ | (2-cyclopentylphenoxymethyl group) | X₂—O—CH(CH₃)₂ | H | 1.23 | 457.3 | 458.3 |
| 1201 | 6-(2,6-diethylphenyl)-4-isopropoxy-2-methyl-3-[(2,3,6-trimethylphenoxy)methyl]pyridine | X₁—CH₃ | (2,3,6-trimethylphenoxymethyl group) | X₂—O—CH(CH₃)₂ | H | 1.2 | 431.3 | 432.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1202 | 6-(2,6-diethylphenyl)-4-isopropoxy-2-methyl-3-{[(2-methyl-1-naphthyl)oxy]methyl}pyridine | X₁—CH₃ | 2-methylnaphthyl-1-oxy-CH₂-X₄ | X₂-O-CH(CH₃)₂ | H | 1.15 | 453.3 | 454.3 |
| 1203 | 3-{[6-(2,6-diethylphenyl)-4-isopropoxy-2-methylpyridin-3-yl]methoxy}-N,N-dimethylaniline | X₁—CH₃ | 3-(N,N-dimethylamino)phenyl-O-CH₂-X₄ | X₂-O-CH(CH₃)₂ | H | 1.1 | 432.3 | 433.3 |
| 1204 | 4-(3-{[6-(2,6-diethylphenyl)-4-isopropoxy-2-methylpyridin-3-yl]methoxy}phenyl)morpholine | X₁—CH₃ | 3-(morpholin-4-yl)phenyl-O-CH₂-X₄ | X₂-O-CH(CH₃)₂ | H | 1.14 | 474.3 | 475.4 |

TABLE 3-continued
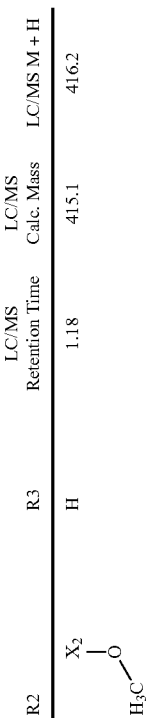
| Cpd # | NAME | R1 | B | R2 | R3 | LC/MS Retention Time | LC/MS Calc. Mass | LC/MS M + H |
|---|---|---|---|---|---|---|---|---|
| 1205 | 5-[(2,5-dichlorophenoxy)methyl]-2-(2,6-diethylphenyl)-4-methoxypyridine | H |  |  | H | 1.18 | 415.1 | 416.2 |
| 1206 | 5-[(2,6-dichlorophenoxy)methyl]-2-(2,6-diethylphenyl)-4-methoxypyridine | H | 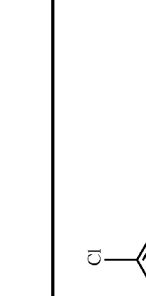 |  | H | 1.16 | 415.1 | 416.2 |
| 1207 | 5-[(2-chloro-4-methyl)phenyl]-2-(2,6-diethylphenyl)-4-methoxypyridine | H |  | 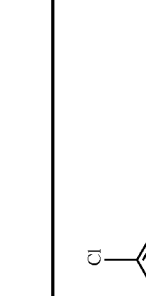 | H | 1.17 | 395.2 | 396.2 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1208 | 5-[(2-chloro-4-methoxyphenoxy)methyl]-2-(2,6-diethylphenyl)-4-methoxypyridine | H |  | 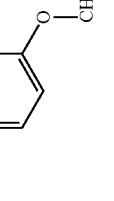 | H | 1.14 | 411.2 | 412.2 |
| 1209 | 2-(2,6-diethylphenyl)-5-[(2-isopropoxyphenoxy)methyl]-4-methoxypyridine | H |  | 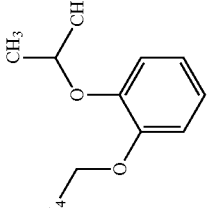 | H | 1.15 | 405.2 | 406.3 |
| 1210 | 2-(2,6-diethylphenyl)-5-{[(2,2-dimethyl-2,3-dihydro-1-benzofuran-7-yl)oxy]methyl}-4-methoxypyridine | H |  | 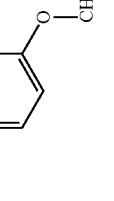 | H | 1.15 | 417.2 | 418.3 |

TABLE 3-continued
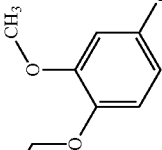
| Cpd # | NAME | R1 | B | R2 | R3 | LC/MS Retention Time | LC/MS Calc. Mass | LC/MS M + H |
|---|---|---|---|---|---|---|---|---|
| 1211 | 2-(2,6-diethylphenyl)-4-methoxy-5-[(2-methoxy-4-methylphenoxy)methyl]pyridine | H | 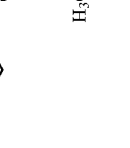 | 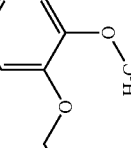 | H | 1.13 | 391.2 | 392.2 |
| 1212 | 2-(2,6-diethylphenyl)-4-methoxy-5-[(2-methoxy-4-propylphenoxy)methyl]pyridine | H | 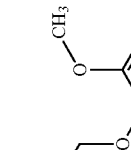 | 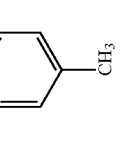 | H | 1.18 | 419.2 | 420.3 |
| 1213 | 2-(2,6-diethylphenyl)-4-methoxy-5-[(2-methoxy-5-methylphenoxy)methyl]pyridine | H |  | 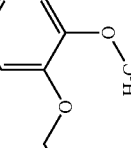 | H | 1.13 | 391.2 | 392.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1214 | 2-(2,6-diethylphenyl)-5-[(4-fluoro-2-methylphenoxy)methyl]-4-methoxypyridine | H | X4–O–(2-methyl-4-fluorophenyl) | X2–O–CH3 | H | 1.15 | 379.2 | 380.2 |
| 1215 | 5-[(2,6-chloro-6-fluorophenoxy)methyl]-2-(2,6-diethylphenyl)-4-methoxypyridine | H | X4–O–(2-chloro-6-fluorophenyl) | X2–O–CH3 | H | 1.14 | 399.1 | 400.2 |
| 1216 | 5-[(2-chloro-6-fluoro-2-methylphenoxy)methyl]-2-(2,6-diethylphenyl)-4-methoxypyridine | H | X4–O–(2-chloro-3-methyl-6-fluorophenyl) | X2–O–CH3 | H | 1.16 | 413.2 | 414.2 |
| 1217 | 5-[(2-chloro-6-methylphenoxy)methyl]-2-(2,6-diethylphenyl)-4-methoxypyridine | H | X4–O–(2-chloro-6-methylphenyl) | X2–O–CH3 | H | 1.16 | 395.2 | 396.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1218 | 5-[(2-chloro-4,5-dimethylphenoxy)methyl]-2-(2,6-diethylphenyl)-4-methoxypyridine | H | X4–O–CH2–(2-Cl-4,5-diMe-phenyl) | X2–O–CH3 | H | 1.19 | 409.2 | 410.2 |
| 1219 | 2-(2,6-diethylphenyl)-4-methoxy-5-{[2-(methylthio)phenoxy]methyl}pyridine | H | X4–O–CH2–(2-SMe-phenyl) | X2–O–CH3 | H | 1.14 | 393.2 | 394.2 |
| 1220 | 2-(2,6-diethylphenyl)-4-methoxy-5-[(1-naphthyloxy)methyl]pyridine | H | X4–O–CH2–(1-naphthyl) | X2–O–CH3 | H | 1.17 | 397.2 | 398.2 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1221 | 5-[[(4-chloro-1-napthyl)oxy]methyl]-2-(2,6-diethylphenyl)-4-methoxypyridine | H | (4-chloro-1-naphthyloxymethyl) | (methoxy via X2) | H | 1.22 | 431.2 | 432.2 |
| 1222 | 2-(2,6-diethylphenyl)-4-methoxy-5-[(2-methylphenoxy)methyl]pyridine | H | (2-methylphenoxymethyl) | (methoxy via X2) | H | 1.14 | 361.2 | 362.2 |
| 1223 | 2-(2,6-diethylphenyl)-5-[(2,4-dimethylphenoxy)methyl]-4-methoxypyridine | H | (2,4-dimethylphenoxymethyl) | (methoxy via X2) | H | 1.18 | 375.2 | 376.2 |

TABLE 3-continued
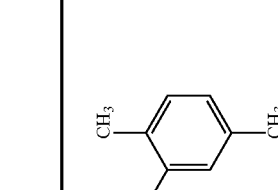
| Cpd # | NAME | R1 | B | R2 | R3 | LC/MS Retention Time | LC/MS Calc. Mass | LC/MS M + H |
|---|---|---|---|---|---|---|---|---|
| 1224 | 2-(2,6-diethylphenyl)-5-[(2,5-dimethylphenoxy)methyl]-4-methoxypyridine | H |  | 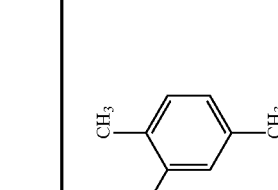 | H | 1.17 | 375.2 | 376.2 |
| 1225 | 2-(2,6-diethylphenyl)-5-[(5-isopropyl-2-methylphenoxy)methyl]-4-methoxypyridine | H |  | 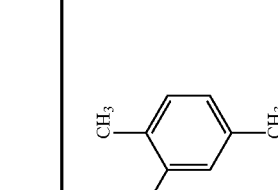 | H | 1.21 | 403.3 | 404.3 |
| 1226 | 2-(2,6-diethylphenyl)-4-methoxy-5-[(2,3,5-trimethylphenoxy)methyl]pyridine | H |  | 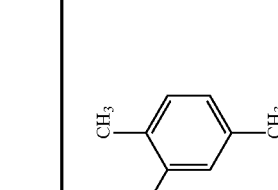 | H | 1.2 | 389.2 | 390.2 |

TABLE 3-continued
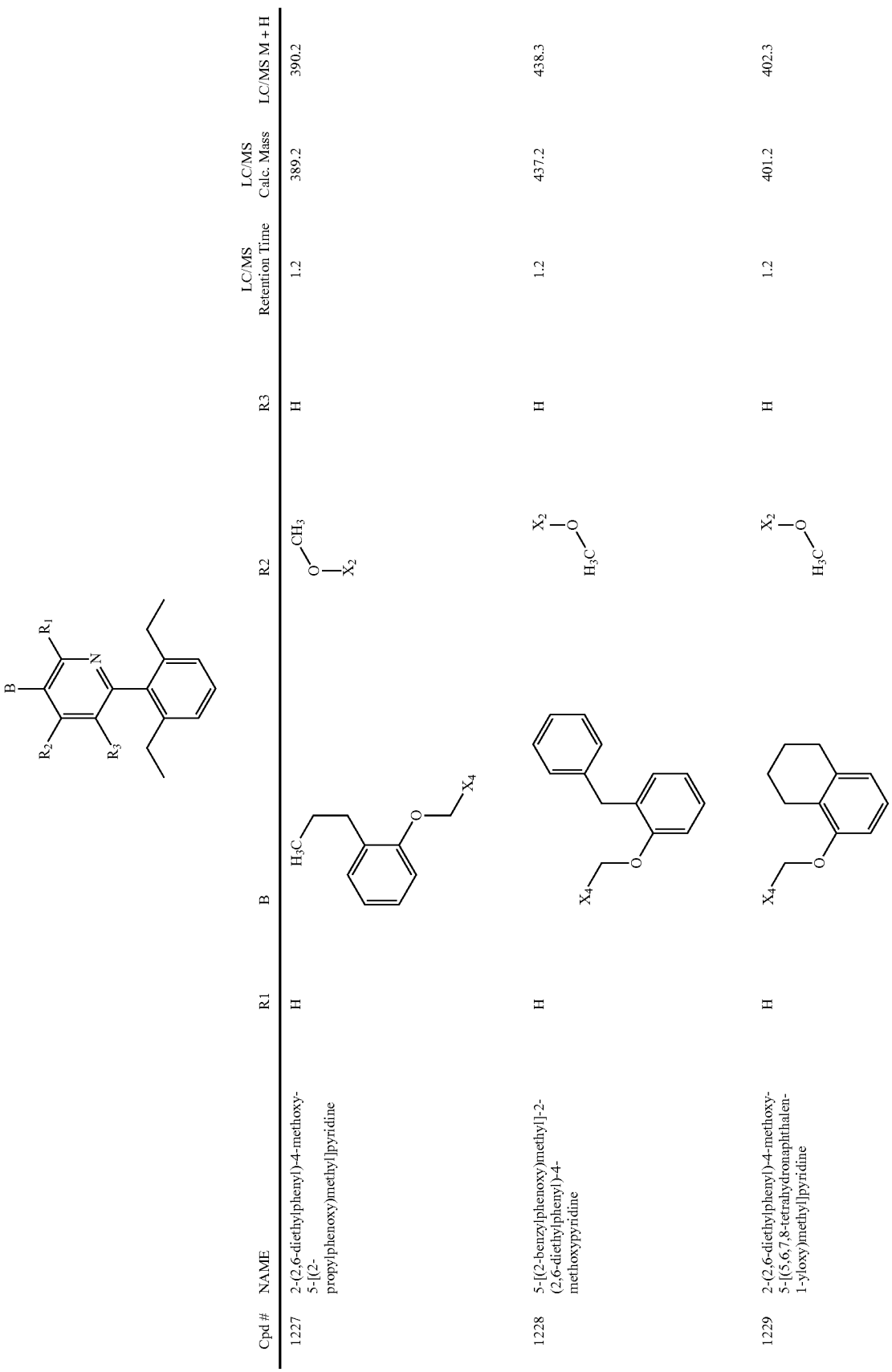
| Cpd # | NAME | R1 | B | R2 | R3 | LC/MS Retention Time | LC/MS Calc. Mass | LC/MS M + H |
|---|---|---|---|---|---|---|---|---|
| 1227 | 2-(2,6-diethylphenyl)-4-methoxy-5-[(2-propylphenoxy)methyl]pyridine | H | | | H | 1.2 | 389.2 | 390.2 |
| 1228 | 5-[(2-benzylphenoxy)methyl]-2-(2,6-diethylphenyl)-4-methoxypyridine | H | | | H | 1.2 | 437.2 | 438.3 |
| 1229 | 2-(2,6-diethylphenyl)-4-methoxy-5-[(5,6,7,8-tetrahydronaphthalen-1-yloxy)methyl]pyridine | H | | | H | 1.2 | 401.2 | 402.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1230 | 2-(2,6-diethylphenyl)-5-[(2-isopropylphenoxy)methyl]-4-methoxypyridine | H |  | 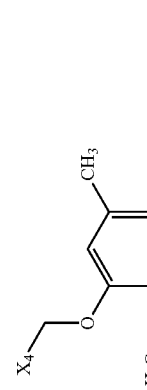 | H | 1.19 | 389.2 | 390.2 |
| 1231 | 2-(2,6-diethylphenyl)-5-[(2-isopropyl-5-methylphenoxy)methyl]-4-methoxypyridine | H |  |  | H | 1.21 | 403.3 | 404.3 |
| 1232 | 5-[(4-chloro-2-isopropyl-5-methylphenoxy)methyl]-2-(2,6-diethylphenyl)-4-methoxypyridine | H |  |  | H | 1.25 | 437.2 | 438.3 |

TABLE 3-continued
| Cpd # | NAME | R1 | B | R2 | R3 | LC/MS Retention Time | LC/MS Calc. Mass | LC/MS M + H |
|---|---|---|---|---|---|---|---|---|
| 1233 | 5-[[2-cyclopentylphenoxy)methyl]-2-(2,6-diethylphenyl)-4-methoxypyridine | H | 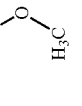 |  | H | 1.22 | 415.3 | 416.3 |
| 1234 | 2-(2,6-diethylphenyl)-4-methoxy-5-[(2,3,6-trimethylphenoxy)methyl]pyridine | H |  |  | H | 1.19 | 389.2 | 390.3 |

TABLE 3-continued

| Cpd # | NAME | R1 | B | R2 | R3 | LC/MS Retention Time | LC/MS Calc. Mass | LC/MS M + H |
|---|---|---|---|---|---|---|---|---|
| 1235 | 2-(2,6-diethylphenyl)-4-methoxy-5-{[(2-methyl)oxy]methyl}pyridine | H | X₄—O—(2-methylnaphthyl) | X₂—O—CH₃ | H | 1.19 | 411.2 | 412.3 |
| 1236 | 3-{[6-(2,6-diethylphenyl)-4-methoxypyridin-3-yl]methoxy}-N,N-dimethylaniline | H | X₄—O—(3-N,N-dimethylaminophenyl) | X₂—O—CH₃ | H | 1.05 | 390.2 | 391.3 |

Example 52

Pharmaceutical Preparations of Oral and Intravenous Administration

A. Tablets containing a C5a antagonist and an anti-arthritic agent that is not a C5a receptor antagonist can be prepared as illustrated below:

| Ingredient | Amount |
| --- | --- |
| C5a receptor antagonist | 5 mg-500 mg |
| C5a receptor-inactive therapeutic agent | 1 mg-500 mg |
| diluent, binder, disintigrant, lubricant, excipients | q.s. 200-400 mg. |

B. Tablets containing a C5a receptor antagonist as the only active ingredient can be prepared as illustrated below.

| Ingredient | mg | mg |
| --- | --- | --- |
| C5a receptor antagonist | 10 | 50 |
| Microcrystalline Cellulose | 70.4 | 352 |
| Granular Mannitol | 15.1 | 75.5 |
| Croscarmellose Sodium | 3.0 | 15.0 |
| Colloidal Silicon Dioxide | 0.5 | 2.5 |
| Magnesium Stearate (Impalpable Powder) | 1.0 | 5.0 |
| Total (mg) | 100 | 500 |

C. Tablets containing a C5a receptor antagonist and a C5a receptor inactive agent may be prepared as follows:

| Ingredient | mg | ms |
| --- | --- | --- |
| C5a receptor antagonist | 10 | 25 |
| C5a receptor inactive therapeutic agent | 10 | 25 |
| Microcrystalline Cellulose | 40 | 100 |
| Modified food corn starch | 1.05 | 4.25 |
| Magnesium stearate | 1.25 | 0.5 |

D. Intravenous formulations containing a C5a receptor antagonist and a C5a receptor inactive agent may be prepared as follows:

| Ingredient | Amount |
| --- | --- |
| C5a receptor antagonist | 0.5-10 mg |
| C5a receptor inactive therapeutic agent | 0.5-10 mg |
| Sodium Citrate | 5-50 mg |
| Citric Acid | 1-15 mg |
| Sodium Chloride | 1-8 mg |
| Water for Injection | to 1.0 liter |

E. Oral suspensions containing a C5a receptor antagonist and a C5a receptor inactive agent may be prepared as follows:

| Ingredient | Amount per 5 mL dose |
| --- | --- |
| C5a receptor antagonist | 5-100 mg |
| C5a receptor inactive therapeutic agent | 5-100 mg |
| Polyvinylpyrrolidone | 150 mg |
| Poly oxyethylene sorbitan monolaurate | 25 mg |
| Benzoic Acid | 10 mg to 5 mL with sorbitol solution (70%) |

Example 53

Preparation of Radiolabeled Probes

Compounds provided herein are prepared as radiolabeled probes by carrying out their synthesis using precursors comprising at least one atom that is a radioisotope. The radioisotope is preferably at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SM International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using a compound provided herein as substrate. In addition, certain precursors may be subjected to tritium-halogen exchange with tritium gas, tritium gas reduction of unsaturated bonds, or reduction using sodium borotritide, as appropriate.

Example 54

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds prepared as described herein.

Example 55

Assay for C5a Receptor Mediated Chemotaxis

This Example provides a standard assay of C5a receptor-mediated chemotaxis.

Human promonocytic U937 cells (or purified human or non-human neutrophils) are treated with dibutyl cAMP for 48 hours prior to performing the assay. Human neutrophils or those from another mammalian species are used directly after isolation. The cells are pelleted and resuspended in culture media containing 0.1% fetal bovine serum (FBS) and 10 µg/mL calcein AM (a fluorescent dye). This suspension is then incubated at 37° C. for 30 minutes such that the cells take up the fluorescent dye. The suspension is then centrifuged briefly to pellet the cells, which are then resuspended in culture media containing 0.1% FBS at a concentration of approximately $3\times10^6$ cells/mL. Aliquots of this cell suspension are transferred to clean test tubes, which contain vehicle (1% DMSO in culture media containing 0.1% FBS) or varying concentrations of a compound of interest, and are incubated at room temperature for at least 30 minutes. The chemotaxis assay is performed in CHEMO TX 101-8, 96 well plates (Neuro Probe, Inc.; Gaithersburg, Md.). The bottom wells of the plate are filled with medium containing 0-10 nM of C5a, preferably derived from the same species of mammal as are the neutrophils or other cells (e.g., human C5a for human U937 cells). The top wells of the plate are filled with cell suspensions (compound or vehicle-treated). The plate is then placed in a tissue culture incubator for 60 minutes. The top surface of the plate is washed with PBS to remove excess cell suspension. The number of cells that have migrated into the bottom well is then determined using a fluorescence reader. Chemotaxis index (the ratio of migrated cells to total number of cells loaded) is then calculated for each compound concentration to determine an $EC_{50}$ value.

As a control to ensure that cells retain chemotactic ability in the presence of the compound of interest, the bottom wells of the plate may be filled with varying concentrations chemoattractants that do not mediate chemotaxis via the C5a receptor, such as zymosan-activated serum (ZAS), N-formylmethionyl-leucyl-phenylalanine (FMLP) or leukotriene B4 (LTB4), rather than C5a, under which conditions compounds provided herein preferably do not detectably inhibit chemotaxis. Preferred C5a receptor modulators exhibit $EC_{50}$ values of less than 1 µM in the above assay for C5a mediated chemotaxis.

Example 56

Expression of A C5a Receptor

A human C5a receptor cDNA is obtained by PCR using 1) a forward primer adding a Kozak ribosome binding site and 2) a reverse primer that adds no additional sequence, and 3) an aliquot of a Stratagene Human Fetal Brain cDNA library as template. The sequence of the resulting PCR product is described in PCT International Application WO 02/49993 as SEQ ID NO:1. The PCR product is subcloned into the cloning vector pCR-Script AMP (STRATAGENE, La Jolla, Calif.) at the Srf I site. It is then excised using the restriction enzymes EcoRI and NotI and subcloned in the appropriate orientation for expression into the baculoviral expression vector pBacPAK 9 (CLONTECH, Palo Alto, Calif.) that has been digested with EcoRI and NotI.

Example 57

Baculoviral Preparations for C5a Expression

The human C5a (hC5a) receptor baculoviral expression vector is co-transfected along with BACULOGOLD DNA (BD PharMingen, San Diego, Calif.) into Sf9 cells. The Sf9 cell culture supernatant is harvested three days post-transfection. The recombinant virus-containing supernatant is serially diluted in Hink's TNM-FH insect medium (JRH Biosciences, Kansas City) supplemented Grace's salts and with 4.1 mM L-Gln, 3.3 g/L LAH, 3.3 g/L ultrafiltered yeastolate and 10% heat-inactivated fetal bovine serum (hereinafter "insect medium") and plaque assayed for recombinant plaques. After four days, recombinant plaques are selected and harvested into 1 mL of insect medium for amplification. Each 1 mL volume of recombinant baculovirus (at passage 0) is used to infect a separate T25 flask containing $2\times10^6$ Sf9 cells in 5 mL of insect medium. After five days of incubation at 27° C., supernatant medium is harvested from each of the T25 infections for use as passage 1 inoculum.

Two of seven recombinant baculoviral clones are then chosen for a second round of amplification, using 1 mL of passage 1 stock to infect $1\times10^8$ cells in 100 mL of insect medium divided into 2 T175 flasks. Forty-eight hours post infection, passage 2 medium from each 100 mL prep is harvested and plaque assayed for titer. The cell pellets from the second round of amplification are assayed by affinity binding as described below to verify recombinant receptor expression. A third round of amplification is then initiated using a multiplicity of infection of 0.1 to infect a liter of Sf9 cells. Forty hours post-infection the supernatant medium is harvested to yield passage 3 baculoviral stock.

The remaining cell pellet is assayed for affinity binding using the protocol of DeMartino et al. (1994) *J. Biol. Chem.* 269(20): 14446-14450 (which is incorporated herein by reference for its teaching of binding assays at page 14447), adapted as follows-Radioligand is 0.005-0.500 nM [$^{125}$I]C5a (human recombinant) (New England Nuclear Corp., Boston, Mass.); the hC5a receptor-expressing baculoviral cells are used instead of 293 cells; the assay buffer contains 50 mM Hepes pH. 7.6, 1 mM $CaCl_2$, 5 mM $MgCl_2$, 0.1% BSA, pH 7.4, 0.1 mM bacitracin, and 100 KIU/mL aprotinin; filtration is carried out using GF/C WHATMAN filters (presoaked in 1.0% polyethyeneimine for 2 hours prior to use); and the filters are washed twice with 5 mL cold binding buffer without BSA, bacitracin, or aprotinin.

Titer of the passage 3 baculoviral stock is determined by plaque assay and a multiplicity of infection, incubation time course, binding assay experiment is carried out to determine conditions for optimal receptor expression.

A multiplicity of infection of 0.1 and a 72-hour incubation period were the best infection parameters found for hC5a receptor expression in up to 1-liter Sf9 cell infection cultures.

Example 58

Baculoviral Infections

Log-phase Sf9 cells (INVITROGEN Corp., Carlsbad Calif.), are infected with one or more stocks of recombinant baculovirus followed by culturing in insect medium at 27° C. Infections are carried out either only with virus directing the expression of the hC5a receptor or with this virus in combination with three G-protein subunit-expression virus stocks: 1) rat $G\square_{i2}$ G-protein-encoding virus stock (BIOSIGNAL #V5J008), 2) bovine b1 G-protein-encoding virus stock (BIOSIGNAL #V5H012), and 3) human g2 G-protein-encoding virus stock (BIOSIGNAL #V613003), which may be obtained from BIOSIGNAL Inc., Montreal.

The infections are conveniently carried out at a multiplicity of infection of 0.1:1.0:0.5:0.5. At 72 hours post-infection, a sample of cell suspension is analyzed for viability by trypan blue dye exclusion, and the remaining Sf9 cells are harvested via centrifugation (3000 rpm/10 minutes/4° C.).

Example 59

Purified Recombinant Insect Cell Membranes

Sf9 cell pellets are resuspended in homogenization buffer (10 mM HEPES, 250 mM sucrose, 0.5 µg/mL leupeptin, 2 µg/mL Aprotinin, 200 µM PMSF, and 2.5 mM EDTA, pH 7.4) and homogenized using a POLYTRON homogenizer (setting 5 for 30 seconds). The homogenate is centrifuged (536×g/10 minutes/4° C.) to pellet the nuclei. The supernatant containing isolated membranes is decanted to a clean centrifuge tube, centrifuged (48,000×g/30 minutes, 4° C.) and the resulting pellet resuspended in 30 mL homogenization buffer. This centrifugation and resuspension step is repeated twice. The final pellet is resuspended in ice cold Dulbecco's PBS containing 5 mM EDTA and stored in frozen aliquots at −80° C. until needed. The protein concentration of the resulting membrane preparation (hereinafter "P2 membranes") is conveniently measured using a Bradford protein assay (Bio-Rad Laboratories, Hercules, Calif.). By this measure, a 1-liter culture of cells typically yields 100-150 mg of total membrane protein.

Example 60

Radioligand Binding Assays

Purified P2 membranes, prepared by the method given above, are resuspended by Dounce homogenization (tight pestle) in binding buffer (50 mM Hepes pH. 7.6, 120 mM NaCl, 1 mM $CaCl_2$, 5 mM $MgCl_2$, 0.1% BSA, pH 7.4, 0.1 mM bacitracin, 100 KIU/mL aprotinin).

For saturation binding analysis, membranes (5-50 μg) are added to polypropylene tubes containing 0.005-0.500 nM [$^{125}$I]C5a (human (recombinant), New England Nuclear Corp., Boston, Mass.) with a final assay volume of 0.25 ml. Nonspecific binding is determined in the presence of 300 nM hC5a (Sigma Chemical Co., St. Louis, Mo.) and accounted for less than 10% of total binding. For evaluation of guanine nucleotide effects on receptor affinity, GTPγS is added to duplicate tubes at the final concentration of 50 μM.

For competition analysis, membranes (5-50 μg) are added to polypropylene tubes containing 0.030 nM [$^{125}$I]C5a (human). Non-radiolabeled displacers are added to separate assays at concentrations ranging from $10^{-10}$ M to $10^{-5}$ M to yield a final volume of 0.250 mL. Nonspecific binding is determined in the presence of 300 nM hC5a (Sigma Chemical Co., St. Louis, Mo.) and accounted for less than 10% of total binding. Following a 2-hour incubation at room temperature, the reaction is terminated by rapid vacuum filtration. Samples are filtered over presoaked (in 1.0% polyethyleneimine for 2 hours prior to use) CF/C WHATMAN filters and rinsed 2 times with 5 mL cold binding buffer without BSA, bacitracin, or aprotinin. Remaining bound radioactivity is quantified by gamma counting. $K_1$ and Hill coefficient ("nH") are determined by fitting the Hill equation to the measured values with the aid of SIGMAPLOT software.

Example 61

Agonist-Induced GTP Binding

Agonist-stimulated GTP-gamma S binding ("GTP binding") activity can be used to identify agonist and antagonist compounds and to differentiate neutral antagonist compounds from those that possess inverse agonist activity. This activity can also be used to detect partial agonism mediated by antagonist compounds. A compound being analyzed in this assay is referred to herein as a "test compound." Agonist-stimulated GTP binding activity is measured as follows: Four independent baculoviral stocks (one directing the expression of the hC5a receptor and three directing the expression of each of the three subunits of a heterotrimeric G-protein) are used to infect a culture of Sf9 cells as described above.

Agonist-stimulated GTP binding on purified membranes (prepared as described above) is assessed using hC5a (Sigma Chemical Co., St. Louis, Mo., USA) as agonist in order to ascertain that the receptor/G-protein-alpha-beta-gamma combination(s) yield a functional response as measured by GTP binding.

P2 membranes are resuspended by Dounce homogenization (tight pestle) in GTP binding assay buffer (50 mM Tris pH 7.0, 120 mM NaCl, 2 mM $MgCl_2$, 2 mM EGTA, 0.1% BSA, 0.1 mM bacitracin, 100 KIU/mL aprotinin, 5 μM GDP) and added to reaction tubes at a concentration of 30 μg protein/reaction tube. After adding increasing doses of the agonist hC5a at concentrations ranging from $10^{-12}$ M to $10^{-6}$ M, reactions are initiated by the addition of 100 μM GTPgamma$^{35}$S with a final assay volume of 025 ml. In competition experiments, non-radiolabeled test compounds (e.g., compounds of Formula I) are added to separate assays at concentrations ranging from $10^{-10}$ M to $10^{-5}$ M along with 10 nM hC5a to yield a final volume of 0.25 mL.

Neutral antagonists are those test compounds that reduce the C5a-stimulated GTP binding activity towards, but not below, baseline (the level of GTP bound by membranes in this assay in the absence of added C5a or other agonist and in the further absence of any test compound).

In contrast, in the absence of added C5a, certain preferred compounds reduce the GTP binding activity of the receptor-containing membranes below baseline, and are thus characterized as inverse agonists. If a test compound that displays antagonist activity does not reduce the GTP binding activity below baseline in the absence of the C5a agonist, it is characterized as a neutral antagonist.

An antagonist test compound that elevates GTP binding activity above baseline in the absence of added hC5a in this assay is characterized as having partial agonist activity. Preferred antagonist compounds provided herein do not elevate GTP binding activity under such conditions more than 10% above baseline, preferably not more than 5% above baseline, and most preferably not more than 2% above baseline.

Following a 60-minute incubation at room temperature, the reactions are terminated by vacuum filtration over CF/C filters (pre-soaked in wash buffer, 0.1% BSA) followed by washing with ice-cold wash buffer (50 mM Tris pH 7.0, 120 mM NaCl). The amount of receptor-bound (and thereby membrane-bound) GTPgamma$^{35}$S is determined by measuring the bound radioactivity, preferably by liquid scintillation spectrometry of the washed filters. Non-specific binding is determined using 10 mM GTPgammaS and typically represents less than 5 percent of total binding. Data is expressed as percent above basal (baseline). The results of these GTP binding experiments is analyzed using SIGMAPLOT software (SPSS Inc., Chicago, Ill.).

Example 62

Calcium Mobilization Assays

A. Response to C5a

U937 cells are grown in differentiation media (1 mM dibutyrl cAMP in RPMI 1640 medium containing 10% fetal bovine serum) for 48 hours at 37° C. then reseeded onto 96-well plates suitable for use in a FLIPR™ Plate Reader (Molecular Devices Corp., Sunnyvale Calif.). Cells are grown an additional 24 hours (to 70-90% confluence) before the assay. The cells are then washed once with Krebs Ringer solution. FLUO-3 calcium sensitive dye (Molecular Probes, Inc. Eugene, Oreg.) is added to 10 μg/mL and incubated with the cells in Krebs Ringer solution at room temperature for 1 to 2 hours. The 96 well plates are then washed to remove excess dye. Fluorescence responses, measured by excitation at 480 nM and emission at 530 nM, are monitored upon the addition of human C5a to the cells to a final concentration of 0.01-30.0 nM, using the FLIPR™ device (Molecular Devices). Differentiated U937 cells typically exhibit signals of 5,000-50,000 Arbitrary Fluorescent Light Units in response to agonist stimulation.

B. Assays for Determination of ATP Responses

Differentiated U937 cells (prepared and tested as described above under "A. Response to C5a") are stimulated by the addition of ATP (rather than C5a) to a final concentration of 0.01 to 30 µM. This stimulation typically triggers a signal of 1,000 to 12,000 arbitrary fluorescence light units. Certain preferred compounds produce less than a 10%, preferably less than a 5%, and most preferably less than a 2% alteration of this calcium mobilization signal when this control assay is carried out in the presence or absence of the compounds.

C. Assays for the Identification of Receptor Modulatory Agents: Antagonists and Agonists Those of skill in the art will recognize that the calcium mobilization assay described above may be readily adapted for identifying test compounds as having agonist or antagonist activity at the human C5a receptor.

For example, in order to identify antagonist compounds, differentiated U937 cells are washed and incubated with Fluo-3 dye as described above. One hour prior to measuring the fluorescence signal, a subset of the cells is incubated with a 1 µM concentration of at least one compound to be tested. The fluorescence response upon the subsequent addition of 0.3 nM (final concentration) human recombinant C5a is monitored using the FLIPR™ plate reader. Antagonist compounds elicit at least a 2-fold decrease in the fluorescence response relative to that measured in the presence of human C5a alone. Preferred antagonist compounds elicit at least a 5-fold, preferably at least a 10-fold, and more preferably at least a 20-fold decrease in the fluorescence response relative to that measured in the presence of human C5a alone. Agonist compounds elicit an increase in fluorescence without the addition of C5a, which increase will be at least partially blocked by a known C5a receptor antagonist.

Example 63

Assays to Evaluate Agonist Activity of Small Molecule C5a Receptor Antagonists

Certain preferred compounds of Formula I are C5a receptor antagonists that do not possess significant (e.g., greater than 5%) agonist activity in any of the C5a mediated functional assays discussed herein. Such agonist activity can be evaluated, for example, in the assay of C5a induced GTP binding given above, by measuring small molecule mediated GTP binding in the absence of the natural agonist, C5a. Similarly, in a calcium mobilization assay such as the assay described above a small molecule compound can be directly assayed for the ability of the compound to stimulate calcium levels in the absence of the natural agonist, C5a. The preferred extent of C5a agonist activity exhibited by certain compounds provided herein is less than 10%, more preferably less than 5% and most preferably less than 2% of the response elicited by the natural agonist, C5a.

Example 64

MDCK Toxicity Assay

This Example illustrates the evaluation of compound toxicity using a Madin Darby canine kidney (MDCK) cell cytotoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagles ATCC catalog #30-2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution" (available as a component of the PACKARD (Meriden, Conn.) ATP-LITE-M Luminescent ATP detection kit) is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD ATP-LITE-M Luminescent ATP detection kit, product no. 6016941, is generally used according to the manufacturers instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

What is claimed is:

1. A compound having the formula:

[chemical structure diagram showing a pyridine ring with substituents $R_1$, $R_2$, $R_3$, $R_8$, $R_9$, $R_{17}$, A, and connected to an indazole-like ring with $R_{12}$, $R_{13}$, $A_1$, NH]

or a pharmaceutically acceptable salt thereof, wherein:

A is $OR_4$, $NR_4R_5$, $CR_6R_7$ or $CH_R6R_7$;

$R_1$ is chosen from:
(i) hydrogen, halogen, amino, and cyano; and
(ii) $C_1$-$C_6$alkyl, $C_2$-$C_6$alkenyl, $C_2$-$C_6$alkynyl, $C_1$-$C_6$alkoxy, $C_1$-$C_4$haloalkyl, $C_1$-$C_4$haloalkoxy, mono- and di-($C_1$-$C_6$alkyl)amino, ($C_3$-$C_7$cycloalkyl)$C_0$-$C_4$alkyl, and —S($O_n$)$C_1$-$C_4$alkyl, each of which is substituted with from 0 to 4 substituents independently chosen from $R_x$;

$R_2$ is halogen, cyano or $XR_y$;

$R_3$ is hydrogen, halogen, hydroxy, amino, cyano, $C_1$-$C_4$alkyl, $C_2$-$C_4$alkenyl, $C_2$-$C_4$alkynyl, $C_1$-$C_4$alkoxy, $C_1$-$C_2$haloalkyl, $C_1$-$C_2$haloalkoxy, mono- or di-($C_1$-$C_4$alkyl)amino or —S($O_n$)$C_1$-$C_4$alkyl;

$R_4$ is:
(i) hydrogen, $C_1$-$C_8$alkyl, $C_2$-$C_8$alkenyl, $C_2$-$C_8$alkynyl, ($C_3$-$C_7$cycloalkyl)$C_0$-$C_4$alkyl, mono- or di-($C_1$-$C_4$alkylamino)$C_0$-$C_4$alkyl, phenyl$C_0$-$C_4$alkyl, or tetrahydronapthyl, each of which is substituted with from 0 to 4 substituents independently chosen from $R_x$, oxo, mono- and di-($C_1$-$C_4$alkyl)amino($C_1$-$C_4$alkyl), mono- and di-$C_1$-$C_4$alkylamino($C_1$-$C_4$alkoxy), $C_2$-$C_4$alkanoyl or $XR_y$;

$R_5$ is hydrogen, $C_1$-$C_6$alkyl, $C_2$-$C_6$alkenyl, $C_2$-$C_6$alkynyl, ($C_3$-$C_7$carbocycle) $C_0$-$C_4$alkyl;

$R_6$ is:
(i) hydrogen, halogen, hydroxy, cyano, amino, $C_1$-$C_6$alkyl, $C_2$-$C_6$alkenyl, $C_2$-$C_6$alkynyl, mono- or di-($C_1$-$C_6$alkylamino)$C_0$-$C_6$alkyl, or ($C_3$-$C_{10}$carbocycle)$C_0$-$C_4$alkyl, each of which is substituted with from 0 to 4 substituents independently chosen from $R_x$, oxo, mono- and di-$C_1$-$C_4$alkylamino($C_1$-$C_4$alkyl), mono- and di-$C_1$-$C_4$alkylamino($C_1$-$C_4$alkoxy), $C_2$-$C_4$alkanoyl and YZ; or
(ii) joined to $R_7$ to form, with the carbon atom to which $R_6$ and $R_7$ are bound, a 3- to 10-membered carbocycle which is substituted with from 0 to 4 substituents independently chosen from $R_7$, oxo, mono- and di-($C_1$-$C_4$alkylamino)$C_1$-$C_4$alkyl, mono- and di-$C_1$-$C_4$alkylamino($C_1$-$C_4$alkoxy), $C_2$-$C_4$alkanoyl and $C_2$-$C_4$alkanoyloxy;

$R_7$ is hydrogen, halogen, hydroxy, cyano, amino, $C_1$-$C_6$alkyl, $C_{2-6}$alkenyl, $C_2$-$C_6$alkynyl, $C_1$-$C_6$alkoxy, ($C_3$-$C_7$cycloalkyl)$C_0$-$C_4$alkyl or joined to $R_6$ to form an optionally substituted carbocycle;

$R_8$ is:
(i) hydrogen, halogen, hydroxy, $C_1$-$C_6$alkyl, $C_2$-$C_6$alkenyl, $C_2$-$C_6$alkynyl, $C_1$-$C_6$alkoxy, $C_1$-$C_6$alkylamino or $C_3$-$C_7$cycloalkyl $C_0$-$C_4$alkyl;
(ii) joined to $R_9$ to form a $C_5$-$C_7$ cycloalkyl ring which is substituted with from 0 to 4 substituents independently chosen from halogen, hydroxy, $C_1$-$C_2$alkyl and $C_1$-$C_2$alkoxy; or
(iii) taken together with $R_9$ to form an oxo group;

$R_9$ is:
(i) absent, hydrogen, halogen, hydroxy, $C_1$-$C_6$alkyl, $C_2$-$C_6$alkenyl, $C_2$-$C_6$alkynyl, $C_1$-$C_6$alkoxy, $C_1$-$C_6$alkylamino or $C_3$-$C_7$cycloalkyl $C_0$-$C_4$alkyl;
(ii) joined to $R_8$ to form an optionally substituted $C_5$-$C_7$ cycloalkyl ring or
(iii) taken together with $R_8$ to form an oxo group;

$R_{12}$ and $R_{13}$ independently represent from 0 to 3 substituents independently chosen from $R_x$;

$R_{17}$ is absent or oxygen;

$A_1$ is N;

X is a single bond, —$CR_AR_B$—, —O—, —C(=O)—, —C(=O)O—, —S(O)$_n$— or —$NR_B$—; and $R_y$ is:
(i) hydrogen; or
(ii) $C_1$-$C_{10}$alkyl, $C_2$-$C_{10}$alkenyl, $C_2$-$C_{10}$alkynyl, or $C_3$-$C_{10}$carbocycle$C_0$-$C_4$alkyl, each of which is substituted with from 0 to 6 substituents independently selected from $R_x$, oxo, —NH($C_1$-$C_6$alkanoyl), —N($C_1$-$C_6$alkyl)$C_1$-$C_6$alkanoyl, —NHS($O_n$)$C_1$-$C_6$alkyl, —N(S($O_n$)$C_1$-$C_6$alkyl)$_2$, —S($O_n$)NH$C_1$-$C_6$alkyl and —S($O_n$)N($C_1$-$C_6$alkyl)$_2$;

Y is a single bond, —$CR_AR_B$—, —$NR_B$—, or —O—;

Z is independently selected at each occurrence from 3- to 7-membered carbocycles which is substituted with from 0 to 4 substituents independently selected from halogen, oxo, —COOH, hydroxy, amino, cyano, $C_1$-$C_6$alkyl, $C_1$-$C_6$alkoxy, $C_1$-$C_6$haloalkyl, $C_1$-$C_6$haloalkoxy, mono- and di-($C_1$-$C_6$alkyl)amino and —S($O_n$) $C_1$-$C_6$alkyl; and $R_A$ and $R_B$ are independently selected at each occurrence from:
(i) hydrogen; and
(ii) $C_1$-$C_{10}$alkyl, $C_2$-$C_{10}$alkenyl, $C_2$-$C_{10}$alkynyl, or saturated or partially saturated ($C_3C_{10}$carbocycle)$C_0$-$C_4$alkyl each of which is substituted with from 0 to 6 substituents independently selected from oxo, hydroxy, halogen, cyano, amino, $C_1$-$C_6$alkoxy, mono- and di-($C_1$-$C_4$alkyl)amino, —COOH, —C(=O)NH$_2$, —NHC(=O)($C_1$-$C_6$alkyl), —N($C_1$-$C_6$alkyl)C(=O)($C_1$-$C_6$alkyl), —NHS($O_n$)$C_1$-$C_6$alkyl, —S($O_n$)$C_1$-$C_6$alkyl, —S($O_n$)NH$C_1$-$C_6$alkyl, —S($O_n$)N($C_1$-$C_6$alkyl)$C_1$-$C_6$alkyl and Z;

$R_x$ is independently chosen at each occurrence from halogen, hydroxy, amino, cyano, nitro, —COOH, —C(=O)NH$_2$, $C_1$-$C_6$alkoxycarbonyl, —C(=O)NH$C_1$-$C_6$alkyl, —C(=O)N($C_1$-$C_6$alkyl)$_2$, $C_1$-$C_6$alkyl, $C_2$-$C_6$alkenyl, $C_2$-$C_6$alkynyl, mono- and di-($C_1$-$C_6$alkyl)amino, $C_1$-$C_6$alkoxy, $C_1$-$C_2$hydroxyalkyl, $C_1$-$C_2$haloalkyl, $C_1$-$C_2$haloalkoxy, ($C_3$-$C_7$cycloalkyl)$C_0$-$C_4$alkyl, and —S($O_n$)$C_1$-$C_6$alkyl; and n is independently selected at each occurrence from 0, 1 and 2.

2. A compound or salt thereof according to claim 1, wherein:

$R_1$ is hydrogen, cyano, $C_1$-$C_4$alkyl or $C_1$-$C_4$alkoxy;

$R_2$ is hydrogen, halogen, cyano or $XR_y$, wherein:

X is a single bond, —C(=O)—, —O—, —S(O)$_n$ or —$NR_B$—; and $R_y$ is $C_1$-$C_8$alkyl, $C_1$-$C_8$alkenyl, $C_1$-$C_8$alkynyl, $C_3$-$C_7$cycloalkyl$C_0$-$C_4$alkyl, or phenyl$C_0$-$C_4$alkyl each of which is substituted with from 0 to 2 substituents independently chosen from hydroxy, halogen, cyano, amino, —COOH, oxo, —C(=O)NH$_2$, —SO$_2$NH$_2$, —SO$_2$NH($C_1$-$C_4$alkyl), $C_1$-$C_8$alkyl, $C_1$-$C_8$hydroxyalkyl, $C_1C_8$alkoxy and $C_3$-$C_7$cycloalkyl;

R₃ is hydrogen, methyl, chloro, fluoro, trifluoromethyl or cyano; and

R$_8$ and R$_9$ are independently chosen from hydrogen, halogen, hydroxy, $C_1$-$C_6$alkyl, $C_1$-$C_6$alkenyl, ($C_3$-$C_6$cycloalkyl)$C_0$-$C_4$alkyl and $C_1$-$C_6$alkoxy.

3. A compound or salt thereof according to claim 2, wherein R$_{12}$ and R$_{13}$ independently represent 0, 1 or 2 substituents independently chosen from methyl, ethyl and isopropyl.

4. The compound or pharmaceutically acceptable salt thereof according to claim 1, wherein the compound is selected from the group consisting of 4-[4-Isopropoxy-5-(5-isopropyl-2-methyl-phenoxymethyl)-6-methyl-pyridin-2-yl]-5-isopropyl-1H-indazole, 5-Ethyl-4-[4-isopropoxy-5-(5-isopropyl-2-methyl-phenoxymethyl)-6-methyl-pyridin-2-yl]-3-methyl-1H-indazole, 4-[4-Ethoxy-5-(5-isopropyl-2-methyl-phenoxymethyl)-6-methyl-pyridin-2-yl]-5-ethyl-3-methyl-1H-indazole, 4-[5-(2,5-Dimethyl-phenoxymethyl)-4-ethoxy-6-methyl-pyridin-2-yl]-5-ethyl-3-methyl-1H-indazole, 3-Ethyl-4-[4-isopropoxy-5-(5-isopropyl-2-methyl-phenoxymethyl)-6-methyl-pyridin-2-yl]-1H-indazole, 4-[4-Isopropoxy-5-(5-isopropyl-2-methyl-phenoxymethyl)-6-methyl-pyridin-2-yl]-3-isopropyl-1H-indazole, 4-[4-Isopropoxy-5-(5-isopropyl-2-methyl-phenoxymethyl)-6-methyl-pyridin-2-yl]-3-methyl-1H-indazole, 4-[5-(Cyclohexyl-methoxy-methyl)-4-isopropoxy-6-methyl-pyridin-2-yl]-5-isopropyl-1H-indazole, 5-Isopropyl-4-[5-(5-isopropyl-2-methyl-phenoxymethyl)-6-methyl-pyridin-2-yl]-1H-indazole, 5-Isopropyl-4-[5-(5-isopropyl-2-methyl-phenoxymethyl)-6-methyl-4-vinyl-pyridin-2-yl]-1H-indazole, Isopropyl-[6-(5-isopropyl-1H-indazol-4-yl)-3-(5-isopropyl-2-methyl-phenoxymethyl)-2-methyl-pyridin-4-ylmethyl]-amine, Cyclobutyl-[6-(5-isopropyl-1H-indazol-4-yl)-3-(5-isopropyl-2-methyl-phenoxymethyl)-2-methyl-pyridin-4-ylmethyl]-amine, Isobutyl-[6-(5-isopropyl-1H-indazol-4-yl)-3-(5-isopropyl-2-methyl-phenoxymethyl)-2-methyl-pyridin-4-ylmethyl]-amine, (2,2-Dimethyl-propyl)-[6-(5-isopropyl-1H-indazol-4-yl)-3-(5-isopropyl-2-methyl-phenoxymethyl)-2-methyl-pyridin-4-ylmethyl]-amine, 2-{[6-(5-Isopropyl-1H-indazol-4-yl)-3-(5-isopropyl-2-methyl-phenoxymethyl)-2-methyl-pyridin-4-ylmethyl]-amino}-2-methyl-propan-1-ol, (S)-(1,2-Dimethyl-propyl)-[6-(5-isopropyl-1H-indazol-4-yl)-3-isopropyl-2-methyl-phenoxymethyl)-2-methyl-pyridin-4-ylmethyl]-amine, and (R)-(1,2-Dimethyl-propyl)-[6-(5-isopropyl-1H-indazol-4-yl)-3-(4-isopropyl-2-methyl-phenoxymethyl)-2-methyl-pyridin-4-ylmethyl]amine.

* * * * *